(12) United States Patent
Corte et al.

(10) Patent No.: US 12,404,274 B2
(45) Date of Patent: Sep. 2, 2025

(54) MACROCYCLES AS FACTOR XIA INHIBITORS

(71) Applicant: Bristol-Myers Squibb Company, Princeton, NJ (US)

(72) Inventors: James R. Corte, Yardley, PA (US); Tianan Fang, Newtown, PA (US); Carl P. Decicco, New Hope, PA (US); Donald J.P. Pinto, Churchville, PA (US); Karen A. Rossi, Newtown, PA (US); Zilun Hu, Jamison, PA (US); Yoon Jeon, Belle Mead, NJ (US); Mimi L Quan, Yardley, PA (US); Joanne M. Smallheer, Yardley, PA (US); Yufeng Wang, Belle Mead, NJ (US); Wu Yang, Princeton Junction, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 841 days.

(21) Appl. No.: 17/493,516

(22) Filed: Oct. 4, 2021

(65) Prior Publication Data
US 2023/0058729 A1 Feb. 23, 2023

Related U.S. Application Data

(62) Division of application No. 16/691,099, filed on Nov. 21, 2019, now Pat. No. 11,136,327, which is a division of application No. 15/718,431, filed on Sep. 28, 2017, now Pat. No. 10,487,086, which is a division of application No. 14/578,846, filed on Dec. 22, 2014, now Pat. No. 9,802,939, which is a division of application No. 13/024,544, filed on Feb. 10, 2011, now Pat. No. 8,940,720.

(60) Provisional application No. 61/405,338, filed on Oct. 21, 2010, provisional application No. 61/303,423, filed on Feb. 11, 2010.

(51) Int. Cl.

| | | |
|---|---|---|
| *C07D 471/18* | (2006.01) | |
| *C07D 471/14* | (2006.01) | |
| *C07D 487/04* | (2006.01) | |
| *C07D 487/06* | (2006.01) | |
| *C07D 487/08* | (2006.01) | |
| *C07D 487/14* | (2006.01) | |
| *C07D 487/16* | (2006.01) | |
| *C07D 487/18* | (2006.01) | |
| *C07D 498/04* | (2006.01) | |
| *C07D 498/06* | (2006.01) | |
| *C07D 498/08* | (2006.01) | |

(52) U.S. Cl.
CPC ......... *C07D 487/04* (2013.01); *C07D 471/14* (2013.01); *C07D 471/18* (2013.01); *C07D 487/06* (2013.01); *C07D 487/08* (2013.01); *C07D 487/14* (2013.01); *C07D 487/16* (2013.01); *C07D 487/18* (2013.01); *C07D 498/04* (2013.01); *C07D 498/06* (2013.01); *C07D 498/08* (2013.01)

(58) Field of Classification Search
None
See application file for complete search history.

(56) References Cited

U.S. PATENT DOCUMENTS

| | | |
|---|---|---|
| 6,951,840 B2 | 10/2005 | Belvo et al. |
| 8,828,983 B2 | 9/2014 | Quan et al. |
| 8,940,720 B2 | 1/2015 | Corte et al. |
| 9,079,918 B2 | 7/2015 | Quan et al. |
| 9,221,818 B2 | 12/2015 | Pinto et al. |
| 9,453,029 B2 | 9/2016 | Quan et al. |
| 9,802,939 B2 | 10/2017 | Corte et al. |
| 10,487,086 B2 | 11/2019 | Corte et al. |
| 11,136,327 B2 | 10/2021 | Corte et al. |

(Continued)

FOREIGN PATENT DOCUMENTS

| | | |
|---|---|---|
| CN | 1403458 A | 3/2003 |
| CN | 101006063 A | 7/2007 |

(Continued)

OTHER PUBLICATIONS

Yoshimura. Chemical Communications, 2007, 3057-3059 (Year: 2007).*

(Continued)

*Primary Examiner* — Noble E Jarrell
(74) *Attorney, Agent, or Firm* — Mintz, Levin, Cohn, Ferris, Glovsky and Popeo, P.C

(57) ABSTRACT

The present invention provides compounds of Formula (I):

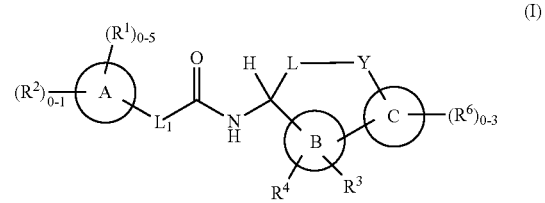

or a stereoisomer, a tautomer, or a pharmaceutically acceptable salt thereof, wherein all the variables are as defined herein. These compounds are selective Factor XIa inhibitors or dual inhibitors of fXIa and plasma kallikrein. This invention also relates to pharmaceutical compositions comprising these compounds and methods of treating thromboembolic and/or inflammatory disorders using the same.

8 Claims, No Drawings

(56) References Cited

U.S. PATENT DOCUMENTS

| | | |
|---|---|---|
| 2003/0130172 A1 | 7/2003 | Belvo et al. |
| 2008/0039470 A1 | 2/2008 | Niu et al. |
| 2012/0041190 A1 | 2/2012 | Corte et al. |
| 2015/0112058 A1 | 4/2015 | Corte et al. |
| 2018/0022753 A1 | 1/2018 | Corte et al. |
| 2020/0087312 A1 | 3/2020 | Corte et al. |

FOREIGN PATENT DOCUMENTS

| | | |
|---|---|---|
| CN | 101341129 A | 1/2009 |
| CN | 101495480 A | 7/2009 |
| CN | 101605779 A | 12/2009 |
| JP | 2001517671 A | 10/2001 |
| JP | 2008502700 A | 1/2008 |
| JP | 2009519966 A | 5/2009 |
| JP | 2009519967 A | 5/2009 |
| JP | 2013519678 A | 5/2013 |
| JP | 2013519679 A | 5/2013 |
| WO | 9915530 A1 | 4/1999 |
| WO | 03106438 A1 | 12/2003 |
| WO | 2004080971 A1 | 9/2004 |
| WO | 2004094372 A2 | 11/2004 |
| WO | 2005099709 A2 | 10/2005 |
| WO | 2005123050 A2 | 12/2005 |
| WO | 2005123680 A1 | 12/2005 |
| WO | 2006076575 A2 | 7/2006 |
| WO | 2006089005 A2 | 8/2006 |
| WO | 2007047608 A2 | 4/2007 |
| WO | 2007070816 A2 | 6/2007 |
| WO | 2007070818 A1 | 6/2007 |
| WO | 2007070826 A1 | 6/2007 |
| WO | 2008076805 A2 | 6/2008 |
| WO | 2008079836 A2 | 7/2008 |
| WO | 2008157162 A1 | 12/2008 |
| WO | 2009038974 A1 | 3/2009 |
| WO | 2009114677 A1 | 9/2009 |
| WO | 2011100401 A1 | 8/2011 |
| WO | 2011100402 A1 | 8/2011 |
| WO | 2013022814 A1 | 2/2013 |
| WO | 2013022818 A1 | 2/2013 |
| WO | 2013055984 A1 | 4/2013 |
| WO | 2013056034 A1 | 4/2013 |
| WO | 2013056060 A1 | 4/2013 |
| WO | 2013093484 A1 | 6/2013 |
| WO | 2013118805 A1 | 8/2013 |
| WO | 2013174937 A1 | 11/2013 |

OTHER PUBLICATIONS

Cho. Bulletin of the Korean Chemical Society, 2013, 34(4), 1212-1220 (Year: 2013).*
How is pulmonary embolism treated, Sep. 6, 2016,.
International Search Report and Written Opinion Issued in International Patent Application No. PCT/US2011/024305, mailed on May 3, 2011, 8 pages.
Pulmonary Embolism, https://www.mayoclinic.org/diseases-conditions/pulmonary-embolism/symptoms-causes/syc-20354647, May 20, 2013, 7 pages.
Boger et al. (1998) "Thermal Atropisomerism of Aglucovancomycin Derivatives: Preparation of (M,M,M)-and (P,M,M)-Aglucovancomysins", Journal of American Chemical Society, 120(35):8920-8926.
Boger et al. (Oct. 15, 1999) "Total Synthesis of the Vancomycin Aglycon", Journal of the American Chemical Society, 121(43):10004-10011.
Chan et al. (Feb. 2001) "The Characterization of Mice with a Targeted Combined Deficiency of Protein C and Factor XI", The American Journal of Pathology, 158(2):469-479.
Evans et al. (1993) "Kinetic and Thermodynamic Atropdiastereoselection in the Synthesis of the M(5-7) Tripeptide Portion of Vancomycin", Tetrahedron Letters, 34(38):6029-6032.
Evans et al. (1998) "Total Synthesis of Vancomycin and Eremomycin Aglycons", Angewandte Chemie, 37(19):2700-2704.
Gailani et al. (Mar. 1997) "A Murine Model of Factor XI Deficiency", Blood Coagulation and Fibrinolysis, 8(2):134-144.
Gailani David. (Feb. 1, 2001) "Gene Targeting in Hemostasis: Factor XI", Frontiers in Bioscience, 6:201-207.
Gruber et al. (Aug. 1, 2003) "Factor XI—Dependence of Surface- and Tissue Factor-Initiated Thrombus Propagation in Primates", Blood, 102(3):953-955.
Hoffman et al. (Sep. 2003) "A Cell-Based Model of Coagulation and the Role of Factor VIIa", Blood Reviews, 17:S1-S5.
Kumar et al. (2013) "Remarkable Photocytotoxicity of a Novel Triazole-Linked Cationic Porphyrin—β-Carboline Conjugate", Chemical Communications, 49(7):683-685.
Meijers et al. (Mar. 9, 2000) "High Levels of Coagulation Factor XI as a Risk Factor for Venous Thrombosis", The New England Journal of Medicine, 342(10):696-701.
Minnema et al. (Nov. 1, 2000) "Activation of Clotting Factors XI and IX in Patients With Acute Myocardial Infarction", Arteriosclerosis, Thrombosis, and Vascular Biology, 20(11):2489-2493.
Murakami et al. (Aug. 1995) "Evaluation of Factor XIa-α1-Antitrypsin in Plasma, a Contact Phase-Activated Coagulation Factor-Inhibitor Complex, in Patients With Coronary Artery Disease", Arteriosclerosis, Thrombosis, and Vascular Biology, 15(8):1107-1113.
Nicolaou et al. (Aug. 4, 1997) "New Technology for the Synthesis of Vancomycin-Type Biaryl Ring Systems", Angewandte Chemie, 36(13-14):1539-1540.
Nicolaou et al. (Sep. 3, 1999) "Total Synthesis of Vancomycin—Part 1: Design and Development of Methodology", Chemistry—A European Journal, 5(9):2584-2601.
Rosen et al. (Apr. 2002) "FXI is Essential for Thrombus Formation Following FeCl3-Induced Injury of the Carotid Artery in the Mouse", Thrombosis and Haemostasis, 87(4):774-776.
Schumacher et al. (2010) "Inhibition of Factor XIa as a New Approach to Anticoagulation", Arteriosclerosis: Thrombosis & Vascular Biology, 30:388-392.
Walsh. (1999) "Platelets and Factor XI Bypass the Contact System of Blood Coagulation", Thrombosis and Haemostasis, 82(2):234-242.
Wang et al. (Apr. 2005) "Effects of Factor IX or Factor XI Deficiency on Ferric Chloride-Induced Carotid Artery Occlusion in Mice", Journal of Thrombosis and Haemostasis, 3(4):695-702.

* cited by examiner

MACROCYCLES AS FACTOR XIA INHIBITORS

CROSS REFERENCE TO RELATED APPLICATIONS

This Divisional application claims the benefit of U.S. Ser. No. 16/691,099 filed Nov. 21, 2019, now allowed, which is a Divisional of U.S. Ser. No. 15/718,431 filed Sep. 28, 2017, now U.S. Pat. No. 10,487,086, which is a Divisional of U.S. Ser. No. 14/578,846 filed Dec. 22, 2014, now U.S. Pat. No. 9,802,939, which is a Divisional of U.S. Ser. No. 13/024,544 filed Feb. 10, 2011, now U.S. Pat. No. 8,940,720, which in turn claims the benefit of U.S. Provisional Application Ser. No. 61/303,423 filed Feb. 11, 2010 and U.S. Provisional Application Ser. No. 61/405,338 filed Oct. 21, 2010, hereby incorporated by reference in their entireties.

FIELD OF THE INVENTION

The present invention relates generally to novel macrocyclic compounds, and their analogues thereof, which are inhibitors of Factor XIa and/or plasma kallikrein, compositions containing them, and methods of using them, for example, for the treatment or prophylaxis of thromboembolic disorders.

BACKGROUND OF THE INVENTION

Thromboembolic diseases remain the leading cause of death in developed countries despite the availability of anticoagulants such as warfarin (COUMADIN®), heparin, low molecular weight heparins (LMWH), and synthetic pentasaccharides and antiplatelet agents such as aspirin and clopidogrel (PLAVIX®). The oral anticoagulant warfarin, inhibits the post-translational maturation of coagulation Factors VII, IX, X and prothrombin, and has proven effective in both venous and arterial thrombosis. However, its usage is limited due to its narrow therapeutic index, slow onset of therapeutic effect, numerous dietary and drug interactions, and a need for monitoring and dose adjustment. Thus, discovering and developing safe and efficacious oral anticoagulants for the prevention and treatment of a wide range of thromboembolic disorders has become increasingly important.

One approach is to inhibit thrombin generation by targeting the inhibition of coagulation Factor XIa (FXIa). Factor XIa is a plasma serine protease involved in the regulation of blood coagulation, which is initiated in vivo by the binding of tissue factor (TF) to Factor VII (FVII) to generate Factor VIIa (FVIIa). The resulting TF:FVIIa complex activates Factor IX (FIX) and Factor X (FX) that leads to the production of Factor Xa (FXa). The generated FXa catalyzes the transformation of prothrombin into small amounts of thrombin before this pathway is shut down by tissue factor pathway inhibitor (TFPI). The process of coagulation is then further propagated via the feedback activation of Factors V, VIII and XI by catalytic amounts of thrombin. (Gailani, D. et al., *Arterioscler. Thromb. Vasc. Biol.*, 27:2507-2513 (2007).) The resulting burst of thrombin converts fibrinogen to fibrin that polymerizes to form the structural framework of a blood clot, and activates platelets, which are a key cellular component of coagulation (Hoffman, M., *Blood Reviews*, 17: S1-S5 (2003)). Therefore, Factor XIa plays a key role in propagating this amplification loop and is thus an attractive target for anti-thrombotic therapy.

SUMMARY OF THE INVENTION

The present invention provides novel macrocyclic compounds, their analogues, including stereoisomers, tautomers, pharmaceutically acceptable salts, or solvates thereof, which are useful as selective inhibitors of serine protease enzymes, especially Factor XIa and/or plasma kallikrein.

The present invention also provides processes and intermediates for making the compounds of the present invention.

The present invention also provides pharmaceutical compositions comprising a pharmaceutically acceptable carrier and at least one of the compounds of the present invention or stereoisomers, tautomers, pharmaceutically acceptable salts, or solvates thereof.

The compounds of the invention may be used in the treatment and/or prophylaxis of thromboembolic disorders.

The compounds of the present invention may be used in therapy.

The compounds of the present invention may be used for the manufacture of a medicament for the treatment and/or prophylaxis of a thromboembolic disorder.

The compounds of the invention can be used alone, in combination with other compounds of the present invention, or in combination with one or more, preferably one to two other agent(s).

These and other features of the invention will be set forth in expanded form as the disclosure continues.

DETAILED DESCRIPTION OF THE INVENTION

I. Compounds of the Invention

In a first aspect, the present invention provides, inter alia, a compound of Formula (I):

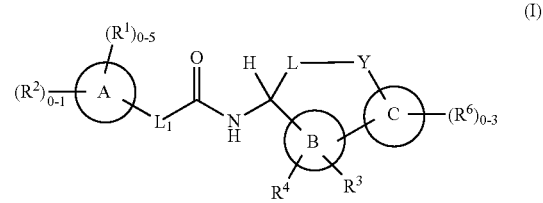

or a stereoisomer, a tautomer, a pharmaceutically acceptable salt, a solvate, or a prodrug thereof, wherein:

ring A is independently a $C_{3-10}$ carbocycle or a 5- to 10-membered heterocycle comprising: carbon atoms and 1-4 heteroatoms selected from N, NH, N($C_{1-4}$ alkyl), O, and $S(O)_p$;

ring B is independently a benzene ring or a 5- to 6-membered heteroaryl comprising: carbon atoms and 1-4 heteroatoms selected from N, O, and $S(O)_p$;

ring C is independently a benzene ring or a 5- to 10-membered heterocycle comprising: carbon atoms and 1-4 heteroatoms selected from N, NH, N($C_{1-4}$ alkyl), O, and $S(O)_p$;

$L_1$ is independently selected from the group consisting of: a bond, —$CHR^5$—, —$CHR^5CHR^5$—, —$CR^5$=$CR^5$—, —$OCH_2$—, —$CHR^5NH$—, —$CH_2O$—, —$SCH_2$—, —$SO_2CH_2$—, —$CH_2NH$—, and —$CR^5R^5$—;

L is independently selected from the group consisting of: $C_{3-8}$ alkylene, $C_{3-8}$ alkenylene, and $C_{4-8}$ alkynylene;

wherein said alkylene, alkenylene and alkynylene are substituted with 0-2 $R^7$ and optionally one or more of the carbon atoms of said alkylene and alkenylene may be replaced by O, S, NH, N($C_{1-4}$ alkyl), CO, CONH, NHCO, OCONH, NHCO$_2$, —NHCONH—, SO$_2$NH, NHSO$_2$, CON($C_{1-4}$ alkyl), or N($C_{1-4}$ alkyl)CO;

Y is independently selected from the group consisting of: CH$_2$, CH($C_{1-4}$ alkyl), C($C_{1-4}$ alkyl)$_2$, CO, O, S, NH, N($C_{1-4}$ alkyl), N(CO$_2$($C_{1-4}$ alkyl)), —N($C_{1-4}$ alkyl)CH$_2$—, —N(CO$_2$($C_{1-4}$ alkyl))CH$_2$—, —N(CH$_2$CO$_2$($C_{1-4}$ alkyl))CH$_2$—, —CONH—, —NHCO—, —CONHCH$_2$—, —CON($C_{1-4}$ alkyl)CH$_2$—, —OCONH—, —OCON($C_{1-4}$ alkyl)-, —NHCONH—, —SO$_2$NH—, —NHCO$_2$—, and —NHSO$_2$—;

alternatively, L-Y is —$C_{3-6}$ alkylene-CH=N—;

$R^1$ is, independently at each occurrence, selected from the group consisting of: halogen, $C_{1-6}$ alkyl, $C_{1-4}$ alkoxy, $C_{1-4}$ alkylthio, $C_{1-4}$ haloalkyl, OH, OCH$_2$F, OCHF$_2$, OCF$_3$, CN, NH$_2$, NH($C_{1-4}$ alkyl), N($C_{1-4}$ alkyl)$_2$, CO$_2$($C_{1-4}$ alkyl), CO($C_{1-4}$ alkyl), —CH$_2$NH$_2$, —CONH$_2$, —CONH($C_{1-4}$ alkyl), —OCH$_2$CO$_2$H, —NHCO($C_{1-4}$ alkyl), —NHCO$_2$($C_{1-4}$ alkyl), —NHSO$_2$($C_{1-4}$ alkyl), —SO$_2$NH$_2$, —C(=NH)NH$_2$, and phenyl substituted with 0-2 $R^a$;

$R^2$ is independently a 5- to 7-membered heterocycle comprising carbon atoms and 1-4 heteroatoms selected from N, NH, N($C_{1-4}$ alkyl), O, and S(O)$_p$, wherein said heterocycle is substituted with 0-2 $R^{2a}$;

$R^{2a}$ is, independently at each occurrence, selected from the group consisting of: halogen, $C_{1-4}$ alkyl, —CH$_2$OH, $C_{1-4}$ alkoxy, OH, CF$_3$, OCF$_3$, CN, NH$_2$, CO$_2$H, CO$_2$($C_{1-4}$ alkyl), COC$_{1-4}$ alkyl, —CONH$_2$, —CONH($C_{1-4}$ alkyl), —CON($C_{1-4}$ alkyl)$_2$, —SO$_2$($C_{1-4}$ alkyl), —SO$_2$NH$_2$, —SO$_2$NH($C_{1-4}$ alkyl), and —SO$_2$N($C_{1-4}$ alkyl)$_2$;

$R^3$ is independently selected from the group consisting of: H, =O, halogen, OH, NH$_2$, CN, $C_{1-4}$ alkyl, $C_{1-4}$ alkoxy, $C_{1-4}$ haloalkyl, —CH$_2$OH, CO$_2$H, CO$_2$($C_{1-4}$ alkyl), —C(O)NH$_2$, —C(O)NH($C_{1-4}$ alkyl), —C(O)N($C_{1-4}$ alkyl)$_2$, —CH$_2$CO$_2$H, and $C_{3-6}$ cycloalkyl;

$R^4$ is independently selected from the group consisting of: H, and $C_{1-4}$ alkyl;

$R^5$ is, independently at each occurrence, selected from the group consisting of: H, halogen, OH, and $C_{1-4}$ alkyl;

$R^6$ is, independently at each occurrence, selected from the group consisting of: halogen, $C_{1-4}$ alkyl, CN, OH, CF$_3$, CO$_2$H, CO$_2$($C_{1-4}$ alkyl), —CH$_2$CO$_2$H, —(CH$_2$)$_2$CO$_2$H, —CH$_2$CO$_2$($C_{1-4}$ alkyl), —(CH$_2$)$_2$CO$_2$($C_{1-4}$ alkyl), NH$_2$, —CH$_2$NH$_2$, —NHCO($C_{1-4}$ alkyl), —NHCOCF$_3$, —NHCO$_2$($C_{1-4}$ alkyl), —NHCO$_2$(CH$_2$)$_2$O($C_{1-4}$ alkyl), —NHCO$_2$(CH$_2$)$_3$O($C_{1-4}$ alkyl), —NHCO$_2$CH$_2$CH($C_{1-4}$ alkyl)O($C_{1-4}$ alkyl), —NHCO$_2$(CH$_2$)$_2$OH, —NHCO$_2$(CH$_2$)$_2$NH$_2$, —NHCO$_2$(CH$_2$)$_2$N($C_{1-4}$ alkyl)$_2$, —NHCO$_2$CH$_2$CO$_2$H, —CH$_2$NHCO$_2$($C_{1-4}$ alkyl), —NHC(O)NH($C_{1-4}$ alkyl), —NHC(O)N($C_{1-4}$ alkyl)$_2$, —NHSO$_2$($C_{1-4}$ alkyl), —SO$_2$NH$_2$, —SO$_2$NH($C_{1-4}$ alkyl), —SO$_2$NH(CH$_2$)$_2$OH, —SO$_2$NH(CH$_2$)$_2$O($C_{1-4}$ alkyl), —CONH$_2$, —CONH($C_{1-4}$ alkyl), —CON($C_{1-4}$ alkyl)$_2$, —CH$_2$CONH$_2$, and —NHCO$_2$(CH$_2$)$_{0-2}$R$^9$;

$R^7$ is, independently at each occurrence, selected from the group consisting of: halogen, OH, NH$_2$, CH$_2$NH$_2$, $C_{1-4}$ haloalkyl, OCH$_2$F, OCHF$_2$, OCF$_3$, —NH($C_{1-4}$ alkyl), —N($C_{1-4}$ alkyl)$_2$, $C_{1-4}$ alkoxy, CH$_2$OH, CH$_2$O($C_{1-4}$ alkyl), CH$_2$O(CH$_2$)$_{1-4}$O($C_{1-4}$ alkyl), CO$_2$H, CO$_2$($C_{1-4}$ alkyl), CO$_2$(CH$_2$)$_2$O($C_{1-4}$ alkyl), CO$_2$($C_{1-4}$ haloalkyl), CO$_2$(CH$_2$)$_2$SO$_2$($C_{1-4}$ alkyl), CH$_2$CO$_2$H, CH$_2$CO$_2$($C_{1-4}$ alkyl), CONH$_2$, CONH($C_{1-4}$ alkyl), CON($C_{1-4}$ alkyl)$_2$, —OCO($C_{1-4}$ alkyl), —CH$_2$NH(CH$_2$)$_2$O($C_{1-4}$ alkyl), —CONH($C_{1-4}$ alkoxy), —CO$_2$(CH$_2$)$_2$O($C_{1-4}$ alkyl), —CO$_2$(CH$_2$)$_2$N($C_{1-4}$ alkyl)$_2$, —CONH(CH$_2$)$_2$O($C_{1-4}$ alkyl), —CONH(CH$_2$)$_2$N($C_{1-4}$ alkyl)$_2$, —CON($C_{1-4}$ alkyl)(CH$_2$)$_2$O($C_{1-4}$ alkyl), —CON($C_{1-4}$ alkyl)(CH$_2$)$_2$N($C_{1-4}$ alkyl)$_2$, $C_{1-4}$ alkyl, —CONHBn, —CONH(OBn), —(CO)$_{0-1}$(CH$_2$)$_{0-3}$—$C_{3-6}$ carbocycle, and —(CH$_2$)$_{0-1}$—(CO)$_{0-1}$—(W)$_{0-1}$—(CH$_2$)$_{0-2}$—(4- to 6-membered heterocycle comprising carbon atoms and 1-4 heteroatoms selected from N, NH, N($C_{1-4}$ alkyl), O, and S(O)$_p$); wherein said carbocycle and heterocycle are substituted with 0-2 $R^8$;

$R^8$ is, independently at each occurrence, selected from the group consisting of: halogen, OH, CHF$_2$, CF$_3$, $C_{1-4}$ alkoxy, CH$_2$OH, CO$_2$H, CO$_2$($C_{1-4}$ alkyl), CONH$_2$, and $C_{1-4}$ alkyl;

$R^9$ is a 4- to 6-membered heterocycle comprising: carbon atoms and 1-4 heteroatoms selected from N, NH, N($C_{1-4}$ alkyl), N(CO$_2$($C_{1-4}$ alkyl)), O, and S(O)$_p$;

$R^a$ is, independently at each occurrence, selected from the group consisting of: halogen, OH, CF$_3$, $C_{1-4}$ alkoxy, and $C_{1-4}$ alkyl;

W is independently selected from the group consisting of: O, NH and N($C_{1-4}$ alkyl); and p is, independently at each occurrence, selected from the group consisting of: 0, 1, and 2.

In a second aspect, the present invention provides compounds of Formula (I), or a stereoisomer, a tautomer, a pharmaceutically acceptable salt, a solvate, or a prodrug thereof, within the scope of the first aspect, wherein:

ring A is independently a 6-membered carbocycle, a 9- to 10-membered carbocycle, or a 5- to 10-membered heterocycle comprising: carbon atoms and 1-3 heteroatoms selected from N, NH, N($C_{1-4}$ alkyl), O, and S(O)$_p$;

ring B is independently selected from the group consisting of: imidazole, oxazole, oxadiazole, triazole, pyridine, pyridazine, pyrimidine, and benzene; and ring C is independently selected from the group consisting of: benzene, pyridine, indazole, indole, benzimidazole, quinoline, isoquinoline, tetrahydroquinoline, tetrahydroisoquinoline, and quinazoline.

In a third aspect, the present invention provides compounds of Formula (I), or a stereoisomer, a tautomer, a pharmaceutically acceptable salt, a solvate, or a prodrug thereof, within the scope of the first or second aspect, wherein:

ring A is independently selected from the group consisting of: benzene, cyclohexane, indane, tetrahydronaphthalene, naphthalene, isoxazoline, isoxazole, pyrazole, imidazole, triazole, piperidine, pyridine, indazole, indole, benzimidazole, quinoline, isoquinoline, tetrahydroquinoline, and tetrahydroisoquinoline;

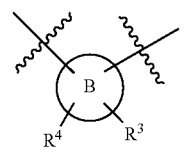

is independently selected from the group consisting of:
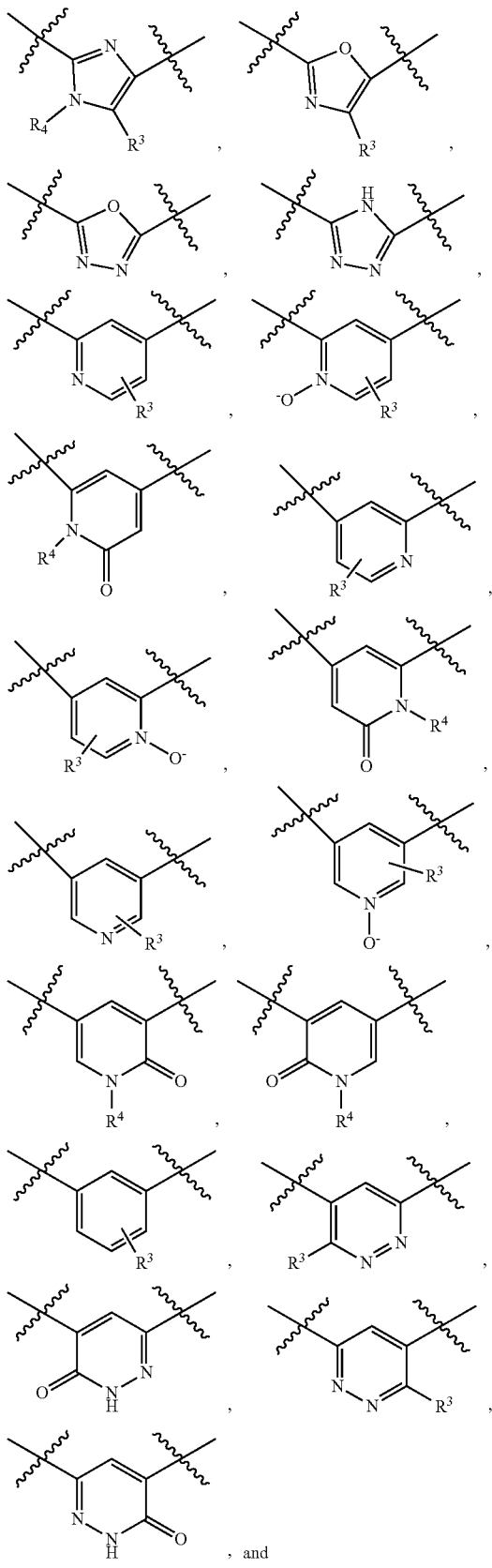
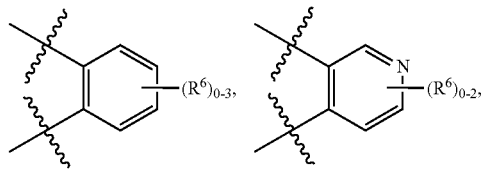
is independently selected from the group consisting of:

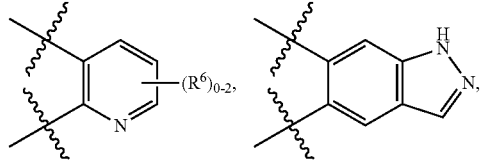
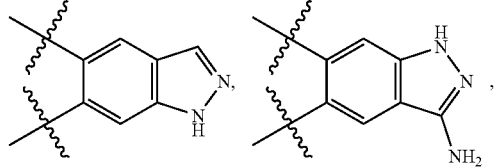
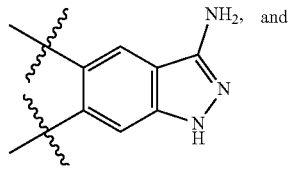
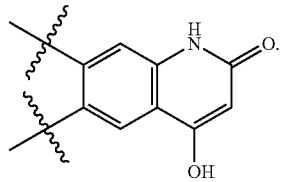
In a fourth aspect, the present invention provides compounds of Formula (II):

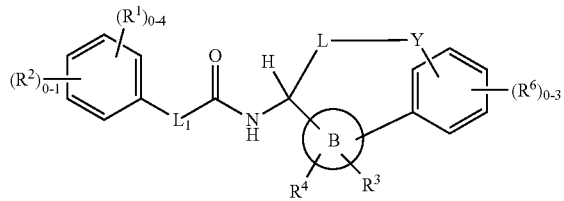

(II)

or a stereoisomer, a tautomer, a pharmaceutically acceptable salt, a solvate, or a prodrug thereof, wherein:

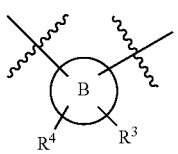

is independently selected from the group consisting of:

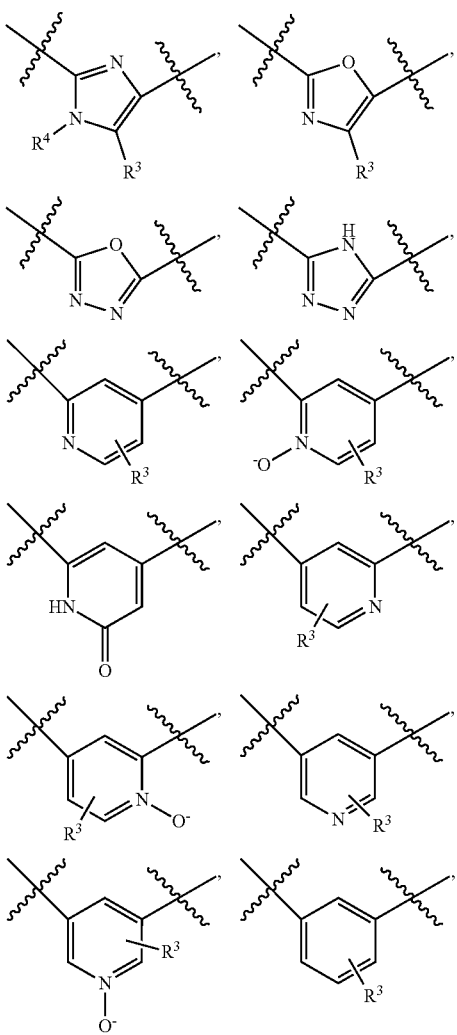

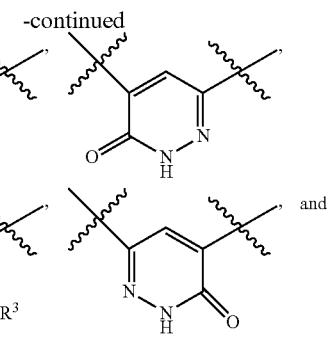

$L_1$ is independently selected from the group consisting of: a bond, —CHR$^5$CHR$^5$—, —CR$^5$=CHR$^5$—, —OCH$_2$—, —CHR$^5$NH—, —CH$_2$O—, —SCH$_2$—, —SO$_2$CH$_2$—, —CH$_2$NH—, and —CR$^5$R$^5$-;

L is independently selected from the group consisting of: $C_{3-8}$ alkylene and $C_{3-8}$ alkenylene; wherein said alkylene and alkenylene are substituted with 0-2 R$^7$ and optionally one or two of the carbon atoms of said alkylene and alkenylene may be replaced by O, CO, S, NH, N(C$_{1-4}$ alkyl), CONH—, NHCO, OCONH, SO$_2$NH, or CON(C$_{1-4}$ alkyl);

Y is independently selected from the group consisting of: CH$_2$, CO, CH(C$_{1-4}$ alkyl), C(C$_{1-4}$ alkyl)$_2$, O, S, NH, N(C$_{1-4}$ alkyl), N(CO$_2$(C$_{1-4}$ alkyl), —N(C$_{1-4}$ alkyl) CH$_2$—, —N(CO$_2$(C$_{1-4}$ alkyl))CH$_2$—, —N(CH$_2$CO$_2$ (C$_{1-4}$ alkyl))CH$_2$—, —CONH—, —NHCO—, —CONHCH$_2$—, —CON(C$_{1-4}$ alkyl)CH$_2$—, —OCONH—, —OCON(C$_{1-4}$ alkyl)-, —NHCONH—, and —SO$_2$NH—;

alternatively, L-Y is —C$_{3-6}$ alkylene-CH=N—;

R$^1$ is, independently at each occurrence, selected from the group consisting of: halogen, C$_{1-6}$ alkyl, C$_{1-4}$ alkoxy, C$_{1-4}$ alkylthio, C$_{1-4}$ haloalkyl, OH, OCH$_2$F, OCHF$_2$, OCF$_3$, CN, NH$_2$, NH(C$_{1-4}$ alkyl), N(C$_{1-4}$ alkyl)$_2$, CO$_2$ (C$_{1-4}$ alkyl), CO(C$_{1-4}$ alkyl), —OCH$_2$CO$_2$H, —CH$_2$NH$_2$, —CONH$_2$, —CONH(C$_{1-4}$ alkyl), —SO$_2$NH$_2$, and —C(=NH)NH$_2$;

R$^2$ is independently a 5- to 6-membered heterocycle comprising carbon atoms and 1-4 heteroatoms selected from N, NH, O, and S(O)$_p$, wherein said heterocycle is substituted with 0-2 R$^{2a}$;

R$^{2a}$ is, independently at each occurrence, selected from the group consisting of: halogen, C$_{1-4}$ alkyl, —CH$_2$OH, C$_{1-4}$ alkoxy, OH, CF$_3$, CN, NH$_2$, CO$_2$H, CO$_2$(C$_{1-4}$ alkyl), COC$_{1-4}$ alkyl, —CONH$_2$, —CONH(C$_{1-4}$ alkyl), and —CON(C$_{1-4}$ alkyl)$_2$;

R$^3$ is independently selected from the group consisting of: H, halogen, OH, NH$_2$, CN, CF$_3$, C$_{1-4}$ alkyl, C$_{1-4}$ alkoxy, —CH$_2$OH, CO$_2$H, CO$_2$(C$_{1-4}$ alkyl), C(O)NH$_2$, —C(O)NH(C$_{1-4}$ alkyl), —C(O)N(C$_{1-4}$ alkyl)$_2$, —CH$_2$CO$_2$H, and C$_{3-6}$ cycloalkyl;

R$^4$ is independently selected from the group consisting of: H and C$_{1-4}$ alkyl;

R$^5$ is, independently at each occurrence, selected from the group consisting of: H, halogen, OH, and C$_{1-4}$ alkyl;

$R^6$ is, independently at each occurrence, selected from the group consisting of: halogen, $C_{1-4}$ alkyl, CN, OH, $CF_3$, $CO_2H$, $CO_2(C_{1-4}$ alkyl), —$CH_2CO_2H$, —$(CH_2)_2CO_2H$, —$CH_2CO_2(C_{1-4}$ alkyl), —$(CH_2)_2CO_2(C_{1-4}$ alkyl), $NH_2$, —$CH_2NH_2$, —$NHCO(C_{1-4}$ alkyl), —$NHCO_2(C_{1-4}$ alkyl), —$NHCO_2(CH_2)_2O(C_{1-4}$ alkyl), —$NHCO_2(CH_2)_3O(C_{1-4}$ alkyl), —$NHCO_2CH_2CH(C_{1-4}$ alkyl)$O(C_{1-4}$ alkyl), —$NHCO_2(CH_2)_2OH$, —$NHCO_2(CH_2)_2NH_2$, —$NHCO_2CH_2CO_2H$, —$CH_2NHCO_2(C_{1-4}$ alkyl), —$NHC(O)NH(C_{1-4}$ alkyl), —$NHC(O)N(C_{1-4}$ alkyl)$_2$, —$NHSO_2(C_{1-4}$ alkyl), —$SO_2NH(CH_2)_2OH$, —$SO_2NH(CH_2)_2O(C_{1-4}$ alkyl), —$CONH(CH_2)_2O(C_{1-4}$ alkyl), $CONH_2$, $CONH(C_{1-4}$ alkyl), $CON(C_{14}$ alkyl)$_2$, —$CH_2CONH_2$, —$NHCO_2(CH_2)_2N(C_{14}$ alkyl)$_2$, —$NHCOCF_3$, and —$NHCO_2(CH_2)_{0-1}R^9$;

$R^7$ is, independently at each occurrence, selected from the group consisting of: halogen, OH, $C_{1-4}$ haloalkyl, $C_{1-4}$ alkoxy, $CH_2OH$, $CH_2O(C_{1-4}$ alkyl), $CO_2H$, $CO_2(C_{1-4}$ alkyl), $CO_2(CH_2)_2O(C_{1-4}$ alkyl)), $CO_2CH_2CF_3$, $CO_2(CH_2)_2SO_2(C_{1-4}$ alkyl, $CH_2CO_2H$, $CH_2CO_2(C_{1-4}$ alkyl), $CONH_2$, $CONH(C_{1-4}$ alkyl), $CON(C_{1-4}$ alkyl)$_2$, —$OCO(C_{1-4}$ alkyl), —$CH_2NH(CH_2)_2O(C_{1-4}$ alkyl), —$CO_2(CH_2)_2N(C_{1-4}$ alkyl)$_2$, —$CONH(CH_2)_2O(C_{1-4}$ alkyl), —$CONH(CH_2)_2N(C_{1-4}$ alkyl)$_2$, —$CON(C_{1-4}$ alkyl)$(CH_2)_2O(C_{1-4}$ alkyl), —$CONH(CH_2)_2N(C_{1-4}$ alkyl)$_2$, —$CON(C_{1-4}$ alkyl)$(CH_2)_2N(C_{1-4}$ alkyl)$_2$, —$CONH(C_{1-4}$ alkoxy), —$CONHBn$, —$CONH(OBn)$, —$(CH_2)_{1-3}Ph$, $C_{1-4}$ alkyl, and —$(CH_2)_{0-1}(CO)_{0-1}(W)_{0-1}(CH_2)_{0-2}$-(4- to 6-membered heterocycle comprising carbon atoms and 1-4 heteroatoms selected from N, NH, $N(C_{1-4}$ alkyl), O, and $S(O)_p$); wherein said heterocycle is substituted with 0-2 $R^8$;

$R^8$ is, independently at each occurrence, selected from the group consisting of: halogen, OH, $CHF_2$, $CF_3$, $C_{1-4}$ alkoxy, and $C_{1-4}$ alkyl;

$R^9$ is a 4- to 6-membered heterocycle comprising: carbon atoms and 1-4 heteroatoms selected from N, NH, $N(C_{1-4}$ alkyl), $N(CO_2(C_{1-4}$ alkyl)), O, and $S(O)_p$;

W is independently selected from the group consisting of: O and NH; and p is, independently at each occurrence, selected from the group consisting of: 0, 1, and 2.

In a fifth aspect, the present invention provides compounds of Formula (IIa) or Formula (IIb):

(IIa)

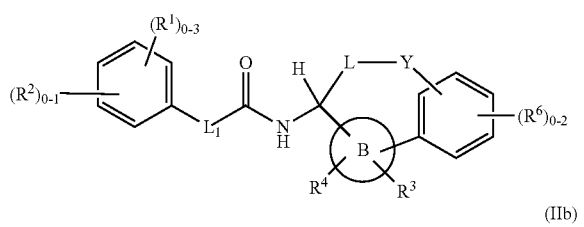

(IIb)

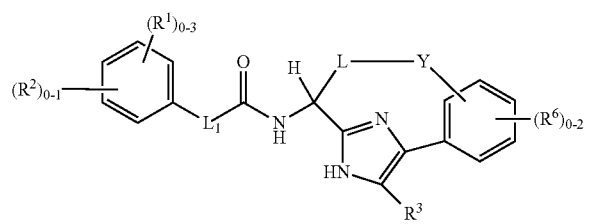

or a stereoisomer, a tautomer, a pharmaceutically acceptable salt, a solvate, or a prodrug thereof, within the scope of the fourth aspect.

In a sixth aspect, the present invention provides compounds of Formula (IIc) or Formula (IId):

(IIc)

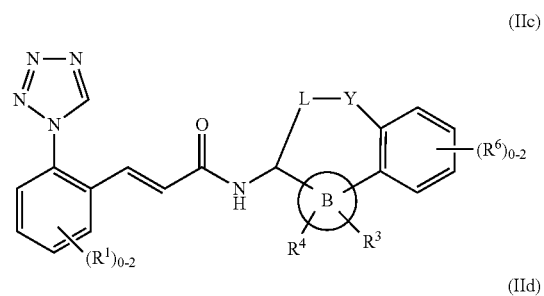

(IId)

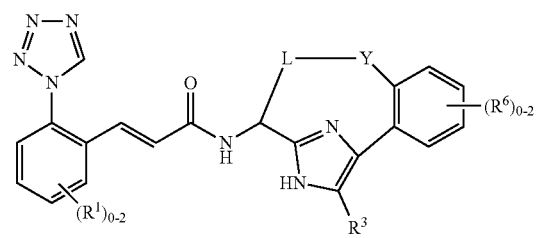

or a stereoisomer, a tautomer, a pharmaceutically acceptable salt, a solvate, or a prodrug thereof, within the scope of the fourth aspect.

In a seventh aspect, the present invention provides compounds of Formula (IIe) or Formula (IIf):

(IIe)

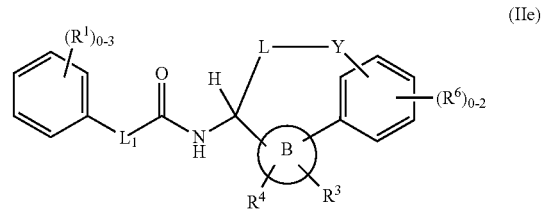

(IIf)

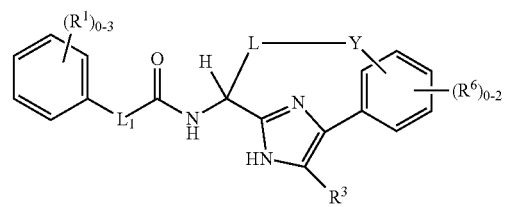

or a stereoisomer, a tautomer, a pharmaceutically acceptable salt, a solvate, or a prodrug thereof, within the scope of the fourth aspect.

In an eighth aspect, the present invention includes compounds of Formula (I), (II), (IIa), (IIb), (IIc), (IId), (IIe) or (IIf) a stereoisomer, a tautomer, a pharmaceutically acceptable salt, a solvate, or a prodrug thereof, within the scope of any of the above aspects, wherein:

$L_1$ is independently selected from the group consisting of: a bond, —$CH_2CH_2$—, —$CH$=$CH$—, —$C(Me)$=$CH$—, —$C$≡$C$—, and —$CH_2NH$— in Formula (I), (II), (IIa), (IIb), (IIe) or (IIf);

L is independently selected from the group consisting of: $C_{3-7}$ alkylene and $C_{3-7}$ alkenylene; wherein said alkylene and alkenylene are substituted with 0-2 $R^7$ and optionally one or two of the carbon atoms of said alkylene and alkenylene may be replaced by O, CO, NH, N($C_{1-4}$ alkyl), CONH, NHCO, or CON($C_{1-4}$ alkyl);

Y is independently selected from the group consisting of: $CH_2$, CO, CH($C_{1-4}$ alkyl), C($C_{1-4}$ alkyl)$_2$, O, S, NH, N($C_{1-4}$ alkyl), N($CO_2$($C_{1-4}$ alkyl)), —N($C_{1-4}$ alkyl) $CH_2$—, —N($CO_2$($C_{1-4}$ alkyl))$CH_2$—, —N($CH_2CO_2$ ($C_{1-4}$ alkyl))$CH_2$—, —CONH—, —NHCO—, —CONHCH$_2$—, —CON($C_{1-4}$ alkyl)$CH_2$—, —OCONH—, —NHCONH—, and —$SO_2$NH—;

alternatively, L-Y is —(CH$_2$)$_{3-6}$—CH=N—;

$R^1$ is, independently at each occurrence, selected from: halogen, CN, OH, OCH$_2$F, OCHF$_2$, OCF$_3$, $C_{1-4}$ haloalkyl, $C_{1-4}$ alkyl, $C_{1-4}$ alkoxy, CO($C_{1-4}$ alkyl), NH$_2$, NH($C_{1-4}$ alkyl), N($C_{1-4}$ alkyl)$_2$, —C(=NH)NH$_2$, —C(O)NH$_2$, —CH$_2$NH$_2$, and —SO$_2$NH$_2$;

$R^3$ is independently selected from the group consisting of: H, halogen, OH, NH$_2$, CN, CF$_3$, $C_{1-4}$ alkyl, $C_{1-4}$ alkoxy, —CH$_2$OH, CO$_2$H, CO$_2$($C_{1-4}$ alkyl), C(O)NH$_2$, —C(O)NH($C_{1-4}$ alkyl), —C(O)N($C_{1-4}$ alkyl)$_2$, —CH$_2$CO$_2$H, and $C_{3-6}$ cycloalkyl; and $R^6$ is, independently at each occurrence, selected from the group consisting of: halogen, $C_{1-4}$ alkyl, CN, OH, CF$_3$, CO$_2$H, CO$_2$($C_{1-4}$ alkyl), —CH$_2$CO$_2$H, —(CH$_2$)$_2$CO$_2$H, —CH$_2$CO$_2$($C_{1-4}$ alkyl), —(CH$_2$)$_2$CO$_2$($C_{1-4}$ alkyl), NH$_2$, —CH$_2$NH$_2$, —NHCO($C_{1-4}$ alkyl), —NHCO$_2$($C_{1-4}$ alkyl), —NHCO$_2$(CH$_2$)$_2$O($C_{1-4}$ alkyl), —NHCO$_2$(CH$_2$)$_3$O($C_{1-4}$ alkyl), —NHCO$_2$CH$_2$CH($C_{1-4}$ alkyl)O($C_{1-4}$ alkyl), —NHCO$_2$(CH$_2$)$_2$OH, —NHCO$_2$(CH$_2$)$_2$NH$_2$, —NHCO$_2$CH$_2$CO$_2$H, —CH$_2$NHCO$_2$($C_{1-4}$ alkyl), —NHC(O)NH($C_{1-4}$ alkyl), —NHC(O)N($C_{1-4}$ alkyl)$_2$, —NHSO$_2$($C_{1-4}$ alkyl), —SO$_2$NH(CH$_2$)$_2$OH, —SO$_2$NH(CH$_2$)$_2$O($C_{1-4}$ alkyl), CONH$_2$, CONH($C_{1-4}$ alkyl), CON($C_{1-4}$ alkyl)$_2$, —NHCO$_2$(CH$_2$)$_2$N($C_{1-4}$ alkyl)$_2$, —NHCOCF$_3$, and —NHCO$_2$(CH$_2$)$_{0-1}$$R^9$.

In a ninth aspect, the present invention includes compounds of Formula (I), (II), (IIa), (IIb), (IIc), (IId), (IIe) or (IIf) or a stereoisomer, a tautomer, a pharmaceutically acceptable salt, a solvate, or a prodrug thereof, within the scope of any of the above aspects, wherein:

$L_1$ is independently selected from the group consisting of: a bond, —CH$_2$CH$_2$— and —CH=CH— in Formula (I), (II), (IIa), (IIb), (IIe) or (IIf);

$R^1$ is, independently at each occurrence, selected from the group consisting of: halogen, CN, $C_{1-4}$ alkyl, OH, $C_{1-4}$ alkoxy, CH$_2$F, CHF$_2$, CF$_3$, OCH$_2$F, OCHF$_2$, OCF$_3$, CO($C_{1-4}$ alkyl), NH$_2$, NH($C_{1-4}$ alkyl)$_2$, N($C_{1-4}$ alkyl)$_2$, —CH$_2$NH$_2$, and —C(=NH)NH$_2$;

$R^3$ is independently selected from the group consisting of: H, halogen, CN, CF$_3$, CO$_2$H, CO$_2$($C_{1-4}$ alkyl), $C_{1-4}$ alkyl, CONH$_2$, CON($C_{14}$ alkyl)$_2$, and $C_{3-6}$ cycloalkyl; and $R^6$ is, independently at each occurrence, selected from the group consisting of: halogen, $C_{1-4}$ alkyl, CN, OH, CF$_3$, CO$_2$H, CO$_2$($C_{1-4}$ alkyl), —CH$_2$CO$_2$H, —CH$_2$CO$_2$ ($C_{1-4}$ alkyl), NH$_2$, —CH$_2$NH$_2$, —NHCO($C_{1-4}$ alkyl), —NHCO$_2$($C_{1-4}$ alkyl), —CH$_2$NHCO$_2$($C_{1-4}$ alkyl), —CONH$_2$, CONH($C_{1-4}$ alkyl), CON($C_{1-4}$ alkyl)$_2$, —NHCO$_2$(CH$_2$)$_2$OH, —NHCO$_2$(CH$_2$)$_2$O($C_{1-4}$ alkyl), —NHCO$_2$CH$_2$CO$_2$H, —NHCO$_2$CH$_2$CH($C_{1-4}$ alkyl)O ($C_{1-4}$ alkyl), —NHCO$_2$(CH$_2$)$_2$N($C_{1-4}$ alkyl)$_2$, —NHCOCF$_3$,

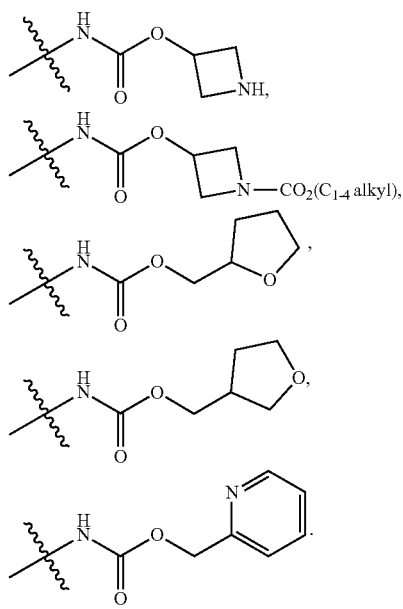

In a tenth aspect, the present invention includes compounds of Formula (I), (II), (IIa), (IIb), (IIc), (IId), (IIe) or (IIf) or a stereoisomer, a tautomer, a pharmaceutically acceptable salt, a solvate, or a prodrug thereof, within the scope of any one of the above aspects, wherein:

$L_1$ is independently selected from the group consisting of: a bond and —CH=CH— in Formula (I), (II), (IIa), (IIb), (IIe) or (IIf);

L is independently selected from the group consisting of: —(CH$_2$)$_{3-6}$—, —(CH$_2$)$_{2-4}$CH($C_{1-4}$ alkyl)(CH$_2$)$_{0-2}$—, —(CH$_2$)$_{1-2}$—CH=CH—(CH$_2$)$_{0-3}$—, —CH$_2$—CH=C($C_{1-4}$ alkyl)-(CH$_2$)$_{1-2}$—, —CH$_2$—C($C_{1-4}$ alkyl)=CH—(CH$_2$)$_{1-2}$—, —CH$_2$—CH=CH—CH$_2$CH ($C_{1-4}$ alkyl)-, —CH$_2$—CH=CH—CH($C_{1-4}$ alkyl)-(CH$_2$)$_{0-2}$—, —CH$_2$—CH=CH—CH$_2$C(halo)$_2$-, —CH$_2$—CH=CH—(CH$_2$)$_{1-2}$CH(CF$_3$)—, —CH$_2$—CH=CH—CH(OH)CH$_2$—, —(CH$_2$)$_3$CH(halo)-, —(CH$_2$)$_{3-4}$C(halo)$_2$-, —(CH$_2$)$_4$CH(CH$_2$OH)—, —(CH$_2$)$_{3-4}$CH($C_{1-4}$ alkoxy)-, —(CH$_2$)$_4$CH(CH$_2$($C_{1-4}$ alkoxy))-, —(CH$_2$)$_4$CH(CO$_2$H)—, —(CH$_2$)$_4$CH (CH$_2$CO$_2$H)—, —(CH$_2$)$_{4-5}$CH(CO$_2$($C_{1-4}$alkyl))-, —(CH$_2$)$_4$CH(CH$_2$CO$_2$($C_{1-4}$ alkyl))-, —(CH$_2$)$_4$CH (CO$_2$CH$_2$CF$_3$)—, —(CH$_2$)$_4$CH(CO$_2$(CH$_2$)$_2$SO$_2$($C_{1-4}$ alkyl))-, —(CH$_2$)$_4$C($C_{1-4}$ alkyl)(CO$_2$($C_{1-4}$ alkyl))-, —(CH$_2$)$_4$C(CF$_3$)(CO$_2$($C_{1-4}$ alkyl))-, —(CH$_2$)$_4$CH (CONH$_2$))—, —(CH$_2$)$_4$CH(CONH($C_{1-4}$alkyl))-, —(CH$_2$)$_4$CH(CON($C_{1-4}$ alkyl)$_2$)-, —(CH$_2$)$_3$CH($C_{1-4}$ alkyl)CH(CONH$_2$)—, —(CH$_2$)$_4$CH(CO$_2$(CH$_2$)$_2$O($C_{1-4}$ alkyl))-, —(CH$_2$)$_4$CH(CH$_2$NH(CH$_2$)$_2$O($C_{1-4}$ alkyl))-, —(CH$_2$)$_4$CH(CONH($C_{1-4}$ alkoxy))-, —(CH$_2$)$_4$CH (CONH(OBn))—, —(CH$_2$)$_4$CH((CH$_2$)$_3$Ph)—, —(CH$_2$)$_4$CH(CO$_2$(CH$_2$)$_2$N($C_{1-4}$ alkyl)$_2$)-, —(CH$_2$)$_4$ CH(CONH(CH$_2$)$_2$O($C_{1-4}$ alkyl))-, —(CH$_2$)$_4$CH (CONH(CH$_2$)$_2$N($C_{1-4}$ alkyl)$_2$)-, —(CH$_2$)$_4$CH(CON ($C_{1-4}$ alkyl)(CH$_2$)$_2$O($C_{1-4}$ alkyl))-, —(CH$_2$)$_4$CH(CON ($C_{1-4}$ alkyl)(CH$_2$)$_2$N($C_{1-4}$ alkyl)$_2$)-, —(CH$_2$)$_4$CH(CH (halo)$_2$)-, —(CH$_2$)$_{4-5}$CH(CF$_3$)—, —(CH$_2$)$_3$C(halo)$_2$CH$_2$—, —(CH$_2$)$_{1-3}$CH(OH)(CH$_2$)$_{1-2}$—, —CH$_2$CH (OH)CH(OH)CH$_2$—, —(CH$_2$)$_3$CH(OCO($C_{1-4}$ alkyl))CH$_2$—, —(CH$_2$)$_3$C(O)CH$_2$—, —CH$_2$O(CH$_2$)$_{2-4}$—, —CH$_2$NH(CH$_2$)$_{2-4}$—, —(CH$_2$)$_{2-3}$NH(CH$_2$)$_{1-2}$—, —CH$_2$)$_{2-4}$N($C_{1-4}$ alkyl)(CH$_2$)$_{0-2}$—, —CH₂CONH(CH₂)₂₋₄—, —CH₂CON(C₁₋₄ alkyl)(CH₂)₂₋₄—, —CH₂NHCOC(halo)₂CH₂—, —(CH₂)₄CH(3-C₁₋₄ alkyl-oxetan-3-yl)-, —(CH₂)₄CH(thiazol-4-yl)-, —(CH₂)₄CH(4-C₁₋₄ alkyl-thiazol-2-yl)-, —(CH₂)₄ CH(1-C₁₋₄ alkyl-imidazol-2-yl)-, —(CH₂)₄ CH(1-C₁₋₄ alkyl-pyrazol-3-yl)-, —(CH₂)₄CH(1-C₁₋₄ alkyl-pyrazol-5-yl)-, —CH₂—CH=CH—CH₂CH(1-C₁₋₄ alkyl-pyrazol-5-yl)-, —(CH₂)₄CH(1-C₁₋₄ alkyl-3-C₁₋₄ alkyl-pyrazol-5-yl)-, —(CH₂)₄CH(1-C₁₋₄ alkyl-4-halo-pyrazol-3-yl)-,
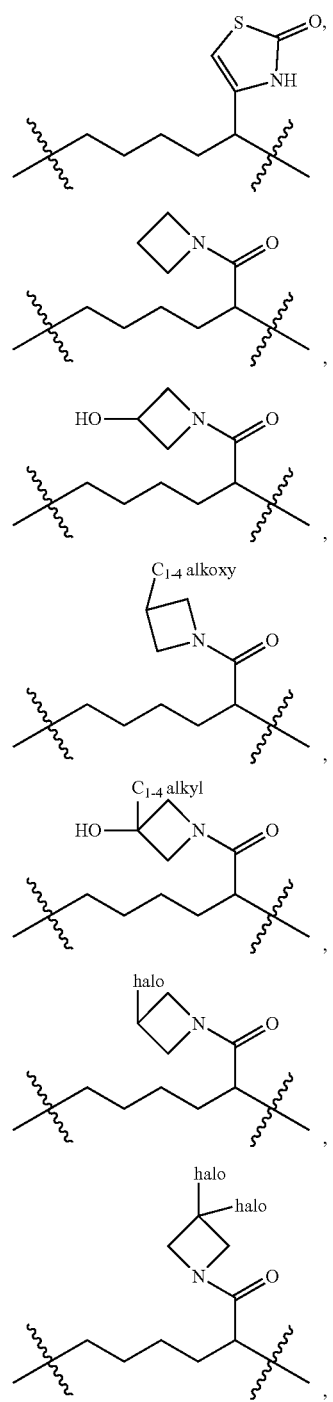
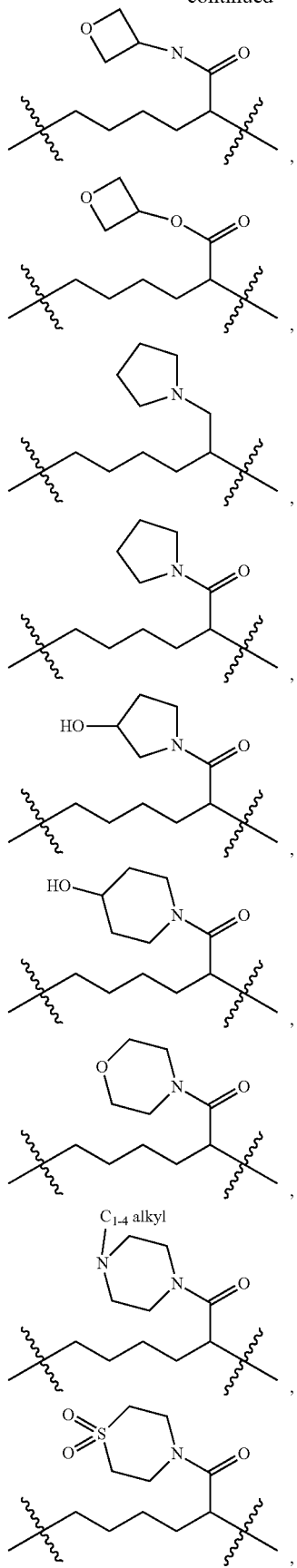

-continued

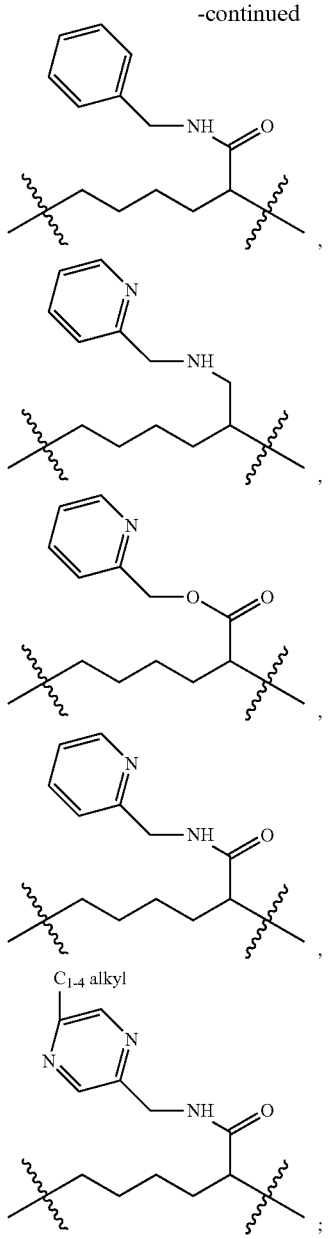

, and

Y is independently selected from the group consisting of: $CH_2$, CO, O, NH, $N(C_{1-4}$ alkyl), $N(CO_2(C_{1-4}$ alkyl)), —$N(C_{1-4}$ alkyl)$CH_2$—, —$N(CO_2(C_{1-4}$ alkyl))$CH_2$—, —$N(CH_2CO_2(C_{1-4}$ alkyl))$CH_2$—, —CONH—, —NHCO—, —CONHCH$_2$—, —CON($C_{1-4}$ alkyl)$CH_2$—, —OCONH—, —NHCONH—, and —$SO_2NH$—; and alternatively, L-Y is —$(CH_2)_{3-6}$—CH=N—;

$R^1$ is, independently at each occurrence, selected from the group consisting of: halogen, $C_{1-4}$ alkyl, OH, $C_{1-4}$ alkoxy, CO($C_{1-4}$ alkyl), CN, $CH_2F$, $CHF_2$, $CF_3$, $OCHF_2$, $NH_2$, $N(C_{1-4}$ alkyl)$_2$, —$CH_2NH_2$, and —C(=NH)NH$_2$;

$R^3$ is independently selected from the group consisting of: H, halogen, $C_{1-4}$ alkyl, CN, $CO_2(C_{1-4}$ alkyl), $CONH_2$, $CON(C_{1-4}$ alkyl)$_2$, and $C_{3-6}$ cycloalkyl; and $R^6$ is, independently at each occurrence, selected from the group consisting of: halogen, $NH_2$, $CO_2H$, $CO_2(C_{1-4}$ alkyl), $CONH_2$, $CONH(C_{1-4}$ alkyl), $CON(C_{1-4}$ alkyl)$_2$, —$NHCO_2(C_{1-4}$ alkyl), —$CH_2NHCO_2(C_{1-4}$ alkyl), —$NHCO_2CH_2CO_2H$, —$NHCO_2(CH_2)_2OH$, —$NHCO_2(CH_2)_2O(C_{1-4}$ alkyl), —$NHCO_2CH_2CH(C_{1-4}$ alkyl)O($C_{1-4}$ alkyl), —$NHCO_2(CH_2)_2N(C_{1-4}$ alkyl)$_2$, —$NHCOCF_3$,

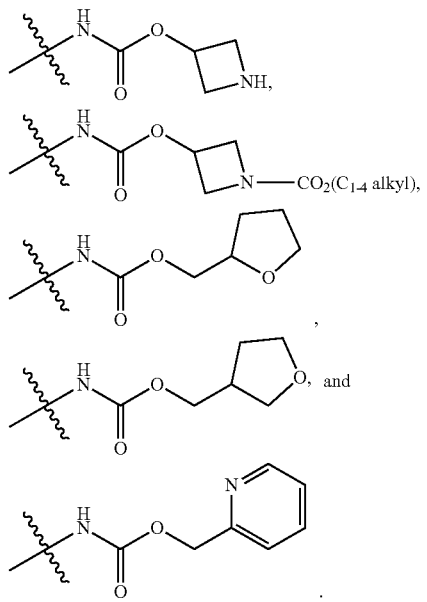

In an 11th aspect, the present invention includes compounds of Formula (III) or Formula (IIIa):

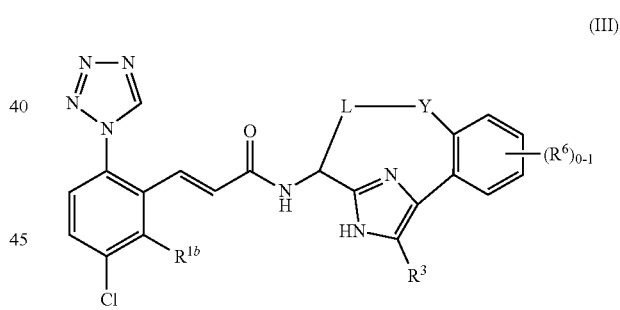

(III)

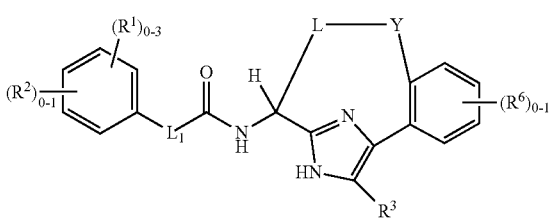

(IIIa)

or a stereoisomer, a tautomer, a pharmaceutically acceptable salt, a solvate, or a prodrug thereof, wherein:
$L_1$ is independently selected from the group consisting of: a bond and —CH=CH— in Formula (IIIa);
L is independently selected from the group consisting of: —$(CH_2)_3$—, —$(CH_2)_4$—, —$(CH_2)_5$—, —$(CH_2)_6$—, —$(CH_2)_3CH(C_{1-4}$ alkyl)-, —$(CH_2)_4CH(C_{1-4}$ alkyl)-, —$(CH_2)_2CH(C_{1-4}$ alkyl)$CH_2$—, —$(CH_2)_3CH(C_{1-4}$ alkyl)$CH_2$—, —$(CH_2)_2CH(C_{1-4}$ alkyl)($CH_2)_2$—, —(CH$_2$)$_3$CH(C$_{1-4}$ alkyl)(CH$_2$)$_2$—, —(CH$_2$)$_4$CH(C$_{1-4}$ alkyl)CH$_2$—, —(CH$_2$)$_4$CH(C$_{1-4}$ alkyl)(CH$_2$)$_2$—, —(CH$_2$)$_2$—CH=CH—, —CH$_2$—CH=CH—CH$_2$—, —CH$_2$—CH=CH—(CH$_2$)$_2$—, —CH$_2$—CH=CH—(CH$_2$)$_3$—, —CH$_2$—CH=C(C$_{1-4}$ alkyl)-(CH$_2$)$_2$—, —CH$_2$—CH=CH—CH$_2$CH(C$_{1-4}$ alkyl)-, —CH$_2$—CH=CH—CH(C$_{1-4}$ alkyl)CH$_2$—, —CH$_2$—CH=CH—CH$_2$C(halo)$_2$-, —CH$_2$—CH=CH—CH$_2$CH(CF$_3$)—, —CH$_2$—CH=CH—(CH$_2$)$_2$CH(CF$_3$)—, —CH$_2$—CH=CH—CH(OH)CH$_2$—, —(CH$_2$)$_3$CH(halo)-, —(CH$_2$)$_3$C(halo)$_2$-, —(CH$_2$)$_4$C(halo)$_2$-, —(CH$_2$)$_4$CH(CH$_2$OH)—, —(CH$_2$)$_3$CH(C$_{1-4}$ alkoxy)-, —(CH$_2$)$_4$CH(CH$_2$(C$_{1-4}$ alkoxy))-, —(CH$_2$)$_4$CH(CO$_2$H)—, —(CH$_2$)$_4$CH(CH$_2$CO$_2$H)—, —(CH$_2$)$_4$CH(CO$_2$(C$_{1-4}$ alkyl))-, —(CH$_2$)$_4$CH(CH$_2$CO$_2$(C$_{1-4}$ alkyl))-, —(CH$_2$)$_4$CH(CO$_2$CH$_2$CF$_3$)—, —(CH$_2$)$_4$CH(CO$_2$(CH$_2$)$_2$SO$_2$(C$_{1-4}$ alkyl))-, —(CH$_2$)$_5$CH(CO$_2$(C$_{1-4}$ alkyl))-, —(CH$_2$)$_4$C(C$_{1-4}$ alkyl)(CO$_2$(C$_{1-4}$ alkyl))-, —(CH$_2$)$_4$C(CF$_3$)(CO$_2$(C$_{1-4}$ alkyl))-, —(CH$_2$)$_4$CH(CONH$_2$)—, —(CH$_2$)$_4$CH(CONH(C$_{1-4}$ alkyl))-, —(CH$_2$)$_4$CH(CON(C$_{1-4}$ alkyl)$_2$)-, —(CH$_2$)$_3$CH(C$_{1-4}$ alkyl)CH(CONH$_2$)—, —(CH$_2$)$_4$CH(CONH(C$_{1-4}$ alkoxy))-, —(CH$_2$)$_4$CH(CONH(OBn))—, —(CH$_2$)$_4$CH((CH$_2$)$_3$Ph)—, —(CH$_2$)$_4$CH(CON(C$_{1-4}$ alkyl)(CH$_2$)$_2$O(C$_{1-4}$ alkyl))-, —(CH$_2$)$_4$CH(CON(C$_{1-4}$ alkyl)(CH$_2$)$_2$N(C$_{1-4}$ alkyl)$_2$)-, —(CH$_2$)$_4$CH(CH(halo)$_2$)-, —(CH$_2$)$_4$CH(CF$_3$)—, —(CH$_2$)$_5$CH(CF$_3$)—, —(CH$_2$)$_3$C(halo)$_2$CH$_2$—, —CH$_2$CH(OH)(CH$_2$)$_2$—, —(CH$_2$)$_2$CH(OH)CH$_2$—, —(CH$_2$)$_3$CH(OH)CH$_2$—, —CH$_2$CH(OH)CH(OH)CH$_2$—, —(CH$_2$)$_3$CH(OCO(C$_{1-4}$ alkyl))CH$_2$—, —(CH$_2$)$_3$C(O)CH$_2$—, —CH$_2$O(CH$_2$)$_3$—, —CH$_2$O(CH$_2$)$_4$—, —CH$_2$NH(CH$_2$)$_2$—, —CH$_2$NH(CH$_2$)$_3$—, —CH$_2$NH(CH$_2$)$_4$—, —(CH$_2$)$_2$N(C$_{1-4}$ alkyl)CH$_2$—, —(CH$_2$)$_2$N(C$_{1-4}$ alkyl)(CH$_2$)$_2$—, —CH$_2$CONH(CH$_2$)$_2$—, —CH$_2$CONH(CH$_2$)$_3$—, —CH$_2$CONH(CH$_2$)$_4$—, —CH$_2$CON(C$_{1-4}$ alkyl)(CH$_2$)$_2$—, —CH$_2$CON(C$_{1-4}$ alkyl)(CH$_2$)$_3$—, —(CH$_2$)$_4$CH(thiazol-4-yl)-, —(CH$_2$)$_4$CH(4-C$_{1-4}$ alkyl-thiazol-2-yl)-, —(CH$_2$)$_4$CH(1-C$_{1-4}$ alkyl-imidazol-2-yl)-, —(CH$_2$)$_4$CH(1-C$_{1-4}$ alkyl-pyrazol-3-yl)-, —(CH$_2$)$_4$CH(1-C$_{1-4}$ alkyl-pyrazol-5-yl)-, —CH$_2$—CH=CH—CH$_2$CH(1-C$_{1-4}$ alkyl-pyrazol-5-yl)-, —(CH$_2$)$_4$CH(1-C$_{1-4}$ alkyl-3-C$_{1-4}$ alkyl-pyrazol-5-yl)-, —(CH$_2$)$_4$CH(1-C$_{1-4}$ alkyl-4-halo-pyrazol-3-yl)-,

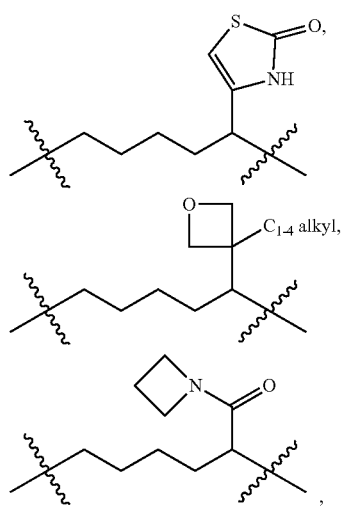

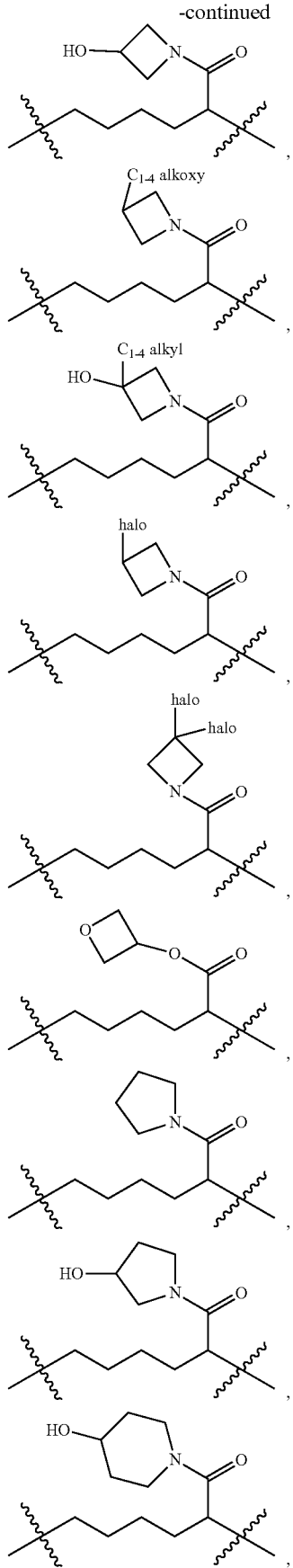

-continued

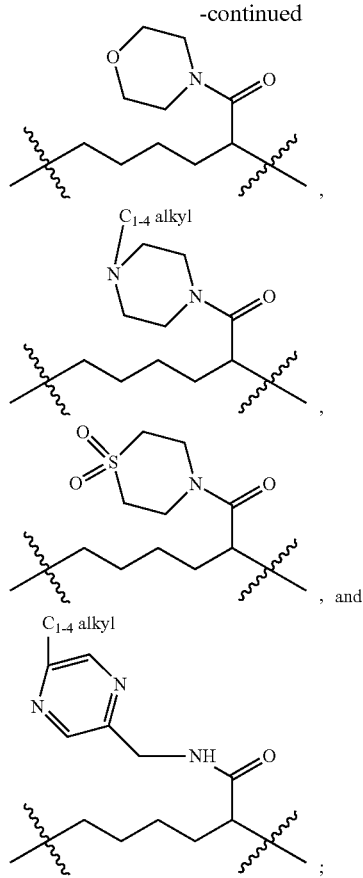

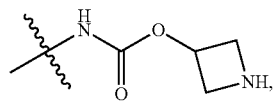

Y is independently selected from the group consisting of: CH$_2$, CO, O, NH, N(C$_{1-4}$ alkyl), N(CO$_2$(C$_{1-4}$ alkyl)), —N(C$_{1-4}$ alkyl)CH$_2$—, —N(CO$_2$(C$_{1-4}$ alkyl))CH$_2$—, —N(CH$_2$CO$_2$(C$_{1-4}$ alkyl))CH$_2$—, —CONH—, —NHCO—, —CONHCH$_2$—, —CON(C$_{1-4}$ alkyl)CH$_2$—, —OCONH—, —NHCONH—, and —SO$_2$NH—;

alternatively, L-Y is —(CH$_2$)$_4$—CH=N—;

R$^1$ is, independently at each occurrence, selected from the group consisting of: halogen, C$_{1-4}$ alkyl, OH, C$_{1-4}$ alkoxy, CO(C$_{1-4}$ alkyl), CN, CH$_2$F, CHF$_2$, CF$_3$, OCHF$_2$, NH$_2$, N(C$_{1-4}$ alkyl)$_2$, —CH$_2$NH$_2$, and —C(=NH)NH$_2$ in Formula (IIIa);

R$^{1b}$ is independently selected from the group consisting of: H and halogen in Formula (III);

R$^2$ is independently a 5-membered heterocycle selected from: triazolyl and tetrazolyl in Formula (IIIa);

R$^3$ is independently selected from the group consisting of: H, halogen, C$_{1-4}$ alkyl, CN, CO$_2$(C$_{1-4}$ alkyl), CONH$_2$, CON(C$_{1-4}$ alkyl)$_2$, and C$_{3-6}$ cycloalkyl; and R$^6$ is independently selected from the group consisting of: halogen, NH$_2$, CO$_2$H, CONH$_2$, CO$_2$(C$_{1-4}$ alkyl), —NHCO$_2$(C$_{1-4}$ alkyl), —NHCO$_2$(CH$_2$)$_2$OH, —NHCO$_2$(CH$_2$)$_2$O(C$_{1-4}$ alkyl), —NHCO$_2$CH$_2$CO$_2$H, —NHCO$_2$CH$_2$CH(C$_{1-4}$ alkyl)O(C$_{1-4}$ alkyl), —NHCO$_2$(CH$_2$)$_2$N(C$_{1-4}$ alkyl)$_2$, —NHCOCF$_3$,

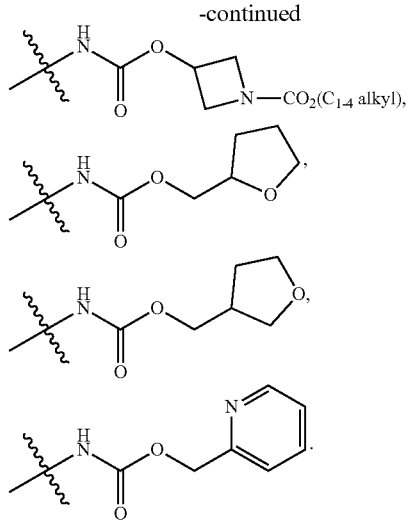

In a 12th aspect, the present invention includes compounds of Formula (III) or Formula (IIIa), or a stereoisomer, a tautomer, a pharmaceutically acceptable salt, a solvate, or a prodrug thereof, within the scope of the 11th aspect, wherein:

L is independently selected from the group consisting of:
—(CH$_2$)$_4$—, —(CH$_2$)$_5$—, —(CH$_2$)$_6$—, —(CH$_2$)$_3$CH(C$_{1-4}$ alkyl)-, —(CH$_2$)$_4$CH(C$_{1-4}$ alkyl)-, —(CH$_2$)$_2$CH(C$_{1-4}$ alkyl)CH$_2$—, —(CH$_2$)$_3$CH(C$_{1-4}$ alkyl)CH$_2$—, —(CH$_2$)$_2$CH(C$_{1-4}$ alkyl)(CH$_2$)$_2$—, —(CH$_2$)$_3$CH(C$_{1-4}$ alkyl)(CH$_2$)$_2$—, —(CH$_2$)$_4$CH(C$_{1-4}$ alkyl)CH$_2$—, —(CH$_2$)$_4$CH(C$_{1-4}$ alkyl)(CH$_2$)$_2$—, —(CH$_2$)$_2$—CH=CH—, —CH$_2$—CH=CH—CH$_2$—, —CH$_2$—CH=CH—(CH$_2$)$_2$—, —CH$_2$—CH=CH—(CH$_2$)$_3$—, —CH$_2$—CH=C(C$_{1-4}$ alkyl)-(CH$_2$)$_2$—, —CH$_2$—CH=CH—CH$_2$CH(C$_{1-4}$ alkyl)-, —CH$_2$—CH=CH—CH(C$_{1-4}$ alkyl)CH$_2$—, —CH$_2$—CH=CH—CH$_2$C(halo)$_2$-, —CH$_2$—CH=CH—CH$_2$CH(CF$_3$)—, —CH$_2$—CH=CH—(CH$_2$)$_2$CH(CF$_3$)—, —CH$_2$—CH=CH—CH(OH)CH$_2$—, —(CH$_2$)$_3$CH(halo)-, —(CH$_2$)$_3$C(halo)$_2$-, —(CH$_2$)$_4$C(halo)$_2$-, —(CH$_2$)$_4$CH(CH$_2$OH)—, —(CH$_2$)$_4$CH(CH$_2$(C$_{1-4}$ alkoxy))-, —(CH$_2$)$_3$CH(C$_{1-4}$ alkoxy)-, —(CH$_2$)$_4$CH(C$_{1-4}$ alkoxy)-, —(CH$_2$)$_4$CH(CO$_2$H)—, —(CH$_2$)$_4$CH(CH$_2$CO$_2$H)—, —(CH$_2$)$_4$CH(CO$_2$(C$_{1-4}$ alkyl))-, —(CH$_2$)$_4$CH(CH$_2$CO$_2$(C$_{1-4}$ alkyl))-, —(CH$_2$)$_4$CH(CO$_2$CH$_2$CF$_3$)—, —(CH$_2$)$_4$CH(CO$_2$(CH$_2$)$_2$SO$_2$(C$_{1-4}$ alkyl))-, —(CH$_2$)$_5$CH(CO$_2$(C$_{1-4}$ alkyl)-, —(CH$_2$)$_4$C(C$_{1-4}$ alkyl)(CO$_2$(C$_{1-4}$ alkyl))-, —(CH$_2$)$_4$C(CF$_3$)(CO$_2$(C$_{1-4}$ alkyl))-, —(CH$_2$)$_4$CH(CONH$_2$)—, —(CH$_2$)$_4$CH(CONH(C$_{1-4}$ alkyl))-, —(CH$_2$)$_4$CH(CON(C$_{1-4}$ alkyl)$_2$)-, —(CH$_2$)$_3$CH(C$_{1-4}$ alkyl)CH(CONH$_2$)—, —(CH$_2$)$_4$CH(CONH(C$_{1-4}$ alkoxy))-, —(CH$_2$)$_4$CH(CONH(OBn))—, —(CH$_2$)$_4$CH(CON(C$_{1-4}$ alkyl)(CH$_2$)$_2$O(C$_{1-4}$ alkyl))-, —(CH$_2$)$_4$CH(CON(C$_{1-4}$ alkyl)(CH$_2$)$_2$N(C$_{1-4}$ alkyl)$_2$)-, —(CH$_2$)$_4$CH(CH(halo)$_2$)-, —(CH$_2$)$_4$CH(CF$_3$)—, —(CH$_2$)$_5$CH(CF$_3$)—, —(CH$_2$)$_3$C(halo)$_2$CH$_2$—, —CH$_2$CH(OH)(CH$_2$)$_2$—, —(CH$_2$)$_2$CH(OH)CH$_2$—, —(CH$_2$)$_3$CH(OH)CH$_2$—, —CH$_2$CH(OH)CH(OH)CH$_2$—, —(CH$_2$)$_3$CH(OCO(C$_{1-4}$ alkyl))CH$_2$—, —(CH$_2$)$_3$C(O)CH$_2$—, —CH$_2$O(CH$_2$)$_3$—, —CH$_2$O(CH$_2$)$_4$—, —CH$_2$NH(CH$_2$)$_2$—, —CH$_2$NH(CH$_2$)$_3$—, —CH$_2$NH(CH$_2$)$_4$—, —(CH$_2$)$_2$N(C$_{1-4}$ alkyl)CH$_2$—, —(CH$_2$)$_2$N(C$_{1-4}$ alkyl)(CH$_2$)$_2$—, —CH$_2$CONH(CH$_2$)$_2$—, —CH$_2$CONH(CH$_2$)$_3$—, —CH₂CONH(CH₂)₄—, —CH₂CON(C₁₋₄ alkyl)(CH₂)₂—, —CH₂CON(C₁₋₄ alkyl)(CH₂)₃—, —(CH₂)₄CH(thiazol-4-yl)-, —(CH₂)₄CH(4-C₁₋₄ alkyl-thiazol-2-yl)-, —(CH₂)₄CH(1-C₁₋₄ alkyl-imidazol-2-yl)-, —(CH₂)₄CH(1-C₁₋₄ alkyl-pyrazol-3-yl)-, —(CH₂)₄CH(1-C₁₋₄ alkyl-pyrazol-5-yl)-, —CH₂—CH=CH—CH₂CH(1-C₁₋₄ alkyl-pyrazol-5-yl)-, —(CH₂)₄CH(1-C₁₋₄ alkyl-3-C₁₋₄ alkyl-pyrazol-5-yl)-, —(CH₂)₄CH(1-C₁₋₄ alkyl-4-halo-pyrazol-3-yl)-,
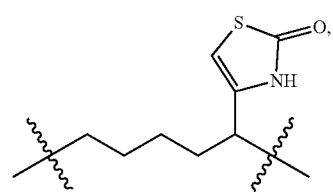
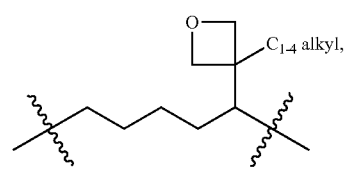
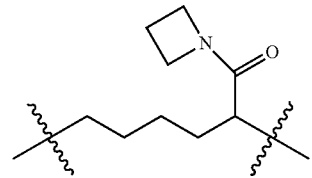
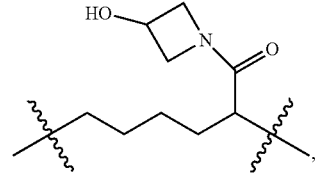
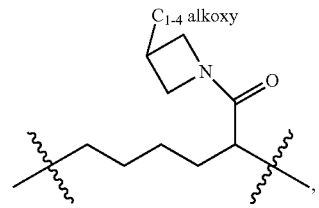
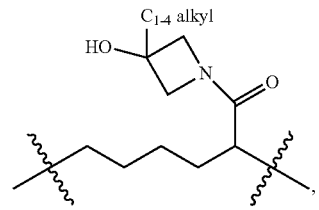
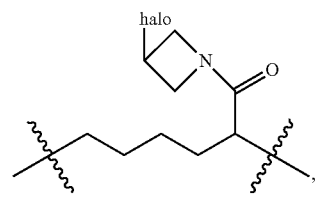
-continued
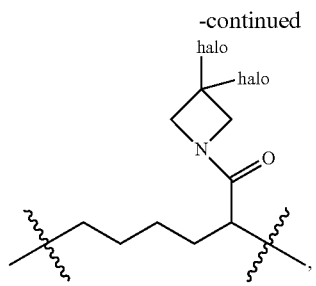
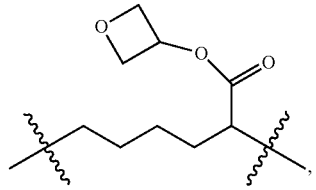
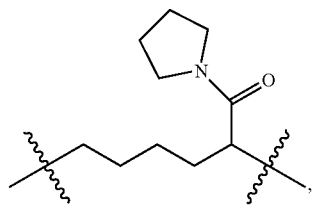
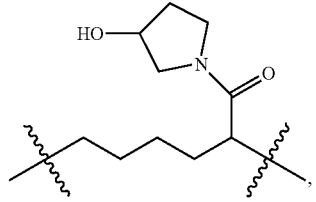
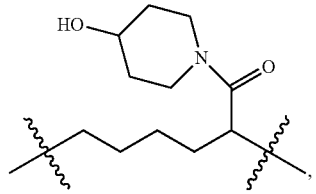
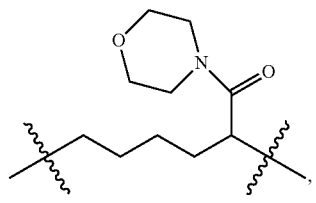
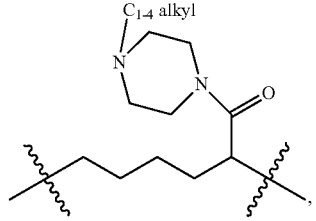
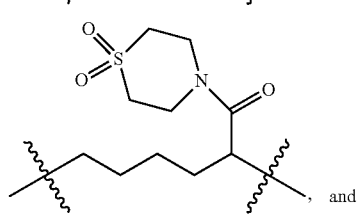
and -continued

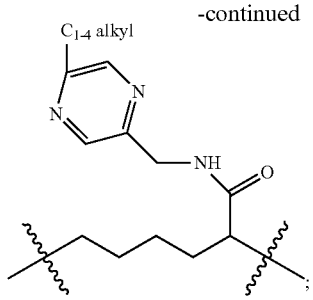

Y is independently selected from the group consisting of: CH$_2$, O, NH, —CONH—, —NHCO—, —CONHCH$_2$—, —CON(C$_{1-4}$ alkyl)CH$_2$—, —N(C$_{1-4}$ alkyl)CH$_2$—, —N(CO$_2$(C$_{1-4}$ alkyl))CH$_2$—, —N(CH$_2$CO$_2$(C$_{1-4}$ alkyl))CH$_2$—, —OCONH—, —NHCONH—, and —SO$_2$NH—;
alternatively, L-Y is —(CH$_2$)$_4$—CH=N—; and
R$^6$ is independently selected from the group consisting of: halogen, NH$_2$, CO$_2$H, CONH$_2$, —NHCO$_2$(C$_{1-4}$ alkyl), —NHCO$_2$(CH$_2$)$_2$OH, —NHCO$_2$(CH$_2$)$_2$O(C$_{1-4}$ alkyl), —NHCO$_2$CH$_2$CH(C$_{1-4}$ alkyl)O(C$_{1-4}$ alkyl), —NHCO$_2$CH$_2$CO$_2$H,

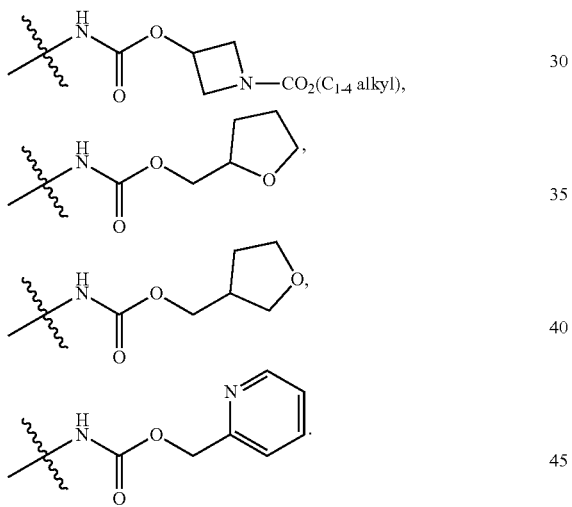

In a 13th aspect, the present invention includes compounds of Formula (III), or a stereoisomer, a tautomer, a pharmaceutically acceptable salt, a solvate, or a prodrug thereof, wherein:
L-Y is independently selected from the group consisting of: —(CH$_2$)$_6$—, —(CH$_2$)$_7$—, —(CH$_2$)$_4$CH(CO$_2$H) CH$_2$—, —(CH$_2$)$_4$CH(CO$_2$(C$_{1-4}$ alkyl))CH$_2$—, —(CH$_2$)$_4$CH(CONH$_2$)CH$_2$—, —(CH$_2$)$_4$CH(CONH (C$_{1-4}$ alkyl))CH$_2$—, —(CH$_2$)$_4$CH(CON(C$_{1-4}$ alkyl)$_2$) CH$_2$—, —(CH$_2$)$_4$CF$_2$CO—, —CH$_2$—CH=CH— (CH$_2$)$_3$—, —CH$_2$—CH=CH—(CH$_2$)$_4$—, —CH$_2$CON(C$_{1-4}$ alkyl)(CH$_2$)$_3$—, —CH$_2$CON(C$_{1-4}$ alkyl)(CH$_2$)$_4$—, —(CH$_2$)$_4$N(C$_{1-4}$ alkyl)CH$_2$—, —(CH$_2$)$_4$N(CO$_2$(C$_{1-4}$ alkyl)CH$_2$—, —(CH$_2$)$_4$N (CH$_2$CO$_2$(C$_{1-4}$ alkyl))CH$_2$—, —(CH$_2$)$_5$O—, —(CH$_2$)$_6$ O—, —(CH$_2$)$_3$CH(C$_{1-4}$ alkyl)(CH$_2$)$_2$O—, —(CH$_2$)$_4$ CH(C$_{1-4}$ alkyl)CH$_2$O—, —CH$_2$CONH(CH$_2$)$_2$O—, —CH$_2$NH(CH$_2$)$_4$O—, —CH$_2$—CH=CH—(CH$_2$)$_2$ O—, —CH$_2$—CH=CH—(CH$_2$)$_3$O—, —(CH$_2$)$_5$ NH—, —(CH$_2$)$_6$NH—, —(CH$_2$)$_3$CH(C$_{1-4}$ alkyl) CH$_2$NH—, —(CH$_2$)$_4$CH(C$_{14}$ alkyl)NH—, —(CH$_2$)$_4$ CH(C$_{1-4}$ alkyl)CH$_2$NH—, —(CH$_2$)$_4$CH(CH$_2$OH) NH—, —(CH$_2$)$_4$CH(CH$_2$(C$_{1-4}$alkoxy))NH—, —(CH$_2$)$_4$ CH(CO$_2$H)NH—, —(CH$_2$)$_4$CH((CH$_2$)$_3$Ph) NH—, —(CH$_2$)$_4$CH(CH$_2$CO$_2$H)NH—, —(CH$_2$)$_4$CH (CH$_2$CO$_2$(C$_{1-4}$ alkyl))NH—, —(CH$_2$)$_4$CH(CO$_2$(C$_{1-4}$ alkyl))NH—, —(CH$_2$)$_4$CH(CO$_2$CH$_2$CF$_3$)NH—, —(CH$_2$)$_4$CH(CO$_2$(CH$_2$)$_2$SO$_2$(C$_{1-4}$ alkyl))NH—, —(CH$_2$)$_5$CH(CO$_2$(C$_{1-4}$ alkyl))NH—, —(CH$_2$)$_4$CH (CONH$_2$)NH—, —(CH$_2$)$_4$CH(CONH(C$_{1-4}$ alkyl)) NH—, —(CH$_2$)$_4$CH(CON(C$_{1-4}$ alkyl)$_2$)NH—, —(CH$_2$)$_4$C(C$_{1-4}$ alkyl)(CO$_2$(C$_{h4}$ alkyl))NH—, —(CH$_2$)$_4$C(CF$_3$)(CO$_2$(C$_{1-4}$ alkyl))NH—, —(CH$_2$)$_3$CH (C$_{1-4}$ alkyl)CH(CONH$_2$)NH—, —(CH$_2$)$_4$CH(CONH (C$_{1-4}$ alkoxy))NH—, —(CH$_2$)$_4$CH(CONH(OBn)) NH—, —(CH$_2$)$_4$CH(CON(C$_{1-4}$ alkyl)(CH$_2$)$_2$O(C$_{1-4}$ alkyl))NH—, —(CH$_2$)$_4$CH(CON(C$_{1-4}$ alkyl)(CH$_2$)$_2$N (C$_{1-4}$ alkyl)$_2$)NH—, —CH$_2$—CH=CH—(CH$_2$)$_2$ NH—, —CH$_2$—CH=CH—(CH$_2$)$_3$NH—, —(CH$_2$)$_4$ CH(CHF$_2$)NH—, —(CH$_2$)$_4$CH(CF$_3$)NH—, —(CH$_2$)$_5$ CH(CF$_3$)NH—, —(CH$_2$)$_3$CF$_2$CH$_2$NH—, —CH$_2$— CH=CH—CH$_2$CH(CF$_3$)NH—, —CH$_2$—CH=CH— (CH$_2$)$_2$CH(CF$_3$)NH—, —CH$_2$CONH(CH$_2$)$_2$NH—, —CH$_2$CONH(CH$_2$)$_3$NH—, —CH$_2$CONH(CH$_2$)$_4$ NH—, —CH$_2$NHCOCF$_2$CH$_2$NH—, —(CH$_2$)$_4$CH(CO-pyrrolidin-1-yl)NH—, —(CH$_2$)$_4$CH(thiazol-4-yl)NH—, —(CH$_2$)$_4$CH(4-C$_{1-4}$ alkyl-thiazol-2-yl)NH—, —(CH$_2$)$_4$CH(1-C$_{1-4}$ alkyl-imidazol-2-yl)NH—, —(CH$_2$)$_4$CH(1-C$_{1-4}$ alkyl-pyrazol-3-yl)NH—, —(CH$_2$)$_4$CH(1-C$_{1-4}$ alkyl-pyrazol-5-yl)NH—, —(CH$_2$)$_4$CH(1-C$_{1-4}$ alkyl-3-C$_{1-4}$ alkyl-pyrazol-5-yl)NH—, —(CH$_2$)$_4$CH(1-C$_{1-4}$ alkyl-4-halo-pyrazol-3-yl)NH—, —CH$_2$—CH=CH—CH$_2$CH(1-C$_{1-4}$ alkyl-pyrazol-5-yl)NH—, —(CH$_2$)$_6$N(C$_{1-4}$ alkyl)-, —(CH$_2$)$_5$N(CO$_2$(C$_{1-4}$ alkyl))-, —(CH$_2$)$_4$ CONH—, —(CH$_2$)$_5$CONH—, —(CH$_2$)$_6$CONH—, —(CH$_2$)$_3$CH(C$_{1-4}$ alkyl)CONH—, —(CH$_2$)$_4$CH(C$_{1-4}$ alkyl)CONH—, —(CH$_2$)$_2$CH(C$_{1-4}$ alkyl) CH$_2$CONH—, —(CH$_2$)$_3$CH(C$_{1-4}$ alkyl)CH$_2$CONH—, —(CH$_2$)$_2$CH(C$_{1-4}$ alkyl)(CH$_2$)$_2$CONH—, —(CH$_2$)$_2$— CH=CH—CONH—, —CH$_2$—CH=CH— CH$_2$CONH—, —CH$_2$—CH=CH—(CH$_2$)$_2$CONH—, —CH$_2$—CH=CH—(CH$_2$)$_3$CONH—, —CH$_2$— CH=CH—CH$_2$CH(C$_{1-4}$ alkyl)CONH—, —CH$_2$— CH=CH—CH(C$_{1-4}$ alkyl)CH$_2$CONH—, —CH$_2$— CH=C(C$_{1-4}$ alkyl)(CH$_2$)$_2$CONH—, —(CH$_2$)$_3$CH(C$_{1-4}$ alkyl)CONH—, —(CH$_2$)$_3$CHFCONH—, —(CH$_2$)$_3$ CF$_2$CONH—, —(CH$_2$)$_4$CF$_2$CONH—, —CH$_2$— CH=CH—CH$_2$CF$_2$CONH—, —(CH$_2$)$_3$CH(CF$_3$) CONH—, —CH$_2$CH(OH)(CH$_2$)$_2$CONH—, —(CH$_2$)$_2$ CH(OH)CH$_2$CONH—, —(CH$_2$)$_3$CH(OH) CH$_2$CONH—, —CH$_2$CH(OH)CH(OH)CH$_2$CONH—, —CH$_2$—CH=CH—CH(OH)CH$_2$CONH—, —(CH$_2$)$_3$ CH(C$_{1-4}$ alkoxy)CONH—, —(CH$_2$)$_3$CH(OCO(C$_{1-4}$ alkyl))CH$_2$CONH—, —(CH$_2$)$_2$C(O)CH$_2$CONH—, —CH$_2$O(CH$_2$)$_3$CONH—, —CH$_2$O(CH$_2$)$_4$CONH—, —CH$_2$NH(CH$_2$)$_2$CONH—, —CH$_2$NH(CH$_2$)$_3$ CONH—, —(CH$_2$)$_2$N(C$_{1-4}$ alkyl)CH$_2$CONH—, —(CH$_2$)$_2$N(C$_{1-4}$ alkyl)(CH$_2$)$_2$CONH—, —(CH$_2$)$_5$ NHCO—, —CH$_2$—CH=CH—(CH$_2$)$_2$NHCO—, —(CH$_2$)$_3$OCONH—, —(CH$_2$)$_4$OCONH—, —CH$_2$— CH=CH—CH$_2$OCONH—, —CH$_2$—CH=CH— CH$_2$NHCONH—, —(CH$_2$)$_4$SO$_2$NH—, —CH$_2$— CH=CH—CH$_2$SO$_2$NH—, —(CH$_2$)$_4$—CH=N—,

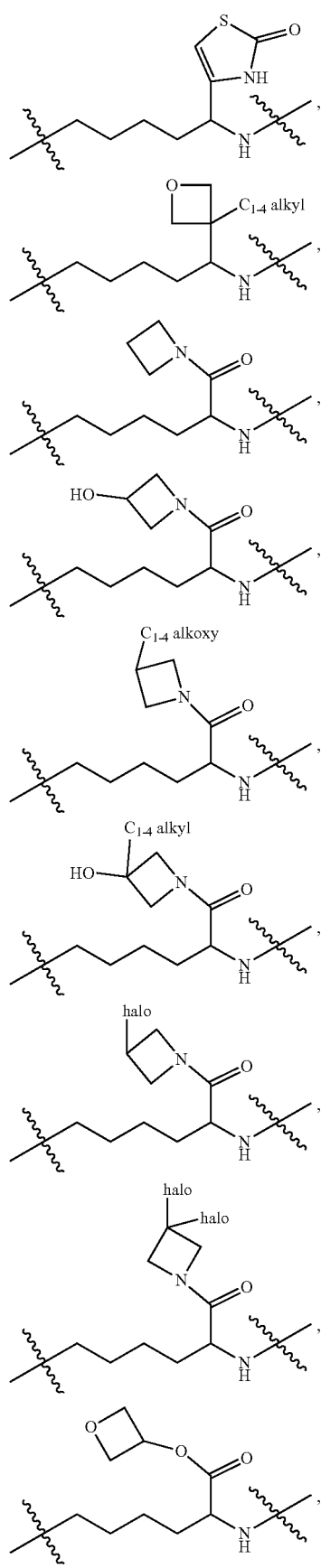
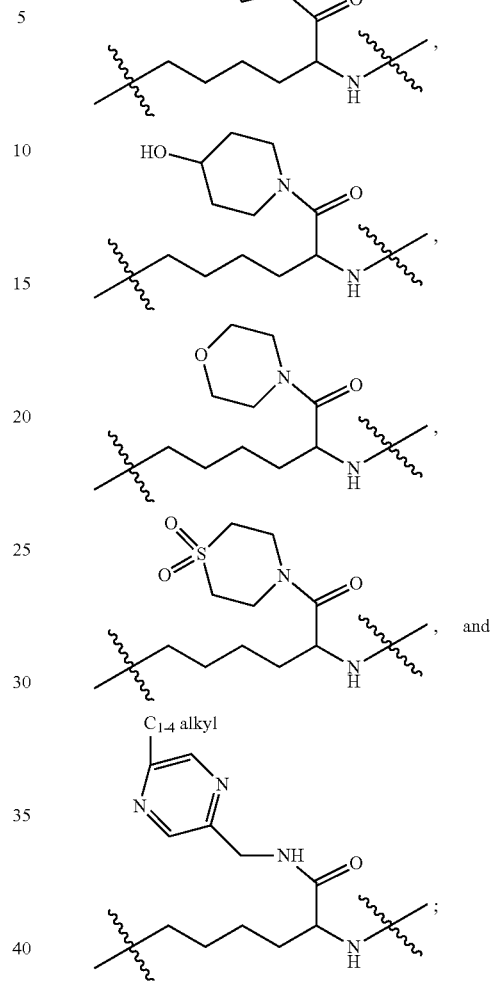

$R^{1b}$ is independently selected from the group consisting of: H and halogen;

$R^3$ is independently selected from the group consisting of: H, halogen, $C_{1-4}$ alkyl, CN, $CO_2(C_{1-4}$ alkyl), $CONH_2$, $CON(C_{1-4}$ alkyl)$_2$, and $C_{3-6}$ cycloalkyl; and $R^6$ is independently selected from the group consisting of: halogen, $NH_2$, $CO_2H$, $CONH_2$, —$NHCO_2(C_{1-4}$ alkyl), —$NHCO_2(CH_2)_2OH$, —$NHCO_2(CH_2)_2O(C_{1-4}$ alkyl), —$NHCO_2CH_2CH(C_{1-4}$ alkyl)$O(C_{1-4}$ alkyl),

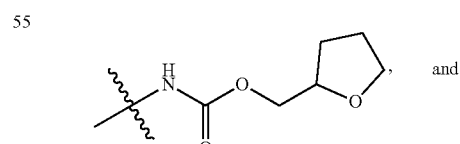
and
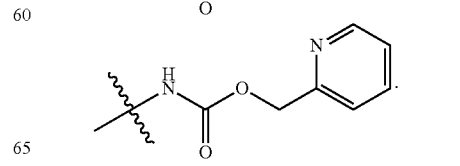

In a 14th aspect, the present invention includes compounds of Formula (III), or a stereoisomer, a tautomer, a pharmaceutically acceptable salt, a solvate, or a prodrug thereof, wherein:

L-Y is independently selected from the group consisting of: —(CH$_2$)$_6$—, —(CH$_2$)$_7$—, —(CH$_2$)$_4$CH(CO$_2$H)CH$_2$—, —(CH$_2$)$_4$CH(CO$_2$(C$_{1-4}$ alkyl))CH$_2$—, —(CH$_2$)$_4$CH(CONH$_2$)CH$_2$—, —(CH$_2$)$_4$CH(CONH(C$_{1-4}$ alkyl))CH$_2$—, —(CH$_2$)$_4$CH(CON(C$_{1-4}$ alkyl)$_2$)CH$_2$—, —CH$_2$—CH=CH—(CH$_2$)$_3$—, —CH$_2$—CH=CH—(CH$_2$)$_4$—, —CH$_2$CON(C$_{1-4}$ alkyl)(CH$_2$)$_3$—, —(CH$_2$)$_5$O—, —(CH$_2$)$_6$O—, —(CH$_2$)$_3$CH(C$_{1-4}$ alkyl)(CH$_2$)$_2$O—, —(CH$_2$)$_4$CH(C$_{1-4}$ alkyl)CH$_2$O—, —CH$_2$NH(CH$_2$)$_4$O—, —CH$_2$—CH=CH—(CH$_2$)$_3$O—, —(CH$_2$)$_5$NH—, —(CH$_2$)$_6$NH—, —(CH$_2$)$_3$CH(C$_{1-4}$ alkyl)CH$_2$NH—, —(CH$_2$)$_4$CH(C$_{1-4}$ alkyl)NH—, —(CH$_2$)$_4$CH(C$_{1-4}$ alkyl)CH$_2$NH—, —(CH$_2$)$_4$CH(CH$_2$OH)NH—, —(CH$_2$)$_4$CH(CH$_2$(C$_{1-4}$ alkoxy))NH—, —(CH$_2$)$_4$CH(CO$_2$H)NH—, —(CH$_2$)$_4$CH(CH$_2$CO$_2$H)NH—, —(CH$_2$)$_4$CH(CH$_2$CO$_2$(C$_{1-4}$ alkyl))NH—, —(CH$_2$)$_4$CH(CO$_2$(C$_{1-4}$ alkyl))NH—, —(CH$_2$)$_4$CH(CO$_2$CH$_2$CF$_3$)NH—, —(CH$_2$)$_4$CH(CO$_2$(CH$_2$)$_2$SO$_2$(C$_{1-4}$ alkyl))NH—, —(CH$_2$)$_5$CH(CO$_2$(C$_{1-4}$ alkyl))NH—, —(CH$_2$)$_4$CH(CONH$_2$)NH—, —(CH$_2$)$_4$CH(CONH(C$_{1-4}$ alkyl))NH—, —(CH$_2$)$_4$CH(CON(C$_{1-4}$ alkyl)$_2$)NH—, —(CH$_2$)$_4$C(C$_{1-4}$ alkyl)(CO$_2$(C$_{1-4}$ alkyl))NH—, —(CH$_2$)$_4$C(CF$_3$)(CO$_2$(C$_{1-4}$ alkyl)NH—, —(CH$_2$)$_3$CH(C$_{1-4}$ alkyl)CH(CONH$_2$)NH—, —(CH$_2$)$_4$CH(CONH(C$_{1-4}$ alkoxy))NH—, —(CH$_2$)$_4$CH(CONH(OBn))NH—, —(CH$_2$)$_4$CH(CON(C$_{1-4}$ alkyl)(CH$_2$)$_2$O(C$_{1-4}$ alkyl))NH—, —(CH$_2$)$_4$CH(CON(C$_{1-4}$ alkyl)(CH$_2$)$_2$N(C$_{1-4}$ alkyl)$_2$)NH—, —CH$_2$—CH=CH—(CH$_2$)$_2$NH—, —CH$_2$—CH=CH—(CH$_2$)$_3$NH—, —(CH$_2$)$_4$CH(CHF$_2$)NH—, —(CH$_2$)$_4$CH(CF$_3$)NH—, —(CH$_2$)$_5$CH(CF$_3$)NH—, —(CH$_2$)$_3$CF$_2$CH$_2$NH—, —CH$_2$—CH=CH—(CH$_2$)$_2$CH(CF$_3$)NH—, —CH$_2$CONH(CH$_2$)$_2$NH—, —CH$_2$CONH(CH$_2$)$_3$NH—, —(CH$_2$)$_4$CH(3-C$_{1-4}$ alkyl-oxetan-3-yl)NH—, —(CH$_2$)$_4$CH(CO-pyrrolidin-1-yl)NH—, —(CH$_2$)$_4$CH(thiazol-4-yl)NH—, —(CH$_2$)$_4$CH(4-C$_{1-4}$ alkyl-thiazol-2-yl)NH—, —(CH$_2$)$_4$CH(1-C$_{1-4}$ alkyl-imidazol-2-yl)NH—, —(CH$_2$)$_4$CH(1-C$_{1-4}$ alkyl-pyrazol-3-yl)NH—, —(CH$_2$)$_4$CH(1-C$_{1-4}$ alkyl-pyrazol-5-yl)NH—, —(CH$_2$)$_4$CH(1-C$_{1-4}$ alkyl-3-C$_{1-4}$ alkyl-pyrazol-5-yl)NH—, —(CH$_2$)$_4$CH(1-C$_{1-4}$ alkyl-4-halo-pyrazol-3-yl)NH—, —CH$_2$—CH=CH—CH$_2$CH(1-C$_{1-4}$ alkyl-pyrazol-5-yl)NH—, —(CH$_2$)$_4$N(CO$_2$(C$_{1-4}$ alkyl))CH$_2$—, —(CH$_2$)$_4$N(CH$_2$CO$_2$(C$_{1-4}$ alkyl))CH$_2$—, —(CH$_2$)$_4$CONH—, —(CH$_2$)$_5$CONH—, —(CH$_2$)$_6$CONH—, —(CH$_2$)$_3$CH(C$_{1-4}$ alkyl)CONH—, —(CH$_2$)$_4$CH(C$_{1-4}$ alkyl)CONH—, —(CH$_2$)$_2$CH(C$_{1-4}$ alkyl)CH$_2$CONH—, —(CH$_2$)$_3$CH(C$_{1-4}$ alkyl)CH$_2$CONH—, —(CH$_2$)$_2$CH(C$_{1-4}$ alkyl)(CH$_2$)$_2$CONH—, —(CH$_2$)$_2$—CH=CH—CONH—, —CH$_2$—CH=CH—CH$_2$CONH—, —CH$_2$—CH=CH—(CH$_2$)$_2$CONH—, —CH$_2$—CH=CH—(CH$_2$)$_3$CONH—, —CH$_2$—CH=CH—CH$_2$CH(C$_{1-4}$ alkyl)CONH—, —CH$_2$—CH=CH—CH(C$_{1-4}$ alkyl)CH$_2$CONH—, —CH$_2$—CH=C(C$_{1-4}$ alkyl)-(CH$_2$)$_2$CONH—, —(CH$_2$)$_3$CH(C$_{1-4}$ alkyl)CONH—, —(CH$_2$)$_3$CHFCONH—, —(CH$_2$)$_3$CF$_2$CONH—, —(CH$_2$)$_4$CF$_2$CONH—, —CH$_2$—CH=CH—CH$_2$CF$_2$CONH—, —(CH$_2$)$_3$CH(CF$_3$)CONH—, —CH$_2$CH(OH)(CH$_2$)$_2$CONH—, —(CH$_2$)$_2$CH(OH)CH$_2$CONH—, —(CH$_2$)$_3$CH(OH)CH$_2$CONH—, —CH$_2$CH(OH)CH(OH)CH$_2$CONH—, —CH$_2$—CH=CH—CH(OH)CH$_2$CONH—, —(CH$_2$)$_3$CH(C$_{1-4}$ alkoxy)CONH—, —(CH$_2$)$_3$CH(OCO(C$_{1-4}$ alkyl))CH$_2$CONH—, —(CH$_2$)$_3$C(O)CH$_2$CONH—, —CH$_2$O(CH$_2$)$_3$CONH—, —CH$_2$O(CH$_2$)$_4$CONH—, —CH$_2$NH(CH$_2$)$_2$CONH—, —CH$_2$NH(CH$_2$)$_3$CONH—, —(CH$_2$)$_2$N(C$_{1-4}$ alkyl)CH$_2$CONH—, —(CH$_2$)$_2$N(C$_{1-4}$ alkyl)(CH$_2$)$_2$CONH—, —(CH$_2$)$_5$NHCO—, —CH$_2$—CH=CH—(CH$_2$)$_2$NHCO—, —CH$_2$—CH=CH—CH$_2$OCONH—, —(CH$_2$)$_4$OCONH—, —CH$_2$—CH=CH—CH$_2$NHCONH—, —(CH$_2$)$_4$SO$_2$NH—, —CH$_2$—CH=CH—CH$_2$SO$_2$NH—, —(CH$_2$)$_4$—CH=N—,

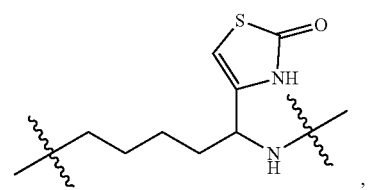

,

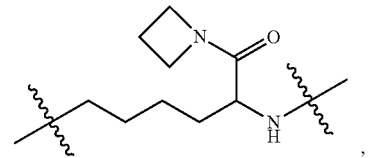

,

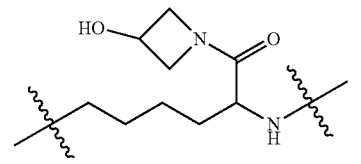

,

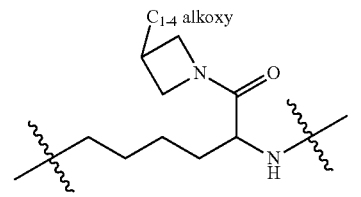

,

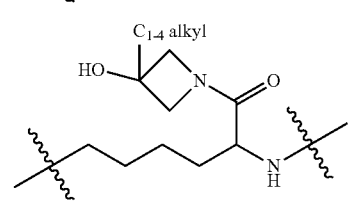

,

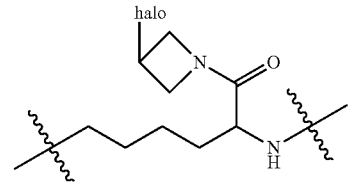

,

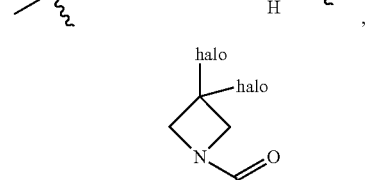

,

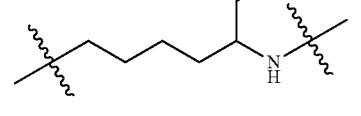

,

-continued

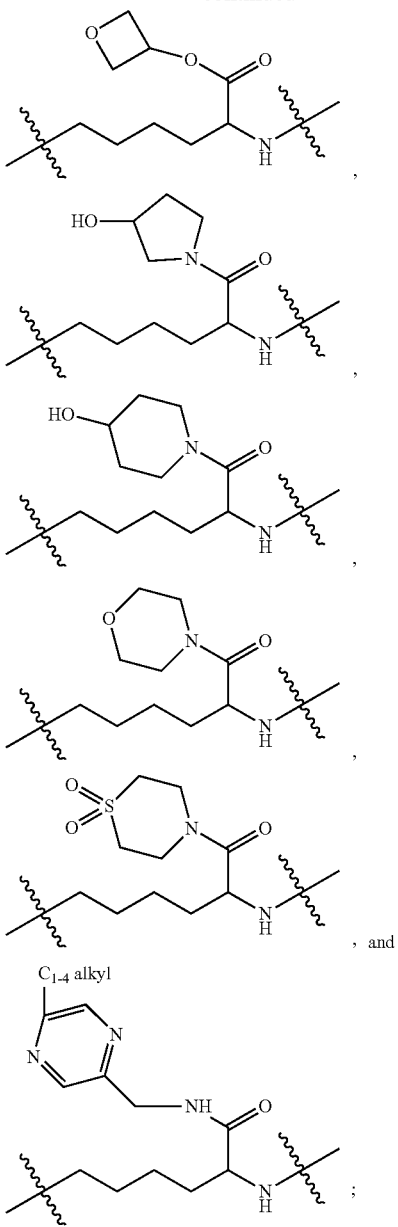

, and

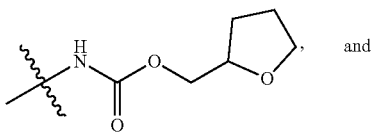

R$^{1b}$ is independently selected from the group consisting of: H and halogen;

R$^3$ is independently selected from the group consisting of: H, halogen, C$_{1-4}$ alkyl, CN, CO$_2$(C$_{1-4}$ alkyl), CONH$_2$, CON(C$_{1-4}$ alkyl)$_2$, and cyclopropyl; and R$^6$ is independently selected from the group consisting of: halogen, NH$_2$, CO$_2$H, CONH$_2$, —NHCO$_2$(C$_{1-4}$ alkyl), —NHCO$_2$(CH$_2$)$_2$OH, —NHCO$_2$(CH$_2$)$_2$O(C$_{1-4}$ alkyl), —NHCO$_2$CH$_2$CH(C$_{1-4}$ alkyl)O(C$_{1-4}$ alkyl), and -continued

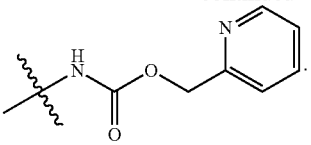

In a 15th aspect, the present invention includes compounds of Formula (III), or a stereoisomer, a tautomer, a pharmaceutically acceptable salt, a solvate, or a prodrug thereof, wherein:

L-Y is independently selected from the group consisting of: —(CH$_2$)$_6$—, —(CH$_2$)$_7$—, —(CH$_2$)$_4$CH(CO$_2$H)CH$_2$—, —(CH$_2$)$_4$CH(CO$_2$Me)CH$_2$—, —(CH$_2$)$_4$CH(CONH$_2$)CH$_2$—, —(CH$_2$)$_4$CH(CONHMe)CH$_2$—, —(CH$_2$)$_4$CH(CON(Me)$_2$)CH$_2$—, —CH$_2$—CH═CH—(CH$_2$)$_3$—, —CH$_2$—CH═CH—(CH$_2$)$_4$—, —CH$_2$CON(CH$_3$)(CH$_2$)$_3$—, —(CH$_2$)$_4$N(CO$_2$Me)CH$_2$—, —(CH$_2$)$_4$N(CH$_2$CO$_2$Et)CH$_2$—, —(CH$_2$)$_5$O—, —(CH$_2$)$_6$O—, —(CH$_2$)$_3$CH(Me)(CH$_2$)$_2$O—, —(CH$_2$)$_4$CH(Me)CH$_2$O—, —CH$_2$NH(CH$_2$)$_4$O—, —CH$_2$—CH═CH—(CH$_2$)$_3$O—, —(CH$_2$)$_5$NH—, —(CH$_2$)$_6$NH—, —(CH$_2$)$_3$CH(Me)CH$_2$NH—, —(CH$_2$)$_4$CH(Me)NH—, —(CH$_2$)$_4$CH(Me)CH$_2$NH—, —(CH$_2$)$_4$CH(CH$_2$OH)NH—, —(CH$_2$)$_4$CH(CH$_2$OMe)NH—, —(CH$_2$)$_4$CH(CO$_2$H)NH—, —(CH$_2$)$_4$CH(CO$_2$Me)NH—, —(CH$_2$)$_4$CH(CO$_2$Et)NH—, —CH$_2$CONH(CH$_2$)$_4$NH—, —(CH$_2$)$_4$CH(CO$_2$(i-Pr))NH—, —(CH$_2$)$_4$CH(CO$_2$(t-Bu))NH—, —(CH$_2$)$_4$CH(CO$_2$CH$_2$CF$_3$)NH—, —(CH$_2$)$_4$CH(CO$_2$(CH$_2$)$_2$SO$_2$Me)NH—, —(CH$_2$)$_5$CH(CO$_2$Me)NH—, —(CH$_2$)$_4$CH(CH$_2$CO$_2$H)NH—, —(CH$_2$)$_4$CH(CH$_2$CO$_2$Me)NH—, —(CH$_2$)$_4$CH(CONH$_2$)NH—, —(CH$_2$)$_4$CH(CONH(Me))NH—, —(CH$_2$)$_4$CH(CONH(t-Bu))NH—, —(CH$_2$)$_4$CH(CON(Me)$_2$)NH—, —(CH$_2$)$_4$CH(CONH(OMe))NH—, —(CH$_2$)$_4$CH(CONH(OBn))NH—, —(CH$_2$)$_4$CH(CON(Me)(CH$_2$)$_2$OMe)NH—, —(CH$_2$)$_4$C(Me)(CO$_2$Me)NH—, —(CH$_2$)$_4$C(CF$_3$)(CO$_2$Me)$_2$)NH—, —(CH$_2$)$_3$CH(Me)CH(CONH$_2$)NH—, —(CH$_2$)$_4$CH(CON(Me)(CH$_2$)$_2$N(Me)$_2$)NH—, —CH$_2$—CH═CH—(CH$_2$)$_2$NH—, —CH$_2$CH═CH—(CH$_2$)$_3$NH—, —(CH$_2$)$_4$CH(CHF$_2$)NH—, —(CH$_2$)$_4$CH(CF$_3$)NH—, —(CH$_2$)$_5$CH(CF$_3$)NH—, —(CH$_2$)$_3$CF$_2$CH$_2$NH—, —CH$_2$—CH═CH—(CH$_2$)$_2$CH(CF$_3$)NH—, —CH$_2$CONH(CH$_2$)$_2$NH—, —CH$_2$CONH(CH$_2$)$_3$NH—, —(CH$_2$)$_4$CH(3-Me-oxetan-3-yl)NH—, —(CH$_2$)$_4$CH(CO-pyrrolidin-1-yl)NH—, —(CH$_2$)$_4$CH(thiazol-4-yl)NH—, —(CH$_2$)$_4$CH(4-Me-thiazol-2-yl)NH—, —(CH$_2$)$_4$CH(1-Me-imidazol-2-yl)NH—, —(CH$_2$)$_4$CH(1-Me-pyrazol-3-yl)NH—, —(CH$_2$)$_4$CH(1(n-Pr)-pyrazol-3-yl)NH—, —(CH$_2$)$_4$CH(1-Me-pyrazol-5-yl)NH—, —(CH$_2$)$_4$CH(1,3-di-Me-pyrazol-5-yl)NH—, —(CH$_2$)$_4$CH(1-Me-4-Cl-pyrazol-3-yl)NH—, —CH$_2$—CH═CH—CH$_2$CH(1-Me-pyrazol-5-yl)NH—, —(CH$_2$)$_4$CONH—, —(CH$_2$)$_5$CONH—, —(CH$_2$)$_6$CONH—, —(CH$_2$)$_3$CH(Me)CONH—, —(CH$_2$)$_4$CH(Me)CONH—, —(CH$_2$)$_2$CH(Me)CH$_2$CONH—, —(CH$_2$)$_3$CH(Me)CH$_2$CONH—, —(CH$_2$)$_2$CH(Me)(CH$_2$)$_2$CONH—, —(CH$_2$)$_2$—CH═CH—CONH—, —CH$_2$CH═CH—CH$_2$CONH—, —CH$_2$—CH═CH—(CH$_2$)$_2$CONH—, —CH$_2$—CH═CH—(CH$_2$)$_3$CONH—, —CH$_2$—CH═CH—CH$_2$CH(Me)CONH—, —CH$_2$—CH═CHCH(Me)CH$_2$CONH—, —CH$_2$—CH═CHCH(Et)CH$_2$CONH—, —CH$_2$—CH═C(Me)—(CH$_2$)$_2$CONH—, —(CH$_2$)$_3$CH(Et)

CH₂CONH—, —(CH₂)₃CH(i-Pr)CONH—, —(CH₂)₃CHFCONH—, —(CH₂)₃CF₂CONH—, —(CH₂)₄CF₂CONH—, —CH₂—CH=CH—CH₂CF₂CONH—, —(CH₂)₃CH(CF₃)CONH—, —CH₂CH(OH)(CH₂)₂CONH—, —(CH₂)₂CH(OH)CH₂CONH—, —(CH₂)₃CH(OH)CH₂CONH—, —CH₂CH(OH)CH(OH)CH₂CONH—, —CH₂—CH=CH—CH(OH)CH₂CONH—, —(CH₂)₃CH(OMe)CONH—, —(CH₂)₃CH(OCOMe)CH₂CONH—, —(CH₂)₃C(O)CH₂CONH—, —CH₂O(CH₂)₃CONH—, —CH₂O(CH₂)₄CONH—, —CH₂NH(CH₂)₂CONH—, —CH₂NH(CH₂)₃CONH—, —(CH₂)₂N(Me)CH₂CONH—, —(CH₂)₂N(Me)(CH₂)₂CONH—, —(CH₂)₅NHCO—, —CH₂—CH=CH—(CH₂)₂NHCO—, —CH₂—CH=CH—CH₂OCONH—, —(CH₂)₄OCONH—, —CH₂—CH=CH—CH₂NHCONH—, —(CH₂)₄SO₂NH—, —CH₂—CH=CH—CH₂SO₂NH—, —(CH₂)₄—CH=N—,

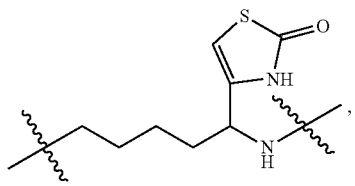

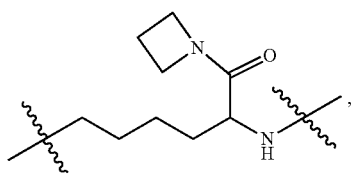

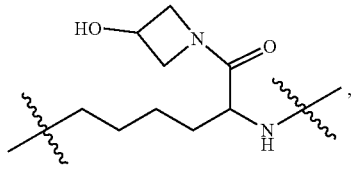

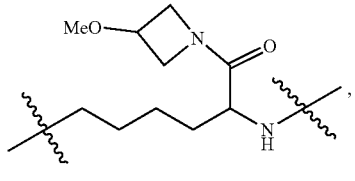

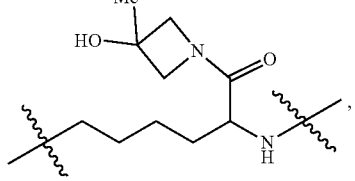

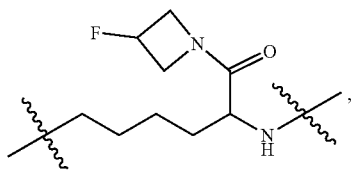

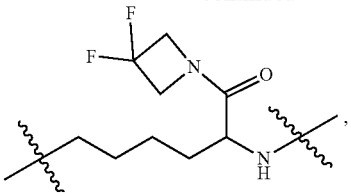

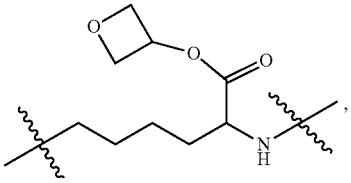

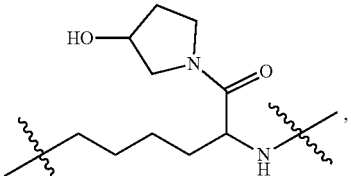

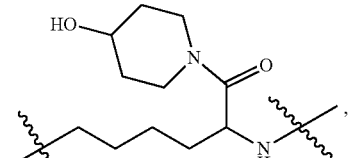

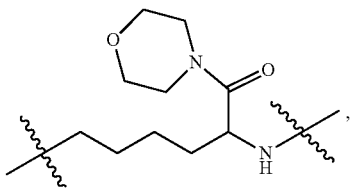

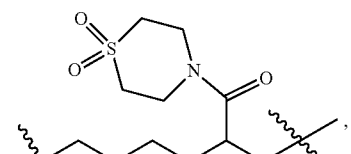

, and

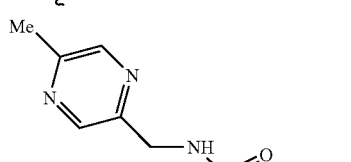

;

$R^{1b}$ is independently selected from the group consisting of: H and F;

$R^3$ is independently selected from the group consisting of: H, F, Cl, Br, CH₃, CN, CO₂Me, CO₂Et, CONH₂, CONMe₂, and cyclopropyl; and $R^6$ is independently selected from the group consisting of: F, NH₂, CO₂H, CONH₂, —NHCO₂Me, —NHCO₂(CH₂)₂OH, —NHCO₂(CH₂)₂OMe, —NHCO₂(CH₂)₂OEt, —NHCO₂CH₂CH(Et)OMe, and

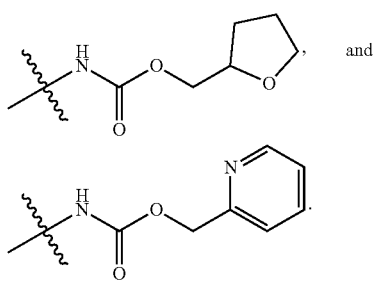

and

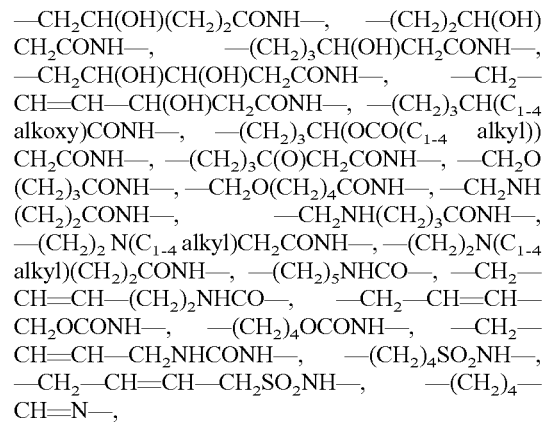

In a 16th aspect, the present invention includes compounds of Formula (III), or a stereoisomer, a tautomer, a pharmaceutically acceptable salt, a solvate, or a prodrug thereof, wherein:

L-Y is independently selected from the group consisting of: —(CH$_2$)$_6$—, —(CH$_2$)$_7$—, —(CH$_2$)$_4$CH(CO$_2$H)CH$_2$—, —(CH$_2$)$_4$CH(CO$_2$(C$_{1-4}$ alkyl))CH$_2$—, —(CH$_2$)$_4$CH(CONH$_2$)CH$_2$—, —(CH$_2$)$_4$CH(CONH(C$_{1-4}$ alkyl))CH$_2$—, —(CH$_2$)$_4$CH(CON(C$_{1-4}$ alkyl)$_2$)CH$_2$—, —CH$_2$—CH═CH—(CH$_2$)$_4$—, —(CH$_2$)$_4$N(CO$_2$(C$_{1-4}$ alkyl))CH$_2$—, —(CH$_2$)$_6$O—, —(CH$_2$)$_3$CH(C$_{1-4}$ alkyl)(CH$_2$)$_2$O—, —CH$_2$NH(CH$_2$)$_4$O—, —(CH$_2$)$_5$NH—, —(CH$_2$)$_6$NH—, —(CH$_2$)$_4$CH(C$_{1-4}$ alkyl)NH—, —(CH$_2$)$_3$CH(C$_{1-4}$ alkyl)CH$_2$NH—(CH$_2$)$_4$CH(C$_{1-4}$ alkyl)CH$_2$NH—, —(CH$_2$)$_4$CH(CH$_2$OH)NH—, —(CH$_2$)$_4$CH(CH$_2$(C$_{1-4}$ alkoxy))NH—, —(CH$_2$)$_4$CH(CO$_2$H)NH—, —(CH$_2$)$_4$CH(CH$_2$CO$_2$H)NH—, —(CH$_2$)$_4$CH(CH$_2$CO$_2$(C$_{1-4}$ alkyl))NH—, —(CH$_2$)$_4$CH(CO$_2$(C$_{1-4}$ alkyl))NH—, —(CH$_2$)$_4$CH(CO$_2$CH$_2$CF$_3$)NH—, —(CH$_2$)$_4$CH(CO$_2$(CH$_2$)$_2$SO$_2$(C$_{1-4}$ alkyl))NH—, —(CH$_2$)$_5$CH(CO$_2$(C$_{1-4}$ alkyl))NH—, —(CH$_2$)$_4$CH(CONH$_2$)NH—, —(CH$_2$)$_4$CH(CONH(C$_{1-4}$ alkyl))NH—, —(CH$_2$)$_4$CH(CON(C$_{1-4}$ alkyl)$_2$)NH—, —(CH$_2$)$_4$CH(CONH(C$_{1-4}$ alkoxy))NH—, —(CH$_2$)$_4$CH(CONH(OBn))NH—, —(CH$_2$)$_4$CH(CON(C$_{1-4}$ alkyl)(CH$_2$)$_2$O(C$_{1-4}$ alkyl))NH—, —(CH$_2$)$_4$CH(CON(C$_{1-4}$ alkyl)(CH$_2$)$_2$N(C$_{1-4}$ alkyl)$_2$)NH—, —CH$_2$—CH═CH—(CH$_2$)$_2$NH—, —CH$_2$—CH═CH—(CH$_2$)$_3$NH—, —(CH$_2$)$_4$CH(CHF$_2$)NH—, —(CH$_2$)$_4$CH(CF$_3$)NH—, —(CH$_2$)$_3$CF$_2$CH$_2$NH—, —CH$_2$—CH═CH—(CH$_2$)$_2$CH(CF$_3$)NH—, —(CH$_2$)$_4$CH(3-C$_{1-4}$ alkyl-oxetan-3-yl)NH—, —(CH$_2$)$_4$CH(CO-pyrrolidin-1-yl)NH—, —(CH$_2$)$_4$CH(thiazol-4-yl)NH—, —(CH$_2$)$_4$CH(4-C$_{1-4}$ alkyl-thiazol-2-yl)NH—, —(CH$_2$)$_4$CH(1-C$_{1-4}$ alkyl-imidazol-2-yl)NH—, —(CH$_2$)$_4$CH(1-C$_{1-4}$ alkyl-pyrazol-3-yl)NH—, —(CH$_2$)$_4$CH(1-C$_{1-4}$ alkyl-pyrazol-5-yl)NH—, —(CH$_2$)$_4$CH(1-C$_{1-4}$ alkyl-3-C$_{1-4}$ alkyl-pyrazol-5-yl)NH—, —(CH$_2$)$_4$CH(1-C$_{1-4}$ alkyl-4-halo-pyrazol-3-yl)NH—, —(CH$_2$)$_4$CONH—, —(CH$_2$)$_5$CONH—, —(CH$_2$)$_6$CONH—, —(CH$_2$)$_3$CH(C$_{1-4}$ alkyl)CONH—, —(CH$_2$)$_4$CH(C$_{1-4}$ alkyl)CONH—, —(CH$_2$)$_2$CH(C$_{1-4}$ alkyl)CH$_2$CONH—, —(CH$_2$)$_3$CH(C$_{1-4}$ alkyl)CH$_2$CONH—, —(CH$_2$)$_2$CH(C$_{1-4}$ alkyl)(CH$_2$)$_2$CONH—, —(CH$_2$)$_2$—CH═CH—CONH—, —CH$_2$—CH═CH—CH$_2$CONH—, —CH$_2$—CH═CH—(CH$_2$)$_2$CONH—, —CH$_2$—CH═CH—(CH$_2$)$_3$CONH—, —CH$_2$—CH═CH—CH$_2$CH(C$_{1-4}$ alkyl)CONH—, —CH$_2$—CH═CH—CH(C$_{1-4}$ alkyl)CH$_2$CONH—, —CH$_2$—CH═C(C$_{1-4}$ alkyl)-(CH$_2$)$_2$CONH—, —(CH$_2$)$_3$CH(C$_{1-4}$ alkyl)CONH—, —(CH$_2$)$_3$CHFCONH—, —(CH$_2$)$_3$CF$_2$CONH—, —(CH$_2$)$_4$CF$_2$CONH—, —CH$_2$—CH═CH—CH$_2$CF$_2$CONH—, —(CH$_2$)$_3$CH(CF$_3$)CONH—, —CH$_2$CH(OH)(CH$_2$)$_2$CONH—, —(CH$_2$)$_2$CH(OH)CH$_2$CONH—, —(CH$_2$)$_3$CH(OH)CH$_2$CONH—, —CH$_2$CH(OH)CH(OH)CH$_2$CONH—, —CH$_2$—CH═CH—CH(OH)CH$_2$CONH—, —(CH$_2$)$_3$CH(C$_{1-4}$ alkoxy)CONH—, —(CH$_2$)$_3$CH(OCO(C$_{1-4}$ alkyl))CH$_2$CONH—, —(CH$_2$)$_3$C(O)CH$_2$CONH—, —CH$_2$O(CH$_2$)$_3$CONH—, —CH$_2$O(CH$_2$)$_4$CONH—, —CH$_2$NH(CH$_2$)$_2$CONH—, —CH$_2$NH(CH$_2$)$_3$CONH—, —(CH$_2$)$_2$N(C$_{1-4}$ alkyl)CH$_2$CONH—, —(CH$_2$)$_2$N(C$_{1-4}$ alkyl)(CH$_2$)$_2$CONH—, —(CH$_2$)$_5$NHCO—, —CH$_2$—CH═CH—(CH$_2$)$_2$NHCO—, —CH$_2$—CH═CH—CH$_2$OCONH—, —(CH$_2$)$_4$OCONH—, —CH$_2$—CH═CH—CH$_2$NHCONH—, —(CH$_2$)$_4$SO$_2$NH—, —CH$_2$—CH═CH—CH$_2$SO$_2$NH—, —(CH$_2$)$_4$—CH═N—,

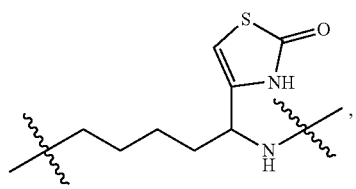

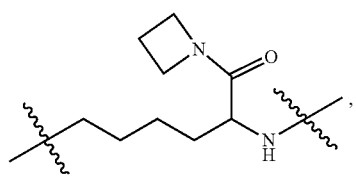

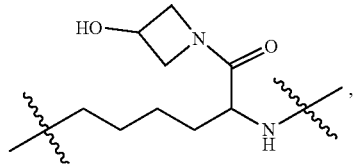

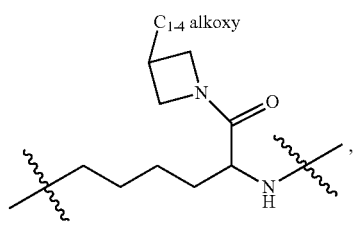

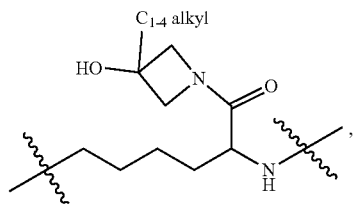

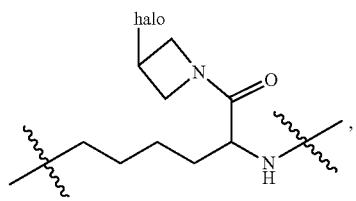

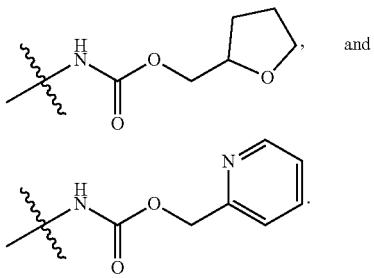

In a 17th aspect, the present invention includes compounds of Formula (III), or a stereoisomer, a tautomer, a pharmaceutically acceptable salt, a solvate, or a prodrug thereof, wherein:

L-Y is independently selected from the group consisting of: —(CH$_2$)$_6$—, —(CH$_2$)$_7$—, —(CH$_2$)$_4$CH(CO$_2$H)CH$_2$—, —(CH$_2$)$_4$CH(CO$_2$Me)CH$_2$—, —(CH$_2$)$_4$CH(CONH$_2$)CH$_2$—, —(CH$_2$)$_4$CH(CONHMe)CH$_2$—, —(CH$_2$)$_4$CH(CON(Me)$_2$)CH$_2$—, —CH$_2$—CH=CH—(CH$_2$)$_4$—, —(CH$_2$)$_4$N(CO$_2$Me)CH$_2$—, —(CH$_2$)$_6$O—, —(CH$_2$)$_3$CH(Me)(CH$_2$)$_2$O—, —CH$_2$NH(CH$_2$)$_4$O—, —(CH$_2$)$_5$NH—, —(CH$_2$)$_6$NH—, —(CH$_2$)$_4$CH(Me)NH—, —(CH$_2$)$_3$CH(Me)CH$_2$NH—, —(CH$_2$)$_4$CH(Me)CH$_2$NH—, —(CH$_2$)$_4$CH(CH$_2$OH)NH—, —(CH$_2$)$_4$CH(CH$_2$OMe)NH—, —(CH$_2$)$_4$CH(CO$_2$H)NH—, —(CH$_2$)$_4$CH(CO$_2$Me)NH—, —(CH$_2$)$_4$CH(CO$_2$Et)NH—, —(CH$_2$)$_4$CH(CO$_2$(i-Pr))NH—, —(CH$_2$)$_4$CH(CO$_2$(t-Bu))NH—, —(CH$_2$)$_4$CH(CO$_2$CH$_2$CF$_3$)NH—, —(CH$_2$)$_4$CH(CO$_2$(CH$_2$)$_2$SO$_2$Me))NH—, —(CH$_2$)$_5$CH(CO$_2$Me)NH—, —(CH$_2$)$_4$CH(CH$_2$CO$_2$H)NH—, —(CH$_2$)$_4$CH(CH$_2$CO$_2$Me)NH—, —(CH$_2$)$_4$CH(CONH$_2$)NH—, —(CH$_2$)$_4$CH(CONH(Me))NH—, —(CH$_2$)$_4$CH(CONH(t-Bu))NH—, —(CH$_2$)$_4$CH(CON(Me)$_2$)NH—, —(CH$_2$)$_4$CH(CONH(OMe))NH—, —(CH$_2$)$_4$CH(CONH(OBn))NH—, —(CH$_2$)$_4$CH(CON(Me)(CH$_2$)$_2$OMe)NH—, —(CH$_2$)$_4$CH(CON(Me)(CH$_2$)$_2$N(Me)$_2$)NH—, —CH$_2$—CH=CH—(CH$_2$)$_2$NH—, —CH$_2$—CH=CH—(CH$_2$)$_3$NH—, —(CH$_2$)$_4$CH(CHF$_2$)NH—, —(CH$_2$)$_4$CH(CF$_3$)NH—, —(CH$_2$)$_3$CF$_2$CH$_2$NH—, —CH$_2$—CH=CH—(CH$_2$)$_2$CH(CF$_3$)NH—, —(CH$_2$)$_4$CH(3-Me-oxetan-3-yl)NH—, —(CH$_2$)$_4$CH(CO-pyrrolidin-1-yl)NH—, —(CH$_2$)$_4$CH(thiazol-4-yl)NH—, —(CH$_2$)$_4$CH(4-Me-thiazol-2-yl)NH—, —(CH$_2$)$_4$CH(1-Me-imidazol-2-yl)NH—, —(CH$_2$)$_4$CH(1-Me-pyrazol-3-yl)NH—, —(CH$_2$)$_4$CH(1-(n-Pr)-pyrazol-3-yl)NH—, —(CH$_2$)$_4$CH(1-Me-pyrazol-5-yl)NH—, —(CH$_2$)$_4$CH(1,3-di-Me-pyrazol-5-yl)NH—, —(CH$_2$)$_4$CH(1-Me-4-Cl-pyrazol-3-yl)NH—, —(CH$_2$)$_4$N(CO$_2$Me)CH$_2$—, —(CH$_2$)$_4$CONH—, —(CH$_2$)$_5$CONH—, —(CH$_2$)$_6$CONH—, —(CH$_2$)$_3$CH(Me)CONH—, —(CH$_2$)$_4$CH(Me)CONH—, —(CH$_2$)$_2$CH(Me)CH$_2$CONH—, —(CH$_2$)$_3$CH(Me)CH$_2$CONH—, —(CH$_2$)$_2$CH(Me)(CH$_2$)$_2$CONH—, —(CH$_2$)$_2$—CH=CH—CONH—, —CH$_2$—CH=CH—CH$_2$CONH—, —CH$_2$—CH=CH—(CH$_2$)$_2$CONH—, —CH$_2$—CH=CH—(CH$_2$)$_3$CONH—, —CH$_2$—CH=CH—CH$_2$CH(Me)CONH—, —CH$_2$—CH=CH—CH(Me)CH$_2$CONH—, —CH$_2$—CH=CHCH(Et)CH$_2$CONH—, —CH$_2$—CH=C(Me)—(CH$_2$)$_2$CONH—, —(CH$_2$)$_3$CH(Me)CONH—, —(CH$_2$)$_3$CH(Et)CONH—, —(CH$_2$)$_3$CH(i-Pr)CONH—, —(CH$_2$)$_3$CHFCONH—, —(CH$_2$)$_3$CF$_2$CONH—, —(CH$_2$)$_4$CF$_2$CONH—, —CH$_2$—

$R^{1b}$ is independently selected from the group consisting of: H and halogen;

$R^3$ is independently selected from the group consisting of: H, halogen, C$_{1-4}$ alkyl, CN, CO$_2$(C$_{1-4}$ alkyl), CONH$_2$, CON(C$_{1-4}$ alkyl)$_2$, and cyclopropyl; and $R^6$ is independently selected from the group consisting of: F, NH$_2$, CO$_2$H, —NHCO$_2$(C$_{1-4}$ alkyl), —NHCO$_2$(CH$_2$)$_2$OH, —NHCO$_2$(CH$_2$)$_2$O(C$_{1-4}$ alkyl), —NHCO$_2$CH$_2$CH(C$_{1-4}$ alkyl)O(C$_{1-4}$ alkyl), and CH=CH—CH₂CF₂CONH—, —(CH₂)₃CH(CF₃)CONH—, —CH₂CH(OH)(CH₂)₂CONH—, —(CH₂)₂CH(OH)CH₂CONH—, —(CH₂)₃CH(OH)CH₂CONH—, —CH₂CH(OH)CH(OH)CH₂CONH—, —CH₂—CH=CH—CH(OH)CH₂CONH—, —(CH₂)₃CH(OMe)CONH—, —(CH₂)₃CH(OCOMe)CH₂CONH—, —(CH₂)₃C(O)CH₂CONH—, —CH₂O(CH₂)₃CONH—, —CH₂O(CH₂)₄CONH—, —CH₂NH(CH₂)₂CONH—, —CH₂NH(CH₂)₃CONH—, —(CH₂)₂N(Me)CH₂CONH—, —(CH₂)₂N(Me)(CH₂)₂CONH—, —(CH₂)₅NHCO—, —CH₂—CH=CH—(CH₂)₂NHCO—, —CH₂—CH=CH—CH₂OCONH—, —(CH₂)₄OCONH—, —CH₂—CH=CH—CH₂NHCONH—, —(CH₂)₄SO₂NH—, —CH₂—CH=CH—CH₂SO₂NH—, —(CH₂)₄CH=N—,

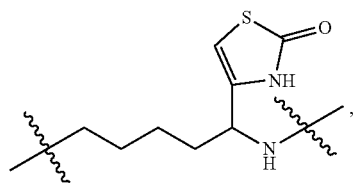

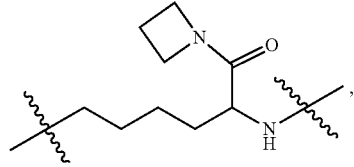

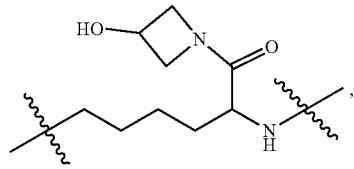

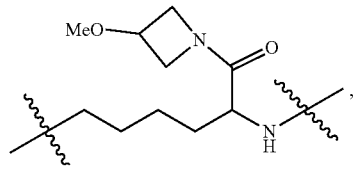

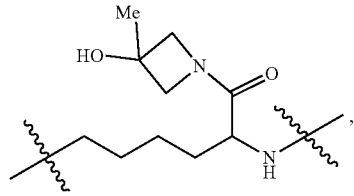

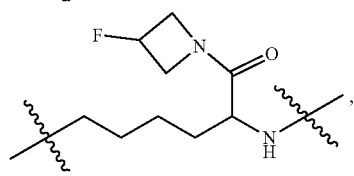

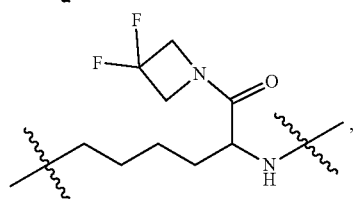

-continued

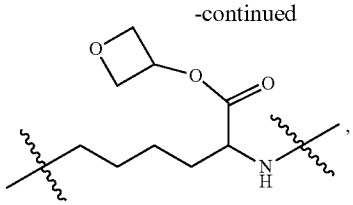

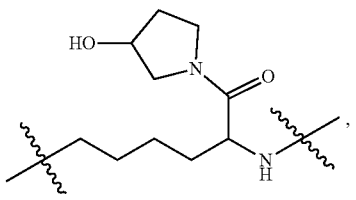

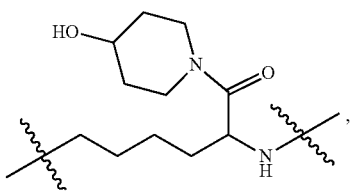

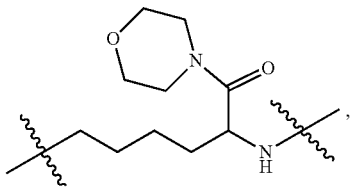

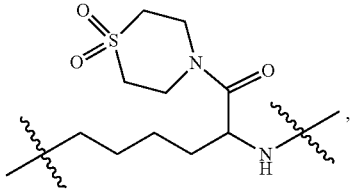

, and

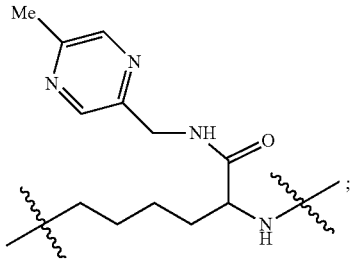

;

$R^{1b}$ is independently selected from the group consisting of: H and F;

$R^3$ is independently selected from the group consisting of: H, F, Cl, Br, CH₃, CN, CO₂Me, CO₂Et, CONH₂, CONMe₂, and cyclopropyl; and $R^6$ is independently selected from the group consisting of: F, NH₂, CO₂H, —NHCO₂Me, —NHCO₂(CH₂)₂OH, —NHCO₂(CH₂)₂OMe, —NHCO₂(CH₂)₂OEt, —NHCO₂CH₂CH(Et)OMe, and

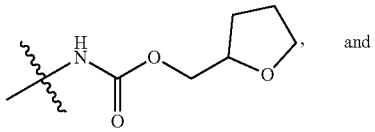

, and

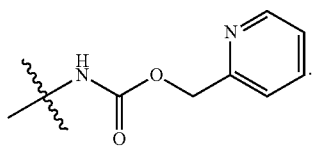

In an 18th aspect, the present invention includes compounds of Formula (IV):

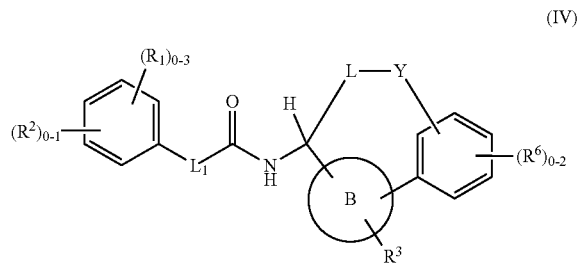

or a stereoisomer, a tautomer, a pharmaceutically acceptable salt, a solvate, or a prodrug thereof, within the scope of any one of the first to tenth aspects, wherein:

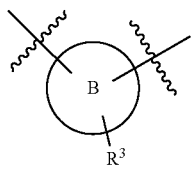

is independently selected from the group consisting of:

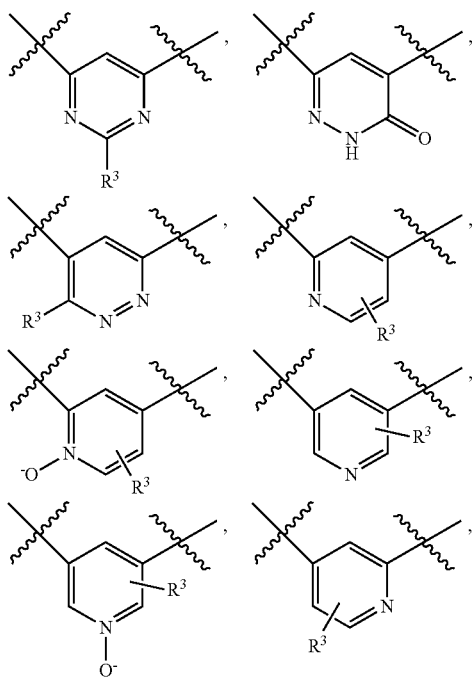

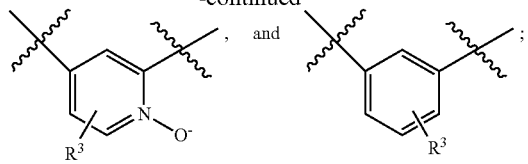

$L_1$ is independently selected from the group consisting of: a bond, —$CH_2CH_2$— and —CH=CH—;
L is independently selected from the group consisting of:
—$CH_2$—CH=CH—$CH_2$—, —$CH_2$—CH=CH—$(CH_2)_2$—, —$(CH_2)_4$—, —$(CH_2)_5$—, —$(CH_2)_3$CH$(C_{1-4}$ alkyl)-, —$CH_2$—CH=CH—$CH_2$CH$(CF_3)$—, —$(CH_2)_4$CH$(CF_3)$—, —$(CH_2)_4$CH$(CH_2OH)$—, —$(CH_2)_4$CH$(CO_2H)$—, —$(CH_2)_4$CH$(CO_2(C_{1-4}$ alkyl))-, —$CH_2$CONH$(CH_2)_2$—, —$(CH_2)_4$CH$(CO_2(CH_2)_2O(C_{1-4}$ alkyl))-, —$(CH_2)_4$CH$(CH_2NH(CH_2)_2O(C_{1-4}$ alkyl))-, —$(CH_2)_4$CH$(CO_2(CH_2)_2N(C_{1-4}$ alkyl)$_2$)-, —$(CH_2)_4$CH$(CON(C_{1-4}$ alkyl)$(CH_2)_2O(C_{1-4}$ alkyl))-, —$(CH_2)_4$CH$(CON(C_{1-4}$ alkyl)$(CH_2)_2N(C_{1-4}$ alkyl)$_2$)-,

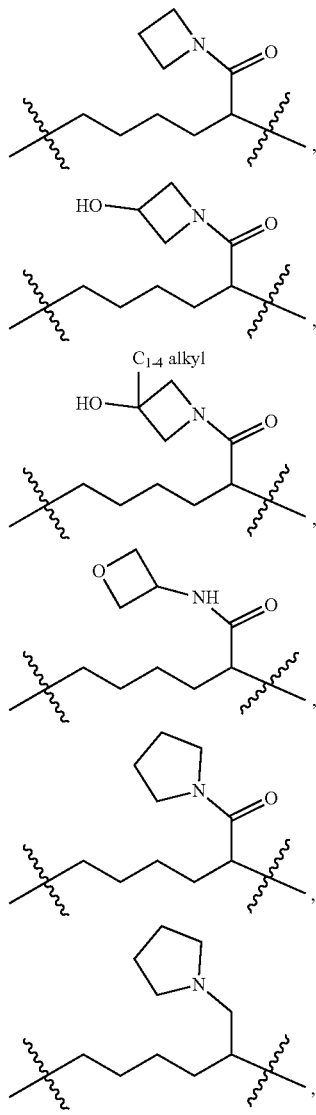

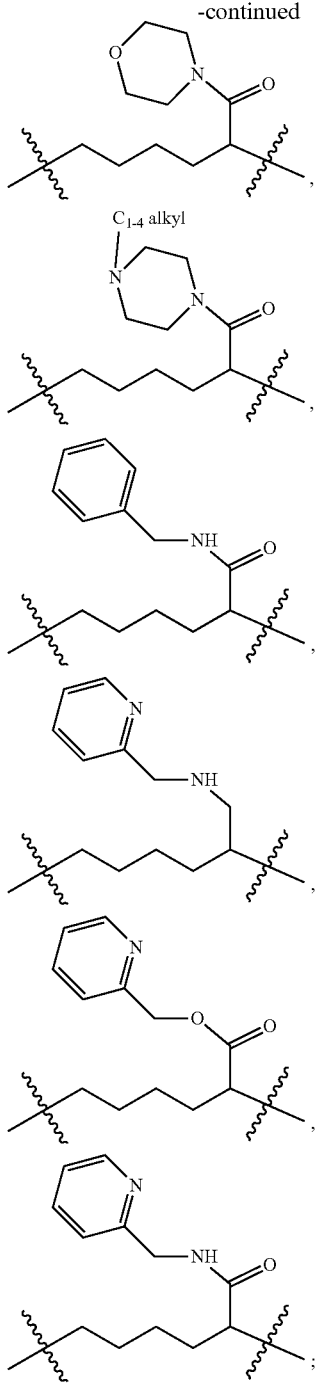

Y is independently —CONH—, O, or NH;
$R^1$ is, independently at each occurrence, selected from: halogen, CN, $OCF_3$, $CHF_2$, $CF_3$, $C_{1-4}$ alkyl, $C_{1-4}$ alkoxy, $CO(C_{1-4}$ alkyl), $NH_2$, —C(=NH)$NH_2$, —C(O)$NH_2$, and —$CH_2NH_2$;
$R^2$ is independently a 5-membered heterocycle selected from: pyrazolyl, imidazolyl, triazolyl, and tetrazolyl;
$R^3$ is independently selected from the group consisting of: H, halogen, and $C_{1-4}$ alkyl; and
$R^6$ is, independently at each occurrence, selected from the group consisting of: H, halogen, CN, —$NHCO_2(C_{1-4}$ alkyl), —$CH_2NHCO_2(C_{1-4}$ alkyl), —$NHCO_2(CH_2)_2O(C_{1-4}$ alkyl), $CO_2H$, and $CONH_2$.

In a 19th aspect, the present invention includes compounds of Formula (IVa):

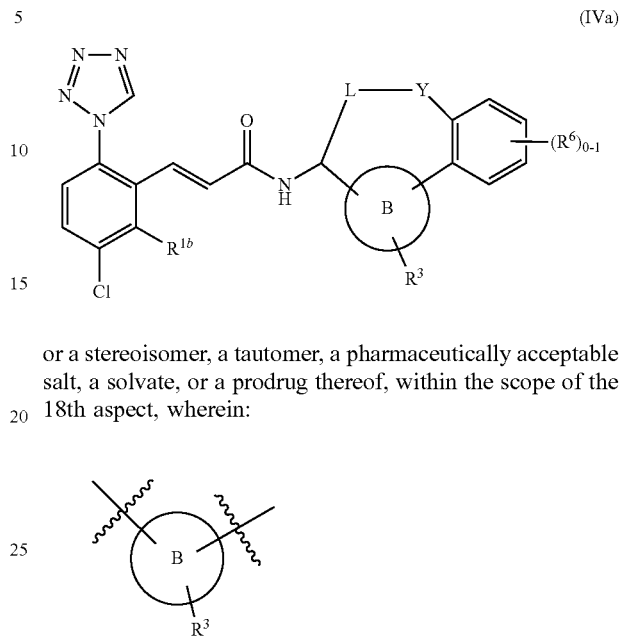

(IVa)

or a stereoisomer, a tautomer, a pharmaceutically acceptable salt, a solvate, or a prodrug thereof, within the scope of the 18th aspect, wherein:

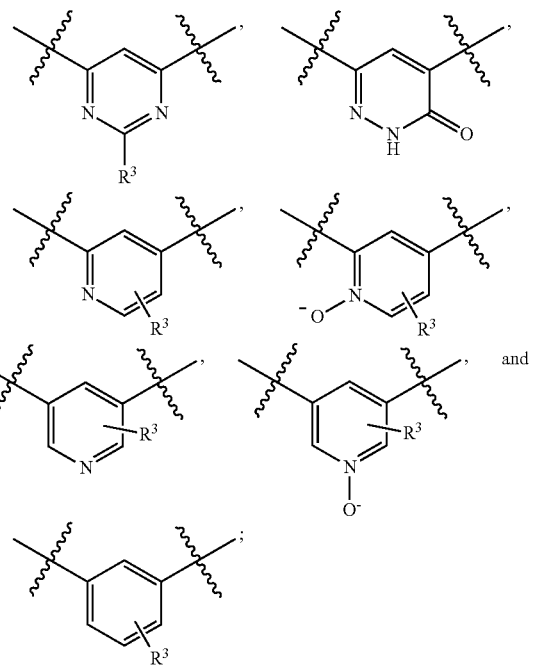

is independently selected from the group consisting of:

Y is independently —CONH— or NH;
$R^3$ is independently selected from the group consisting of: H, F, Cl, and $C_{1-4}$ alkyl; and
$R^6$ is independently selected from the group consisting of: F, —$NHCO_2(C_{1-4}$ alkyl), —$CH_2NHCO_2(C_{1-4}$ alkyl), $CO_2H$, $CONH_2$, and —$NHCO_2(CH_2)_2O(C_{1-4}$ alkyl).

In a 20th aspect, the present invention includes compounds of Formula (V):

(V)

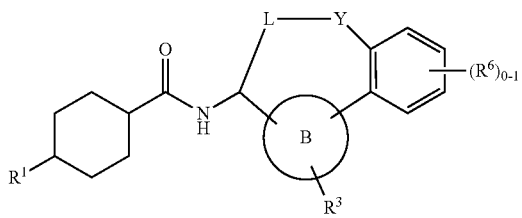

or a stereoisomer, a tautomer, a pharmaceutically acceptable salt, a solvate, or a prodrug thereof, within the scope of the first, second or third aspect, wherein:
 ring B is independently selected from the group consisting of: imidazole and pyridine; and
 $R^1$ is independently selected from the group consisting of: $C_{1-4}$ alkyl and $CH_2NH_2$.

In another aspect, the present invention includes compounds of Formula (V): or a stereoisomer, a tautomer, a pharmaceutically acceptable salt, a solvate, or a prodrug thereof, wherein:
 ring B is independently selected from the group consisting of:

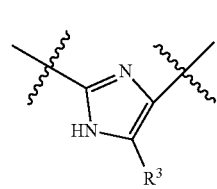 and 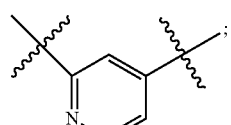;

L is independently selected from the group consisting of:
 —$CH_2$—CH=CH—$(CH_2)_2$—, —$CH_2$—CH=CH—$CH_2CF_2$—, —$(CH_2)_4$—, and —$(CH_2)_4CH(CF_3)$—;
Y is independently selected from the group consisting of: —$CH_2$—, —CONH—, and NH;
$R^3$ is independently selected from the group consisting of: H, F, Cl, and Me; and
$R^{6a}$ is independently selected from the group consisting of: H and —$NHCO_2Me$.

In a 21st aspect, the present invention provides a compound selected from the exemplified examples or a stereoisomer, a tautomer, a pharmaceutically acceptable salt, or a solvate thereof.

In another aspect, the present invention provides a compound selected from any subset list of compounds within the scope of the 24th aspect.

In another aspect, the present invention provides compounds of Formula (I), (II), (IIa), (IIc), or (IIe), or a stereoisomer, a tautomer, a pharmaceutically acceptable salt, a solvate, or a prodrug thereof, within the scope of the fourth aspect, wherein:

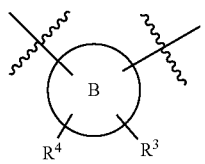

is independently selected from the group consisting of:

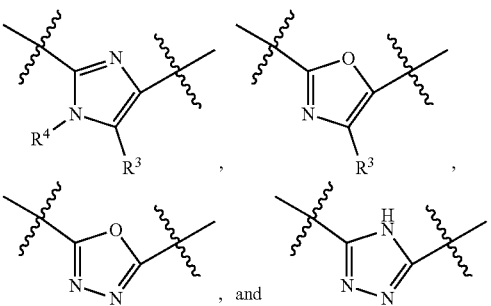, and

In another aspect wherein:

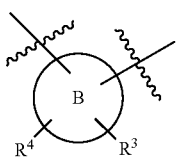

is independently selected from the group consisting of:

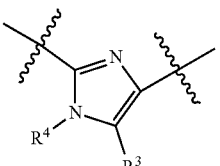

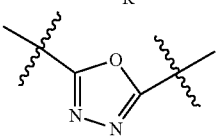.

In another aspect, wherein:

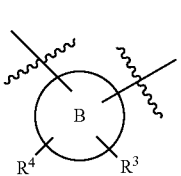 is 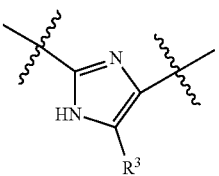.

In another aspect, the present invention provides compounds of Formula (I), (II), (IIa), (IIc), or (IIe), or a stereoisomer, a tautomer, a pharmaceutically acceptable salt, a solvate, or a prodrug thereof, within the scope of the fourth aspect, wherein:

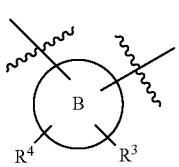

is independently selected from the group consisting of:
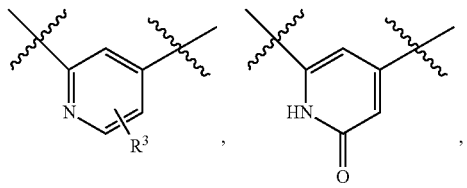
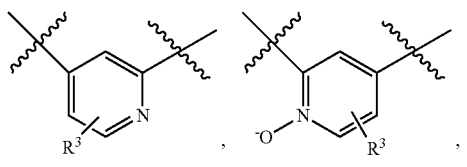
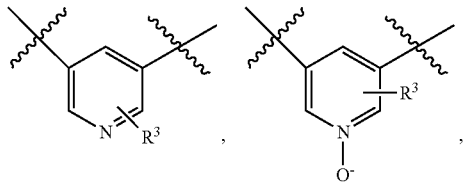
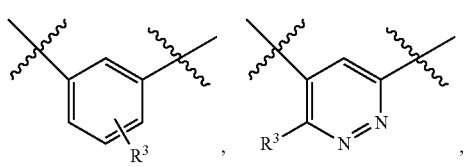
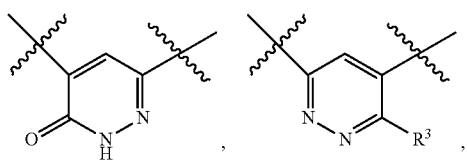
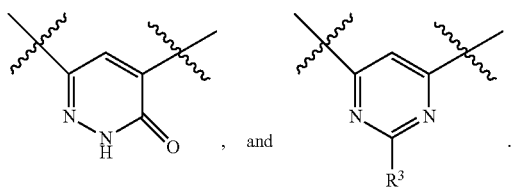
In another aspect wherein:
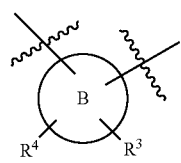
is independently selected from the group consisting of:
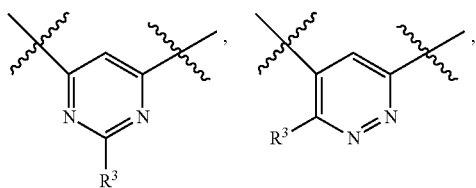
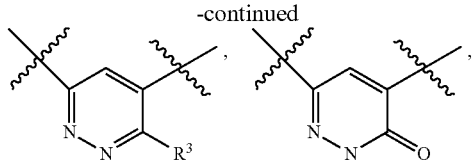
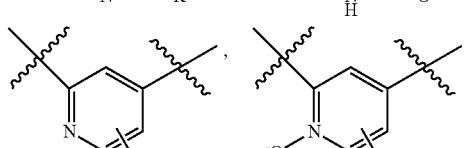
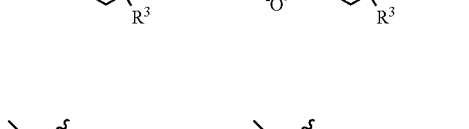
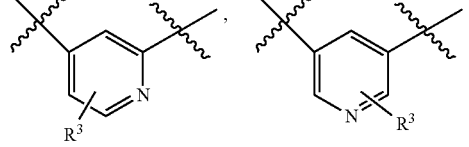
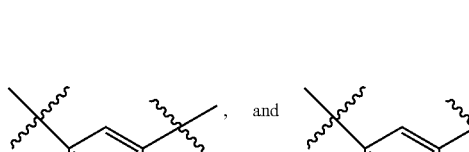
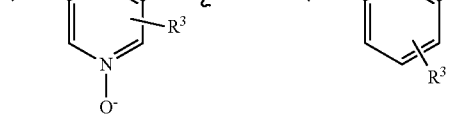
In another aspect wherein:
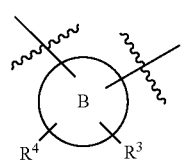
is independently selected from the group consisting of:
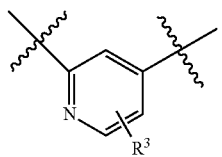 and 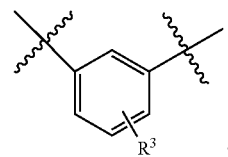
In another aspect wherein:
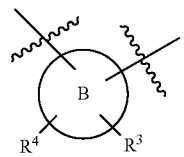 is 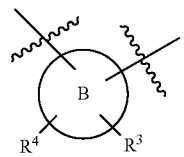

In another aspect wherein:

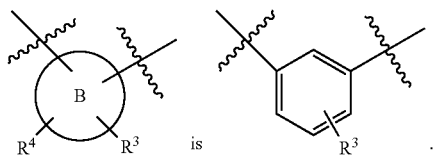

In another aspect, the present invention includes compounds of Formula (I), (II), (IIa), or (IIb), a stereoisomer, a tautomer, a pharmaceutically acceptable salt, a solvate, or a prodrug thereof, within the scope of any of the above aspects, wherein:

$R^2$ is independently a 5-membered heterocycle substituted with 0-1 $R^{2a}$, wherein said heterocycle is selected from: pyrazolyl, imidazolyl, triazolyl, and tetrazolyl; and $R^{2a}$ is, independently at each occurrence, selected from the group consisting of: halogen, OH, $NH_2$, $CH_2OH$, $CO_2H$, $C_{1-4}$ alkyl, —$CONH_2$, —$CONH(C_{1-4}$ alkyl), and —$CON(C_{1-4}$ alkyl$)_2$.

In another aspect, the present invention includes compounds of Formula (I), (II), (IIa), or (IIb), a stereoisomer, a tautomer, a pharmaceutically acceptable salt, a solvate, or a prodrug thereof, within the scope of any of the above aspects, wherein:

$R^2$ is independently selected from the group consisting of: triazolyl and tetrazolyl.

In another embodiment, ring A is independently selected from the group consisting of: phenyl, cyclohexyl, and 5,6,7,8-tetrahydroisoquinolinyl.

In another embodiment, ring A is phenyl.
In another embodiment, ring A is cyclohexyl.
In another embodiment, ring A is tetrahydroisoquinoline.
In another aspect, ring A is

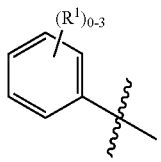

wherein $R^1$ is, independently at each occurrence, selected from the group consisting of: halogen, $C_{1-4}$ alkyl, OH, $C_{1-4}$ alkoxy, $CO(C_{1-4}$ alkyl), CN, $CH_2F$, $CHF_2$, $OCHF_2$, $NH_2$, $N(C_{1-4}$ alkyl$)_2$, —$CH_2NH_2$, —$CH_2NHCO_2(C_{1-4}$ alkyl), and —$C(=NH)NH_2$.

In another aspect, ring A is

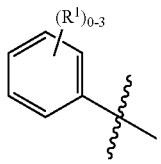

is independently selected from the group consisting of:

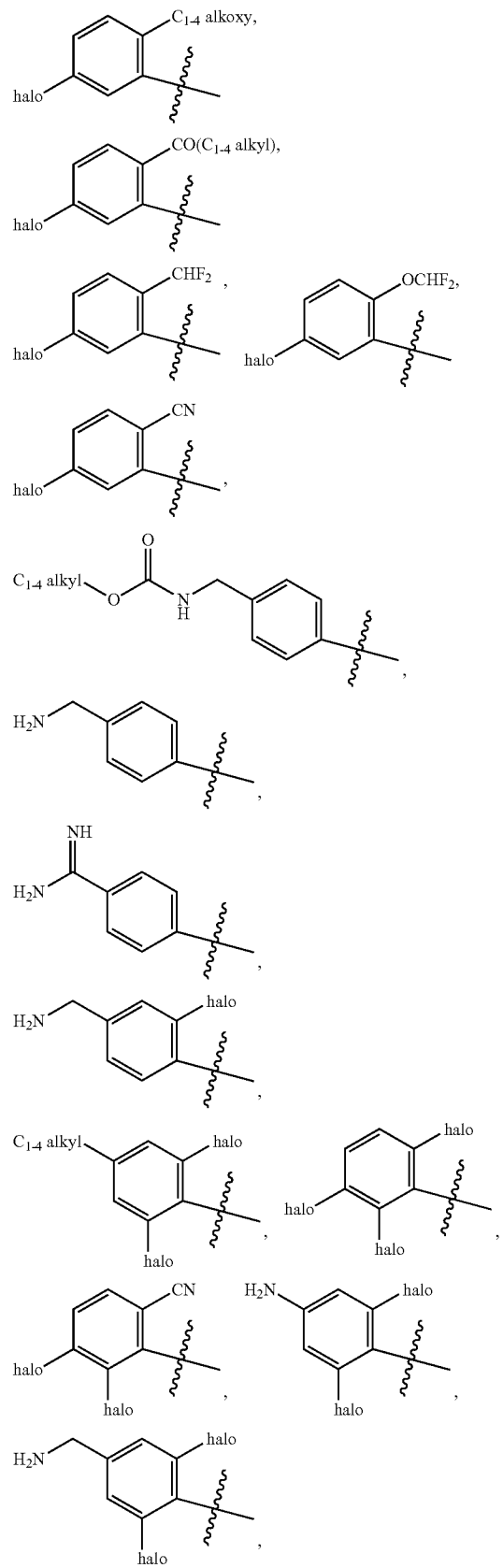

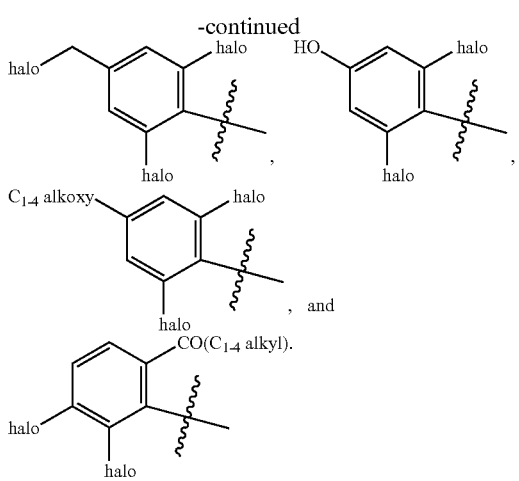

In another embodiment, ring B is independently selected from the group consisting of: imidazole, oxadiazole, pyridine, pyridazine, and benzene.

In another embodiment,

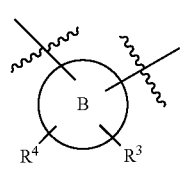

is independently selected from the group consisting of:

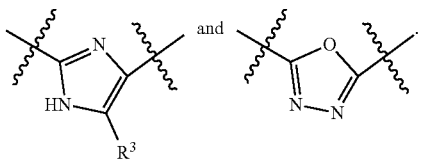

In another embodiment,

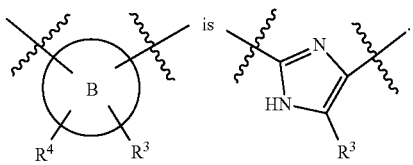

In another embodiment,

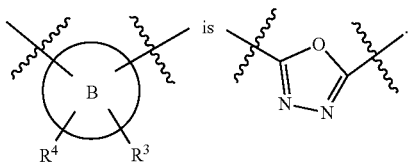

In another embodiment,

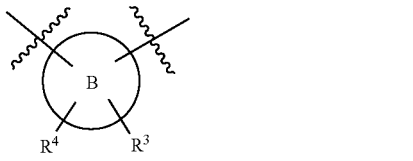

is independently selected from the group consisting of:

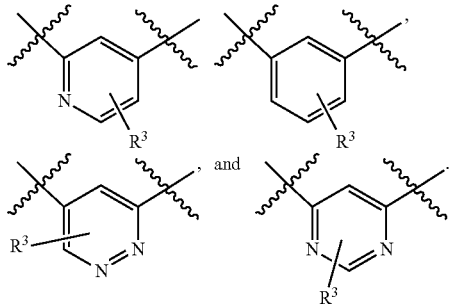

In another embodiment,

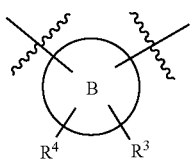

In another embodiment,

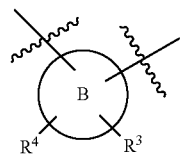

is independently selected from the group consisting of:

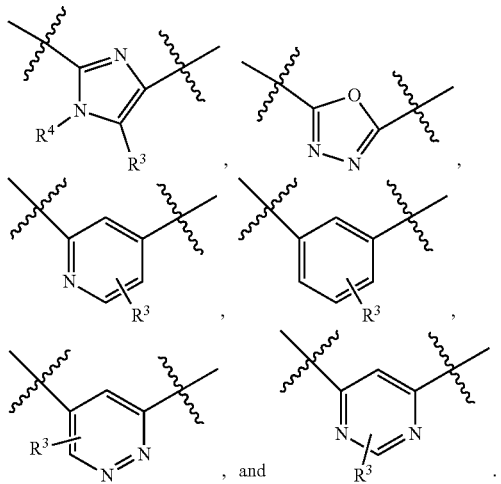

In another embodiment, is independently selected from the group consisting of:

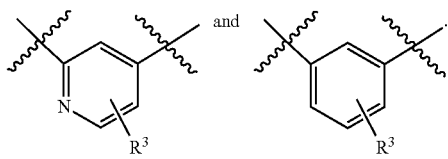

In another embodiment,

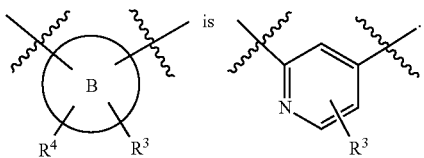

In another embodiment,

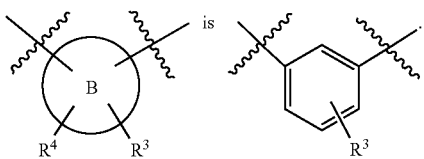

In another embodiment,

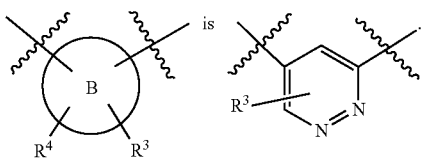

In another embodiment,

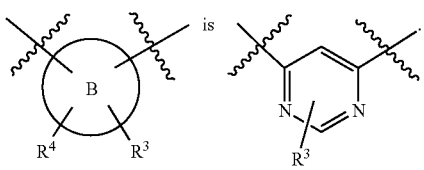

In another embodiment, $L_1$ is independently selected from the group consisting of: a bond, —CH$_2$CH$_2$—, —CH=CH—, —C(Me)=CH—, and —CH$_2$NH—.

In another embodiment, $L_1$ is independently selected from the group consisting of: a bond, —CH$_2$CH$_2$—, —CH=CH—, and —C(Me)=CH.

In another embodiment, $L_1$ is independently selected from the group consisting of: a bond, —CH$_2$CH$_2$— and —CH=CH—.

In another embodiment, $L_1$ is a bond.

In another embodiment, $L_1$ is —CH=CH—.

In another embodiment, L is independently selected from the group consisting of: $C_{3-7}$ alkylene and $C_{3-7}$ alkenylene; wherein said alkylene and alkenylene are substituted with 0-2 $R^7$ and optionally one or two of the carbon atoms of said alkylene and alkenylene may be replaced by O, NH, N($C_{1-4}$ alkyl), CONH, NHCO, or CON($C_{1-4}$ alkyl).

In another embodiment, L is independently selected from the group consisting of: $C_{3-7}$ alkylene and $C_{4-7}$ alkenylene; wherein said alkylene and alkenylene are optionally substituted with 1-2 $R^7$; optionally one or two of the carbon atoms of said alkylene and alkenylene may be replaced by O, NH, N($C_{1-4}$ alkyl), CONH, or CON($C_{1-4}$ alkyl).

In another embodiment, L is $C_{3-7}$ alkylene, wherein said alkylene is optionally substituted with 1-2 $R^7$; optionally one or two of the carbon atoms of said alkylene may be replaced by O, NH, N($C_{1-4}$ alkyl), CONH, or CON($C_{1-4}$ alkyl).

In another embodiment, L is $C_{4-7}$ alkenylene, wherein said alkenylene is optionally substituted with 1-2 $R^7$; optionally one or two of the carbon atoms of said alkenylene may be replaced by O, NH, N($C_{1-4}$ alkyl), CONH, or CON($C_{1-4}$ alkyl).

In another embodiment, Y is independently selected from the group consisting of: —CH$_2$—, O, NH, N($C_{1-4}$ alkyl), —NHCO—, —CONH—, —CONHCH$_2$—, —CON($C_{1-4}$ alkyl)CH$_2$—, —OCONH—, —NHCONH—, and —SO$_2$NH—.

In another embodiment, Y is independently selected from the group consisting of: —CH$_2$—, O, NH, NMe, —CONH—, —NHCO—, —CONHCH$_2$—, —CONMeCH$_2$—, —OCONH—, —NHCONH—, and —SO$_2$NH—.

In another embodiment, Y is —CONH—.

In another embodiment, $R^1$ is, independently at each occurrence, selected from the group consisting of: halogen, $C_{1-6}$ alkyl, $C_{1-4}$ alkoxy, $C_{1-4}$ alkylthio, OH, CH$_2$F, CHF$_2$, CF$_3$, OCH$_2$F, OCHF$_2$, OCF$_3$, CN, NH$_2$, NH($C_{1-4}$ alkyl)$^2$, N($C_{1-4}$ alkyl)$_2$, CO$_2$($C_{1-4}$ alkyl), CO($C_{1-4}$ alkyl), —OCH$_2$CO$_2$H, —CH$_2$NH$_2$, —CONH$_2$, —CONH($C_{1-4}$ alkyl), —CH$_2$NHCO$_2$($C_{1-4}$ alkyl), —SO$_2$NH$_2$, and —C(=NH)NH$_2$.

In another embodiment, $R^1$ is, independently at each occurrence, selected from the group consisting of: halogen, $C_{1-6}$ alkyl, $C_{1-4}$ alkoxy, $C_{1-4}$ alkylthio, OH, CHF$_2$, CF$_3$, OCF$_3$, CN, NH$_2$, CO$_2$($C_{1-4}$ alkyl), CO($C_{1-4}$ alkyl), —OCH$_2$CO$_2$H, —CH$_2$NH$_2$, —CONH$_2$, —CONH($C_{1-4}$ alkyl), —SO$_2$NH$_2$, and —C(=NH)NH$_2$.

In another embodiment, $R^1$ is, independently at each occurrence, selected from: halogen, CN, OH, CH$_2$F, CHF$_2$, CF$_3$, OCH$_2$F, OCHF$_2$, OCF$_3$, $C_{1-4}$ alkyl, $C_{1-4}$ alkoxy, CO($C_{1-4}$ alkyl), NH$_2$, NH($C_{1-4}$ alkyl)$_2$, N($C_{1-4}$ alkyl)$_2$, —C(=NH)NH$_2$, —C(C)NH$_2$, —CH$_2$NH$_2$, —CH$_2$NHCO$_2$($C_{1-4}$ alkyl), and —SO$_2$NH$_2$.

In another embodiment, $R^1$ is, independently at each occurrence, selected from: halogen, CN, OH, OCF$_3$, CHF$_2$, CF$_3$, $C_{1-4}$ alkyl, $C_{1-4}$ alkoxy, CO($C_{1-4}$ alkyl), NH$_2$, —C(=NH)NH$_2$, —C(O)NH$_2$, —CH$_2$NH$_2$, and —SO$_2$NH$_2$.

In another embodiment, $R^1$ is selected from the group consisting of: halogen, $C_{1-4}$ alkyl, CHF$_2$, and CO($C_{1-4}$ alkyl).

In another embodiment, $R^2$ is a 5-membered heterocycle substituted with 0-1 $R^{2a}$, wherein said heterocycle is independently selected from: pyrazolyl, imidazolyl, triazolyl, and tetrazolyl.

In another embodiment, $R^2$ is independently selected from the group consisting of: triazolyl and tetrazolyl.

In another embodiment, $R^2$ is tetrazolyl.

In another embodiment, $R^3$ is independently selected from the group consisting of: H, halogen, $C_{1-4}$ alkyl, CN, CO$_2$ ($C_{1-4}$ alkyl), CONH$_2$, and cyclopropyl.

In another embodiment, $R^3$ is independently selected from the group consisting of: H, $C_{1-4}$ alkyl, and halogen.

In another embodiment, $R^3$ is independently selected from the group consisting of: H and halogen.

In another embodiment, $R^3$ is independently selected from the group consisting of: H and Cl.

In another embodiment, $R^3$ is H.

In another embodiment, $R^3$ is Cl.

In another embodiment, $R^4$ is H.

In another embodiment, $R^5$ is, independently at each occurrence, selected from the group consisting of: H and $C_{1-4}$ alkyl.

In another embodiment, $R^5$ is, independently at each occurrence, selected from the group consisting of: H and methyl.

In another embodiment, $R^6$ is, independently at each occurrence, selected from the group consisting of: halogen, $C_{1-4}$ alkyl, CN, OH, $CF_3$, $CO_2H$, $CO_2(C_{1-4}$ alkyl), —$CH_2CO_2H$, —$(CH_2)_2CO_2H$, —$CH_2CO_2(C_{1-4}$ alkyl), —$(CH_2)_2CO_2(C_{1-4}$ alkyl), $NH_2$, —$CH_2NH_2$, —$NHCO(C_{1-4}$ alkyl), —$NHCO_2(C_{1-4}$ alkyl), —$NHCO_2(CH_2)_2O(C_{1-4}$ alkyl), —$NHCO_2(CH_2)_3O(C_{1-4}$ alkyl), —$NHCO_2CH_2CH(C_{1-4}$ alkyl)$O(C_{1-4}$ alkyl), —$NHCO_2(CH_2)_2OH$, —$NHCO_2(CH_2)_2NH_2$, —$NHCO_2CH_2CO_2H$, —$CH_2NHCO_2(C_{1-4}$ alkyl), —$NHC(O)NH(C_{1-4}$ alkyl), —$NHC(O)N(C_{1-4}$ alkyl)$_2$, —$NHSO_2(C_{1-4}$ alkyl), —$SO_2NH(CH_2)_2OH$, —$SO_2NH(CH_2)_2O(C_{1-4}$ alkyl), —$C(O)NH(CH_2)_2O(C_{1-4}$ alkyl), $CONH_2$, $CONH(C_{1-4}$ alkyl), $CON(C_{1-4}$ alkyl)$_2$, —$CH_2CONH_2$,

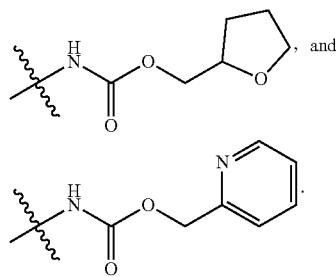

In another embodiment, $R^6$ is, independently at each occurrence, selected from the group consisting of: halogen, $C_{1-4}$ alkyl, CN, OH, $CF_3$, $CO_2H$, $CO_2(C_{1-4}$ alkyl), —$CH_2CO_2H$, —$(CH_2)_2CO_2H$, —$CH_2CO_2(C_{1-4}$ alkyl), —$(CH_2)_2CO_2(C_{1-4}$ alkyl), $NH_2$, —$CH_2NH_2$, —$NHCO(C_{1-4}$ alkyl), —$NHCO_2(C_{1-4}$ alkyl), —$NHCO_2(CH_2)_2O(C_{1-4}$ alkyl), —$NHCO_2(CH_2)_3O(C_{1-4}$ alkyl), —$NHCO_2(CH_2)_2OH$, —$NHCO_2(CH_2)_2NH_2$, —$CH_2NHCO_2(C_{1-4}$ alkyl), —$NHC(O)NH(C_{1-4}$ alkyl), —$NHC(O)N(C_{1-4}$ alkyl)$_2$, —$NHSO_2(C_{1-4}$ alkyl), —$SO_2NH(CH_2)_2OH$, —$SO_2NH(CH_2)_2O(C_{1-4}$ alkyl), and —$CONH_2$.

In another embodiment, $R^6$ is, independently at each occurrence, selected from the group consisting of: halogen, $C_{1-4}$ alkyl, CN, OH, $CF_3$, $CO_2H$, $CO_2(C_{1-4}$ alkyl), —$CH_2CO_2H$, —$CH_2CO_2(C_{1-4}$ alkyl), $NH_2$, —$CH_2NH_2$, —$NHCO(C_{1-4}$ alkyl), —$NHCO_2(C_{1-4}$ alkyl), —$CH_2NHCO_2(C_{1-4}$ alkyl), —$CONH_2$, —$NHCO_2(CH_2)_2OH$, —$NHCO_2(CH_2)_2O(C_{1-4}$ alkyl), —$NHCO_2CH_2CO_2H$, —$NHCO_2CH_2CH(C_{1-4}$ alkyl)$O(C_{1-4}$ alkyl),

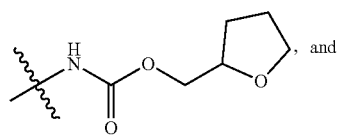

In another embodiment, $R^6$ is, independently at each occurrence, selected from the group consisting of: halogen, $NH_2$, $CO_2H$, $CO_2(C_{1-4}$ alkyl), $CONH_2$, $CONH(C_{1-4}$ alkyl), $CON(C_{1-4}$ alkyl)$_2$, —$NHCO_2(C_{1-4}$ alkyl), —$CH_2NHCO_2(C_{1-4}$ alkyl), —$NHCO_2CH_2CO_2H$, —$NHCO_2(CH_2)_2OH$, —$NHCO_2(CH_2)_2O(C_{1-4}$ alkyl), —$NHCO_2CH_2CH(C_{1-4}$ alkyl)$O(C_{1-4}$ alkyl),

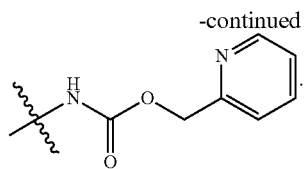

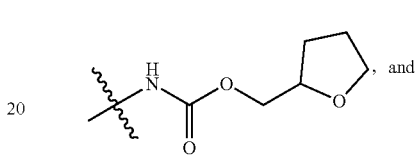

In another embodiment, $R^6$ is, independently at each occurrence, selected from the group consisting of: halogen, $C_{1-4}$ alkyl, CN, OH, $CF_3$, $CO_2H$, $CO_2(C_{1-4}$ alkyl), —$CH_2CO_2H$, —$CH_2CO_2(C_{1-4}$ alkyl), $NH_2$, —$CH_2NH_2$, —$NHCO(C_{1-4}$ alkyl), —$NHCO_2(C_{1-4}$ alkyl), —$CH_2NHCO_2(C_{1-4}$ alkyl), and —$CONH_2$.

In another embodiment, $R^6$ is, independently at each occurrence, selected from the group consisting of: halogen, $CO_2H$, $CO_2(C_{1-4}$ alkyl), $NH_2$, $NHCO_2(C_{1-4}$ alkyl), and —$CH_2NHCO_2(C_{1-4}$ alkyl).

In another embodiment, $R^6$ is, independently at each occurrence, is selected from the group consisting of: halogen, $NH_2$, $NHCO_2(C_{1-4}$ alkyl), and —$CH_2NHCO_2(C_{1-4}$ alkyl).

In another embodiment, $R^6$ is, independently at each occurrence, is selected from the group consisting of: F, $NH_2$, $NHCO_2Me$, and —$CH_2NHCO_2Me$.

In another embodiment, $R^{6a}$ is independently selected from the group consisting of: H, halogen, $NH_2$, $CO_2H$, $CONH_2$, —$NHCO_2(C_{1-4}$ alkyl), —$NHCO_2(CH_2)_2OH$, —$NHCO_2(CH_2)_2O(C_{1-4}$ alkyl), —$NHCO_2CH_2CH(C_{1-4}$ alkyl)$O(C_{1-4}$ alkyl),

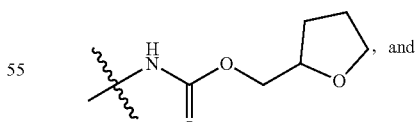

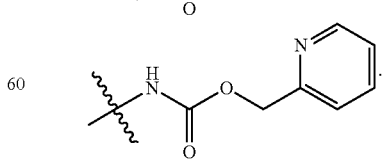

In another embodiment, $R^{6a}$ is independently selected from the group consisting of: H, halogen, $NH(C_{1-4}$ alkyl), and $NHCO_2(C_{1-4}$ alkyl).

In another embodiment, $R^{6a}$ is independently selected from the group consisting of: H, halogen, and $NHCO_2(C_{1-4}$ alkyl).

In another embodiment, $R^{6a}$ is independently selected from the group consisting of: H, F, and NHCO₂Me.

In another embodiment, $R^7$ is, independently at each occurrence, selected from the group consisting of: halogen, OH, $CHF_2$, $CF_3$, $C_{1-4}$ alkoxy, $CH_2OH$, $CH_2O(C_{1-4}$ alkyl), $CO_2H$, $CO_2(C_{1-4}$ alkyl), $CH_2CO_2H$, $CH_2CO_2(C_{1-4}$ alkyl), $CONH_2$, $CONH(C_{1-4}$ alkyl), $CON(C_{1-4}$ alkyl)$_2$, —OCO ($C_{1-4}$ alkyl), —CON($C_{1-4}$ alkyl)($CH_2$)$_2$N($C_{1-4}$ alkyl)$_2$, —CONH($C_{1-4}$ alkoxy), $C_{1-4}$ alkyl, and —(CO)$_{0-1}$-(4- to 6-membered heterocycle comprising carbon atoms and 1-4 heteroatoms selected from N, NH, N($C_{1-4}$ alkyl), O, and S(O)$_p$); wherein said heterocycle is substituted with 0-2 $R^8$.

In another embodiment, $R^7$ is independently selected from the group consisting of: halogen, $C_{1-4}$ alkyl, and N($C_{1-4}$ alkyl)$_2$.

In another embodiment, $R^7$ is independently selected from the group consisting of: halogen, and $C_{1-4}$ alkyl.

In another aspect, the present invention provides, inter alia, a compound of Formula (I-1):

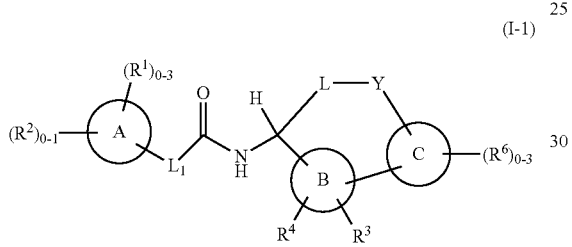

(I-1)

or a stereoisomer, a tautomer, a pharmaceutically acceptable salt, a solvate, or a prodrug thereof, wherein:
ring A is a $C_{3-10}$ carbocycle or a 5- to 10-membered heterocycle comprising: carbon atoms and 1-4 heteroatoms selected from N, O, and S(O)$_p$;
ring B is a benzene ring or a 5- to 6-membered heteroaryl comprising: carbon atoms and 1-4 heteroatoms selected from N, O, and S(O)$_p$;
ring C is a benzene ring or a 5- to 10-membered heterocycle comprising: carbon atoms and 1-4 heteroatoms selected from N, O, and S(O)$_p$;
$L_1$ is selected from the group consisting of: a bond, —$CHR^5CHR^5$—, —$CR^5$=$CR^5$—, —C≡—, —$OCH_2$—, —$CHR^5NH$—, —$CH_2O$—, —$SCH_2$—, —$SO_2CH_2$—, —$CH_2NH$—, and —$CR^5R^5$—;
L is selected from the group consisting of: $C_{3-8}$ alkylene, $C_{4-8}$ alkenylene and $C_{4-8}$ alkynylene; wherein said alkylene, alkenylene and alkynylene are optionally substituted with 1-2 $R^7$; optionally one or more of the carbon atoms of said alkylene and alkenylene may be replaced by O, S, NH, N($C_{1-4}$ alkyl), CO, CONH, NHCO, OCONH, SO₂NH, or CON($C_{1-4}$ alkyl);
Y is selected from the group consisting of: O, S, NH, N($C_{1-4}$ alkyl), $CH_2$, CH($C_{1-4}$ alkyl), C($C_{1-4}$ alkyl)$_2$, —CONH—, —NHCO—, —CONHCH₂—, —CON ($C_{1-4}$ alkyl)$CH_2$—, —OCONH—, —OCON($C_{1-4}$ alkyl)-, —NHCONH—, —SO₂NH—, —NHCO₂—, and —NHSO₂—;
$R^1$ is, independently at each occurrence, selected from the group consisting of: halogen, $C_{1-6}$ alkyl, $C_{1-4}$ alkoxy, $C_{1-4}$ alkylthio, OH, $CHF_2$, $CF_3$, $OCF_3$, CN, $NH_2$, —$CO_2(C_{1-4}$ alkyl), —$CO(C_{1-4}$ alkyl), —$CH_2NH_2$, —$CONH_2$, —$CONH(C_{1-4}$ alkyl), —$OCH_2CO_2H$, —$NHCO(C_{1-4}$ alkyl), —$NHCO_2(C_{1-4}$ alkyl), —$NHSO_2(C_{1-4}$ alkyl), —$SO_2NH_2$, and —C(=NH)$NH_2$;
$R^2$ is a 5- to 7-membered heterocycle comprising carbon atoms and 1-4 heteroatoms selected from N, O, and S(O)$_p$, wherein said heterocycle is substituted with 0-2 $R^{2a}$;
$R^{2a}$ is, independently at each occurrence, selected from the group consisting of: $C_{1-4}$ alkyl, —$CH_2OH$, $C_{1-4}$ alkoxy, OH, $CF_3$, $OCF_3$, CN, $NH_2$, $CO_2H$, $CO_2(C_{1-4}$ alkyl), $COC_{1-4}$ alkyl, —$CONH_2$, —$CONH(C_{1-4}$ alkyl), —$CON(C_{1-4}$ alkyl)$_2$, —$SO_2(C_{1-4}$ alkyl), —$SO_2NH_2$, —$SO_2NH(C_{1-4}$ alkyl), and —$SO_2N(C_{1-4}$ alkyl)$_2$;
$R^3$ is selected from the group consisting of: H, halogen, OH, $NH_2$, $CF_3$, $C_{1-4}$ alkyl, $C_{1-4}$ alkoxy, —$CH_2OH$, $CO_2H$, $CO_2(C_{1-4}$ alkyl), —C(O)$NH_2$, —C(O)NH($C_{1-4}$ alkyl), —C(O)N($C_{1-4}$ alkyl)$_2$, and —$CH_2CO_2H$;
$R^4$ is selected from the group consisting of: H and $C_{1-4}$ alkyl;
$R^5$ is, independently at each occurrence, selected from the group consisting of: H, halogen, OH, and $C_{1-4}$ alkyl;
$R^6$ is, independently at each occurrence, selected from the group consisting of: halogen, $C_{1-4}$ alkyl, CN, OH, $CF_3$, $CO_2H$, $C^O_2(C_{1-4}$ alkyl), —$CH_2CO_2H$, —($CH_2$)$_2CO_2H$, —$CH_2CO_2(C_{1-4}$ alkyl), —($CH_2$)$_2CO_2(C_{1-4}$ alkyl), $NH_2$, —$CH_2NH_2$, —NHCO($C_{1-4}$ alkyl), —$NHCO_2$ ($C_{1-4}$ alkyl), —$NHCO_2(CH_2)_2O(C_{1-4}$ alkyl), —$NHCO_2$ ($CH_2$)$_3O(C_{1-4}$ alkyl), —$NHCO_2(CH_2)_2OH$, —$NHCO_2$ ($CH_2$)$_2NH_2$, —$CH_2NHCO_2(C_{1-4}$ alkyl), —NHC(O) NH($C_{1-4}$ alkyl), —NHC(O)N($C_{1-4}$ alkyl)$_2$, —$NHSO_2$ ($C_{1-4}$ alkyl), —$SO_2NH_2$, —$SO_2NH(C_{1-4}$ alkyl), —$SO_2NH(CH_2)_2OH$, —$SO_2NH(CH_2)_2O(C_{1-4}$ alkyl), —$CONH_2$, —$CONH(C_{1-4}$ alkyl), —$CON(C_{1-4}$ alkyl)$_2$, and —$CH_2CONH_2$;
$R^7$ is, independently at each occurrence, selected from the group consisting of: halogen, OH, $NH_2$, —$CH_2NH_2$, $CHF_2$, $CF_3$, —NH($C_{1-4}$ alkyl), —N(($C_{1-4}$ alkyl)$_2$, $C_{1-4}$ alkoxy, and $C_{1-4}$ alkyl; and
p is, independently at each occurrence, selected from the group consisting of: 0, 1, and 2.

In another aspect, the present invention provides compounds of Formula (I-1), or a stereoisomer, a tautomer, a pharmaceutically acceptable salt, a solvate, or a prodrug thereof, wherein:
ring A is a 6-membered carbocycle or 5,6,7,8-tetrahydroisoquinoline;
ring B is selected from the group consisting of: imidazole, oxadiazole, pyridine, pyridazine, pyrimidine, and benzene; and
ring C is selected from the group consisting of: benzene and pyridine.

In another aspect, the present invention provides compounds of Formula (Ia), or a stereoisomer, a tautomer, a pharmaceutically acceptable salt, a solvate, or a prodrug thereof, wherein:
ring A is selected from the group consisting of: benzene, cyclohexane, and 5,6,7,8-tetrahydroisoquinoline;

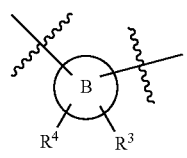

is selected from the group consisting of:

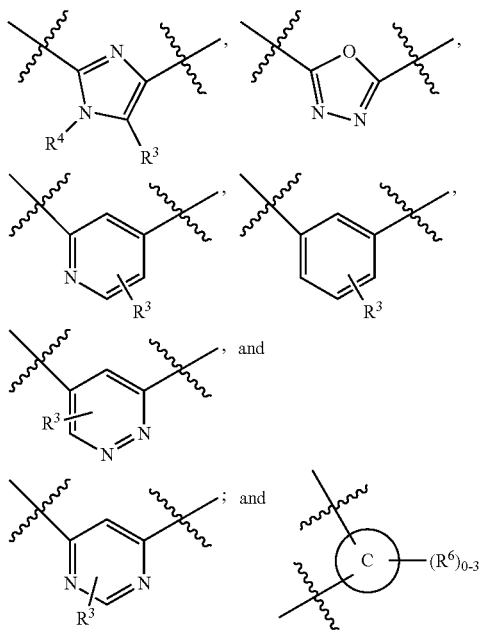

is selected from the group consisting of:

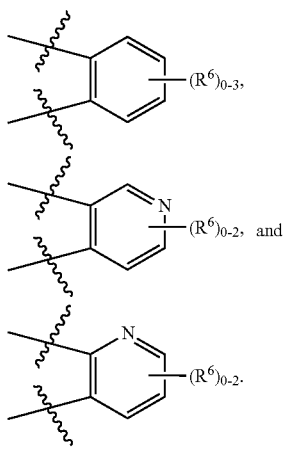

In another aspect, the present invention provides compounds of Formula (II-1):

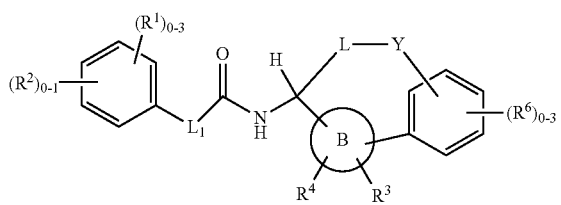

(II-1)

or a stereoisomer, a tautomer, a pharmaceutically acceptable salt, a solvate, or a prodrug thereof, wherein:

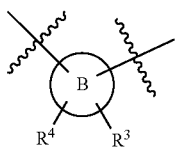

is selected from the group consisting of:

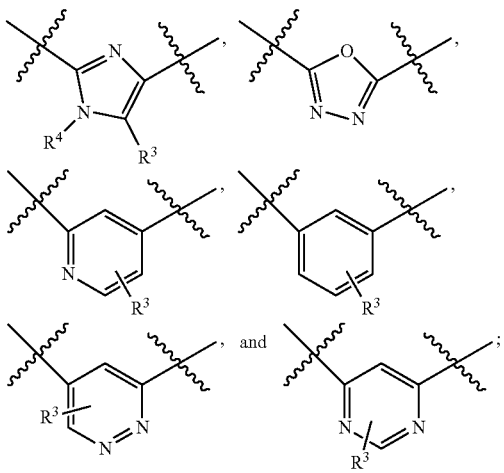

$L_1$ is selected from the group consisting of: a bond, —CHR$^5$CHR$^5$—, —CR$^5$=CHR$^5$—, —OCH$_2$—, —CHR$^5$NH—, —CH$_2$O—, —SCH$_2$—, —SO$_2$CH$_2$—, —CH$_2$NH—, and —CR$^5$R$^5$—;

L is selected from the group consisting of: $C_{3-8}$ alkylene and $C_{4-8}$ alkenylene; wherein said alkylene and alkenylene are optionally substituted with 1-2 R$^7$; optionally one or two of the carbon atoms of said alkylene and alkenylene may be replaced by O, S, NH, N($C_{1-4}$ alkyl), CONH—, or CON($C_{1-4}$ alkyl);

Y is selected from the group consisting of: CH$_2$, CH($C_{1-4}$ alkyl), C($C_{1-4}$ alkyl)$_2$, O, S, NH, N($C_{1-4}$ alkyl), —CONH—, —NHCO—, —CONHCH$_2$—, —CON($C_{1-4}$ alkyl)CH$_2$—, —OCONH—, —OCON($C_{1-4}$ alkyl)-, —NHCONH—, and —SO$_2$NH—;

R$^1$ is, independently at each occurrence, selected from the group consisting of: halogen, $C_{1-6}$ alkyl, $C_{1-4}$ alkoxy, $C_{1-4}$ alkylthio, OH, CHF$_2$, CF$_3$, OCF$_3$, CN, NH$_2$, CO$_2$($C_{1-4}$ alkyl), CO($C_{1-4}$ alkyl), —OCH$_2$CO$_2$H, —CH$_2$NH$_2$, —CONH$_2$, —CONH($C_{1-4}$ alkyl), —SO$_2$NH$_2$, and —C(=NH)NH$_2$;

R$^2$ is a 5- to 6-membered heterocycle comprising carbon atoms and 1-4 heteroatoms selected from N, O, and S(O)$_p$, wherein said heterocycle is substituted with 0-2 R$^{2a}$;

R$^{2a}$ is, independently at each occurrence, selected from the group consisting of: $C_{1-4}$ alkyl, —CH$_2$OH, $C_{1-4}$ alkoxy, OH, CF$_3$, CN, NH$_2$, CO$_2$H, CO$_2$($C_{1-4}$ alkyl), COC$_{1-4}$ alkyl, —CONH$_2$, —CONH($C_{1-4}$ alkyl), and —CON($C_{1-4}$ alkyl)$_2$;

R$^3$ is selected from the group consisting of: H, halogen, OH, NH$_2$, CF$_3$, $C_{1-4}$ alkyl, $C_{1-4}$ alkoxy, —CH$_2$OH, CO$_2$H, CO$_2$($C_{1-4}$ alkyl), —C(O)NH$_2$, —C(O)NH($C_{1-4}$ alkyl), —C(O)N($C_{1-4}$ alkyl)$_2$, and —CH$_2$CO$_2$H;

R$^4$ is selected from the group consisting of: H and $C_{1-4}$ alkyl;

$R^5$ is, independently at each occurrence, selected from the group consisting of: H, halogen, OH, and $C_{1-4}$ alkyl;

$R^6$ is, independently at each occurrence, selected from the group consisting of: halogen, $C_{1-4}$ alkyl, CN, OH, $CF_3$, $CO_2H$, $CO_2(C_{1-4}$ alkyl), —$CH_2CO_2H$, —$(CH_2)_2CO_2H$, —$CH_2CO_2(C_{1-4}$ alkyl), —$(CH_2)_2CO_2(C_{1-4}$ alkyl), $NH_2$, —$CH_2NH_2$, —$NHCO(C_{1-4}$ alkyl), —$NHCO_2(C_{1-4}$ alkyl), —$NHCO_2(CH_2)_2O(C_{1-4}$ alkyl), —$NHCO_2(CH_2)_3O(C_{1-4}$ alkyl), —$NHCO_2(CH_2)_2OH$, —$NHCO_2(CH_2)_2NH_2$, —$CH_2NHCO_2(C_{1-4}$ alkyl), —$NHC(O)NH(C_{1-4}$ alkyl), —$NHC(O)N(C_{1-4}$ alkyl)$_2$, —$NHSO_2(C_{1-4}$ alkyl), —$SO_2NH(CH_2)_2OH$, —$SO_2NH(CH_2)_2O(C_{1-4}$ alkyl), —$CONH_2$, —$C(O)NH(CH_2)_2O(C_{1-4}$ alkyl), and —$CH_2CONH_2$;

$R^7$ is, independently at each occurrence, selected from the group consisting of: halogen, OH, $CF_3$, $C_{1-4}$ alkoxy and $C_{1-4}$ alkyl; and p is, independently at each occurrence, selected from the group consisting of: 0, 1, and 2.

In another aspect, the present invention provides compounds of Formula (I), (II), (IIa), (IIc), or (IIe), or a stereoisomer, a tautomer, a pharmaceutically acceptable salt, a solvate, or a prodrug thereof, wherein:

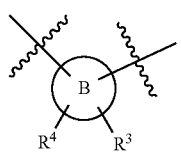

is selected from the group consisting of:

1p;1p 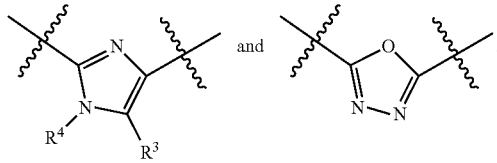

In another aspect, the present invention provides compounds of Formula (I-1), (II-1), (IIa), (IIc), or (IIe), or a stereoisomer, a tautomer, a pharmaceutically acceptable salt, a solvate, or a prodrug thereof, wherein:

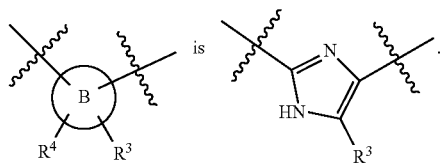

In another aspect, the present invention provides compounds of Formula (I-1), (II-1), (IIa), (IIc), or (IIe), or a stereoisomer, a tautomer, a pharmaceutically acceptable salt, a solvate, or a prodrug thereof, wherein:

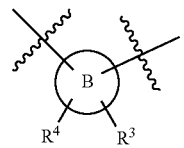

is selected from the group consisting of:

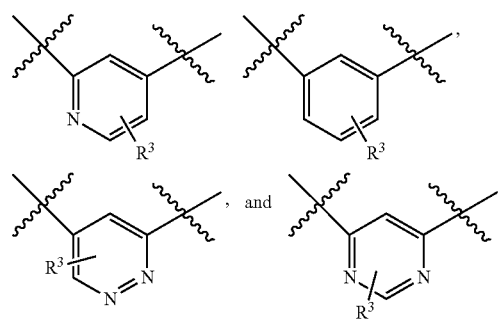

In another aspect, the present invention provides compounds of Formula (I-1), (II-1), (IIa), (IIc), or (IIe), or a stereoisomer, a tautomer, a pharmaceutically acceptable salt, a solvate, or a prodrug thereof, wherein:

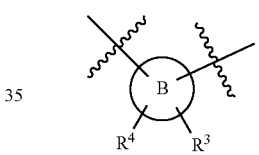

is selected from the group consisting of:

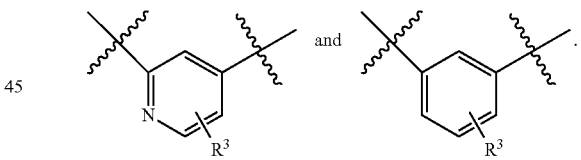

In another aspect, the present invention provides compounds of Formula (I-1), (II-1), (IIa), (IIc), or (IIe), or a stereoisomer, a tautomer, a pharmaceutically acceptable salt, a solvate, or a prodrug thereof, wherein:

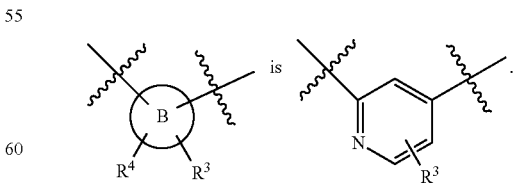

In another aspect, the present invention provides compounds of Formula (I-1), (II-1), (IIa), (IIc), or (IIe), or a stereoisomer, a tautomer, a pharmaceutically acceptable salt, a solvate, or a prodrug thereof, wherein:

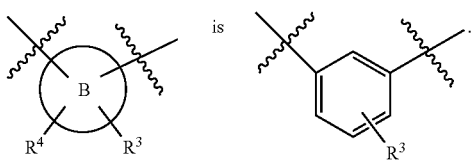 is

In another aspect, the present invention includes compounds of Formula (I-1), (II-1), (IIa), or (IIb), a stereoisomer, a tautomer, a pharmaceutically acceptable salt, a solvate, or a prodrug thereof, wherein:
$R^2$ is a 5-membered heterocycle substituted with 0-1 $R^{2a}$, wherein said heterocycle is selected from: pyrazolyl, imidazolyl, triazolyl, and tetrazolyl; and
$R^{2a}$ is, independently at each occurrence, selected from the group consisting of: OH, $NH_2$, $CH_2OH$, $CO_2H$, $C_{1-4}$ alkyl, —$CONH_2$, —$CONH(C_{1-4}$ alkyl), and —$CON(C_{1-4}$ alkyl$)_2$ In another aspect, the present invention includes compounds of Formula (I-1), (II-1), (IIa), or (IIb), a stereoisomer, a tautomer, a pharmaceutically acceptable salt, a solvate, or a prodrug thereof, wherein:
$R^2$ is selected from the group consisting of: triazolyl and tetrazolyl.

In another aspect, the present invention includes compounds of Formula (I-1), (II-1), (IIa), (IIb), (IIc), (IId), (IIe) or (IIf) a stereoisomer, a tautomer, a pharmaceutically acceptable salt, a solvate, or a prodrug thereof, wherein:
$L_1$ is selected from the group consisting of: a bond, —$CH_2CH_2$—, —CH=CH—, —C(Me)=CH—, and —$CH_2NH$—;
L is selected from the group consisting of: $C_{3-7}$ alkylene and $C_{4-7}$ alkenylene; wherein said alkylene and alkenylene are optionally substituted with 1-2 $R^7$; optionally one or two of the carbon atoms of said alkylene and alkenylene may be replaced by O, NH, N($C_{1-4}$ alkyl), CONH, or CON($C_{1-4}$ alkyl);
Y is selected from the group consisting of: $CH_2$, $CH(C_{1-4}$ alkyl), $C(C_{1-4}$ alkyl$)_2$, O, S, NH, N($C_{1-4}$ alkyl), —CONH—, —NHCO—, —$CONHCH_2$—, —CON($C_{1-4}$ alkyl)$CH_2$—, —OCONH—, —NHCONH—, and —$SO_2NH$—;
$R^1$ is, independently at each occurrence, selected from: halogen, CN, OH, $OCF_3$, $CHF_2$, $CF_3$, $C_{1-4}$ alkyl, $C_{1-4}$ alkoxy, $CO(C_{1-4}$ alkyl), $NH_2$, —C(=NH)$NH_2$, —C(O)$NH_2$, —$CH_2NH_2$, and —$SO_2NH_2$;
$R^3$ is selected from the group consisting of: H, halogen, OH, $NH_2$, $CF_3$, $C_{1-4}$ alkyl, $C_{1-4}$ alkoxy, —$CH_2OH$, $CO_2H$, $CO_2(C_{1-4}$ alkyl), —C(O)$NH_2$, —C(O)NH($C_{1-4}$ alkyl), —C(O)N($C_{1-4}$ alkyl$)_2$, and —$CH_2CO_2H$; and
$R^6$ is, independently at each occurrence, selected from the group consisting of: halogen, $C_{1-4}$ alkyl, CN, OH, $CF_3$, $CO_2H$, $CO_2(C_{1-4}$ alkyl), —$CH_2CO_2H$, —$(CH_2)_2CO_2H$, —$CH_2CO_2(C_{1-4}$ alkyl), —$(CH_2)_2CO_2(C_{1-4}$ alkyl), $NH_2$, —$CH_2NH_2$, —NHCO($C_{1-4}$ alkyl), —$NHCO_2(C_{1-4}$ alkyl), —$NHCO_2(CH_2)_2O(C_{1-4}$ alkyl), —$NHCO_2(CH_2)_3O(C_{1-4}$ alkyl), —$NHCO_2(CH_2)_2OH$, —$NHCO_2(CH_2)_2NH_2$, —$CH_2NHCO_2(C_{1-4}$ alkyl), —NHC(O)NH($C_{1-4}$ alkyl), —NHC(O)N($C_{1-4}$ alkyl$)_2$, —$NHSO_2(C_{1-4}$ alkyl), —$SO_2NH(CH_2)_2OH$, —$SO_2NH(CH_2)_2O(C_{1-4}$ alkyl), and —$CONH_2$.

In another aspect, the present invention includes compounds of Formula (I-1), (II-1), (IIa), (IIb), (IIc), (IId), (IIe) or (IIf) or a stereoisomer, a tautomer, a pharmaceutically acceptable salt, a solvate, or a prodrug thereof, wherein:
$L_1$ is selected from the group consisting of: a bond, —$CH_2CH_2$— and —CH=CH—;
$R^1$ is, independently at each occurrence, selected from the group consisting of: halogen, CN, $C_{1-4}$ alkyl, $CHF_2$, $CF_3$, $CO(C_{1-4}$ alkyl), $NH_2$, —$CH_2NH_2$, and —C(=NH)$NH_2$;
$R^3$ is selected from the group consisting of: H, halogen, $CF_3$, $CO_2H$, $CO_2(C_{1-4}$ alkyl), and $C_{1-4}$ alkyl; and
$R^6$ is, independently at each occurrence, selected from the group consisting of: halogen, $C_{1-4}$ alkyl, CN, OH, $CF_3$, $CO_2H$, $CO_2(C_{1-4}$ alkyl), —$CH_2CO_2H$, —$CH_2CO_2(C_{1-4}$ alkyl), $NH_2$, —$CH_2NH_2$, —NHCO($C_{1-4}$ alkyl), —$NHCO_2(C_{1-4}$ alkyl), —$CH_2NHCO_2(C_{1-4}$ alkyl), and —$CONH_2$.

In another aspect, the present invention includes compounds of Formula (I-1), (II-1), (IIa), (IIb), (IIc), (IId), (IIe) or (IIf) or a stereoisomer, a tautomer, a pharmaceutically acceptable salt, a solvate, or a prodrug thereof, wherein:
$L_1$ is selected from the group consisting of: a bond, —$CH_2CH_2$— and —CH=CH—;
L is selected from the group consisting of: —$CH_2$—CH=CH—$CH_2$—, —$CH_2$—CH=CH—$(CH_2)_2$—, —$CH_2$—CH=CH—$(CH_2)_3$—, —$CH_2$—CH=C($C_{1-4}$ alkyl)-$(CH_2)_2$—, —$CH_2$—CH=CH—CH($C_{1-4}$ alkyl)-$CH_2$—, —$CH_2$—C($C_{1-4}$ alkyl)=CH—$(CH_2)_2$—, —$(CH_2)_3$CH($C_{1-4}$ alkyl)$CH_2$—, —$(CH_2)_2$CH($C_{1-4}$ alkyl)$(CH_2)_2$—, —$(CH_2)_3$CH($C_{1-4}$ alkyl)$(CH_2)_2$—, —$(CH_2)_3$CH($C_{1-4}$ alkyl)-, —$(CH_2)_3$—, —$(CH_2)_4$—, —$(CH_2)_5$—, —$(CH_2)_6$—, —$CH_2O(CH_2)_3$—, —$CH_2O(CH_2)_4$—, —$(CH_2)_4CF_2$—, —$(CH_2)_4CH(CF_3)$—, —$CH_2$—CH=CH—$CH_2CF_2$—, —$CH_2NHCOCF_2CH_2$—, —$CH_2NH(CH_2)_2$—, —$CH_2NH(CH_2)_3$—, —$CH_2NH(CH_2)_4$—, —$(CH_2)_2NHCH_2$—, —$(CH_2)_2N(C_{1-4}$ alkyl)$CH_2$—, —$(CH_2)_2N(C_{1-4}$ alkyl)$(CH_2)_2$—, —$CH_2$—CONH—$(CH_2)_2$—, —$CH_2$—CONH—$(CH_2)_3$—, —$CH_2$—CONH—$(CH_2)_4$—, —$CH_2$—CON($C_{1-4}$ alkyl)-$(CH_2)_2$—, —$CH_2$—CON($C_{1-4}$ alkyl)-$(CH_2)_3$—, —$CH_2CH(OH)(CH_2)_2$—, —$(CH_2)_2CH(OH)CH_2$—, and —$CH_2CH(OH)CH(OH)CH_2$—;
Y is selected from the group consisting of: —$CH_2$—, O, NH, N($C_{1-4}$ alkyl), —NHCO—, —CONH—, —$CONHCH_2$—, —CON($C_{1-4}$ alkyl)$CH_2$—, —OCONH—, —NHCONH—, and —$SO_2NH$—;
$R^3$ is selected from the group consisting of: H, $C_{1-4}$ alkyl, and halogen; and
$R^6$ is, independently at each occurrence, selected from the group consisting of: halogen, $CO_2H$, $CO_2(C_{1-4}$ alkyl), $NH_2$, $NHCO_2(C_{1-4}$ alkyl), and —$CH_2NHCO_2(C_{1-4}$ alkyl).

In another aspect, the present invention includes compounds of Formula (I-1), (II-1), (IIa), (IIb), (IIc), (IId), (IIe) or (IIf) or a stereoisomer, a tautomer, a pharmaceutically acceptable salt, a solvate, or a prodrug thereof, wherein:
L is selected from the group consisting of: —$CH_2$—CH=CH—$CH_2$—, —$CH_2$—CH=CH—$(CH_2)_2$—, —$CH_2$—CH=CH—$(CH_2)_3$—, —$CH_2$—CH=C($C_{1-4}$ alkyl)-$(CH_2)_2$—, —$CH_2$—CH=CH—CH($C_{1-4}$ alkyl)-$CH_2$—, —$CH_2$—C($C_{1-4}$ alkyl)=CH—$(CH_2)_2$—, —$(CH_2)_3$CH($C_{1-4}$ alkyl)$CH_2$—, —$(CH_2)_3$CH($C_{1-4}$ alkyl)$(CH_2)_2$—, —$(CH_2)_3$CH($C_{1-4}$ alkyl)-, —$(CH_2)_3$—, —$(CH_2)_4$—, —$(CH_2)_5$—, —$(CH_2)_6$—, —$CH_2O(CH_2)_3$—, —$CH_2O(CH_2)_4$—, —$(CH_2)_4CF_2$—, —$(CH_2)_4CH(CF_3)$—, —$CH_2$—CH=CH—$CH_2CF_2$—, —$CH_2NHCOCF_2CH_2$—, —$CH_2NH(CH_2)_2$—, —$CH_2NH(CH_2)_3$—, —$CH_2NH(CH_2)_4$—, —$(CH_2)_2NHCH_2$—, —$(CH_2)_2N(C_{1-4}$ alkyl)$CH_2$—, —$(CH_2)_2N(C_{1-4}$ alkyl)$(CH_2)_2$—, —$CH_2$—CONH—$(CH_2)_2$—, —CH$_2$—CONH—(CH$_2$)$_3$—, —CH$_2$—CONH—(CH$_2$)$_4$—, —CH$_2$—CON(C$_{1-4}$ alkyl)-(CH$_2$)$_2$—, —CH$_2$—CON(C$_{1-4}$ alkyl)-(CH$_2$)$_3$—, —CH$_2$CH(OH)(CH$_2$)$_2$—, —(CH$_2$)$_2$CH(OH)CH$_2$—, and —CH$_2$CH(OH)CH(OH)CH$_2$—;

Y is selected from the group consisting of: CH$_2$, O, NH, N(C$_{1-4}$ alkyl), —NHCO—, —CONH—, —CONHCH$_2$—, —CON(C$_{1-4}$ alkyl)CH$_2$—, —OCONH—, —NHCONH—, and —SO$_2$NH—;

R$^1$ is selected from the group consisting of: halogen, C$_{1-4}$ alkyl, CHF$_2$, CN, and CO(C$_{1-4}$ alkyl);

R$^3$ is selected from the group consisting of: H, C$_{1-4}$ alkyl, and halogen; and R$^6$ is, independently at each occurrence, is selected from the group consisting of: halogen, NH$_2$, NHCO$_2$(C$_{1-4}$ alkyl), and —CH$_2$NHCO$_2$(C$_{1-4}$ alkyl).

In another aspect, the present invention includes compounds of Formula (I-1), (II-1), (IIa), (IIb), (IIc), (IId), (IIe) or (IIf) or a stereoisomer, a tautomer, a pharmaceutically acceptable salt, a solvate, or a prodrug thereof, wherein:

L is selected from the group consisting of: —CH$_2$—CH=CH—CH$_2$—, —CH$_2$—CH=CH—(CH$_2$)$_2$—, —CH$_2$—CH=CH—(CH$_2$)$_3$—, —CH$_2$—CH=C(CH$_3$)—(CH$_2$)$_2$—, —CH$_2$—CH=CH—CH(CH$_3$)CH$_2$—, —(CH$_2$)$_3$CH(CH$_3$)CH$_2$—, —(CH$_2$)$_2$CH(CH$_3$)(CH$_2$)$_2$—, —(CH$_2$)$_3$CH(CH$_3$)—, —(CH$_2$)$_3$—, —(CH$_2$)$_4$—, —(CH$_2$)$_5$—, —(CH$_2$)$_6$—, —CH$_2$O(CH$_2$)$_3$—, —CH$_2$O(CH$_2$)$_4$—, —(CH$_2$)$_4$CF$_2$—, —(CH$_2$)$_4$CH(CF$_3$)—, —CH$_2$—CH=CH—CH$_2$CF$_2$—, —CH$_2$NHCOCF$_2$CH$_2$—, —CH$_2$NH(CH$_2$)$_2$—, —CH$_2$NH(CH$_2$)$_3$—, —CH$_2$NH(CH$_2$)$_4$—, —(CH$_2$)$_2$NHCH$_2$—, —(CH$_2$)$_2$N(CH$_3$)CH$_2$—, —(CH$_2$)$_2$N(CH$_3$)(CH$_2$)$_2$—, —CH$_2$—CONH—(CH$_2$)$_2$—, —CH$_2$—CONH—(CH$_2$)$_3$—, —CH$_2$—CONH—(CH$_2$)$_4$—, —CH$_2$—CON(CH$_3$)—(CH$_2$)$_2$—, —CH$_2$—CON(CH$_3$)—(CH$_2$)$_3$—, —CH$_2$CH(OH)(CH$_2$)$_2$—, —(CH$_2$)$_2$CH(OH)CH$_2$—, and —CH$_2$CH(OH)CH(OH)CH$_2$—;

Y is selected from the group consisting of: CH$_2$, O, NH, —NMe, —CONH—, —NHCO—, —CONHCH$_2$—, —CONMeCH$_2$—, —OCONH—, —NHCONH—, and —SO$_2$NH—;

R$^1$ is selected from the group consisting of: H, F, Cl, Me, COMe, and CHF$_2$;

R$^3$ is selected from the group consisting of: H, Me, and Cl; and

R$^6$ is, independently at each occurrence, selected from the group consisting of: F, NH$_2$, NHCO$_2$Me, and —CH$_2$NHCO$_2$Me.

In another aspect, the present invention includes compounds of Formula (I-1), (II-1), (IIa), (IIb), (IIc), (IId), (IIe) or (IIf) or a stereoisomer, a tautomer, a pharmaceutically acceptable salt, a solvate, or a prodrug thereof, within the scope of any one of the above aspects, wherein:

L is selected from the group consisting of: —CH$_2$—CH=CH—CH$_2$—, —CH$_2$—CH=CH—(CH$_2$)$_2$—, —CH$_2$—CH=CH—(CH$_2$)$_3$—, —CH$_2$—CH=C(CH$_3$)—(CH$_2$)$_2$—, —CH$_2$—CH=CH—CH(CH$_3$)CH$_2$—, —(CH$_2$)$_3$CH(CH$_3$)CH$_2$—, —(CH$_2$)$_2$CH(CH$_3$)(CH$_2$)$_2$—, —(CH$_2$)$_4$—, —(CH$_2$)$_5$—, —(CH$_2$)$_6$—, —CH$_2$O(CH$_2$)$_3$—, —CH$_2$O(CH$_2$)$_4$—, —(CH$_2$)$_4$CF$_2$—, —CH$_2$—CH=CH—CH$_2$CF$_2$—, —CH$_2$NH(CH$_2$)$_2$—, —CH$_2$NH(CH$_2$)$_3$—, —(CH$_2$)$_2$N(CH$_3$)CH$_2$—, —(CH$_2$)$_2$N(CH$_3$)(CH$_2$)$_2$—, —CH$_2$—CONH—(CH$_2$)$_3$—, —CH$_2$—CONH—(CH$_2$)$_4$—, —CH$_2$—CON(CH$_3$)—(CH$_2$)$_2$—, and —CH$_2$CH(OH)CH(OH)CH$_2$—;

Y is selected from the group consisting of: CH$_2$, O, NH, —CONH—, —NHCO—, —CONHCH$_2$—, —CONMeCH$_2$—, —OCONH—, —NHCONH—, and —SO$_2$NH—; and R$^3$ is selected from the group consisting of: H and Cl.

In another aspect, the present invention includes compounds of Formula (IIe) or (IIf) or a stereoisomer, a tautomer, a pharmaceutically acceptable salt, a solvate, or a prodrug thereof, wherein:

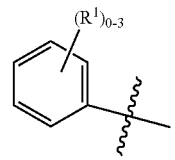

is selected from the group consisting of:

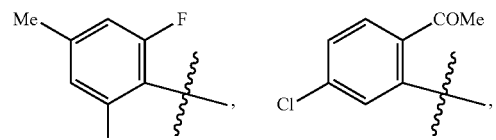

and

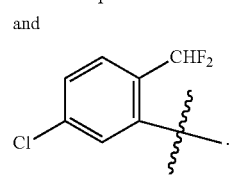

In another aspect, the present invention includes compounds of Formula (I-1), (II-1), (IIa), (IIb), (IIc), (IId), (IIe) or (IIf) or a stereoisomer, a tautomer, a pharmaceutically acceptable salt, a solvate, or a prodrug thereof, wherein:

L is selected from the group consisting of: —CH$_2$—CH=CH—CH$_2$—, —CH$_2$—CH=CH—(CH$_2$)$_2$—, —CH$_2$—CH=CH—(CH$_2$)$_3$—, —CH$_2$—CH=C(CH$_3$)—(CH$_2$)$_2$—, —CH$_2$—CH=CH—CH(CH$_3$)CH$_2$—, —(CH$_2$)$_3$CH(CH$_3$)CH$_2$—, —(CH$_2$)$_2$CH(CH$_3$)(CH$_2$)$_2$—, —(CH$_2$)$_3$CH(CH$_3$)—, —(CH$_2$)$_3$—, —(CH$_2$)$_4$—, —(CH$_2$)$_5$—, —(CH$_2$)$_6$—, —CH$_2$O(CH$_2$)$_3$—, —CH$_2$O(CH$_2$)$_4$—, —(CH$_2$)$_4$CF$_2$—, —(CH$_2$)$_4$CH(CF$_3$)—, —CH$_2$—CH=CH—CH$_2$CF$_2$—, —CH$_2$NHCOCF$_2$CH$_2$—, —CH$_2$NH(CH$_2$)$_2$—, —CH$_2$NH(CH$_2$)$_3$—, —CH$_2$NH(CH$_2$)$_4$—, —(CH$_2$)$_2$NHCH$_2$—, —(CH$_2$)$_2$N(CH$_3$)CH$_2$—, —(CH$_2$)$_2$N(CH$_3$)(CH$_2$)$_2$—, —CH$_2$—CONH—(CH$_2$)$_2$—, —CH$_2$—CONH—(CH$_2$)$_3$—, —CH$_2$—CONH—(CH$_2$)$_4$—, —CH$_2$—CON(CH$_3$)—(CH$_2$)$_2$—, —CH$_2$—CON(CH$_3$)—(CH$_2$)$_3$—, —CH$_2$CH(OH)(CH$_2$)$_2$—, —(CH$_2$)$_2$CH(OH)CH$_2$—, and —CH$_2$CH(OH)CH(OH)CH$_2$—;

Y is selected from the group consisting of: CH$_2$, O, NH, NMe, —CONH—, —NHCO—, —CONHCH$_2$—, —CONMeCH$_2$—, —OCONH—, —NHCONH—, and —SO$_2$NH—;

R¹ is selected from the group consisting of: H, F, Cl, Me, COMe, and CHF₂;

R³ is selected from the group consisting of: H, Me, and Cl; and

R⁶ is, independently at each occurrence, selected from the group consisting of: F, NH₂, NHCO₂Me, and —CH₂NHCO₂Me.

In another aspect, the present invention includes compounds of Formula (I-1), (II-1), (IIa), (IIb), (IIc), (IId), (IIe) or (IIf) or a stereoisomer, a tautomer, a pharmaceutically acceptable salt, a solvate, or a prodrug thereof, wherein:

L is selected from the group consisting of: —CH₂—CH=CH—CH₂—, —CH₂—CH=CH—(CH₂)₂—, —CH₂—CH=CH—(CH₂)₃—, —CH₂—CH=C(CH₃)—(CH₂)₂—, —CH₂—CH=CH—CH(CH₃)CH₂—, —(CH₂)₃CH(CH₃)CH₂—, —(CH₂)₂CH(CH₃)(CH₂)₂—, —(CH₂)₄—, —(CH₂)₅—, —(CH₂)₆—, —CH₂O(CH₂)₃—, —CH₂O(CH₂)₄—, —(CH₂)₄CF₂—, —CH₂—CH=CH—CH₂CF₂—, —CH₂NH(CH₂)₂—, —CH₂NH(CH₂)₃—, —(CH₂)₂N(CH₃)CH₂—, —(CH₂)₂N(CH₃)(CH₂)₂—, —CH₂—CONH—(CH₂)₃—, —CH₂—CONH—(CH₂)₄—, —CH₂—CON(CH₃)—(CH₂)₂—, and —CH₂CH(OH)CH(OH)CH₂—;

Y is selected from the group consisting of: CH₂, O, NH, —CONH—, —NHCO—, —CONHCH₂—, —CONMeCH₂—, —OCONH—, —NHCONH—, and —SO₂NH—; and R³ is selected from the group consisting of: H and Cl.

In another aspect, the present invention includes compounds of Formula (IIe) or (IIf) or a stereoisomer, a tautomer, a pharmaceutically acceptable salt, a solvate, or a prodrug thereof, wherein:

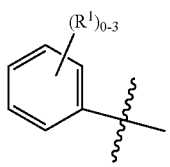

is selected from the group consisting of:

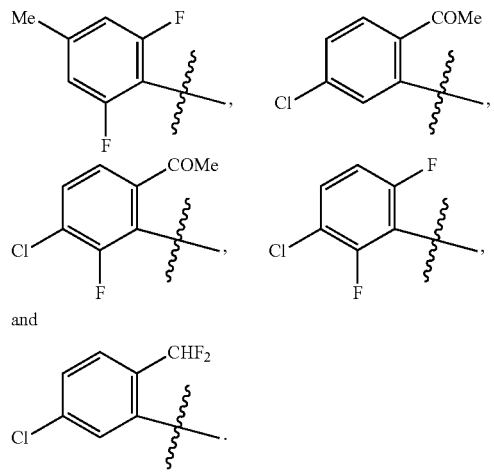

In another aspect, the present invention includes compounds of Formula (III):

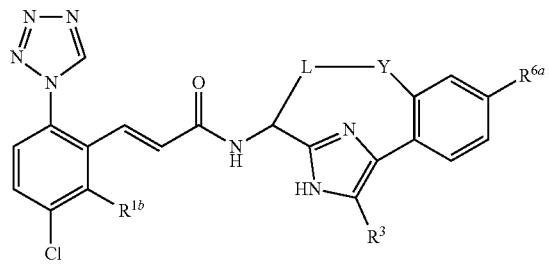

or a stereoisomer, a tautomer, a pharmaceutically acceptable salt, a solvate, or a prodrug thereof, wherein:

L is selected from the group consisting of: —CH₂—CH=CH—CH₂—, —CH₂—CH=CH—(CH₂)₂—, —CH₂—CH=CH—(CH₂)₃—, —CH₂—CH=C(CH₃)—(CH₂)₂—, —CH₂—CH=CH—CH(CH₃)CH₂—, —(CH₂)₃CH(CH₃)CH₂—, —(CH₂)₂CH(CH₃)(CH₂)₂—, —(CH₂)₃CH(CH₃)—, —(CH₂)₃—, —(CH₂)₄—, —(CH₂)₅—, —(CH₂)₆—, —CH₂O(CH₂)₃—, —CH₂O(CH₂)₄—, —(CH₂)₄CF₂—, —(CH₂)₄CH(CF₃)—, —CH₂—CH=CH—CH₂CF₂—, —CH₂NHCOCF₂CH₂—, —CH₂NH(CH₂)₂—, —CH₂NH(CH₂)₃—, —CH₂NH(CH₂)₄—, —(CH₂)₂NHCH₂—, —(CH₂)₂N(CH₃)CH₂—, —(CH₂)₂N(CH₃)(CH₂)₂—, —CH₂—CONH—(CH₂)₂—, —CH₂—CONH—(CH₂)₃—, —CH₂—CONH—(CH₂)₄—, —CH₂—CON(CH₃)—(CH₂)₂—, —CH₂—CON(CH₃)—(CH₂)₃—, —CH₂CH(OH)(CH₂)₂—, —(CH₂)₂CH(OH)CH₂—, and —CH₂CH(OH)CH(OH)CH₂—;

Y is selected from the group consisting of: CH₂, O, NH, NMe, —CONH—, —NHCO—, —CONHCH₂—, —CONMeCH₂—, —OCONH—, —NHCONH—, and —SO₂NH—;

R¹ᵇ is selected from the group consisting of: H and F;

R³ is selected from the group consisting of: H, Me, and Cl; and

R⁶ᵃ is selected from the group consisting of: H, F, NH₂, and NHCO₂Me.

In another aspect, the present invention includes compounds of Formula (III), or a stereoisomer, a tautomer, a pharmaceutically acceptable salt, a solvate, or a prodrug thereof, wherein:

L is selected from the group consisting of: —CH₂—CH=CH—CH₂—, —CH₂—CH=CH—(CH₂)₂—, —CH₂—CH=CH—(CH₂)₃—, —CH₂—CH=C(CH₃)—(CH₂)₂—, —CH₂—CH=CH—CH(CH₃)CH₂—, —(CH₂)₃CH(CH₃)CH₂—, —(CH₂)₂CH(CH₃)(CH₂)₂—, —(CH₂)₄—, —(CH₂)₅—, —(CH₂)₆—, —CH₂O(CH₂)₃—, —CH₂O(CH₂)₄—, —(CH₂)₄CF₂—, —CH₂—CH=CH—CH₂CF₂—, —CH₂NH(CH₂)₂—, —CH₂NH(CH₂)₃—, —(CH₂)₂N(CH₃)CH₂—, —(CH₂)₂N(CH₃)(CH₂)₂—, —CH₂—CONH—(CH₂)₃—, —CH₂—CONH—(CH₂)₄—, —CH₂—CON(CH₃)—(CH₂)₂—, and —CH₂CH(OH)CH(OH)CH₂—;

Y is selected from the group consisting of: CH₂, O, NH, —CONH—, —NHCO—, —CONHCH₂—, —CONMeCH₂—, —OCONH—, —NHCONH—, and —SO₂NH—;

R¹ᵇ is selected from the group consisting of: H and F;

R³ is selected from the group consisting of: H and Cl; and

R⁶ᵃ is selected from the group consisting of: H, F, NH₂, and NHCO₂Me.

In another aspect, the present invention includes compounds of Formula (III), or a stereoisomer, a tautomer, a pharmaceutically acceptable salt, a solvate, or a prodrug thereof, wherein:

L is selected from the group consisting of: —CH₂—CH=CH—CH₂—, —CH₂—CH=CH—(CH₂)₂—, —CH₂—CH=CH—(CH₂)₃—, —CH₂—CH=C(CH₃)—(CH₂)₂—, —CH₂—CH=CH—CH(CH₃)CH₂—, —(CH₂)₃CH(CH₃)—, —(CH₂)₃CH(CH₃)CH₂—, —(CH₂)₂CH(CH₃)(CH₂)₂—, —(CH₂)₄—, —(CH₂)₅—, —(CH₂)₆—, —CH₂O(CH₂)₃—, —CH₂O(CH₂)₄—, —(CH₂)₄CF₂—, —(CH₂)₄CH(CF₃)—, —CH₂—CH=CH—CH₂CF₂—, —CH₂NH(CH₂)₂—, —CH₂NH(CH₂)₃—, —CH₂NH(CH₂)₄—, —(CH₂)₂N(CH₃)CH₂—, —(CH₂)₂N(CH₃)(CH₂)₂—, —CH₂CH(OH)(CH₂)₂—, —(CH₂)₂CH(OH)CH₂—, and —CH₂CH(OH)CH(OH)CH₂—;

Y is selected from the group consisting of: CH₂, O, NH, —CONH—, —NHCO—, —OCONH—, —NHCONH—, —CONHCH₂—, and —SO₂NH—; and R³ is selected from the group consisting of: H and Cl.

In another aspect, the present invention includes compounds of Formula (IV):

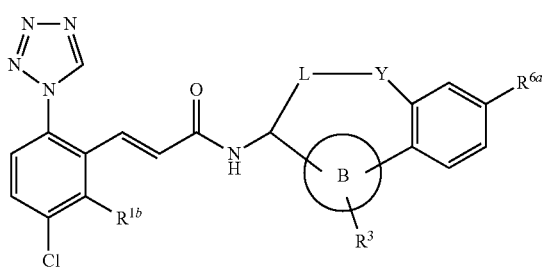

(IV)

or a stereoisomer, a tautomer, a pharmaceutically acceptable salt, a solvate, or a prodrug thereof, within the scope of any one of the above aspects, wherein:

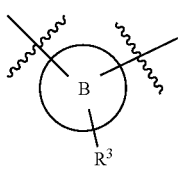

is selected from the group consisting of:

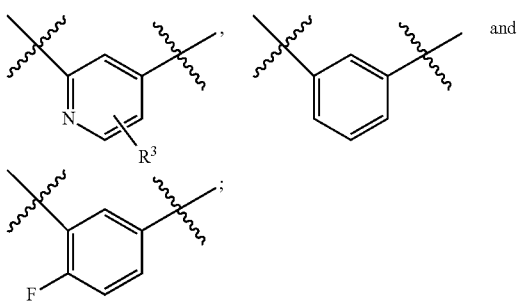

L is selected from the group consisting of: —CH₂—CH=CH—CH₂—, —CH₂—CH=CH—(CH₂)₂—, —(CH₂)₄—, and —(CH₂)₅—;

Y is —CONH—;

R³ is selected from the group consisting of: H and Cl; and

R⁶ᵃ is selected from the group consisting of: H, F, —NHCO₂Me, and —CH₂NHCO₂Me.

In another aspect, the present invention includes compounds of Formula (V): or a stereoisomer, a tautomer, a pharmaceutically acceptable salt, a solvate, or a prodrug thereof, wherein:

ring B is selected from the group consisting of:

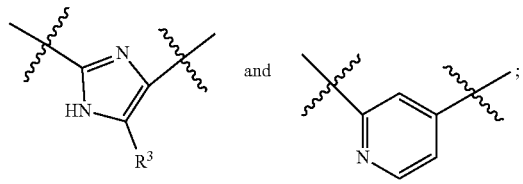

L is selected from the group consisting of: —CH₂—CH=CH—(CH₂)₂—, —CH₂—CH=CH—CH₂CF₂—, and —(CH₂)₄—;

Y is selected from the group consisting of: CH₂ and —CONH—;

R³ is selected from the group consisting of: H and Cl; and

R⁶ᵃ is selected from the group consisting of: H and —NHCO₂Me.

In another embodiment, the compounds of the present invention have Factor XIa Ki values≤10 μM.

In another embodiment, the compounds of the present invention have Factor XIa Ki values≤1 μM.

In another embodiment, the compounds of the present invention have Factor XIa Ki values≤0.5 μM.

In another embodiment, the compounds of the present invention have Factor XIa Ki values≤0.1 μM.

II. Other Embodiments of the Invention

In another embodiment, the present invention provides a composition comprising at least one of the compounds of the present invention or a stereoisomer, a tautomer, a pharmaceutically acceptable salt, or a solvate thereof.

In another embodiment, the present invention provides a pharmaceutical composition comprising a pharmaceutically acceptable carrier and at least one of the compounds of the present invention or a stereoisomer, a tautomer, a pharmaceutically acceptable salt, or a solvate, thereof.

In another embodiment, the present invention provides a pharmaceutical composition, comprising: a pharmaceutically acceptable carrier and a therapeutically effective amount of at least one of the compounds of the present invention or a stereoisomer, a tautomer, a pharmaceutically acceptable salt, or a solvate thereof.

In another embodiment, the present invention provides a process for making a compound of the present invention.

In another embodiment, the present invention provides an intermediate for making a compound of the present invention.

In another embodiment, the present invention provides a pharmaceutical composition further comprising additional therapeutic agent(s). In a preferred embodiment, the present invention provides pharmaceutical composition, wherein the additional therapeutic agent(s) are an anti-platelet agent or a combination thereof. Preferably, the anti-platelet agent(s) are clopidogrel and/or aspirin, or a combination thereof.

In another embodiment, the present invention provides a method for the treatment and/or prophylaxis of a thromboembolic disorder comprising administering to a patient in need of such treatment and/or prophylaxis a therapeutically effective amount of at least one of the compounds of the present invention or a stereoisomer, a tautomer, a pharmaceutically acceptable salt, or a solvate thereof.

In another embodiment, the present invention provides a compound of the present invention or a stereoisomer, a tautomer, a pharmaceutically acceptable salt, or a solvate thereof, for use in therapy.

In another embodiment, the present invention provides a compound of the present invention or a stereoisomer, a tautomer, a pharmaceutically acceptable salt, or a solvate thereof, for use in therapy for the treatment and/or prophylaxis of a thromboembolic disorder.

In another embodiment, the present invention also provides the use of a compound of the present invention or a stereoisomer, a tautomer, a pharmaceutically acceptable salt, or a solvate thereof, for the manufacture of a medicament for the treatment and/or prophylaxis of a thromboembolic disorder.

In another embodiment, the present invention provides a method for treatment and/or prophylaxis of a thromboembolic disorder, comprising: administering to a patient in need thereof a therapeutically effective amount of a first and second therapeutic agent, wherein the first therapeutic agent is a compound of the present invention or a stereoisomer, a tautomer, a pharmaceutically acceptable salt, or a solvate thereof, and the second therapeutic agent is at least one agent selected from a second Factor Xa inhibitor, an anti-coagulant agent, an anti-platelet agent, a thrombin inhibiting agent, a thrombolytic agent, and a fibrinolytic agent. Preferably, the second therapeutic agent is at least one agent selected from warfarin, unfractionated heparin, low molecular weight heparin, synthetic pentasaccharide, hirudin, argatroban, aspirin, ibuprofen, naproxen, sulindac, indomethacin, mefenamate, droxicam, diclofenac, sulfinpyrazone, piroxicam, ticlopidine, clopidogrel, tirofiban, eptifibatide, abciximab, melagatran, desulfatohirudin, tissue plasminogen activator, modified tissue plasminogen activator, anistreplase, urokinase, and streptokinase. Preferably, the second therapeutic agent is at least one anti-platelet agent. Preferably, the anti-platelet agent(s) are clopidogrel and/or aspirin, or a combination thereof.

The thromboembolic disorder includes arterial cardiovascular thromboembolic disorders, venous cardiovascular thromboembolic disorders, arterial cerebrovascular thromboembolic disorders, and venous cerebrovascular thromboembolic disorders. Examples of the thromboembolic disorder include, but are not limited to, unstable angina, an acute coronary syndrome, atrial fibrillation, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis.

In another embodiment, the present invention provides a method for the treatment and/or prophylaxis of an inflammatory disorder comprising: administering to a patient in need of such treatment and/or prophylaxis a therapeutically effective amount of at least one of the compounds of the present invention or a stereoisomer, a tautomer, a pharmaceutically acceptable salt, or a solvate thereof. Examples of the inflammatory disorder include, but are not limited to, sepsis, acute respiratory distress syndrome, and systemic inflammatory response syndrome.

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in treatment and/or prophylaxis of a thromboembolic disorder.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also to be understood that each individual element of the embodiments is its own independent embodiment. Furthermore, any element of an embodiment is meant to be combined with any and all other elements from any embodiment to describe an additional embodiment.

III. Chemistry

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

The term "stereoisomer" refers to isomers of identical constitution that differ in the arrangement of their atoms in space. Enantiomers and diastereomers are examples of stereoisomers. The term "enantiomer" refers to one of a pair of molecular species that are mirror images of each other and are not superimposable. The term "diastereomer" refers to stereoisomers that are not mirror images. The term "racemate" or "racemic mixture" refers to a composition composed of equimolar quantities of two enantiomeric species, wherein the composition is devoid of optical activity.

The symbols "R" and "S" represent the configuration of substituents around a chiral carbon atom(s). The isomeric descriptors "R" and "S" are used as described herein for indicating atom configuration(s) relative to a core molecule and are intended to be used as defined in the literature (IUPAC Recommendations 1996, Pure and Applied Chemistry, 68:2193-2222 (1996)).

The term "chiral" refers to the structural characteristic of a molecule that makes it impossible to superimpose it on its mirror image. The term "homochiral" refers to a state of enantiomeric purity. The term "optical activity" refers to the degree to which a homochiral molecule or nonracemic mixture of chiral molecules rotates a plane of polarized light.

As used herein, the term "alkyl" or "alkylene" is intended to include both branched and straight-chain saturated aliphatic hydrocarbon groups having the specified number of carbon atoms. For example, "$C_1$ to $C_{10}$ alkyl" or "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$ to $C_6$ alkyl" or "$C_1$-$C_6$ alkyl" denotes alkyl having 1 to 6 carbon atoms. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl). When "$C_0$ alkyl" or "$C_0$ alkylene" is used, it is intended to denote a direct bond.

"Alkenyl" or "alkenylene" is intended to include hydrocarbon chains of either straight or branched configuration having the specified number of carbon atoms and one or more, preferably one to two, carbon-carbon double bonds that may occur in any stable point along the chain. For example, "$C_2$ to Co alkenyl" or "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, and 4-methyl-3-pentenyl.

"Alkynyl" or "alkynylene" is intended to include hydrocarbon chains of either straight or branched configuration having one or more, preferably one to three, carbon-carbon triple bonds that may occur in any stable point along the chain. For example, "$C_2$ to $C_6$ alkynyl" or "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl.

The term "alkoxy" or "alkyloxy" refers to an —O-alkyl group. "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S— and ethyl-S—.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_1$ to $C_6$ haloalkoxy" or "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

The term "cycloalkyl" refers to cyclized alkyl groups, including mono-, bi- or poly-cyclic ring systems. "$C_3$ to $C_7$ cycloalkyl" or "$C_{3-7}$ cycloalkyl" is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl".

As used herein, "carbocycle" or "carbocyclic residue" is intended to mean any stable 3-, 4-, 5-, 6-, 7-, or 8-membered monocyclic or bicyclic or 7-, 8-, 9-, 10-, 11-, 12-, or 13-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2] bicyclooctane). Preferred carbocycles, unless otherwise specified, are cyclopropyl, cyclobutyl, cyclopentyl, cyclohexyl, phenyl, and indanyl. When the term "carbocycle" is used, it is intended to include "aryl". A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

As used herein, the term "bicyclic carbocycle" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

"Aryl" groups refer to monocyclic or polycyclic aromatic hydrocarbons, including, for example, phenyl, naphthyl, and phenanthranyl. Aryl moieties are well known and described, for example, in *Hawley's Condensed Chemical Dictionary* (13th Edition), Lewis, R. J., ed., J. Wiley & Sons, Inc., New York (1997). "$C_6$ or $C_{10}$ aryl" or "$C_{6-10}$ aryl" refers to phenyl and naphthyl. Unless otherwise specified, "aryl", "$C_6$ or $C_{10}$ aryl" or "$C_{6-10}$ aryl" or "aromatic residue" may be unsubstituted or substituted with 1 to 5 groups, preferably 1 to 3 groups, OH, $OCH_3$, Cl, F, Br, I, CN, $NO_2$, $NH_2$, $N(CH_3)H$, $N(CH_3)_2$, $CF_3$, $OCF_3$, $C(=O)CH_3$, $SCH_3$, $S(=O)CH_3$, $S(=O)_2CH_3$, $CH_3$, $CH_2CH_3$, $CO_2H$, and $CO_2CH_3$.

The term "benzyl," as used herein, refers to a methyl group on which one of the hydrogen atoms is replaced by a phenyl group, wherein said phenyl group may optionally be substituted with 1 to 5 groups, preferably 1 to 3 groups, OH, $OCH_3$, Cl, F, Br, I, CN, $NO_2$, $NH_2$, $N(CH_3)H$, $N(CH_3)_2$, $CF_3$, $OCF_3$, $C(=O)CH_3$, $SCH_3$, $S(=O)CH_3$, $S(=O)_2CH_3$, $CH_3$, $CH_2CH_3$, $CO_2H$, and $CO_2CH_3$.

As used herein, the term "heterocycle" or "heterocyclic group" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and $S(O)_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Examples of 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Examples of 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydrobenzofuranyl, chromanyl, 1,2,3,4-tetrahydro-quinoxalinyl, and 1,2,3,4-tetrahydro-quinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

Bridged rings are also included in the definition of heterocycle. A bridged ring occurs when one or more atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "counterion" is used to represent a negatively charged species such as chloride, bromide, hydroxide, acetate, and sulfate.

When a dotted ring is used within a ring structure, this indicates that the ring structure may be saturated, partially saturated or unsaturated.

As referred to herein, the term "substituted" means that at least one hydrogen atom is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R groups, then said group may optionally be substituted with up to three R groups, and at each occurrence R is selected independently from the definition of R. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 18th Edition, Mack Publishing Company, Easton, PA (1990), the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) *Design of Prodrugs*, Bundgaard, H., ed., Elsevier (1985), and *Methods in Enzymology,* 112:309-396, Widder, K. et al., eds., Academic Press (1985);

b) Bundgaard, H., Chapter 5: "Design and Application of Prodrugs," *A Textbook of Drug Design and Development*, pp. 113-191, Krosgaard-Larsen, P. et al., eds., Harwood Academic Publishers (1991);

c) Bundgaard, H., *Adv. Drug Deliv. Rev.,* 8:1-38 (1992);

d) Bundgaard, H. et al., *J. Pharm. Sci.,* 77:285 (1988); and e) Kakeya, N. et al., *Chem. Pharm. Bull.,* 32:692 (1984).

Compounds containing a carboxy group can form physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, *Medicinal Chemistry: Principles and Practice*, King, F. D., ed. The Royal Society of Chemistry, Cambridge, UK (1994); Testa, B. et al., *Hydrolysis in Drug and Prodrug Metabolism. Chemistry, Biochemistry and Enzymology*, VCHA and Wiley-VCH, Zurich, Switzerland (2003); *The Practice of Medicinal Chemistry*, Wermuth, C. G., ed., Academic Press, San Diego, CA (1999).

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or $S(O)H$ group.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1H$" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Me methyl
Et ethyl
Pr propyl
i-Pr isopropyl
Bu butyl
i-Bu isobutyl
t-Bu tert-butyl
Ph phenyl
Bn benzyl
Boc tert-butyloxycarbonyl
AcOH or HOAc acetic acid
$AlCl_3$ aluminum chloride
AIBN azobisisobutyronitrile
$BBr_3$ boron tribromide
$BCl_3$ boron trichloride
BEMP 2-tert-butylimino-2-diethylamino-1,3-dimethylperhydro-1,3,2-diazaphosphorine
BOP reagent benzotriazol-1-yloxytris(dimethylamino)phosphonium hexafluorophosphate
Burgess reagent 1-methoxy-N-triethylammoniosulfonyl-methanimidate
CBz carbobenzyloxy
$CH_2Cl_2$ dichloromethane
$CH_3CN$ or ACN acetonitrile
$CDCl_3$ deutero-chloroform
$CDCl_3$ chloroform
mCPBA or m-meta-chloroperbenzoic acid
CPBA
$Cs_2CO_3$ cesium carbonate
$Cu(OAc)_2$ copper (II) acetate
$Cy_2NMe$ N-cyclohexyl-N-methylcyclohexanamine
DBU 1,8-diazabicyclo[5.4.0]undec-7-ene
DCE 1,2 dichloroethane
DCM dichloromethane
DEA diethylamine
Dess-Martin 1,1,1-tris(acetyloxy)-1,1-dihydro-1,2-benziodoxol-3-(1H)-one
DIC or DIPCDI diisopropylcarbodiimide
DIEA, DIPEA or diisopropylethylamine Hunig's base
DMAP 4-dimethylaminopyridine
DME 1,2-dimethoxyethane
DMF dimethyl formamide
DMSO dimethyl sulfoxide
cDNA complimentary DNA
Dppp (R)-(+)-1,2-bis(diphenylphosphino)propane
DuPhos (+)-1,2-bis((2S,5S)-2,5-diethylphospholano)benzene
EDC N-(3-dimthylaminopropyl)-N'-ethylcarbodiimide
EDCI N-(3-dimthylaminopropyl)-N'-ethylcarbodiimide hydrochloride
EDTA ethylenediaminetetraacetic acid
(S,S)-EtDuPhosRh(I) (+)-1,2-bis((2S,5S)-2,5-diethylphospholano)benzene(1,5-cyclooctadiene)rhodium (I) trifluoromethanesulfonate
$Et_3N$ or TEA triethylamine
EtOAc ethyl acetate
$Et_2O$ diethyl ether
EtOH ethanol
GMF glass microfiber filter Grubbs (II) (1,3-bis(2,4,6-trimethylphenyl)-2-imidazo-lidinylidene)dichloro(phenylmethylene) (triycyclohex-ylphosphine)ruthenium
HCl hydrochloric acid
HATU O-(7-azabenzotriazol-1-yl)-N,N,N',N'-tetramethy-luronium hexafluorophosphate
HEPES 4-(2-hydroxyethyl)piperaxine-1-ethanesulfonic acid
Hex hexane
HOBt or HOBT 1-hydroxybenzotriazole
H$_2$SO$_4$ sulfuric acid
K$_2$CO$_3$ potassium carbonate
KOAc potassium acetate
K$_3$PO$_4$ potassium phosphate
LAH lithium aluminum hydride
LG leaving group
LiOH lithium hydroxide
MeOH methanol
MgSO$_4$ magnesium sulfate
MsOH or MSA methylsulfonic acid
NaCl sodium chloride
NaH sodium hydride
NaHCO$_3$ sodium bicarbonate
Na$_2$CO$_3$ sodium carbonate
NaOH sodium hydroxide
Na$_2$SO$_3$ sodium sulfite
Na$_2$SO$_4$ sodium sulfate
NBS N-bromosuccinimide
NCS N-chlorosuccinimide
NH$_3$ ammonia
NH$_4$Cl ammonium chloride
NH$_4$OH ammonium hydroxide
OTf triflate or trifluoromethanesulfonate
Pd$_2$(dba)$_3$ tris(dibenzylideneacetone)dipalladium(0)
Pd(OAc)$_2$ palladium(II) acetate
Pd/C palladium on carbon
Pd(dppf)Cl$_2$ [1,1'-bis(diphenylphosphino)-ferrocene]dichloropalladium(II)
Ph$_3$PCl$_2$ triphenylphosphine dichloride
PG protecting group
PL-HCO$_3$ MP SPE Solid phase anion exchange
POCl$_3$ phosphorus oxychloride
i-PrOH or IPA isopropanol
PS polystyrene
SEM-Cl 2-(trimethysilyl)ethoxymethyl chloride
SiO$_2$ silica oxide
SnCl$_2$ tin(II) chloride
TBAI tetra-n-butylammonium iodide
TEA triethylamine
TFA trifluoroacetic acid
THF tetrahydrofuran
TMSCHN$_2$ trimethylsilyldiazomethane
T3P propane phosphonic acid anhydride
TRIS tris(hydroxymethyl)aminomethane The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al. (*Protective Groups in Organic Synthesis*, 4th Edition, Wiley-Interscience (2006)).

Imidazole derivatives useful for the synthesis of the compounds of this invention may be synthesized according to the general method outlined in Scheme 1 (Contour-Galcera et al., *Bioorg. Med. Chem. Lett.*, 11(5):741-745 (2001)). Alkylation of the potassium or cesium carboxylate of an appropriately protected or derivatized alpha amino acid 1a with a suitably substituted alpha-bromoketone 1b (ring C is aryl or heteroaryl) provides the keto ester 1c. The imidazole 1d is formed by heating the keto ester 1c to reflux in a suitable solvent, such as toluene or xylenes, in the presence of excess ammonium acetate using a Dean-Stark trap to remove water. Formation of the imidazole can also be carried out by combining the keto ester 1c and ammonium acetate in a suitable solvent, such as xylene or ethanol or a combination of solvents such as dimethylformamide and ethanol (1:1) and using microwave heating. Imidazole 1d can then be protected with as suitable protecting group. For example, imidazole 1d can be reacted with SEM-Cl, in the presence of base, such as sodium hydride or dicyclohexylmethyl amine, and in a solvent such as dimethylformamide or tetrahydrofuran to give 1e.

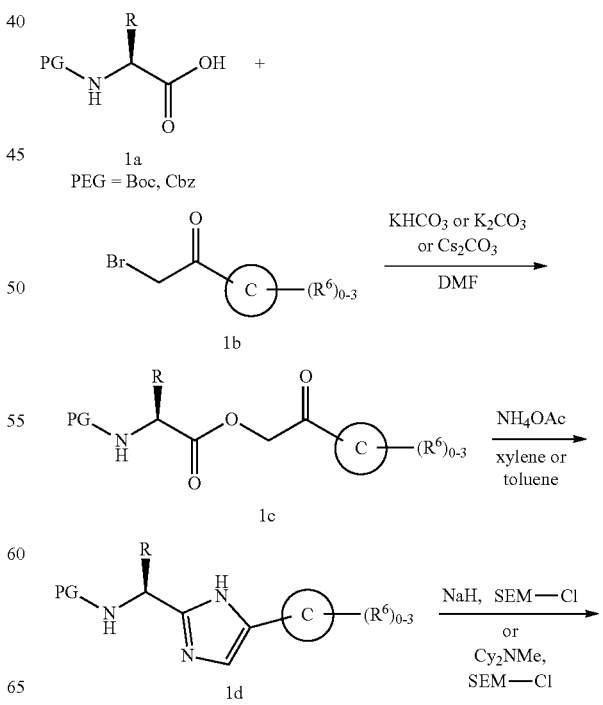

Scheme 1

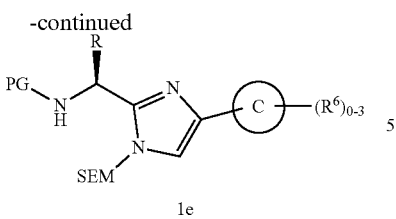

1e

Imidazole containing macrocycles of this invention wherein Y is —CH₂— can be prepared according to Scheme 2. Suzuki-Miyaura coupling between 2a, prepared as described in Scheme 1, and a suitably substituted alkyl boronic acid 2b in the presence of silver(I) oxide and a base, such as potassium carbonate, using a precatalyst such as Pd(dppf)Cl₂·CH₂Cl₂ complex, in a solvent such as tetrahydrofuran at elevated temperatures provides 2c (Falck, J. R., *Tetrahedron Letters*, 42:7213 (2001)). Using a modified procedure described by Lovely (*Tetrahedron Letters*, 44:1379 (2003)), 2c, following pretreatment with p-toluenesulfonic acid to form the imidazolium ion, can be cyclized via ring-closing metathesis using a catalyst, such as Grubbs (II), in a suitable solvent, such as dichloromethane, dichloroethane, or toluene at elevated temperature, to give the imidazole-containing macrocycle as a mixture of olefin isomers (E-alkene 2d and Z-alkene 2e). The olefins can be separated, and then deprotection of both the Boc and SEM groups with aqueous 5M hydrochloric acid in methanol or ethanol at elevated temperature provides amines 2f and 2g. Alternatively, the deprotection can be performed under anhydrous conditions with 4M hydrochloric acid in dioxane at elevated temperatures. The mixture of olefin isomers (E-alkene 2d and Z-alkene 2e) can be reduced with hydrogen over either palladium on carbon or platinum oxide and subsequent deprotection as described above gives the saturated amine 2h. Amide coupling between amines 2f-h, with an appropriately substituted carboxylic acid 2k, employing suitable coupling reagents, such as EDCI, HOBt, and base generates 2m-o (for alternative coupling reagents see: Han, S.-Y. et al., *Tetrahedron*, 60:2447 (2004)). Alternately, amines 2f-h can be coupled with an activated carboxylic ester 2l in the presence of a base such as Hunig's base and in a solvent such as dimethylformamide to give 2m-o. Further functional group incorporation on the imidazole ring may be achieved by chlorination of the C-5 of the imidazole ring with N-chlorosuccinimide, using a suitable solvent such as methylene chloride, acetonitrile or chloroform to give compounds 2p-r. Further functional group incorporation on the imidazole ring may also be achieved by fluorination of the C-5 of the imidazole ring with Accufluor, using a suitable solvent such as dimethylformamide in the presence of a base, such as sodium carbonate.

Scheme 2

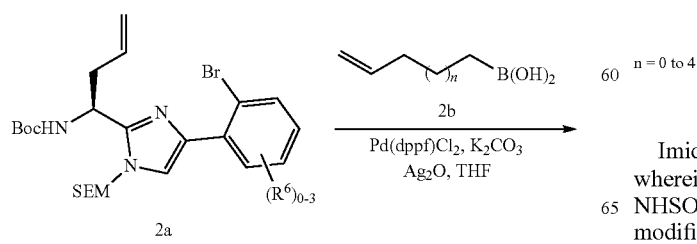

2a

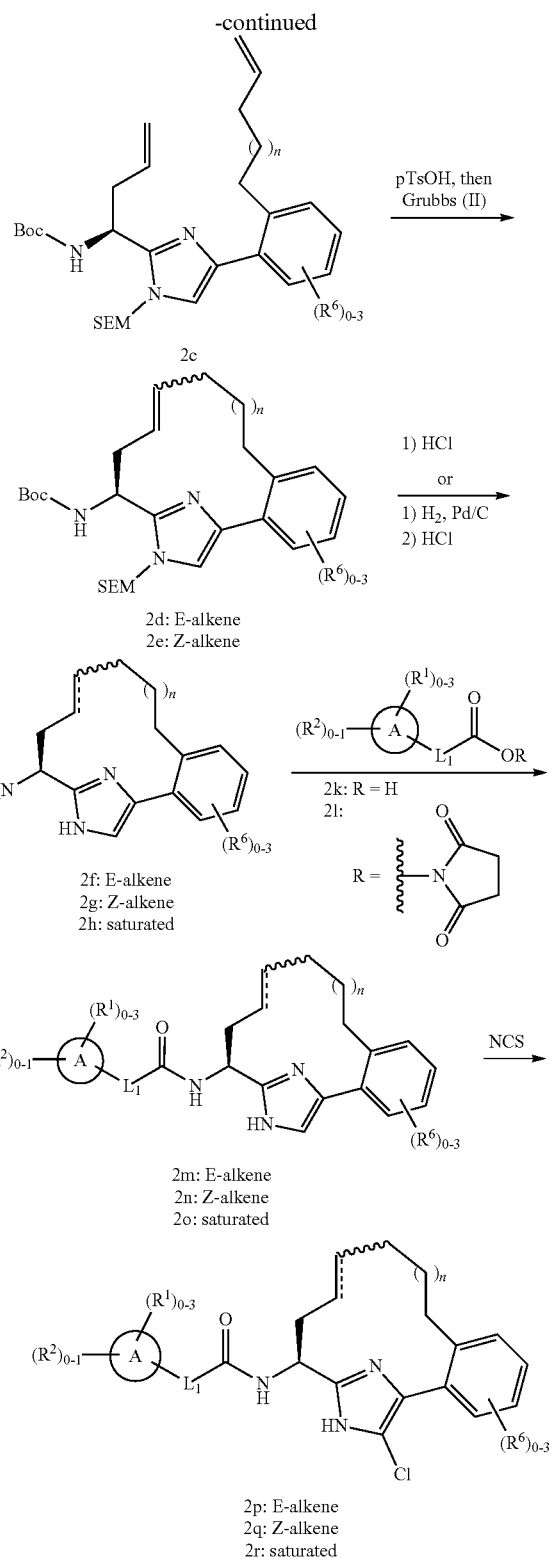

n = 0 to 4

Imidazole containing macrocycles of this invention wherein Y is NH, NHC(O), NHCO₂, NHC(O)NH, and NHSO₂ can be prepared according to Scheme 3. Using a modified procedure described by Ma (*Synthesis*, 3:496 (2005)), bromide 2a can be coupled with an appropriately substituted amine 3a employing copper (I) iodide and L-proline in the presence of a base such as potassium carbonate, in a solvent such as dimethylsulfoxide at elevated temperature to give the substituted aniline 3g. Alternatively, bromide 2a can be converted to the unsubstituted aniline 3b under similar reaction conditions (Chang, S., *Chem. Commun.,* 3052 (2008)). The aniline 3b can then be coupled with an appropriately substituted carboxylic acid 3c using T3P in a solvent such as ethyl acetate or dimethylformamide to give the amide 3h. The aniline 3b can also be coupled with an appropriately substituted chloroformate 3d, isocyanate 3e, or sulfonyl chloride 3f to provide the carbamate 3k, urea 3l, and the sulfonamide 3m, respectively. Compounds of the formula 3g, 3h, and 3k-m can be converted to compounds 3n-r according to Scheme 2. For the preparation of compounds of the formulae 3n, the preferred method for removing both the Boc and SEM, as described in Scheme 2, employs anhydrous 4M hydrochloric acid in dioxane at elevated temperatures with either cysteine or O-methyl hydroxylamine as a formaldehyde scavenger.

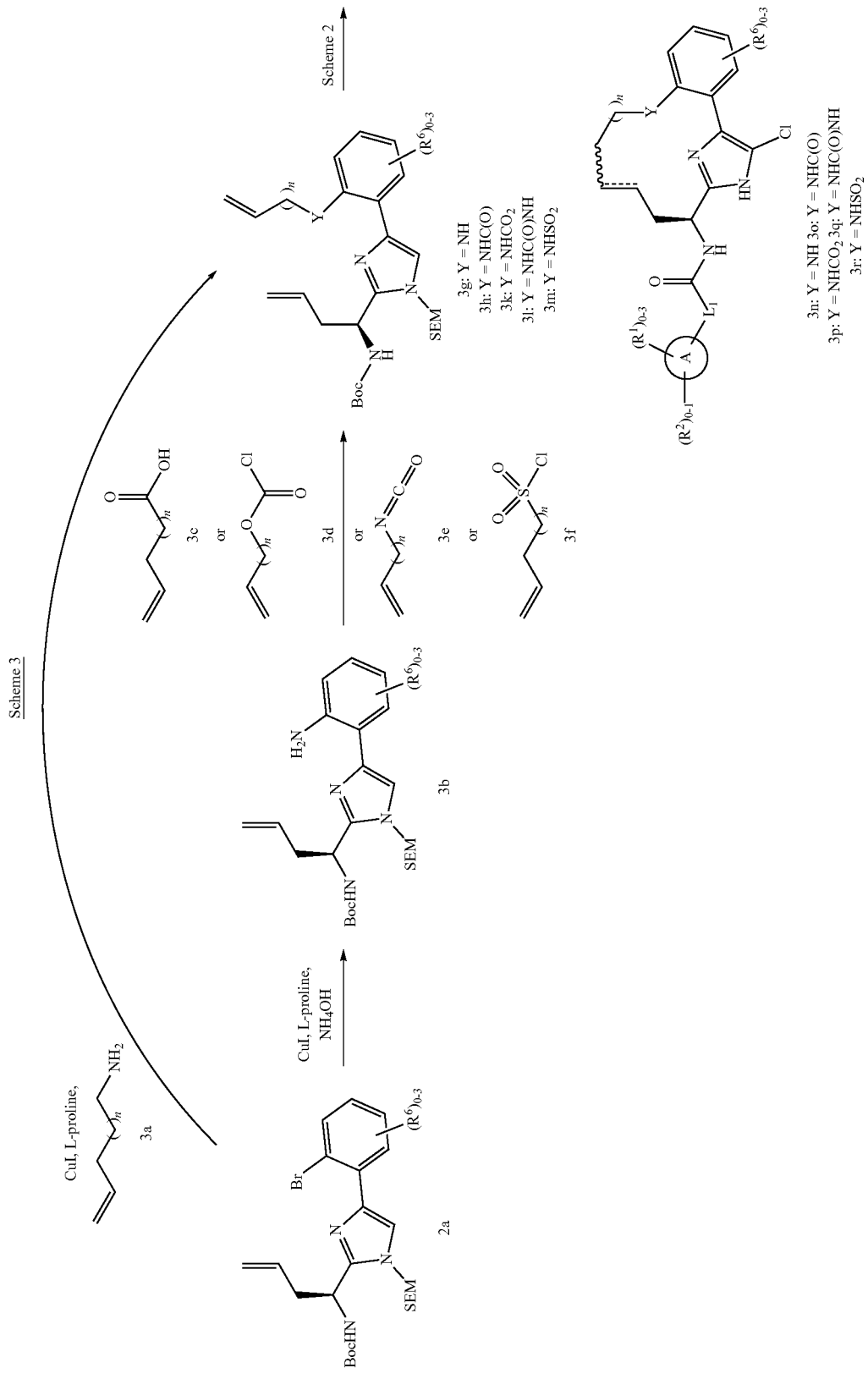
n = 0 to 4

Imidazole-containing macrocycles of this invention wherein Y is C(O)NH can be prepared according to Scheme 4. Subjecting 2a to methyllithium followed by metal-halogen exchange with n-butyllithium and quenching the intermediate anion with carbon dioxide provides the carboxylic acid 4a. Amide coupling with an appropriately substituted amine 4b, as previously described for the conversion of 3b to 3h, gives amide 4c. Amide 4c can be converted to compounds 4d-f according to Scheme 2.

chloroform to give 6b. Alternatively, acetophenone derivatives 6a can be treated with either copper (II) bromide in a solvent such as ethyl acetate at elevated temperature or phenyltrimethylammonium tribromide in a solvent such as tetrahydrofuran at low temperature to provide 6b. Benzoic acid derivatives 6c can be treated sequentially with oxalyl chloride in a suitable solvent, such as dichloromethane, containing a few drops of DMF, and then treated with trimethylsilyldiazomethane in a suitable solvent or solvent combination, such as acetonitrile and hexane. The intermediate diazoketone is isolated and treated with aqueous hydrobromic acid and dichloromethane to provide 6b. Alternatively the benzoic acid derivatives 6c can be converted to the acetophenone derivatives 6a in three steps as described in Scheme 6. Alternatively, Stille coupling between a suitably substituted aryl halide or triflate and tributyl-(1-ethoxyvinyl)stannane with a palladium catalyst, such as bis-(triphenylphosphine)palladium dichloride, in a suitable solvent, such as toluene, at elevated temperature yields the enol ether 6e. The resulting enol ether 6e can be converted to 6b with N-bromosuccinimide.

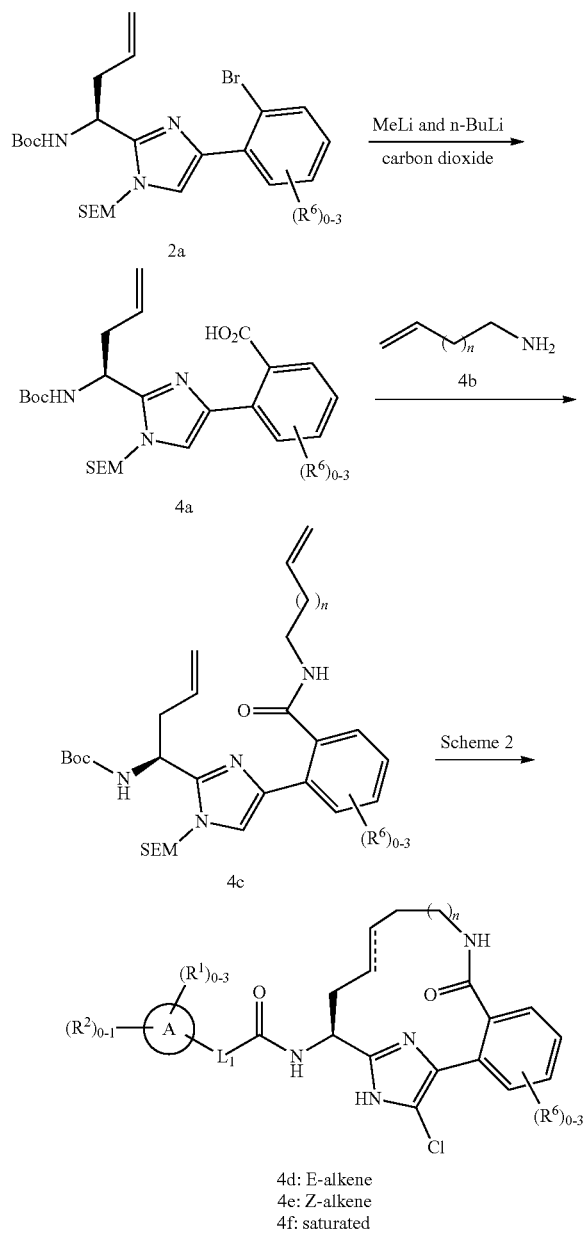

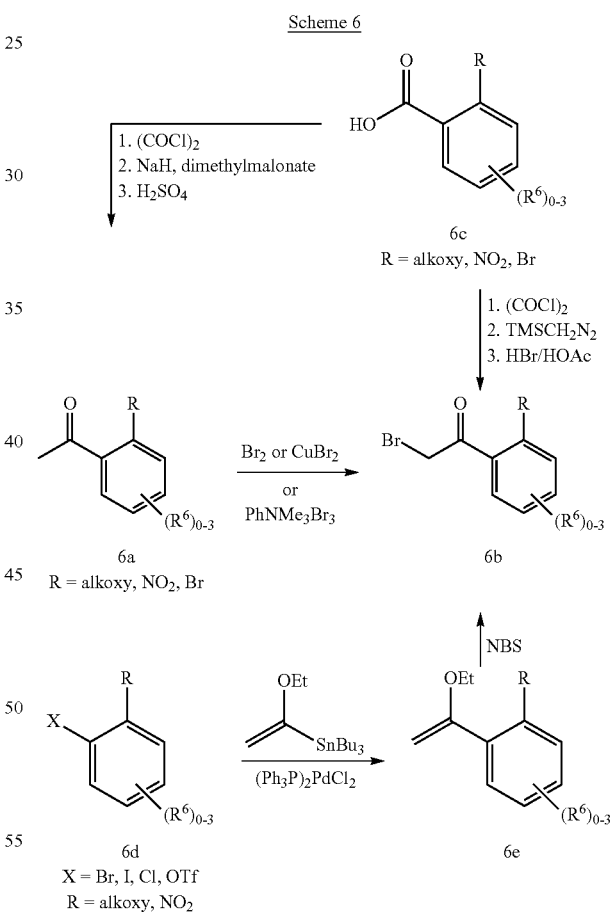

Certain 2-bromoacetophenone analogs (1b, C=aryl) that are not commercially available may be synthesized from commercially available starting materials as described in Scheme 6. Acetophenone derivatives 6a can be treated with a brominating reagent such as bromine in a solvent such The syntheses of appropriately substituted carboxylic acids of formulae 2k, where A=aryl and where $L_1$=—$CH_2CH_2$—, —CH=CH—, —C≡C—, —$OCH_2$—, —$S(O)_p$$CH_2$—, or —$CH_2NH$—, useful for the synthesis of amide compounds of this invention as outlined in Scheme 2 are described in PCT International Application No. WO 2009/114677 published Sep. 17, 2009, which is incorporated in its entirety herein by reference. In addition, 1-amino-5,6,7,8- tetrahydroisoquinoline-6-carboxylic acid useful for the synthesis of amide compounds of this invention as outlined in Scheme 2 is described in U.S. Patent Application No. 2005/0282805 published Dec. 22, 2005, which is incorporated in its entirety herein by reference.

Representative pyridine (ring B=pyridine) containing macrocycles of this invention wherein Y is NHCO can be prepared as shown in Scheme 7. Condensation of aldehyde 7a, prepared according to a modified procedure described by Negi (*Synthesis,* 991 (1996)), with (S)-2-methylpropane-2-sulfinamide in the presence of anhydrous copper sulfate in a solvent such as dichloromethane gives the sulfinimine 7b (Ellman, J., *J. Org. Chem.,* 64:1278 (1999).) Using a modified procedure described by Kuduk (*Tetrahedron Letters,* 45:6641 (2004)), suitably substituted Grignard reagents, for example allylmagnesium bromide, can be added to sulfinimine 7b to give a sulfinamide 7c, as a mixture of diastereomers which can be separated at various stages of the sequence. Suzuki-Miyaura coupling between 4-chloropyridine 7c and an appropriately substituted aryl or heteroaryl boronic acid or ester 7d in the presence of a base such as potassium phosphate in a solvent mixture, such dimethylsulfoxide and water, or dimethylformamide, using a precatalyst such as Pd(dppf)Cl$_2$·CH$_2$Cl$_2$ complex provides 7e. Protecting group interconversion can be accomplished in two steps to give 7f. The aniline 7f can then be coupled with an appropriately substituted carboxylic acid 3c using propane phosphonic acid anhydride (T3P) to give the amide 7g. Ring closing metathesis, as described previously in Scheme 2, affords the pyridine containing macrocycle 7h, as the E-alkene. Boc deprotection on 7h with either TFA in dichloromethane or 4M hydrochloric acid in dioxane gives amine 7k. Alternatively, hydrogenation of 7h followed by Boc deprotection with TFA in dichloromethane provides amine 7l. Compounds 7k and 7l can be converted to compounds 3m and 3n according to Scheme 2.

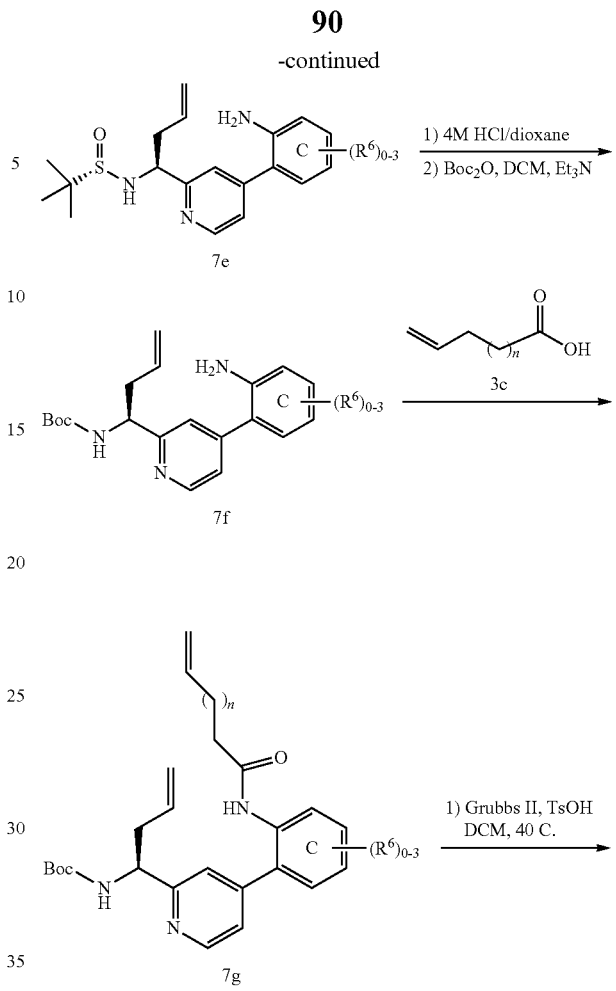

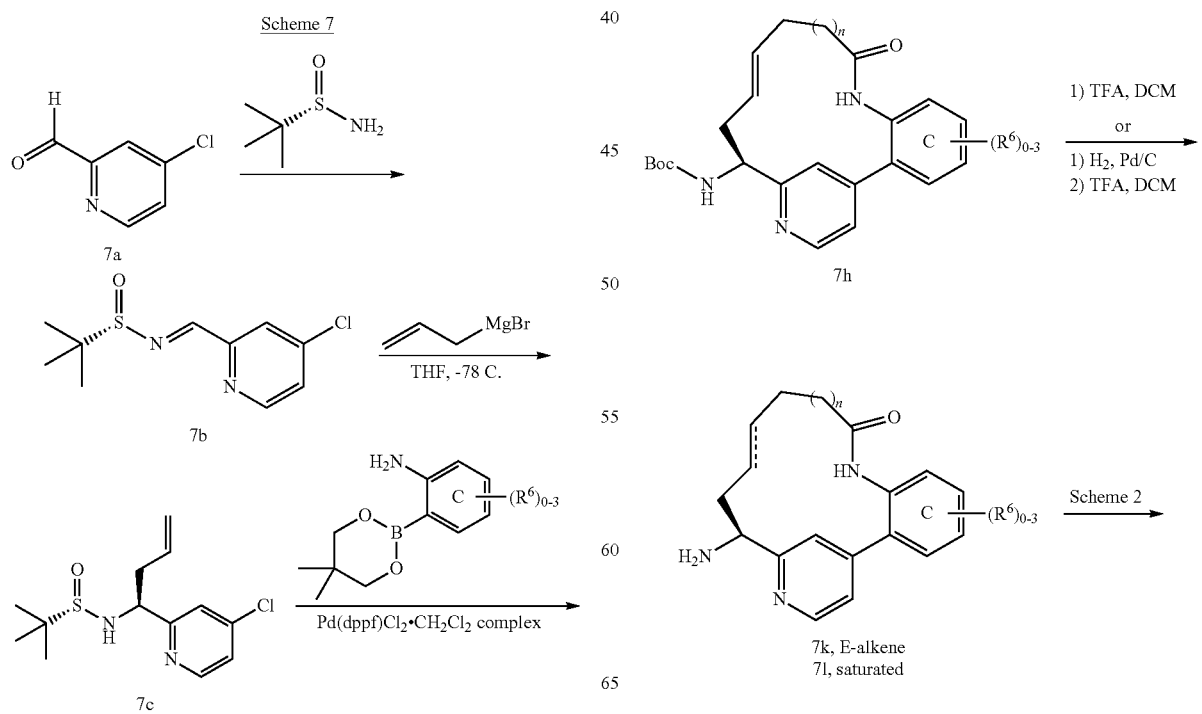

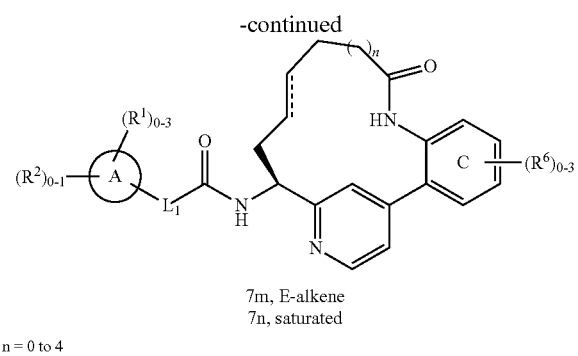

7m, E-alkene
7n, saturated n = 0 to 4

Additional pyridine (ring B=pyridine) containing macrocycles of this invention wherein Y is NHCO$_2$, NHC(O)NH, and NHSO$_2$ can be prepared according to Scheme 7 by replacing 3c with an appropriately substituted chloroformate 3d, isocyanate 3e, or sulfonyl chloride 3f. Additional macrocycles containing regioisomeric pyridine scaffolds to the one described in Scheme 7 can be prepared by an analogous sequence.

Methods for synthesis of a large variety of substituted pyridine compounds useful as starting materials for the preparation of compounds of the present invention are well known in the art and have been extensively reviewed. (For examples of methods useful for the preparation of pyridine starting materials see: Kroehnke, F., Synthesis, 1 (1976); "Pyridine and Its Derivatives", The Chemistry of Heterocyclic Compounds, 14(Suppl. 1-4), Abramovitch, R. A., ed., John Wiley & Sons, New York (1974); Comprehensive Heterocyclic Chemistry, 2:165-524, Boulton, A. J. et al., eds., Pergamon Press, New York (1984); Comprehensive Heterocyclic Chemistry, 5:1-300, McKillop, A., ed., Pergamon Press, New York (1996)).

In cases where suitably substituted boronic acids are not commercially available, a modification to this approach may be adopted wherein an aryl halide is subjected to a palladium mediated coupling with a diboron species such as bis(pinacolato) diboron or bis(neopentyl glycolato)diboron to provide the corresponding 4,4,5,5-tetramethyl-[1,3,2]dioxaborolane or the 5,5-dimethyl-[1,3,2]dioxaborolane intermediates using the method of Ishiyama, T. et al. (J. Org. Chem., 60(23):7508-7510 (1995)). Alternately, this same intermediate can be prepared by reaction of the intermediate halide with the corresponding dialkoxyhydroborane as described by Murata et al. (J. Org. Chem., 62(19):6458-6459 (1997)). The boron pinacolate intermediates can be used in place of boronic acids for coupling to the aryl/heteroaryl halides or triflates or the boron pinacolate intermediate can be converted to the boronic acids. Alternately, the corresponding boronic acids can be prepared by metal-halogen exchange of the aryl/heteroaryl halide, quenching with a trialkoxyborate reagent, and aqueous workup to provide the boronic acids (Miyaura, N. et al., Chem. Rev., 95:2457 (1995)).

It is also realized that the scope of intermediate synthesis can be further extended outside the use of Suzuki-Miyaura coupling methodology since the precursor aryl halides or triflates described above are also precursors for Stille, Negishi, Hiyama, and Kumada-type cross coupling methodologies (Tsuji, J., Transition Metal Reagents and Catalysts: Innovations in Organic Synthesis, John Wiley & Sons (2000); Tsuji, J., Palladium Reagents and Catalysts: Innovations in Organic Synthesis, John Wiley & Sons (1996).)

Representative phenyl (ring B=phenyl) containing macrocycles of this invention wherein Y is NHCO can be prepared as shown in Scheme 8. Using a modification of the procedure described by Hart (J. Org. Chem., 48(3):289-294 (1983)), in situ generation of N-trimethylsilylaldimines from a suitably substituted benzaldehyde 8a and lithium bis(trimethylsilyl)amide, followed by the addition of Grignard or alkyllithium reagents 8b, for instance allylmagnesium bromide, gives after aqueous work up the amine 8c. The amine can be protected as the Boc. Compounds of the formula 8e and 8f can be prepared following the sequence described in Scheme 7, by replacing 7c with 8d.

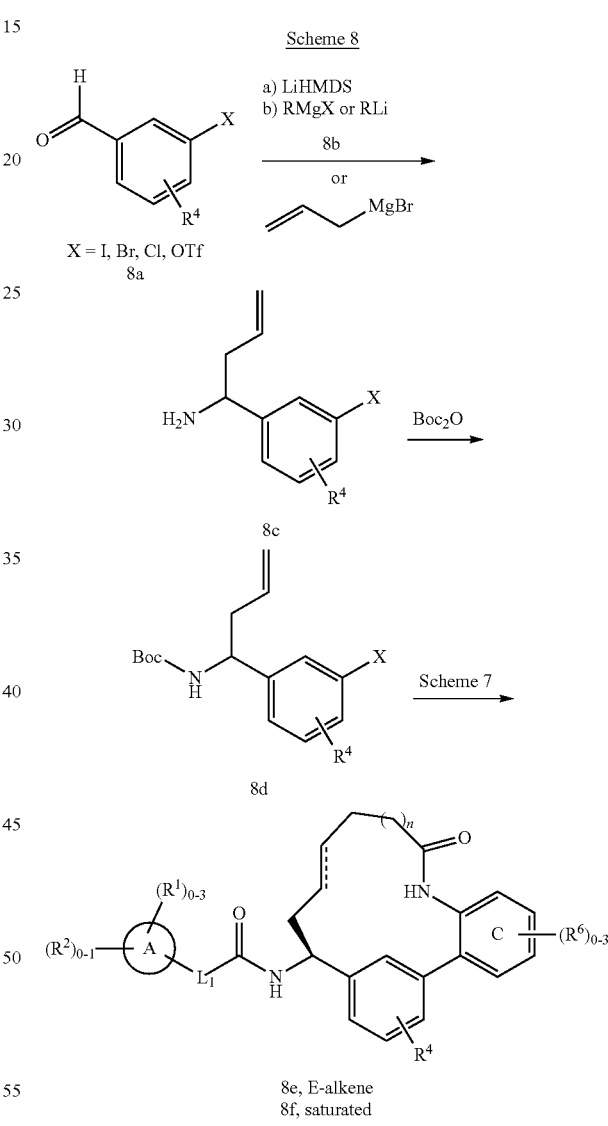

8e, E-alkene
8f, saturated n = 0 to 4

Representative pyridazine (ring B=pyridazine) containing macrocycles of this invention wherein Y is NHCO can be prepared as shown in Scheme 9. Using a modification of the Minisci reaction described by Cowden (Org. Lett., 5:4497-4499 (2003)), an appropriately protected or derivatized alpha amino acid 1a and 3,6-dichloropyridazine 9a can be coupled at elevated temperature in the presence of silver nitrate, ammonium persulfate, and an acid, such as trifluoroacetic acid, in a solvent, such as water or a water/dimethylformamide mixture, to give compounds of the formulae 9b. Compound 9b wherein R=H, prepared using an appropriately protected glycine derivative of 1a, can be further functionalized by deprotonation with sec-BuLi and subsequent alkylation with an appropriately substituted alkyl halide, for instance allyl bromide, to give compound 9c. Suzuki-Miyaura coupling between chloropyridazine 9c and an appropriately substituted aryl or heteroaryl boronic acid or ester 7d in the presence of a base such as potassium phosphate in a solvent mixture, such dimethylsulfoxide and water, or dimethylformamide, using a precatalyst such as $Pd(dppf)Cl_2 \cdot CH_2Cl_2$ complex provides 9d. Compounds of the formula 9e and 9f can be prepared following the sequence described in Scheme 7, by replacing 7f with 9d.

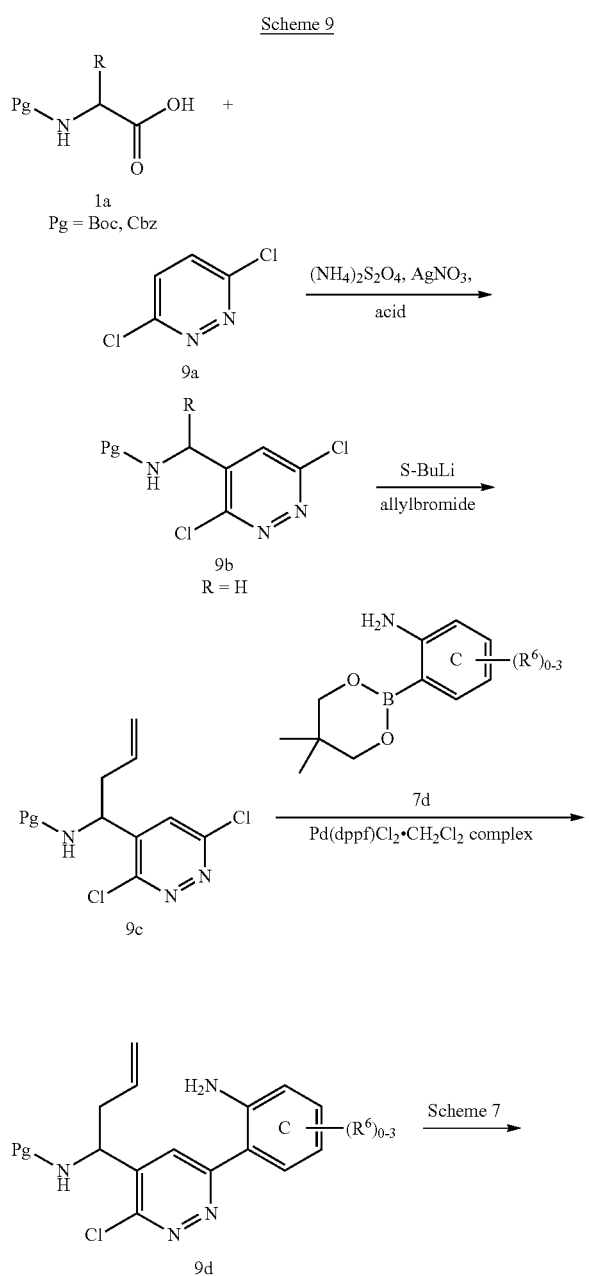

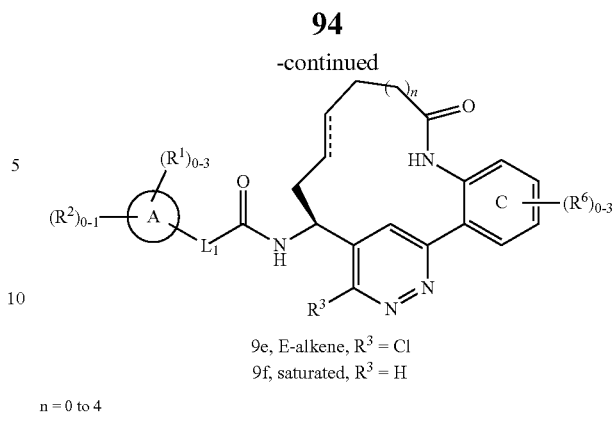

9e, E-alkene, $R^3$ = Cl
9f, saturated, $R^3$ = H n = 0 to 4

Methods for the synthesis of a large variety of substituted pyridazines useful for the preparation of compounds of the present invention are well known in the art. (For examples of methods useful for the preparation of pyridazine starting materials see: "Pyridazines", *The Chemistry of Heterocyclic Compounds*, Vol. 28, Castle, R. N., ed., John Wiley & Sons, New York (1973); "The Pyridazines", *The Chemistry of Heterocyclic Compounds,* 57(Suppl. 1), Brown, D. J., ed., John Wiley & Sons, New York (2000); *Comprehensive Heterocyclic Chemistry II,* 6:1-93, Boulton, A. J., ed., Elsevier Science Inc., New York (1996)).

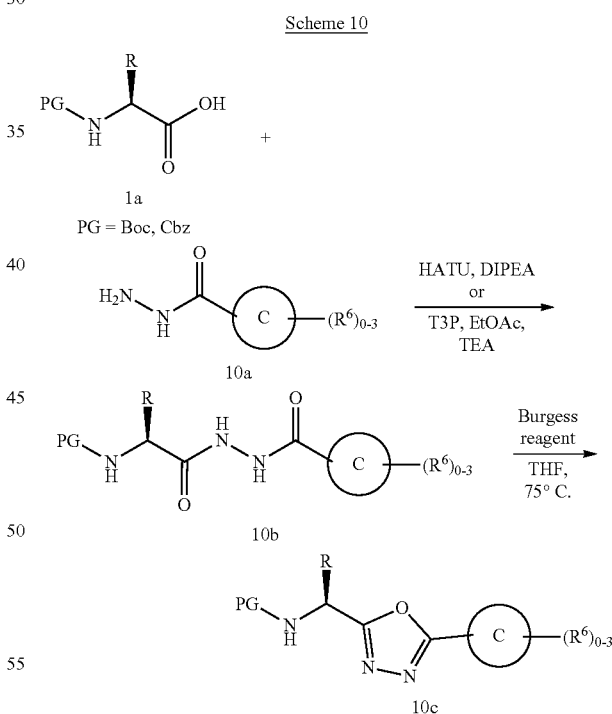

Oxadiazole derivatives useful for the synthesis of the compounds of this invention may be synthesized according to the general method outlined in Scheme 10. A suitably protected amino acid 1a is coupled to a hydrazide of formula 10a in the presence of a coupling reagent such as HATU or T3P to provide acylhydrazide 10b which is cyclized to the corresponding oxadiazole 10c by heating in the presence of Burgess reagent in a suitable solvent such as THF.

Scheme 10a

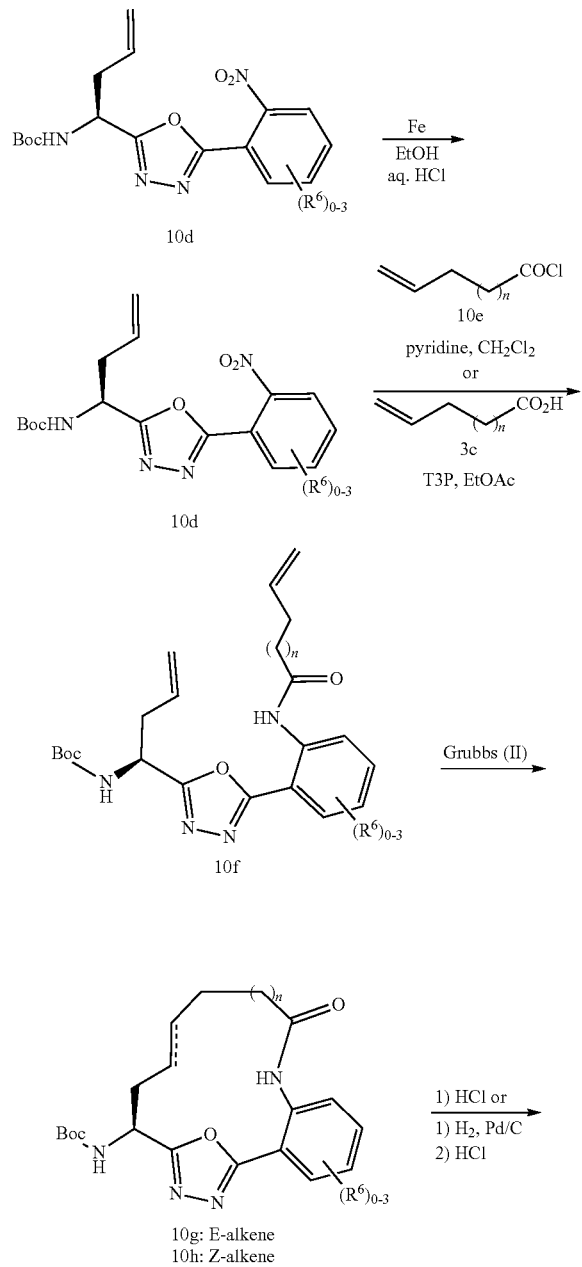

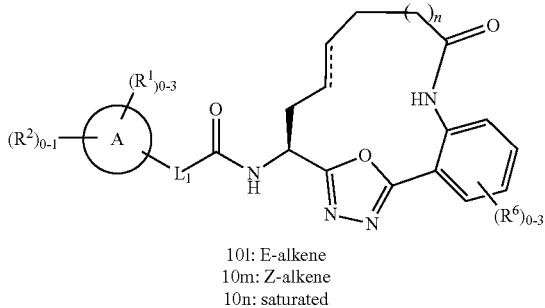

10l: E-alkene
10m: Z-alkene
10n: saturated n = 0 to 4

Representative oxadiazole (ring B=oxadiazole) containing macrocycles of this invention wherein Y is NHCO can be prepared as shown in Scheme 10a. Thus from N-Boc-allylglycine and a suitably substituted 2-nitrophenylhydrazine, compounds of formula 10d can be obtained and then converted into macrocyclic compounds of this invention using similar chemistry to that described above in Scheme 7.

It should be recognized to one skilled in the art of organic synthesis that additional macrocyclic compounds of this invention can be prepared by alternative cyclization strategies which are not limited to the ring-closing metathesis strategy described in Scheme 2. For instance, macrolactamization can also be used as described in Scheme 11. Slow addition of a solution 11a and Hunig's base in DMF to a solution BOP reagent in a mixture dichloromethane and DMF, provides macrocycle 11b. Hydrogenolysis of the Cbz provides the amine 11c. Amide coupling of the amine 11c with 2k or 2l, as described in Scheme 2, and global deprotection gives 11d.

Scheme 11

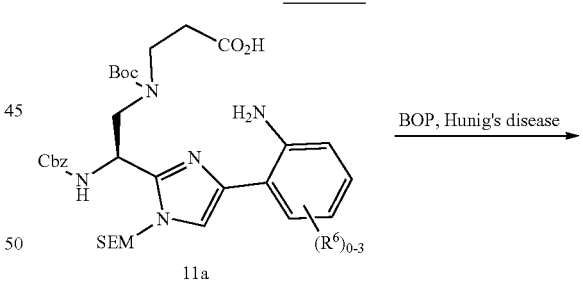

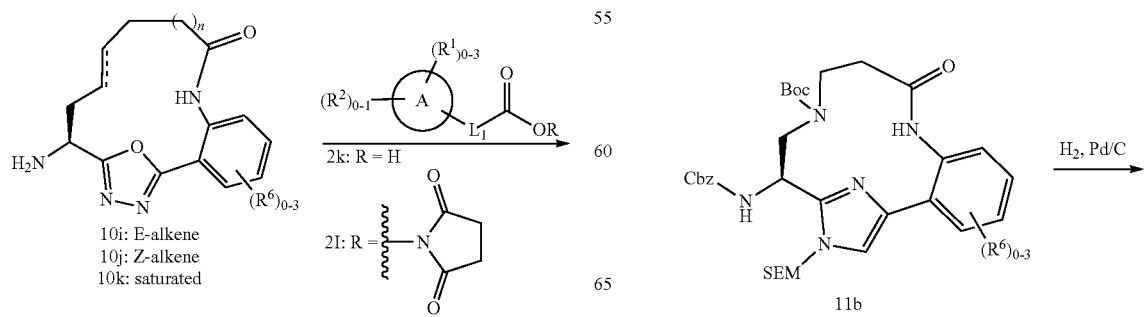

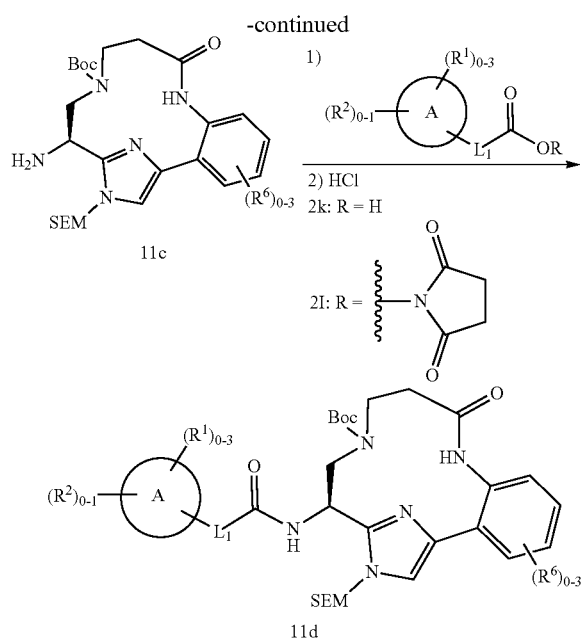

Additional imidazole containing macrocycles of this invention wherein Y is NH can be prepared according to Scheme 14. Using a modified procedure described by Ma (*Synthesis*, 3:496 (2005)), bromide 2a can be coupled with an appropriately substituted amine or amino acid ($R^7$=$CO_2H$) 14a employing copper (I) iodide and L-proline in the presence of a base such as potassium carbonate, in a solvent such as dimethylsulfoxide at elevated temperature, followed by alkylation of the carboxylic acid moiety with an alkyl iodide such as methyl iodide, gives the substituted aniline 14b. Alternatively, 14b can be prepared using a modified procedure described by Zhao (*Synthesis*, 19:3189 (2006)). Combining aniline 3b with appropriately substituted aldehdydes 14c in the presence of maleic acid and allyltributyltin provides 14b. Alternatively, aniline 3b can be condensed with trifluoroacealdehyde ethyl hemiacetal followed by the addition of Grignard reagents, such as allylmagnesium bromide, which gives 14d. Compounds of the formula 14b and 14d can be converted to compounds 14e and 14f according to Scheme 2. For the preparation of compounds of the formulae 14e and 14f, the preferred method for removing both the Boc and SEM, as described in Scheme 2, employs anhydrous 4M hydrochloric acid in dioxane at elevated temperatures with either cysteine or O-methyl hydroxylamine as a formaldehyde scavenger. Further manipulation of functional groups on $R^7$ using methods known to one skilled in the art of organic synthesis will give additional compounds of the invention.

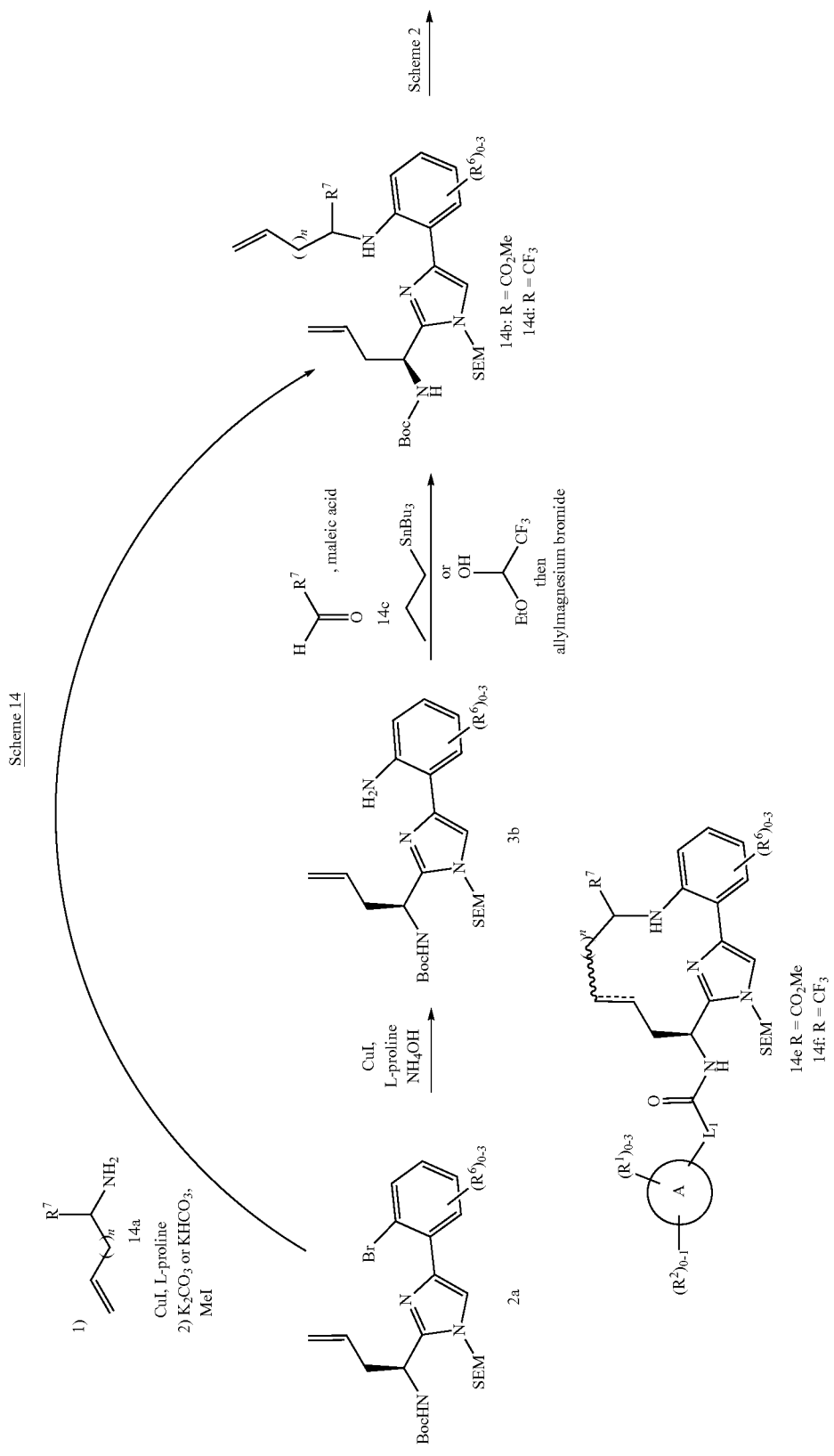

Additional imidazole macrocycles of this invention wherein $R^3$ is CN, can be prepared according to Scheme 15. Deprotection of intermediates 15g and 15h followed by amide coupling as described above will then provide additional compounds of this invention. Further manipulation of functional groups at $R^7$ and $R^3$ using methods known to one skilled in the art of organic synthesis and as exemplified in the specific examples given below will give additional compounds of the invention.

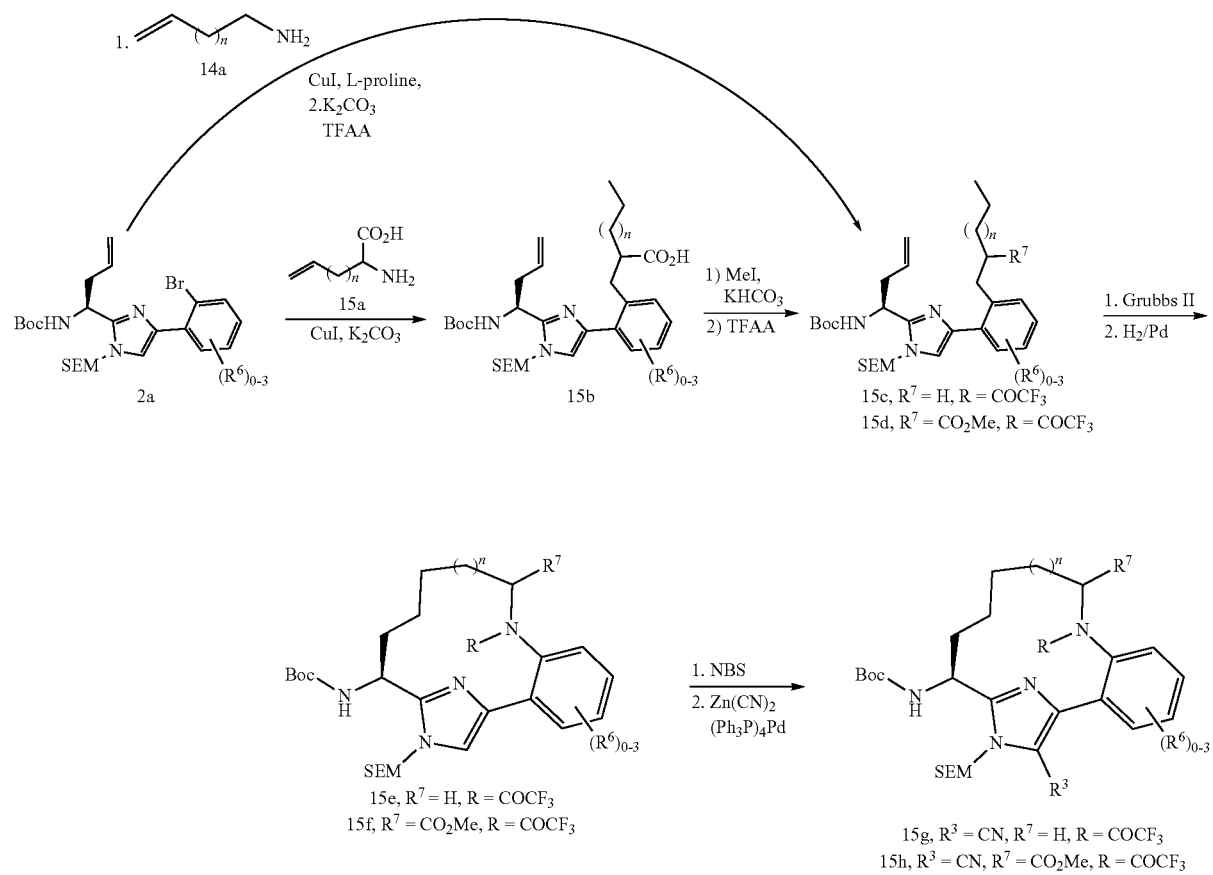

Scheme 15

Additional imidazole containing macrocycles of this invention can be prepared according to Scheme 16. Regioselective protection of the 2,4-dibromo imidazole with SEM-Cl provides 16b. Metal-halogen exchange of 16b with n-BuLi followed by quenching with dimethylformamide affords a mixture of the C2 and C4 aldehydes. Condensation of the C2-aldehyde with (S)-2-methylpropane-2-sulfinamide in the presence of anhydrous copper sulfate in a solvent such as dichloromethane gives the sulfinimine 16c. Appropriately substituted Grignard reagents, for example allylmagnesium bromide, can be added to sulfinimine 16c to give sulfinamine 16d, as a mixture of diastereomers which can be separated at various stages of the sequence. Alternatively, the 2, 4, 5-tribromo imidazole 16e can be converted to 16h according to the four step sequence described above. Regioselective halogen-magnesium exchange of 16h with isopropylmagnesium chloride, followed by quenching with saturated ammonium chloride, provides 16d. Suzuki-Miyaura coupling between bromoimidazole 16d and an appropriately substituted aryl or heteroaryl boronic acid or ester 7d in the presence of a base such as potassium carbonate in a solvent, such as dioxane, using a catalyst such as $Pd(tBu_3P)_2$ provides 16k. Protecting group interconversion can be accomplished in two steps to give 3b. Compound 3b can be converted to compound 3o according to Scheme 3.

Scheme 16

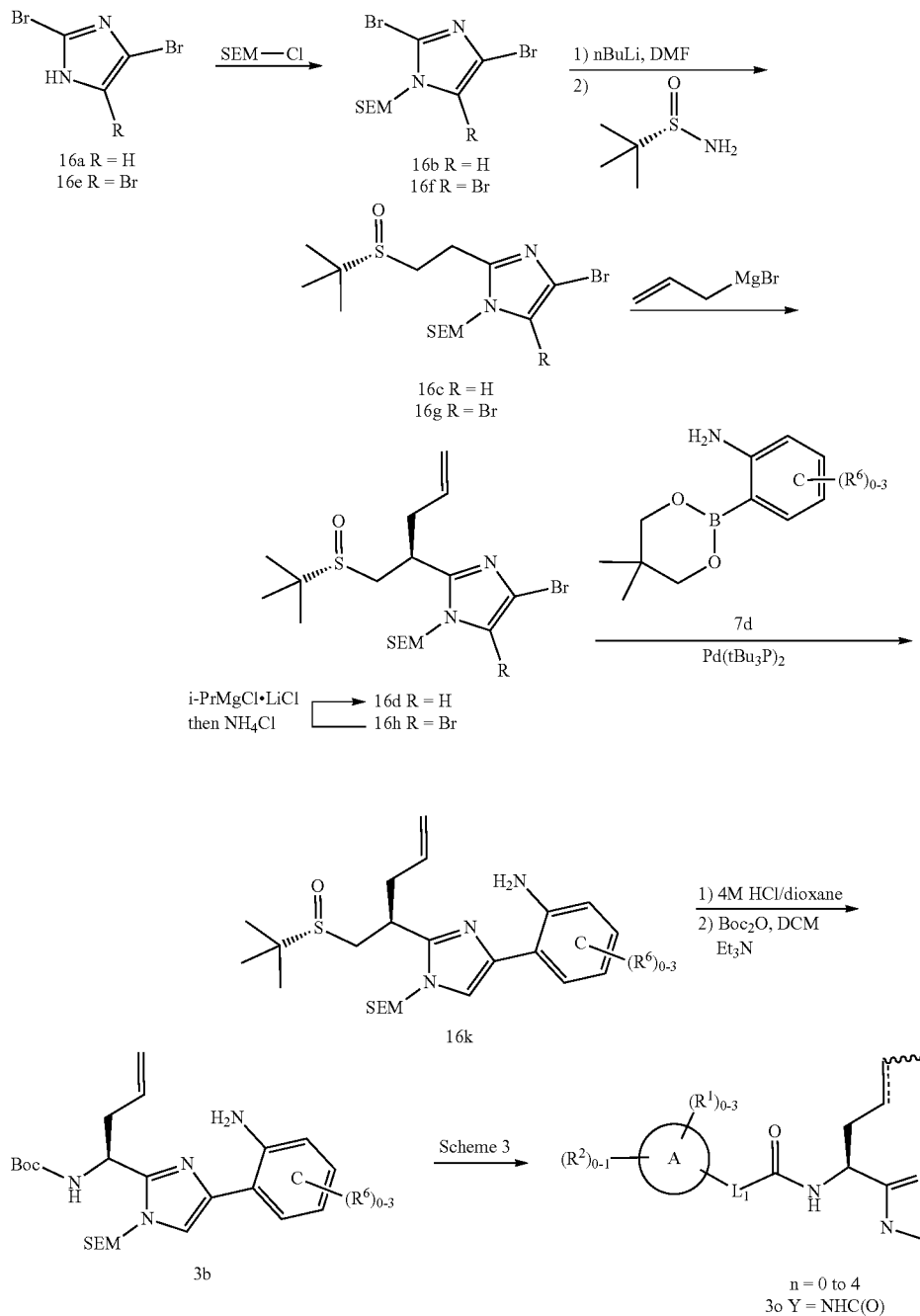

Representative pyridone (ring B=pyridone) containing macrocycles of this invention can be prepared as shown in Scheme 17. Compound 17d can be prepared in two steps according to a modified procedure described by Resmini (Resmini, M. et al., *Tetrahedron Asymmetry*, 15:1847 (2004)). A suitably substituted amino ester 17a can be converted to the corresponding β-ketophosphonate 17b by treatment with lithium dimethylmethylphosphonate. Horner-Wadsworth-Emmons reaction of 17b and a suitably substituted aldehyde 17c in the presence of base such as potassium carbonate in a solvent such as ethanol or tetrahydrofuran gives the α,β-unsaturated ketone 17d. Condensation of 17d with 1-(ethoxycarbonylmethyl)-pyrdinium chloride or 1-(carbamoylmethyl)-pyridinium chloride in the presence of ammonium acetate in a solvent such as ethanol or glacial acetic acid generates the pyridone 17e. The nitro group can be reduced to the aniline 17f with zinc and ammonium chloride in methanol. Alternatively, alkylation of the cesium salt of the pyridone 17e with methyl iodide, followed by reduction of the nitro as described above, can yield the N-Me pyridone derivative 17g. Compounds of formula 17f and 17g can be converted to compounds 17h-k, according to Scheme 7, or to compounds 17l-m, according to Scheme 14.

Scheme 17

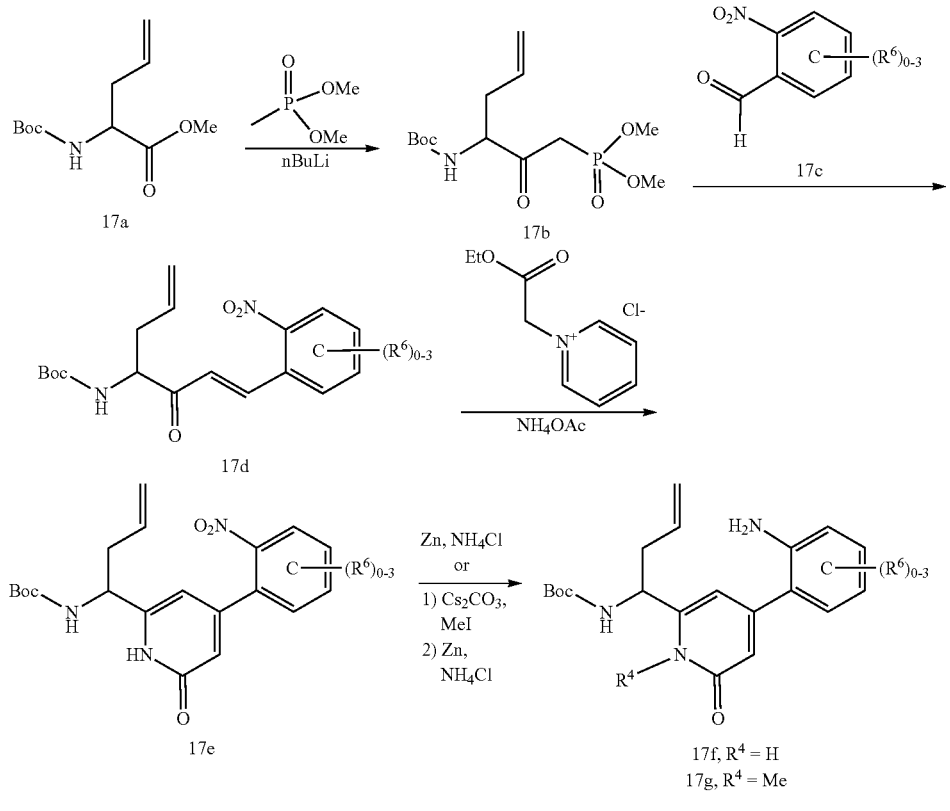

Representative pyrimidine (ring B=pyrimidine) containing macrocycles of this invention can be prepared as shown in Scheme 18. Condensation of the β-ketoester 18b, prepared according to a modified procedure of Maibaum (*J. Org. Chem.*, 53:869 (1988)), with a suitably substituted amidine under basic conditions, such as formamidine and sodium methoxide in methanol, yields the pyrimidone 18c. The pyrimidone can be converted to the chloro pyrimidine 18d in two steps with phosphorus oxychloride and then reprotection of the amine with Boc-anhydride. Alternatively, the pyrimidone can be converted directly to the corresponding triflate 18e with sodium hydride and N-phenyltrifluoromethanesulfonimide. Suzuki-Miyaura coupling between 18d or 18e and an appropriately substituted aryl or heteroaryl boronic acid or ester 7d in the presence of a base such as potassium phosphate in a solvent mixture, such as dimethylsulfoxide and water, or dimethylformamide, using a precatalyst such as Pd(dppf)Cl$_2$·CH$_2$Cl$_2$ complex provides 18f. Compounds of the formula 18f can be converted to compounds 18g-h, according to Scheme 7, or to compounds 18i, according to Scheme 14.

Scheme 18

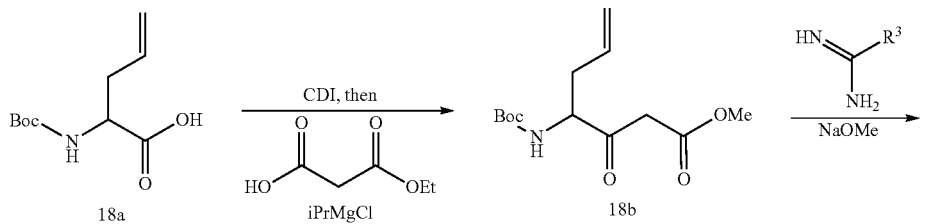

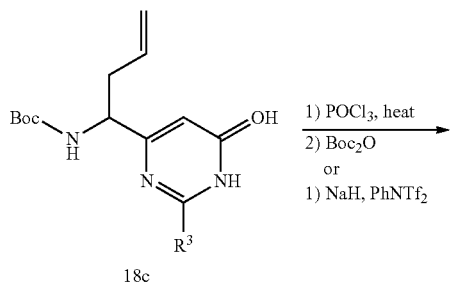

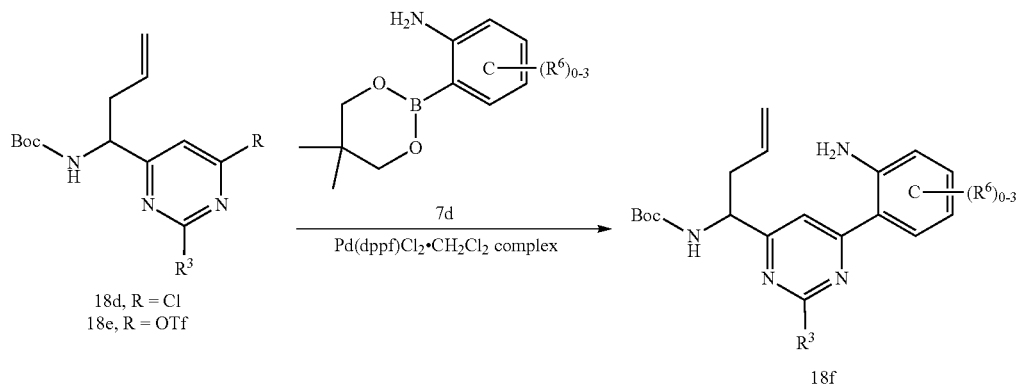

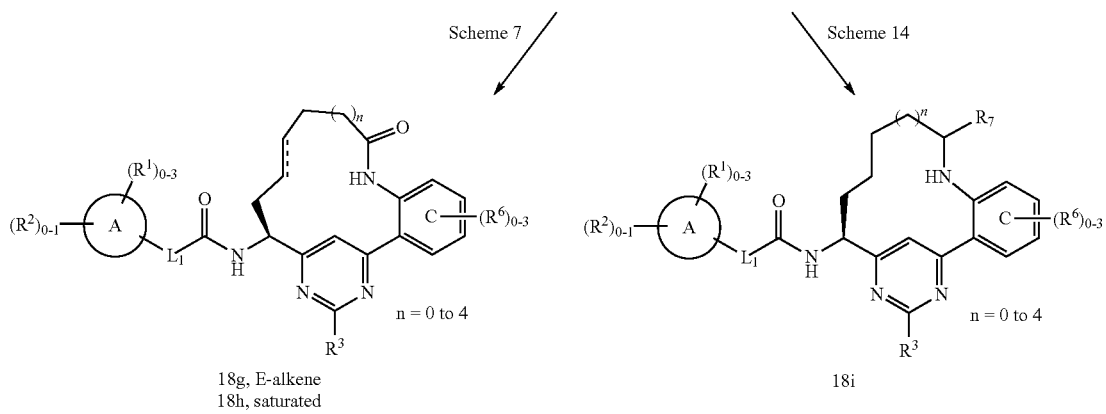

Representative pyridazinone (ring B=pyridazinone) containing macrocycles of this invention can be prepared as shown in Scheme 19. Condensation of the potassium salt of 17b with a suitably substituted a-ketoester 19a, which is either commercially available or prepared using a modified procedure described by Domagala (*Tetrahedron Lett.*, 21:4997-5000), in a solvent such as tetrahydrofuran generates the α,β-unsaturated ketone derivative which can then be condensed with a suitably substituted hydrazine derivative to give pyridazinone 19b. The nitro group can be reduced to the aniline 19c with zinc and ammonium chloride in methanol. Compounds of the formula 19c can be converted to compounds 19d according to Scheme 14.

Scheme 19

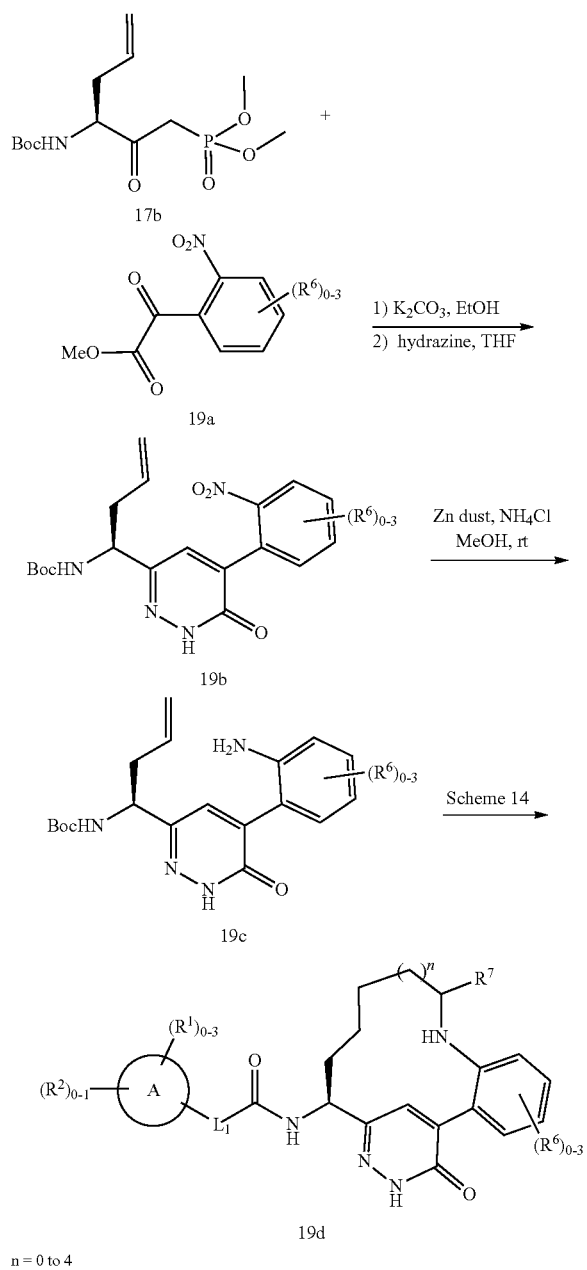

n = 0 to 4

It should be recognized that additional deprotection steps and further functional group manipulations of compounds obtained via Schemes 1-19 using methods known in the art will then provide additional compounds of this invention.

Purification of intermediates and final products was carried out via either normal or reverse phase chromatography. Normal phase chromatography was carried out using pre-packed $SiO_2$ cartridges eluting with either gradients of hexanes and ethyl acetate or dichloromethane and methanol unless otherwise indicated. Reverse phase preparative HPLC was carried out using C18 columns eluting with gradients of Solvent A (90% water, 10% methanol, 0.1% TFA) and Solvent B (10% water, 90% methanol, 0.1% TFA, UV 220 nm) or with gradients of Solvent A (90% water, 10% acetonitrile, 0.1% TFA) and Solvent B (10% water, 90% acetonitrile, 0.1% TFA, UV 220 nm) or with gradients of Solvent A (98% water, 2% acetonitrile, 0.05% TFA) and Solvent B (98% acetonitrile, 2% water, 0.05% TFA, UV 254 nm).

Unless otherwise stated, analysis of final products was carried out by reverse phase analytical HPLC using the Waters SunFire column (3.5 μm C18, 3.0×150 mm). Gradient elution (1.0 mL/min) from 10-100% Solvent B for 12 min and then 100% Solvent B for 3 min was used. Solvent A is (95% water, 5% acetonitrile, 0.05% TFA) and Solvent B is (5% water, 95% acetonitrile, 0.05% TFA, UV 254 nm). Method B: Agilent ZORBAX® (3.5 μm C18, 4.6×75 mm) eluted at 2.5 mL/min with an 8 min gradient from 100% A to 100% B (A: 10% methanol, 89.9% water, 0.1% $H_3PO_4$; B: 10% water, 89.9% methanol, 0.1% $H_3PO_4$, UV 220 nm). Method C: Waters SunFire column (3.5 μm C18, 4.6×150 mm) eluted at 1 mL/min with a gradient from 10-100% Solvent B for 10 min and then 100% Solvent B for 5 min. (A: 0.01 M $NH_4HCO_3$ in water:methanol 95:5. B: 0.01 M $NH_4HCO_3$ in water:methanol 5:95. UV 254 nm). Method D: Waters SunFire column (3.5 μm C18, 3.0×150 mm). Gradient elution (1.0 mL/min) from 10-100% Solvent B for 10 min and then 100% Solvent B for 5 min was used. Solvent A is (95% water, 5% acetonitrile, 0.05% TFA) and Solvent B is (5% water, 95% acetonitrile, 0.05% TFA, UV 254 nm).

IV. Biology

While blood coagulation is essential to the regulation of an organism's hemostasis, it is also involved in many pathological conditions. In thrombosis, a blood clot, or thrombus, may form and obstruct circulation locally, causing ischemia and organ damage. Alternatively, in a process known as embolism, the clot may dislodge and subsequently become trapped in a distal vessel, where it again causes ischemia and organ damage. Diseases arising from pathological thrombus formation are collectively referred to as thromboembolic disorders and include acute coronary syndrome, unstable angina, myocardial infarction, thrombosis in the cavity of the heart, ischemic stroke, deep vein thrombosis, peripheral occlusive arterial disease, transient ischemic attack, and pulmonary embolism. In addition, thrombosis occurs on artificial surfaces in contact with blood, including catheters, stents, artificial heart valves, and hemodialysis membranes.

Some conditions contribute to the risk of developing thrombosis. For example, alterations of the vessel wall, changes in the flow of blood, and alterations in the composition of the vascular compartment. These risk factors are collectively known as Virchow's triad. (*Hemostasis and Thrombosis, Basic Principles and Clinical Practice*, 5th Edition, p. 853, Colman, R. W. et al., eds., Lippincott Williams & Wilkins (2006))

Antithrombotic agents are frequently given to patients at risk of developing thromboembolic disease because of the presence of one or more predisposing risk factors from Virchow's triad to prevent formation of an occlusive thrombus (primary prevention). For example, in an orthopedic surgery setting (e.g., hip and knee replacement), an antithrombotic agent is frequently administered prior to a surgical procedure. The antithrombotic agent counterbalances the prothrombotic stimulus exerted by vascular flow alterations (stasis), potential surgical vessel wall injury, as well as changes in the composition of the blood due to the acute phase response related to surgery. Another example of the use of an antithrombotic agent for primary prevention is dosing with aspirin, a platelet activation inhibitor, in patients at risk for developing thrombotic cardiovascular disease.

Well recognized risk factors in this setting include age, male gender, hypertension, diabetes mellitus, lipid alterations, and obesity.

Antithrombotic agents are also indicated for secondary prevention, following an initial thrombotic episode. For example, patients with mutations in Factor V (also known as Factor V Leiden) and additional risk factors (e.g., pregnancy), are dosed with anticoagulants to prevent the reoccurrence of venous thrombosis. Another example entails secondary prevention of cardiovascular events in patients with a history of acute myocardial infarction or acute coronary syndrome. In a clinical setting, a combination of aspirin and clopidogrel (or other thienopyridines) may be used to prevent a second thrombotic event.

Antithrombotic agents are also given to treat the disease state (i.e., by arresting its development) after it has already started. For example, patients presenting with deep vein thrombosis are treated with anticoagulants (i.e., heparin, warfarin, or LMWH) to prevent further growth of the venous occlusion. Over time, these agents also cause a regression of the disease state because the balance between prothrombotic factors and anticoagulant/profibrinolytic pathways is changed in favor of the latter. Examples on the arterial vascular bed include the treatment of patients with acute myocardial infarction or acute coronary syndrome with aspirin and clopidogrel to prevent further growth of vascular occlusions and eventually leading to a regression of thrombotic occlusions.

Thus, antithrombotic agents are used widely for primary and secondary prevention (i.e., prophylaxis or risk reduction) of thromboembolic disorders, as well as treatment of an already existing thrombotic process. Drugs that inhibit blood coagulation, or anticoagulants, are "pivotal agents for prevention and treatment of thromboembolic disorders" (Hirsh, J. et al., *Blood*, 105:453-463 (2005)).

An alternative way of initiation of coagulation is operative when blood is exposed to artificial surfaces (e.g., during hemodialysis, "on-pump" cardiovascular surgery, vessel grafts, bacterial sepsis), on cell surfaces, cellular receptors, cell debris, DNA, RNA, and extracellular matrices. This process is also termed contact activation. Surface absorption of Factor XII leads to a conformational change in the Factor XII molecule, thereby facilitating activation to proteolytic active Factor XII molecules (Factor XIIa and Factor XIIf). Factor XIIa (or XIIf) has a number of target proteins, including plasma prekallikrein and Factor XI. Active plasma kallikrein further activates Factor XII, leading to an amplification of contact activation. Alternatively, the serine protease prolylcarboxylpeptidase can activate plasma kallikrein complexed with high molecular weight kininogen in a multiprotein complex formed on the surface of cells and matrices (Shariat-Madar et al., *Blood*, 108:192-199 (2006)). Contact activation is a surface mediated process responsible in part for the regulation of thrombosis and inflammation, and is mediated, at least in part, by fibrinolytic-, complement-, kininogen/kinin-, and other humoral and cellular pathways (for review, Coleman, R., "Contact Activation Pathway", *Hemostasis and Thrombosis*, pp. 103-122, Lippincott Williams & Wilkins (2001); Schmaier, A. H., "Contact Activation", *Thrombosis and Hemorrhage*, pp. 105-128 (1998)). The biological relevance of the contact activation system for thromboembolic diseases is supported by the phenotype of Factor XII deficient mice. More specifically, Factor XII deficient mice were protected from thrombotic vascular occlusion in several thrombosis models as well as stroke models and the phenotype of the XII deficient mice was identical to XI deficient mice (Renne et al., *J. Exp. Med.*, 202:271-281 (2005); Kleinschmitz et al., *J. Exp. Med.*, 203:513-518 (2006)). The fact that Factor XI is down-stream from Factor XIIa, combined with the identical phenotype of the XII and XI deficient mice suggest that the contact activation system could play a major role in Factor XI activation in vivo.

Factor XI is a zymogen of a trypsin-like serine protease and is present in plasma at a relatively low concentration. Proteolytic activation at an internal R369-I370 bond yields a heavy chain (369 amino acids) and a light chain (238 amino acids). The latter contains a typical trypsin-like catalytic triad (H413, D464, and S557). Activation of Factor XI by thrombin is believed to occur on negatively charged surfaces, most likely on the surface of activated platelets. Platelets contain high affinity (0.8 nM) specific sites (130-500/platelet) for activated Factor XI. After activation, Factor XIa remains surface bound and recognizes Factor IX as its normal macromolecular substrate. (Galiani, D., *Trends Cardiovasc. Med.*, 10:198-204 (2000))

In addition to the feedback activation mechanisms described above, thrombin activates thrombin activated fibrinolysis inhibitor (TAFI), a plasma carboxypeptidase that cleaves C-terminal lysine and arginine residues on fibrin, reducing the ability of fibrin to enhance tissue-type plasminogen activator (tPA) dependent plasminogen activation. In the presence of antibodies to FXIa, clot lysis can occur more rapidly independent of plasma TAFI concentration. (Bouma, B. N. et al., *Thromb. Res.*, 101:329-354 (2001).) Thus, inhibitors of Factor XIa are expected to be anticoagulant and profibrinolytic.

Further evidence for the anti-thromboembolic effects of targeting Factor XI is derived from mice deficient in Factor XI. It has been demonstrated that complete fXI deficiency protected mice from ferric chloride ($FeCl_3$)-induced carotid artery thrombosis (Rosen et al., *Thromb. Haemost.*, 87:774-777 (2002); Wang et al., *J. Thromb. Haemost.*, 3:695-702 (2005)). Also, Factor XI deficiency rescues the perinatal lethal phenotype of complete protein C deficiency (Chan et al., *Amer. J. Pathology*, 158:469-479 (2001)). Furthermore, baboon cross-reactive, function blocking antibodies to human Factor XI protect against baboon arterial venous shunt thrombosis (Gruber et al., *Blood*, 102:953-955 (2003)). Evidence for an antithrombotic effect of small molecule inhibitors of Factor XIa is also disclosed in published U.S. Patent Application No. 2004/0180855A1. Taken together, these studies suggest that targeting Factor XI will reduce the propensity for thrombotic and thromboembolic diseases.

Genetic evidence indicates that Factor XI is not required for normal homeostasis, implying a superior safety profile of the Factor XI mechanism compared to competing antithrombotic mechanisms. In contrast to hemophilia A (Factor VIII deficiency) or hemophilia B (Factor IX deficiency), mutations of the Factor XI gene causing Factor XI deficiency (hemophilia C) result in only a mild to moderate bleeding diathesis characterized primarily by postoperative or post-traumatic, but rarely spontaneous hemorrhage. Postoperative bleeding occurs mostly in tissue with high concentrations of endogenous fibrinolytic activity (e.g., oral cavity, and urogenital system). The majority of the cases are fortuitously identified by preoperative prolongation of aPTT (intrinsic system) without any prior bleeding history.

The increased safety of inhibition of XIa as an anticoagulation therapy is further supported by the fact that Factor XI knock-out mice, which have no detectable Factor XI protein, undergo normal development, and have a normal life span. No evidence for spontaneous bleeding has been noted. The aPTT (intrinsic system) is prolonged in a gene dose-dependent fashion. Interestingly, even after severe stimulation of the coagulation system (tail transection), the bleeding time is not significantly prolonged compared to wild-type and heterozygous litter mates. (Gailani, D., *Frontiers in Bioscience*, 6:201-207 (2001); Gailani, D. et al., *Blood Coagulation and Fibrinolysis*, 8:134-144 (1997).) Taken together, these observations suggest that high levels of inhibition of Factor XIa should be well tolerated. This is in contrast to gene targeting experiments with other coagulation factors, excluding Factor XII.

In vivo activation of Factor XI can be determined by complex formation with either C1 inhibitor or alpha 1 antitrypsin. In a study of 50 patients with acute myocardial infarction (AMI), approximately 25% of the patients had values above the upper normal range of the complex ELISA. This study can be viewed as evidence that at least in a subpopulation of patients with AMI, Factor XI activation contributes to thrombin formation (Minnema, M. C. et al., *Arterioscler. Thromb. Vasc. Biol.*, 20:2489-2493 (2000)). A second study establishes a positive correlation between the extent of coronary arteriosclerosis and Factor XIa in complex with alpha 1 antitrypsin (Murakami, T. et al., *Arterioscler. Thromb. Vasc. Biol.*, 15:1107-1113 (1995)). In another study, Factor XI levels above the 90th percentile in patients were associated with a 2.2-fold increased risk for venous thrombosis (Meijers, J. C. M. et al., *N Engl. J. Med.*, 342:696-701 (2000)).

Plasma kallikrein is a zymogen of a trypsin-like serine protease and is present in plasma at 35 to 50 µg/mL. The gene structure is similar to that of Factor XI. Overall, the amino acid sequence of plasma kallikrein has 58% homology to Factor XI. Proteolytic activation by Factor XIIa at an internal I 389-R390 bond yields a heavy chain (371 amino acids) and a light chain (248 amino acids). The active site of plasma kallikrein is contained in the light chain. The light chain of plasma kallikrein reacts with protease inhibitors, including alpha 2 macroglobulin and C1-inhibitor. Interestingly, heparin significantly accelerates the inhibition of plasma kallikrein by antithrombin III in the presence of high molecular weight kininogen (HMWK). In blood, the majority of plasma kallikrein circulates in complex with HMWK. Plasma kallikrein cleaves HMWK to liberate bradykinin. Bradykinin release results in increase of vascular permeability and vasodilation (for review, Coleman, R., "Contact Activation Pathway", *Hemostasis and Thrombosis*, pp. 103-122, Lippincott Williams & Wilkins (2001); Schmaier A. H., "Contact Activation", *Thrombosis and Hemorrhage*, pp. 105-128 (1998)).

Also, it is preferred to find new compounds with improved activity in in vitro clotting assays, compared with known serine protease inhibitors, such as the activated partial thromboplastin time (aPTT) or prothrombin time (PT) assay. (for a description of the aPTT and PT assays see, Goodnight, S. H. et al., "Screening Tests of Hemostasis", *Disorders of Thrombosis and Hemostasis: A Clinical Guide*, 2nd Edition, pp. 41-51, McGraw-Hill, New York (2001)).

It is also desirable and preferable to find compounds with advantageous and improved characteristics compared with known serine protease inhibitors, in one or more of the following categories that are given as examples, and are not intended to be limiting: (a) pharmacokinetic properties, including oral bioavailability, half life, and clearance; (b) pharmaceutical properties; (c) dosage requirements; (d) factors that decrease blood concentration peak-to-trough characteristics; (e) factors that increase the concentration of active drug at the receptor; (f) factors that decrease the liability for clinical drug-drug interactions; (g) factors that decrease the potential for adverse side-effects, including selectivity versus other biological targets; and (h) factors that improve manufacturing costs or feasibility.

Pre-clinical studies demonstrated significant antithrombotic effects of small molecule Factor XIa inhibitors in rabbit and rat model of arterial thrombosis, at doses that preserved hemostasis. (Wong P. C. et al., *American Heart Association Scientific Sessions*, Abstract No. 6118, November 12-15, 2006; Schumacher, W. et al., *J. Thromb. Haemost*, 3(Suppl. 1):P1228 (2005); Schumacher, W. A. et al., *Eur. J. Pharmacol.*, 167-174 (2007)). Furthermore, it was observed that in vitro prolongation of the aPTT by specific XIa inhibitors is a good predictor of efficacy in our thrombosis models. Thus, the in vitro aPTT test can be used as a surrogate for efficacy in vivo.

As used herein, the term "patient" encompasses all mammalian species.

As used herein, "treating" or "treatment" cover the treatment of a disease-state in a mammal, particularly in a human, and include: (a) inhibiting the disease-state, i.e., arresting it development; and/or (b) relieving the disease-state, i.e., causing regression of the disease state.

As used herein, "prophylaxis" or "prevention" cover the preventive treatment of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population. "Prophylaxis" therapies can be divided into (a) primary prevention and (b) secondary prevention. Primary prevention is defined as treatment in a subject that has not yet presented with a clinical disease state, whereas secondary prevention is defined as preventing a second occurrence of the same or similar clinical disease state.

As used herein, "risk reduction" covers therapies that lower the incidence of development of a clinical disease state. As such, primary and secondary prevention therapies are examples of risk reduction.

"Therapeutically effective amount" is intended to include an amount of a compound of the present invention that is effective when administered alone or in combination to inhibit Factor XIa and/or plasma kallikrein and/or to prevent or treat the disorders listed herein. When applied to a combination, the term refers to combined amounts of the active ingredients that result in the preventive or therapeutic effect, whether administered in combination, serially, or simultaneously.

The term "thrombosis", as used herein, refers to formation or presence of a thrombus (pl. thrombi); clotting within a blood vessel that may cause ischemia or infarction of tissues supplied by the vessel. The term "embolism", as used herein, refers to sudden blocking of an artery by a clot or foreign material that has been brought to its site of lodgment by the blood current. The term "thromboembolism", as used herein, refers to obstruction of a blood vessel with thrombotic material carried by the blood stream from the site of origin to plug another vessel. The term "thromboembolic disorders" entails both "thrombotic" and "embolic" disorders (defined above).

The term "thromboembolic disorders" as used herein includes arterial cardiovascular thromboembolic disorders, venous cardiovascular or cerebrovascular thromboembolic disorders, and thromboembolic disorders in the chambers of the heart or in the peripheral circulation. The term "thromboembolic disorders" as used herein also includes specific disorders selected from, but not limited to, unstable angina or other acute coronary syndromes, atrial fibrillation, first or recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. The medical implants or devices include, but are not limited to: prosthetic valves, artificial valves, indwelling catheters, stents, blood oxygenators, shunts, vascular access ports, ventricular assist devices and artificial hearts or heart chambers, and vessel grafts. The procedures include, but are not limited to: cardiopulmonary bypass, percutaneous coronary intervention, and hemodialysis. In another embodiment, the term "thromboembolic disorders" includes acute coronary syndrome, stroke, deep vein thrombosis, and pulmonary embolism.

In another embodiment, the present invention provides a method for the treatment of a thromboembolic disorder, wherein the thromboembolic disorder is selected from unstable angina, an acute coronary syndrome, atrial fibrillation, myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the treatment of a thromboembolic disorder, wherein the thromboembolic disorder is selected from acute coronary syndrome, stroke, venous thrombosis, atrial fibrillation, and thrombosis resulting from medical implants and devices.

In another embodiment, the present invention provides a method for the primary prophylaxis of a thromboembolic disorder, wherein the thromboembolic disorder is selected from unstable angina, an acute coronary syndrome, atrial fibrillation, myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the primary prophylaxis of a thromboembolic disorder, wherein the thromboembolic disorder is selected from acute coronary syndrome, stroke, venous thrombosis, and thrombosis resulting from medical implants and devices.

In another embodiment, the present invention provides a method for the secondary prophylaxis of a thromboembolic disorder, wherein the thromboembolic disorder is selected from unstable angina, an acute coronary syndrome, atrial fibrillation, recurrent myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the secondary prophylaxis of a thromboembolic disorder, wherein the thromboembolic disorder is selected from acute coronary syndrome, stroke, atrial fibrillation and venous thrombosis.

The term "stroke", as used herein, refers to embolic stroke or atherothrombotic stroke arising from occlusive thrombosis in the carotid communis, carotid interna, or intracerebral arteries.

It is noted that thrombosis includes vessel occlusion (e.g., after a bypass) and reocclusion (e.g., during or after percutaneous transluminal coronary angioplasty). The thromboembolic disorders may result from conditions including but not limited to atherosclerosis, surgery or surgical complications, prolonged immobilization, arterial fibrillation, congenital thrombophilia, cancer, diabetes, effects of medications or hormones, and complications of pregnancy.

Thromboembolic disorders are frequently associated with patients with atherosclerosis. Risk factors for atherosclerosis include but are not limited to male gender, age, hypertension, lipid disorders, and diabetes mellitus. Risk factors for atherosclerosis are at the same time risk factors for complications of atherosclerosis, i.e., thromboembolic disorders.

Similarly, arterial fibrillation is frequently associated with thromboembolic disorders. Risk factors for arterial fibrillation and subsequent thromboembolic disorders include cardiovascular disease, rheumatic heart disease, nonrheumatic mitral valve disease, hypertensive cardiovascular disease, chronic lung disease, and a variety of miscellaneous cardiac abnormalities as well as thyrotoxicosis.

Diabetes mellitus is frequently associated with atherosclerosis and thromboembolic disorders. Risk factors for the more common type 2 include but are not limited to are family history, obesity, physical inactivity, race/ethnicity, previously impaired fasting glucose or glucose tolerance test, history of gestational diabetes mellitus or delivery of a "big baby", hypertension, low HDL cholesterol, and polycystic ovary syndrome.

Risk factors for congenital thrombophilia include gain of function mutations in coagulation factors or loss of function mutations in the anticoagulant- or fibrinolytic pathways.

Thrombosis has been associated with a variety of tumor types, e.g., pancreatic cancer, breast cancer, brain tumors, lung cancer, ovarian cancer, prostate cancer, gastrointestinal malignancies, and Hodgkins or non-Hodgkins lymphoma. Recent studies suggest that the frequency of cancer in patients with thrombosis reflects the frequency of a particular cancer type in the general population (Levitan, N. et al., *Medicine* (Baltimore), 78(5):285-291 (1999); Levine M. et al., *N Engl. J. Med.,* 334(11):677-681 (1996); Blom, J. W. et al., *JAMA,* 293(6):715-722 (2005)). Hence, the most common cancers associated with thrombosis in men are prostate, colorectal, brain, and lung cancer, and in women are breast, ovary, and lung cancer. The observed rate of venous thromboembolism (VTE) in cancer patients is significant. The varying rates of VTE between different tumor types are most likely related to the selection of the patient population. Cancer patients at risk for thrombosis may possess any or all of the following risk factors: (i) the stage of the cancer (i.e., presence of metastases), (ii) the presence of central vein catheters, (iii) surgery and anticancer therapies including chemotherapy, and (iv) hormones and antiangiogenic drugs. Thus, it is common clinical practice to dose patients having advanced tumors with heparin or low molecular heparin to prevent thromboembolic disorders. A number of low molecular heparin preparations have been approved by the FDA for these indications.

There are three main clinical situations when considering the prevention of VTE in a medical cancer patient: (i) the patient is bedridden for prolonged periods of time; (ii) the ambulatory patient is receiving chemotherapy or radiation; and (iii) the patient is with indwelling central vein catheters. Unfractionated heparin (UFH) and low molecular weight heparin (LMWH) are effective antithrombotic agents in cancer patients undergoing surgery. (Mismetti, P. et al., *Brit. J. Surg.*, 88:913-930 (2001).)

A. In Vitro Assays

The effectiveness of compounds of the present invention as inhibitors of the coagulation Factors XIa, VIIa, IXa, Xa, XIIa, plasma kallikrein or thrombin, can be determined using a relevant purified serine protease, respectively, and an appropriate synthetic substrate. The rate of hydrolysis of the chromogenic or fluorogenic substrate by the relevant serine protease was measured both in the absence and presence of compounds of the present invention. Hydrolysis of the substrate resulted in the release of pNA (para nitroaniline), which was monitored spectrophotometrically by measuring the increase in absorbance at 405 nm, or the release of AMC (amino methylcoumarin), which was monitored spectrofluorometrically by measuring the increase in emission at 460 nm with excitation at 380 nm. A decrease in the rate of absorbance or fluorescence change in the presence of inhibitor is indicative of enzyme inhibition. Such methods are known to one skilled in the art. The results of this assay are expressed as the inhibitory constant, $K_i$.

Factor XIa determinations were made in 50 mM HEPES buffer at pH 7.4 containing 145 mM NaCl, 5 mM KCl, and 0.1% PEG 8000 (polyethylene glycol; JT Baker or Fisher Scientific). Determinations were made using purified human Factor XIa at a final concentration of 25-200 pM (Haematologic Technologies) and the synthetic substrate S-2366 (pyroGlu-Pro-Arg-pNA; CHROMOGENIX® or AnaSpec) at a concentration of 0.0002-0.001 M.

Factor VIIa determinations were made in 0.005 M calcium chloride, 0.15 M sodium chloride, 0.05 M HEPES buffer containing 0.1% PEG 8000 at a pH of 7.5. Determinations were made using purified human Factor VIIa (Haematologic Technologies) or recombinant human Factor VIIa (Novo Nordisk) at a final assay concentration of 0.5-10 nM, recombinant soluble tissue factor at a concentration of 10-40 nM and the synthetic substrate H-D-Ile-Pro-Arg-pNA (S-2288; CHROMOGENIX® or BMPM-2; AnaSpec) at a concentration of 0.001-0.0075 M.

Factor IXa determinations were made in 0.005 M calcium chloride, 0.1 M sodium chloride, 0.0000001 M Refludan (Berlex), 0.05 M TRIS base and 0.5% PEG 8000 at a pH of 7.4. Refludan was added to inhibit small amounts of thrombin in the commercial preparations of human Factor IXa. Determinations were made using purified human Factor IXa (Haematologic Technologies) at a final assay concentration of 20-100 nM and the synthetic substrate PCIXA2100-B (CenterChem) or Pefafluor IXa 3688 (H-D-Leu-Plf Gly-Arg-AMC; CenterChem) at a concentration of 0.0004-0.0005 M.

Factor Xa determinations were made in 0.1 M sodium phosphate buffer at a pH of 7.5 containing 0.2 M sodium chloride and 0.5% PEG 8000. Determinations were made using purified human Factor Xa (Haematologic Technologies) at a final assay concentration of 150-1000 pM and the synthetic substrate S-2222 (Bz-Ile-Glu (gamma-OMe, 50%)-Gly-Arg-pNA; CHROMOGENIX®) at a concentration of 0.0002-0.00035 M.

Factor XIIa determinations were made in 50 mM HEPES buffer at pH 7.4 containing 145 mM NaCl, 5 mM KCl, and 0.1% PEG 8000. Determinations were made using purified human Factor XIIa at a final concentration of 4 nM (American Diagnostica) and the synthetic substrate SPECTROZYME® #312 (H-D-CHT-Gly-L-Arg-pNA.2AcOH; American Diagnostica) at a concentration of 0.00015 M.

Plasma kallikrein determinations were made in 0.1 M sodium phosphate buffer at a pH of 7.5 containing 0.1-0.2 M sodium chloride and 0.5% PEG 8000. Determinations were made using purified human kallikrein (Enzyme Research Laboratories) at a final assay concentration of 200 pM and the synthetic substrate S-2302 (H-(D)-Pro-Phe-Arg-pNA; CHROMOGENIX®) at a concentration of 0.00008-0.0004 M. The $K_m$ value used for calculation of $K_i$ was 0.00005 to 0.00007 M.

Thrombin determinations were made in 0.1 M sodium phosphate buffer at a pH of 7.5 containing 0.2 M sodium chloride and 0.5% PEG 8000. Determinations were made using purified human alpha thrombin (Haematologic Technologies or Enzyme Research Laboratories) at a final assay concentration of 200-250 pM and the synthetic substrate S-2366 (pyroGlu-Pro-Arg-pNA; CHROMOGENIX® or AnaSpec) at a concentration of 0.0002-0.0004 M.

The Michaelis constant, $K_m$, for substrate hydrolysis by each protease, was determined at 25° C. using the method of Lineweaver and Burk. Values of $K_i$ were determined by allowing the protease to react with the substrate in the presence of the inhibitor. Reactions were allowed to go for periods of 20-180 minutes (depending on the protease) and the velocities (rate of absorbance or fluorescence change versus time) were measured. The following relationships were used to calculate $K_i$ values:

$(v_o-v_s)/v_s=I/(K_i(1+S/K_m))$ for a competitive inhibitor with one binding site; or $v_s/v_o=A+((B-A)/1+((IC_{50}/(I)_n)))$; and $K_i=IC_{50}/(1+S/K_m)$ for a competitive inhibitor where:
$v_o$ is the velocity of the control in the absence of inhibitor;
$v_s$ is the velocity in the presence of inhibitor;
I is the concentration of inhibitor;
A is the minimum activity remaining (usually locked at zero);
B is the maximum activity remaining (usually locked at 1.0);
n is the Hill coefficient, a measure of the number and cooperativity of potential inhibitor binding sites;
$IC_{50}$ is the concentration of inhibitor that produces 50% inhibition under the assay conditions;
$K_i$ is the dissociation constant of the enzyme:inhibitor complex;
S is the concentration of substrate; and
$K_m$ is the Michaelis constant for the substrate.

The selectivity of a compound may be evaluated by taking the ratio of the $K_i$ value for a given protease with the $K_i$ value for the protease of interest (i.e., selectivity for FXIa versus protease P=$K_i$ for protease P/$K_i$ for FXIa). Compounds with selectivity ratios>20 are considered selective. Compounds with selectivity ratios>100 are preferred, and compounds with selectivity ratios>500 are more preferred.

The effectiveness of compounds of the present invention as inhibitors of coagulation can be determined using a standard or modified clotting assay. An increase in the plasma clotting time in the presence of inhibitor is indicative of anticoagulation. Relative clotting time is the clotting time in the presence of an inhibitor divided by the clotting time in the absence of an inhibitor. The results of this assay may be expressed as IC1.5x or IC2x, the inhibitor concentration required to increase the clotting time by 50 or 100 percent, respectively. The IC1.5x or IC2x is found by linear interpolation from relative clotting time versus inhibitor concentration plots using inhibitor concentration that spans the IC1.5x or IC2x.

Clotting times are determined using citrated normal human plasma as well as plasma obtained from a number of laboratory animal species (e.g., rat, or rabbit). A compound is diluted into plasma beginning with a 10 mM DMSO stock solution. The final concentration of DMSO is less than 2%. Plasma clotting assays are performed in an automated coagulation analyzer (Sysmex, Dade-Behring, Illinois). Similarly, clotting times can be determined from laboratory animal species or humans dosed with compounds of the invention.

Activated Partial Thromboplastin Time (aPTT) is determined using ALEXIN® (Trinity Biotech, Ireland) or ACTIN® (Dade-Behring, Illinois) following the directions in the package insert. Plasma (0.05 mL) is warmed to 37° C. for 1 minute. ALEXIN® or ACTIN® (0.05 mL) is added to the plasma and incubated for an additional 2 to 5 minutes. Calcium chloride (25 mM, 0.05 mL) is added to the reaction to initiate coagulation. The clotting time is the time in seconds from the moment calcium chloride is added until a clot is detected.

Prothrombin Time (PT) is determined using thromboplastin (Thromboplastin C Plus, Dade-Behring, Illinois) following the directions in the package insert. Plasma (0.05 mL) is warmed to 37° C. for 1 minute. Thromboplastin (0.1 mL) is added to the plasma to initiate coagulation. The clotting time is the time in seconds from the moment thromboplastin is added until a clot is detected.

The exemplified Examples disclosed below were tested in the Factor XIa assay described above and found having Factor XIa inhibitory activity. A range of Factor XIa inhibitory activity (Ki values) of ≤10 μM (10000 nM) was observed. Table 1 below lists Factor XIa Ki values measured for the following examples.

TABLE 1

| Example No. | Factor XIa Ki (nM) |
| --- | --- |
| 1 | 2983 |
| 3 | 6174 |
| 4 | 636 |
| 6 | 34 |
| 9 | 249 |
| 10 | <5 |
| 11 | 6 |
| 19 | 96 |
| 21 | 4515 |
| 61 | <5 |
| 89 | 1057 |
| 90 | <5 |
| 93 | <5 |
| 121 | <5 |
| 122 | 25 |
| 136 | 962 |
| 137 | 192 |
| 138 | 20 |
| 167 | 157 |
| I-4 | <5 |
| I-5 | <5 |
| I-9 | 1872 |
| I-10 | 217 |
| I-13 | 311 |

TABLE 1-continued

| Example No. | Factor XIa Ki (nM) |
| --- | --- |
| I-14 | 2920 |
| I-17 | 351 |
| I-21 | <5 |
| I-57 | 6.6 |
| I-59 | <5 |
| I-60 | 616 |
| I-67 | 203 |
| I-70 | 270 |
| I-72 | 289 |
| I-77 | <5 |
| I-80 | <5 |
| I-84 | 580 |
| I-94 | 3851 |
| I-99 | 1322 |
| I-104 | 435 |
| I-106 | 24 |
| I-107 | 29 |
| I-108 | 3869 |
| I-114 | 296 |
| I-115 | <5 |
| I-121 | 736 |
| I-124 | <5 |
| I-134 | <5 |
| I-136 | 183 |
| I-137 | 2979 |
| I-151 | <5 |
| I-152 | 21 |
| I-153 | 1652 |
| I-183 | 4949 |
| I-211 | 2171 |
| I-227 | <5 |
| I-242 | 456 |
| I-251 | <5 |
| I-258 | 947 |
| I-262 | 675 |
| I-265 | 133 |
| I-268 | 9 |
| I-270 | 1745 |
| I-278 | <5 |
| I-284 | 102 |
| I-299 | 19 |
| I-309 | 9 |
| I-311 | <5 |
| II-3 | <5 |
| II-4 | 111 |
| II-10 | 23 |
| II-13 | <5 |
| II-15 | 4156 |
| II-18 | 572 |
| II-35 | <5 |
| II-43 | 938 |
| II-58 | 21 |
| II-62 | <5 |

B. In Vivo Assays

The effectiveness of compounds of the present invention as antithrombotic agents can be determined using relevant in vivo thrombosis models, including In Vivo Electrically-induced Carotid Artery Thrombosis Models and In Vivo Rabbit Arterio-venous Shunt Thrombosis Models.

a. In Vivo Electrically-Induced Carotid Artery Thrombosis (ECAT) Model

The rabbit ECAT model, described by Wong et al. (*J. Pharmacol. Exp. Ther.*, 295:212-218 (2000)), can be used in this study. Male New Zealand White rabbits are anesthetized with ketamine (50 mg/kg+50 mg/kg/h IM) and xylazine (10 mg/kg+10 mg/kg/h IM). These anesthetics are supplemented as needed. An electromagnetic flow probe is placed on a segment of an isolated carotid artery to monitor blood flow. Test agents or vehicle will be given (i.v., i.p., s.c., or orally) prior to or after the initiation of thrombosis. Drug treatment prior to initiation of thrombosis is used to model the ability of test agents to prevent and reduce the risk of thrombus formation, whereas dosing after initiation is used to model the ability to treat existing thrombotic disease. Thrombus formation is induced by electrical stimulation of the carotid artery for 3 min at 4 mA using an external stainless-steel bipolar electrode. Carotid blood flow is measured continuously over a 90-min period to monitor thrombus-induced occlusion. Total carotid blood flow over 90 min is calculated by the trapezoidal rule. Average carotid flow over 90 min is then determined by converting total carotid blood flow over 90 min to percent of total control carotid blood flow, which would result if control blood flow had been maintained continuously for 90 min. The $ED_{50}$ (dose that increased average carotid blood flow over 90 min to 50% of the control) of compounds are estimated by a nonlinear least square regression program using the Hill sigmoid $E_{max}$ equation (DeltaGraph; SPSS Inc., Chicago, IL).

b. In Vivo Rabbit Arterio-Venous (AV) Shunt Thrombosis Model

The rabbit AV shunt model, described by Wong et al. (Wong, P. C. et al., *J. Pharmacol. Exp. Ther.*, 292:351-357 (2000)), can be used in this study. Male New Zealand White rabbits are anesthetized with ketamine (50 mg/kg+50 mg/kg/h IM) and xylazine (10 mg/kg+10 mg/kg/h IM). These anesthetics are supplemented as needed. The femoral artery, jugular vein and femoral vein are isolated and catheterized. A saline-filled AV shunt device is connected between the femoral arterial and the femoral venous cannulae. The AV shunt device consists of an outer piece of tygon tubing (length=8 cm; internal diameter=7.9 mm) and an inner piece of tubing (length=2.5 cm; internal diameter=4.8 mm). The AV shunt also contains an 8-cm-long 2-0 silk thread (Ethicon, Somerville, NJ). Blood flows from the femoral artery via the AV-shunt into the femoral vein. The exposure of flowing blood to a silk thread induces the formation of a significant thrombus. Forty minutes later, the shunt is disconnected and the silk thread covered with thrombus is weighed. Test agents or vehicle will be given (i.v., i.p., s.c., or orally) prior to the opening of the AV shunt. The percentage inhibition of thrombus formation is determined for each treatment group. The $ID_{50}$ values (dose that produces 50% inhibition of thrombus formation) are estimated by a nonlinear least square regression program using the Hill sigmoid $E_{max}$ equation (DeltaGraph; SPSS Inc., Chicago, IL).

The anti-inflammatory effect of these compounds can be demonstrated in an Evans Blue dye extravasation assay using C1-esterase inhibitor deficient mice. In this model, mice are dosed with a compound of the present invention, Evans Blue dye is injected via the tail vein, and extravasation of the blue dye is determined by spectrophotometric means from tissue extracts.

The ability of the compounds of the current invention to reduce or prevent the systemic inflammatory response syndrome, for example, as observed during on-pump cardiovascular procedures, can be tested in in vitro perfusion systems, or by on-pump surgical procedures in larger mammals, including dogs and baboons. Read-outs to assess the benefit of the compounds of the present invention include for example reduced platelet loss, reduced platelet/white blood cell complexes, reduced neutrophil elastase levels in plasma, reduced activation of complement factors, and reduced activation and/or consumption of contact activation proteins (plasma kallikrein, Factor XII, Factor XI, high molecular weight kininogen, C1-esterase inhibitors).

The compounds of the present invention may also be useful as inhibitors of additional serine proteases, notably human thrombin, human plasma kallikrein and human plasmin. Because of their inhibitory action, these compounds are indicated for use in the prevention or treatment of physiological reactions, including blood coagulation, fibrinolysis, blood pressure regulation and inflammation, and wound healing catalyzed by the aforesaid class of enzymes. Specifically, the compounds have utility as drugs for the treatment of diseases arising from elevated thrombin activity of the aforementioned serine proteases, such as myocardial infarction, and as reagents used as anticoagulants in the processing of blood to plasma for diagnostic and other commercial purposes.

V. Pharmaceutical Compositions, Formulations and Combinations

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 18th Edition (1990).

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to about 1000 mg/kg of body weight, preferably between about 0.01 to about 100 mg/kg of body weight per day, and most preferably between about 0.1 to about 20 mg/kg/day. Intravenously, the most preferred doses will range from about 0.001 to about 10 mg/kg/minute during a constant rate infusion. Compounds of this invention may be administered in a single daily dose, or the total daily dosage may be administered in divided doses of two, three, or four times daily.

Compounds of this invention can also be administered by parenteral administration (e.g., intra-venous, intra-arterial, intramuscularly, or subcutaneously. When administered intra-venous or intra-arterial, the dose can be given continuously or intermittent. Furthermore, formulation can be developed for intramuscularly and subcutaneous delivery that ensure a gradual release of the active pharmaceutical ingredient.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 1000 milligrams of active ingredient per dosage unit. In these pharmaceutical compositions the active ingredient will ordinarily be present in an amount of about 0.1-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfate, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Where the compounds of this invention are combined with other anticoagulant agents, for example, a daily dosage may be about 0.1 to about 100 milligrams of the compound of the present invention and about 0.1 to about 100 milligrams per kilogram of patient body weight. For a tablet dosage form, the compounds of this invention generally may be present in an amount of about 5 to about 100 milligrams per dosage unit, and the second anti-coagulant in an amount of about 1 to about 50 milligrams per dosage unit.

Where the compounds of the present invention are administered in combination with an anti-platelet agent, by way of general guidance, typically a daily dosage may be about 0.01 to about 25 milligrams of the compound of the present invention and about 50 to about 150 milligrams of the anti-platelet agent, preferably about 0.1 to about 1 milligrams of the compound of the present invention and about 1 to about 3 milligrams of antiplatelet agents, per kilogram of patient body weight.

Where the compounds of the present invention are administered in combination with thrombolytic agent, typically a daily dosage may be about 0.1 to about 1 milligrams of the compound of the present invention, per kilogram of patient body weight and, in the case of the thrombolytic agents, the usual dosage of the thrombolyic agent when administered alone may be reduced by about 50-80% when administered with a compound of the present invention.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

In another embodiment, the present invention provides a pharmaceutical composition further comprising additional therapeutic agent(s) selected from potassium channel openers, potassium channel blockers, calcium channel blockers, sodium hydrogen exchanger inhibitors, antiarrhythmic agents, antiatherosclerotic agents, anticoagulants, anti-thrombotic agents, prothrombolytic agents, fibrinogen antagonists, diuretics, antihypertensive agents, ATPase inhibitors, mineralocorticoid receptor antagonists, phospodiesterase inhibitors, antidiabetic agents, anti-inflammatory agents, antioxidants, angiogenesis modulators, antiosteoporosis agents, hormone replacement therapies, hormone receptor modulators, oral contraceptives, antiobesity agents, antidepressants, antianxiety agents, antipsychotic agents, antiproliferative agents, antitumor agents, antiulcer and gastroesophageal reflux disease agents, growth hormone agents and/or growth hormone secretagogues, thyroid mimetics, anti-infective agents, antiviral agents, antibacterial agents, antifungal agents, cholesterol/lipid lowering agents and lipid profile therapies, and agents that mimic ischemic preconditioning and/or myocardial stunning, or a combination thereof.

In another embodiment, the present invention provides a pharmaceutical composition further comprising additional therapeutic agent(s) selected from an anti-arrhythmic agent, an anti-hypertensive agent, an anti-coagulant agent, an anti-platelet agent, a thrombin inhibiting agent, a thrombolytic agent, a fibrinolytic agent, a calcium channel blocker, a potassium channel blocker, a cholesterol/lipid lowering agent, or a combination thereof.

In another embodiment, the present invention provides a pharmaceutical composition further comprising additional therapeutic agent(s) selected from warfarin, unfractionated heparin, low molecular weight heparin, synthetic pentasaccharide, hirudin, argatroban, aspirin, ibuprofen, naproxen, sulindac, indomethacin, mefenamate, dipyridamol, droxicam, diclofenac, sulfinpyrazone, piroxicam, ticlopidine, clopidogrel, tirofiban, eptifibatide, abciximab, melagatran, ximelagatran, disulfatohirudin, tissue plasminogen activator, modified tissue plasminogen activator, anistreplase, urokinase, and streptokinase, or a combination thereof.

In another embodiment, the present invention provides a pharmaceutical composition wherein the additional therapeutic agent is an antihypertensive agent selected from ACE inhibitors, AT-1 receptor antagonists, beta-adrenergic receptor antagonists, ETA receptor antagonists, dual ETA/AT-1 receptor antagonists, renin inhibitors (alliskerin) and vasopepsidase inhibitors, an antiarrythmic agent selected from IKur inhibitors, an anticoagulant selected from thrombin inhibitors, antithrombin-III activators, heparin co-Factor II activators, other Factor XIa inhibitors, other kallikrein inhibitors, plasminogen activator inhibitor (PAI-1) antagonists, thrombin activatable fibrinolysis inhibitor (TAFI) inhibitors, Factor VIIa inhibitors, Factor IXa inhibitors, and Factor Xa inhibitors, or an antiplatelet agent selected from GPIIb/IIIa blockers, GP Ib/IX blockers, protease activated receptor 1 (PAR-1) antagonists, protease activated receptor4 (PAR-4) antagonists, prostaglandin E2 receptor EP3 antagonists, collagen receptor antagonists, phosphodiesterase-III inhibitors, $P2Y_1$ receptor antagonists, $P2Y_{12}$ antagonists, thromboxane receptor antagonists, cyclooxygense-1 inhibitors, and aspirin, or a combination thereof.

In another embodiment, the present invention provides pharmaceutical composition, wherein the additional therapeutic agent(s) are an anti-platelet agent or a combination thereof.

In another embodiment, the present invention provides a pharmaceutical composition, wherein the additional therapeutic agent is the anti-platelet agent clopidogrel.

The compounds of the present invention can be administered alone or in combination with one or more additional therapeutic agents. By "administered in combination" or "combination therapy" it is meant that the compound of the present invention and one or more additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

Compounds that can be administered in combination with the compounds of the present invention include, but are not limited to, anticoagulants, anti-thrombin agents, anti-platelet agents, fibrinolytics, hypolipidemic agents, antihypertensive agents, and anti-ischemic agents.

Other anticoagulant agents (or coagulation inhibitory agents) that may be used in combination with the compounds of this invention include warfarin, heparin (either unfractionated heparin or any commercially available low molecular weight heparin, for example LOVENOX®), synthetic pentasaccharide, direct acting thrombin inhibitors including hirudin and argatroban, as well as other Factor VIIa inhibitors, Factor IXa inhibitors, Factor Xa inhibitors (e.g., ARIXTRAC®, apixaban, rivaroxaban, LY-517717, DU-176b, DX-9065a, and those disclosed in WO 98/57951, WO 03/026652, WO 01/047919, and WO 00/076970), Factor XIa inhibitors, and inhibitors of activated TAFI and PAI-1 known in the art.

The term anti-platelet agents (or platelet inhibitory agents), as used herein, denotes agents that inhibit platelet function, for example, by inhibiting the aggregation, adhesion or granule-content secretion of platelets. Such agents include, but are not limited to, the various known non-steroidal anti-inflammatory drugs (NSAIDs) such as acetaminophen, aspirin, codeine, diclofenac, droxicam, fentaynl, ibuprofen, indomethacin, ketorolac, mefenamate, morphine, naproxen, phenacetin, piroxicam, sufentanyl, sulfinpyrazone, sulindac, and pharmaceutically acceptable salts or prodrugs thereof. Of the NSAIDs, aspirin (acetylsalicylic acid or ASA) and piroxicam are preferred. Other suitable platelet inhibitory agents include glycoprotein IIb/IIIa antagonists (e.g., tirofiban, eptifibatide, abciximab, and integrelin), thromboxane-A2-receptor antagonists (e.g., ifetroban), thromboxane-A-synthetase inhibitors, phosphodiesterase-III (PDE-III) inhibitors (e.g., dipyridamole, cilostazol), and PDE-V inhibitors (such as sildenafil), protease-activated receptor 1 (PAR-1) antagonists (e.g., E-5555, SCH-530348, SCH-203099, SCH-529153 and SCH-205831), and pharmaceutically acceptable salts or prodrugs thereof.

Other examples of suitable anti-platelet agents for use in combination with the compounds of the present invention, with or without aspirin, are ADP (adenosine diphosphate) receptor antagonists, preferably antagonists of the purinergic receptors $P2Y_1$ and $P2Y_{12}$, with $P2Y_{12}$ being even more preferred. Preferred $P2Y_{12}$ receptor antagonists include clopidogrel, ticlopidine, prasugrel, ticagrelor, and cangrelor, and pharmaceutically acceptable salts or prodrugs thereof. Ticlopidine and clopidogrel are also preferred compounds since they are known to be more gentle than aspirin on the gastro-intestinal tract in use. Clopidogrel is an even more preferred agent.

A preferred example is a triple combination of a compound of the present invention, aspirin, and another anti-platelet agent. Preferably, the anti-platelet agent is clopidogrel or prasugrel, more preferably clopidogrel.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the secretion of platelet granule contents including serotonin) and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin, argatroban, dabigatran, AZD-0837, and those disclosed in WO 98/37075 and WO 02/044145, and pharmaceutically acceptable salts and prodrugs thereof. Boroarginine derivatives and boropeptides include N-acetyl and peptide derivatives of boronic acid, such as C-terminal a-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin.

The term thrombolytic (or fibrinolytic) agents (or thrombolytics or fibrinolytics), as used herein, denotes agents that lyse blood clots (thrombi). Such agents include tissue plasminogen activator (TPA, natural or recombinant) and modified forms thereof, anistreplase, urokinase, streptokinase, tenecteplase (TNK), lanoteplase (nPA), Factor VIIa inhibitors, thrombin inhibitors, inhibitors of Factors IXa, Xa, and XIa, PAI-I inhibitors (i.e., inactivators of tissue plasminogen activator inhibitors), inhibitors of activated TAFI, alpha-2-antiplasmin inhibitors, and anisoylated plasminogen streptokinase activator complex, including pharmaceutically acceptable salts or prodrugs thereof. The term anistreplase, as used herein, refers to anisoylated plasminogen streptokinase activator complex, as described, for example, in European Patent Application No. 028489, the disclosure of which is hereby incorporated herein by reference herein. The term urokinase, as used herein, is intended to denote both dual and single chain urokinase, the latter also being referred to herein as prourokinase.

Examples of suitable cholesterol/lipid lowering agents and lipid profile therapies for use in combination with the compounds of the present invention include HMG-CoA reductase inhibitors (e.g., pravastatin, lovastatin, simvastatin, fluvastatin, atorvastatin, rosuvastatin, and other statins), low-density lipoprotein (LDL) receptor activity modulators (e.g., HOE-402, PCSK9 inhibitors), bile acid sequestrants (e.g., cholestyramine and colestipol), nicotinic acid or derivatives thereof (e.g., NIASPAN®), GPR109B (nicotinic acid receptor) modulators, fenofibric acid derivatives (e.g., gemfibrozil, clofibrate, fenofibrate and benzafibrate) and other peroxisome proliferator-activated receptors (PPAR) alpha modulators, PPARdelta modulators (e.g., GW-501516), PPARgamma modulators (e.g., rosiglitazone), compounds that have multiple functionality for modulating the activities of various combinations of PPARalpha, PPARgamma and PPARdelta, probucol or derivatives thereof (e.g., AGI-1067), cholesterol absorption inhibitors and/or Niemann-Pick C1-like transporter inhibitors (e.g., ezetimibe), cholesterol ester transfer protein inhibitors (e.g., CP-529414), squalene synthase inhibitors and/or squalene epoxidase inhibitors or mixtures thereof, acyl coenzyme A: cholesteryl acyltransferase (ACAT) 1 inhibitors, ACAT2 inhibitors, dual ACAT1/2 inhibitors, ileal bile acid transport inhibitors (or apical sodium co-dependent bile acid transport inhibitors), microsomal triglyceride transfer protein inhibitors, liver-X-receptor (LXR) alpha modulators, LXRbeta modulators, LXR dual alpha/beta modulators, FXR modulators, omega 3 fatty acids (e.g., 3-PUFA), plant stanols and/or fatty acid esters of plant stanols (e.g., sitostanol ester used in BENECOL® margarine), endothelial lipase inhibitors, and HDL functional mimetics which activate reverse cholesterol transport (e.g., apoAI derivatives or apoAI peptide mimetics).

The compounds of the present invention are also useful as standard or reference compounds, for example as a quality standard or control, in tests or assays involving the inhibition of thrombin, Factor VIIa, IXa, Xa, XIa, and/or plasma kallikrein. Such compounds may be provided in a commercial kit, for example, for use in pharmaceutical research involving thrombin, Factor VIIa, IXa, Xa, XIa, and/or plasma kallikrein. XIa. For example, a compound of the present invention could be used as a reference in an assay to compare its known activity to a compound with an unknown activity. This would ensure the experimentor that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving thrombin, Factor VIIa, IXa, Xa, XIa, and/or plasma kallikrein. For example, the presence of thrombin, Factor VIIa, IXa, Xa XIa, and/or plasma kallikrein in an unknown sample could be determined by addition of the relevant chromogenic substrate, for example S2366 for Factor XIa, to a series of solutions containing test sample and optionally one of the compounds of the present invention. If production of pNA is observed in the solutions containing test sample, but not in the presence of a compound of the present invention, then one would conclude Factor XIa was present.

Extremely potent and selective compounds of the present invention, those having $K_i$ values less than or equal to 0.001 µM against the target protease and greater than or equal to 0.1 µM against the other proteases, may also be used in diagnostic assays involving the quantitation of thrombin, Factor VIIa, IXa, Xa, XIa, and/or plasma kallikrein in serum samples. For example, the amount of Factor XIa in serum samples could be determined by careful titration of protease activity in the presence of the relevant chromogenic substrate, S2366, with a potent and selective Factor XIa inhibitor of the present invention.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a thromboembolic and/or inflammatory disorder (as defined previously). In another embodiment, the package insert states that the pharmaceutical composition can be used in combination (as defined previously) with a second therapeutic agent to treat a thromboembolic and/or inflammatory disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Other features of the invention will become apparent in the course of the following descriptions of exemplary embodiments that are given for illustration of the invention and are not intended to be limiting thereof. The following Examples have been prepared, isolated and characterized using the methods disclosed herein.

Intermediate 1. (E)-2,5-Dioxopyrrolidin-1-yl 3-(5-chloro-2-(1H-tetrazol-1-yl)phenyl)acrylate

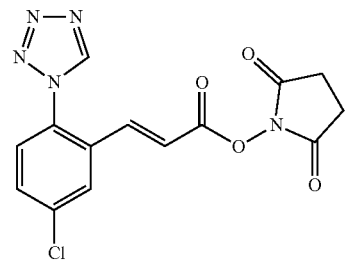 [SMILES: O=C(/C=C/c1cc(Cl)ccc1-n1cnnn1)ON1C(=O)CCC1=O]

The synthesis was described as Intermediate 1 in PCT International Application No. WO 2009/114677 published Sep. 17, 2009.

Intermediate 2. (E)-3-(5-Chloro-2-tetrazol-1-yl-phenyl)-acrylic Acid

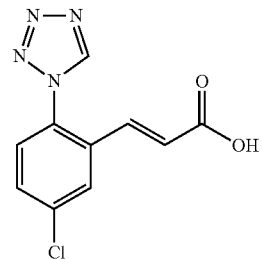

The synthesis was described as Intermediate 1B in PCT International Application No. WO 2009/114677 published Sep. 17, 2009.

Intermediate 3. (E)-3-(3-Chloro-2-fluoro-6-tetrazol-1-yl-phenyl)-acrylic Acid 2,5-dioxo-pyrrolidin-1-yl ester

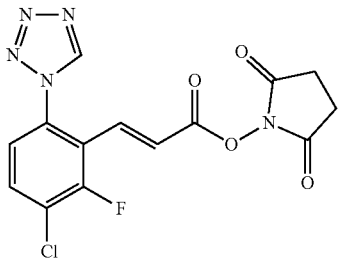 [SMILES: O=C(/C=C/c1c(-n2cnnn2)ccc(Cl)c1F)ON1C(=O)CCC1=O]

Intermediate 3A. (E)-3-(3-Chloro-2-fluoro-6-(1H-tetrazol-1-yl)phenyl)acrylic acid: The synthesis of Intermediate 3A was described as Intermediate 7 in PCT International Application No. WO 2009/114677 published Sep. 17, 2009.

Intermediate 3. To a slightly turbid mixture of Intermediate 3A (1.0 g, 3.72 mmol) in THF (18.70 mL) and DMF (1.870 mL) was added 1-hydroxypyrrolidine-2,5-dione (0.471 g, 4.09 mmol) and DIC (0.638 mL, 4.09 mmol). The reaction was stirred at rt and a white precipitate formed overtime. The solid was collected by suction filtration and washed with MeOH, water, MeOH, air-dried, and dried under vacuum to give Intermediate 3 (0.98 g, 72.0% yield), as a white solid. MS (ESI) m/z: 366.2 (M+H)+.

Intermediate 4. (E)-3-(2-Acetyl-5-chlorophenyl)acrylic Acid

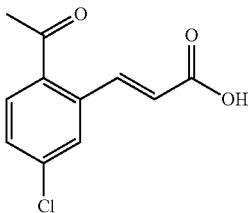

Intermediate 4A. (E)-tert-Butyl 3-(2-acetyl-5-chlorophenyl)acrylate: To a degassed solution of 1-(2-bromo-4-chlorophenyl)ethanone (1.0 g, 4.28 mmol), tributylamine (2.041 mL, 8.57 mmol), and tert-butyl acrylate (1.255 mL, 8.57 mmol) in DMF (10 mL) was added palladium on carbon (0.456 g, 0.428 mmol) and palladium(II) acetate (0.096 g, 0.428 mmol). The reaction mixture was warmed to 100° C. After 16 h, the reaction was cooled to rt. The reaction was filtered and the solid was rinsed with DMF. The filtrate was diluted with EtOAc, washed with water (2×), brine, dried over sodium sulfate, filtered and concentrated. Purification by normal phase chromatography afforded Intermediate 4A (0.760 g, 63%), as a brown oil. MS (ESI) m/z: 225.0 (M–C4H8+H)+.

Intermediate 4. A solution of Intermediate 4A (0.048 g, 0.171 mmol) in 50% TFA/DCM (2 mL) was stirred at rt. After 1 h, the reaction was concentrated to give Intermediate 4 (0.038 g, 100% yield) as a yellow solid. The material was used without further purification. MS (ESI) m/z: 225.1 (M+H)+.

Intermediate 5. 1-Amino-5,6,7,8-tetrahydroisoquinoline-6-carboxylic Acid

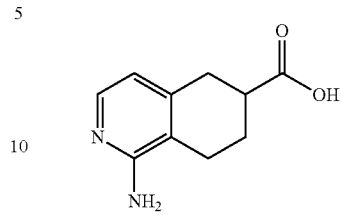

The synthesis was described as Example 147, Part E in U.S. Patent Application No. 2005/0282805 published Dec. 22, 2005.

Intermediate 6. 2-Bromo-1-(2-(but-3-enyloxy)phenyl)ethanone

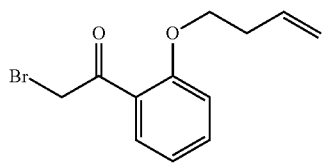

Intermediate 6A. 1-(2-But-3-enyloxy-phenyl)-ethanone: To a white suspension of potassium carbonate (15.2 g, 110 mmol) in acetone (29.4 mL) was added 5-bromobut-1-ene (3.73 mL, 36.7 mmol) and 1-(2-hydroxyphenyl)ethanone (4.42 mL, 36.7 mmol). The resulting off-white suspension was warmed to reflux and stirred overnight. The reaction was cooled to rt, filtered and the filtrate was concentrated. The residue was partitioned between water and EtOAc and the layers were separated. The aqueous layer was extracted with EtOAc (2×20 mL). The combined organic layers were washed with brine, dried over Na2SO4, filtered and concentrated. Purification by normal phase chromatography gave 1.12 g (15%) of Intermediate 6A, as a dark purple oil. MS (ESI) m/z: 205.2 (M+H)+.

Intermediate 6. A suspension of Intermediate 6A (1.1153 g, 5.86 mmol) and copper (II) bromide (2.62 g, 11.73 mmol) in EtOAc (10.47 mL) was warmed to reflux. After 1 h, the suspension was cooled to rt, filtered, and the filtrate was concentrated to give a greenish-brown residue. The greenish-brown residue was taken up in EtOAc (100 mL) and washed with water (2×100 mL). The organic layer was then washed with brine, dried over Na2SO4, filtered, and concentrated. Purification by normal phase chromatography gave 0.773 g (44%) of Intermediate 6, as a yellow oil. MS (ESI) m/z: 271.1 (M+H)+.

Intermediate 7. Methyl 4-(2-bromoacetyl)-3-(but-3-enyloxy)phenylcarbamate

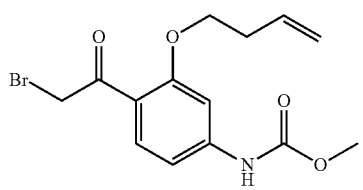 [SMILES: C=CCCOc1cc(NC(=O)OC)ccc1C(=O)CBr]

Intermediate 7A. 1-(4-Amino-2-(but-3-enyloxy)phenyl)ethanone: A suspension of 1-(4-amino-2-hydroxyphenyl)ethanone (3 g, 19.85 mmol), 4-bromobut-1-ene (6.04 mL, 59.5 mmol) and $K_2CO_3$ (16.46 g, 119 mmol) in acetone (30 mL) was heated in a sealed tube at 60° C. After 18 h, another 2 eq. of 4-bromobut-1-ene was added and the reaction was heated at 60° C. for 18 h. This process was repeated one more time, and the reaction was cooled to rt, diluted with EtOAc, washed with water, brine, dried over sodium sulfate, filtered and concentrated. Purification by normal phase chromatography afforded 1.055 g (14.24%) of Intermediate 7A, as a yellow solid. MS (ESI) m/z: 206.0 $(M+H)^+$.

Intermediate 7B. Methyl 4-acetyl-3-(but-3-enyloxy)phenylcarbamate: To a cooled (0° C.), clear yellow solution of Intermediate 7A (1.055 g) in DCM (9.42 mL) and pyridine (0.252 mL, 3.11 mmol) was added dropwise methyl chloroformate (0.230 mL, 2.97 mmol). The resulting yellow suspension was stirred at 0° C. for 2 h. The reaction was partitioned between EtOAc/sat. sodium bicarbonate and the layers were separated. The aqueous layer was extracted with EtOAc (1×). The combined organic layers were washed with brine, dried over sodium sulfate, filtered and concentrated to give a yellow solid. The solid was purified by trituration from DCM. The solid was collected via Buchner funnel filtration and rinsed with DCM (3×2 mL), air-dried, and dried under vacuum to give 0.91 g of Intermediate 7B as a white solid. MS (ESI) m/z: 264.0 $(M+H)^+$.

Intermediate 7 was prepared following the procedure described in Intermediate 6, by replacing Intermediate 6A with Intermediate 7B. The material was used without further purification. MS (ESI) m/z: 341.9 $(M+H)^+$ and 343.9 $(M+2+H)^+$.

Intermediate 8. [3-Bromo-4-(2-bromo-acetyl)-phenyl]-carbamic Acid methyl ester

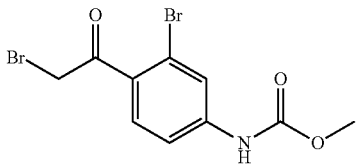 [SMILES: COC(=O)Nc1ccc(C(=O)CBr)c(Br)c1]

Intermediate 8A. 1-(4-Amino-2-bromophenyl)ethanone: (Caution, possible explosion hazard!) A clear, colorless solution of 1-(2-bromo-4-fluorophenyl)ethanone (22.8 g, 0.105 mol) in DMSO (105 mL) and ammonium hydroxide (68.2 mL, 0.526 mol) was divided into nineteen 20-mL microwave vials. The vials were sealed, microwaved at 150° C. for 1.5 h, and then cooled to rt. All the reactions were combined, partitioned between DCM and water (400 mL) and the layers were separated. The aqueous layer was extracted with DCM (2×). The combined organic layers were washed with brine, dried over sodium sulfate, filtered, and concentrated to give 35 g of Intermediate 8A as an orange oil. The material was carried onto the next step without further purification. MS (ESI) m/z: 212.4 $(M+H)^+$ and 214.4 $(M+2+H)^+$.

Intermediate 8 was prepared following the procedures described in Intermediate 7, by replacing Intermediate 7A with Intermediate 8A. MS (ESI) m/z: 352.1 $(M+H)^+$ and 354.1 $(M+2+H)^+$.

An alternative preparation of Intermediate 8 is highlighted below:

Alternative Intermediate 8A. 1-(4-Amino-2-bromophenyl)ethanone: To a solution of Intermediate 10C (19 g, 0.077 mol) in ethanol (400 mL) was added in portions tin(II) chloride (74 g, 0.39 mol). Following the addition, the reaction was heated to reflux overnight. The reaction was concentrated and the residue was dissolved in 10% aq. sodium hydroxide (200 mL). The solution was extracted with ethyl acetate (2×200 mL). The combined organic layers were washed with brine and concentrated to afford an oil. Petroleum ether (25 mL) was added to give a suspension. The petroleum ether was decanted and the solid was suspended in 20% ethyl acetate/petroleum ether. The solid was collected to afford 14 g of Intermediate 8A.

Alternative Intermediate 8B. (4-Acetyl-3-bromo-phenyl)-carbamic acid methyl ester: To a cooled (10° C.) mixture of alternative Intermediate 8A (14 g, 0.065 mol) and Hunig's base (12.7 g, 0.098 mol) in dry dioxane (140 mL) was added dropwise methyl chloroformate (7.4 g, 0.078 m). After 3 h, the reaction was quenched with water (100 mL) and then extracted with ethyl acetate (2×150 mL). The combined organic layers were washed with brine, dried over sodium sulfate, filtered, and concentrated. Purification by trituration from isopropanol provided 14 g of the alternative Intermediate 8B. MS (ESI) m/z: 271.7 $(M+H)^+$. $^1H$ NMR (400 MHz, DMSO-$d_6$) δ: 2.50 (s, 3H), 3.71 (s, 3H), 7.53-7.56 (m, 1H), 7.78 (d, J=8.8 Hz, 1H), 7.86 (d, J=2.0 Hz, 1H), 10.14 (s, 1H).

Alternative Intermediate 8. To a cooled (10° C.) solution of alternative Intermediate 8B (90 g, 0.33 mol) in dry dioxane (900 mL) was added a solution of bromine (52.9 g, 0.33 mol) in dioxane (430 mL) dropwise over 1 h. After 2 h, ice cold water (500 mL) was added and the reaction was extracted with ethyl acetate (2×500 mL). The combined organic layers were washed with brine, dried over sodium sulfate, filtered, and concentrated to afford 110 g of crude product. A suspension of the crude product in ethanol (1 L) was warmed to 50° C. After a clear solution formed, water (1.0 L) was added dropwise and the mixture was gradually cooled to 35° C. The precipitated solid was collected by filtration, washed with ethanol (200 mL), air-dried, and then dried at 50° C. under vacuum for 30 min to yield 70 g of alternative Intermediate 8.

Intermediate 9. Methyl 4-(2-bromoacetyl)-3-nitrophenylcarbamate

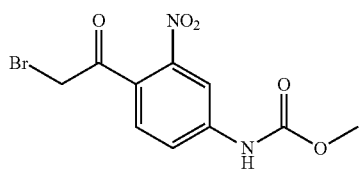 [SMILES: COC(=O)Nc1ccc(C(=O)CBr)c([N+](=O)[O-])c1]

Intermediate 9A. Methyl 4-iodo-3-nitrophenylcarbamate: To a cooled (0° C.), yellow suspension of 4-iodo-3-nitroaniline (8.46 g, 32.0 mmol) in DCM (320 mL) and pyridine (2.85 mL, 35.2 mmol) was added dropwise methyl chloroformate (2.61 mL, 33.6 mmol). The resulting clear, light yellow solution was stirred at 0° C. After 1.5 h, the reaction was diluted with DCM, washed with sat. $NaHCO_3$, brine, dried over $MgSO_4$, filtered and concentrated. The residue was dissolved in a minimal amount of DCM (~100 mL) and then hexane (600 mL) was added to give a yellow suspension. The suspension was filtered, and the solid was rinsed with hexane and then dried to give Intermediate 9A (10.3 g, 100%), as yellow solid. MS (ESI) m/z: 321.3 (M−H)⁻.

Intermediate 9B. Methyl 4-(1-ethoxyvinyl)-3-nitrophenylcarbamate: A solution of Intermediate 9A (6 g, 18.63 mmol), tributyl(1-ethoxyvinyl)stannane (7.55 mL, 22.36 mmol), and bis(triphenylphosphine)palladium(II) chloride (0.654 g, 0.932 mmol) in toluene (37.3 mL) was heated at 110° C. After 2 h, the reaction was cooled to rt. The reaction mixture was filtered through a 0.45 micron GMF, rinsing with EtOAc. The filtrate was concentrated. Purification by normal phase chromatography gave Intermediate 9B (3.59 g, 72.4% yield), as a brown solid. MS (ESI) m/z: 267.4 (M+H)⁺.

Intermediate 9. To a slightly cloudy orange mixture of Intermediate 9B (3.59 g, 13.48 mmol) in THF (20 mL) and water (7 mL) was added NBS (2.400 g, 13.48 mmol). The resulting clear, yellow solution was stirred at rt for 20 min and then the reaction was partitioned between EtOAc/brine. The layers were separated and the organic layer washed with brine, dried over Na₂SO₄, filtered, and concentrated to afford Intermediate 9 (4.28 g, 100% yield), as a yellow foam. This material was used without further purification. MS (ESI) m/z: 317.3 (M+H)⁺, 319.3 (M+2+H)⁺.

Alternatively, Intermediate 9B can be hydrolyzed with aqueous 1N HCl to give the methyl ketone which can then be brominated with copper (II) bromide according to the procedure described in Intermediate 6.

Intermediate 10.
2-Bromo-1-(2-bromo-4-nitrophenyl)ethanone

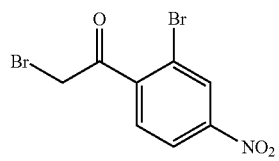 [SMILES: O=C(CBr)c1ccc([N+](=O)[O-])cc1Br]

Intermediate 10A. 2-Bromo-4-nitro-benzoic acid: To a warm (80° C.) solution of pyridine (500 mL) and water (1.0 L) was added 4-nitro-2-bromo toluene (100 g, 0.46 mol). The resulting suspension was stirred until it became a clear solution. Next, KMnO₄ (600 g, 3.8 mol) was added in portions over 1.5 h. The reaction was stirred overnight. The reaction mixture was cooled to RT and then 10% aq. sodium hydroxide (200 mL) was added. After 15 min, the reaction was filtered to remove the solid. The solid was rinsed with 10% aq. sodium hydroxide (5×100 mL). The filtrate was extracted with MTBE (3×250 mL). The clear aqueous layer was cooled to 10° C. and then it was acidified with concentrated HCl. The aqueous layer was extracted with MTBE (4×500 mL). The organic layers were combined, dried over sodium sulfate, filtered and concentrated to afford 72 g of Intermediate 10A. ¹h NMR (400 MHz, DMSO-d₆) δ: 7.96 (d, J=8 Hz, 1H), 8.28-8.48 (m, 1H), 8.49 (d, J=2.4 Hz, 1H), 14.1 (br. s, 1H).

Intermediate 10B. 2-(2-Bromo-4-nitro-benzoyl)-malonic acid diethyl ester: To a solution of Intermediate 10A (50 g, 0.2 mol) in toluene (500 mL) was added triethylamine (24.6 g, 0.24 mol). The reaction was cooled to 15° C. and ethyl chloroformate (24 g, 0.22 mol) was added. After 45 min, the mixed anhydride solution was cooled to 0° C.

In a separate flask: To a suspension of Mg turnings (5.4 g) in dry ether (300 mL) was added ethanol (3.0 mL), carbon tetrachloride (2.0 mL), and diethyl malonate (34 mL, 0.22 mol). The mixture was stirred at 40° C. for an hour to ensure that the magnesium dissolved completely. After the reaction became a clear solution, it was added to the cooled solution of the mixed anhydride. After 2 h, the reaction was quenched with 2N sulfuric acid (200 mL) and then extracted with ethyl acetate (4×100 mL). The combined organic layers were dried over sodium sulfate, filtered and concentrated to give 80 g of Intermediate 10B. This was used in the next step without further purification.

Intermediate 10C. 1-(2-Bromo-4-nitro-phenyl)-ethanone: A mixture of Intermediate 10B (80 g, 0.2 mol) in acetic acid (400 mL) and sulfuric acid (400 mL) was stirred at 105° C. After 3 h, the reaction was cooled to RT and then extracted with ethyl acetate (2×500 mL). The combined organic layers were washed with 20% aq. sodium hydroxide, dried over sodium sulfate, filtered and concentrated to give 43.0 g of Intermediate 10C. ¹H NMR (400 MHz, CDCl₃) δ: 2.66 (s, 3H), 7.57 (d, J=8 Hz, 1H), 8.21-8.24 (dd, 1H), 8.48 (d, J=2.0 Hz, 1H).

Intermediate 10. To a cooled (10° C.) solution of the Intermediate 10C (43 g, 0.17 mol) in dry dioxane (430 mL) was added a dropwise over 1.5 h a solution of bromine (31 g) in dioxane (430 mL). The reaction was stirred for 30 min and then ice cold water (150 mL) was added. The reaction was extracted with ethyl acetate (2×200 mL). The combined organic layers were washed with brine, dried over sodium sulfate, filtered and concentrated. Purification by normal phase chromatography (petroleum ether/ethyl acetate) gave 30 g of Intermediate 10. ¹H NMR (400 MHz, CDCl₃) δ4.46 (s, 2H), 7.62 (d, J=8.4 Hz, 1H), 8.25-8.27 (dd, 1H), 8.50 (d, J=2.4 Hz, 1H).

Intermediate 11. Methyl 4-(2-bromoacetyl)-3-(pent-4-enyloxy)phenylcarbamate

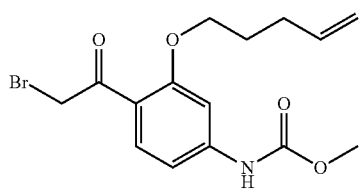 [SMILES: C=CCCCOc1cc(NC(=O)OC)ccc1C(=O)CBr]

This compound was prepared following the procedures described in Intermediate 7, by replacing 4-bromobut-1-ene with 5-bromopent-1-ene. MS (ESI) m/z: 355.9 (M+H)⁺, 357.9 (M+2+H)⁺.

Intermediate 12. 2-(5,5-Dimethyl-1,3,2-dioxaborinan-2-yl)-5-nitro-phenylamine

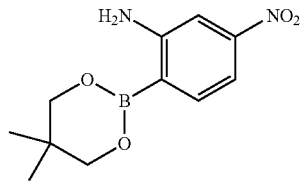 [SMILES: CC1(C)COB(c2ccc([N+](=O)[O-])cc2N)OC1]

To a flame-dried flask, equipped with a reflux condensor, containing 2-bromo-5-nitroaniline (10.0 g, 46.1 mmol), bis (neopentyl glycolato)diboron (13.01 g, 57.6 mmol), potassium acetate (13.57 g, 138 mmol), and PdCl₂(dppf)·CH₂Cl₂ adduct (0.941 g, 1.152 mmol) was added DMSO (132 mL). The resulting dark red-brown suspension was degassed with argon for 30 min. and then the reaction was warmed to 80° C. After 4 h, the reaction was stopped and cooled to rt. The reaction was poured slowly into vigorously stirred ice-cold water (300 mL) to give a brown suspension. After stirring for 10 min, the suspension was filtered to collect the solid. The solid was rinsed with water (3×125 mL), air-dried, and then dried under a vacuum to give a brown solid. Purification by normal phase chromatography gave 4.36 g of Intermediate 12 as an orange solid. MS (ESI) m/z: 183.1 (M–$C_5H_8$+H)$^+$.

Intermediate 13. 4-(5,5-Dimethyl-1,3,2-dioxaborinan-2-yl)-3-[2-(1,3-dioxo-1,3-dihydro-isoindol-2-yl)-ethoxy]-benzoic acid methyl ester

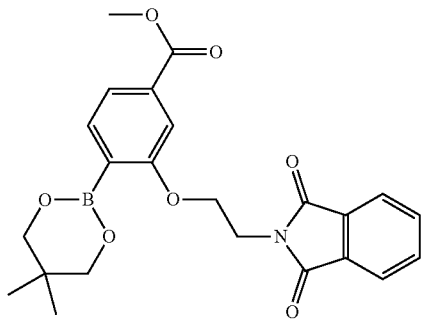 [SMILES: COC(=O)c1ccc(B2OCC(C)(C)CO2)c(OCCN2C(=O)c3ccccc3C2=O)c1]

Intermediate 13A. 4-Bromo-3-[2-(1,3-dioxo-1,3-dihydro-isoindol-2-yl)-ethoxy]-benzoic acid methyl ester: To a solution of methyl 4-bromo-3-hydroxybenzoate (2.0 g, 8.66 mmol) and 2-(2-bromoethyl)isoindoline-1,3-dione (2.419 g, 9.52 mmol) in DMF (10 mL) was added NaH (0.866 g, 21.64 mmol) in small portions at 0° C. The reaction was stirred under argon at 0° C. for 2 h. The reaction was warmed to 60° C. and stirred for 4 h. After cooling to rt, the reaction mixture was diluted with EtOAc, washed with 1M HCl, saturated NaHCO$_3$ and brine. The organic phase was dried over MgSO$_4$, filtered and concentrated. Purification by normal phase chromatography gave Intermediate 13A (0.36 g, 10.3% yield) as a white solid. MS (ESI) m/z: 404.0/406.0 (M+H)$^+$.

Intermediate 13 was prepared following the procedure described in Intermediate 12, by replacing 2-bromo-5-nitroaniline with Intermediate 13A and running the reaction in acetonitrile at 90° C. MS (ESI) m/z: 352.1 (M+H)$^+$.

Intermediate 14. [3-[(Benzyloxycarbonyl-methyl-amino)-methyl]-4-(2-bromo-acetyl)-phenyl]-carbamic Acid methyl ester

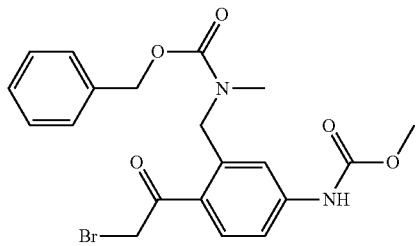 [SMILES: COC(=O)Nc1ccc(C(=O)CBr)c(CN(C)C(=O)OCc2ccccc2)c1]

Intermediate 14A. Benzyl 5-amino-2-bromobenzyl(methyl)carbamate: To a mixture of benzyl 2-bromo-5-nitrobenzyl(methyl)carbamate (3.0 g, 7.91 mmol) in MeOH (60 mL) was added ammonium chloride (2.116 g, 39.6 mmol) and zinc (2.59 g, 39.6 mmol) at 0° C. The reaction mixture was warmed up to rt and stirred under argon for 3 h. The solid was filtered off and the solvent was removed to give Intermediate 14A (2.72 g, 98% yield) as a light tan solid. MS (ESI) m/z: 350.8 (M+H)$^+$.

Intermediate 14 was prepared following the procedures described in Intermediate 9, by replacing 4-iodo-3-nitroaniline with Intermediate 14A. MS (ESI) m/z: 449.0 (M+H)$^+$.

Intermediate 15. (E)-3-(3-Chloro-2,6-difluoro-phenyl)-acrylic Acid

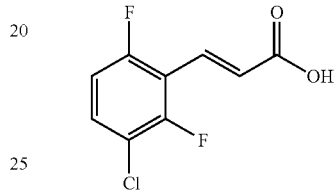

Intermediate 15A. 3-Chloro-2,6-difluorobenzaldehyde: To a solution of (3-chloro-2,6-difluorophenyl)methanol (1.07 g, 5.99 mmol) in CH$_2$Cl$_2$ (20 ml) was added Dess-Martin periodinane (3.05 g, 7.19 mmol). After 2h, the reaction was concentrated. Purification by normal phase chromatography gave Intermediate 15A (0.94 g, 89% yield), as a white solid. MS (ESI) m/z: 177.1 (M+H)$^+$.

Intermediate 15B. (E)-tert-Butyl 3-(3-chloro-2,6-difluorophenyl)acrylate: To a solution of Intermediate 15A (0.94 g, 5.32 mmol) in THF (30 ml) were added tert-butyl 2-(dimethoxyphosphoryl)acetate (1.194 g, 5.32 mmol) and KOtBu (0.896 g, 7.99 mmol). After 2 h, the reaction was diluted with EtOAc, washed with H$_2$O, brine, dried over MgSO$_4$, filtered and concentrated. Purification by normal phase chromatography provided Intermediate 15B (0.866 g, 59.2% yield), as a clear colorless oil. MS (ESI) m/z: 219.2 (M–$^t$Bu+H)$^+$.

Intermediate 15. To a solution of Intermediate 15B (0.866 g, 3.15 mmol) in DCM (7.0 ml) was added TFA (3.0 mL, 38.9 mmol). After 1.5 h, the reaction was concentrated and the residue was dried in vacuo to give Intermediate 15 (0.689 g, 100% yield) as an off-white solid. MS (ESI) m/z: 219.1 (M+H)$^+$.

Intermediate 17.
2-Bromo-1-(2-bromo-4-fluoro-phenyl)-ethanone

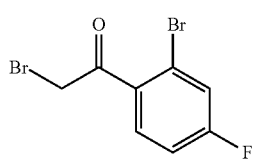 [SMILES: O=C(CBr)c1ccc(F)cc1Br]

The synthesis was described as Method A-1, Page 92 in PCT International Application No. WO 2005/014566 published Feb. 17, 2005.

Intermediate 18. (E)-3-(6-Acetyl-3-chloro-2-fluorophenyl)-acrylic Acid

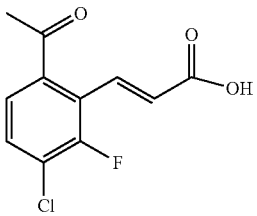 [SMILES: CC(=O)c1ccc(Cl)c(F)c1/C=C/C(=O)O]

Intermediate 18A. 2-Bromo-4-chloro-3-fluorobenzoic acid: To a cooled (−78° C.) solution of DIEA (4.9 mL, 48 mmol) in THF was added dropwise n-BuLi (132 mL, 2.3 eq, 2.5 M solution). The mixture was stirred at −30° C. for 30 min. Again the reaction mixture was cooled to −78° C., and a solution of 4-chloro-3-fluorobenzoic acid (25 g, 143 mmol) in THF was added over 1 h. The reaction was stirred at −78° C. overnight. The next day a solution of 1,2-dibromo-1,1,2,2-tetrachloroethane (87 g, 267 mmol) in THF was added and the reaction was stirred at −78° C. for further 2 h and then RT for 4 h. The reaction mixture was quenched with water, the layers were separated, and the aqueous layer washed with Et$_2$O. The aqueous layer was acidified with 1.5 N HCl and then extracted in EtOAc (2×200 mL). The combined organic layers were dried over anhydrous Na$_2$SO$_4$, filtered and concentrated to afford Intermediate 18A (30 g, 83.3%). MS (ESI) m/z: 252.6 (M−H)$^+$.

Intermediate 18B. Diethyl 2-((2-bromo-4-chloro-3-fluorophenyl) (hydroxy)methylene)malonate: To a suspension of Intermediate 18A (14.6 g, 57 mmol) in DCM (200 mL) was added thionyl chloride (6.6 mL, 88 mmol). The mixture was stirred at reflux for 3 h. The solvent was removed and the residue was dried in vacuum to give the acid chloride as a light brown solid.

To a cooled (0° C.) suspension of sodium hydride (3.66 g (60%), 91.5 mmol) in THF was added a solution of diethyl malonate (0.612 g, 3.82 mmol) in THF (5 mL). After 10 min, a solution of the acid chloride (16.4 g, 60 mmol) in THF (160 mL) was added slowly. Following the addition, the reaction was warmed to RT. After 30 min, the solvent was removed and the residue was treated with cold (0° C.) 1.2 M HCl (150 mL). The mixture was extracted with EtOAc (3×250 mL). The combined organic layers were washed with brine, dried over Na$_2$SO$_4$, filtered and concentrated to give Intermediate 18B (20 g, 87%) as a solid. MS (ESI) m/z: 395/397 (M+H)$^+$.

Intermediate 18C. 1-(2-Bromo-4-chloro-3-fluorophenyl)ethanone: A solution of Intermediate 18B (18.6 g, 47 mmol) in acetic acid (200 mL), H$_2$O (150 mL) and H$_2$SO$_4$ (2.0 mL) was stirred at 110° C. for 4 h. Most of the solvent was removed and the residue was diluted with EtOAc (400 mL), washed with water (5×20 mL), saturated NaHCO$_3$, 1N NaOH, and brine. The solvent was removed to give Intermediate 18C (10 g, 84%) as a low melting solid. $^1$H NMR (400 MHz, DMSO-d$_6$) δ: 7.42 (q, J=6.8, 6.4 Hz, 1H), 7.24 (q, J=6.4, 5.2 Hz, 1H), 2.5 (s, 3H).

Intermediate 18D. (E)-tert-Butyl 3-(6-acetyl-3-chloro-2-fluorophenyl)acrylate: To the mixture of Intermediate 18C (50 g, 198 mmol), tert-butyl acrylate (50.9 g, 397 mmol) and TEA (55 mL, 397 mmol) in DMF (500 mL) was added Pd(OAc)$_2$ (8.9 g, 39.7 mmol). The resulting mixture was stirred at 90° C. overnight. The reaction was cooled to RT, filtered, and the filtrate was concentrated. Purification by normal phase chromatography gave Intermediate 18D (30 g, 50.8%) as a light yellow solid. MS (ESI) m/z: 242.7 (M+H)$^+$.

Intermediate 18. A solution of Intermediate 18D (25 g, 84 mmol) in DCM (330 mL) and TFA (330 mL) was stirred at RT. After 1.5 h, the solvent was concentrated to give Intermediate 18 (19.5 g, 97.0) as a white solid. $^1$H NMR (400 MHz, DMSO-d$_6$) δ: 12.69 (bs, 1H), 7.80-7.76 (m, 2H), 7.62 (d, J=12.1 Hz, 1H), 6.30 (dd, J=2.4, 2.0 Hz, 1H), 2.6 (s, 3H). MS (ESI) m/z: 241 (M−H)$^+$.

Intermediate 19. (E)-3-(5-Chloro-2-(difluoromethyl)phenyl)acrylic Acid

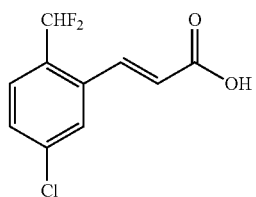 [SMILES: O=C(O)/C=C/c1cc(Cl)ccc1C(F)F]

Intermediate 19A. 2-Bromo-4-chloro-1-(difluoromethyl)benzene: To a solution of 2-bromo-4-chlorobenzaldehyde (1 g, 4.56 mmol) in DCM (15 mL) was added DAST (0.903 mL, 6.83 mmol) at 0° C. The reaction was allowed to warm to rt and stir overnight. The reaction mixture was diluted with EtOAc, washed with sat NaHCO$_3$ and brine. The organic phase was dried over magnesium sulfate, filtered and concentrated to give Intermediate 19A (0.88g. 80% yield) as a clear oil. MS (ESI) m/z: 261.2 (M+Na)$^+$.

Intermediate 19B. (E)-tert-Butyl 3-(5-chloro-2-(difluoromethyl)phenyl)acrylate: To a solution of Intermediate 19A (0.88 g, 3.64 mmol) in DMF (10 mL) was added tert-butyl acrylate (1.401 g, 10.93 mmol), TEA (1.270 mL, 9.11 mmol) and palladium acetate (0.082 g, 0.364 mmol). The reaction was warmed to 90° C. After 5 h, the reaction was cooled to rt and then filtered to remove the solid. The filtrate was diluted with EtOAc, washed with 1M HCl, sat NaHCO$_3$ and brine. The organic phase was dried over magnesium sulfate, filtered and concentrated. Purification by normal phase chromatography gave Intermediate 19B (232 mg, 22% yield) as a tan oil. MS (ESI) m/z: 233.1 (M−tBu)$^+$.

Intermediate 19. A solution of Intermediate 19B (232 mg, 0.804 mmol) in DCM (2.0 mL) was added TFA (2.0 mL, 26.0 mmol). The reaction was stirred under argon at rt. After 1 h, the solvent was removed and the residue was dried to give Intermediate 19 (191 mg, 100% yield) as tan solid. $^1$H NMR (400 MHz, CD$_3$OD) δ 7.99 (dt, J=15.8, 1.5 Hz, 1H), 7.83 (s, 1H), 7.60 (d, J=8.3 Hz, 1H), 7.55-7.48 (m, 1H), 7.01 (t, J=54.6 Hz, 1H), 6.51 (d, J=15.8 Hz, 1H). $^{19}$F NMR (376 MHz, CD$_3$OD) δ −111.67 (s, 2F). MS (EST) m/z: 233.1 (M+H)$^+$.

Intermediate 20. (E)-3-(5-Chloro-2-(1H-1,2,4-tri-azol-1-yl)phenyl)acrylic Acid

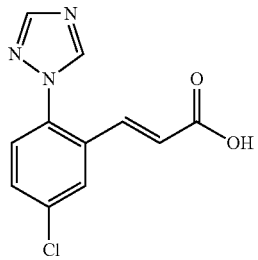 [SMILES: O=C(O)/C=C/c1cc(Cl)ccc1-n1cncn1]

Intermediate 20A. 5-Chloro-2-(1H-1,2,4-triazol-1-yl)benzaldehyde: A mixture of 5-chloro-2-fluorobenzaldehyde (0.634 g, 4 mmol), 1H-1,2,4-triazole (0.290 g, 4.20 mmol), and cesium carbonate (1.564 g, 4.80 mmol) in DMF (6 mL) was stirred at 50° C. After 20 h, the reaction was cooled to RT, partitioned between water and EtOAc and the layers were separated. The organic layer was washed with water, brine, dried over $Na_2SO_4$, filtered and concentrated. The residue was suspended in DCM (5 mL) and then it was filtered. The solid was washed with hexane, air-dried, and dried under vacuum to give 0.22 g (26.5%) of Intermediate 20A, as a yellow solid. MS (ESI) m/z: 208.1 (M+H)+. $^1$H NMR (400 MHz, $CDCl_3$) δ: 7.48 (d, J=8.2 Hz, 1H), 7.72 (dd, J=2.2 Hz, 8.2 Hz, 1H), 8.06 (d, J=2.2 Hz, 1H), 8.20 (s, 1H), 8.48 (s, 1H), 9.99 (s, 1H).

Intermediate 20B. (E)-tert-Butyl 3-(5-chloro-2-(1H-1,2,4-triazol-1-yl)phenyl)acrylate: To a suspension of NaH (60%, 0.100 g, 2.495 mmol) in THF (4 mL) was added dropwise tert-butyl 2-(dimethoxyphosphoryl)acetate (0.530 mL, 2.67 mmol). The cloudy reaction mixture was stirred at RT for 45 min and then cooled to 0° C. Next a solution of Intermediate 20A (0.37 g, 1.78 mmol) in THF (14 mL) was added. The reaction mixture turned orange. After 30 min, the reaction was quenched with saturated $NH_4Cl$ and then the reaction was diluted with EtOAc and water. The layers were separated and the organic layer was washed with brine, dried over $Na_2SO_4$, filtered and concentrated. Purification by normal phase chromatography afforded 0.178 g (26%) of Intermediate 20B, as a yellow gum. MS (ESI) m/z: 306.3 (M+H)+. $^1$H NMR (400 MHz, $CDCl_3$) δ ppm 1.49 (s, 9H), 6.38 (d, J=15.9 Hz, 1H), 7.34-7.42 (m, 2H), 7.48 (dd, J=8.3, 2.2 Hz, 1H), 7.73 (d, J=2.2 Hz, 1H), 8.17 (s, 1H), 8.29 (s, 1H).

Intermediate 20. To a solution of Intermediate 20B (0.178 g, 0.582 mmol) in DCM (1 ml) was added TFA (1 ml, 12.98 mmol). The reaction mixture was stirred at rt for 1 h and then it was concentrated to dryness. MeOH (3 mL) was added to give a white suspension. The solid was collected by filtration, rinsing with a small amount of methanol. The solid was air-dried and dried under vacuum to give 0.076 g (52%) of Intermediate 20 as a white solid. MS (ESI) m/z: 250.1 (M+H)+. $^1$H NMR (400 MHz, DMSO-$d_6$) δ ppm 6.65 (d, 15.9 Hz, 1H), 7.21 (d, 15.9 Hz, 1H), 7.60 (d, J=8.2 Hz, 1 H), 7.68 (dd, J=2.2 Hz, 8.2 Hz, 1H), 8.16 (d, J=2.2 Hz, 1H), 8.32 (s, 1H), 8.93 (s, 1H), 12.64 (s, 1H).

Intermediate 21. (E)-3-(5-Chloro-2-(4H-1,2,4-tri-azol-4-yl)phenyl)acrylic Acid

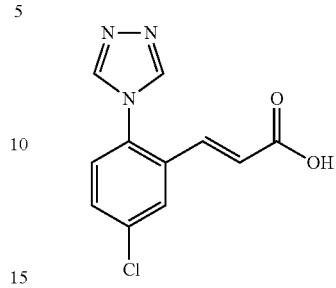

Intermediate 21A. 4-(4-Chloro-2-iodophenyl)-4H-1,2,4-triazole: To a suspension of 4-chloro-2-iodoaniline (0.760 g, 3 mmol) and N'-formylformohydrazide (0.793 g, 9 mmol) in pyridine (12 ml) was added dropwise chlorotrimethylsilane (5.71 ml, 45 mmol) followed by TEA (2.84 ml, 20.4 mmol). The reaction mixture was heated at 100° C. After 4 h, the reaction was cooled to rt and the reaction was concentrated to give a solid. The solid was suspended in water and the solid was collected by filtration, washing with water. The solid was air-dried and dried under vacuum to give 0.8 g as an off-white solid. Purification by normal phase chromatography afforded 0.59 g (64%) of Intermediate 21A, as a white solid. MS (ESI) m/z: 306.1 (M+H)+. $^1$H NMR (400 MHz, DMSO-$d_6$) δ ppm 7.56 (d, J=8.2 Hz, 1H), 7.67 (dd, J=2.2 Hz, 8.2 Hz, 1H), 8.17 (d, J=2.2 Hz, 1H), 8.78 (s, 2H).

Intermediate 21B. (E)-tert-Butyl 3-(5-chloro-2-(4H-1,2,4-triazol-4-yl)phenyl)acrylate: To a degassed solution of Intermediate 21A (0.48 g, 1.571 mmol), tributylamine (0.749 mL, 3.14 mmol), and tert-butyl acrylate (1.151 mL, 7.86 mmol) in DMF (7.86 mL) was added palladium on carbon (10% w/w, 0.167 g, 0.157 mmol) and palladium(II) acetate (0.035 g, 0.157 mmol). The reaction was heated at 100° C. for 18 h. Additional tert-butyl acrylate (1.151 mL, 7.86 mmol) and palladium(II) acetate (0.035 g, 0.157 mmol) was added and the reaction was stirred at 100° C. for another 48 h. The reaction was cooled to RT, filtered through a 0.45 µm GMF, and rinsed with EtOAc. The filtrate was diluted with EtOAc, washed with water, brine, dried over $Na_2SO_4$, filtered and concentrated. Purification by normal phase chromatography followed by reverse phase chromatography gave 0.122 g (25%) of Intermediate 21B, as a white solid. $^1$H NMR (500 MHz, $CD_3OD$) δ ppm 1.47 (s, 9H), 6.51 (d, J=16.0 Hz, 1H), 7.12 (d, J=15.7 Hz, 1H), 7.52 (d, J=8.5 Hz, 1H), 7.62 (dd, J=8.5, 2.2 Hz, 1H), 7.97 (d, J=2.2 Hz, 1H), 8.86 (s, 2H).

Intermediate 21. To the solution of Intermediate 21B (0.122 g, 0.399 mmol) in DCM (0.5 mL) was added TFA (0.5 mL, 6.49 mmol). The reaction was stirred at rt for 2 h, then it was concentrated to afford 0.100 g (100%) of Intermediate 21, as a white solid. MS (ESI) m/z: 249.9 (M+H)+.

Intermediate 22.
4-(N-(tert-Butoxycarbonyl)carbamimidoyl)benzoic Acid, 2 NaOH Salt

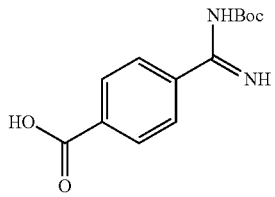 [SMILES: CC(C)(C)OC(=O)NC(=N)c1ccc(C(=O)O)cc1]

Intermediate 22A. Methyl 4-(N-hydroxycarbamimidoyl)benzoate: To a solution of methyl 4-cyanobenzoate (1.003 g, 6.22 mmol) in MeOH (15 mL) was added hydroxylamine hydrochloride (2.162 g, 31.1 mmol) and TEA (4.34 mL, 31.1 mmol). The reaction was stirred at rt for 24 h, then the reaction was concentrated to give a white solid. Water and DCM were added to give a suspension. The suspension was filtered and the solid was rinsed with water and then air-dried to give 1.14 g (94%) of Intermediate 22A, as a white solid. MS (ESI) m/z: 195.0 (M+H)+. $^1$H NMR (500 MHz, $CD_3OD$) δ ppm 3.91 (s, 3H), 7.74-7.77 (m, 2H), 8.01-8.04 (m, 2H). The material was carried onto the next step without further purification.

Intermediate 22B. Methyl 4-carbamimidoylbenzoate, 1 acetic acid salt: To a solution of Intermediate 22A (1.14 g, 5.87 mmol) in acetic acid (5 mL) was added acetic anhydride (2 mL, 21.20 mmol). The reaction turned to a white gel. After 10 min, MeOH (50 mL) was added followed by palladium on carbon (10% w/w, 0.625 g, 0.587 mmol). Hydrogen gas was bubbled through the reaction mixture for a few minutes, then the reaction was stirred under a $H_2$-balloon. After 24 h, the reaction was filtered through a 0.45 µm GMF rinsing with MeOH. The filtrate was concentrated to give 1.32 g (94%) of Intermediate 22B as a white solid. MS (ESI) m/z: 179.0 (M+H)+. $^1$H NMR (400 MHz, $CD_3OD$) δ ppm 1.90 (s, 3H), 3.96 (s, 3H), 7.89 (d, J=8.8 Hz, 2H), 8.22 (d, J=8.8 Hz, 2H).

Intermediate 22C. Methyl 4-(N-(tert-butoxycarbonyl)carbamimidoyl)benzoate: To a white suspension of Intermediate 22B (1.82 g, 7.64 mmol) in DCM (102 mL) was added di-tert-butyl dicarbonate (2.452 g, 11.24 mmol) and TEA (4.27 mL, 30.6 mmol). The reaction mixture was stirred at rt. Overtime, the reaction became a clear solution. After 72 h, additional di-tert-butyl dicarbonate (0.4 eq, 0.879 g) was added, and the reaction was stirred at rt. After an additional 24 h, the reaction was concentrated. Purification by normal phase chromatography afforded 0.84 g (30%) of Intermediate 22C as a white solid. MS (ESI) m/z: 277.3 (M–H)−. $^1$H NMR (500 MHz, $CD_3OD$) δ ppm 1.52 (s, 9H), 3.93 (s, 3H), 7.86-7.91 (m, 2H), 8.07-8.10 (m, 2H).

Intermediate 22. To a solution of Intermediate 22C (0.84 g, 3.02 mmol) in MeOH (15.09 mL) was added 1N NaOH (6.04 mL, 6.04 mmol) to give a cloudy white mixture. Additional MeOH (15.09 mL) was added and the resulting clear solution was stirred at rt. After 24 h, the reaction was concentrated to give 0.895 g (86%) of Intermediate 22, as a white solid. MS (ESI) m/z: 265.3 (M+H)+. The material was used in the next step without further purification.

Intermediate 23. (E)-3-(5-Chloro-2-1,2,3-triazol-1-yl-phenyl)-acrylic Acid

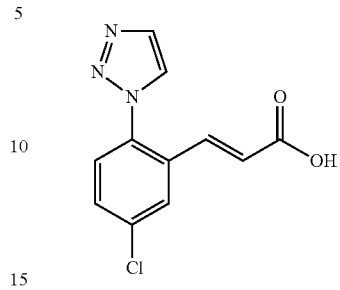

Intermediate 23A. 5-Chloro-2-1,2,3-triazol-1-yl-benzaldehyde and Intermediate 23B. 5-Chloro-2-1,2,3-triazol-2-yl-benzaldehyde: To a solution of 5-chloro-2-fluorobenzaldehyde (1 g, 6.31 mmol) in DMF (12.6 mL) was added 1H-1,2,3-triazole (0.365 ml, 6.31 mmol) and $Cs_2CO_3$ (4.11 g, 12.61 mmol). The reaction was stirred at rt for 18 h. Water was added to the reaction, and the resulting suspension was acidified with 1N HCl to pH<3, and then the reaction was filtered. The filtrate was extracted with EtOAc (3×). The organic layers were combined and washed with water, brine, dried over $Na_2SO_4$, filtered and concentrated. Trituration with DCM/hexane gave 0.35 g as a mixture of Intermediate 23A and Intermediate 23B as a yellow solid. The material was used in the next step without further purification.

Intermediate 23C. (E)-3-(5-Chloro-2-1,2,3-triazol-1-yl-phenyl)-acrylic acid tert-butyl ester and Intermediate 23D. (E)-3-(5-Chloro-2-1,2,3-triazol-2-yl-phenyl)-acrylic acid tert-butyl ester: The title compounds were prepared according to the procedure described in Intermediate 20B, by replacing Intermediate 20A with a mixture of Intermediate 23A and Intermediate 23B. The triazole regioisomers were separated by normal phase chromatography which gave 0.147 g (28.5%) of Intermediate 23C. MS (ESI) m/z: 306.1 (M+H)+. $^1$H NMR (500 MHz, $CDCl_3$) δ ppm 1.48 (s, 9H), 6.36 (d, J=16.0 Hz, 1H), 7.21 (d, J=16.0 Hz, 1H), 7.44 (d, J=8.5 Hz, 1H), 7.48-7.52 (dd, J=8.5, 2.2 Hz, 1H), 7.74 (d, J=2.2 Hz, 1H), 7.79 (d, J=1.1 Hz, 1H), 7.89 (d, J=1.1 Hz, 1H).

Intermediate 23. The title compound was prepared according to the procedure described in Intermediate 20, by replacing Intermediate 20B with Intermediate 23C. MS (ESI) m/z: 250.0 (M+H)+. $^1$H NMR (500 MHz, $CD_3OD$) δ ppm 6.51 (d, J=15.7 Hz, 1H), 7.22 (d, J=16.0 Hz, 1H), 7.53 (d, J=8.5 Hz, 1H), 7.63 (dd, J=8.4, 2.3 Hz, 1H), 7.96 (d, J=0.83 Hz, 1H), 8.00 (d, J=2.2 Hz, 1H), 8.30 (d, J=0.83 Hz, 1H).

Intermediate 24. (E)-3-(5-Chloro-2-difluoromethoxy-phenyl)-acrylic Acid

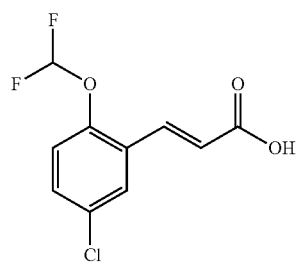 [SMILES: O=C(O)/C=C/c1cc(Cl)ccc1OC(F)F]

Intermediate 24A. (E)-3-(5-Chloro-2-difluoromethoxy-phenyl)-acrylic acid tert-butyl ester: To a cooled (0° C.) solution of potassium tert-butoxide (0.407 g, 3.63 mmol) in THF (10 mL) was added tert-butyl 2-(dimethoxyphosphoryl)acetate (0.528 mL, 2.66 mmol) and 5-chloro-2-(difluoromethoxy)benzaldehyde (0.50g, 2.420 mmol). The reaction was allowed to warm to RT. After 4 h, the reaction was quenched with the addition of sat. ammonium chloride. The reaction was diluted with EtOAc, washed with sat. ammonium chloride, sat NaHCO$_3$ and brine. The organic layer was dried over sodium sulfate, filtered and concentrated. Purification by normal phase chromatography gave 550 mg (74%) of Intermediate 24A as a white solid. $^1$H NMR (400 MHz, CDCl$_3$) δ ppm 7.77 (1H, d, J=16.31 Hz), 7.58 (1H, d, J=2.51 Hz), 7.31 (1H, dd, J=8.66, 2.64 Hz), 7.12 (1H, d, J=8.78 Hz), 6.52 (1H, t, J=72.78 Hz) 6.40 (1H, d, J=16.31 Hz), 1.53 (9H, s). $^{19}$F NMR (376 MHz, CDCl$_3$) δ ppm −81.11. MS (ESI) m/z: 327.0 (M+Na)$^+$.

Intermediate 24. To a solution of Intermediate 24A (458 mg, 1.503 mmol) in DCM (4.0 mL) was added TFA (2.0 mL, 26.0 mmol). The reaction was stirred under argon at RT for 1 h. The solvent was removed to give Intermediate 24 as a white solid. MS (ESI) m/z: 249.0 (M+H)$^+$.

Intermediate 25.
3-(5-Chloro-2-tetrazol-1-yl-phenyl)-propionic Acid

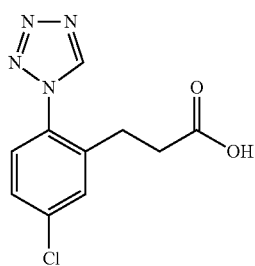 [SMILES: O=C(O)CCc1cc(Cl)ccc1-n1cnnn1]

The synthesis was described as Example 63A in PCT International Application No. WO 2007/070826 published Jun. 21, 2007.

Intermediate 26: 3-(3-Chlorophenyl)-4,5-dihydroisoxazole-5-carboxylic Acid

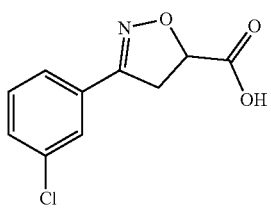 [SMILES: O=C(O)C1CC(c2cccc(Cl)c2)=NO1]

Intermediate 26 was obtained via the procedure described in U.S. Pat. No. 4,889,551 A1 (1989).

Intermediate 27:
3-(3-Chlorophenyl)isoxazole-5-carboxylic Acid

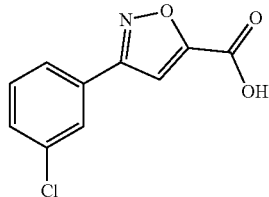 [SMILES: O=C(O)c1cc(-c2cccc(Cl)c2)no1]

Intermediate 27 was obtained via the procedure described by Gruenanger, F., *Gazz. Chim. Ital.*, 89:598-609 (1959).

Intermediate 28:
1-(3-Chlorophenyl)-1H-1,2,3-triazole-4-carboxylic Acid

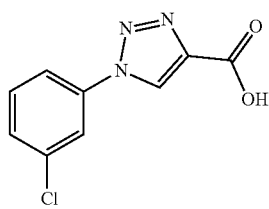 [SMILES: O=C(O)c1cn(-c2cccc(Cl)c2)nn1]

Intermediate 28 was obtained via the procedure described by Sader Al, B. H. et al., *Tetrahedron Letters*, 4661-4664 (1985).

Intermediate 29. 4-(tert-Butoxycarbonylaminomethyl)-2,6-difluoro-benzoic Acid

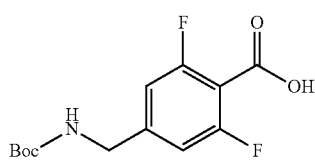 [SMILES: CC(C)(C)OC(=O)NCc1cc(F)c(C(=O)O)c(F)c1]

Intermediate 29A. 4-Cyano-2,6-difluoro-benzoic acid: To a cooled (−78° C.) clear, colorless solution of 3,5-difluorobenzonitrile (1 g, 7.19 mmol) in THF (28.8 mL) was added dropwise 1.6M n-butyllithium in hexane (4.49 ml, 7.19 mmol) to give a red-orange solution. After 45 min, carbon dioxide (sublimation of dry ice passing through a drierite tower) was bubbled through the reaction to eventually give a thick off-white suspension. After 25 min, the reaction was quenched with 1M HCl (aq) and the reaction was allowed to warm to RT. The reaction was extracted with EtOAc(2×). The organic layers were combined, washed with brine, dried over Na$_2$SO$_4$, filtered and concentrated to a white residue. The crude residue was partitioned between EtOAc and 1M NaOH (aq) and the layers were separated. The organic layer was extracted with 1 N NaOH (aq) (2×). The aqueous layers were combined and then washed with EtOAc (2×). The aqueous layer was then acidified to pH~2 to give a cloudy white suspension. The aqueous layer was then extracted with EtOAc (2×). The organic layers were combined, washed with brine, dried over Na$_2$SO$_4$, filtered and concentrated to a give 922.5 mg (65.3%) of Intermediate 29A as a white solid. MS (ESI) m/z: 184.0 (M+H)$^+$.

Intermediate 29B. 4-Aminomethyl-2,6-difluoro-benzoic acid: A black suspension of Intermediate 29A (922.5 mg, 5.04 mmol) and Pd/C (268 mg, 0.126 mmol) in EtOH (50.4 mL) was degassed with hydrogen (balloon) for several minutes. The reaction was stirred under hydrogen atmosphere for 24 h. The reaction was filtered through CELITE® eluting with 1M HCl (aq) and MeOH. The filtrate was concentrated to a pale yellow solid. The solid was dissolved in (1:1) 1 N HCl and EtOAc and the layers were separated. The aqueous layer was neutralized to pH 7 and extracted with 15% isopropanol/chloroform. The aqueous layer still contained some product, so both the organic and aqueous layers were concentrated and combined to give Intermediate 29B as an off-white solid. MS (ESI) m/z: 188.0 (M+H)$^+$. The product was used as is without further purification.

Intermediate 29. To a suspension of Intermediate 29B (943 mg, 4.22 mmol) in DCM (14.1 mL) was added triethylamine (2.351 mL, 16.87 mmol) followed by BOC$_2$O (1.077 mL, 4.64 mmol). DMF (5 mL) was added to facilitate mixing. After stirring for 1.5 h, the slightly purple suspension was diluted with water and DCM and the layers were separated. The aqueous layer was neutralized to pH~7 using 1 N HCl (aq) and then extracted with EtOAc (2×). The organic layers were combined, washed with brine, dried over Na$_2$SO$_4$, filtered and concentrated to give a viscous, pink oil. Purification by normal phase chromatography (0-10% DCM:MeOH) gave 803.2 mg (55.0%) of Intermediate 29, as a clear oil. MS (ESI) m/z: 232.2 (M–C$_4$H$_8$+H)$^+$. $^1$H NMR (500 MHz, CD$_3$OD) δ: 1.46 (s, 9H), 4.24 (s, 2H), 6.95 (d, J=9.3 Hz, 2H).

Intermediate 30. 4,6-Difluoro-1-methyl-1H-benzo[d]imidazole-5-carboxylic

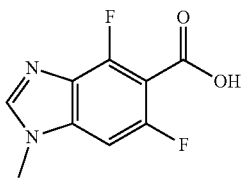

Intermediate 30A. 3,5-Difluoro-N-methyl-2-nitroaniline: To a solution of 1,3,5-trifluoro-2-nitrobenzene (1.0 g, 5.65 mmol) and methanamine (8.47 mL, 16.94 mmol) in MeOH (10 mL) was stirred for 4 h at 80° C. Reaction mixture was concentrated in vacuo, yielding oil, which was subjected to the following reaction w/o any further purification. MS (ESI) m/z: 189.2 (M+H)$^+$.

Intermediate 30B. 4,6-Difluoro-1-methyl-1H-benzo[d]imidazole: Solution of Intermediate 30A (1.063 g, 5.65 mmol) in formic acid (5 mL) was heated at 80° C. for 12 h. Rxn mixture after concentration was diluted in EtOAc (100 mL) and washed with 1 N aq NaOH. Organic solution was dried over Na$_2$SO$_4$ and concentrated in vacuo, yielding oily mixture. It was purified on normal phase column chromatography to yield Intermediate 30B (0.39 g, 41.1%).

Intermediate 30. (Reference: WO 2009/083526) To a solution of Intermediate 30B (227 mg, 1.35 mmol) in THF (10 mL) was added BuLi (0.74 mL, 1.485 mmol) dropwise and the resulting solution was stirred for 0.5 h at –78° C. To the solution was added bromotrimethylsilane (0.175 mL, 1.350 mmol) dropwise and solution was stirred for 15 min. To the solution was added sec-butyllithium (1.298 mL, 1.688 mmol) dropwise and solution was stirred for 0.5 h. The solution was then poured into THF solution of dry ice (2 pieces). The solution was stirred for 1 h at –78° C. The reaction was then quenched by adding 1 N HCl and the reaction was warmed to RT. The reaction was concentrated and then it was purified by reverse phase chromatography which gave Intermediate 30 (121 mg, 41.0%). $^1$H NMR (400 MHz, CD$_3$OD) δ ppm 8.80 (s, 1H), 7.51 (d, J=9.0 Hz, 1H), 3.99 (s, 3H). MS(ESI) m/z: 213.0 (M+H)$^+$.

Intermediate 31.
4,6-Difluoro-1-methyl-1H-indazole-5-carboxylic Acid

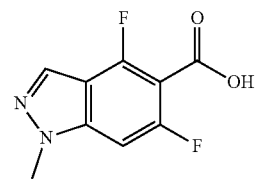

Intermediate 31A. (E)-1-Methyl-2-(2,4,6-trifluorobenzylidene)hydrazine: A solution of monomethyl hydrazine (2.158 g, 46.8 mmol) and 2,4,6-trifluorobenzaldehyde (2.5 g, 15.6 mmol) in THF (20 mL) was stirred at RT for 5 h. The reaction mixture was concentrated in vacuo, yielding oily residue, which was subjected to the following reaction w/o further purification. MS (ESI) m/z: 189.4 (M+H)$^+$.

Intermediate 31B. 4,6-Difluoro-1-methyl-1H-indazole: A solution of Intermediate 31A (8.84 g, 47 mmol) in DMF (5 mL) and pyridine (5.00 mL) was stirred at 90° C. for 12 h. The reaction mixture was concentrated in vacuo, yielding an oily mixture, which was purified on normal phase chromatography to provide Intermediate 31B (2.3 g, 29.1%). $^1$H NMR (400 MHz, CDCl$_3$) δ ppm 7.94 (s, 1H), 6.78 (d, J=8.5 Hz, 1H), 6.55 (td, J=9.7, 1.8 Hz, 1H), 3.95 (s, 3H). MS (ESI) m/z: 169.0 (M+H)$^+$.

Intermediate 31. To a solution of Intermediate 31B (250 mg, 1.48 mmol) in THF (15 mL) was added LDA (0.89 µL, 1.78 mmol) in several portions and the resulting dark solution was stirred for 0.5 h at –78° C. To the solution was added a few pieces of dry ice. The resulting solution was stirred at –78° C. for 0.5 h and at 25° C. for 0.5 h. It was diluted with EtOAc (40 mL) and washed with 1 N HCl. Organic solution was dried over MgSO$_4$ and concentrated in vacuo, yielding oil, which was then purified on reverse phase chromatography to yield Intermediate 31 (0.26 g, 82%). $^1$H NMR (400 MHz, CD$_3$OD) δ ppm 8.15 (s, 1H), 7.27 (d, J=10.0 Hz, 1H), 4.04 (s, 3H). MS (ESI) m/z: 212.9 (M+H)$^+$.

Intermediate 32:
4,6-Difluoro-1-methyl-1H-indole-5-carboxylic Acid

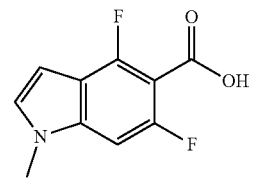

Intermediate 32A. 4,6-Difluoro-1-methyl-1H-indole: The synthesis is described in WO 2009/050235.

Intermediate 32. In a flame-dried 25 ml RBF, diisopropylamine (0.352 ml, 2.51 mmol) in 10 ml dry THF was cooled down to 0° C. under Ar, butyllithium (1.6M in Hexane) (1.571 ml, 2.51 mmol) was added, stirred at 0° C. for 30 mins, before cooling down to −78° C. Intermediate 32A (382 mg, 2.285 mmol) in 2 ml dry THF was added dropwise, stirred at −78° C. for 1 hrs, before dry ice was added to the reaction. The reaction was stirred at −78° C. for 30 mins and then warmed up to rt and stirred at rt overnight. The reaction was concentrated, diluted with EtOAc, washed with $H_2O$, washed again with EtOAc. The aqueous layer was acidified with 1 N HCl, white precipitate formed immediately. It was extracted with EtOAc twice. EtOAc layers washed with brine, dried over $MgSO_4$, filtered off solid, concentrated to give Intermediate 32 as a pale yellow solid (177 mg, 38%). MS (ESI) m/z: 212.1 $(M+H)^+$.

Intermediate 33: 4-Amino-2,6-difluoro-benzoic Acid

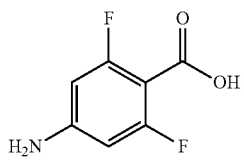

Intermediate 33A. 4-Bromo-2,6-difluorobenzoic acid methyl ester: To a solution of 4-bromo-2,6-difluorobenzoic acid (1.00 g, 4.22 mmol) in 30 mL methanol was added TMS-Cl (1.1 ml, 8.61 mmol), and the mixture was heated at 60° C. under $N_2$ over night. An additional 1 mL TMS-Cl was added and heating continued at 60° C. for an additional 4 h. Reaction mixture was cooled to RT and diluted with aq. NaOH, then extracted with EtOAc. The combined organic extracts were washed with dilute aq. NaOH to remove unreacted starting material, then dried over $Na_2SO_4$, filtered and evaporated to obtain Intermediate 33A as a pale pink solid (0.86g, 81%) MS (ESI) m/z: 251.05 $(M+H)^+$.

Intermediate 33B. 4-(Benzhydrylidene-amino)-2,6-difluoro-benzoic acid methyl ester: Intermediate 33A (0.600 g, 2.390 mmol) and cesium carbonate (1.324 g, 4.06 mmol) were weighed into a 50 mL 3-necked rbf and flushed with $N_2$. Palladium(II) acetate (10.73 mg, 0.048 mmol) and rac-2,2'-bis(diphenylphosphino)-1,1'-binaphthyl (0.045 g, 0.072 mmol) were added, followed by 7.5 mL toluene. Benzophenone imine (0.521 ml, 3.11 mmol) was then added to the above mixture, and the reaction was heated with stirring at 100° C. overnight. The reaction mixture was diluted with 50 mL $Et_2O$, and filtered. The filtrate was evaporated and the residue was purified by flash chromatography to provide Intermediate 33B as a yellow oil which was used without further purification in the next step. MS (ESI) m/z: 352.2 $(M+H)^+$.

Intermediate 33. Intermediate 33B (0.840 g, 2.39 mmol) was dissolved in MeOH (16 mL), and hydroxylamine hydrochloride (0.332 g, 4.78 mmol) and sodium acetate (0.490 g, 5.98 mmol) were added. The mixture was stirred for 1 h and then diluted with water and extracted with EtOAc. The combined organic layers were washed with water and brine, then dried over $Na_2SO_4$ filtered and evaporated. The crude product was dissolved in EtOH (~12 mL) and 1M NaOH (6 mL, 6.0 mmol) was added. The mixture was stirred for 3 days at room temperature. Reaction mixture was neutralized with 1M HCl and then evaporated to remove ethanol. The residue was redissolved in MeOH, filtered and evaporated (2×) to remove the bulk of the inorganic salts. The filtrate was evaporated and the residue was purified by reverse phase HPLC to provide Intermediate 33 (0.36g, 88%) as a white solid. $^1H$ NMR (400 MHz, DMSO-$d_6$) δ ppm 5.99 (s, 2H) 6.10 (d, J=10.99 Hz, 2H). $^{19}F$ NMR (376 MHz, DMSO-$d_6$) δ ppm −111.82 (s, 2F).

Intermediate 34. 4,6-Difluoro-1-(2-fluoro-ethyl)-1H-benzoimidazole-5-carboxylic Acid

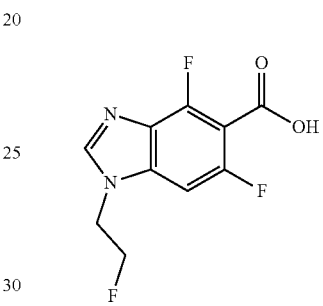

Intermediate 34 was prepared following the procedures described in Intermediate 30, by replacing methylamine with 2-fluoroethanamine, HCl. MS (ESI) m/z: 245.1 $(M+H)^+$.

Intermediate 35. 7-Chloro-4,6-difluoro-1-methyl-1H-benzo[d]imidazole-5-carboxylic Acid

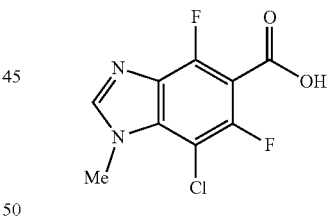

Intermediate 35A. 2-Chloro-3,5-difluoro-N-methyl-6-nitroaniline: Solution of Intermediate 30A (1.1 g, 5.85 mmol) and NCS (0.781 g, 5.85 mmol) in acetonitrile (25 mL) was stirred for 12 h at 70° C. The reaction mixture was concentrated in vacuo, yielding yellow solid, which was redissolved in EtOAc and washed with aq. $NaHCO_3$ and brine. Concentration of organic solution provided oily residue, which was purified on normal phase chromatography to provide Intermediate 35A (0.78 g, 60%). MS (ESI) m/z: 222.9/224.8 $(M+H)^+$.

Intermediate 35. Intermediate 35 was prepared following the procedures described in Intermediate 30, by replacing Intermediate 30A with Intermediate 35A. $^1H$ NMR (400 MHz, $CD_3OD$) δ ppm 8.18 (s, 1H), 4.16 (s, 3H). MS (ESI) m/z: 246.9/248.8 $(M+H)^+$.

Intermediate 36. 4,6-Difluoro-1-fluoromethyl-1H-benzoimidazole-5-carboxylic Acid

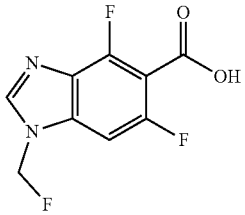 [SMILES: O=C(O)c1c(F)cc2c(ncn2CF)c1F]

Intermediate 36A. 4,6-Difluoro-1-(fluoromethyl)-1H-benzo[d]imidazole: (Reference: *Tetrahedron*, 63:10569-10575 (2007).) To a solution of 4,6-difluoro-1H-benzo[d]imidazole (100 mg, 0.649 mmol) in DMF (5 mL) was added NaH (57.1 mg, 1.43 mmol) and the resulting solution was stirred for 0.5 h at rt. The solution was cooled down to −78° C. and FCH$_2$Cl was bubbled in for 10 min. The reaction mixture was then sealed in the microwave vial and stirred at 80° C. for 2h. The reaction mixture was diluted with EtOAc (30 ml) and washed with 1 N HCl (20 mL), then aq NH$_4$Cl. Organic solution was concentrated and purified on reverse phase chromatography to provide Intermediate 36A (52 mg, 43%). $^1$H NMR (500 MHz, CDCl$_3$) δ ppm 8.02 (d, 2H), 7.29-7.40 (m, 1H), 7.00-7.13 (m, 1H), 6.82-6.98 (m, 2H), 6.29 (s, 1H), 6.18 (d, J=5.5 Hz, 2H), 6.07 (s, 1H), 1.59 (s, 2H). MS (ESI) m/z: 187.0 (M+H)$^+$.

Intermediate 36. Intermediate 36 was prepared following the procedure described in Intermediate 30, by replacing Intermediate 30B with Intermediate 36A. MS (ESI) m/z: 231.1 (M+H)$^+$.

Intermediate 37. 2-Methyl-propane-2-sulfinic Acid {(S)-1-[4-bromo-1-(2-trimethylsilanyl-ethoxymethyl)-1H-imidazol-2-yl]-but-3-enyl}-amide

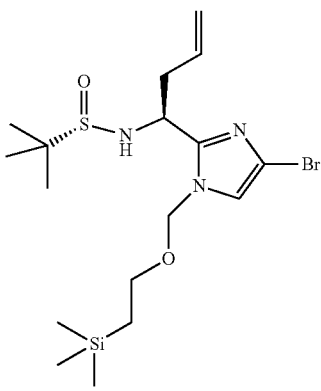 [SMILES: C=CC[C@H](N[S@@](=O)C(C)(C)C)c1nc(Br)cn1COCC[Si](C)(C)C]

Intermediate 37A. 2,4,5-Tribromo-1-(2-trimethylsilanyl-ethoxymethyl)-1H-imidazole: To a cooled (0° C.) suspension of sodium hydride (0.9 g, 0.03 mole) in THF (50 mL) was added dropwise a solution of 2, 4, 5-tribromo imidazole (5 g, 0.016 mol) in THF (50 mL). After 1 h, a solution of trimethylsilylethoxymethyl chloride (SEMCl) (3 mL, 0.017 mol) in THF (30 mL) was added dropwise. The reaction mixture was quenched with saturated ammonium chloride solution and then the reaction was extracted with ethyl acetate [3×100 mL]. The organic layers were combined and washed with 10% sodium bicarbonate solution, water, brine, dried over sodium sulfate, filtered and concentrated to yield 7.2 g of Intermediate 37A as pale, yellow oil which solidified on standing. The material was used in the next step without further purification. MS (ESI) m/z: 435 (M+2+H)$^+$.

Intermediate 37B. 4,5-Dibromo-1-(2-trimethylsilanyl-ethoxymethyl)-1H-imidazole-2-carbaldehyde: To a cooled (−78° C.) solution of Intermediate 37A (16 g, 0.03 mol) in THF (160 mL) was added a solution of n-BuLi (13.5 mL, 3M in hexane; 0.04 mol) dropwise. After 1 h, DMF (14 mL, 0.2 mol) was added dropwise. After 1 h, the reaction was quenched with saturated ammonium chloride solution and then the reaction was allowed to warm to RT. The reaction was extracted with ethyl acetate [2×100 mL]. The organic layers were combined and washed with 10% sodium bicarbonate solution, water, brine and then concentrated. Purification by normal phase chromatography (gradient elution pet ether: ethyl acetate) gave 11.5 g (40%) of Intermediate 37B. MS (ESI) m/z: 384.1 (M)$^+$.

Intermediate 37C. (S,E)-N-((4,5-Dibromo-1-((2-(trimethylsilyl)ethoxy)methyl)-1H-imidazol-2-yl)methylene)-2-methylpropane-2-sulfinamide: To a solution of Intermediate 37B (35 g, 0.09 mol) in methylene chloride (350 mL) was added (S)-(−)-2-Methyl-2-propanesulfinamide (22 g, 0.18 mole) and anhydrous copper sulfate (72 gc 0.45 mol). The resulting suspension was stirred at RT. After 20 h, the reaction was filtered through CELITE®. The filtrate was concentrated and purification by normal phase chromatography (gradient elution pet ether:ethyl acetate) gave 42 g (94%) of Intermediate 37C as a pale yellow oil which solidified on standing. MS (ESI) m/z: 487.3 (M+H)$^+$.

Intermediate 37D. 2-Methyl-propane-2-sulfinic acid {(S)-1-[4,5-dibromo-1-(2-trimethylsilanyl-ethoxymethyl)-1H-imidazol-2-yl]-but-3-enyl}-amide: To a cooled (−78° C.) solution of Intermediate 37C (17 g, 0.03 mole) in THF (170 mL) was added allylmagnesium bromide (1M in diethylether, 52.3 mL, 0.05 mol) dropwise. After 1 h, the reaction was quenched with saturated ammonium chloride solution and then the reaction was allowed to warm to RT. The reaction mixture was extracted with ethyl acetate (2×250 mL). The organic layers were combined and washed with sodium bicarbonate solution, brine, water, dried over anhydrous sodium sulfate, filtered and concentrated. Purification by normal phase chromatography (gradient elution; hexane: ethyl acetate) gave 25 g (67%) of Intermediate 37D, as a pale yellow oil. $^1$H NMR (400 MHz, CDCl$_3$) δ: 5.71 (m, 1H), 5.60 (d, 1H, J=11.6 Hz), 5.28 (m, 1H), 5.06 (m, 2H), 4.57 (q, 1H, J=7.2 Hz), 3.98 (d, 1H, J=8.4 Hz), 3.55 (m, 2H), 2.70 (t, 2H, 7.2 Hz), 1.2 (s, 9H), 0.92 (m, 2H), −0.01 (s, 9H). MS (ESI) m/z: 529.4 (M+H)$^+$.

Intermediate 37. A solution of Intermediate 37D (5.25 g, 9.92 mmol) in THF (33.1 mL) was degassed with argon for 15 min. The solution was cooled to −3° C. (ice/brine) and isopropylmagnesium chloride, lithium chloride complex in THF (8.00 mL, 10.4 mmol) was added dropwise over 20 min, keeping the temperature below 0° C. during the addition. After 30 min, the second equivalent of isopropylmagnesium chloride, lithium chloride complex in THF (8.00 mL, 10.4 mmol) was added dropwise over 20 min, keeping the temperature below 0° C. during the addition. After 30 min, the reaction was quenched with sat. ammonium chloride (30 mL) and the reaction was allowed to warm to RT. The reaction was partitioned between EtOAc and sat. ammonium chloride and the layers were separated. The aqueous layer was extracted with EtOAc (1×). The organic layers were combined and washed with sat. NaHCO$_3$, brine, dried over sodium sulfate, filtered and concentrated to give clear, yellow viscous oil weighing 4.67 g. Purification by normal phase chromatography gave 3.98 g (89%) of Intermediate 37, as a white solid. $^1$H NMR (500 MHz, CD$_3$OD) δ ppm 7.20 (s, 1H), 5.69-5.82 (m, 1H), 5.49 (d, J=11.3 Hz, 1H), 5.30 (d, J=11.3 Hz, 1H), 5.09 (dd, J=17.1, 1.7 Hz, 1H), 5.04 (d, J=10.5 Hz, 1H), 4.62 (t, J=7.3 Hz, 1H), 3.51-3.67 (m, 2H), 2.69 (t, J=7.3 Hz, 2H), 1.20 (s, 9H), 0.85-1.04 (m, 2H), 0.00 (s, 9H). MS (ESI) m/z: 450.1 (M+H)$^+$. [α]$_D^{23.6}$=+70.13 (c=1.70; chloroform).

Alternatively, Intermediate 37 can be prepared by the following sequence:

Intermediate 37E. 2,4-Dibromo-1-(2-trimethylsilanyl-ethoxymethyl)-1H-imidazole: To a cooled (0° C.) suspension of NaH (1.062 g, 26.6 mmol) in THF (44.3 mL) was added dropwise over 20 min. a clear, pale yellow solution of 2,4-dibromo-1H-imidazole (5.00 g, 22.14 mmol) in THF (20 mL). The resulting purple-gray suspension was stirred at 0° C. for 1h. Next, SEMCl (4.71 mL, 26.6 mmol) was added dropwise. The reaction was maintained at 0° C. for 1 h and then it was quenched with the slow addition of sat. ammonium chloride. The reaction was diluted with EtOAc and the layers were separated. The aqueous layer was extracted with EtOAc (2×). The combined organic layers were washed with sat. NaHCO$_3$, brine, dried over sulfate, filtered and concentrated to give a clear liquid weighing 9.06 g. Purification by normal phase chromatography gave 5.97 g (76%) of Intermediate 37E, as a clear, colorless liquid. Ratio of regioisomers by HPLC was 14.7:1. MS (ESI) m/z: 357.0 (M+2+H)$^+$.

Intermediate 37F. 4-Bromo-1-(2-trimethylsilanyl-ethoxymethyl)-1H-imidazole-2-carbaldehyde: To a cooled (−78° C.) clear, colorless solution of Intermediate 37E (1.0 g, 2.81 mmol) in THF (9.36 mL) was added dropwise over 10 min. n-BuLi (1.930 mL, 3.09 mmol). The resulting clear, golden yellow solution was stirred at −78° C. for 1 h and then DMF (1.087 mL, 14.04 mmol) was added. The reaction was stirred at −78° C. for 1 h and then the reaction was quenched with sat. ammonium chloride and the reaction was allowed to warm to RT. The reaction was partitioned between EtOAc and water and the layers were separated. The organic layer was washed with sat. NaHCO$_3$, brine, dried over sodium sulfate, filtered, and concentrated. Purification by normal phase chromatography gave 0.130 g (16%) of Intermediate 37F, as a white solid. MS (ESI) m/z: 339.1 (M+CH$_4$O+2+H)$^+$, consistent with hemiacetal of methanol addition to the aldehyde.

Intermediate 37. Intermediate 37 was prepared by following the procedures described in Intermediate 37C, by replacing Intermediate 37B with Intermediate 37F; followed by procedure described in Intermediate 37D which gave a 9:1 mixture of diastereomers.

Intermediate 38.
4,6-Difluoro-1,3-dimethyl-1H-indazole-5-carboxylic Acid

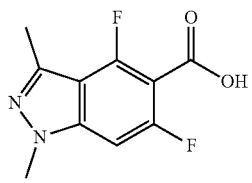 [SMILES: Cc1nn(C)c2cc(F)c(C(=O)O)c(F)c12]

Intermediate 38A. 4,6-Difluoro-1,3-dimethyl-1H-indazole: K$_2$CO$_3$ (1.191 g, 8.61 mmol) and copper(II) oxide (0.023 g, 0.287 mmol) were weighed into a microwave tube. Vacuum and filled with Ar for several times. Methylhydrazine (0.363 ml, 6.89 mmol) was added. The reaction was cooled down to 0° C. 1-(2,4,6-trifluorophenyl)ethanone (0.767 ml, 5.74 mmol) was added dropwise. The tube was placed in an oil bath and heated at 100° C. for 4 hrs, then cooled down to rt overnight. The reaction mixture was diluted with EtOAc, washed with H$_2$O, brine, dried over MgSO$_4$. Purification by normal phase chromatography gave 877 mg (84%) of Intermediate 38A as a white solid. MS (ESI) m/z: 183.0 (M+H)$^+$.

Intermediate 38. In a flame-dried 25 ml RBF, diisopropylamine (0.494 ml, 3.52 mmol) in THF (14.68 ml) was cooled down to 0° C. under Ar. Butyllithium (1.6M in Hexane) (1.571 ml, 2.51 mmol) was added. The reaction was stirred at 0° C. for 1 hr, before cooling down to −78° C. 4,6-difluoro-1,3-dimethyl-1H-indazole (535 mg, 2.94 mmol) in 4 ml dry THF was added dropwise. The reaction was stirred at −78° C. for 1 hrs, before dry ice was added to the reaction. The reaction was stirred at −78° C. for 30 mins and then warmed up to rt and stirred at rt overnight. The reaction was concentrated, diluted with EtOAc, washed with H$_2$O. The aqueous layer was acidified with 1 N HCl. It was filtered and the white solid was dried in a vacuum oven to give 160 mg (24%) of Intermediate 38 as a white solid. MS (ESI) m/z: 227.0 (M+H)$^+$.

Intermediate 39. 4-Amino-3-(5,5-dimethyl-1,3,2-dioxaborinan-2-yl)-benzoic Acid methyl ester

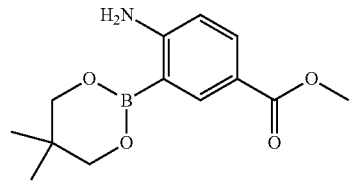

A flame-dried flask, equipped with a reflux condensor, containing methyl 4-amino-3-bromobenzoate (2.5 g, 10.87 mmol), bis(neopentyl glycolato)diboron (3.07 g, 13.58 mmol), potassium acetate (3.20 g, 32.6 mmol), and PdCl$_2$ (dppf)-CH$_2$Cl$_2$ adduct (0.222 g, 0.272 mmol) was added degassed DMSO (31.0 mL). The resulting dark red-brown suspension was warmed to 85° C. After 2.5 h, the resulting dark black reaction was cooled to RT and poured into cold water (100 mL) to give a suspension. The suspension was extracted with EtOAc (3×). The combined organic layers were washed with sat. NaHCO$_3$, brine, dried over sodium sulfate, filtered and concentrated to give a brown solid weighing 3.1 g. Purification by normal phase chromatography gave 1.64 g (55%) of Intermediate 39 as a pale, yellow solid. $^1$H NMR (500 MHz, CDCl$_3$) δ ppm 8.35 (d, J=2.20 Hz, 1H), 7.84 (dd, J=8.53, 2.20 Hz, 1H), 6.52 (d, J=8.53 Hz, 1H), 5.25 (br. s., 2H), 3.84 (s, 3H), 3.79 (s, 4H), 1.03 (s, 6H). MS (ESI) m/z: 196.0 (M−C$_5$H$_8$+H)$^+$.

Intermediate 40. (E)-3-(3-Chloro-2-fluoro-6-(trifluoromethyl)phenyl)acrylic Acid

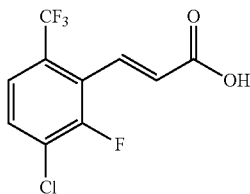

Intermediate 40 was prepared following the procedures described in Intermediate 24, by replacing 5-chloro-2-(difluoromethoxy) benzaldehyde with 3-chloro-2-fluoro-6-(trifluoromethyl)benzaldehyde. MS (ESI) m/z: 292 (M+Na)+. 1H NMR (400 MHz, CDCl3) δ ppm 7.87 (1H, dd, J=16.17, 2.02 Hz), 7.49-7.62 (2H, m), 6.67 (1H, dd, J=16.30, 1.39 Hz).

Example 1

(E)-3-(5-Chloro-2-tetrazol-1-yl-phenyl)-N-(E)-(S)-8-oxa-16,18-diaza-tricyclo[13.2.1.0$^{2,7}$]octadeca-1(17),2,4,6,11,15(18)-hexaen-14-yl-acrylamide, 1 TFA Salt

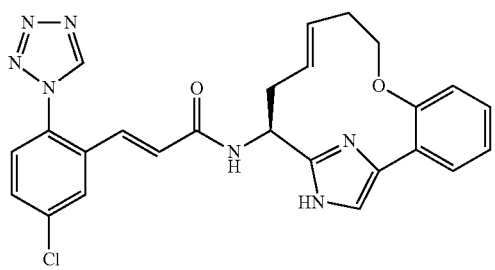 [SMILES: O=C(/C=C/c1cc(Cl)ccc1-n1cnnn1)N[C@H]1C/C=C/CCOc2ccccc2-c2c[nH]c1n2]

1A. (S)-2-tert-Butoxycarbonylamino-pent-4-enoic acid 2-(2-but-3-enyloxy-phenyl)-2-oxo-ethyl ester: A suspension of (S)-2-(tert-butoxycarbonylamino)pent-4-enoic acid (515 mg, 2.394 mmol) and potassium hydrogen carbonate (0.288 g, 2.87 mmol) in DMF (12.00 mL) was stirred at rt for 20 min. The reaction was then cooled to 0° C. and Intermediate 6 (0.773g, 2.87 mmol) was added. The resulting yellow solution was allowed to warm to rt. After stirring overnight, the reaction was cooled to 0° C. and then poured into cold water to give a white suspension. The white suspension was then extracted with EtOAc (3×75 mL). The combined organic layers were washed with brine, dried over Na$_2$SO$_4$, filtered, and concentrated to give 1.072 g of 1A as a yellow oil. This was used without further purification. MS (ESI) m/z: 304.3 (M–C$_5$H$_8$O$_2$+H)+.

1B. {(S)-1-[4-(2-But-3-enyloxy-phenyl)-1H-imidazol-2-yl]-but-3-enyl}-carbamic acid tert-butyl ester: Compound 1A (1.07 g, 2.66 mmol) was dissolved in xylene (26.6 mL) and divided evenly between two 20-mL microwave vials. Next ammonium acetate (2.047 g, 26.6 mmol) was added to each vial. The vials were microwaved at 140° C. for 30 min. The resulting bright orange solutions were combined, partitioned between EtOAc and sat. NaHCO$_3$ and the layers were separated. The aqueous layer was extracted with EtOAc (2×100 mL). The combined organic layers were washed with brine, dried over Na$_2$SO$_4$, filtered and concentrated to give a peach residue. Purification by normal phase chromatography gave 0.626 g (62%) of 1B as a sticky, yellow solid. MS (ESI) m/z: 384.4 (M+H)+.

1C. {(S)-1-[4-(2-But-3-enyloxy-phenyl)-1-(2-trimethylsilanyl-ethoxymethyl)-1H-imidazol-2-yl]-but-3-enyl}-carbamic acid tert-butyl ester: To a cooled (0° C.) suspension of NaH (58.7 mg, 1.468 mmol) in DMF (2.06 mL) was added dropwise a solution of 1B (536.2 mg, 1.40 mmol) in DMF (1.3 mL). The resulting orange solution was allowed to warm to rt. After 1 h, the reaction was cooled to 0° C. and SEMCl (0.27 mL, 1.52 mmol) was added dropwise. The resulting peach solution was allowed to warm to rt. After 1 h and 45 min, the cloudy yellow mixture was cooled to 0° C. and quenched with water (20 mL). The reaction was extracted with EtOAc (3×20 mL). The combined organic layers were washed with water (3×6 mL), dried over Na$_2$SO$_4$, filtered and concentrated. Purification by normal phase chromatography gave 462.5 mg (64%) of 1C as a pale yellow oil. MS (ESI) m/z: 514.3 (M+H)+.

1D. [(E)-(S)-16-(2-Trimethylsilanyl-ethoxymethyl)-8-oxa-16,18-diaza-tricyclo[13.2.1.0$^{2,7}$]octadeca-1(17),2,4,6,11,15(18)-hexaen-14-yl]-carbamic acid tert-butyl ester, 1 TFA salt; and 1E. [(Z)-(S)-16-(2-Trimethylsilanyl-ethoxymethyl)-8-oxa-16,18-diaza-tricyclo[13.2.1.02,7]octadeca-1(17),2,4,6,11,15(18)-hexaen-14-yl]-carbamic acid tert-butyl ester, 1 TFA salt: (Flask 1): To a flame-dried RBF was added Grubbs (II) (681 mg, 0.802 mmol). The flask was degassed with argon for several minutes and then degassed DCM (10 mL) was added to give a clear, burgundy solution. (Flask 2): To a separate flame-dried RBF was added 1C (412 mg, 0.802 mmol), pTsOH monohydrate (168 mg, 0.882 mmol) and DCM (779 mL). The flask was equipped with a reflux condenser and the solution was degassed with argon for 30 min. Next, the reaction was warmed to 40° C. After 1 h, the solution of Grubbs (II) was added dropwise. After 1 h, the reaction was cooled to rt and washed with NaHCO$_3$, brine, dried over MgSO$_4$, filtered and concentrated. Purification by normal phase chromatography gave a pale, brown oil. Further purification by reverse phase chromatography gave 78.6 mg (20%) of 1D (E-alkene) as a pale brown oil and 33.2 mg (9%) of 1E (Z-alkene) as a pale, brown oil. For 1D: MS (ESI) m/z: 486.5 (M+H)+. For 1E: MS (ESI) m/z: 486.5 (M+H)+.

1F. (E)-(S)-(8-Pxa-16,18-diaza-tricyclo[13.2.1.0$^{2,7}$]octadeca-1(17),2,4,6,11,15(18)-hexaen-14-yl)amine, 2 TFA: A yellow solution of 1D (59.2 mg, 0.122 mmol) in 5M HCl (2.50 mL, 82 mmol) and EtOH (2.44 mL) was heated to 50° C. After stirring overnight, the reaction was concentrated to remove EtOH and the remaining aqueous layer was adjusted to pH >10 with sat. K$_2$CO$_3$. The reaction was extracted with EtOAc (3×). The combined organic layers were dried over Na$_2$SO$_4$, filtered and concentrated to give a brown residue. Purification by reverse phase chromatography gave 0.0246 g (42%) of 1F as a clear, colorless oil. MS (ESI) m/z: 256.3 (M+H)+.

1G. Example 1: To a solution of Intermediate 1 (33.5 mg, 0.096 mmol) and 1F (24.6 mg, 0.096 mmol) in DMF (0.321 mL) was added Hunig's Base (0.084 mL, 0.482 mmol). After 45 min, water was added to give a suspension. The solid was collected by filtration. Purification by reverse phase chromatography gave after concentration and lyophilization 0.0195 g (33%) of Example 1 as a white solid. 1H NMR (400 MHz, CD$_3$OD) δ ppm 2.40-2.71 (m, 3H), 2.76-2.88 (m, 1H), 3.68-3.84 (m, 1H), 4.21-4.42 (m, 1H), 5.13-5.28 (m, 2H), 5.77-5.91 (m, 1H), 6.81 (d, J=15.9 Hz, 1H), 7.14-7.23 (m, 2H), 7.29 (dd, J=8.2, 1.1 Hz, 1H), 7.47

(td, J=7.7, 1.6 Hz, 1H), 7.55 (s, 1H), 7.57-7.62 (m, 2H), 7.69 (dd, J=8.8, 2.2 Hz, 1H), 8.00 (d, J=2.2 Hz, 1H), 9.54 (s, 1H). MS (ESI) m/z: 488.3 (M+H)+. Analytical HPLC: RT=5.35 min.

Example 2

(E)-3-(5-Chloro-2-tetrazol-1-yl-phenyl)-N-(S)-16,18-diaza-tricyclo[13.2.1.0$^{2,7}$]octadeca-1(17),2,4,6,15(18)-pentaen-14-yl-acrylamide, 1 TFA Salt

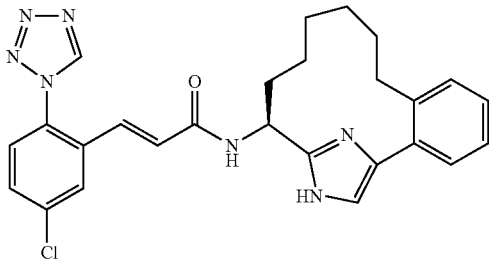 [SMILES: O=C(/C=C/c1cc(Cl)ccc1-n1cnnn1)N[C@H]1CCCCCCc2ccccc2-c2c[nH]c1n2]

2A. (S)-2-(2-Bromophenyl)-2-oxoethyl 2-(tert-butoxycarbonylamino)pent-4-enoate: To a clear, colorless solution of (S)-2-(tert-butoxycarbonylamino)pent-4-enoic acid (3.33 g, 15.47 mmol) in DMF (38.7 mL) was added potassium hydrogen carbonate (1.859 g, 18.57 mmol). The reaction was stirred for 20 min at rt and then it was cooled to 0° C. Next a solution of 2-bromo-1-(2-bromophenyl)ethanone (4.3 g, 15.47 mmol) in DMF (38.7 mL) was added dropwise and the reaction was allowed to warm to rt. After 3 h, the reaction was cooled to 0° C., poured into ice-cold water, and then extracted with EtOAc (3×). The combined organic layers were washed with water (1×), brine (1×), dried over sodium sulfate, filtered and concentrated to give 2A (6.37 g) as a yellow oil which solidified on storage in the freezer. MS (ESI) m/z: 410.2 (M−H)−, 412.2 (M+2−H)−. The material was used in the next step without further purification.

2B. (S)-tert-Butyl 1-(5-(2-bromophenyl)-1H-imidazol-2-yl)but-3-enylcarbamate: To the clear, yellow solution of 2A (6.37 g, 15.45 mmol) in xylene (155 mL) was added ammonium acetate (11.91 g, 155 mmol). The reaction mixture was heated to reflux with a Dean-Stark trap to remove water azeotropically. After 4 h, the reaction was cooled to rt, diluted with EtOAc (500 mL) and then washed with sat. sodium bicarbonate, brine, dried over sodium sulfate, filtered, and concentrated to give a brown residue. Purification by normal phase chromatography afforded 2B (2.768 g, 45.7%) as a yellow solid. MS (ESI) m/z: 392.3 (M+H)+, 394.3 (M+2+H)+.

2C. (S)-tert-Butyl 1-(4-(2-bromophenyl)-1-((2-(trimethylsilyl)ethoxy)methyl)-1H-imidazol-2-yl)but-3-enylcarbamate: To a cooled (0° C.), suspension of NaH (60% dispersion in mineral oil, 0.299 g, 7.48 mmol) in THF (10.0 mL) was added dropwise a solution of 2B (2.668 g, 6.80 mmol) in THF (15.0 mL). Gas evolution was observed. The flask containing 2B was rinsed with THF (2.2 mL) and then this solution was added to the reaction mixture. The resulting clear orange solution was stirred at 0° C. for 30 min, then SEM-Cl (1.206 mL, 6.80 mmol) was added dropwise. The resulting orange solution was maintained at 0° C. After 3 h, the reaction was quenched with sat. ammonium chloride and diluted with EtOAc (200 mL) and water. The layers were separated and the aqueous layer was extracted with EtOAc (1×). The combined organic layers were washed with brine, dried over sodium sulfate, filtered, and concentrated to give clear orange oil. Purification by normal phase chromatography gave 2C (2.76 g, 78%) as a yellow oil. MS (ESI) m/z: 522.5 (M+H)+, 524.5 (M+2+H)+.

2D. (S)-tert-Butyl 1-(4-(2-(pent-4-enyl)phenyl)-1-((2-(trimethylsilyl)ethoxy)methyl)-1H-imidazol-2-yl)but-3-enylcarbamate: To a flame-dried, thick-walled vial was placed 2C (1.085 g, 2.076 mmol), pent-4-enylboronic acid (0.757 g, 6.64 mmol), silver oxide (1.203 g, 5.19 mmol), potassium carbonate (1.722 g, 12.46 mmol), and PdCl$_2$(dppf)-CH$_2$Cl$_2$ adduct (0.170 g, 0.208 mmol). The vial was purged with argon for several minutes and then degassed THF (8.3 mL) was added. The vial was sealed with a teflon-coated screw cap and the black suspension was warmed to 80° C. After 16 h the reaction was cooled to rt. The reaction mixture was diluted with EtOAc, washed with water, sat. sodium bicarbonate, brine, dried over sodium sulfate, filtered and concentrated to give an orange-brown residue. Purification by normal phase chromatography yielded a clear, colorless oil which was a mixture of 2D and starting material. The material was purified further by reverse phase chromatography. The pure fractions were neutralized with sat. sodium bicarbonate and then concentrated to remove the organic solvent. The remaining residue was extracted with EtOAc (2×). The combined organic layers were washed with brine, dried over sodium sulfate, filtered and concentrated to afford 2D (0.21 g, 20%) as a clear, colorless oil. MS (ESI) m/z: 512.6 (M+H)+.

2E. [(E)-(S)-16-(2-Trimethylsilanyl-ethoxymethyl)-16,18-diaza-tricyclo[13.2.1.0$^{2,7}$]octadeca-1(17),2,4,6,11,15(18)-hexaen-14-yl]-carbamic acid tert-butyl ester and 2F. [(Z)-(S)-16-(2-Trimethylsilanyl-ethoxymethyl)-16,18-diaza-tricyclo[13.2.1.0$^{2,7}$]octadeca-1(17),2,4,6,11,15(18)-hexaen-14-yl]-carbamic acid tert-butyl ester: (Flask 1): To a flame-dried flask was added Grubbs (II) (0.139 g, 0.164 mmol). The flask was degassed with argon for several minutes and then degassed DCM (2 mL) was added to give a clear, burgundy solution. (Flask 2): To a separate flame-dried RBF was added 2D (0.21 g, 0.410 mmol), p-toluenesulfonic acid monohydrate (0.086 g, 0.451 mmol) and DCM (420 mL). The flask was equipped with a reflux condenser and the solution was degassed with argon for 30 min. The reaction was heated to 40° C. After 1 h, the solution of Grubbs (II) was added dropwise. After 1 h, the reaction was cooled to rt, washed with sat. sodium bicarbonate, brine, dried over MgSO$_4$, filtered and concentrated to give a brown foam. Purification by reverse phase chromatography gave, after neutralization and extractive workup as described in 2D, 2E (0.09 g, 45.3%, E-alkene) as a yellow solid and 2F (0.035 g, 17.6%, Z-alkene) as a yellow solid. For 2E: MS (ESI) m/z: 484.6 (M+H)+. For 2F: MS (ESI) m/z: 484.6 (M+H)+.

2G. [(S)-16-(2-Trimethylsilanyl-ethoxymethyl)-16,18-diaza-tricyclo[13.2.1.0$^{2,7}$]octadeca-1(17),2,4,6,15(18)-pentaen-14-yl]-carbamic acid tert-butyl ester: To the solution of 2E and 2F (mixture of E/Z isomers) (0.049 g, 0.101 mmol) in MeOH (3 mL) was added 10% palladium on carbon (10.78 mg, 10.13 µmol). The reaction mixture was stirred under H$_2$-balloon. After 2 h, the reaction was filtered through a 0.45 µm glass microfiber filter (GMF) and the Pd/C was rinsed with MeOH. The filtrate was concentrated to give 2G (0.046 g, 93%) as a clear, colorless residue. MS (ESI) m/z: 486.7 (M+H)+. The material was used in the next step without further purification.

2H. Example 2 was prepared by following the procedures described in step 1F, by replacing 1D with 2G; followed by step 1G. ¹H NMR (500 MHz, 50° C., CD₃OD) δ ppm 9.47 (s, 1H), 7.96 (d, J=2.2 Hz, 1H), 7.67 (dd, J=8.8, 2.2 Hz, 1H), 7.57 (d, J=8.8 Hz, 1H), 7.43-7.49 (m, 3H), 7.32-7.39 (m, 2H), 7.18 (d, J=16.0 Hz, 1H), 6.76 (dd, J=15.7, 3.6 Hz, 1H), 4.99-5.04 (m, 1H), 2.52-2.60 (m, 1H), 2.40-2.48 (m, 1H), 2.18-2.26 (m, 1H), 1.84-1.90 (m, 1H), 1.31-1.58 (m, 4H), 1.21-1.29 (m, 2H), 0.87-1.01 (m, 1H), 0.40-0.54 (m, 1H). MS (ESI) m/z: 488.0 (M+H)⁺. Analytical HPLC: RT=5.78 min.

Example 3

2 TFA Salt

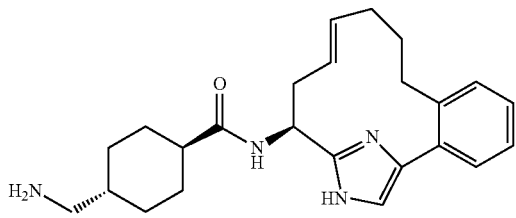 [SMILES: NC[C@H]1CC[C@H](C(=O)N[C@H]2C/C=C/CCCc3ccccc3-c3c[nH]c2n3)CC1]

3A. (E)-(S)-(16,18-Diaza-tricyclo[13.2.1.0²,⁷]octadeca-1 (17),2,4,6,11,15(18)-hexaen-14-yl)amine, 2 TFA salt: This compound was prepared following the procedures described in 1F, by replacing 1D with 2E. MS (ESI) m/z: 254.5 (M+H)⁺.

3B. {4-[(E)-(S)-(16,18-Diaza-tricyclo[13.2.1.0²,⁷]octadeca-1(17),2,4,6,11,15(18)-hexaen-14-yl)carbamoyl]-cyclohexylmethyl}-carbamic acid tert-butyl ester: To a solution of 3A (0.014 g, 0.029 mmol) in DMF (0.5 mL) was added (1r,4r)-4-((tert-butoxycarbonylamino)methyl)cyclohexanecarboxylic acid (8.23 mg, 0.032 mmol), EDC (0.011 g, 0.058 mmol), HOBt (8.91 mg, 0.058 mmol) and Hunig's base (0.015 g, 0.116 mmol). The reaction was stirred at rt for 16 h and then quenched with water to give a suspension. The solid was collected by filtration and then the solid was rinsed with water, air-dried, and then dried in a vacuum oven (50° C.) for 2 h to afford 3B (0.010 g, 69.8%) as white solid. MS (ESI) m/z: 293.7 (M+H)⁺. The material was used in the next step without further purification.

3C. Example 3: To a solution of 3B (0.01 g, 0.020 mmol) in DCM (0.3 mL) was added TFA (0.3 mL, 3.89 mmol). The reaction was stirred at rt for 1 h, and then concentrated. Purification by reverse phase chromatography afforded Example 3 (0.0095 g, 73.7%) as a white solid. ¹H NMR (500 MHz, 50° C., CD₃OD) δ ppm 7.40-7.45 (m, 2H), 7.38 (s, 1H), 7.29-7.37 (m, 2H), 5.48-5.56 (m, 1H), 5.07-5.15 (m, 1H), 5.01 (dd, J=10.4, 4.9 Hz, 1H), 2.75-2.84 (m, 3H), 2.58-2.66 (m, 1H), 2.43-2.51 (m, 2H), 2.35-2.45 (m, 1H), 1.82-2.03 (m, 6H), 1.44-1.69 (m, 4H), 1.20-1.30 (m, 1H), 1.06-1.18 (m, 2H). MS (ESI) m/z: 393.6 (M+H)⁺. Analytical HPLC: RT=3.70 min.

Example 4

{(E)-(S)-14-[(E)-3-(5-Chloro-2-tetrazol-1-yl-phenyl)-acryloylamino]-16,18-diaza-tricyclo[13.2.1.0²,⁷]octadeca-1(17),2,4,6,11,15(18)-hexaen-5-yl}-carbamic acid methyl ester, 1 TFA Salt

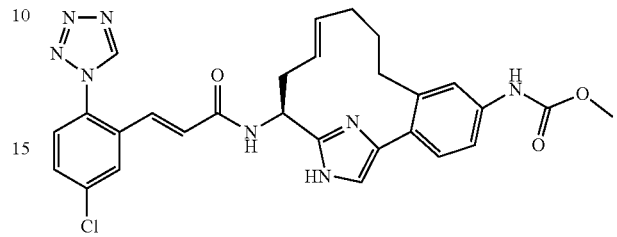

Example 4 was prepared following the procedures described in step 2A, by replacing 2-bromo-1-(2-bromophenyl)ethanone with Intermediate 8; followed by steps 2B-2E; 1F; and 1G. ¹H NMR (50° C., 500 MHz, CD₃OD) δ ppm 9.47 (s, 1H), 7.96 (d, J=1.6 Hz, 1H), 7.67 (d, J=8.8 Hz, 1H), 7.58 (d, J=8.2 Hz, 1H), 7.46 (s, 1H), 7.39 (d, J=8.3 Hz, 1H), 7.29-7.37 (m, 2H), 7.19 (d, J=15.4 Hz, 1H), 6.76 (d, J=15.4 Hz, 1H), 5.50-5.60 (m, 1H), 5.09-5.19 (m, 1H), 5.02-5.09 (m, 1H), 3.75 (s, 3H), 2.77-2.86 (m, 1H), 2.40-2.60 (m, 3H), 1.95-2.05 (m, 1H), 1.85-1.95 (m, 1H), 1.49-1.62 (m, 1H), 1.25-1.38 (m, 1H). MS (ESI) m/z: 559.1 (M+H)⁺ and 561.1 (M+2+H)⁺. Analytical HPLC (Method D): RT=5.42 min.

Example 5

(E)-N—((S)-17-Chloro-16,18-diaza-tricyclo[13.2.1.0²,⁷]octadeca-1(17),2,4,6,15(18)-pentaen-14-yl)-3-(5-chloro-2-tetrazol-1-yl-phenyl)-acrylamide, 1 TFA Salt

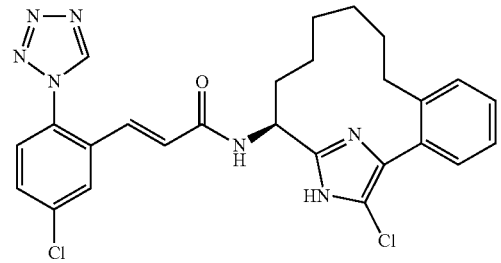 [SMILES: O=C(/C=C/c1cc(Cl)ccc1-n1cnnn1)N[C@H]1CCCCCCc2ccccc2-c2nc1[nH]c2Cl]

5A. [(S)-17-Chloro-16-(2-trimethylsilanyl-ethoxymethyl)-16,18-diaza-tricyclo[13.2.1.0²,⁷]octadeca-1(17),2,4,6,15(18)-pentaen-14-yl]-carbamic acid tert-butyl ester: To a solution of 2G (0.068 g, 0.140 mmol) in acetonitrile (0.5 mL)/CHCl₃ (0.5 mL) was added NCS (0.022 g, 0.168 mmol). The vial was sealed with a teflon-coated screw cap and the reaction was warmed to 65° C. After 3 h, the reaction was cooled to rt. The reaction was diluted with EtOAc, washed with brine, dried over sodium sulfate, filtered and concentrated. Purification by reverse phase chromatography gave, after neutralization of pure fractions and workup as described in step 2D, 0.020 g (27.5%) of 5A as a white solid. MS (ESI) m/z: 520.7 (M+H)⁺.

5B. Example 5 was prepared by following the procedures described in step 1F, by replacing 1D with 5A; followed by step 1G. $^1$H NMR (500 MHz, 50° C., CD$_3$OD) δ ppm 9.46 (s, 1H), 7.97 (d, J=2.2 Hz, 1H), 7.65 (dd, J=8.2, 2.2 Hz, 1H), 7.56 (d, J=8.8 Hz, 1H), 7.35-7.39 (m, 2H), 7.32 (s, 1H), 7.26-7.31 (m, 2H), 7.14 (d, J=15.4 Hz, 1H), 6.77 (d, J=15.4 Hz, 1H), 4.86 (dd, J=10.4, 5.5 Hz, 1H), 2.48-2.56 (m, 1H), 2.36-2.43 (m, 1H), 2.08-2.16 (m, 1H), 1.60-1.70 (m, 1H), 1.33-1.55 (m, 3H), 1.11-1.31 (m, 3H), 0.97-1.08 (m, 1H), 0.28-0.41 (m, 1H). MS (ESI) m/z: 522.4 (M+H)$^+$. Analytical HPLC: RT=8.48 min.

Example 6

{(S)-14-[(E)-3-(5-Chloro-2-tetrazol-1-yl-phenyl)-acryloylamino]-16,18-diaza-tricyclo[13.2.1.0$^{2,7}$]octadeca-1(17),2,4,6,15(18)-pentaen-5-yl}-carbamic Acid methyl ester, 1 TFA Salt

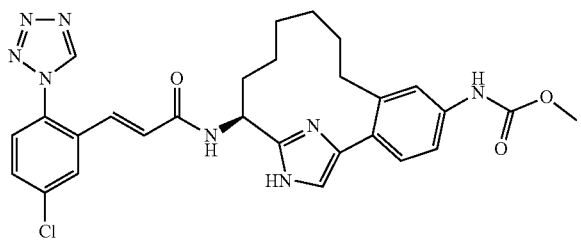 [SMILES: COC(=O)Nc1ccc2c(c1)CCCCCC[C@H](NC(=O)/C=C/c1cc(Cl)ccc1-n1cnnn1)c1nc-2c[nH]1]

Example 6 was prepared following the procedures described in step 2A, by replacing 2-bromo-1-(2-bromophenyl)ethanone with Intermediate 8; followed by steps 2B-2G; 1F, by replacing ethanol with methanol and by running the reaction at 75° C.; and 1G. $^1$H NMR (500 MHz, 50° C., CD$_3$OD) δ ppm 9.47 (s, 1H), 7.95 (d, J=2.2 Hz, 1H), 7.67 (dd, J=8.8, 2.2 Hz, 1H), 7.57 (d, J=8.2 Hz, 1H), 7.46 (d, J=2.2 Hz, 1H), 7.41-7.44 (m, 2H), 7.37 (d, J=8.3 Hz, 1H), 7.17 (d, J=15.9 Hz, 1H), 6.77 (d, J=15.9 Hz, 1H), 5.01 (dd, 5.8 Hz, 1H), 3.75 (s, 3H), 2.47-2.56 (m, 1H), 2.36-2.44 (m, 1H), 2.17-2.25 (m, 1H), 1.82-1.91 (m, 1H), 1.31-1.56 (m, 4H), 1.23-1.26 (m, 2H), 0.87-0.98 (m, 1H), 0.38-0.53 (m, 1H). MS (ESI) m/z: 561.1 (M+H)$^+$. Analytical HPLC: RT=5.45 min.

Example 7

{(S)-17-Chloro-14-[(E)-3-(5-chloro-2-tetrazol-1-yl-phenyl)-acryloylamino]-16,18-diaza-tricyclo[13.2.1.0$^{2,7}$]octadeca-1(17),2,4,6,15(18)-pentaen-5-yl}-carbamic Acid methyl ester, 1 TFA Salt

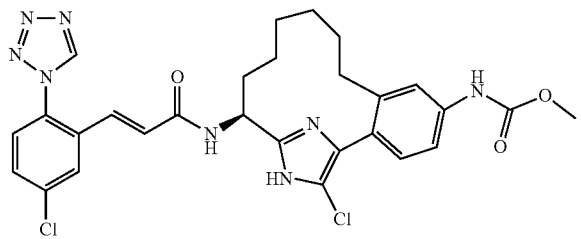 [SMILES: COC(=O)Nc1ccc2c(c1)OCCCCC[C@H](NC(=O)/C=C/c1cc(Cl)ccc1-n1cnnn1)c1nc-2c(Cl)[nH]1]

To the solution of Example 6 (0.012 g, 0.018 mmol) in acetonitrile (0.3 mL)/chloroform (0.300 mL) was added NCS (2.85 mg, 0.021 mmol). The vial was sealed with a teflon-coated screw cap and the reaction was warmed to 65° C. After 4 h, additional NCS (2.85 mg, 0.021 mmol) was added. After another 1 h, the reaction was cooled to rt, and then concentrated. Purification by reverse phase chromatography afforded 0.0040 g (30.9%) of Example 7 as a yellow solid. $^1$H NMR (500 MHz, 50° C., CD$_3$OD) δ ppm 9.46 (s, 1H), 7.97 (d, J=2.2 Hz, 1H), 7.65 (dd, J=8.8, 2.2 Hz, 1H), 7.55 (d, J=8.3 Hz, 1H), 7.40 (d, J=2.2 Hz, 1H), 7.36 (dd, J=8.3, 1.6 Hz, 1H), 7.27 (d, J=8.2 Hz, 1H), 7.13 (d, J=15.4 Hz, 1H), 6.77 (d, J=15.9 Hz, 1H), 4.85 (dd, J=10.4, 5.5 Hz, 1H), 3.75 (s, 3H), 2.43-2.52 (m, 1H), 2.31-2.40 (m, 1H), 2.05-2.15 (m, 1H), 1.57-1.68 (m, 1H), 1.10-1.53 (m, 6H), 0.95-1.07 (m, 1H), 0.26-0.38 (m, 1H). MS (ESI) m/z: 561.1 (M+H)$^+$. Analytical HPLC: RT=7.48 min.

Example 8

{(S)-14-[(E)-3-(5-Chloro-2-tetrazol-1-yl-phenyl)-acryloylamino]-8-oxa-16,18-diaza-tricyclo[13.2.1.0$^{2,7}$]octadeca-1(17),2,4,6,15(18)-pentaen-5-yl}-carbamic Acid methyl ester, 1 TFA Salt

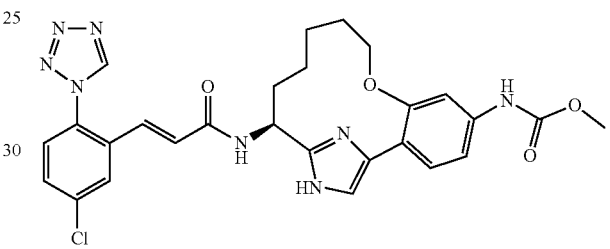

Example 8 was prepared following the procedures described in step 2A, by replacing 2-bromo-1-(2-bromophenyl)ethanone with Intermediate 7; followed by steps 2B-2C; 2E/2F-2G; 1F, by replacing ethanol with methanol and by running the reaction at 75° C.; and 1G. $^1$H NMR (500 MHz, CD$_3$OD) δ ppm 9.52 (s, 1H), 7.98 (d, J=2.2 Hz, 1H), 7.68 (dd, J=8.2, 2.2 Hz, 1H), 7.59 (d, J=8.2 Hz, 1H), 7.48-7.52 (m, 2H), 7.46 (d, J=8.2 Hz, 1H), 7.21 (dd, J=8.8, 2.2 Hz, 1H), 7.16 (d, J=15.9 Hz, 1H), 6.78 (d, J=15.9 Hz, 1H), 5.14 (dd, J=10.4, 6.0 Hz, 1H), 3.82-3.88 (m, 1H), 3.75 (s, 3H), 3.67-3.72 (m, 1H), 2.19-2.28 (m, 1H), 1.84-1.99 (m, 2H), 1.46-1.62 (m, 2H), 1.35-1.45 (m, 1H), 1.11-1.21 (m, 1H), 0.88-0.99 (m, 1H). MS (ESI) m/z: 562.9 (M+H)$^+$. Analytical HPLC: RT=5.65 min.

Example 9

{(S)-17-Chloro-14-[(E)-3-(5-chloro-2-tetrazol-1-yl-phenyl)-acryloylamino]-8-oxa-16,18-diaza-tricyclo[13.2.1.0$^{2,7}$]octadeca-1(17),2,4,6,15(18)-pentaen-5-yl}-carbamic Acid methyl ester, 1 TFA Salt

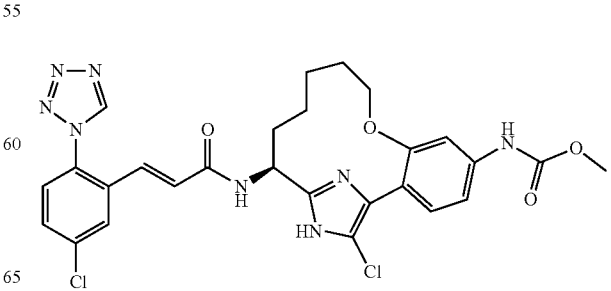

To a solution of Example 8 (0.013 g, 0.019 mmol) in acetonitrile (0.5 mL)/chloroform (0.500 mL) was added Hunig's base (6.69 µL, 0.038 mmol). The reaction was stirred at rt for 10 min, then NCS (3.08 mg, 0.023 mmol) was added. The vial was sealed with a teflon-coated screw cap and the reaction was warmed to 65° C. After 4 h, additional NCS (3.08 mg, 0.023 mmol) was added. After another 2 h, the reaction was cooled to rt and then concentrated. Purification by reverse phase chromatography afforded 0.0050 g (35.5%) of Example 9 as a yellow solid. $^1$H NMR (500 MHz, CD$_3$OD) δ ppm 9.52 (s, 1H), 7.98 (d, J=2.2 Hz, 1H), 7.67 (dd, J=8.5, 2.5 Hz, 1H), 7.58 (d, J=8.3 Hz, 1H), 7.47-7.51 (m, 2H), 7.20 (dd, J=8.8, 2.2 Hz, 1H), 7.15 (d, J=15.4 Hz, 1H), 6.77 (d, J=15.4 Hz, 1H), 5.05 (dd, J=10.4, 6.0 Hz, 1H), 3.80-3.85 (m, 1H), 3.75 (s, 3H), 3.64-3.70 (m, 1H), 2.13-2.22 (m, 1H), 1.81-1.92 (m, 2H), 1.49-1.61 (m, 2H), 1.30-1.41 (m, 1H), 1.10-1.20 (m, 1H), 0.89-1.01 (m, 1H). MS (ESI) m/z: 597.0 (M+H)$^+$. Analytical HPLC: RT=8.09 min.

Example 10

{(S)-14-[(E)-3-(5-Chloro-2-tetrazol-1-yl-phenyl)-acryloylamino]-9-oxo-8,16,18-triaza-tricyclo[13.2.1.0$^{2,7}$]octadeca-1(17),2,4,6,15(18)-pentaen-5-yl}-carbamic Acid methyl ester, 1 TFA Salt

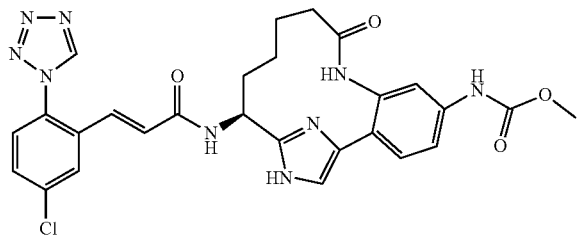 [SMILES: COC(=O)Nc1ccc2c(c1)NC(=O)CCCC[C@H](NC(=O)/C=C/c1cc(Cl)ccc1-n1cnnn1)c1nc-2c[nH]1]

10A. {3-Bromo-4-[2-((S)-1-tert-butoxycarbonylamino-but-3-enyl)-3H-imidazol-4-yl]-phenyl}-carbamic acid methyl ester: This compound was prepared following the procedures described in step 2A, by replacing 2-bromo-1-(2-bromophenyl)ethanone with Intermediate 8; followed by step 2B. MS (ESI) m/z: 467.1 (M+2+H)$^+$.

10B. {3-Bromo-4-[2-((S)-1-tert-butoxycarbonylamino-but-3-enyl)-1-(2-trimethylsilanyl-ethoxymethyl)-1H-imidazol-4-yl]-phenyl}-carbamic acid methyl ester: (The following is an alternative procedure to procedure 2C). To a cooled (0° C.) solution of 10A (15 g, 32.2 mmol) in THF (77 mL) was added N,N-dicyclohexylmethylamine (7.52 mL, 35.5 mmol) followed by the dropwise addition of SEM-Cl (6.29 mL, 35.5 mmol). The reaction was stirred at 0° C. for 2 h and then it was allowed to warm slowly to rt. After 18 h, the yellow suspension was diluted with EtOAc, washed with sat. sodium bicarbonate, brine, dried over MgSO$_4$, filtered and concentrated. Purification by normal phase chromatography gave 12.24 g (63.8%) of 10B as an off-white solid. MS (ESI) m/z: 595.1 (M+H)$^+$ and 597.2 (M+2+H)$^+$.

10C. {3-Amino-4-[2-((S)-1-tert-butoxycarbonylamino-but-3-enyl)-1-(2-trimethylsilanyl-ethoxymethyl)-1H-imidazol-4-yl]-phenyl}-carbamic acid methyl ester: A thick-walled vial containing 10B (2 g, 3.36 mmol), copper(I) iodide (0.128 g, 0.672 mmol), L-proline (0.155 g, 1.343 mmol) and potassium carbonate (1.392 g, 10.07 mmol) in DMSO (6.72 mL) was vacuumed and back-filled with argon three times. Then 28% aq. ammonium hydroxide (0.607 mL, 4.37 mmol) was added. The vial was sealed with a teflon-coated screw cap and the reaction was warmed to 85° C. After 20 h, the reaction was cooled to rt, diluted with EtOAc, washed with water, brine, dried over sodium sulfate, filtered and concentrated. Purification by normal phase chromatography afforded 1.05 g (58.8%) of 10C as a yellow solid. MS (ESI) m/z: 532.5 (M+H)$^+$.

10C (Alternative route). Compound 10B (1.0 g, 1.679 mmol), copper(I) iodide (0.032 g, 0.168 mmol), L-proline (0.058 g, 0.504 mmol) and sodium azide (0.131 g, 2.015 mmol) were added to a 35 mL pressure tube. Next, EtOH (2.52 mL), water (0.839 mL), and 1 N NaOH (0.504 mL, 0.504 mmol) were added. The reaction vessel was vacuumed and back-filled with argon three times. The pressure tube was sealed with a teflon screw cap, containing a viton O-ring, and then the reaction was warmed to 95° C. After 20 h, the reaction was cooled to rt, and additional sodium azide (0.131 g, 2.015 mmol), L-proline (0.058 g, 0.504 mmol), copper(I) iodide (0.032 g, 0.168 mmol), NaOH (0.504 mL, 0.504 mmol) and EtOH (2.52 mL) were added. The vessel was sealed and the reaction was warmed to 95° C. After another 24 h, the reaction was cooled to rt, diluted with EtOAc, washed with water, brine, dried over sodium sulfate, filtered and concentrated. Purification by normal phase chromatography gave 0.475 g (53.2%) of 10C as an orange solid. MS (ESI) m/z: 532.4 (M+H)$^+$.

10D. {3-But-3-enoylamino-4-[2-((S)-1-tert-butoxycarbonylamino-but-3-enyl)-1-(2-trimethylsilanyl-ethoxymethyl)-1H-imidazol-4-yl]-phenyl}-carbamic acid methyl ester: To a cooled (−10° C.) solution of Hunig's base (0.300 mL, 1.715 mmol), but-3-enoic acid (0.049 g, 0.572 mmol) and 10C (0.304 g, 0.572 mmol) in ethyl acetate (16.34 mL) was added 1-propanephosphonic acid cyclic anhydride (T3P) (50% in EtOAc, 0.674 mL, 1.143 mmol). After 5 min, the reaction was allowed to warm to rt. After 1 h at rt, the reaction was concentrated. Purification by normal phase chromatography gave 0.30 g (87%) of 10D as a yellow solid. MS (ESI) m/z: 600.3 (M+H)$^+$.

10E. [(E)-(S)-14-tert-Butoxycarbonylamino-9-oxo-16-(2-trimethylsilanyl-ethoxymethyl)-8,16,18-triaza-tricyclo[13.2.1.0$^{2,7}$]octadeca-1(17),2,4,6,11,15(18)-hexaen-5-yl]-carbamic acid methyl ester; and 10F. [(Z)-(S)-14-tert-Butoxycarbonylamino-9-oxo-16-(2-trimethylsilanyl-ethoxymethyl)-8,16,18-triaza-tricyclo[13.2.1.0$^{2,7}$]octadeca-1(17),2,4,6,11,15(18)-hexaen-5-yl]-carbamic acid methyl ester: Compound 10E, the E-alkene, and compound 10F, the Z-alkene, were prepared following the procedure described in 2E/2F, by replacing 2D with 10D. MS (ESI) m/z: 572.2 (M+H)$^+$.

10G. [(S)-14-tert-Butoxycarbonylamino-9-oxo-16-(2-trimethylsilanyl-ethoxymethyl)-8,16,18-triaza-tricyclo[13.2.1.0$^{2,7}$]octadeca-1(17),2,4,6,15(18)-pentaen-5-yl]-carbamic acid methyl ester: To a suspension of 10E (0.25 g, 0.437 mmol) in MeOH (10 mL)/EtOAc (5 mL) was added 10% palladium on carbon (0.047 g, 0.044 mmol). Hydrogen was bubbled through the reaction mixture for 5 min and then the reaction was stirred vigorously under a hydrogen atmosphere (balloon). After 24 h, the reaction was filtered through a 0.45 µm GMF, rinsing with MeOH, DCM and EtOAc. The filtrate was concentrated and purification by reverse phase chromatography afforded 0.220 g (88%) of 10G, as an off-white solid. MS (ESI) m/z: 574.4 (M+H)$^+$.

10H. ((S)-14-Amino-9-oxo-8,16,18-triaza-tricyclo[13.2.1.0$^{2,7}$]octadeca-1(17),2,4,6,15(18)-pentaen-5-yl)-carbamic acid methyl ester, 2 HCl salt: A mixture of 10G (0.099 g, 0.173 mmol) and 4M HCl in dioxane (2 mL, 8.00 mmol)

in a sealed tube was heated at 50° C. After 2 h, the yellow suspension was cooled to rt and then concentrated. The residue was suspended in MeOH (0.2 mL) and Et$_2$O. The solid was collected by filtration. The solid was rinsed with Et$_2$O, air-dried (very hygroscopic) to afford 0.053 g (73.8%) of 10H as a yellow solid. MS (ESI) m/z: 344.2 (M+H)$^+$.

10I. Example 10 was prepared following the procedure described in 1G, by replacing 1F with 10H. $^1$H NMR (400 MHz, CD$_3$OD) δ ppm 9.51 (s, 1H), 7.97 (d, J=2.2 Hz, 1H), 7.67 (dd, J=8.2, 2.2 Hz, 1H), 7.55-7.60 (m, 2H), 7.50 (d, J=8.2 Hz, 1H), 7.44 (s, 1H), 7.42 (dd, J=8.3, 2.2 Hz, 1H), 7.13 (d, J=15.4 Hz, 1H), 6.76 (d, J=15.9 Hz, 1H), 5.13 (dd, J=10.2, 6.3 Hz, 1H), 3.75 (s, 3H), 2.42-2.52 (m, 1H), 2.17-2.29 (m, 1H), 2.05-2.15 (m, 1H), 1.96 (m, 1H), 1.51-1.71 (m, 2H), 1.36-1.49 (m, 1H), 0.92-1.07 (m, 1H). MS (ESI) m/z: 576.3 (M+H)$^+$. Analytical HPLC: RT=4.60 min.

Example 11

{(S)-14-[(E)-3-(5-Chloro-2-tetrazol-1-yl-phenyl)-acryloylamino]-8,16,18-triaza-tricyclo[13.2.1.0$^{2,7}$]octadeca-1(17),2,4,6,15(18)-pentaen-5-yl}-carbamic Acid methyl ester, 2 TFA Salt

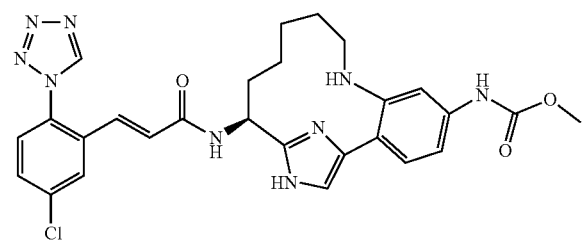

Example 11 was prepared following the procedures described in step 10C, by replacing ammonium hydroxide with but-3-enylamine and running the reaction at 90° C.; followed by steps 10E/F; 10G, by replacing the methanol/EtOAc mixture with EtOAc; 1F, by replacing ethanol with methanol and running the reaction at 75° C.; and 1G. $^1$H NMR (400 MHz, CD$_3$OD) δ ppm 9.54 (s, 1H), 8.01 (d, J=2.2 Hz, 1H), 7.82 (s, 1H), 7.69 (dd, J=8.8, 2.2 Hz, 1H), 7.61 (d, J=8.8 Hz, 1H), 7.55 (d, J=8.2 Hz, 1H), 7.40 (s, 1H), 7.28 (dd, J=8.8, 2.2 Hz, 1H), 7.24 (d, J=15.9 Hz, 1H), 6.81 (d, J=15.4 Hz, 1H), 5.29 (dd, J=10.7, 6.3 Hz, 1H), 3.72 (s, 3H), 3.16-3.24 (m, 1H), 2.93 (t, J=11.5 Hz, 1H), 2.00-2.20 (m, 3H), 1.82-1.92 (m, 1H), 1.62-1.76 (m, 2H), 1.27-1.41 (m, 1H), 0.78-0.87 (m, 1H). MS (ESI) m/z: 562.2 (M+H)$^+$. Analytical HPLC: RT=5.59 min.

Example 12

{(E)-(S)-14-[(E)-3-(5-Chloro-2-tetrazol-1-yl-phenyl)-acryloylamino]-9-oxo-8,16,18-triaza-tricyclo[13.2.1.0$^{2,7}$]octadeca-1(17),2,4,6,11,15(18)-hexaen-5-yl}-carbamic Acid methyl ester, 1 TFA Salt

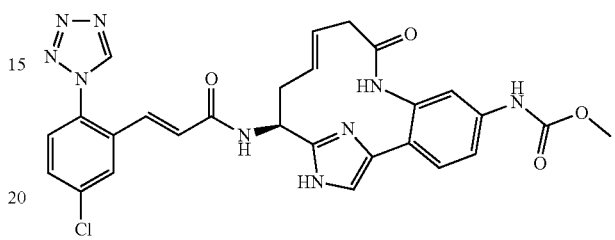

Example 12 was prepared following the procedures described in step 10H, by replacing 10G with 10E; followed by step 1G. $^1$H NMR (500 MHz, CD$_3$OD) δ ppm 9.52 (s, 1H), 7.98 (d, J=2.2 Hz, 1H), 7.66-7.72 (m, 2H), 7.59 (d, J=8.2 Hz, 1H), 7.45 (s, 2H), 7.35 (s, 1H), 7.16 (d, J=15.4 Hz, 1H), 6.76 (d, J=15.4 Hz, 1H), 5.73-5.82 (m, 1H), 5.21-5.29 (m, 1H), 5.10 (dd, J=9.1, 5.2 Hz, 1H), 3.75 (s, 3H), 2.91-3.03 (m, 2H), 2.81-2.89 (m, 1H), 2.48-2.59 (m, 1H). MS (ESI) m/z: 574.1 (M+H)$^+$. Analytical HPLC: RT=4.78 min.

Example 13

{(S)-14-[(E)-3-(3-Chloro-2-fluoro-6-tetrazol-1-yl-phenyl)-acryloylamino]-9-oxo-8,16,18-triaza-tricyclo[13.2.1.0$^{2,7}$]octadeca-1(17),2,4,6,15(18)-pentaen-5-yl}-carbamic Acid methyl ester, 1 TFA Salt

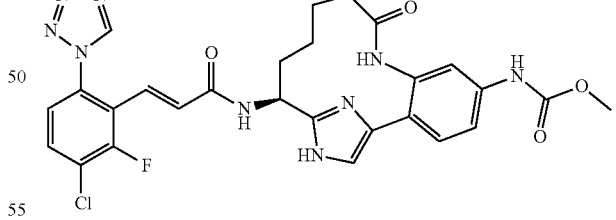

Example 13 was prepared following the procedure described in 1G, by replacing 1F with 10H and by replacing Intermediate 1 with Intermediate 3. $^1$H NMR (500 MHz, CD$_3$OD) δ ppm 9.52 (s, 1H), 7.78 (t, J=8.2 Hz, 1H), 7.56 (s, 1H), 7.40-7.52 (m, 4H), 7.00 (d, J=15.9 Hz, 1H), 6.81 (d, J=15.9 Hz, 1H), 5.12 (dd, J=9.9, 6.6 Hz, 1H), 3.75 (s, 3H), 2.42-2.51 (m, 1H), 2.16-2.26 (m, 1H), 2.04-2.13 (m, 1H), 1.89-2.00 (m, 1H), 1.51-1.69 (m, 2H), 1.36-1.48 (m, 1H), 0.90-1.03 (m, 1H). MS (ESI) m/z: 594.3 (M+H)$^+$. Analytical HPLC: RT=4.79 min.

Example 14

{(S)-14-[(E)-3-(2-Acetyl-5-chloro-phenyl)-acryloylamino]-9-oxo-8,16,18-triaza-tricyclo[13.2.1.0$^{2,7}$]octadeca-1(17),2,4,6,15(18)-pentaen-5-yl}-carbamic Acid methyl ester, 1 TFA Salt

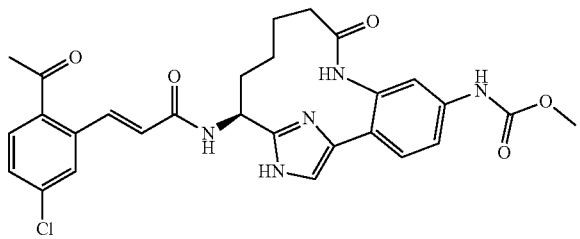 [SMILES: COC(=O)Nc1ccc2c(c1)NC(=O)CCCC[C@H](NC(=O)/C=C/c1cc(Cl)ccc1C(C)=O)c1nc-2c[nH]1]

Example 14 was prepared following the procedure described in step 1G, by replacing 1F with 10H, by replacing Intermediate 1 with Intermediate 4, and by using EDC, HOBt, and triethylamine. $^1$H NMR (400 MHz, CD$_3$OD) δ ppm 7.97 (d, J=15.4 Hz, 1H), 7.91 (d, J=8.2 Hz, 1H), 7.65 (d, J=1.6 Hz, 1H), 7.58 (d, J=2.2 Hz, 1H), 7.50-7.55 (m, 2H), 7.47 (s, 1H), 7.43 (dd, J=8.8, 2.2 Hz, 1H), 6.54 (d, J=15.9 Hz, 1H), 5.17 (dd, J=10.2, 6.3 Hz, 1H), 3.76 (s, 3H), 2.59 (s, 3H), 2.45-2.53 (m, 1H), 2.20-2.31 (m, 1H), 2.05-2.15 (m, 1H), 1.92-2.02 (m, 1H), 1.55-1.72 (m, 2H), 1.40-1.52 (m, 1H), 0.94-1.07 (m, 1H). MS (ESI) m/z: 550.2 (M+H)$^+$. Analytical HPLC: RT=5.01 min.

Example 15

(E)-3-(5-Chloro-2-tetrazol-1-yl-phenyl)-N—((S)-9-oxo-8,16,18-triaza-tricyclo[13.2.1.0$^{2,7}$]octadeca-1(17),2,4,6,15(18)-pentaen-14-yl)-acrylamide, 1 TFA Salt

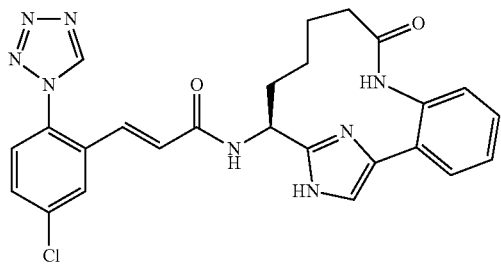 [SMILES: O=C(/C=C/c1cc(Cl)ccc1-n1cnnn1)N[C@H]1CCCCC(=O)Nc2ccccc2-c2c[nH]c1n2]

15A. {(S)-1-[4-(2-Nitro-phenyl)-1-(2-trimethylsilanyl-ethoxymethyl)-1H-imidazol-2-yl]-but-3-enyl}-carbamic acid tert-butyl ester: This compound was prepared following the procedures described in step 2A, by replacing 2-bromo-1-(2-bromophenyl)ethanone with 2-bromo-1-(2-nitrophenyl)ethanone; followed by steps 2B, by replacing xylene with toluene; and 2C. MS (ESI) m/z: 489.4 (M+H)$^+$.

15B. {(S)-1-[4-(2-Amino-phenyl)-1-(2-trimethylsilanyl-ethoxymethyl)-1H-imidazol-2-yl]-but-3-enyl}-carbamic acid tert-butyl ester: To a yellow solution of 15A (1.0441 g, 2.137 mmol) in MeOH (14.15 mL) was added zinc dust (1.397 g, 21.37 mmol) and ammonium chloride (1.143 g, 21.37 mmol). The gray suspension was stirred vigorously at rt. After 1 h, the flask was equipped with a reflux condenser and the reaction was warmed to 60° C. After 1 h, the reaction was cooled to rt and allowed to stir overnight. The reaction was filtered through a 0.45 μm GMF, eluting with methanol. The filtrate was concentrated to give a yellow solid. The solid was partitioned between EtOAc and 0.5M HCl (aq). The layers were separated and the aqueous layer was extracted with EtOAc (1×). The combined organic layers were washed with sat. NaHCO$_3$, brine, dried over Na$_2$SO$_4$, filtered and concentrated to give an orange oil. Purification by normal phase chromatography gave 0.818g (83%) of 15B as a yellow foam. MS (ESI) m/z: 459.4 (M+H)$^+$.

15C. (S)-14-Amino-8,16,18-triaza-tricyclo[13.2.1.0$^{2,7}$]octadeca-1(17),2,4,6,15(18)-pentaen-9-one, 2HCl: This compound was prepared following the procedures in step 10D, by replacing 10C with 15B; followed by steps 2E/2F; 2G, by replacing the hydrogen balloon with hydrogen (50-55 psi); and 10H. MS (ESI) m/z: 489.4 (M+H)$^+$.

15D. Example 15: A suspension of Intermediate 2 (0.074 g, 0.296 mmol), 15C (0.113 g, 0.329 mmol), EDC (0.095 g, 0.494 mmol), and HOBT (0.076 g, 0.494 mmol) in DMF (1.65 mL) and Hunig's Base (0.172 mL, 0.988 mmol) was stirred at rt overnight. Water was added to the brown solution to give a suspension. The mixture was extracted with EtOAc (2×). The organic layers were combined and washed with sat. NaHCO$_3$, brine, dried over Na$_2$SO$_4$, filtered and concentrated. Purification by reverse phase chromatography gave 0.0964 g (47%) of Example 15 as a white solid. $^1$H NMR (500 MHz, CD$_3$OD) δ ppm 0.96-1.13 (m, 1H), 1.37-1.50 (m, 1H), 1.51-1.72 (m, 2H), 1.90-2.01 (m, 1H), 2.05-2.15 (m, 1H), 2.18-2.28 (m, 1H), 2.44-2.50 (m, 1H), 5.13 (dd, J=10.2, 6.3 Hz, 1H), 6.75 (d, J=15.7 Hz, 1H), 7.14 (d, J=15.7 Hz, 1H), 7.31 (dd, J=7.8, 0.7 Hz, 1H), 7.44 (td, J=7.6, 1.1 Hz, 1H), 7.49 (s, 1H), 7.53 (td, J=7.7, 1.4 Hz, 1H), 7.58 (d, J=8.5 Hz, 1H), 7.61 (dd, J=7.7, 1.4 Hz, 1H), 7.67 (dd, 2.5 Hz, 1H), 7.97 (d, J=2.2 Hz, 1H), 9.50 (s, 1H). MS (ESI) m/z: 503.3 (M+H)$^+$. Analytical HPLC: RT=4.72 min.

Example 16

4-Aminomethyl-cyclohexanecarboxylic Acid ((S)-9-oxo-8,16,18-triaza-tricyclo[13.2.1.0$^{2,7}$]octadeca-1(17),2,4,6,15(18)-pentaen-14-yl)-amide, 2 TFA Salt

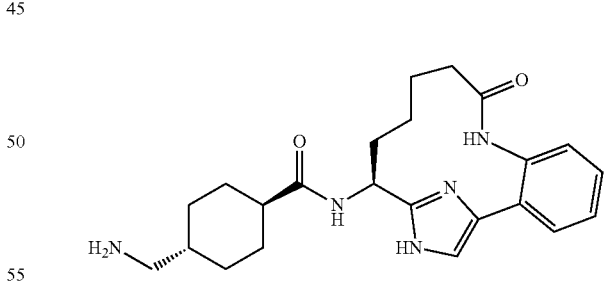

16A. [4-((S)-9-Oxo-8,16,18-triaza-tricyclo[13.2.1.0$^{2,7}$]octadeca-1(17),2,4,6,15(18)-pentaen-14-ylcarbamoyl)-cyclohexylmethyl]-carbamic acid tert-butyl ester: This compound was prepared following the procedure described in 3B, by replacing 3A with 15C. MS (ESI) m/z: 510.4 (M+H)$^+$.

16B. Example 16 was prepared following the procedure described in 3C, by replacing 3B with 16A. $^1$H NMR (500 MHz, CD$_3$OD) δ ppm 0.91-1.18 (m, 3H), 1.28-1.75 (m, 6H), 1.84-1.98 (m, 5H), 2.07-2.23 (m, 2H), 2.33 (tt, J=12.1, 3.3 Hz, 1H), 2.43-2.53 (m, 1H), 2.79 (d, J=6.9 Hz, 2H), 5.05

(dd, J=10.7, 6.3 Hz, 1H), 7.32 (dd, J=7.8, 1.0 Hz, 1H), 7.44 (td, J=7.7, 1.3 Hz, 1H), 7.49 (s, 1H), 7.53 (td, J=7.7, 1.5 Hz, 1H), 7.60 (dd, J=7.7, 1.4 Hz, 1H). MS (ESI) m/z: 410.4 (M+H)$^+$. Analytical HPLC: RT=1.56, 2.10 min.

Example 17

4-Aminomethyl-cyclohexanecarboxylic Acid ((S)-17-chloro-9-oxo-8,16,18-triaza-tricyclo[13.2.1.0$^{2,7}$]octadeca-1(17),2,4,6,15(18)-pentaen-14-yl)-amide, 2 TFA Salt

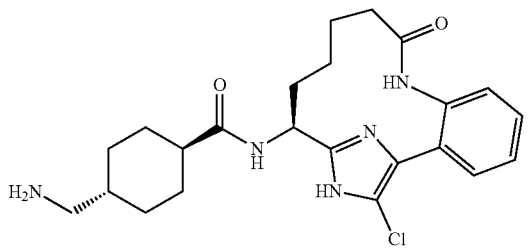 [SMILES: NC[C@H]1CC[C@H](C(=O)N[C@H]2CCCCC(=O)Nc3ccccc3-c3nc2[nH]c3Cl)CC1]

17A. [4-((S)-17-Chloro-9-oxo-8,16,18-triaza-tricyclo[13.2.1.0$^{2,7}$]octadeca-1(17),2,4,6,15(18)-pentaen-14-ylcarbamoyl)-cyclohexylmethyl]-carbamic acid tert-butyl ester: Compound 16A was dissolved in EtOAc and washed with sat. NaHCO$_3$, brine, dried over Na$_2$SO$_4$, filtered and concentrated to give the free base of 16A. To a suspension of the free base of 16A (0.067 g, 0.131 mmol) in acetonitrile (1.32 mL) and chloroform (1.32 mL) was added NCS (0.018 mg, 0.131 mmol). The thick-walled vial was sealed with a teflon coated screw cap and the reaction was heated to 65° C. After 1 h and 35 min, the reaction was cooled to rt and partitioned between EtOAc and water. The layers were separated and the aqueous layer was extracted with EtOAc (1×). The organic layers were combined, washed with sat. NaHCO$_3$, brine, dried over Na$_2$SO$_4$, filtered and concentrated. Purification by reverse phase chromatography gave 0.018 g (17%) of 17A as a white solid. MS (ESI) m/z: 544.3 (M+H)$^+$.

17B. Example 17 was prepared following the procedure described in 3C, by replacing 3B with 17A. $^1$H NMR (500 MHz, CD$_3$OD) δ ppm 0.93-1.17 (m, 3H), 1.34-1.80 (m, 7H), 1.86-2.10 (m, 6H), 2.25-2.34 (m, 1H), 2.36-2.43 (m, 1H), 2.80 (d, J=7.2 Hz, 2H), 4.93 (dd, J=10.7, 6.1 Hz, 1H), 7.27 (dd, J=7.7, 1.4 Hz, 1H), 7.41 (td, J=7.6, 1.3 Hz, 1H), 7.46 (td, J=7.6, 1.6 Hz, 1H), 7.60 (dd, J=7.4, 1.4 Hz, 1H). MS (ESI) m/z: 444.2 (M+H)$^+$. Analytical HPLC: RT=3.36 min.

Example 18

{(S)-14-[(E)-3-(5-Chloro-2-tetrazol-1-yl-phenyl)-acryloylamino]-9,9-dioxo-9λ$^6$-thia-8,16,18-triaza-tricyclo[13.2.1.0$^{2,7}$]octadeca-1(17),2,4,6,15 (18)-pentaen-5-yl}-carbamic Acid methyl ester, 1 TFA Salt

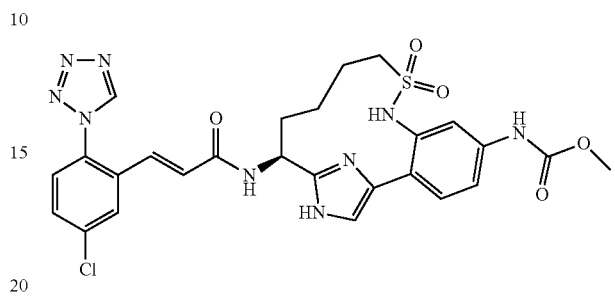

18A. [4-[2-((S)-1-tert-Butoxycarbonylamino-but-3-enyl)-1-(2-trimethylsilanyl-ethoxymethyl)-1H-imidazol-4-yl]-3-(prop-2-ene-1-sulfonylamino)-phenyl]-carbamic acid methyl ester: To a solution of 10C (178 mg, 0.335 mmol) in CH$_2$Cl$_2$ (2 mL) was added DIEA (0.117 mL, 0.670 mmol). The reaction was cooled to 0° C. Next, a solution of prop-2-ene-1-sulfonyl chloride (54.5 mg, 0.368 mmol) in DCM (1 ml) was added dropwise. The resulting mixture was stirred at 0° C. for 2 h. The reaction was concentrated and purification by normal phase chromatography gave 18A as a pale yellow solid (124 mg, 58%). MS (ESI) m/z: 636.4 (M+H)$^+$.

18B. Example 18 was prepared following the procedures described in step 2E/2F, by replacing 2D with 18A; followed by steps 2G; 10H; and 1G. $^1$H NMR (400 MHz, CD$_3$OD) δ ppm 9.52 (s, 1H), 7.98 (d, J=2.2 Hz, 1H), 7.64-7.75 (m, 2H), 7.54-7.64 (m, 2H), 7.43-7.54 (m, 2H), 7.16 (d, J=15.4 Hz, 1H), 6.78 (d, J=15.4 Hz, 1H), 5.04 (dd, J=9.3, 4.9 Hz, 1H), 3.75 (s, 3H), 2.92-3.01 (m, 2H), 2.16-2.27 (m, 1H), 1.88-1.98 (m, 1H), 1.69-1.81 (m, 1H), 1.52-1.66 (m, 1H), 1.08-1.25 (m, 1H), 0.72-0.93 (m, 1H). MS (ESI) m/z: 612.3 (M+H)$^+$. Analytical HPLC: RT=3.92 min (Method B).

Example 19

{(E)-(S)-14-[(E)-3-(5-Chloro-2-tetrazol-1-yl-phenyl)-acryloylamino]-9,9-dioxo-9λ$^6$-thia-8,16,18-triaza-tricyclo[13.2.1.0$^{2,7}$]octadeca-1(17),2,4,6,11,15 (18)-hexaen-5-yl}-carbamic Acid methyl ester, 1 TFA Salt

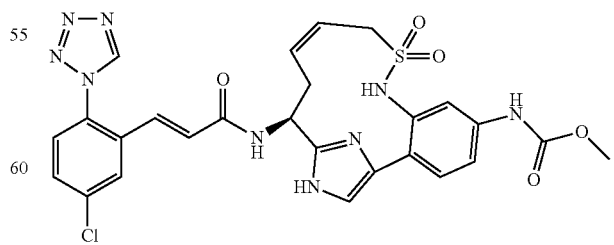

Example 19 was prepared following the procedures described in step 2E, by replacing 2D with 18A; followed by steps 10H; and 1G. $^1$H NMR (400 MHz, CD$_3$OD) δ ppm 9.50 (s, 1H), 7.98 (d, J=2.3 Hz, 1H), 7.74 (s, 1H), 7.68 (dd, J=8.6, 2.3 Hz, 1H), 7.54-7.62 (m, 1H), 7.46-7.54 (m, 2H), 7.43 (s, 1H), 7.17 (d, J=15.7 Hz, 1H), 6.78 (d, J=15.7 Hz, 1H), 5.88-6.06 (m, 1H), 5.07-5.22 (m, 2H), 3.85-4.08 (m, 2H), 3.76 (s, 3H), 2.81-2.95 (m, 1H), 2.47-2.64 (m, 1H). MS (ESI) m/z: 610.3 (M+H)+. Analytical HPLC: RT=3.49 min (Method B).

Example 20

{(S)-14-[(E)-3-(5-Chloro-2-tetrazol-1-yl-phenyl)-acryloylamino]-9-oxo-8,12,16,18-tetraaza-tricyclo[13.2.1.0$^{2,7}$]octadeca-1(17),2,4,6,15-pentaen-5-yl}-carbamic Acid methyl ester, 2 TFA Salt

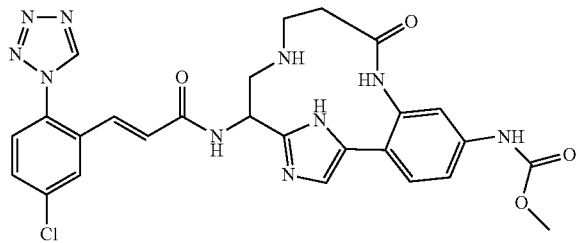 [SMILES: COC(=O)Nc1ccc2c(c1)NC(=O)CCNCC(NC(=O)/C=C/c1cc(Cl)ccc1-n1cnnn1)c1ncc-2[nH]1]

20A. {(S)-2-Benzyloxycarbonylamino-2-[4-(2-bromo-4-methoxycarbonylamino-phenyl)-1-(2-trimethylsilanyl-ethoxymethyl)-1H-imidazol-2-yl]-ethyl}-carbamic acid tert-butyl ester: This compound was prepared following the procedures described in step 2A, by replacing (S)-2-(tert-butoxycarbonylamino)pent-4-enoic acid with (S)-2-benzyloxycarbonylamino-3-tert-butoxycarbonylamino-propionic acid and by replacing 2-bromo-1-(2-bromophenyl)ethanone with Intermediate 8; followed by steps 2B; and 10B. MS (ESI) m/z: 720.5 (M+H)+.

20B. {4-[2-((S)-2-Amino-1-benzyloxycarbonylamino-ethyl)-1-(2-trimethylsilanyl-ethoxymethyl)-1H-imidazol-4-yl]-3-bromo-phenyl}-carbamic acid methyl ester: This compound was prepared following the procedure described in 3C, by replacing 3B with 20A. MS (ESI) m/z: 620.3 (M+H)+.

20C. 3-{(S)-2-Benzyloxycarbonylamino-2-[4-(2-bromo-4-methoxycarbonylamino-phenyl)-1-(2-trimethylsilanyl-ethoxymethyl)-1H-imidazol-2-yl]-ethylamino}-propionic acid methyl ester: To a mixture of 20B (204 mg, 0.330 mmol), methyl acrylate (0.089 mL, 0.989 mmol) and triethylamine (0.230 mL, 1.649 mmol) was added isopropyl alcohol (3 mL) in a sealed microwave tube. The reaction was stirred at 80° C. overnight. The reaction mixture was concentrated to give 20C (208 mg, 90% yield) as a beige solid. MS (ESI) m/z: 706.4 (M+H)+.

20D. 3-({(S)-2-Benzyloxycarbonylamino-2-[4-(2-bromo-4-methoxycarbonylamino-phenyl)-1-(2-trimethylsilanyl-ethoxymethyl)-1H-imidazol-2-yl]-ethyl}-tert-butoxycarbonyl-amino)-propionic acid methyl ester: To a solution of 20C (208 mg, 0.295 mmol) in CH$_2$Cl$_2$ (2952 μL) at 0° C. was added di-tert-butyl dicarbonate (64.4 mg, 0.295 mmol) and DMAP (3.61 mg, 0.030 mmol). The reaction mixture was stirred at 0° C. and allowed to warm slowly to rt. After 4 h, the reaction mixture was concentrated and purified by normal phase chromatography to give 20D (180 mg, 0.224 mmol, 76% yield) as a pale yellow solid. MS (ESI) m/z: 806.2 (M+H)+.

20E. 3-({(S)-2-[4-(2-Amino-4-methoxycarbonylamino-phenyl)-1-(2-trimethylsilanyl-ethoxymethyl)-1H-imidazol-2-yl]-2-benzyloxycarbonylamino-ethyl}-tert-butoxycarbonyl-amino)-propionic acid: This compound was prepared following the procedure described in 10C (alternative route), by replacing 10B with 20D. MS (ESI) m/z: 727.6 (M+H)+.

20F. (S)-14-Benzyloxycarbonylamino-5-methoxycarbonylamino-9-oxo-16-(2-trimethylsilanyl-ethoxymethyl)-8,12,16,18-tetraaza-tricyclo[13.2.1.0$^{2,7}$]octadeca-1(17),2,4,6,15(18)-pentaene-12-carboxylic acid tert-butyl ester: To a solution of BOP (50.2 mg, 0.113 mmol) in DCM (44.900 ml) and DMF (0.449 ml) at rt was added a solution of 20E (33 mg, 0.045 mmol) and DIEA (0.079 ml, 0.454 mmol) in DMF (3 mL) via a syringe pump over 5 h. The reaction mixture was concentrated to remove DCM, then diluted with ethyl acetate and washed with saturated aqueous sodium bicarbonate. The aqueous layer was extracted with ethyl acetate, and the combined organic layers were washed with water, brine, dried over magnesium sulfate, filtered, and concentrated. Normal phase chromatography gave 20F (28 mg, 87% yield) as an off-white solid. MS (ESI) m/z: 709.3 (M+H)+.

20G. Example 20 was prepared following the procedures described in step 2G, by replacing 2E/2F with 20F; followed by steps 1G; and 3C. $^1$H NMR (400 MHz, MeOD-d$_4$) δ ppm 9.49 (s, 1H) 7.93 (d, J=2.2 Hz, 1H) 7.66 (dd, J=8.79, 2.2 Hz, 1H) 7.57 (d, J=8.24 Hz, 2H) 7.42 (m, 3H) 7.22 (d, J=15.94 Hz, 1H) 6.62 (d, J=15.39 Hz, 1H) 5.40 (dd, J=6.05, 2.75 Hz, 1H) 3.74 (s, 3H) 3.51-3.69 (m, 2H) 3.25-3.39 (m, 2H) 2.89-2.98 (m, 2H). MS (ESI) m/z: 577.3 (M+H)+. Analytical HPLC: RT=4.72 min.

Example 21

{(S)-14-[(E)-3-(5-Chloro-2-tetrazol-1-yl-phenyl)-acryloylamino]-10,10-difluoro-11-oxo-8,12,16,18-tetraaza-tricyclo[13.2.1.02,7]octadeca-1(17),2,4,6,15(18)-pentaen-5-yl}-carbamic Acid methyl ester, 1 TFA Salt

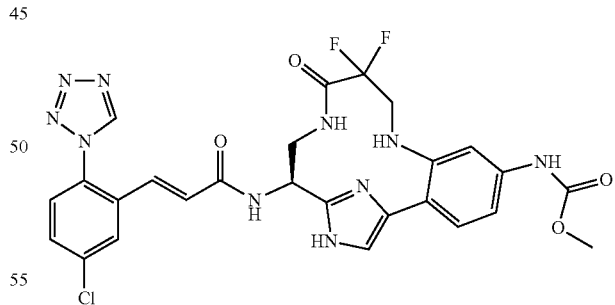

Example 21 was prepared following the procedures described in step 10C (alternative route), by replacing sodium azide with 3-amino-2,2-difluoropropanoic acid and by replacing 10B with 20A; followed by steps 3C; 20F; 2G; 1G; and 3C. MS (ESI) m/z: 613.3 (M+H)+. Analytical HPLC: RT=5.24 min.

Example 22

{(S)-14-[(E)-3-(5-Chloro-2-tetrazol-1-yl-phenyl)-acryloylamino]-9-oxo-10-oxa-8,16,18-triaza-tricyclo[13.2.1.0$^{2,7}$]octadeca-1(17),2,4,6,15(18)-pentaen-5-yl}-carbamic Acid methyl ester, 1 TFA Salt

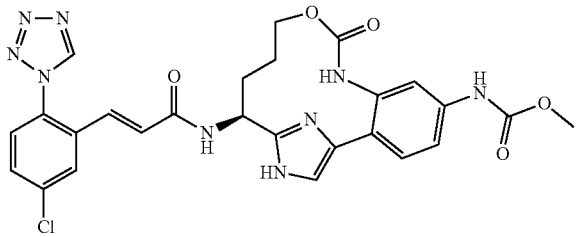 [SMILES: COC(=O)Nc1ccc2c(c1)NC(=O)OCCC[C@H](NC(=O)/C=C/c1cc(Cl)ccc1-n1cnnn1)c1nc-2c[nH]1]

22A. (S)-2-(2-Bromo-4-nitrophenyl)-2-oxoethyl 5-(benzyloxy)-2-(tert-butoxycarbonylamino)pentanoate: This compound was prepared following the procedure described in 2A, by replacing (S)-2-(tert-butoxycarbonylamino)pent-4-enoic acid with (S)-5-(benzyloxy)-2-(tert-butoxycarbonylamino)pentenoic acid and replacing 2-bromo-1-(2-bromophenyl)ethanone with Intermediate 10. MS (ESI) m/z: 565.4 (M+2−H)$^−$.

22B. (S)-2-(4-Amino-2-bromophenyl)-2-oxoethyl 5-(benzyloxy)-2-(tert-butoxycarbonylamino)pentanoate: To a solution of 22A (2.6 g, 4.60 mmol) in ethanol (30 mL) was added iron powder (2.57 g, 46.0 mmol). The suspension was mixed briefly and then 1.0 M aqueous hydrochloric acid (2.299 mL, 2.299 mmol) was added. The reaction mixture was heated to 50° C. After 2 h, the reaction was cooled to rt, diluted with ethyl acetate, and filtered through a pad of CELITE®, eluting with ethyl acetate. The filtrate was concentrated, re-dissolved in ethyl acetate, washed with sat. NaHCO$_3$, brine, dried over sodium sulfate and concentrated to give 22B (1.954 g, 79% yield) as a yellow solid. The material was used in the next step without further purification. MS (ESI) m/z: 537.4 (M+2+H)$^+$.

22C. {3-Amino-4-[2-((S)-4-benzyloxy-1-tert-butoxycarbonylamino-butyl)-1-(2-trimethylsilanyl-ethoxymethyl)-1H-imidazol-4-yl]-phenyl}-carbamic acid methyl ester: This compound was prepared following the procedures described in step Intermediate 7B, by replacing Intermediate 7A with 22B; followed by steps 1B; 10B; and 10C (alternate). MS (ESI) m/z: 640.5 (M+H)$^+$.

22D. {3-Amino-4-[2-((S)-1-tert-butoxycarbonylamino-4-hydroxy-butyl)-1-(2-trimethylsilanyl-ethoxymethyl)-1H-imidazol-4-yl]-phenyl}-carbamic acid methyl ester: To a solution of 22C (0.446 g, 0.697 mmol) in EtOAc (10 mL) was added TFA (0.081 mL, 1.046 mmol). The reaction was stirred at rt for 5 min, then 10% palladium on carbon (0.074 g, 0.070 mmol) was added. Hydrogen was bubbled through the reaction for a few minutes, then the reaction was stirred vigorously under a hydrogen atmosphere (balloon). After 17 h, the reaction was filtered through a 0.45 micron GMF, rinsing with EtOAc and MeOH. The filtrate was concentrated, redissolved in EtOAc, washed with sat. sodium bicarbonate, brine, dried over sodium sulfate, filtered and concentrated to afford 22D (0.35 g, 91%) as a yellow solid. MS (ESI) m/z: 550.4 (M+H)$^+$. The material was used in the next step without further purification.

22E. [(S)-5-Methoxycarbonylamino-9-oxo-16-(2-trimethylsilanyl-ethoxymethyl)-10-oxa-8,16,18-triaza-tricyclo[13.2.1.0$^{2,7}$]octadeca-1(17),2,4,6,15(18)-pentaen-14-yl]-carbamic acid tert-butyl ester: To a solution of 22D (0.19 g, 0.346 mmol) in DCM (15.03 mL) at 0° C. was added TEA (0.096 mL, 0.691 mmol) followed by 4-nitrophenyl carbonochloridate (0.077 g, 0.380 mmol). After 1 h, the reaction was warmed to rt. After 18 h, the reaction was concentrated. Purification by reverse phase chromatography afforded 22E (0.049 g, 24.63%), as a yellow solid. MS (ESI) m/z: 576.5 (M+H)$^+$.

22F. Example 22 was prepared following the procedures described in step 1F, by replacing 1E with 22E, by replacing ethanol with methanol, and by running the reaction at 75° C.; followed by step 1G. $^1$H NMR (400 MHz, CD$_3$OD) δ ppm 9.42 (s, 1H), 7.76 (d, J=2.2 Hz, 1H), 7.59-7.68 (m, 2H), 7.46-7.55 (m, 2H), 7.22 (d, J=8.3 Hz, 1H), 7.16 (dd, J=8.8, 2.2 Hz, 1H), 6.88 (d, J=15.4 Hz, 1H), 6.65 (d, J=15.4 Hz, 1H), 5.26 (t, J=7.7 Hz, 1H), 3.71 (s, 3H), 3.61 (t, J=6.0 Hz, 2H), 2.08-2.22 (m, 2H), 1.54-1.74 (m, 2H). MS (ESI) m/z: 578.3 (M+H)$^+$. Analytical HPLC: RT=4.70 min.

Example 23

{(S)-14-[(E)-3-(5-Chloro-2-tetrazol-1-yl-phenyl)-acryloylamino]-11-methyl-12-oxo-11,16,18-triaza-tricyclo[13.2.1.0$^{2,7}$]octadeca-1(17),2,4,6,15(18)-pentaen-5-yl}-carbamic Acid methyl ester, 1 TFA Salt

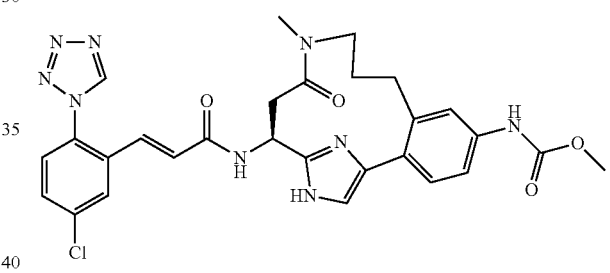

23A. (S)-3-[4-(2-Bromo-4-methoxycarbonylamino-phenyl)-1-(2-trimethylsilanyl-ethoxymethyl)-1H-imidazol-2-yl]-3-tert-butoxycarbonylamino-propionic acid benzyl ester: This compound was prepared following the procedures described in 2A, by replacing (S)-2-(tert-butoxycarbonylamino)pent-4-enoic acid with (S)-2-tert-butoxycarbonylamino-succinic acid 4-benzyl ester, by replacing 2-bromo-1-(2-bromophenyl)ethanone with Intermediate 8 and by replacing potassium hydrogen carbonate with potassium carbonate; followed by steps 2B, by replacing xylene with toluene; and 10B. MS (ESI) m/z: 703.3, 705.3 (M+H)$^+$.

23B. Methyl-prop-2-ynyl-carbamic acid benzyl ester: To a solution of N-methylprop-2-yn-1-amine (3.50 g, 50.6 mmol) in DCM (50 mL) were added TEA (8.47 mL, 60.8 mmol) and Cbz-Cl (7.95 mL, 55.7 mmol) dropwise at 0° C. The reaction was stirred under argon at 0° C. for 1 h. The reaction mixture was diluted with CH$_2$Cl$_2$, washed with 1M HCl, saturated NaHCO$_3$ and brine. The organic phase was dried over MgSO$_4$, filtered and concentrated to give 23B (10.02 g, 97% yield) as a clear oil. MS (ESI) m/z: 204.1 (M+H)$^+$.

23C. (S)-3-[4-{2-[3-(Benzyloxycarbonyl-methyl-amino)-prop-1-ynyl]-4-methoxycarbonylamino-phenyl}-1-(2-trimethylsilanyl-ethoxymethyl)-1H-imidazol-2-yl]-3-tert-butoxycarbonylamino-propionic acid benzyl ester: To a solution of 23A (200 mg, 0.284 mmol) in DMF (5 mL) was added 23B (69.3 mg, 0.341 mmol), CuI (10.83 mg, 0.057 mmol), TEA (0.119 mL, 0.853 mmol) and Pd(Ph₃P)₄ (32.8 mg, 0.028 mmol). The reaction was purged with argon for 3 min and then stirred under argon at 90° C. for 6 h. The reaction was cooled to rt and diluted with EtOAc. The organic layer was washed with saturated NaHCO₃ and brine, dried over MgSO₄, filtered and concentrated. The crude product was purified by normal phase chromatography to give 23C (205 mg, 87% yield) as a solid. LC-MS (ESI) m/z: 826.5 (M+H)⁺.

23D. (S)-3-(tert-Butoxycarbonylamino)-3-(4-(4-(methoxycarbonylamino)-2-(3-(methylamino)propyl)phenyl)-1-((2-(trimethylsilyl)ethoxy)methyl)-1H-imidazol-2-yl)propanoic acid, TFA salt: This compound was prepared following the procedure described in 2G, by replacing 2E with 23C. MS (ESI) m/z: 606.4 (M+H)⁺.

23E. [(S)-5-Methoxycarbonylamino-11-methyl-12-oxo-16-(2-trimethylsilanyl-ethoxymethyl)-11,16,18-triaza-tricyclo[13.2.1.0²,⁷]octadeca-1(17),2,4,6,15(18)-pentaen-14-yl]-carbamic acid tert-butyl ester: To a solution of DMAP (23.19 mg, 0.190 mmol), DIEA (0.166 mL, 0.949 mmol) and BOP (168 mg, 0.380 mmol) in DCM (20 mL) was added a solution of 23D (115 mg, 0.190 mmol) in DMF (2 mL) at rt through a syringe pump over 1.5 h. Upon addition, the reaction was stirred for another 30 min and the solvent was removed. The crude product was purified by reverse phase chromatography to give 23E (44 mg, 39.4% yield) as a solid. MS (ESI) m/z: 588.4 (M+H)⁺.

23F. Example 23 was prepared following the procedures described in step 1F, by replacing 1D with 23E and by replacing ethanol with methanol; followed by step 1G. ¹H NMR (400 MHz, CD₃OD, rotamers) δ ppm 9.52 (two singlets, 1H), 9.36 (s, 1H), 8.00 (d, J=1.8 Hz, 1H), 7.68 (ddd, J=8.6, 6.3, 2.3 Hz, 1H), 7.59 (dd, J=8.5, 5.5 Hz, 1H), 7.49-7.43 (m, 1H), 7.41-7.33 (m, 3H), 7.19 (two doublets, J=16.0 Hz, 1H), 6.81 (two doublets, J=15.6 Hz, 1H), 5.49 (dd, J=8.7, 4.8 Hz, 1H), 4.12 (ddd, J=7.3, 6.0, 3.7 Hz, 1H), 3.75 (two singlets, 3H), 3.55-3.43 (m, J=9.2, 7.6, 5.9 Hz, 1H), 3.00 (two singlets, 3H), 2.81 (dd, J=13.9, 4.8 Hz, 1H), 2.69-2.57 (m, 2H), 2.48-2.28 (m, 1H), 1.91-1.76 (m, 1H), 1.64-1.44 (m, 1H). LC-MS (ESI) m/z: 590.2 (M+H)⁺. Analytical HPLC: RT=5.328 min.

Example 24

(E)-N—((S)-18-Chloro-17,19-diaza-tricyclo[14.2.1.0²,⁷]nonadeca-1(18),2,4,6,16(19)-pentaen-15-yl)-3-(5-chloro-2-tetrazol-1-yl-phenyl)-acrylamide, 1 TFA Salt

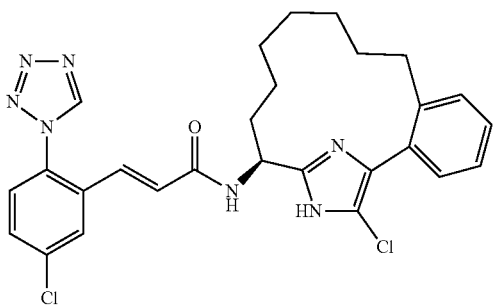 [SMILES: O=C(/C=C/c1cc(Cl)ccc1-n1cnnn1)N[C@H]1CCCCCCCc2ccccc2-c2nc1[nH]c2Cl]

Example 24 was prepared following the procedures described in step 2D, by replacing pent-4-enylboronic acid with hex-5-enylboronic acid; followed by steps 2E/2F; 2G; 1F; 1G; and 7. ¹H NMR (500 MHz, CD₃OD) δ ppm 9.45 (s, 1H), 7.95 (d, J=2.2 Hz, 1H), 7.64 (dd, J=8.2, 2.2 Hz, 1H), 7.55 (d, J=8.3 Hz, 1H), 7.24-7.35 (m, 4H), 7.13 (d, J=15.4 Hz, 1H), 6.76 (d, J=15.9 Hz, 1H), 4.91 (dd, J=9.6, 4.1 Hz, 1H), 2.68-2.76 (m, 1H), 2.39-2.48 (m, 1H), 2.06-2.14 (m, 1H), 1.89-1.99 (m, 1H), 1.56-1.65 (m, 1H), 1.23-1.45 (m, 7H), 0.76-0.86 (m, 1H), 0.49-0.59 (m, 1H). MS (ESI) m/z: 536.4 (M+H)⁺. Analytical HPLC: RT=8.84 min.

Example 25

{(E)-(S)-15-[(E)-3-(5-Chloro-2-tetrazol-1-yl-phenyl)-acryloylamino]-17,19-diaza-tricyclo[14.2.1.0²,⁷]nonadeca-1(18),2,4,6,12,16(19)-hexaen-5-yl}-carbamic Acid methyl ester, 1 TFA Salt

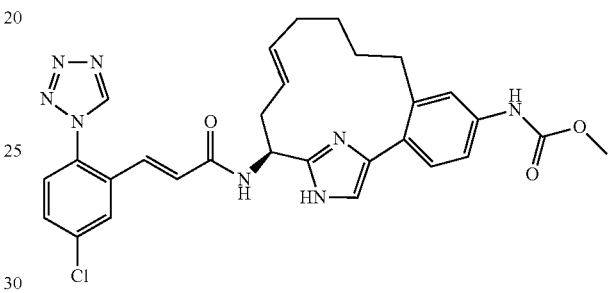

Example 25 was prepared following the procedures described in step 2D, by replacing 2C with 10B and by replacing pent-4-enylboronic acid with hex-5-enylboronic acid; followed by steps 2E; 1F, by replacing ethanol with methanol and by running the reaction at 50-75° C.; and 1G. ¹H NMR (500 MHz, 50° C., CD₃OD) δ ppm 9.46 (s, 1H), 7.96 (d, J=2.7 Hz, 1H), 7.64-7.70 (m, 1H), 7.58 (d, J=8.2 Hz, 1H), 7.37-7.46 (m, 2H), 7.32-7.35 (m, 1H), 7.28 (d, J=8.2 Hz, 1H), 7.19 (d, J=15.9 Hz, 1H), 6.74 (d, J=15.9 Hz, 1H), 5.48-5.58 (m, 1H), 5.22-5.31 (m, 1H), 5.09 (dd, J=9.9, 4.4 Hz, 1H), 3.75 (s, 3H), 2.81-2.89 (m, 1H), 2.69-2.78 (m, 1H), 2.52-2.62 (m, 1H), 2.38-2.48 (m, 1H), 2.06-2.23 (m, 2H), 1.38-1.59 (m, 2H), 1.09-1.19 (m, 2H). MS (ESI) m/z: 573.4 (M+H)⁺. Analytical HPLC: RT=5.63 min.

Example 26

{(S)-15-[(E)-3-(5-Chloro-2-tetrazol-1-yl-phenyl)-acryloylamino]-17,19-diaza-tricyclo[14.2.1.0²,⁷]nonadeca-1(18),2,4,6,16(19)-pentaen-5-yl}-carbamic Acid methyl ester, 1 TFA Salt

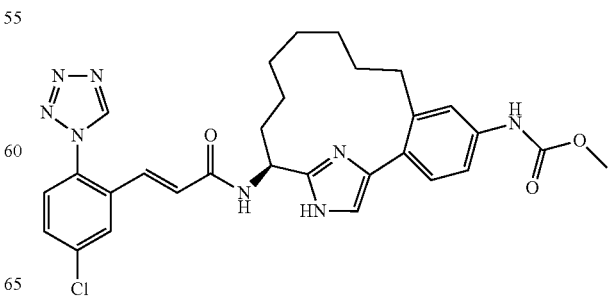

Example 26 was prepared following the procedures described in step 2D, by replacing 2C with 10B and by replacing pent-4-enylboronic acid with hex-5-enylboronic acid; followed by steps 2E/2F; 2G; 1F, by replacing ethanol with methanol and running the reaction at 50-75° C.; and 1G. ¹H NMR (500 MHz, CD₃OD) δ ppm 9.51 (s, 1H), 7.97 (d, J=2.2 Hz, 1H), 7.67 (dd, J=8.2, 2.2 Hz, 1H), 7.58 (d, J=8.8 Hz, 1H), 7.43-7.46 (m, 2H), 7.41 (dd, J=8.3, 2.2 Hz, 1H), 7.31 (d, J=8.2 Hz, 1H), 7.14 (d, J=15.4 Hz, 1H), 6.77 (d, J=15.4 Hz, 1H), 5.00 (dd, J=9.9, 4.4 Hz, 1H), 3.75 (s, 3H), 2.56-2.67 (m, 2H), 2.21-2.30 (m, 1H), 2.03-2.13 (m, 1H), 1.66-1.76 (m, 1H), 1.25-1.57 (m, 7H), 0.47-0.60 (m, 2H). MS (ESI) m/z: 575.5 (M+H)⁺. Analytical HPLC: RT=5.73 min.

Example 27

{(Z)-(S)-15-[(E)-3-(5-Chloro-2-tetrazol-1-yl-phenyl)-acryloylamino]-17,19-diaza-tricyclo[14.2.1.0²,⁷]nonadeca-1(18),2,4,6,12,16(19)-hexaen-5-yl}-carbamic Acid methyl ester, 1 TFA Salt

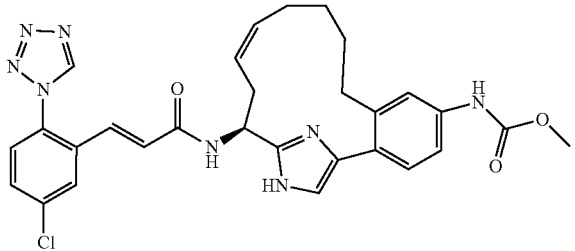 [SMILES: COC(=O)Nc1ccc2c(c1)CCCC/C=C\C[C@H](NC(=O)/C=C/c1cc(Cl)ccc1-n1cnnn1)c1nc-2c[nH]1]

Example 27 was prepared following the procedures described in step 2D, by replacing 2C with 10B and by replacing pent-4-enylboronic acid with hex-5-enylboronic acid; followed by steps 2F; 1F, by replacing ethanol with methanol and running the reaction at 50-75° C.; and 1G. ¹H NMR (500 MHz, CD₃OD) δ ppm 9.52 (s, 1H), 7.98 (d, J=2.2 Hz, 1H), 7.67 (dd, J=8.2, 2.2 Hz, 1H), 7.58 (d, J=8.2 Hz, 1H), 7.44 (s, 1H), 7.41 (dd, J=8.3, 4.7 Hz, 1H), 7.32 (s, 1H), 7.30 (d, J=8.2 Hz, 1H), 7.16 (d, J=15.4 Hz, 1H), 6.78 (d, J=15.4 Hz, 1H), 5.33-5.48 (m, 2H), 5.10-5.17 (m, 1H), 3.74 (s, 3H), 2.71-2.97 (m, 3H), 2.44-2.61 (m, 1H), 1.99-2.23 (m, 2H), 1.48-1.58 (m, 2H), 0.99-1.25 (m, 2H). MS (ESI) m/z: 573.5 (M+H)⁺. Analytical HPLC: RT=5.67 min.

Example 28

{(S)-18-Chloro-15-[(E)-3-(5-chloro-2-tetrazol-1-yl-phenyl)-acryloylamino]-17,19-diaza-tricyclo[14.2.1.0²,⁷]nonadeca-1(18),2,4,6,16(19)-pentaen-5-yl}-carbamic Acid methyl ester, 1 TFA Salt

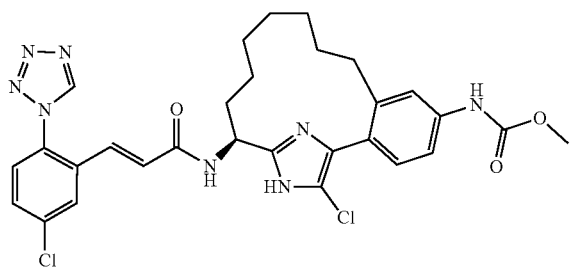 [SMILES: COC(=O)Nc1ccc2c(c1)CCCCCCC[C@H](NC(=O)/C=C/c1cc(Cl)ccc1-n1cnnn1)c1nc-2c(Cl)[nH]1]

Example 28 was prepared following the procedure described in 7, by replacing Example 6 with Example 26. ¹H NMR (500 MHz, 50° C., CD₃OD) δ ppm 9.45 (s, 1H), 7.95 (d, J=2.2 Hz, 1H), 7.64 (dd, J=8.8, 2.2 Hz, 1H), 7.55 (d, J=8.2 Hz, 1H), 7.40 (d, J=2.2 Hz, 1H), 7.35 (dd, J=8.2, 2.2 Hz, 1H), 7.25 (d, J=8.2 Hz, 1H), 7.13 (d, J=15.4 Hz, 1H), 6.75 (d, J=15.9 Hz, 1H), 4.90 (dd, J=9.9, 4.4 Hz, 1H), 3.75 (s, 3H), 2.62-2.73 (m, 1H), 2.35-2.45 (m, 1H), 2.07-2.16 (m, 1H), 1.89-1.99 (m, 1H), 1.56-1.67 (m, 1H), 1.22-1.45 (m, 7H), 0.72-0.86 (m, 1H), 0.47-0.58 (d, 1H). MS (ESI) m/z: 609.1 (M+H)⁺. Analytical HPLC: RT=7.81 min.

Example 29

{(E)-(S)-15-[(E)-3-(5-Chloro-2-tetrazol-1-yl-phenyl)-acryloylamino]-8-oxa-17,19-diaza-tricyclo[14.2.1.0²,⁷]nonadeca-1(18),2,4,6,12,16(19)-hexaen-5-yl}-carbamic Acid methyl ester, 1 TFA Salt

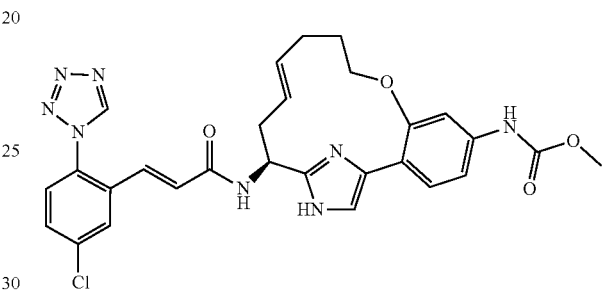

Example 29 was prepared following the procedures described in step 2A, by replacing 2-bromo-1-(2-bromophenyl)ethanone with Intermediate 11; followed by steps 2B; 2C; 2E; 1F, by replacing ethanol with methanol and running the reaction at 75° C.; and 1G. ¹H NMR (500 MHz, CD₃OD) δ ppm 9.52 (s, 1H), 7.99 (d, J=2.2 Hz, 1H), 7.68 (dd, J=8.2, 2.2 Hz, 1H), 7.59 (d, J=8.2 Hz, 1H), 7.46 (s, 1H), 7.42 (s, 1H), 7.37 (d, J=8.2 Hz, 1H), 7.17 (d, J=15.4 Hz, 1H), 7.05 (dd, J=8.3, 1.6 Hz, 1H), 6.79 (d, J=15.4 Hz, 1H), 5.66-5.74 (m, 1H), 5.48-5.56 (m, 1H), 5.11 (dd, J=10.2, 3.6 Hz, 1H), 4.09-4.16 (m, 2H), 3.75 (s, 3H), 2.69-2.77 (m, 1H), 2.52-2.61 (m, 1H), 2.33-2.47 (m, 2H), 2.01-2.09 (m, 1H), 1.91-2.00 (m, 1H). MS (ESI) m/z: 575.0 (M+H)⁺. Analytical HPLC: RT=6.15 min.

Example 30

{(S)-15-[(E)-3-(5-Chloro-2-tetrazol-1-yl-phenyl)-acryloylamino]-8-oxa-17,19-diaza-tricyclo[14.2.1.0²,⁷]nonadeca-1(18),2,4,6,16(19)-pentaen-5-yl}-carbamic Acid methyl ester, 1 TFA Salt

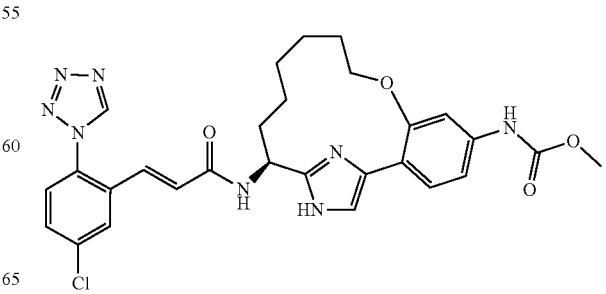

Example 30 was prepared following the procedures described in step 2A, by replacing 2-bromo-1-(2-bromophenyl)ethanone with Intermediate 11; followed by steps 2B; 2C; 2E/2F; 2G; 1F, by replacing ethanol with methanol and running the reaction at 75° C.; and 1G. $^1$H NMR (500 MHz, CD$_3$OD) δ ppm 9.52 (s, 1H), 7.97 (d, J=2.2 Hz, 1H), 7.67 (dd, J=8.8, 2.2 Hz, 1H), 7.58 (d, J=8.8 Hz, 1H), 7.40 (s, 1H), 7.33-7.38 (m, 2H), 7.14 (d, J=15.4 Hz, 1H), 7.06 (d, J=8.2 Hz, 1H), 6.78 (d, J=15.9 Hz, 1H), 5.04 (dd, J=9.9, 4.4 Hz, 1H), 4.05-4.10 (m, 1H), 3.93 (td, J=8.2, 2.7 Hz, 1H), 3.75 (s, 3H), 2.19-2.27 (m, 1H), 1.94-2.03 (m, 1H), 1.69-1.83 (m, 2H), 1.49-1.63 (m, 4H), 0.91-1.09 (m, 2H). MS (ESI) m/z: 577.1 (M+H)$^+$. Analytical HPLC: RT=6.16 min.

Example 31

{(Z)-(S)-15-[(E)-3-(5-Chloro-2-tetrazol-1-yl-phenyl)-acryloylamino]-8-oxa-17,19-diaza-tricyclo[14.2.1.0$^{2,7}$]nonadeca-1(18),2,4,6,12,16(19)-hexaen-5-yl}-carbamic Acid methyl ester, 1 TFA Salt

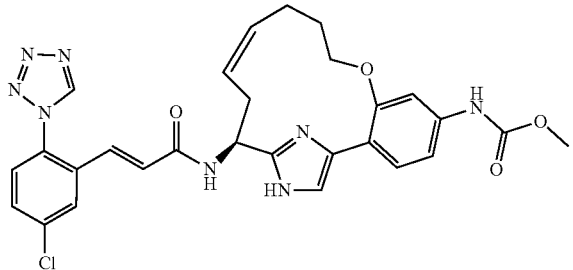 [SMILES: COC(=O)Nc1ccc2c(c1)OCCC/C=C\C[C@H](NC(=O)/C=C/c1cc(Cl)ccc1-n1cnnn1)c1nc-2c[nH]1]

Example 31 was prepared following the procedures described in step 2A, by replacing 2-bromo-1-(2-bromophenyl)ethanone with Intermediate 11; followed by steps 2B; 2C; 2F; 1F, by replacing ethanol with methanol and running the reaction at 75° C.; and 1G. $^1$H NMR (500 MHz, CD$_3$OD) δ ppm 9.52 (s, 1H), 7.97 (d, J=2.2 Hz, 1H), 7.68 (dd, J=8.3, 2.2 Hz, 1H), 7.59 (d, J=8.2 Hz, 1H), 7.50 (d, J=1.6 Hz, 1H), 7.44 (s, 1H), 7.38 (d, J=8.2 Hz, 1H), 7.15-7.21 (m, 2H), 6.74 (d, J=15.9 Hz, 1H), 5.41-5.51 (m, 2H), 5.20-5.25 (m, 1H), 3.74-3.82 (m, 4H), 3.66-3.72 (m, 1H), 2.95-3.06 (m, 1H), 2.79-2.89 (m, 1H), 2.47-2.58 (m, 1H), 2.23-2.34 (m, 1H), 1.89-2.03 (m, 1H), 1.65-1.77 (m, 1H). MS (ESI) m/z: 575.1 (M+H)$^+$. Analytical HPLC: RT=5.94 min.

Example 32

{(S)-18-Chloro-15-[(E)-3-(5-chloro-2-tetrazol-1-yl-phenyl)-acryloylamino]-8-oxa-17,19-diaza-tricyclo[14.2.1.0$^{2,7}$]nonadeca-1(18),2,4,6,16(19)-pentaen-5-yl}-carbamic Acid methyl ester, 1 TFA Salt

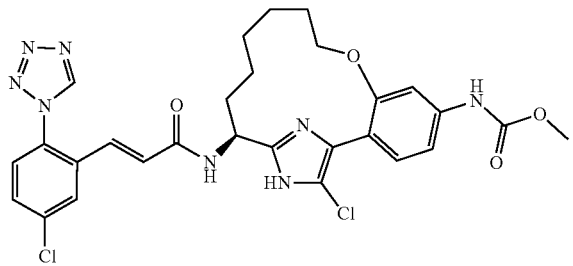 [SMILES: COC(=O)Nc1ccc2c(c1)OCCCCCC[C@H](NC(=O)/C=C/c1cc(Cl)ccc1-n1cnnn1)c1nc-2c(Cl)[nH]1]

Example 32 was prepared following the procedure described in 9, by replacing Example 8 with Example 30. $^1$H NMR (500 MHz, CD$_3$OD) δ ppm 9.46 (s, 1H), 7.94 (d, J=2.2 Hz, 1H), 7.64 (dd, J=8.3, 2.2 Hz, 1H), 7.55 (d, J=8.8 Hz, 1H), 7.32-7.37 (m, 2H), 7.15 (d, J=15.9 Hz, 1H), 7.05 (d, J=8.2 Hz, 1H), 6.74 (d, J=15.4 Hz, 1H), 4.94 (dd, J=9.6, 3.6 Hz, 1H), 4.00-4.06 (m, 1H), 3.88-3.94 (m, 1H), 3.76 (s, 3H), 2.12-2.20 (m, 1H), 1.75-1.93 (m, 2H), 1.65-1.74 (m, 1H), 1.46-1.60 (m, 4H), 1.0-1.12 (m, 1H), 0.92-1.02 (m, 1H). MS (ESI) m/z: 610.9 (M+H)$^+$. Analytical HPLC: RT=7.74 min.

Example 33

{(S)-15-[(E)-3-(5-Chloro-2-tetrazol-1-yl-phenyl)-acryloylamino]-8-methyl-8,17,19-triaza-tricyclo[14.2.1.0$^{2,7}$]nonadeca-1(18),2,4,6,16(19)-pentaen-5-yl}-carbamic Acid methyl ester, 2 TFA Salt

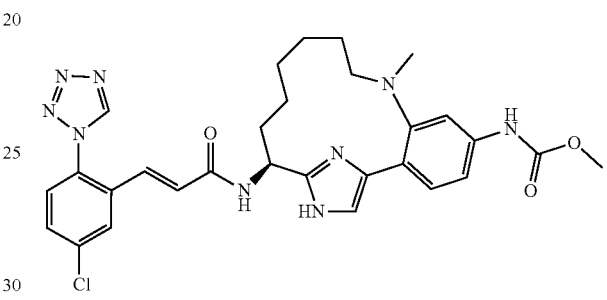

Example 33 was prepared following the procedures described in step 10C, by replacing ammonium hydroxide with pent-4-enylamine and running the reaction at 90° C.; followed by steps 2E/2F; 2G (N-methylation occurred during the hydrogenation step in the presence of methanol); 1F, by replacing ethanol with methanol and running the reaction at 75° C.; and 1G. $^1$H NMR (500 MHz, 50° C., CD$_3$OD) δ ppm 9.52 (s, 1H), 7.96 (d, J=2.2 Hz, 1H), 7.63-7.71 (m, 2H), 7.55-7.60 (m, 2H), 7.46 (d, J=8.2 Hz, 1H), 7.28 (dd, J=8.3, 2.2 Hz, 1H), 7.14 (d, J=15.4 Hz, 1H), 6.73 (d, J=15.4 Hz, 1H), 5.08 (t, J=6.9 Hz, 1H), 3.76 (s, 3H), 2.94 (s, 3H), 2.87-2.92 (m, 2H), 2.15-2.22 (m, 2H), 1.66-1.85 (m, 2H), 1.39-1.65 (m, 4H), 0.75-0.87 (m, 2H). MS (ESI) m/z: 590.3 (M+H)$^+$. Analytical HPLC: RT=6.26 min.

Example 34

{(S)-15-[(E)-3-(5-Chloro-2-tetrazol-1-yl-phenyl)-acryloylamino]-9-oxo-8,17,19-triaza-tricyclo[14.2.1.0$^{2,7}$]nonadeca-1(18),2,4,6,16(19)-pentaen-5-yl}-carbamic Acid methyl ester, 1 TFA Salt

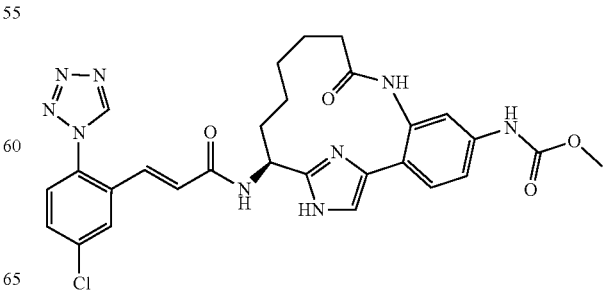

Example 34 was prepared following the procedures described in step 10D, by replacing but-3-enoic acid with pent-4-enoic acid; followed by steps 2E/2F; 2G; 1F, by replacing ethanol with methanol and running the reaction at 75° C.; and 1G. $^1$H NMR (400 MHz, CD$_3$OD) δ ppm 9.50 (s, 1H), 7.96 (d, J=2.2 Hz, 1H), 7.67 (dd, J=8.8, 2.2 Hz, 1H), 7.61 (s, 1H), 7.57 (d, J=8.2 Hz, 1H), 7.38-7.45 (m, 3H), 7.12 (d, J=15.9 Hz, 1H), 6.74 (d, J=15.9 Hz, 1H), 5.01 (dd, J=10.2, 4.7 Hz, 1H), 3.75 (s, 3H), 2.28-2.41 (m, 2H), 2.15-2.25 (m, 1H), 1.95-2.07 (m, 1H), 1.41-1.76 (m, 4H), 0.71-0.98 (m, 2H). MS (ESI) m/z: 590.1 (M+H)$^+$. Analytical HPLC: RT=4.96 min.

Example 35

{(S)-15-[(E)-3-(5-Chloro-2-tetrazol-1-yl-phenyl)-acryloylamino]-8,17,19-triaza-tricyclo[14.2.1.0$^{2,7}$]nonadeca-1(18),2,4,6,16(19)-pentaen-5-yl}-carbamic Acid methyl ester, 2 TFA Salt

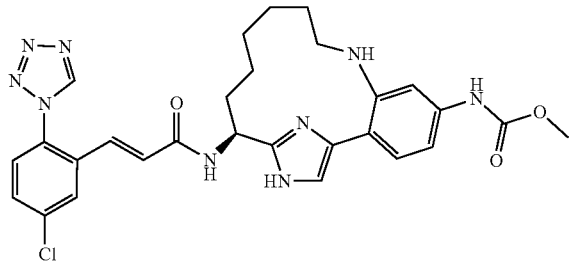

Example 35 was prepared following the procedures described in step 10C, by replacing ammonium hydroxide with pent-4-enylamine and running the reaction at 90° C.; followed by steps 2E/2F; 2G by replacing MeOH with EtOAc; 1F, by replacing ethanol with methanol and running the reaction at 75° C.; and 1G. $^1$H NMR (400 MHz, CD$_3$OD) δ ppm 9.52 (s, 1H), 7.95 (d, J=2.2 Hz, 1H), 7.82 (s, 1H), 7.66 (dd, J=8.2, 2.2 Hz, 1H), 7.60 (d, J=8.8 Hz, 1H), 7.56-7.59 (m, 2H), 7.26 (dd, J=8.8, 2.2 Hz, 1H), 7.16 (d, J=15.4 Hz, 1H), 6.68 (d, J=15.9 Hz, 1H), 5.12 (dd, J=9.9, 3.3 Hz, 1H), 3.76 (s, 3H), 3.09-3.24 (m, 2H), 2.31-2.43 (m, 1H), 1.89-2.10 (m, 2H), 1.53-1.85 (m, 5H), 1.07-1.27 (m, 2H). MS (ESI) m/z: 576.3 (M+H)$^+$. Analytical HPLC: RT=5.91 min.

Example 36

{(E)-(S)-15-[(E)-3-(5-Chloro-2-tetrazol-1-yl-phenyl)-acryloylamino]-8,17,19-triaza-tricyclo[14.2.1.0$^{2,7}$]nonadeca-1(18),2,4,6,12,16(19)-hexaen-5-yl}-carbamic Acid methyl ester, 2 TFA Salt

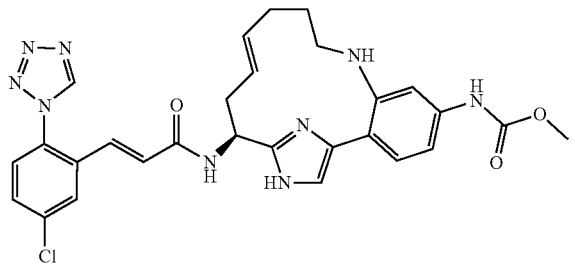

Example 36 was prepared following the procedures described in step 10C, by replacing ammonium hydroxide with pent-4-enylamine and running the reaction at 90° C.; followed by steps 2E; 1F, by replacing ethanol with methanol and running the reaction at 75° C.; and 1G. $^1$H NMR (400 MHz, CD$_3$OD) δ ppm 9.52 (s, 1H), 7.98 (d, J=2.2 Hz, 1H), 7.68 (dd, J=8.8, 2.2 Hz, 1H), 7.59 (d, J=8.8 Hz, 1H), 7.43 (s, 1H), 7.28-7.32 (m, 2H), 7.18 (d, J=15.4 Hz, 1H), 6.98 (dd, J=8.8, 2.2 Hz, 1H), 6.76 (d, J=15.9 Hz, 1H), 5.69-5.79 (m, 1H), 5.45-5.54 (m, 1H), 5.15 (dd, J=9.3, 4.4 Hz, 1H), 3.74 (s, 3H), 3.03-3.20 (m, 2H), 2.72-2.82 (m, 1H), 2.56-2.68 (m, 1H), 2.28-2.48 (m, 2H), 1.82-2.03 (m, 2H). MS (ESI) m/z: 574.2 (M+H)$^+$. Analytical HPLC: RT=5.85 min.

Example 37

{(Z)-(S)-15-[(E)-3-(5-Chloro-2-tetrazol-1-yl-phenyl)-acryloylamino]-8,17,19-triaza-tricyclo[14.2.1.0$^{2,7}$]nonadeca-1(18),2,4,6,12,16(19)-hexaen-5-yl}-carbamic Acid methyl ester, 2 TFA Salt

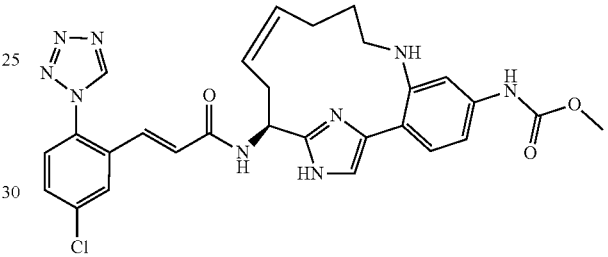

Example 37 was prepared following the procedures described in step 10C, by replacing ammonium hydroxide with pent-4-enylamine and running the reaction at 90° C.; followed by steps 2F; 1F, by replacing ethanol with methanol and running the reaction at 75° C.; and 1G. $^1$H NMR (500 MHz, CD$_3$OD) δ ppm 9.48 (s, 1H), 7.86-7.95 (m, 2H), 7.69 (d, J=8.2 Hz, 1H), 7.65 (dd, J=8.8, 2.2 Hz, 1H), 7.54-7.58 (m, 2H), 7.33 (dd, J=8.2, 2.2 Hz, 1H), 7.21 (d, J=15.9 Hz, 1H), 6.65 (d, J=15.9 Hz, 1H), 5.52-5.60 (m, 1H), 5.36-5.44 (m, 1H), 5.30 (dd, J=9.9, 3.3 Hz, 1H), 3.78 (s, 3H), 3.10-3.28 (m, 3H), 2.60-2.76 (m, 2H), 2.36-2.47 (m, 1H), 2.15-2.25 (m, 1H), 1.96-2.07 (m, 1H). MS (ESI) m/z: 574.2 (M+H)$^+$. Analytical HPLC: RT=5.88 min.

Example 38

{(S)-18-Chloro-15-[(E)-3-(5-chloro-2-tetrazol-1-yl-phenyl)-acryloylamino]-9-oxo-8,17,19-triaza-tricyclo[14.2.1.0$^{2,7}$]nonadeca-1(18),2,4,6,16(19)-pentaen-5-yl}-carbamic Acid methyl ester, 1 TFA Salt

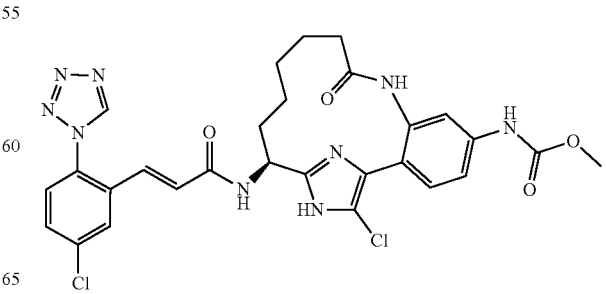

Example 38 was prepared following the procedure described in 7, by replacing Example 6 with Example 34. $^1$H NMR (500 MHz, DMSO-$d_6$+2 drops of $D_2O$) δ ppm 9.76 (s, 1H), 7.90 (d, J=1.6 Hz, 1H), 7.67 (dd, J=8.8, 2.2 Hz, 1H), 7.63 (d, J=8.3 Hz, 1H), 7.38 (s, 1H), 7.30-7.36 (m, 2H), 6.77-6.84 (m, 2H), 4.76 (dd, J=10.4, 4.4 Hz, 1H), 3.62 (s, 3H), 2.07-2.21 (m, 2H), 1.83-1.91 (m, 1H), 1.56-1.66 (m, 1H), 1.44-1.54 (m, 1H), 1.34-1.44 (m, 1H), 1.19-1.31 (m, 2H), 0.85-0.96 (m, 1H), 0.38-0.49 (m, 1H). MS (ESI) m/z: 624.3 (M+H)$^+$. Analytical HPLC: RT=6.32 min.

Example 39

{(E)-(S)-15-[(E)-3-(5-Chloro-2-tetrazol-1-yl-phenyl)-acryloylamino]-9-oxo-8,17,19-triaza-tricyclo[14.2.1.0$^{2,7}$]nonadeca-1(18),2,4,6,12,16(19)-hexaen-5-yl}-carbamic Acid methyl ester, 1 TFA Salt

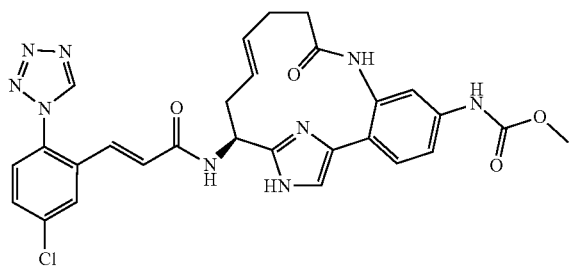 [SMILES: COC(=O)Nc1ccc2c(c1)NC(=O)CCCCC[C@H](NC(=O)/C=C/c1cc(Cl)ccc1-n1cnnn1)c1nc-2c[nH]1]

39A. ((E)-(S)-15-tert-Butoxycarbonylamino-9-oxo-8,17,19-triaza-tricyclo[14.2.1.0$^{2,7}$]nonadeca-1(18),2,4,6,12,16(19)-hexaen-5-yl)-carbamic acid methyl ester: This compound was prepared following the procedures described in step 10D, by replacing but-3-enoic acid with pent-4-enoic acid; followed by step 2E. MS (ESI) m/z: 586.4 (M+H)$^+$.

39B. Example 39 was prepared following the procedures described step 10H, by replacing 10G with 39A; followed by step 1G. $^1$H NMR (500 MHz, $CD_3OD$) δ ppm 9.51 (s, 1H), 7.97 (d, J=2.2 Hz, 1H), 7.68 (dd, J=8.5, 2.5 Hz, 1H), 7.58 (d, J=8.2 Hz, 2H), 7.37-7.41 (m, 3H), 7.14 (d, J=15.4 Hz, 1H), 6.76 (d, J=15.4 Hz, 1H), 5.50-5.59 (m, 1H), 5.37-5.45 (m, 1H), 5.08 (dd, J=10.2, 4.7 Hz, 1H), 3.75 (s, 3H), 2.76-2.84 (m, 1H), 2.32-2.60 (m, 5H). MS (ESI) m/z: 588.1 (M+H)$^+$. Analytical HPLC: RT=4.79 min Example 40

{(E)-(S)-15-[(E)-3-(5-Chloro-2-tetrazol-1-yl-phenyl)-acryloylamino]-9-oxo-10-oxa-8,17,19-triaza-tricyclo[14.2.1.0$^{2,7}$]nonadeca-1(18),2,4,6,12,16(19)-hexaen-5-yl}-carbamic Acid methyl ester, 1 TFA Salt

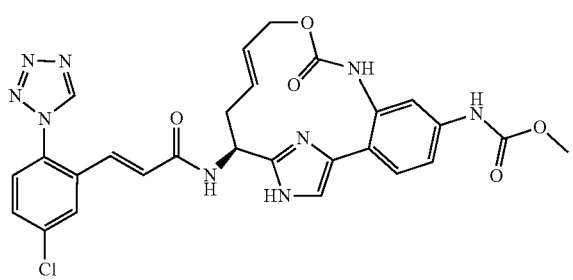

Example 40 was prepared following the procedures described in Intermediate 7B, by replacing Intermediate 7A with 10C and by replacing methyl chloroformate with allyl chloroformate; followed by steps 2E; 10H; and 1G. $^1$H NMR (500 MHz, $CD_3OD$) δ ppm 9.50 (s, 1H), 7.98 (d, J=2.2 Hz, 1H), 7.68 (dd, J=8.5, 2.5 Hz, 1H), 7.58 (d, J=8.5 Hz, 1H), 7.50 (br. s., 1H), 7.34-7.43 (m, 3H), 7.14 (d, J=15.7 Hz, 1H), 6.76 (d, J=15.7 Hz, 1H), 5.83-5.93 (m, 1H), 5.68-5.76 (m, 1H), 5.13 (dd, J=10.2, 5.2 Hz, 1H), 4.28-4.43 (m, 2H), 3.75 (s, 3H), 2.88-2.97 (m, 1H), 2.53-2.65 (m, 1H). MS (ESI) m/z: 590.2 (M+H)$^+$. Analytical HPLC: RT=4.90 min.

Example 41

{(S)-15-[(E)-3-(5-Chloro-2-tetrazol-1-yl-phenyl)-acryloylamino]-9-oxo-10-oxa-8,17,19-triaza-tricyclo[14.2.1.0$^{2,7}$]nonadeca-1(18),2,4,6,16(19)-pentaen-5-yl}-carbamic Acid methyl ester, 1 TFA Salt

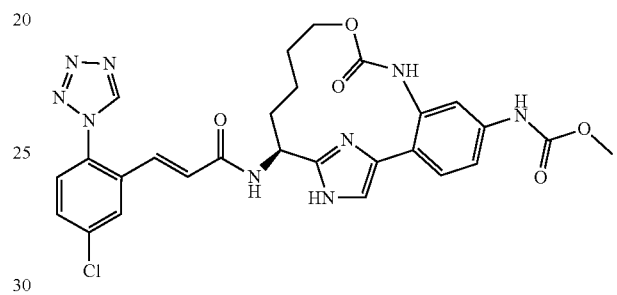

Example 41 was prepared following the procedures described in Intermediate 7B, by replacing Intermediate 7A with 10C and by replacing methyl chloroformate with allyl chloroformate; followed by steps 2E/2F; 2G, by replacing methanol with EtOAc; 1F, by replacing ethanol with methanol and running the reaction at 75° C. for 2 h; and 1G. $^1$H NMR (400 MHz, $CD_3OD$) δ ppm 9.50 (s, 1H), 7.96 (d, J=2.2 Hz, 1H), 7.68 (dd, J=8.8, 2.2 Hz, 1H), 7.58 (d, J=8.2 Hz, 1H), 7.55 (d, J=1.6 Hz, 1H), 7.43-7.47 (m, 2H), 7.39 (dd, J=8.3, 2.2 Hz, 1H), 7.12 (d, J=15.4 Hz, 1H), 6.74 (d, J=15.4 Hz, 1H), 4.98 (dd, J=10.4, 4.9 Hz, 1H), 4.13-4.26 (m, 1H), 3.89-4.03 (m, 1H), 3.75 (s, 3H), 2.18-2.31 (m, 1H), 1.84-1.98 (m, 1H), 1.42-1.65 (m, 3H), 1.19-1.35 (m, 1H). MS (ESI) m/z: 592.2 (M+H)$^+$. Analytical HPLC: RT=5.11 min.

Example 42

{(S)-15-[(E)-3-(5-Chloro-2-tetrazol-1-yl-phenyl)-acryloylamino]-11-methyl-9-oxo-8,17,19-triaza-tricyclo[14.2.1.0$^{2,7}$]nonadeca-1(18),2,4,6,16(19)-pentaen-5-yl}-carbamic Acid methyl ester, 1 TFA Salt. Mixture of diastereomers

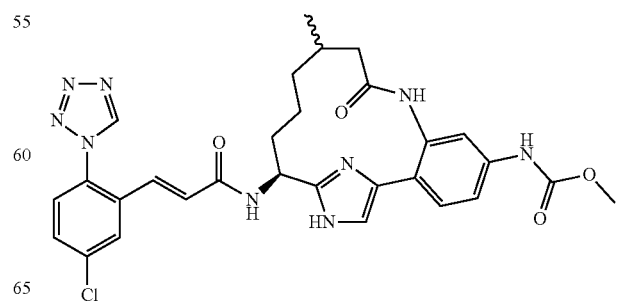

Example 42 (mixture of diastereomers) was prepared following the procedures described in step 10D, by replacing but-3-enoic acid with 3-methylpent-4-enoic acid; followed by steps 2E/2F; 2G; 10H; and 1G. $^1$H NMR (500 MHz, CD$_3$OD) δ ppm 9.50, 9.51 (s, 1H), 7.94-7.98 (m, 1H), 7.64-7.69 (m, 1H), 7.55-7.60 (m, 2H), 7.37-7.44 (m, 3H), 7.08-7.15 (m, 1H), 6.70-6.82 (m, 1H), 4.96-5.02 (m, 1H), 3.75 (s, 3H), 2.38-2.47 (m, 1H), 2.19-2.26 (m, 0.5H), 2.10-2.18 (m, 0.5H), 1.87-2.07 (m, 3H), 1.54-1.70 (m, 1H), 1.36-1.52 (m, 1H), 0.95-1.02 (m, 3.5H), 0.80-0.89 (m, 0.5H), 0.67-0.77 (m, 0.5H), 0.46-0.55 (m, 0.5H). MS (ESI) m/z: 604.3 (M+H)$^+$. Analytical HPLC: RT=5.11 min.

Example 43

{(11S,15S)-15-[(E)-3-(5-Chloro-2-tetrazol-1-yl-phenyl)-acryloylamino]-11-methyl-9-oxo-8,17,19-triaza-tricyclo[14.2.1.0$^{2,7}$]nonadeca-1(18),2,4,6,16(19)-pentaen-5-yl}-carbamic Acid methyl ester, 1 TFA Salt; and

Example 44

{(11R,15S)-15-[(E)-3-(5-Chloro-2-tetrazol-1-yl-phenyl)-acryloylamino]-11-methyl-9-oxo-8,17,19-triaza-tricyclo[14.2.1.0$^{2,7}$]nonadeca-1(18),2,4,6,16(19)-pentaen-5-yl}-carbamic Acid methyl ester, 1 TFA Salt Example 43

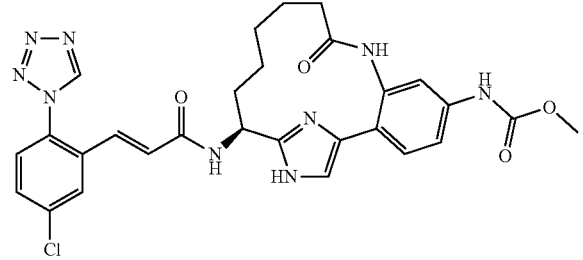

Example 44

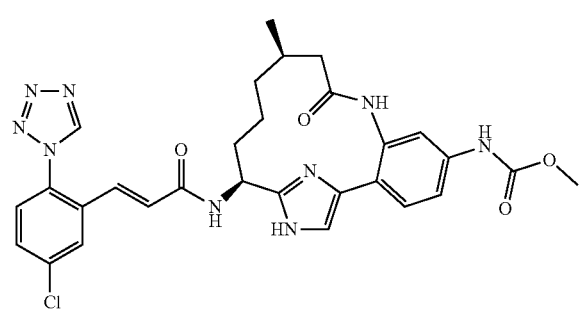

The diastereomers of Example 42 were separated on CHIRALCEL® OD-H column (isocratic; 30% 1:1 MeOH:EtOH/Heptane; 20 mL/min; 254 nm detection). The pure fractions were concentrated, dissolved in methanol containing two drops of TFA, concentrated and then lyophilized to give 0.0047 g of Example 43, as a white solid and 0.0042 g of Example 44, as a white solid.

Example 43: $^1$H NMR (500 MHz, CD$_3$OD) δ ppm 9.52 (s, 1H), 7.98 (d, J=2.2 Hz, 1H), 7.68 (dd, J=8.8, 2.2 Hz, 1H), 7.56-7.62 (m, 2H), 7.37-7.44 (m, 3H), 7.14 (d, J=15.9 Hz, 1H), 6.77 (d, J=15.9 Hz, 1H), 5.00 (dd, J=9.3, 4.4 Hz, 1H), 3.75 (s, 3H), 2.43 (d, J=10.4 Hz, 1H), 2.18-2.30 (m, 1H), 1.84-1.98 (m, 3H), 1.61-1.74 (m, 1H), 1.34-1.49 (m, 1H), 0.93-1.05 (m, 4H), 0.46-0.58 (m, 1H). MS (ESI) 604.3 (M+H)$^+$ and 606.2 (M+2+H)$^+$. Analytical HPLC (Method D): RT=4.63 min. CHIRALCEL® OD (40% 1:1 MeOH:EtOH/Heptane; 4.6×250 mm; 1 mL/min.; 220 nm): 10.08 min. (>99% de).

Example 44: $^1$H NMR (500 MHz, CD$_3$OD) □□δ ppm 9.60 (s, 1H, exchangeable), 9.50 (s, 1H), 7.95 (d, J=1.6 Hz, 1H), 7.66 (dd, J=8.2, 2.2 Hz, 1H), 7.59 (br. s., 1H), 7.57 (d, J=8.8 Hz, 1H), 7.36-7.45 (m, 3H), 7.11 (d, J=15.9 Hz, 1H), 6.71 (d, J=15.9 Hz, 1H), 4.98 (dd, J=10.4, 4.4 Hz, 1H), 3.75 (s, 3H), 2.42 (d, J=11.0 Hz, 1H), 2.08-2.19 (m, 1H), 1.91-2.08 (m, 3H), 1.56-1.65 (m, 1H), 1.41-1.52 (m, 1H), 0.99 (d, J=6.6 Hz, 3H), 0.81-0.94 (m, 1H), 0.69-0.79 (m, 1H). MS (ESI) m/z: 604.3 (M+H)$^+$ and 606.2 (M+2+H)$^+$. Analytical HPLC (Method D): RT=4.69 min. CHIRALCEL® OD (40% 1:1 MeOH:EtOH/Heptane; 4.6×250 mm; 1 mL/min.; 220 nm): 13.74 min. (>99% de).

Example 45

{(E)-(S)-15-[(4-Aminomethyl-cyclohexanecarbonyl)-amino]-9-oxo-8,17,19-triaza-tricyclo[14.2.1.0$^{2,7}$]nonadeca-1(18),2,4,6,12,16(19)-hexaen-5-yl}-carbamic Acid methyl ester, 2 TFA Salt

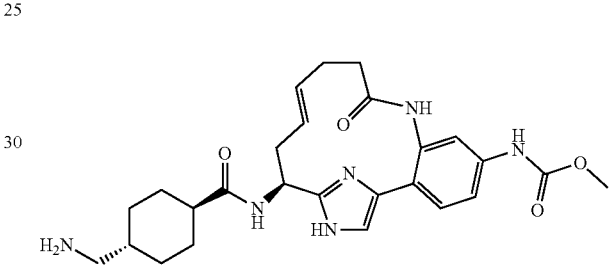

Example 45 was prepared following the procedures described in step 10H, by replacing 10G with 39A; followed by steps 3B, by replacing Hunig's base with triethylamine and running the reaction at 50° C.; and 3C. $^1$H NMR (400 MHz, CD$_3$OD) δ ppm 7.55 (d, J=1.6 Hz, 1H), 7.43 (dd, J=8.2, 2.2 Hz, 1H), 7.37-7.40 (m, 2H), 5.46-5.56 (m, 1H), 5.34-5.43 (m, 1H), 4.98 (dd, J=10.4, 4.4 Hz, 1H), 3.75 (s, 3H), 2.71-2.82 (m, 3H), 2.27-2.55 (m, 6H), 1.83-1.99 (m, 4H), 1.56-1.67 (m, 1H), 1.39-1.53 (m, 2H), 1.01-1.17 (m, 2H). MS (ESI) m/z: 495.3 (M+H)$^+$. Analytical HPLC: RT=1.8, 2.4 min.

Example 46

{(S)-4,18-Dichloro-15-[(E)-3-(5-chloro-2-tetrazol-1-yl-phenyl)-acryloylamino]-9-oxo-8,17,19-triaza-tricyclo[14.2.1.0$^{2,7}$]nonadeca-1(18),2,4,6,16(19)-pentaen-5-yl}-carbamic Acid methyl ester, 1 TFA Salt

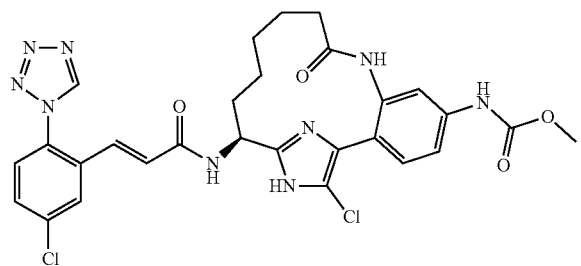 [SMILES: COC(=O)Nc1ccc2c(c1)NC(=O)CCCCC[C@H](NC(=O)/C=C/c1cc(Cl)ccc1-n1cnnn1)c1nc-2c(Cl)[nH]1]

To a solution of Example 34 (0.023 g, 0.033 mmol) in acetonitrile (1 mL)/chloroform (1.000 mL) was added NCS (5.23 mg, 0.039 mmol). The thick-walled vial was sealed with a teflon coated screw cap and the reaction was warmed to 65° C. After 6 h, additional NCS (5.23 mg, 0.039 mmol) was added. After another 4 h, the reaction was cooled to rt and concentrated. Purification by reverse phase chromatography afforded Example 46 (0.006 g, 23.2%) as a yellow solid. $^1$H NMR (400 MHz, CD$_3$OD) δ ppm 9.50 (s, 1H), 7.93-8.02 (m, 2H), 7.62-7.68 (m, 1H), 7.53-7.59 (m, 2H), 7.10 (d, J=15.4 Hz, 1H), 6.75 (d, J=15.4 Hz, 1H), 4.79-4.98 (m, 1H), 3.78 (s, 3H), 2.26-2.37 (m, 2H), 2.01-2.12 (m, 1H), 1.84-1.95 (m, 1H), 1.59-1.72 (m, 2H), 1.32-1.50 (m, 2H), 1.05-1.19 (m, 1H), 0.73-0.86 (m, 1H). MS (ESI) m/z: 656.4 (M−H)$^−$. Analytical HPLC: RT=7.49 min.

Example 47

{(S)-15-[(E)-3-(5-Chloro-2-tetrazol-1-yl-phenyl)-acryloylamino]-12-methyl-9-oxo-8,17,19-triaza-tricyclo[14.2.1.0$^{2,7}$]nonadeca-1(18),2,4,6,12,16(19)-hexaen-5-yl}-carbamic Acid methyl ester, 1 TFA Salt

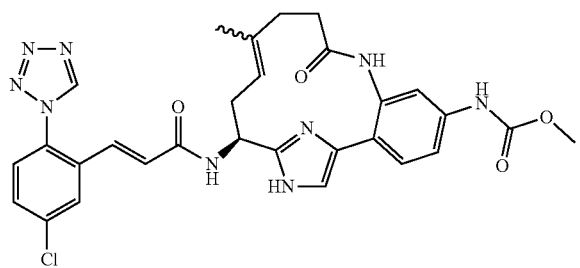

Example 47 was prepared following the procedures described in step 10D, by replacing but-3-enoic acid with 4-methylpent-4-enoic acid; followed by steps 2E/2F; 10H; and 1G. $^1$H NMR (400 MHz, CD$_3$OD) δ ppm 9.52 (s, 1H), 7.99 (d, J=2.2 Hz, 1H), 7.69 (dd, J=8.8, 2.2 Hz, 1H), 7.55-7.62 (m, 2H), 7.33-7.44 (m, 3H), 7.15 (d, J=15.9 Hz, 1H), 6.78 (d, J=15.9 Hz, 1H), 5.14-5.21 (m, 1H), 5.06 (dd, J=10.2, 5.2 Hz, 1H), 3.76 (s, 3H), 2.75-2.83 (m, 1H), 2.48-2.69 (m, 3H), 2.34-2.42 (m, 2H), 1.56 (s, 3H). MS (ESI) m/z: 602.3 (M+H)$^+$. Analytical HPLC: RT=5.09 min.

Example 48

(E)-3-(5-Chloro-2-tetrazol-1-yl-phenyl)-N-((Z)-(S)-9-oxo-8,17,19-triaza-tricyclo[14.2.1.0$^{2,7}$]nonadeca-1(18),2,4,6,12,16(19)-hexaen-15-yl)-acrylamide, 1 TFA Salt

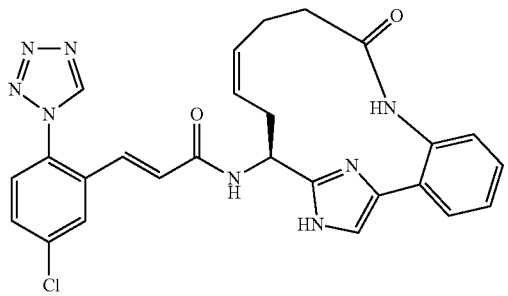 [SMILES: O=C(/C=C/c1cc(Cl)ccc1-n1cnnn1)N[C@H]1C/C=C\CCC(=O)Nc2ccccc2-c2c[nH]c1n2]

Example 48 was prepared following the procedures described in step 10D, by replacing 10C with 15B and by replacing but-3-enoic acid with pent-4-enoic acid; followed by 2F; 10H; and 15D. $^1$H NMR (500 MHz, CD$_3$OD) δ ppm 2.25-3.00 (m, 6H), 5.14-5.24 (m, 1H), 5.41-5.54 (m, 1H), 5.57-5.70 (m, 1H), 6.75 (d, J=15.7 Hz, 1H), 7.17 (d, J=15.7 Hz, 1H), 7.33-7.40 (m, 3H), 7.48-7.54 (m, 2H), 7.58 (d, J=8.5 Hz, 1H), 7.67 (dd, J=8.5, 2.2 Hz, 1H), 7.98 (d, J=2.2 Hz, 1H), 9.51 (s, 1H). MS (ESI) m/z: 515.3 (M+H)$^+$. Analytical HPLC: RT=5.06 min.

Example 49

(E)-3-(5-Chloro-2-tetrazol-1-yl-phenyl)-N-((E)-(S)-9-oxo-8,17,19-triaza-tricyclo[14.2.1.0$^{2,7}$]nonadeca-1(18),2,4,6,12,16(19)-hexaen-15-yl)-acrylamide, 1 TFA Salt

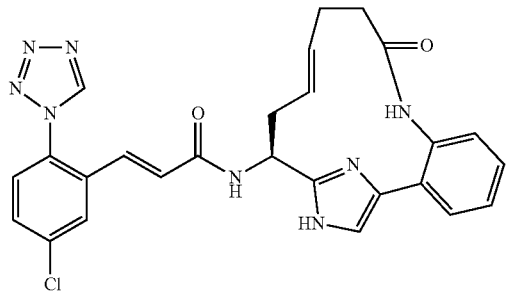 [SMILES: O=C(/C=C/c1cc(Cl)ccc1-n1cnnn1)N[C@H]1C/C=C/CCC(=O)Nc2ccccc2-c2c[nH]c1n2]

Example 49 was prepared following the procedures described in step 10D, by replacing 10C with 15B and by replacing but-3-enoic acid with pent-4-enoic acid; followed by steps 2E; 10H; and 15D. $^1$H NMR (500 MHz, CD$_3$OD) δ ppm 2.32-2.62 (m, 5H), 2.77-2.86 (m, 1H), 5.09 (dd, J=10.2, 4.7 Hz, 1H), 5.38-5.47 (m, 1H), 5.52-5.61 (m, 1H), 6.76 (d, J=15.4 Hz, 1H), 7.15 (d, J=15.4 Hz, 1H), 7.34 (dd, J=8.0, 0.8 Hz, 1H), 7.41 (td, J=7.6, 1.2 Hz, 1H), 7.44 (s, 1H), 7.52 (dd, J=7.7, 1.4 Hz, 1H), 7.55 (td, J=7.7, 1.6 Hz, 1H), 7.59 (d, J=8.5 Hz, 1H), 7.68 (dd, 2.5 Hz, 1H), 7.98 (d, J=2.2 Hz, 1H), 9.51 (s, 1H). MS (ESI) m/z: 515.3 (M+H)$^+$. Analytical HPLC: RT=5.00 min.

Example 50

(E)-N-((E)-(S)-18-Chloro-9-oxo-8,17,19-triaza-tricyclo[14.2.1.0$^{2,7}$]nonadeca-1(18),2,4,6,12,16(19)-hexaen-15-yl)-3-(5-chloro-2-tetrazol-1-yl-phenyl)-acrylamide, 1 TFA Salt

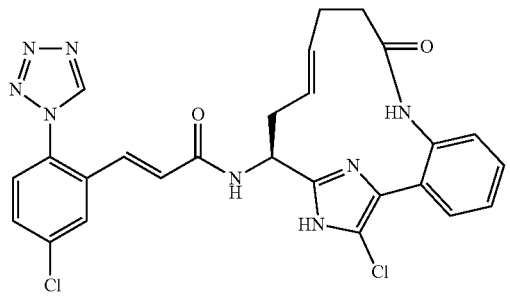 [SMILES: O=C(/C=C/c1cc(Cl)ccc1-n1cnnn1)N[C@H]1C/C=C/CCC(=O)Nc2ccccc2-c2nc1[nH]c2Cl]

Example 50 was prepared following the procedure described in 17A, by replacing 16A with Example 49. $^1$H NMR (500 MHz, CD$_3$OD) δ ppm 2.30-2.53 (m, 5H), 2.66-2.76 (m, 1H), 4.97 (dd, J=10.3, 4.3 Hz, 1H), 5.32-5.42 (m, 1H), 5.49-5.59 (m, 1H), 6.77 (d, J=15.7 Hz, 1H), 7.14 (d, J=15.7 Hz, 1H), 7.32 (dd, J=7.7, 1.2 Hz, 1H), 7.40 (td, J=7.6, 1.3 Hz, 1H), 7.48-7.53 (m, 2H), 7.58 (d, J=8.3 Hz, 1H), 7.67 (dd, J=8.5, 2.2 Hz, 1H), 7.98 (d, J=2.2 Hz, 1H), 9.51 (s, 1H). MS (ESI) m/z: 549.2 (M+H)$^+$. Analytical HPLC: RT=6.87 min.

Example 51

4-Aminomethyl-cyclohexanecarboxylic acid ((E)-(S)-9-oxo-8,17,19-triaza-tricyclo[14.2.1.0$^{2,7}$]nonadeca-1(18),2,4,6,12,16(19)-hexaen-15-yl)-amide, 2 TFA Salt

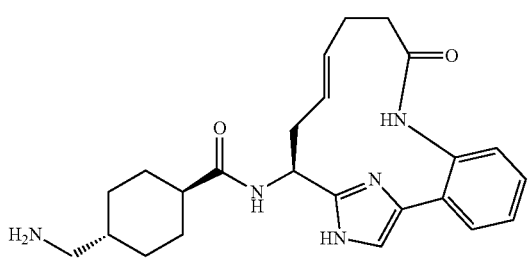 [SMILES: NC[C@H]1CC[C@H](C(=O)N[C@H]2C/C=C/CCC(=O)Nc3ccccc3-c3c[nH]c2n3)CC1]

Example 51 was prepared following the procedures described in step 10D, by replacing 10C with 15B and by replacing but-3-enoic acid with pent-4-enoic acid; followed by steps 2E; 10H; 3B; and 3C. $^1$H NMR (500 MHz, CD$_3$OD) δ ppm 1.03-1.17 (m, 2H), 1.40-1.53 (m, 2H), 1.56-1.67 (m, 1H), 1.83-2.00 (m, 4H), 2.29-2.45 (m, 4H), 2.45-2.55 (m, 2H), 2.72-2.81 (m, 3H), 5.00 (dd, J=10.6, 4.8 Hz, 1H), 5.35-5.44 (m, 1H), 5.47-5.56 (m, 1H), 7.33 (dd, J=8.0, 0.8 Hz, 1H), 7.42 (td, J=7.6, 1.3 Hz, 1H), 7.44 (s, 1H), 7.50 (dd, J=7.7, 1.7 Hz, 1H), 7.55 (td, J=7.7, 1.7 Hz, 1H). MS (ESI) m/z: 422.3 (M+H)$^+$. Analytical HPLC: RT=1.62 min.

Example 52

{(R)-15-[(E)-3-(5-Chloro-2-tetrazol-1-yl-phenyl)-acryloylamino]-9-oxo-13-oxa-8,17,19-triaza-tricyclo[14.2.1.0$^{2,7}$]nonadeca-1(18),2,4,6,16(19)-pentaen-5-yl}-carbamic Acid methyl ester, 1 TFA Salt

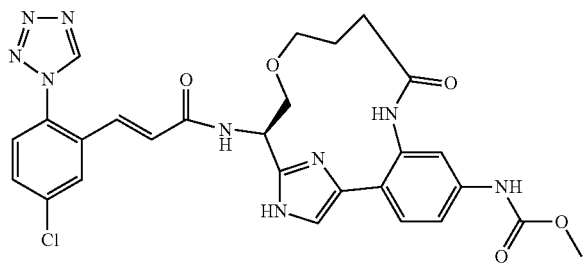 [SMILES: COC(=O)Nc1ccc2c(c1)NC(=O)CCCOC[C@H](NC(=O)/C=C/c1cc(Cl)ccc1-n1cnnn1)c1nc-2c[nH]1]

52A. (S)-3-Allyloxy-2-tert-butoxycarbonylamino-propionic acid methyl ester: This compound was prepared following a procedure described in *Organic Letters*, 10(17): 3883 (2008). To a solution of N-(tert-butoxycarbonyl)-L-serine methyl ester (0.781 mL, 3.85 mmol) in THF (15 mL) was added allyl methyl carbonate (0.524 mL, 4.61 mmol). The solution was purged with N$_2$, followed by the addition of tetrakis(triphenylphosphine)palladium(0) (444 mg, 0.385 mmol). The vessel was sealed and heated at 60° C. overnight. The reaction mixture was diluted with ethyl acetate, washed with sat NaHCO$_3$, and brine. The organic layer was concentrated. Purification by normal phase chromatography provided 52A (550 mg, 55.2% yield) as a yellow oil. $^1$H NMR (400 MHz, CDCl$_3$) δ ppm 5.75-5.94 (m, 1H) 5.32-5.47 (m, 1H) 5.11-5.29 (m, 2H) 4.35-4.53 (m, 1H) 3.92-4.03 (m, 2H) 3.80-3.89 (m, 1H) 3.76 (m, 3H) 3.61-3.70 (m, 1H) 1.46 (m, 9H).

52B. (S)-3-Allyloxy-2-tert-butoxycarbonylamino-propionic acid: A solution of 52A (1000 mg, 3.86 mmol) and lithium hydroxide (486 mg, 11.57 mmol) in THF, water and MeOH was stirred at rt for 4 h. The solution was acidified using 5M HCl in water (pH ~3). The mixture was extracted with EtOAc. The combined organic layers were concentrated to give 52B (0.96 g, 100% yield) as a yellow oil. MS (ESI) m/z: 146.0 (M+H-boc)$^+$.

52C. (S)-3-Allyloxy-2-tert-butoxycarbonylamino-propionic acid 2-(2-bromo-4-nitro-phenyl)-2-oxo-ethyl ester: To a solution of 52B (0.95 g, 3.87 mmol) and Intermediate 10 (1.376 g, 4.26 mmol) in DMF (20 mL) was added potassium bicarbonate (0.465 g, 4.65 mmol). After 1.5 h at rt, the reaction was diluted with EtOAc, washed with water, saturated sodium bicarbonate solution, then brine, dried over magnesium sulfate, filtered, and concentrated to give 52C (1.82 g, 96% yield) as a thick orange oil. MS (ESI) m/z: 389.0 (M+H-boc)$^+$.

52D. (S)-3-Allyloxy-2-tert-butoxycarbonylamino-propionic acid 2-(4-amino-2-bromo-phenyl)-2-oxo-ethyl ester: To a mixture of 52C (1700 mg, 3.49 mmol) and iron (3896 mg, 69.8 mmol) in ethanol (15 mL) and water (15.00 mL) was added 12M conc. HCl (0.204 mL, 2.442 mmol). The suspension was heated at 50° for 2 hr. The dark suspension was filtered, washed with methanol and concentrated to give 52D (1.7 g, 100%). MS (ESI) m/z: 359.0 (M+H-boc)$^+$.

52E. (S)-3-Allyloxy-2-tert-butoxycarbonylamino-propionic acid 2-(2-bromo-4-methoxycarbonylamino-phenyl)-2-oxo-ethyl ester: To a cooled (ice bath) solution 52D (1670 mg, 3.65 mmol) and pyridine (0.325 mL, 4.02 mmol) in dichloromethane (50 mL) was added methyl chloroformate (0.297 mL, 3.83 mmol). The reaction mixture was stirred for 10 min, washed with brine, dried (MgSO$_4$) and concentrated to give 52E (1.8 g, 96% yield) as a yellow foam. MS (EST) m/z: 417.1 (M+H-boc)$^+$.

52F. {4-[2-((R)-2-Allyloxy-1-tert-butoxycarbonylamino-ethyl)-1-(2-trimethylsilanyl-ethoxymethyl)-1H-imidazol-4-yl]-3-amino-phenyl}-carbamic acid methyl ester: This compound was prepared following the procedures described in step 1B, by replacing 1A with 52E; followed by steps 10B; and 10C (alternative). MS (ESI) m/z: 562.3 (M+H)$^+$.

52G. {3-Acryloylamino-4-[2-((R)-2-allyloxy-1-tert-butoxycarbonylamino-ethyl)-1-(2-trimethylsilanyl-ethoxymethyl)-1H-imidazol-4-yl]-phenyl}-carbamic acid methyl ester: A solution of 52F (50 mg, 0.089 mmol), and DIEA (50 μL, 0.286 mmol) in THF (2 mL) was cooled in ice bath. Acryloyl chloride (10 μL, 0.123 mmol) was added into the solution in a portion. Then, the ice bath was removed and reaction mixture was stirred for 1 hr at rt. To the reaction mixture was added sat. NaHCO$_3$ and the mixture was extracted with EtOAc. The combined organic layer were washed with brine and concentrated to provide an oily residue, which has gel like material insoluble in CH$_2$Cl$_2$. The soluble portion of the residue was purified by normal phase chromatography to give 52G (43 mg, 78% yield). MS(ESI) m/z: 616.4 (M+H)$^+$.

52H. Example 52 was prepared following the procedures described in step 2E/2F, by replacing 2D with 52G; followed by steps 2G; 10H; and 1G. $^1$H NMR (400 MHz, CDCl$_3$) δ ppm 8.94 (s, 1H) 7.79 (s, 1H) 7.50-7.62 (m, 1H) 7.42 (t, J=7.91 Hz, 2H) 7.10 (br. s., 1H) 6.60 (d, J=15.31 Hz, 1H) 5.22 (br. s., 1H) 4.04-4.18 (m, 1H) 3.92-4.02 (m, 1H) 3.78 (s, 4H) 3.60 (d, J=6.27 Hz, 2H) 3.28-3.49 (m, 1H) 2.81 (t, J=7.28 Hz, 1H) 2.34 (s, 1H) 2.05 (d, J=5.02 Hz, 2H) 1.63 (br. s., 1H) 0.88 (t, J=6.90 Hz, 2H). MS(ESI) m/z: 592.3 (M+H)$^+$. Analytical HPLC: RT=5.16 min.

Example 53

(E)-3-(5-Chloro-2-tetrazol-1-yl-phenyl)-N-((E)-(S)-11-methyl-9-oxo-8,17,19-triaza-tricyclo[14.2.1.0$^{2,7}$]nonadeca-1(18),2,4,6,12,16(19)-hexaen-15-yl)-acrylamide, 1 TFA Salt

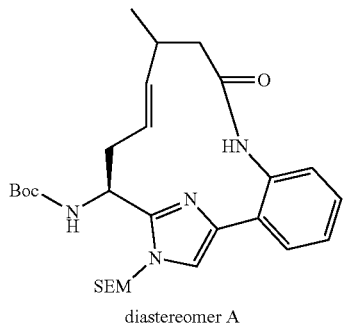

diastereomer A,

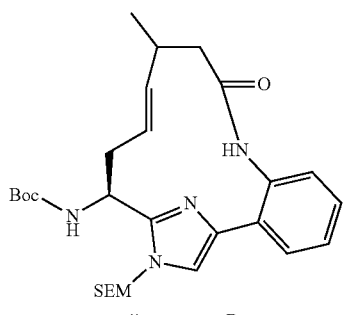

diastereomer B,

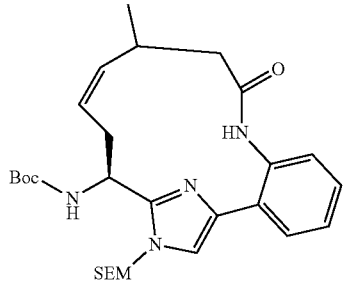

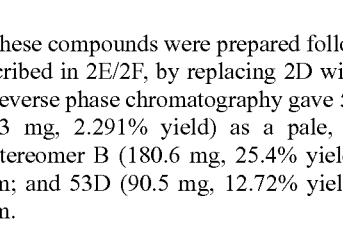

53A. {(S)-1-[4-[2-(3-Methyl-pent-4-enoylamino)-phenyl]-1-(2-trimethylsilanyl-ethoxymethyl)-1H-imidazol-2-yl]-but-3-enyl}-carbamic acid tert-butyl ester: This compound was prepared following the procedure described in 10D, by replacing 10C with 15B and by replacing but-3-enoic acid with 3-methyl-4-pentenoic acid. MS (ESI) m/z: 555.5 (M+H)$^+$.

53B. [(E)-(S)-11-Methyl-9-oxo-17-(2-trimethylsilanyl-ethoxymethyl)-8,17,19-triaza-tricyclo[14.2.1.0$^{2,7}$]nonadeca-1(18),2,4,6,12,16(19)-hexaen-15-yl]-carbamic acid tert-butyl ester, 1 TFA salt, diastereomer A; 53C. [(E)-(S)-11-Methyl-9-oxo-17-(2-trimethylsilanyl-ethoxymethyl)-8,17,19-triaza-tricyclo[14.2.1.0$^{2,7}$]nonadeca-1(18),2,4,6,12,16(19)-hexaen-15-yl]-carbamic acid tert-butyl ester, 1 TFA salt, diastereomer B; and 53D. [(Z)-(S)-11-Methyl-9-oxo-17-(2-trimethylsilanyl-ethoxymethyl)-8,17,19-triaza-tricyclo[14.2.1.0$^{2,7}$]nonadeca-1(18),2,4,6,12,16(19)-hexaen-15-yl]-carbamic acid tert-butyl ester, 1 TFA salt These compounds were prepared following the procedure described in 2E/2F, by replacing 2D with 53A. Purification by reverse phase chromatography gave 53B, diastereomer A (16.3 mg, 2.291% yield) as a pale, purple foam; 53C, diastereomer B (180.6 mg, 25.4% yield) as a pale, purple foam; and 53D (90.5 mg, 12.72% yield) as a pale, purple foam.

53E. Example 53 was prepared following the procedures described in step 10H, by replacing 10G with 53C; followed by step 15D. $^1$H NMR (500 MHz, CD$_3$OD) δ ppm 1.06 (d, J=6.9 Hz, 3H), 2.13 (dd, J=13.9, 11.7 Hz, 1H), 2.43-2.53 (m, 2H), 2.65-2.77 (m, 1H), 2.83-2.91 (m, 1H), 5.05 (dd, J=11.8, 4.7 Hz, 1H), 5.28 (ddd, J=15.1, 9.4, 1.1 Hz, 1H), 5.53 (ddd, J=15.1, 10.5, 4.1 Hz, 1H), 6.77 (d, J=15.7 Hz, 1H), 7.17 (d, J=15.7 Hz, 1H), 7.34 (d, J=8.0 Hz, 1H), 7.39-7.44 (m, 2H), 7.51 (dd, J=7.7, 1.4 Hz, 1H), 7.56 (td, J=7.7, 1.4 Hz, 1H), 7.59 (d, J=8.5 Hz, 1H), 7.69 (dd, J=8.5, 2.2 Hz, 1H), 7.99 (d, J=2.2 Hz, 1H), 9.52 (s, 1H). MS (ESI) m/z: 529.3 (M+H)$^+$. Analytical HPLC: RT=5.39 min.

Example 54

4-Aminomethyl-cyclohexanecarboxylic Acid ((E)-(S)-18-chloro-9-oxo-8,17,19-triaza-tricyclo[14.2.1.0²,⁷]nonadeca-1(18),2,4,6,12,16(19)-hexaen-15-yl)-amide, 2 TFA Salt

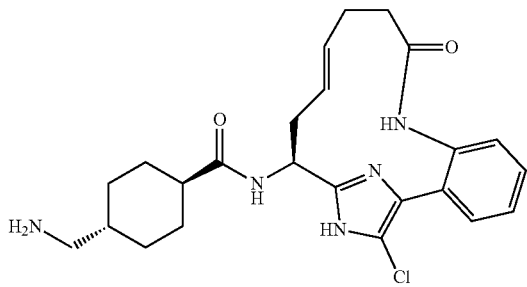 [SMILES: NC[C@H]1CC[C@H](C(=O)N[C@H]2C/C=C/CCC(=O)Nc3ccccc3-c3nc2[nH]c3Cl)CC1]

Example 54 was prepared following the procedures described in step 10D, by replacing 10C with 15B and by replacing but-3-enoic acid with pent-4-enoic acid; followed by steps 2E; 10H; 3B; 17A; and 3C. $^1$H NMR (500 MHz, CD$_3$OD) δ ppm 1.02-1.18 (m, 2H), 1.40-1.55 (m, 2H), 1.56-1.68 (m, 1H), 1.84-1.98 (m, 4H), 2.26-2.53 (m, 6H), 2.68-2.76 (m, 1H), 2.79 (d, J=7.2 Hz, 2H), 4.88-4.92 (m, 1H), 5.33-5.43 (m, 1H), 5.46-5.55 (m, 1H), 7.33 (dd, J=8.0, 0.8 Hz, 1H), 7.43 (td, J=7.6, 1.1 Hz, 1H), 7.51 (dd, J=7.7, 1.4 Hz, 1H), 7.55 (td, J=7.7, 1.6 Hz, 1H). MS (ESI) m/z: 456.2 (M+H)$^+$. Analytical HPLC: RT=3.36 min.

Example 55

(E)-3-(5-Chloro-2-tetrazol-1-yl-phenyl)-N-((Z)-(S)-11-methyl-9-oxo-8,17,19-triaza-tricyclo[14.2.1.0²,⁷]nonadeca-1(18),2,4,6,12,16(19)-hexaen-15-yl)-acrylamide, 1 TFA Salt

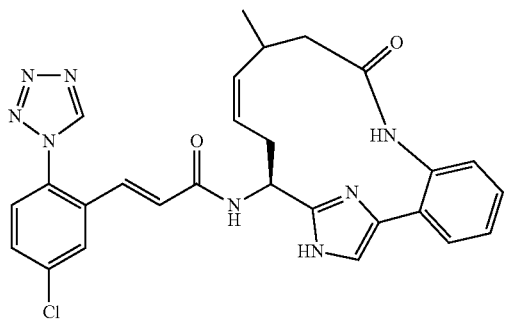 [SMILES: CC1/C=C\C[C@H](NC(=O)/C=C/c2cc(Cl)ccc2-n2cnnn2)c2nc(c[nH]2)-c2ccccc2NC(=O)C1]

Example 55 was prepared following the procedures described in step 10H, by replacing 10G with 53D; followed by step 15D. $^1$H NMR (500 MHz, CD$_3$OD) δ ppm 1.06 (d, J=6.6 Hz, 3H), 2.08 (t, J=12.0 Hz, 1H), 2.47 (dd, J=12.4, 2.5 Hz, 1H), 2.58-2.67 (m, 1H), 2.83-2.96 (m, 1H), 2.99-3.08 (m, 1H), 5.14 (dd, J=12.4, 4.4 Hz, 1H), 5.33 (td, J=11.5, 3.4 Hz, 1H), 5.46-5.54 (m, 1H), 6.74 (d, J=15.7 Hz, 1H), 7.14 (d, J=15.4 Hz, 1H), 7.27 (d, J=8.0 Hz, 1H), 7.36-7.42 (m, 2H), 7.47-7.53 (m, 2H), 7.56 (d, J=8.5 Hz, 1H), 7.65 (dd, J=8.5, 2.5 Hz, 1H), 7.97 (d, J=2.2 Hz, 1H), 9.50 (s, 1H). MS (ESI) m/z: 529.3 (M+H)$^+$. Analytical HPLC: RT=5.35 min.

Example 56

(E)-N-((E)-(S)-18-Chloro-11-methyl-9-oxo-8,17,19-triaza-tricyclo[14.2.1.0²,⁷]nonadeca-1(18),2,4,6,12,16(19)-hexaen-15-yl)-3-(5-chloro-2-tetrazol-1-yl-phenyl)-acrylamide, 1 TFA Salt

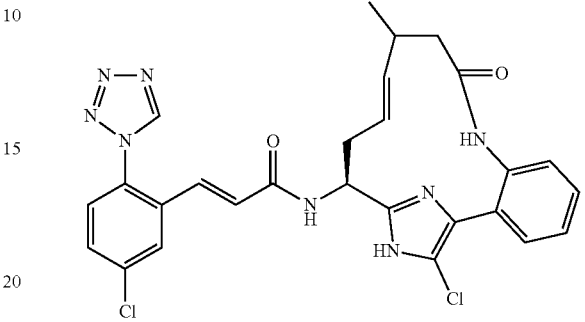

Example 56 was prepared following the procedure described in 17A, by replacing 16A with Example 53. $^1$H NMR (500 MHz, CD$_3$OD) δ ppm 1.05 (d, J=6.9 Hz, 3H), 2.16 (dd, J=13.9, 11.7 Hz, 1H), 2.30-2.39 (m, 1H), 2.42 (dd, J=13.9, 3.2 Hz, 1H), 2.64-2.79 (m, 2H), 4.92 (dd, J=11.8, 4.1 Hz, 1H), 5.19 (ddd, J=15.1, 9.4, 1.1 Hz, 1H), 5.52 (ddd, J=14.9, 10.7, 4.1 Hz, 1H), 6.79 (d, J=15.7 Hz, 1H), 7.15 (d, J=15.7 Hz, 1H), 7.32 (dd, J=7.8, 1.0 Hz, 1H), 7.40 (td, J=7.6, 1.2 Hz, 1H), 7.47 (dd, J=7.7, 1.4 Hz, 1H), 7.51 (td, J=7.7, 1.5 Hz, 1H), 7.58 (d, J=8.5 Hz, 1H), 7.67 (dd, J=8.5, 2.2 Hz, 1H), 8.01 (d, J=2.5 Hz, 1H), 9.52 (s, 1H). MS (ESI) m/z: 563.3 (M+H)$^+$. Analytical HPLC: RT=7.22 min.

Example 57

(E)-3-Chloro-2-tetrazol-1-yl-phenyl)-N-((E)-(S)-11-methyl-9-oxo-8,17,19-triaza-tricyclo[14.2.1.0²,⁷]nonadeca-1(18),2,4,6,12,16(19)-hexaen-15-yl)-acrylamide, 1 TFA Salt

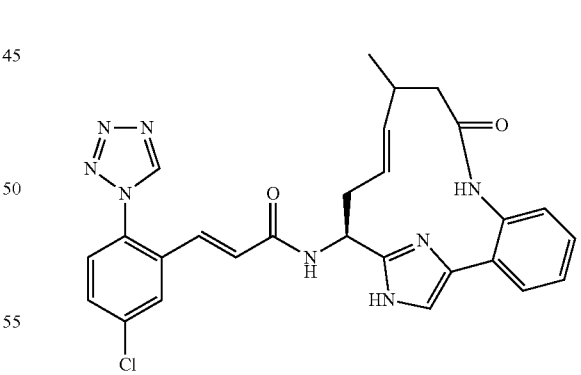

Example 57 was prepared following the procedures described in step 10H, by replacing 10G with 53B; followed by step 15D. $^1$H NMR (500 MHz, CD$_3$OD) δ ppm 1.08 (d, J=6.9 Hz, 3H), 2.26 (dd, J=14.3, 11.6 Hz, 1H), 2.49 (dd, J=14.4, 3.7 Hz, 1H), 2.63-2.75 (m, 3H), 5.18 (dd, J=6.7, 5.4 Hz, 1H), 5.44 (dd, J=15.5, 8.7 Hz, 1H), 5.55-5.64 (m, 1H), 6.76 (d, J=15.4 Hz, 1H), 7.14 (d, J=15.7 Hz, 1H), 7.31 (d, J=8.0 Hz, 1H), 7.40 (td, J=7.6, 1.1 Hz, 1H), 7.48 (s, 1H), 7.50-7.56 (m, 2H), 7.58 (d, J=8.5 Hz, 1H), 7.68 (dd, J=8.5, 2.2 Hz, 1H), 7.96 (d, J=2.2 Hz, 1H), 9.50 (s, 1H). MS (ESI) m/z: 529.3 (M+H)⁺. Analytical HPLC: RT=6.03 min.

Example 58

(E)-N-((Z)-(S)-18-Chloro-11-methyl-9-oxo-8,17,19-triaza-tricyclo[14.2.1.0$^{2,7}$]nonadeca-1(18),2,4,6,12,16(19)-hexaen-15-yl)-3-(5-chloro-2-tetrazol-1-yl-phenyl)-acrylamide, 1 TFA Salt

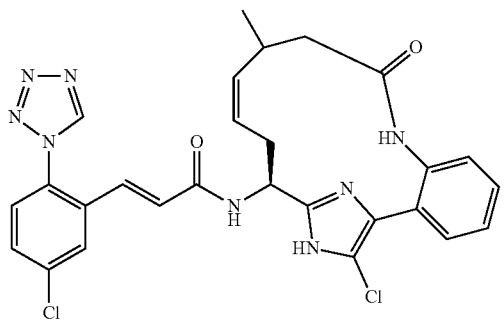 [SMILES: CC1/C=C\C[C@H](NC(=O)/C=C/c2cc(Cl)ccc2-n2cnnn2)c2nc(c(Cl)[nH]2)-c2ccccc2NC(=O)C1]

Example 58 was prepared following the procedure described in 17A, by replacing 16A with Example 55. ¹H NMR (500 MHz, CD₃OD) δ ppm 1.06 (d, J=6.9 Hz, 3H), 2.16 (t, J=12.1 Hz, 1H), 2.40 (dd, J=12.8, 2.3 Hz, 1H), 2.54-2.63 (m, 1H), 2.81-2.96 (m, 2H), 4.97 (dd, J=12.0, 4.3 Hz, 1H), 5.35 (td, J=11.5, 3.4 Hz, 1H), 5.50 (td, J=10.6, 1.7 Hz, 1H), 6.71 (d, J=15.7 Hz, 1H), 7.16 (d, J=15.7 Hz, 1H), 7.30 (dd, 0.8 Hz, 1H), 7.39 (td, J=7.6, 1.3 Hz, 1H), 7.50 (td, J=7.8, 1.5 Hz, 1H), 7.54 (dd, 1.4 Hz, 1H), 7.57 (d, J=8.5 Hz, 1H), 7.66 (dd, J=8.5, 2.2 Hz, 1H), 7.97 (d, J=2.2 Hz, 1H), 9.51 (s, 1H). MS (ESI) m/z: 563.3 (M+H)⁺. Analytical HPLC: RT=6.93 min.

Example 59

(E)-3-(5-Chloro-2-tetrazol-1-yl-phenyl)-N—((S)-11-methyl-9-oxo-8,17,19-triaza-tricyclo[14.2.1.0$^{2,7}$]nonadeca-1(18),2,4,6,16(19)-pentaen-15-yl)-acrylamide, 1 TFA Salt

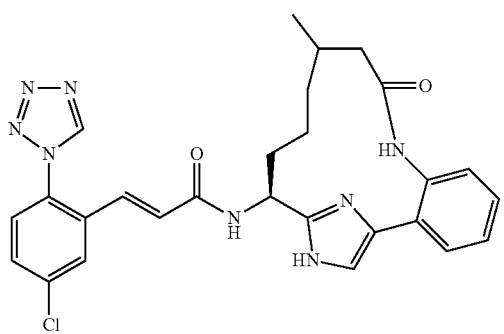 [SMILES: CC1CCC[C@H](NC(=O)/C=C/c2cc(Cl)ccc2-n2cnnn2)c2nc(c[nH]2)-c2ccccc2NC(=O)C1]

Example 59 was prepared following the procedures described in step 2G, by replacing 2E/2F with a mixture of 53B and 53C and by replacing the hydrogen balloon with hydrogen (50 psi); followed by steps 10H; and 15D. MS (ESI) m/z: 531.3 (M+H)⁺. Analytical HPLC: RT=5.79 min.

Example 60

(E)-3-(5-Chloro-2-tetrazol-1-yl-phenyl)-N—((S)-11-methyl-9-oxo-8,17,19-triaza-tricyclo[14.2.1.0$^{2,7}$]nonadeca-1(18),2,4,6,16(19)-pentaen-15-yl)-acrylamide, 1 TFA Salt

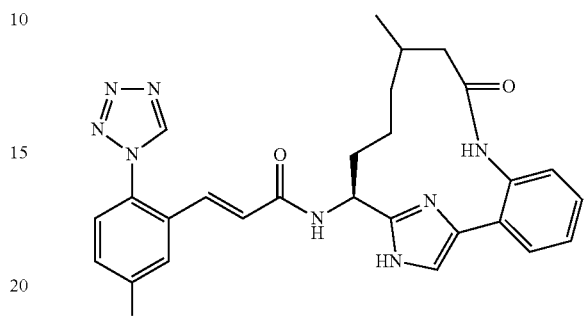

Example 60 was prepared following the procedures described in step 2G, by replacing 2E/2F with 53C and by replacing the hydrogen balloon with hydrogen (50 psi); followed by steps 10H; and 15D. ¹H NMR (500 MHz, CD₃OD) δ ppm 0.48-0.60 (m, 1H), 0.98-1.02 (m, 4H), 1.34-1.49 (m, 1H), 1.58-1.74 (m, 1H), 1.86-2.02 (m, 3H), 2.22-2.29 (m, 1H), 2.40-2.47 (m, 1H), 5.00 (dd, J=9.6, 4.4 Hz, 1H), 6.77 (d, J=15.7 Hz, 1H), 7.14 (d, J=15.7 Hz, 1H), 7.33 (dd, J=8.0, 0.8 Hz, 1H), 7.41-7.47 (m, 2H), 7.51-7.60 (m, 3H), 7.68 (dd, J=8.5, 2.2 Hz, 1H), 7.97 (d, J=2.2 Hz, 1H), 9.50 (s, 1H). MS (ESI) m/z: 531.3 (M+H)⁺. Analytical HPLC: RT=5.01 min.

Example 61

{(S)-15-[(E)-3-(5-Chloro-2-tetrazol-1-yl-phenyl)-acryloylamino]-12-methyl-9-oxo-8,17,19-triaza-tricyclo[14.2.1.0$^{2,7}$]nonadeca-1(18),2,4,6,16(19)-pentaen-5-yl}-carbamic Acid methyl ester, 1 TFA Salt, diastereomer A; and Example 62

{(S)-15-[(E)-3-(5-Chloro-2-tetrazol-1-yl-phenyl)-acryloylamino]-12-methyl-9-oxo-8,17,19-triaza-tricyclo[14.2.1.0$^{2,7}$]nonadeca-1(18),2,4,6,16(19)-pentaen-5-yl}-carbamic Acid methyl ester, 1 TFA Salt, diastereomer B

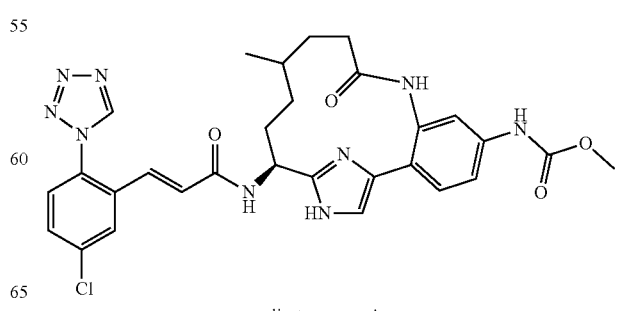

diastereomer A

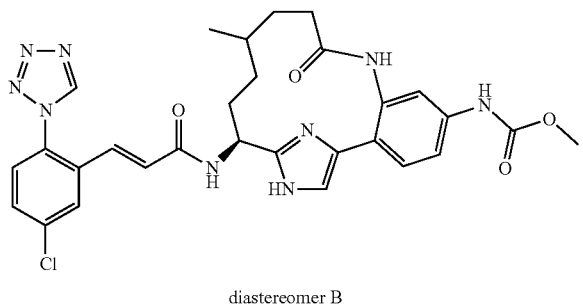

diastereomer B 61A. (S)-Methyl N-4-(2-(1-(tert-butoxycarbonylamino)but-3-enyl)-1-((2-(trimethylsilyl)ethoxy)methyl)-1H-imidazol-4-yl)-3-(4-methylpent-4-enamido)phenylmethanimidoperoxoate: This compound was prepared following the procedure described in 10D, by replacing but-3-enoic acid with 4-methylpent-4-enoic acid. MS (ESI) m/z: 628.2 (M+H)+.

61B. To a solution of 61A (0.066 g, 0.105 mmol) in DCE (1 mL) was added Grubbs (II) (0.018 g, 0.021 mmol). The reaction mixture was vacuumed and back-filled with argon three times, and then the microwave vial was capped. The reaction was microwaved at 120° C. for 20 min, cooled to rt and concentrated. Purification by reverse phase chromatography afforded 61B (mixture of E/Z isomers) (0.026 g, 34.6%) as a brown solid. MS (ESI) m/z: 600.5 (M+H)+ for both peaks.

61C. Example 61 and Example 62 were prepared following the procedures described in step 2G, by replacing 2E/2F with 61B (mixture of E/Z-isomers); followed by steps 10H; and 1G. The diastereomers were then separated by reverse phase chromatography to give Example 61 (diastereomer A) and Example 62 (diastereomer B).

Example 61: $^1$H NMR (500 MHz, CD$_3$OD) δ ppm 9.50 (s, 1H), 7.97 (d, J=2.2 Hz, 1H), 7.68 (dd, J=8.5, 2.2 Hz, 1H), 7.57-7.60 (m, 2H), 7.38-7.44 (m, 3H), 7.14 (d, J=15.7 Hz, 1H), 6.75 (d, J=15.7 Hz, 1H), 4.95 (dd, J=10.6, 4.5 Hz, 1H), 3.76 (s, 3H), 2.47-2.54 (m, 1H), 2.23-2.33 (m, 2H), 1.91-2.00 (m, 1H), 1.53-1.61 (m, 1H), 1.37-1.51 (m, 3H), 0.86 (d, J=6.3 Hz, 3H), 0.27-0.36 (m, 1H). MS (ESI) m/z: 604.3 (M+H)+. Analytical HPLC: RT=5.28 min.

Example 62: $^1$H NMR (500 MHz, CD$_3$OD) δ ppm 9.49 (s, 1H), 7.95 (d, J=2.2 Hz, 1H), 7.66 (dd, J=8.5, 2.2 Hz, 1H), 7.55-7.60 (m, 2H), 7.40-7.45 (m, 3H), 7.12 (d, J=15.7 Hz, 1H), 6.71 (d, J=15.4 Hz, 1H), 5.00 (dd, J=9.5, 5.4 Hz, 1H), 3.75 (s, 3H), 2.41-2.48 (m, 1H), 2.24-2.32 (m, 1H), 2.11-2.21 (m, 2H), 1.60-1.69 (m, 1H), 1.44-1.53 (m, 1H), 1.27-1.42 (m, 2H), 0.90 (d, J=6.3 Hz, 3H), 0.68-0.78 (m, 1H). MS (ESI) m/z: 604.3 (M+H)+. Analytical HPLC: RT=5.36 min.

Example 63

(E)-N—((S)-18-Chloro-11-methyl-9-oxo-8,17,19-triaza-tricyclo[14.2.1.0$^{2,7}$]nonadeca-1(18),2,4,6,16(19)-pentaen-15-yl)-3-(5-chloro-2-tetrazol-1-yl-phenyl)-acrylamide, 1 TFA Salt

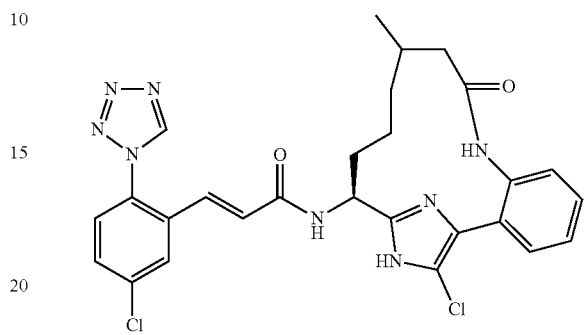

Example 63 was prepared following the procedure described in 17A, by replacing 16A with Example 60. $^1$H NMR (500 MHz, CD$_3$OD) δ ppm 0.65-0.76 (m, 1H), 0.99 (d, J=6.3 Hz, 3H), 1.08-1.18 (m, 1H), 1.31-1.45 (m, 1H), 1.47-1.61 (m, 1H), 1.80-1.91 (m, 1H), 1.93-2.01 (m, 2H), 2.06-2.15 (m, 1H), 2.35-2.38 (m, 1H), 4.90 (dd, J=10.2, 4.4 Hz, 1H), 6.79 (d, J=15.7 Hz, 1H), 7.12 (d, J=15.7 Hz, 1H), 7.33 (d, J=8.0 Hz, 1H), 7.38-7.44 (m, 1H), 7.48-7.53 (m, 2H), 7.57 (d, J=8.5 Hz, 1H), 7.66 (dd, J=8.4, 2.3 Hz, 1H), 7.99 (d, J=2.5 Hz, 1H), 9.51 (s, 1H). MS (ESI) m/z: 565.3 (M+H)+. Analytical HPLC: RT=7.41 min.

Example 64

(E)-3-(5-Chloro-2-tetrazol-1-yl-phenyl)-N—((S)-9-oxo-8,17,19-triaza-tricyclo[14.2.1.0$^{2,7}$]nonadeca-1(18),2,4,6,16(19)-pentaen-15-yl)-acrylamide, 1 TFA Salt

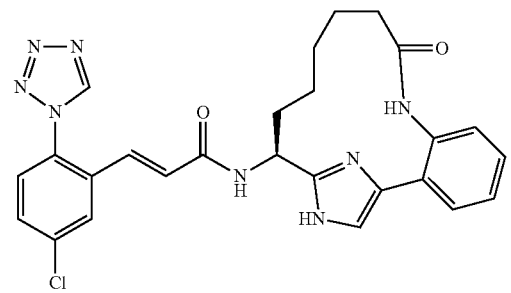 [SMILES: O=C(/C=C/c1cc(Cl)ccc1-n1cnnn1)N[C@H]1CCCCCC(=O)Nc2ccccc2-c2c[nH]c1n2]

Example 64 was prepared following the procedures described in step 10D, by replacing 10C with 15B and by replacing but-3-enoic acid with pent-4-enoic acid; followed by steps 2F; 2G, by replacing the hydrogen balloon with hydrogen (50 psi); 10H; and 15D. $^1$H NMR (500 MHz, CD$_3$OD) δ ppm 0.72-0.82 (m, 1H), 0.83-0.94 (m, 1H), 1.42-1.59 (m, 2H), 1.59-1.77 (m, 2H), 1.98-2.10 (m, 1H), 2.16-2.25 (m, 1H), 2.29-2.44 (m, 2H), 5.05 (dd, J=10.0, 4.8 Hz, 1H), 6.77 (d, J=15.7 Hz, 1H), 7.11 (d, J=15.7 Hz, 1H), 7.33 (d, J=8.0 Hz, 1H), 7.40-7.45 (m, 1H), 7.49 (s, 1H), 7.52-7.58 (m, 3H), 7.65 (dd, J=8.5, 2.2 Hz, 1H), 7.95 (d, J=2.2 Hz, 1H), 9.49 (s, 1H). MS (ESI) m/z: 517.3 (M+H)⁺. Analytical HPLC: RT=5.02 min.

Example 65

(E)-N—((S)-18-Chloro-9-oxo-8,17,19-triaza-tricyclo [14.2.1.0²,⁷]nonadeca-1(18),2,4,6,16(19)-pentaen-15-yl)-3-(5-chloro-2-tetrazol-1-yl-phenyl)-acrylamide, 1 TFA Salt

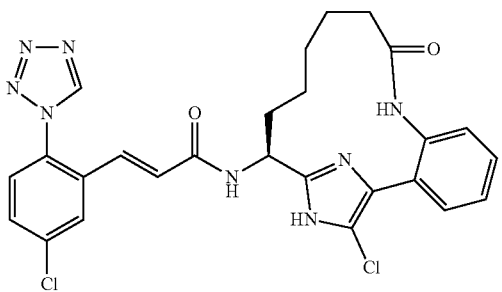 [SMILES: O=C(/C=C/c1cc(Cl)ccc1-n1cnnn1)N[C@H]1CCCCCC(=O)Nc2ccccc2-c2nc1[nH]c2Cl]

Example 65 was prepared following the procedure described in 17A, by replacing 16A with Example 64. ¹H NMR (500 MHz, CD₃OD) δ ppm 0.75-0.94 (m, 1H), 1.07-1.21 (m, 1H), 1.33-1.54 (m, 2H), 1.62-1.72 (m, 2H), 1.86-1.99 (m, 1H), 2.05-2.16 (m, 1H), 2.30-2.36 (m, 2H), 4.90 (dd, J=10.6, 4.5 Hz, 1H), 6.75 (d, J=15.4 Hz, 1H), 7.12 (d, J=15.7 Hz, 1H), 7.34 (dd, J=7.8, 1.0 Hz, 1H), 7.41 (td, J=7.7, 1.4 Hz, 1H), 7.50 (td, J=7.7, 1.6 Hz, 1H), 7.54 (dd, J=7.7, 1.4 Hz, 1H), 7.57 (d, J=8.5 Hz, 1H), 7.66 (dd, J=8.5, 2.2 Hz, 1H), 7.97 (d, J=2.2 Hz, 1H), 9.50 (s, 1H). MS (ESI) m/z: 551.3 (M+H)⁺. Analytical HPLC: RT=6.98 min.

Example 66

{(S)-15-[(E)-3-(5-Chloro-2-tetrazol-1-yl-phenyl)-acryloylamino]-8-oxo-9,17,19-triaza-tricyclo [14.2.1.0²,⁷]nonadeca-1(18),2,4,6,16(19)-pentaen-5-yl}-carbamic Acid methyl ester, 1 TFA Salt

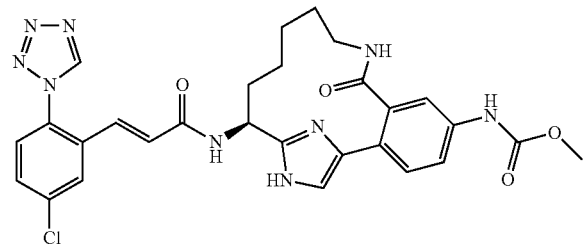 [SMILES: COC(=O)Nc1ccc2c(c1)C(=O)NCCCCC[C@H](NC(=O)/C=C/c1cc(Cl)ccc1-n1cnnn1)c1nc-2c[nH]1]

66A. 2-[2-((S)-1-tert-Butoxycarbonylamino-but-3-enyl)-1-(2-trimethylsilanyl-ethoxymethyl)-1H-imidazol-4-yl]-5-methoxycarbonylamino-benzoic acid: To a solution of 10B (230 mg, 0.386 mmol) in dry THF(2 ml) at −78° C. under Ar was added methyllithium in THF (0.515 mL, 0.772 mmol). The reaction was stirred at −78° C. for 30 min after which butyllithium in THF (0.232 mL, 0.579 mmol) was added dropwise. After 30 min, solid dry ice was added to the reaction mixture and the mixture was stirred at −78° C. for 30 min. The reaction mixture was quenched with conc. NH₄Cl (aq). It was extracted with ether and the ether layer was washed with brine, dried over Na₂SO₄, filtered and concentrated to yield 66A as a white solid. This was a mixture of product and starting material. The mixture was used in the next step without further purification. MS (ESI) m/z: 561.2 (M+H)⁺.

66B. Example 66 was prepared following the procedures described in step 3B, by replacing (1R,4R)-4-((tert-butoxycarbonylamino)methyl) cyclohexanecarboxylic acid with 66A and by replacing 3A with but-3-en-1-amine; followed by steps 2E/2F; 2G; 10H; and 1G. ¹H NMR (400 MHz, CD₃OD) δ ppm 9.51 (s, 1H), 7.96 (d, J=2.2 Hz, 1H), 7.63-7.70 (m, 2H), 7.54-7.63 (m, 2H), 7.51 (s, 1H), 7.30 (d, J=8.2 Hz, 1H), 7.14-7.24 (d, J=15.7 Hz, 1H), 6.70-6.81 (d, J=15.7 Hz, 1H) 4.99-5.13 (m, 1H), 3.68 (s, 3H), 3.25-3.35 (m, 2H), 2.24-2.44 (m, 1H), 1.87-2.09 (m, 1H), 1.42-1.82 (m, 4H), 0.60-0.89 (m, 1H), 0.30-0.60 (m, 1H) MS (ESI) m/z: 590.3 (M+H)⁺. Analytical HPLC: RT=4.28 min (Method B).

Example 67

{(Z)-(S)-15-[(E)-3-(5-Chloro-2-tetrazol-1-yl-phenyl)-acryloylamino]-8-oxo-9,17,19-triaza-tricyclo [14.2.1.0²,⁷]nonadeca-1(18),2,4,6,12,16(19)-hexaen-5-yl}-carbamic Acid methyl ester, 1 TFA Salt

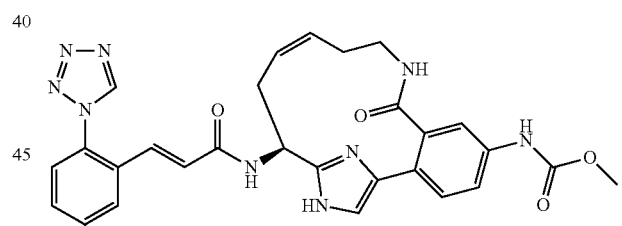

Example 67 was prepared following the procedures described in step 3B, by replacing (1r,4r)-4-((tert-butoxycarbonylamino)methyl)cyclohexanecarboxylic acid with 66A and by replacing 3A with but-3-en-1-amine; followed by steps 2F;10H; and 1G. ¹H NMR (400 MHz, CD₃OD) δ ppm 9.52 (s, 1H), 7.98 (d, J=2.2 Hz, 1H), 7.53-7.71 (m, 4H), 7.41 (s, 1H), 7.35 (d, J=8.8 Hz, 1H), 7.17 (d, J=15.4 Hz, 1H), 6.79 (d, J=15.4 Hz, 1H), 5.59-5.73 (m, 1H), 5.29-5.41 (m, 1H), 5.05-5.14 (m, 1H), 3.73 (s, 3H), 3.33-3.46 (m, 2H), 2.72-2.87 (m, 1H), 2.51-2.65 (m, 1H), 2.41-2.51 (m, 1H), 2.34 (none, 1H) MS (ESI) m/z: 588.3 (M+H)⁺. Analytical HPLC: RT=3.60 min (Method B).

Example 68

{(E)-(S)-15-[(E)-3-(5-Chloro-2-tetrazol-1-yl-phenyl)-acryloylamino]-8-oxo-9,17,19-triaza-tricyclo[14.2.1.0$^{2,7}$]nonadeca-1(18),2,4,6,12,16(19)-hexaen-5-yl}-carbamic Acid methyl ester, 1 TFA Salt

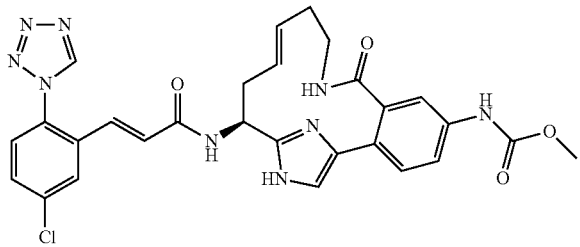 [SMILES: COC(=O)Nc1ccc2c(c1)C(=O)NCC/C=C/C[C@H](NC(=O)/C=C/c1cc(Cl)ccc1-n1cnnn1)c1nc-2c[nH]1]

Example 68 was prepared following the procedures described in step 3B, by replacing (1r,4r)-4-((tert-butoxycarbonylamino)methyl)cyclohexanecarboxylic acid with 66A and by replacing 3A with but-3-en-1-amine; followed by steps 2E;10H; and 1G. $^1$H NMR (400 MHz, CD$_3$OD) δ ppm 9.51 (s, 1H), 7.95 (d, J=2.2 Hz, 1H), 7.65-7.70 (m, 1H), 7.57 (d, J=8.8 Hz, 2H), 7.46-7.54 (m, 1H), 7.41 (s, 1H), 7.24-7.36 (m, 1H), 7.13-7.17 (m, 1H), 6.71-6.85 (m, 1H), 5.50-5.62 (m, 1H), 5.10-5.29 (m, 1H), 3.69 (s, 3H), 2.95-3.21 (m, 1H), 2.63-2.87 (m, 1H), 2.29-2.51 (m, 1H), 2.06-2.29 (m, 1H). MS (ESI) m/z: 588.3 (M+H)$^+$. Analytical HPLC: RT=3.62 min. (Method B).

Example 69

(E)-3-(5-Chloro-2-tetrazol-1-yl-phenyl)-N-((E)-(S)-9-oxo-8,10,17,19-tetraaza-tricyclo[14.2.1.0$^{2,7}$]nonadeca-1(18),2,4,6,12,16(19)-hexaen-15-yl)-acrylamide, 1 TFA Salt

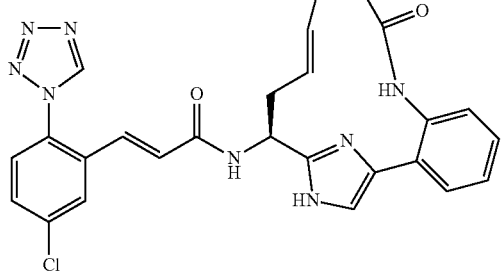

69A. {(S)-1-[4-[2-(3-Allyl-ureido)-phenyl]-1-(2-trimethylsilanyl-ethoxymethyl)-1H-imidazol-2-yl]-but-3-enyl}-carbamic acid tert-butyl ester: To a cooled (0° C.), orange solution of 15B (150 mg, 0.327 mmol) and pyridine (26.5 μL, 0.327 mmol) in DCM (1308 μL) was added dropwise allyl isocyanate (28.9 μL, 0.327 mmol). After 35 min, additional allyl isocyanate (28.9 μL, 0.327 mmol) was added. After an additional 30 min, sat. NaHCO$_3$(aq) (1.31 mL) was added and the reaction was stirred vigorously. The reaction was allowed to warm to rt and stir overnight. The reaction was partitioned between 1:1 mixture of DCM and sat. NaHCO$_3$(aq) and the layers were separated. The aqueous layer was extracted with DCM (2×). The organic layers were combined, washed with brine, dried over MgSO$_4$, filtered and concentrated to give an orange residue. Purification by normal phase chromatography gave 69A (109.8 mg, 59.5% yield) as a yellow foam. MS (ESI) m/z: 542.5 (M+H)$^+$.

69B. Example 69 was prepared following the procedures described in step 2E, by replacing 2D with 69A; followed by steps 10H; and 15D. $^1$H NMR (500 MHz, CD$_3$OD) δ ppm 2.52-2.70 (m, 1H), 2.81-2.93 (m, 1H), 3.48-3.59 (m, 2H), 5.15 (dd, J=10.0, 5.4 Hz, 1H), 5.56-5.73 (m, 2H), 6.77 (d, J=15.4 Hz, 1H), 7.15 (d, J=15.4 Hz, 1H), 7.28 (d, J=8.0 Hz, 1H), 7.33 (td, J=7.6, 1.1 Hz, 1H), 7.39 (s, 1H), 7.46-7.50 (m, 2H), 7.58 (d, J=8.5 Hz, 1H), 7.68 (dd, J=8.5, 2.2 Hz, 1H), 7.98 (d, J=2.2 Hz, 1H), 9.51 (s, 1H). MS (ESI) m/z: 516.2 (M+H)$^+$. Analytical HPLC: RT=4.77 min.

Example 70

{(E)-(S)-15-[(E)-3-(2-Acetyl-5-chloro-phenyl)-acryloylamino]-9-oxo-8,17,19-triaza-tricyclo[14.2.1.0$^{2,7}$]nonadeca-1(18),2,4,6,12,16(19)-hexaen-5-yl}-carbamic Acid methyl ester, 1 TFA Salt

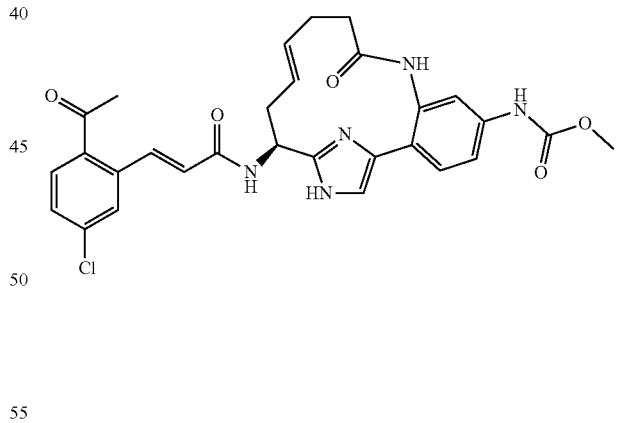

Example 70 was prepared following the procedures described in step 10H, by replacing 10G with 39A; followed by step 15D, by replacing Intermediate 2 with Intermediate 4 and by replacing Hunig's base with triethylamine. $^1$H NMR (500 MHz, CD$_3$OD) δ ppm 7.98 (d, J=15.9 Hz, 1H), 7.91 (d, J=8.2 Hz, 1H), 7.66 (d, J=2.2 Hz, 1H), 7.59 (s, 1H), 7.54 (dd, J=8.8, 2.2 Hz, 1H), 7.41-7.43 (m, 3H), 6.55 (d, J=15.9 Hz, 1H), 5.54-5.62 (m, 1H), 5.38-5.46 (m, 1H), 5.13 (dd, J=9.9, 4.4 Hz, 1H), 3.75 (s, 3H), 2.79-2.87 (m, 1H), 2.34-2.63 (m, 8H). MS (ESI) m/z: 562.5 (M+H)$^+$. Analytical HPLC: RT=5.36 min.

Example 71

(E)-N-((E)-(S)-18-Chloro-9-oxo-8,10,17,19-tetraaza-tricyclo[14.2.1.0²,⁷]nonadeca-1(18),2,4,6,12,16(19)-hexaen-15-yl)-3-(5-chloro-2-tetrazol-1-yl-phenyl)-acrylamide, 1 TFA Salt

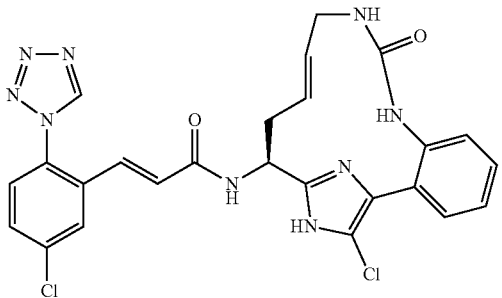 [SMILES: O=C(/C=C/c1cc(Cl)ccc1-n1cnnn1)N[C@H]1C/C=C/CNC(=O)Nc2ccccc2-c2nc1[nH]c2Cl]

Example 71 was prepared following the procedure described in 17A, by replacing 16A with Example 69. ¹H NMR (500 MHz, CD₃OD) δ ppm 2.40-2.57 (m, 1H), 2.72-2.84 (m, 1H), 3.45-3.68 (m, 2H), 5.03 (dd, J=9.9, 4.9 Hz, 1H), 5.37-5.53 (m, 1H), 5.54-5.67 (m, 1H), 6.78 (d, J=15.4 Hz, 1H), 7.15 (d, J=15.4 Hz, 1H), 7.28-7.34 (m, 2H), 7.43-7.48 (m, 2H), 7.58 (d, J=8.8 Hz, 1H), 7.67 (dd, J=8.8, 2.2 Hz, 1H), 7.97-8.00 (m, 1H), 9.52 (s, 1H). MS (ESI) m/z: 550.2 (M+H)⁺. Analytical HPLC: RT=6.48 min.

Example 72

{(S)-15-[(E)-3-(5-Chloro-2-tetrazol-1-yl-phenyl)-acryloylamino]-12-methyl-13-oxo-12,17,19-triaza-tricyclo[14.2.1.0²,⁷]nonadeca-1(18),2,4,6,16(19)-pentaen-5-yl}-carbamic Acid methyl ester, 1 TFA Salt

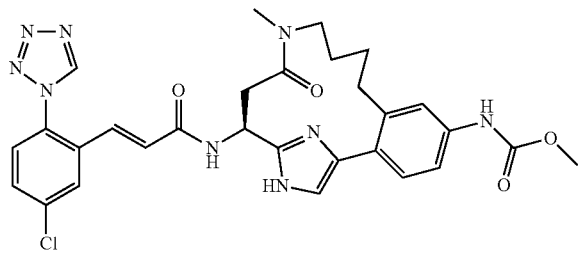 [SMILES: COC(=O)Nc1ccc2c(c1)CCCCN(C)C(=O)C[C@H](NC(=O)/C=C/c1cc(Cl)ccc1-n1cnnn1)c1nc-2c[nH]1]

72A. (S)-3-[4-(2-Allyl-4-methoxycarbonylamino-phenyl)-1-(2-trimethylsilanyl-ethoxymethyl)-1H-imidazol-2-yl]-3-tert-butoxycarbonylamino-propionic acid benzyl ester: 23A (0.30 g, 0.426 mmol), allyltributylstannane (0.282 g, 0.853 mmol), CsF (0.162 g, 1.065 mmol), Pd₂dba₃ (0.020 g, 0.021 mmol), and tri-(tert-butyl)phosphine (0.173 g, 0.085 mmol) were added together with dioxane (10 mL). The mixture was heated to 90° C. under argon. After 2.5 h, an additional two equivalents of allyltributylstannane and CsF, and a catalytic amount of Pd₂dba₃ and tri-(tert-butyl)phosphine were added. The mixture was stirred at 90° C. under argon for 3 h. The solvent was removed and the residue was partitioned between EtOAc and water. The EtOAc solution was washed with brine, dried over Na₂SO₄ and concentrated. The crude product was purified by normal phase chromatography to give 72A (0.26 g, 92% yield). MS (ESI) m/z: 665.3 (M+H)⁺.

72B. (S)-3-(4-(2-Allyl-4-(methoxycarbonylamino)phenyl)-1-((2-(trimethylsilyl)ethoxy)methyl)-1H-imidazol-2-yl)-3-(tert-butoxycarbonylamino)propanoic acid: 72A (0.26 g, 0.39 mmol) was dissolved in THF (6 mL) and 2N LiOH (2 mL) was added. The mixture was stirred at rt under argon for 20 h. The solvent was removed and the residue was diluted with water and acidified to pH about 5 with 1N HCl. The mixture was extracted with EtOAc. The combined EtOAc solution was washed with brine, dried over Na₂SO₄ and concentrated to give 72B (0.24 g, 100% yield). MS (ESI) m/z: 575.3 (M+H)⁺.

72C. {3-Allyl-4-[2-[(S)-2-(allyl-methyl-carbamoyl)-1-tert-butoxycarbonylamino-ethyl]-1-(2-trimethylsilanyl-ethoxymethyl)-1H-imidazol-4-yl]-phenyl}-carbamic acid methyl ester: To a solution of 72B in DMF (4 mL) were added PyBOP (0.26 g, 0.47 mmol), Et₃N (0.22 mL, 1.56 mmol), and methylallylamine (0.71 g, 0.998 mmol). The mixture was stirred at rt under argon for 1.5 h. Water was added and the mixture was extracted with EtOAc. The combined EtOAc solution was washed with brine, dried over Na₂SO₄ and concentrated. The crude product was purified by normal phase chromatography to give 72C (0.16 g, 64% yield). MS (ESI) m/z: 628.4 (M+H)⁺.

72D. Example 72 was prepared following the procedures described in step 2E/2F, by replacing 2D with 72C; followed by steps 2G; 1F, by replacing ethanol with methanol; and 1G. ¹H NMR (400 MHz, CD₃OD, rotamers) δ ppm 9.52 (s, 1H), 9.30 (s, 1H), 8.00 (dd, J=14.56 and 2.26 Hz, 1H), 7.64-7.77 (m, 1H), 7.55-7.63 (m, 1H), 7.46 (dd, J=10.42 and 2.13 Hz, 1H), 7.36-7.43 (m, 1H), 7.35 (d, J=1.25 Hz, 1H), 7.30 (d, J=8.03 Hz, 1H), 7.21 (dd, J=15.69 and 5.14 Hz, 1H), 5.67 (m, 1H), 5.53 (m, 1H), 4.46 (m, 1H), 3.75 (two singlets, 3H), 3.47 (m, 1H), 3.28 (m, 2H), 3.25 (m, 1H), 2.92 (two singlets, 3H), 2.68 (m, 2H), 2.29 (m, 1H), 1.29 (m, 1H). LC-MS (ESI) m/z: 604.3 (M+H)⁺. Analytical HPLC: RT=6.22/6.49 min (two rotational isomers).

Example 73

{(E)-(S)-15-[(E)-3-(5-Chloro-2-tetrazol-1-yl-phenyl)-acryloylamino]-10,10-difluoro-9-oxo-8,17,19-triaza-tricyclo[14.2.1.0²,⁷]nonadeca-1(18),2,4,6,12,16(19)-hexaen-5-yl}-carbamic Acid methyl ester, 1 TFA Salt

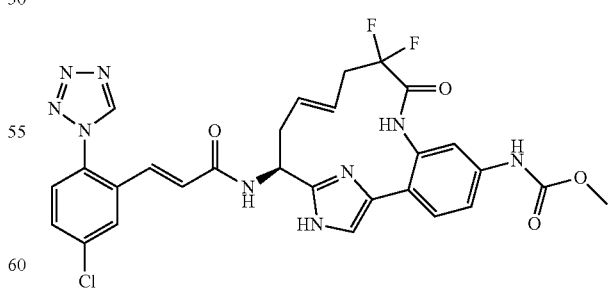

Example 73 was prepared following the procedures described in step 10D, by replacing but-3-enoic acid with 2,2-difluoropent-4-enoic acid; followed by steps 2E; 10H; and 1G. ¹H NMR (400 MHz, CD₃OD) δ ppm 9.52 (s, 1H), 7.97 (s, 1H), 7.67 (s, 1H), 7.54-7.62 (m, 2H), 7.49 (s, 1H), 7.38-7.47 (m, 2H), 7.12-7.16 (d, J=15.4 Hz, 1H), 6.74-6.78 (d, J=15.4 Hz, 1H), 5.69-5.81 (m, 1H), 5.23-5.35 (m, 1H), 5.06-5.14 (m, 1H), 3.76 (s, 3H), 2.75-3.00 (m, 3H), 2.53-2.68 (m, 1H) MS (ESI) m/z: 624.3 (M+H)$^+$. Analytical HPLC: RT=4.31 min. (Method B).

Example 74

{(Z)-(S)-15-[(E)-3-(5-Chloro-2-tetrazol-1-yl-phenyl)-acryloylamino]-10,10-difluoro-9-oxo-8,17,19-triaza-tricyclo[14.2.1.0$^{2,7}$]nonadeca-1(18),2,4,6,12,16(19)-hexaen-5-yl}-carbamic Acid methyl ester, 1 TFA Salt

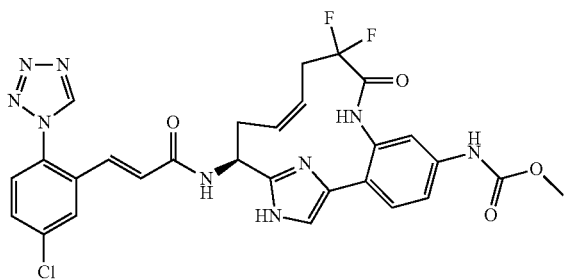 [SMILES: COC(=O)Nc1ccc2c(c1)NC(=O)C(F)(F)C/C=C\C[C@H](NC(=O)/C=C/c1cc(Cl)ccc1-n1cnnn1)c1nc-2c[nH]1]

Example 74 was prepared following the procedures described in step 10D, by replacing but-3-enoic acid with 2,2-difluoropent-4-enoic acid; followed by steps 2F; 10H; and 1G. $^1$H NMR (400 MHz, CD$_3$OD) δ ppm 9.51 (s, 1H), 7.98 (s, 1H), 7.52-7.76 (m, 3H), 7.27-7.52 (m, 3H), 7.04-7.27 (m, 1H), 6.66-6.87 (m, 1H), 5.50-5.75 (m, 2H), 5.09-5.29 (m, 1H), 3.76 (s, 3H), 2.52-3.18 (m, 4H). MS (ESI) m/z: 624.2 (M+H)$^+$. Analytical HPLC: RT=4.24 min. (Method B).

Example 75

{(S)-15-[(E)-3-(5-Chloro-2-tetrazol-1-yl-phenyl)-acryloylamino]-8-oxa-13,17,19-triaza-tricyclo[14.2.1.0$^{2,7}$]nonadeca-1(18),2,4,6,16(19)-pentaen-5-yl}-carbamic Acid methyl ester, 2 TFA Salt

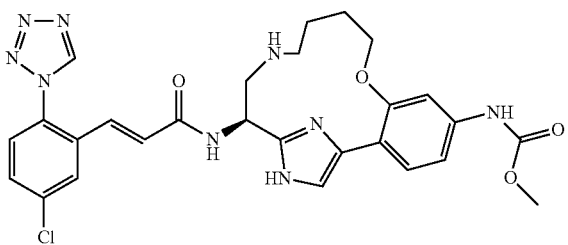 [SMILES: COC(=O)Nc1ccc2c(c1)OCCCCNC[C@H](NC(=O)/C=C/c1cc(Cl)ccc1-n1cnnn1)c1nc-2c[nH]1]

75A. (S)-2-Benzyloxycarbonylamino-3-tert-butoxycarbonylamino-propionic acid 2-(2-hydroxy-4-methoxycarbonylamino-phenyl)-2-oxo-ethyl ester: This compound was prepared following the procedures described in 2A, by replacing (S)-2-(tert-butoxycarbonylamino)pent-4-enoic acid with (S)-2-Benzyloxycarbonylamino-3-tert-butoxycarbonylamino-propionic acid and by replacing 2-bromo-1-(2-bromophenyl)ethanone with methyl 4-(2-bromoacetyl)-3-hydroxyphenylcarbamate. MS (ESI) m/z: 546.3 (M+H)$^+$.

75B. (S)-2-Benzyloxycarbonylamino-3-tert-butoxycarbonylamino-propionic acid 2-(2-allyloxy-4-methoxycarbonylamino-phenyl)-2-oxo-ethyl ester: To a solution of 75A (3.3 g, 6.05 mmol) in DMF (8.5 mL) was added potassium carbonate (1.254 g, 9.07 mmol), followed by addition of 3-bromoprop-1-ene (0.580 mL, 6.65 mmol). The reaction was heated at 70° C. for 2 hr. The reaction mixture turned dark red. It was cooled down, partitioned between water and EtOAc. The organic layer was washed with water, brine, dried over MgSO$_4$, filtered off solid and concentrated. Purification by normal phase chromatography gave 75B as a pale yellow foam (2.05 g, 58%). MS (ESI) m/z: 586.4 (M+H)$^+$.

75C. {4-[2-((S)-2-Allylamino-1-benzyloxycarbonylamino-ethyl)-1-(2-trimethylsilanyl-ethoxymethyl)-1H-imidazol-4-yl]-3-allyloxy-phenyl}-carbamic acid methyl ester: This compound was prepared following the procedures described in step 2B, by replacing 2A with 75B; followed by steps 3C; and 75B. MS (ESI) m/z: 636.5 (M+H)$^+$.

75D. Example 75 was prepared following the procedures described in step 20D, by replacing 20C with 75C; followed by steps 2E/2F; 2G; 1G; and 10H. $^1$H NMR (400 MHz, CD$_3$OD) δ ppm 9.54 (s, 1H), 7.98 (d, J=2.2 Hz, 1H), 7.68 (dd, J=8.5, 2.5 Hz, 1H), 7.60 (d, J=8.3 Hz, 1H), 7.45 (d, J=8.2 Hz, 1H), 7.40 (s, 1H), 7.34 (s, 1H), 7.23 (d, J=15.9 Hz, 1H), 6.98-7.02 (m, 1H), 6.68 (d, J=15.9 Hz, 1H), 5.42 (dd, J=7.1, 3.3 Hz, 1H), 4.14 (s, 2H), 3.75 (s, 3H), 3.51-3.59 (m, 1H), 3.42-3.49 (m, 1H), 3.10-3.22 (m, 2H), 1.95-2.09 (m, 4H). MS (ESI) m/z: 578.3 (M+H)$^+$. Analytical HPLC: RT=3.63 min. (Method B).

Example 76

{(E)-(S)-15-[(E)-3-(2-Acetyl-5-chloro-phenyl)-acryloylamino]-18-chloro-9-oxo-8,17,19-triaza-tricyclo[14.2.1.0$^{2,7}$]nonadeca-1(18),2,4,6,12,16(19)-hexaen-5-yl}-carbamic Acid methyl ester, 1 TFA Salt

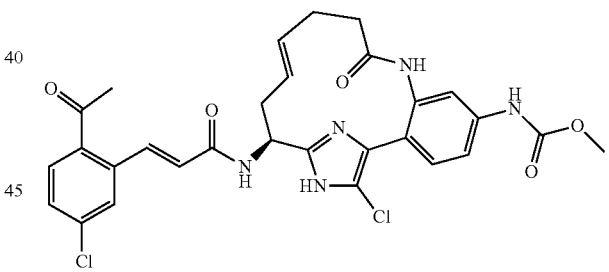

76A. [(E)-(S)-18-Chloro-5-methoxycarbonylamino-9-oxo-17-(2-trimethylsilanylethoxymethyl)-8,17,19-triaza-tricyclo[14.2.1.0$^{2,7}$]nonadeca-1(18),2,4,6,12,16(19)-hexaen-15-yl]-carbamic acid tert-butyl ester: To a solution of 39A (0.37 g, 0.632 mmol) in acetonitrile (3 mL)/chloroform (3 mL) was added NCS (0.101 g, 0.758 mmol). The reaction was heated at 65° C. for 3 h, cooled to rt and concentrated. Purification by reverse phase chromatography gave 76A (0.205 g, 0.331 mmol, 52.3%) as a white solid. MS (ESI) m/z: 620.1 (M+H)$^+$.

76B. ((E)-(S)-15-Amino-18-chloro-9-oxo-8,17,19-triaza-tricyclo[14.2.1.0$^{2,7}$]nonadeca-1(18),2,4,6,12,16(19)-hexaen-5-yl)-carbamic acid methyl ester, 2 HCl salt: The mixture of 76A (0.205 g, 0.279 mmol) and 4M HCl in dioxane (2 mL, 8.00 mmol) in a sealed tube was heated at 75° C. After 2 h, the reaction was cooled to rt. The solid was collected by filtration, rinsed with hexane, and then dried to afford 76B (0.12 g, 93%) as a white solid. MS (ESI) m/z: 390.1 (M+H)$^+$.

76C. Example 76 was prepared following the procedure described in step 15D, by replacing 15C with 76B, by replacing Intermediate 2 with Intermediate 4 and by replacing Hunig's base with triethylamine. $^1$H NMR (500 MHz, CD$_3$OD) δ ppm 7.97 (d, J=15.4 Hz, 1H), 7.89 (d, J=8.2 Hz, 1H), 7.67 (d, J=2.2 Hz, 1H), 7.59 (s, 1H), 7.52 (dd, J=8.2, 2.2 Hz, 1H), 7.41 (s, 2H), 6.55 (d, J=15.9 Hz, 1H), 5.52-5.60 (m, 1H), 5.34-5.42 (m, 1H), 5.02 (dd, J=10.4, 4.4 Hz, 1H), 3.75 (s, 3H), 2.72-2.79 (m, 1H), 2.59 (s, 3H), 2.32-2.53 (m, 5H). MS (ESI) m/z: 596.0 (M+H)$^+$. Analytical HPLC: RT=6.86 min.

Example 77

{(E)-(S)-18-Chloro-15-[(E)-3-(5-chloro-2-tetrazol-1-yl-phenyl)-acryloylamino]-9-oxo-8,17,19-triaza-tricyclo[14.2.1.0$^{2,7}$]nonadeca-1(18),2,4,6,12,16(19)-hexaen-5-yl}-carbamic Acid methyl ester, 1 TFA Salt

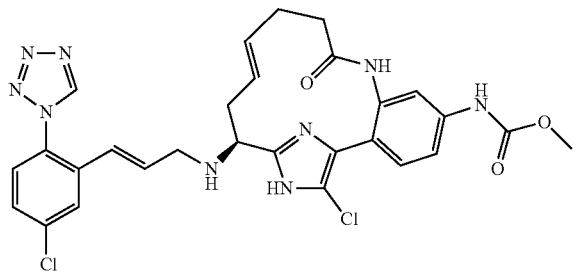 [SMILES: COC(=O)Nc1ccc2c(c1)NC(=O)CC/C=C/C[C@H](NC/C=C/c1cc(Cl)ccc1-n1cnnn1)c1nc-2c(Cl)[nH]1]

Example 77 was prepared following the procedure described in 1G, by replacing 1F with 76B. $^1$H NMR (400 MHz, DMSO-d$_6$+2 drops D$_2$O) δ ppm 9.76 (s, 1H), 7.92 (d, J=2.2 Hz, 1H), 7.68 (dd, J=8.2, 2.2 Hz, 1H), 7.64 (d, J=8.2 Hz, 1H), 7.38 (s, 1H), 7.31 (dd, J=8.8, 2.2 Hz, 1H), 7.26 (d, J=8.3 Hz, 1H), 6.77-6.87 (m, 2H), 5.37-5.47 (m, 1H), 5.12-5.21 (m, 1H), 4.87 (dd, J=10.2, 4.1 Hz, 1H), 3.61 (s, 3H), 2.12-2.33 (m, 6H). MS (ESI) m/z: 622.0 (M+H)$^+$. Analytical HPLC: RT=6.46 min.

Example 78

{(S)-15-[(E)-3-(5-Chloro-2-tetrazol-1-yl-phenyl)-acryloylamino]-10,10-difluoro-9-oxo-8,17,19-triaza-tricyclo[14.2.1.0$^{2,7}$]nonadeca-1(18),2,4,6,16(19)-pentaen-5-yl}-carbamic Acid methyl ester 1 TFA Salt

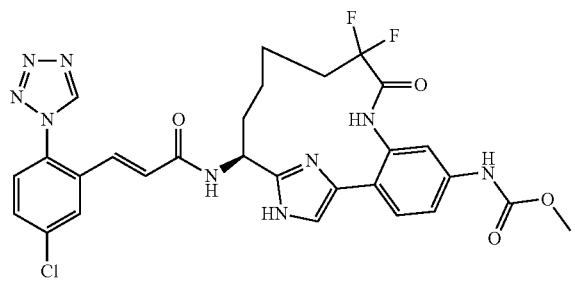 [SMILES: COC(=O)Nc1ccc2c(c1)NC(=O)C(F)(F)CCCC[C@H](NC(=O)/C=C/c1cc(Cl)ccc1-n1cnnn1)c1nc-2c[nH]1]

Example 78 was prepared following the procedures described in step 10D, by replacing but-3-enoic acid with 2,2-difluoropent-4-enoic acid; followed by steps 2E/2F; 2G; 10H; and 1G. $^1$H NMR (400 MHz, CD$_3$OD) δ ppm 9.50 (s, 1H), 7.96 (d, J=2.2 Hz, 1H), 7.67 (d, J=2.2 Hz, 1H), 7.65 (d, J=2.2 Hz, 1H), 7.61 (s, 1H), 7.57 (d, J=8.8 Hz, 1H), 7.51 (s, 1H), 7.47-7.50 (m, 1H), 7.11 (d, J=15.9 Hz, 1H), 6.75 (d, J=15.4 Hz, 1H), 5.53-5.65 (m, 1H), 3.76 (s, 3H), 1.95-2.29 (m, 4H), 1.56 (d, J=4.9 Hz, 2H), 0.68-0.94 (m, 2H). MS (ESI) m/z: 626.3 (M+H)$^+$. Analytical HPLC: RT=4.27 min. (Method B).

Example 79

{(S)-15-[(E)-3-(5-Chloro-2-tetrazol-1-yl-phenyl)-acryloylamino]-13-oxo-8,12,17,19-tetraaza-tricyclo[14.2.1.0$^{2,7}$]nonadeca-1(18),2,4,6,16(19)-pentaen-5-yl}-carbamic Acid methyl ester, 2 TFA Salt

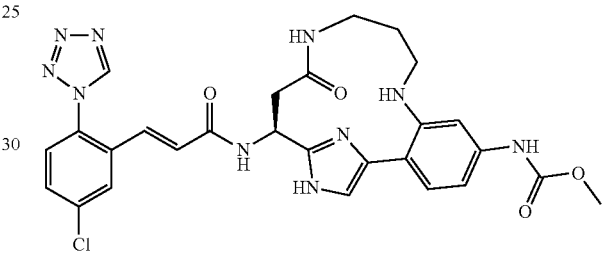

79A. (S)-Benzyl 3-(4-(2-(3-(benzyloxycarbonylamino)propylamino)-4-(methoxycarbonylamino)phenyl)-1-((2-(trimethylsilyl)ethoxy)methyl)-1H-imidazol-2-yl)-3-(tert-butoxycarbonylamino)propanoate: To a solution of 23A (200 mg, 0.284 mmol) in DMSO were added benzyl 3-aminopropylcarbamate, HCl salt (83 mg, 0.341 mmol), L-proline (6.54 mg, 0.057 mmol), CuI (5.41 mg, 0.028 mmol) and K$_2$CO$_3$ (118 mg, 0.853 mmol). The reaction was purged with argon for 3 min. The reaction was stirred at 80° C. for 16 h. The reaction was cooled to rt and then was diluted with EtOAc, washed with H$_2$O, saturated NaHCO$_3$ and brine. The organic phase was dried over MgSO$_4$, filtered and concentrated. The crude product was purified by normal phase chromatography to give 79A (47 mg, 20% yield) as a light tan solid. LC-MS (ESI) m/z: 831.4 (M+H)$^+$.

79B. Example 79 was prepared following the procedures described in step 2G, by replacing 2E with 79A; followed by steps 23E;1F, by replacing ethanol with methanol; and 1G. $^1$H NMR (400 MHz, CD$_3$OD) δ ppm 9.52 (1H, s), 7.99 (1H, d, J=2.26 Hz), 7.83 (1H, s), 7.64-7.71 (2H, m), 7.55-7.62 (2H, m), 7.25 (1H, dd, J=8.53, 2.01 Hz), 7.21 (1H, d, J=15.56 Hz), 6.74 (1H, d, J=15.56 Hz), 5.60 (1H, dd, J=9.29, 4.27 Hz), 3.77 (3H, s), 3.61-3.71 (1H, m), 3.43-3.51 (1H, m), 3.34-3.40 (2H, m), 2.85-2.94 (1H, m), 2.75-2.84 (1H, m), 2.13-2.27 (2H, m). LC-MS (ESI) m/z: 591.2 (M+H)$^+$. Analytical HPLC: RT=4.836 min.

Example 80

{(E)-(S)-15-[(4-Aminomethyl-cyclohexanecarbonyl)-amino]-18-chloro-9-oxo-8,17,19-triaza-tricyclo[14.2.1.0²,⁷]nonadeca-1(18),2,4,6,12,16(19)-hexaen-5-yl}-carbamic Acid methyl ester, 2 TFA Salt

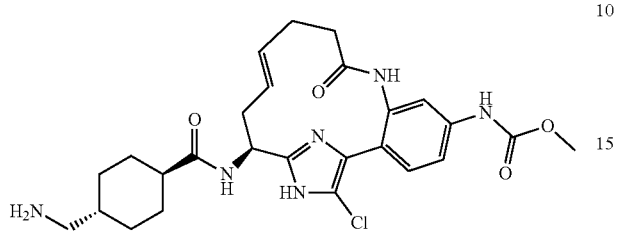

Example 80 was prepared following the procedures described in step 3B, by replacing 3A with 76B and by running the reaction at 55° C.; followed by step 3C. ¹H NMR (500 MHz, CD₃OD) δ ppm 7.53 (d, J=1.4 Hz, 1H), 7.42 (dd, J=8.5, 2.2 Hz, 1H), 7.36 (d, J=8.5 Hz, 1H), 5.46-5.54 (m, 1H), 5.27-5.36 (m, 1H), 4.79-4.90 (m, 1H), 3.75 (s, 3H), 2.79 (d, J=6.9 Hz, 2H), 2.58-2.66 (m, 1H), 2.26-2.48 (m, 6H), 1.85-1.98 (m, 4H), 1.57-1.67 (m, 1H), 1.42-1.55 (m, 2H), 1.03-1.16 (m, 2H). MS (ESI) m/z: 529.1 (M+H)⁺. Analytical HPLC: RT=3.31 min.

Example 82

[(E)-(S)-18-Chloro-15-(2,6-difluoro-4-methyl-benzoylamino)-9-oxo-8,17,19-triaza-tricyclo[14.2.1.0²,⁷]nonadeca-1(18),2,4,6,12,16(19)-hexaen-5-yl]-carbamic Acid methyl ester, 1 TFA Salt

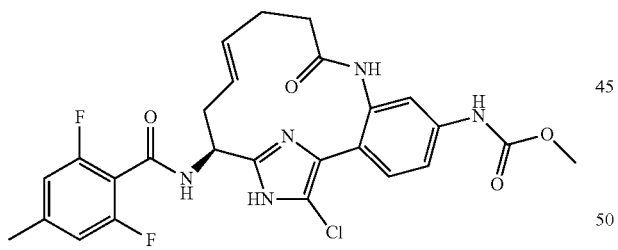

Example 82 was prepared following the procedure described in step 15D, by replacing 15C with 76B, by replacing Intermediate 2 with 2,6-difluoro-4-methyl benzoic acid, by replacing Hunig's base with triethylamine and running the reaction at 55° C. ¹H NMR (500 MHz, DMSO-d₆+2 drops D₂O) δ ppm 7.39 (d, J=1.6 Hz, 1H), 7.33 (dd, J=8.8, 2.2 Hz, 1H), 7.29 (d, J=8.3 Hz, 1H), 6.93 (d, J=8.8 Hz, 2H), 5.40-5.48 (m, 1H), 5.17-5.24 (m, 1H), 5.06 (dd, J=9.1, 4.1 Hz, 1H), 3.62 (s, 3H), 2.37-2.43 (m, 1H), 2.24-2.36 (m, 6H), 2.15-2.22 (m, 2H). MS (ESI) m/z: 544.2 (M+H)⁺. Analytical HPLC: RT=6.67 min.

Example 83

{(E)-(S)-18-Chloro-15-[(4-methyl-cyclohexanecarbonyl)-amino]-9-oxo-8,17,19-triaza-tricyclo[14.2.1.0²,⁷]nonadeca-1(18),2,4,6,12,16(19)-hexaen-5-yl}-carbamic Acid methyl ester, 1 TFA Salt

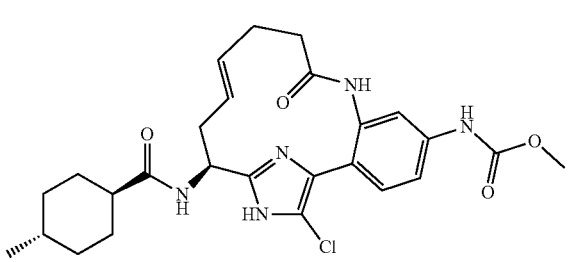

Example 83 was prepared following the procedure described in step 15D, by replacing 15C with 76B, by replacing Intermediate 2 with 4-methylcyclohexanecarboxylic acid, by replacing Hunig's base with triethylamine and running the reaction at 55° C. ¹H NMR (500 MHz, DMSO-d₆+2 drops D₂O) δ ppm 7.40 (d, J=2.2 Hz, 1H), 7.32 (dd, J=8.8, 2.2 Hz, 1H), 7.27 (d, J=8.8 Hz, 1H), 5.37-5.45 (m, 1H), 5.13-5.21 (m, 1H), 4.81 (dd, J=9.6, 4.1 Hz, 1H), 3.62 (s, 3H), 2.14-2.38 (m, 6H), 2.03-2.11 (m, 1H), 1.56-1.70 (m, 4H), 1.16-1.32 (m, 3H), 0.75-0.89 (m, 5H). MS (ESI) m/z: 514.2 (M+H)⁺. Analytical HPLC: RT=6.84 min.

Example 84

{(E)-(S)-15-[(1-Amino-5,6,7,8-tetrahydro-isoquinoline-6-carbonyl)-amino]-18-chloro-9-oxo-8,17,19-triaza-tricyclo[14.2.1.0²,⁷]nonadeca-1(18),2,4,6,12,16(19)-hexaen-5-yl}-carbamic Acid methyl ester, 2 TFA Salt (Mixture of Diastereomers)

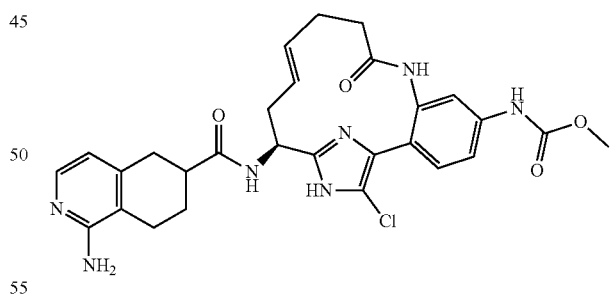

Example 84 was prepared following the procedure described in 15D, by replacing 15C with 76B, by replacing Intermediate 2 with Intermediate 5, by replacing Hunig's base with triethylamine and running the reaction at 55° C. ¹H NMR (500 MHz, DMSO-d₆+2 drops D₂O) δ ppm 7.65-7.70 (m, 1H), 7.42 (s, 1H), 7.35-7.39 (m, 1H), 7.28-7.33 (m, 1H), 6.69-6.74 (m, 1H), 5.42-5.51 (m, 1H), 5.16-5.26 (m, 1H), 4.86-4.92 (m, 1H), 3.65 (s, 3H), 2.77-2.85 (m, 2H), 2.63-2.72 (m, 1H), 2.45-2.53 (m, 1H), 2.18-2.44 (m, 7H), 2.00-2.09 (m, 1H), 1.63-1.78 (m, 1H). MS (ESI) m/z: 564.2 (M+H)⁺. Analytical HPLC: RT=3.56 min.

Example 85

[(E)-(S)-15-(4-Aminomethyl-benzoylamino)-18-chloro-9-oxo-8,17,19-triaza-tricyclo[14.2.1.0²,⁷]nonadeca-1(18),2,4,6,12,16(19)-hexaen-5-yl]-carbamic Acid methyl ester, 2 TFA Salt

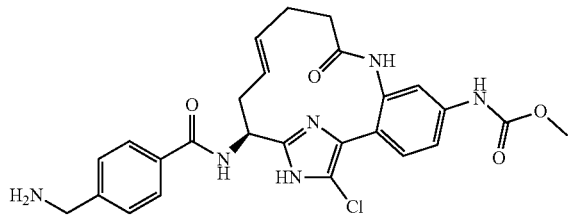 [SMILES: COC(=O)Nc1ccc2c(c1)NC(=O)CC/C=C/C[C@H](NC(=O)c1ccc(CN)cc1)c1nc-2c(Cl)[nH]1]

85A. {(E)-(S)-15-[4-(tert-Butoxycarbonylaminomethyl)-benzoylamino]-18-chloro-9-oxo-8,17,19-triaza-tricyclo[14.2.1.0²,⁷]nonadeca-1(18),2,4,6,12,16(19)-hexaen-5-yl}-carbamic acid methyl ester, 1 TFA salt: This compound was prepared following the procedure described in 15D, by replacing 15C with 76B, by replacing Intermediate 2 with 4-((tert-butoxycarbonylamino)methyl)benzoic acid, by replacing Hunig's base with triethylamine and running the reaction at 55° C. MS (ESI) m/z: 623.3 (M+H)⁺.

85B. Example 85 was prepared following the procedure described in 3C, by replacing 3B with 85A. ¹H NMR (500 MHz, DMSO-d₆+2 drops D₂O) δ ppm 7.93 (d, J=8.5 Hz, 2H), 7.54 (d, J=8.3 Hz, 2H), 7.46 (s, 1H), 7.39 (dd, J=8.5, 2.2 Hz, 1H), 7.32 (d, J=8.5 Hz, 1H), 5.52-5.60 (m, 1H), 5.24-5.32 (m, 1H), 5.15 (dd, J=9.4, 4.7 Hz, 1H), 4.09 (s, 2H), 3.68 (s, 3H), 2.23-2.54 (m, 6H). MS (ESI) m/z: 523.1 (M+H)⁺. Analytical HPLC: RT=3.44 min.

Example 87

(E)-3-(5-Chloro-2-tetrazol-1-yl-phenyl)-N-((E)-(S)-9-oxo-10-oxa-8,17,19-triaza-tricyclo[14.2.1.0²,⁷]nonadeca-1(18),2,4,6,12,16(19)-hexaen-15-yl)-acrylamide, 1 TFA Salt

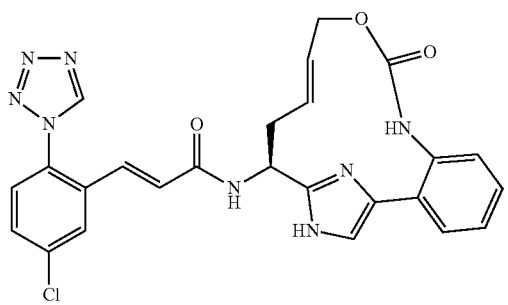 [SMILES: O=C(/C=C/c1cc(Cl)ccc1-n1cnnn1)N[C@H]1C/C=C/COC(=O)Nc2ccccc2-c2c[nH]c1n2]

Example 87 was prepared following the procedures described in step 69A, by replacing allyl isocyanate with allyl chloroformate; followed by steps 2E; 10H; and 15D. ¹H NMR (500 MHz, CD₃OD) δ ppm 2.53-2.69 (m, 1H), 2.88-2.98 (m, 1H), 4.28-4.43 (m, 2H), 5.16 (dd, J=10.5, 5.2 Hz, 1H), 5.63-5.79 (m, 1H), 5.84-5.94 (m, 1H), 6.78 (d, J=15.7 Hz, 1H), 7.14 (d, J=15.7 Hz, 1H), 7.25 (d, J=7.7 Hz, 1H), 7.39 (t, J=7.4 Hz, 1H), 7.44 (s, 1H), 7.48-7.54 (m, 2H), 7.58 (d, J=8.5 Hz, 1H), 7.68 (dd, J=8.5, 2.2 Hz, 1H), 7.98 (d, J=2.2 Hz, 1H), 9.51 (s, 1H). MS (ESI) m/z: 517.2 (M+H)⁺. Analytical HPLC: RT=5.12 min.

Example 88

{(E)-(S)-15-[(E)-3-(5-Chloro-2-tetrazol-1-yl-phenyl)-acryloylamino]-9-oxo-8,17-diaza-tricyclo[14.3.1.0²,⁷]icosa-1(20),2(7),3,5,12,16,18-heptaen-5-yl}-carbamic Acid methyl ester, 1 TFA Salt

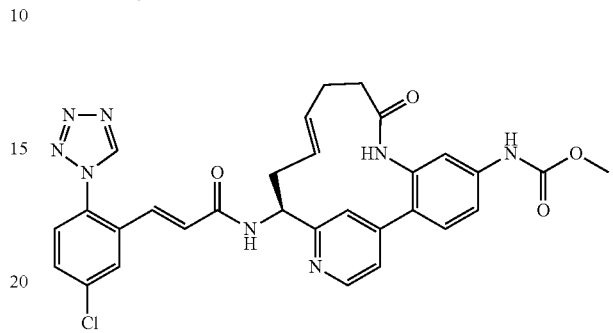

88A. (S,E)-N-((4-Chloropyridin-2-yl)methylene)-2-methylpropane-2-sulfinamide: Reference: Liu, G. et al., *J. Org. Chem.*, 64:1278 (1999). To a solution of S-(−)-t-butylsulfinamide (0.856 g, 7.06 mmol) in dichloromethane (14.13 mL) was added sequentially copper(II) sulfate (2.481 g, 15.54 mmol) and 4-chloropicolinaldehyde [1.0 g, 7.06 mmol, prepared according to a modified described by Negi (*Synthesis*, 991 (1996))]. The white suspension was stirred at rt. After 3h, the brown suspension was filtered through CELITE®, eluting with DCM, to give a clear brown filtrate. Concentration gave a brown oil weighing 1.85 g. Purification by normal phase chromatography gave 1.31 g of 88A as a clear, yellow oil. MS (ESI) m/z: 245.0 (M+H)⁺.

88B. (S)—N—((S)-1-(4-Chloropyridin-2-yl)but-3-enyl)-2-methylpropane-2-sulfinamide: Using a modified procedure described by Kuduk (*Tetrahedron Letters*, 45:6641 (2004)). To a cooled (−78° C.), clear, yellow solution of 88A (2.50 g, 10.21 mmol) in THF (34.0 mL) was added dropwise allylmagnesium bromide (1.0 M in diethyl ether, 14.30 mL, 14.30 mmol) over 25 min. The resulting orange-brown suspension was stirred at −78° C. After 30 min, additional allylmagnesium bromide (1.40 mL) was added. After 1 h, the reaction was stopped by quenching with sat. NH₄Cl. The resulting orange-brown suspension was allowed to warm to rt. The reaction was partitioned between water and EtOAc and the layers were separated. The aqueous layer was extracted with EtOAc (1×). The combined organic layers were washed with sat. NaHCO₃, brine, dried over Na₂SO₄, filtered and concentrated to give a blue oil weighing 3.22 g. Purification by normal phase chromatography gave 2.55 g (87%) of 88B as an orange-brown solid. The diastereomeric excess based on HPLC of the reaction mixture was 1:5.7 diastereomer A:diastereomer B. MS (ESI) m/z: 287.1 (M+H)⁺.

88C. (S)—N—((S)-1-(4-(2-Amino-4-nitrophenyl)pyridin-2-yl)but-3-enyl)-2-methylpropane-2-sulfinamide: To a RBF was added 88B (1.40 g, 4.88 mmol), Intermediate 12 (2.441 g, 9.76 mmol), PdCl₂(dppf)-CH₂Cl₂ adduct (0.399 g, 0.488 mmol), and potassium phosphate, tribasic (2.072 g, 9.76 mmol). The RBF was equipped with a reflux condensor then the apparatus was purged with argon for several minutes. Next, degassed DMSO (24.41 mL) was added followed by degassed water (0.440 mL, 24.41 mmol). The bright orange suspension was warmed to 90° C. After 5 h, the reaction was stopped and cooled to rt. The black mixture was filtered to remove the solid, rinsing with EtOAc. The filtrate was then partitioned between EtOAc and water and the layers were separated. The aqueous layer was extracted with EtOAc (1×). The combined organic layers were washed with brine, dried over sodium sulfate, filtered and concentrated to give a thick black oil weighing 3.8 g. Purification by normal phase chromatography gave 1.70 g as a mixture of diastereomers. The diastereomers were separated by reverse phase chromatography. Pure fractions of diastereomer A were neutralized and worked up as described in 2D to give 0.139 g of diastereomer A as an orange foam. Pure fractions of diastereomer B were neutralized and worked up as described in 2D to give 0.996 g of 88C, as an orange foam. Diastereomer B: MS (ESI) m/z: 389.2 (M+H)⁺.

88D. {(S)-1-[4-(2-Amino-4-nitro-phenyl)-pyridin-2-yl]-but-3-enyl}-carbamic acid tert-butyl ester: To a clear, orange solution of 88C (1.22 g, 3.14 mmol) in methanol (31.4 mL) was added 4 M HCl in dioxane (15.70 mL, 62.8 mmol). The reaction was slightly exothermic to the touch, so a water bath was used. After 1 h, the orange solution was concentrated to give an orange residue. The residue was suspended in DCM and concentrated. The residue was again suspended in DCM and then concentrated to give the amine as an orange solid. MS (ESI) m/z: 285.2 (M+H)⁺. The orange solid was suspended in DCM (10.46 mL) and then BOC₂O (0.802 mL, 3.45 mmol) was added. Next, triethylamine (1.750 mL, 12.56 mmol) was added and the reaction became an orange-brown suspension. The reaction was stirred at rt. After 2 h, the reaction was diluted with EtOAc and washed with sat. NaHCO₃. The aqueous layer was extracted with EtOAc (1×). The combined organic layers were washed with brine, dried over sodium sulfate, filtered, and concentrated to give a dark brown foam weighing 1.53 g. Purification by normal phase chromatography gave 1.15 g (95%) of 88D as a yellow foam. MS (ESI) m/z: (M+H)⁺.

88E. {(S)-1-[4-(4-Nitro-2-pent-4-enoylamino-phenyl)-pyridin-2-yl]-but-3-enyl}-carbamic acid tert-butyl ester: To a cooled (−5° C.) clear, yellow solution of 88D (0.413 g, 1.074 mmol) and pent-4-enoic acid (0.220 mL, 2.149 mmol) in ethyl acetate (10.74 mL) was added Hunig's Base (0.563 mL, 3.22 mmol) and propane phosphonic acid anhydride (1.266 mL, 2.149 mmol). Following the addition, the reaction was allowed to warm to rt and stir overnight. After 17.5 h, additional pent-4-enoic acid (2×0.220 mL, 2.149 mmol), Hunig's Base (2×0.563 mL, 3.22 mmol) and propane phosphonic acid anhydride (2×1.266 mL, 2.149 mmol) were added. After an additional 24 h, the reaction was stopped, partitioned between EtOAc and sat. NaHCO₃, and the layers were separated. The aqueous layer was extracted with EtOAc (1×). The combined organic layers were washed with brine, dried over sodium sulfate, filtered and concentrated to give an orange oil weighing 0.739 g. Purification by normal phase chromatography gave 0.448 g (88%) of 88E as a pale, yellow foam. MS (ESI) m/z: 467.3 (M+H)⁺.

88F. {4-[2-((S)-1-tert-Butoxycarbonylamino-but-3-enyl)-pyridin-4-yl]-3-pent-4-enoylamino-phenyl}-carbamic acid methyl ester: To a clear, yellow solution of 88E (0.330 g, 0.707 mmol) in MeOH (14.15 mL) was added zinc dust (0.463 g, 7.07 mmol) and ammonium chloride (0.378 g, 7.07 mmol). The gray suspension was stirred vigorously at rt. After 2 h, the reaction was stopped and then filtered through a 0.45 micron nylon filter, eluting with methanol. The filtrate was concentrated to give a clear, pale yellow residue. The residue was partitioned between EtOAc and 0.25 M HCl (20 mL) and the layers were separated. The organic layer was extracted with 0.25 M HCl (2×10 mL). The acid layer was basified with 1.5 M K₂HPO₄ and then extracted with EtOAc (3×). The combined organic layers were washed with brine, dried over sodium sulfate, filtered and concentrated to give the aniline as a pale, yellow foam weighing 0.3047 g. MS (ESI) m/z: 437.3 (M+H)⁺. To a cooled (−5° C.) clear, pale yellow solution of the aniline (0.3047 g, 0.698 mmol) in dichloromethane (6.98 mL) was added pyridine (0.056 mL, 0.698 mmol) and methyl chloroformate (0.054 mL, 0.698 mmol). The resulting bright yellow solution was stirred at −5° C. for 1 h. The reaction was diluted with EtOAc and washed with sat. NaHCO₃. The aqueous layer was extracted with EtOAc (2×). The combined organic layers were washed with brine, dried over sodium sulfate, filtered and concentrated to give a white foam weighing 0.345 g. Purification by normal phase chromatography gave 0.312 g (90%) of 88F, as a white foam. MS (ESI) m/z: 495.3 (M+H)⁺.

88G. ((E)-(S)-15-tert-Butoxycarbonylamino-9-oxo-8,17-diaza-tricyclo[14.3.1.0²,⁷]icosa-1(20),2(7),3,5,12,16,18-heptaen-5-yl)-carbamic acid methyl ester, 1 TFA salt: To a flame-dried 500 mL RBF was added 88F (0.116 g, 0.235 mmol), pTsOH monohydrate (0.049 g, 0.258 mmol), and DCM (235 mL). The flask was equipped with a reflux condensor and the clear, colorless solution was degassed with argon for 30 min. The reaction was then warmed to 40° C. for 1 h. In a separate, flame-dried RBF was added Grubbs (II) (0.020 g, 0.023 mmol) and the flask was purged with argon for several minutes. Degassed DCM (2 mL) was added to give a clear, burgundy solution. The solution of Grubbs (II) was added dropwise over 5 min to the above reaction. The resulting clear yellow solution was stirred at 40° C. The reaction was stopped after a total of 1.5 h. Upon cooling to rt, the reaction was washed with sat. NaHCO₃, brine, dried over sodium sulfate, filtered, and concentrated to give dark brown solid weighing 0.134 g. Purification by reverse phase chromatography gave 0.102 g (75%) of 88 G, as an off-white solid. MS (ESI) m/z: 467.3 (M+H)⁺.

88H. Example 88 was prepared following the procedures described in step 3C, by replacing 3B with 88G; followed by step 1G. ¹H NMR (500 MHz, DMSO-d₆ and D₂O) δ ppm 9.89 (s, 1H), 9.81 (s, 1H), 8.63 (d, J=5.5 Hz, 1H), 7.95 (d, J=2.2 Hz, 1H), 7.73 (dd, J=8.8, 2.2 Hz, 1H), 7.69 (d, J=8.2 Hz, 1H), 7.38-7.48 (m, 3H), 7.31 (d, J=8.2 Hz, 1H), 7.18 (s, 1H), 6.98 (d, J=15.4 Hz, 1H), 6.80 (d, J=15.4 Hz, 1H), 5.37-5.48 (m, 1H), 5.18-5.28 (m, 1H), 4.93 (dd, J=9.1, 3.6 Hz, 1H), 3.67 (s, 3H), 2.50-2.55 (m, 1H), 2.17-2.37 (m, 5H). MS (ESI) m/z: 599.3 (M+H)⁺. Analytical HPLC (Method D): RT=4.57 min.

Example 89

{(E)-17-Chloro-15-[(E)-3-(5-chloro-2-tetrazol-1-yl-phenyl)-acryloylamino]-9-oxo-8,18,19-triaza-tricyclo[14.3.1.0²,⁷]icosa-1(20),2,4,6,12,16,18-heptaen-5-yl}-carbamic Acid methyl ester

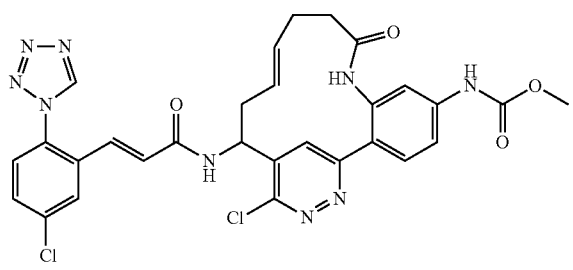 [SMILES: COC(=O)Nc1ccc2c(c1)NC(=O)CC/C=C/CC(NC(=O)/C=C/c1cc(Cl)ccc1-n1cnnn1)c1cc-2nnc1Cl]

89A. tert-Butyl 1-(3,6-dichloropyridazin-4-yl)but-3-enyl-carbamate: To a cooled (−78° C.) solution of tert-butyl (3,6-dichloropyridazin-4-yl)methylcarbamate (3.28 g, 11.79 mmol) prepared by following a literature procedure (Cowden, C. J., Org. Lett., 4497-4499 (2003)) in THF (15 mL) was added TMEDA (1.780 mL, 11.79 mmol). Then sec-butyllithium (1.4M in cyclohexane, 21.06 mL, 29.5 mmol) was added dropwise at −78° C. The reaction was warmed to −40° C. over 30 min before it was cooled to −78° C. Allyl bromide (1.496 mL, 17.69 mmol) was added at −78° C. The reaction was stirred under argon at −78° C. for 30 min and then was quenched with NH$_4$Cl solution. The reaction mixture was diluted with EtOAc, washed with 1M HCl, saturated NaHCO$_3$ and brine. The organic phase was dried over MgSO$_4$, filtered and concentrated. The crude product was purified by normal phase chromatography to give 89A (1.49 g, 40% yield) as a solid. LC-MS (ESI) m/z: 318.1 (M+H)$^+$.

89B. tert-Butyl 1-(6-(2-amino-4-nitrophenyl)-3-chloro-pyridazin-4-yl)but-3-enylcarbamate: A flask containing 89A (1.49 g, 4.68 mmol), 2-(5,5-dimethyl-1,3,2-dioxaborinan-2-yl)-5-nitroaniline (1.756 g, 7.02 mmol) and Cs$_2$CO$_3$ (3.81 g, 11.71 mmol) was purged with argon. To it were added dioxane (40 mL), tri-tert-butylphosphine tetrafluoroborate (0.204 g, 0.702 mmol) and Pd$_2$dba$_3$ (0.429 g, 0.468 mmol) at rt. The reaction was stirred under argon at 90° C. for 3 h. The reaction was cooled to rt. The solid was filtered off and the solvent was removed to give a dark solid. The crude product was purified by normal phase chromatography to give 89B (0.66 g, 34% yield) as a dark brown solid. LC-MS (ESI) m/z: 420.2 (M+H)$^+$.

89C. tert-Butyl 1-(3-chloro-6-(4-nitro-2-pent-4-enamid-ophenyl)pyridazin-4-yl)but-3-enylcarbamate: To a solution of 89B (0.66 g, 1.572 mmol) in DCM (20 mL) were added TEA (0.438 mL, 3.14 mmol) and pent-4-enoyl chloride (0.208 mL, 1.886 mmol) at 0° C. The reaction was stirred under argon at 0° C. for 1.5 h. The reaction mixture was diluted with DCM, washed with 1M HCl, saturated NaHCO$_3$ and brine. The organic phase was dried over sodium sulfate, filtered and concentrated to give 89C (0.79 g, 100% yield) as a brown solid. LC-MS (ESI) m/z: 502.2 (M+H)$^+$.

89D. tert-Butyl 1-(6-(4-amino-2-pent-4-enamidophenyl)-3-chloropyridazin-4-yl)but-3-enylcarbamate: To a solution of 89C (0.79 g, 1.574 mmol) in methanol (30 mL) were added zinc powder (0.515 g, 7.87 mmol) and ammonium chloride (0.842 g, 15.74 mmol) at 0° C. The reaction was stirred under argon at rt for 4 h. The solid was filtered through a pad of CELITE® and the filtrate was concentrated to give 89D (0.74 g, 100% yield) as a dark brown solid. LC-MS (ESI) m/z: 472.4 (M+H)$^+$.

89E. {4-[5-(1-tert-Butoxycarbonylamino-but-3-enyl)-6-chloro-pyridazin-3-yl]-3-pent-4-enoylamino-phenyl}-car-bamic acid methyl ester: To a solution of 89D (0.74 g, 1.568 mmol) in DCM (20 mL) and DMF (2 mL)(to make it more soluble) were added pyridine (0.254 mL, 3.14 mmol) and methyl chloroformate (0.121 mL, 1.568 mmol) at 0° C. The reaction was stirred under argon at 0° C. for 30 min. Water was added to quench the reaction. Most DCM was evaporated. The reaction mixture was diluted with EtOAc, washed with 1M HCl, saturated NaHCO$_3$ and brine. The organic phase was dried over MgSO$_4$, filtered and concentrated. The crude product was purified by normal phase chromatography to give 89E (501 mg, 60% yield) as a brown solid. LC-MS (ESI) m/z: 530.3$^+$.

89F. ((E)-17-Chloro-5-methoxycarbonylamino-9-oxo-8,18,19-triaza-tricyclo[14.3.1.0$^{2,7}$]icosa-1(20),2,4,6,12,16,18-heptaen-15-yl)-carbamic acid tert-butyl ester: To a solution of 89E (350 mg, 0.660 mmol) in DCM (100 mL) was added Grubbs (II) (168 mg, 0.198 mmol) at rt. The solution was purged with argon for 3 min and then was stirred under argon at reflux for 1 h. Solvent was removed. The residue was dissolved in EtOAc, which was washed with water and brine. Organic phase was dried over MgSO$_4$, filtered and concentrated to give a dark solid. The crude product was purified by normal phase chromatography to give 89F (185 mg, 56% yield) as a brown solid. LC-MS (ESI) m/z: 502.3 (M+H)$^+$.

89G. Example 89 was prepared following the procedures described in step 3C, by replacing 3B with 89F; followed by step 1G. $^1$H NMR (400 MHz, MeOD) δ ppm 9.48 (s, 1H), 8.67 (d, J=4.3 Hz, 1H), 8.14 (s, 1H), 8.00 (s, 1H), 7.92 (s, 1H), 7.64 (dd, J=8.5, 1.9 Hz, 1H), 7.55 (d, J=8.6 Hz, 1H), 7.45 (dd, J=14.0, 7.6 Hz, 1H), 7.07 (d, J=15.6 Hz, 1H), 6.59 (d, J=15.8 Hz, 1H), 5.34-5.11 (m, 2H), 4.58-4.36 (m, 1H), 3.76 (s, 3H), 3.10-2.96 (m, 1H), 2.64-2.51 (m, 1H), 2.19 (dd, J=17.9, 11.0 Hz, 3H), 1.30 (t, J=7.3 Hz, 1H). LC-MS (ESI) m/z: 634.3 (M+H)$^+$. Analytical HPLC: RT=7.596 min.

Example 90

{(E)-(S)-15-[(4-Aminomethyl-cyclohexanecarbo-nyl)-amino]-9-oxo-8,17-diaza-tricyclo[14.3.1.0$^{2,7}$]icosa-1(20),2(7),3,5,12,16,18-heptaen-5-yl}-car-bamic Acid methyl ester, 2 TFA Salt

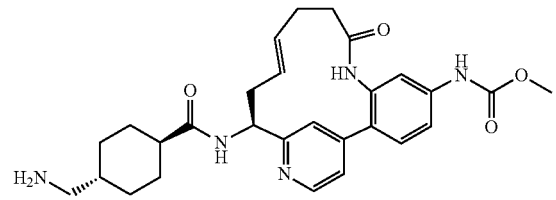 [SMILES: COC(=O)Nc1ccc2c(c1)NC(=O)CC/C=C/C[C@H](NC(=O)[C@H]1CC[C@H](CN)CC1)c1cc-2ccn1]

Example 90 was prepared following the procedures described in step 3C, by replacing 3B with 88G; followed by steps 3B; and 3C. $^1$H NMR (500 MHz, CD$_3$OD) δ ppm 8.70 (d, J=6.0 Hz, 1H), 7.75 (dd, J=6.0, 1.6 Hz, 1H), 7.53-7.63 (m, 2H), 7.49 (dd, J=8.8, 2.2 Hz, 1H), 7.39 (d, J=8.2 Hz, 1H), 5.46-5.59 (m, 1H), 5.36 (dd, J=15.7, 5.5 Hz, 1H), 4.97 (dd, J=9.3, 4.4 Hz, 1H), 3.75 (s, 3H), 2.77 (d, J=7.1 Hz, 2H), 2.67-2.75 (m, 1H), 2.44-2.58 (m, 2H), 2.30-2.44 (m, 4H), 1.79-1.97 (m, 4H), 1.51-1.65 (m, 1H), 1.32-1.50 (m, 2H), 0.99-1.15 (m, 2H). MS (ESI) m/z: 506.4 (M+H)$^+$. Analytical HPLC (Method C): RT=6.97 min.

Example 91

{(S)-15-[(E)-3-(5-Chloro-2-tetrazol-1-yl-phenyl)-acryloylamino]-9-oxo-8,17-diaza-tricyclo[14.3.1.0$^{2,7}$]icosa-1(20),2(7),3,5,16,18-hexaen-5-yl}-carbamic Acid methyl ester, 1 TFA Salt

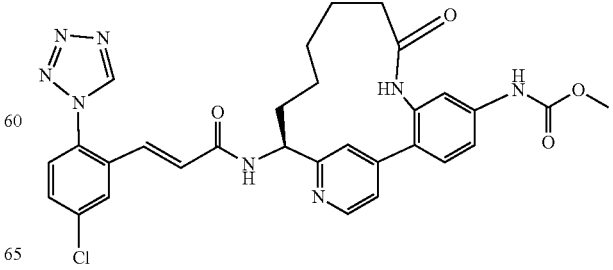

91A. ((S)-15-Amino-9-oxo-8,17-diaza-tricyclo[14.3.1.0$^{2,7}$]icosa-1(20),2(7),3,5,16,18-hexaen-5-yl)-carbamic acid methyl ester, 2 TFA salt: Compound 91A was prepared following the procedures described in step 2G, by replacing 2E/2F with 88G; followed by step 3C. MS (ESI) m/z: 369.1 (M+H)$^+$.

91B. Example 91 was prepared following the procedure described in step 1G, by replacing 1F with 91A. $^1$H NMR (500 MHz, DMSO-d$_6$)) δ ppm 9.81 (s, 1H), 9.78 (s, 1H), 9.36 (s, 1H), 8.56 (d, J=4.9 Hz, 1H), 8.53 (d, J=7.7 Hz, 1H), 7.87 (d, J=1.6 Hz, 1H), 7.66 (dd, J=8.8, 2.2 Hz, 1H), 7.64 (d, J=8.8 Hz, 1H), 7.37-7.43 (m, 2H), 7.28 (d, J=8.2 Hz, 1H), 7.21 (dd, J=4.9, 1.1 Hz, 1H), 7.11 (s, 1H), 6.93 (d, J=15.4 Hz, 1H), 6.73 (d, J=15.9 Hz, 1H), 4.76-4.83 (m, 1H), 3.62 (s, 3H), 2.09-2.20 (m, 2H), 1.76-1.88 (m, 1H), 1.56-1.68 (m, 2H), 1.30-1.42 (m, 1H), 1.07-1.26 (m, 3H), 0.70-0.82 (m, 1H). MS (ESI) m/z: 601.3 (M+H)$^+$ and 603.2 (M+2+H)$^+$. Analytical HPLC (Method D): RT=4.56 min.

Example 92

{15-[(E)-3-(5-Chloro-2-tetrazol-1-yl-phenyl)-acryloylamino]-9-oxo-8,18,19-triaza-tricyclo[14.3.1.0$^{2,7}$]icosa-1(20),2,4,6,16,18-hexaen-5-yl}-carbamic Acid methyl ester

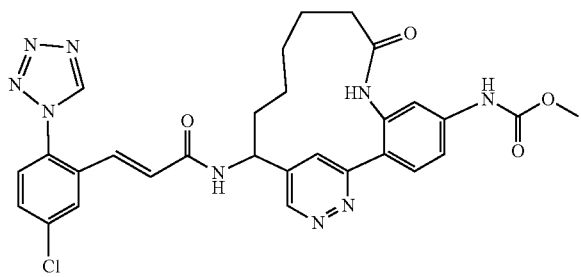 [SMILES: COC(=O)Nc1ccc2c(c1)NC(=O)CCCCCC(NC(=O)/C=C/c1cc(Cl)ccc1-n1cnnn1)c1cnnc-2c1]

Example 92 was prepared by following the procedures described in step 2G, by replacing 2E with 89F; followed by steps 3C; and 1G. $^1$H NMR (400 MHz, CD$_3$OD) δ ppm 9.44 (s, 1H), 9.27 (d, J=5.4 Hz, 1H), 8.32 (d, J=1.5 Hz, 1H), 7.99 (d, J=5.4 Hz, 1H), 7.85 (d, J=2.2 Hz, 1H), 7.65-7.59 (m, 1H), 7.55-7.48 (m, 2H), 7.23 (d, J=8.5 Hz, 1H), 6.91 (d, J=15.6 Hz, 1H), 6.41 (d, J=15.7 Hz, 1H), 4.76-4.64 (m, 1H), 3.76 (s, 3H), 2.37-2.23 (m, 2H), 2.04-1.91 (m, 1H), 1.82-1.70 (m, 1H), 1.58-1.17 (m, 6H). LC-MS (ESI) m/z: 602.3 (M+H)$^+$. Analytical HPLC: RT=6.253 min.

Example 93

{(E)-15-[(E)-3-(5-Chloro-2-tetrazol-1-yl-phenyl)-acryloylamino]-9-oxo-8-aza-tricyclo[14.3.1.02,7]icosa-1(20),2,4,6,12,16,18-heptaen-5-yl}-carbamic Acid methyl ester

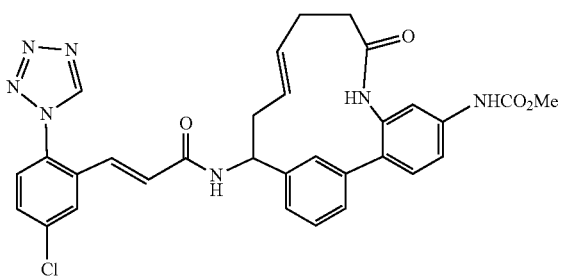

93A. [1-(3-Bromo-phenyl)-but-3-enyl]-carbamic acid tert-butyl ester: Lithium hexamethyldisilazane solution (1M in THF, 7.30 mL, 7.3 mmol) was added to a cold (0° C.) THF (25 mL) solution of the 3-bromobenzaldehyde (1.33 g, 7.3 mmol) and stirred cold for 0.5 h. The reaction mixture was cooled to −78° C., followed by the addition of allyl MgBr (1M, 7.30 mL, 7.3 mmol) dropwise. The cold reaction mixture was stirred at this temperature for 1.5 h, than quenched with sat. NH$_4$Cl and gradually allowed to warm up to room temperature. Extracted the organic materials with EtOAc (2×100 mL), dried (MgSO$_4$) and evaporated to an oil (1.1 g). $^1$H NMR (400 MHz, CDCl$_3$) δ ppm 7.52 (s, 1H), 7.45-7.2 (m, 3H), 5.77-5.68 (m, 1H), 5.15-5.09 (m, 2H), 3.99-3.95 (m, 1H), 2.49-2.30 (m, 2H). MS (ESI) m/z: 326.0 (M+H)$^+$. The crude reaction mixture was dissolved in dioxane (50 mL), and, to this was added Boc$_2$O (0.74g, 3.4 mmol) followed by the addition of TEA (1 mL) and subsequently stirred at room temperature overnight. Quenched the reaction mixture with water (100 mL) and the desired product was extracted with EtOAc (2×100 mL), dried (MgSO$_4$) and evaporated to a semi-solid mass which gradually solidified (1.25 g, 79%). $^1$H NMR (400 MHz, CDCl$_3$) δ ppm 7.45-7.18 (m, 4H), 5.66-5.61 (m, 1H), 5.17-5.08 (m, 2H), 4.89 (bs, 1H), 4.68 (bs, 1H), 2.48 (bm, 2H), 1.41 (bs, 9H)ppm. MS (ESI) m/z: 3499 (M+Na)$^+$.

93B. Example 93 was prepared following the procedures described in step 88C, by replacing 88B with 93A; followed by steps 88E; 88F, by replacing methanol with acetone and by replacing solid ammonium chloride with a saturated aqueous solution of ammonium chloride; 88G, by running the reaction without pTsOH; 3C; and 1G. $^1$H NMR (400 MHz, DMSO-d$_6$) δ ppm 9.77 (s, 1H), 9.68 (bs, 1H), 9.12 (s, 1H), 8.61 (d, J=7.7 Hz, 1H), 7.98 (s, 1H), 7.66 (m, 2H), 7.40-7.10 (m, 4H), 6.95 (s, 1H), 6.81 (q, 2H), 5.40-5.20, m, 2H), 4.78 (m, 1H), 3.62 (s, 3H), 2.25 (m, 4H), 1.16 (m, 2H)ppm. MS (ESI) m/z: 598.4 (M+H)$^+$. Analytical HPLC: RT=7.851 min.

Example 94

16-Chloro-14-[(E)-3-(5-chloro-2-tetrazol-1-yl-phenyl)-acryloylamino]-12-oxo-8-oxa-11,17,18-triaza-tricyclo[13.3.1.0$^{2,7}$]nonadeca-1(19),2,4,6,15,17-hexaene-5-carboxylic Acid methyl ester

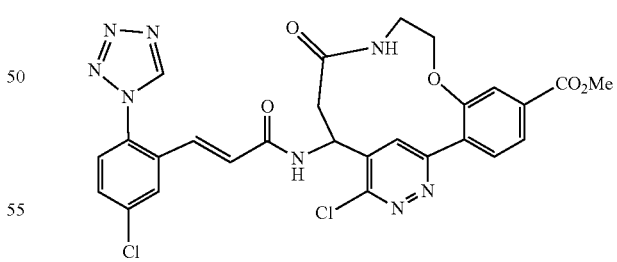

94A. 4-[5-(2-Benzyloxycarbonyl-1-tert-butoxycarbonylamino-ethyl)-6-chloro-pyridazin-3-yl]-3-[2-(1,3-dioxo-1,3-dihydro-isoindol-2-yl)-ethoxy]-benzoic acid methyl ester: To a solution of benzyl 3-(tert-butoxycarbonylamino)-3-(3,6-dichloropyridazin-4-yl)propanoate (200 mg, 0.469 mmol) prepared by following a literature procedure (Cowden, C. J., Org. Lett., 4497-4499 (2003)) in dioxane (10 mL) were added Intermediate 13 (308 mg, 0.704 mmol), Cs$_2$CO$_3$ (382 mg, 1.173 mmol) and tri-tert-butylphosphine tetrafluoroborate (13.61 mg, 0.047 mmol). The solution was purged with argon for 2 min and then Pd$_2$dba$_3$ (21.48 mg, 0.023 mmol) was added. The reaction was stirred under argon at 90° C. for 2 h. The solid was filtered-off and the solvent was removed. The crude mixture was purified by normal phase chromatography to give 94A (128 mg, 38% yield) as a yellow solid. LC-MS (ESI) m/z: 715.2 (M+H)$^+$.

94B. 4-[5-(1-tert-Butoxycarbonylamino-2-carboxy-ethyl)-6-chloro-pyridazin-3-yl]-3-[2-(1,3-dioxo-1,3-di-hydro-isoindol-2-yl)-ethoxy]-benzoic acid methyl ester: To a solution of 94A (128 mg, 0.179 mmol) in MeOH (5 mL) and ethyl acetate (5 mL) (more soluble in EtOAc) was added catalytic amount of 10% Pd/C. The reaction was stirred under a hydrogen balloon at rt for 3 h. The catalyst was filtered off and the solvent was removed to give 94B (102 mg, 91% yield) as a yellow solid. LC-MS (ESI) m/z: 625.2 (M+H)$^+$.

94C. 3-(2-Amino-ethoxy)-4-[5-(1-tert-butoxycarbonylamino-2-carboxy-ethyl)-6-chloro-pyridazin-3-yl]-benzoic acid methyl ester, TFA salt: To a solution of 94B (102 mg, 0.163 mmol) in EtOH (5 mL) was added hydrazine (0.1 mL, 3.19 mmol) at rt. The reaction was stirred under argon at reflux for 30 min. the solvent was removed. Purification by reverse phase chromatography gave 94C (25 mg, 25.2% yield) as a solid. LC-MS (ESI) m/z: 495.1 (M+H)$^+$.

94D. 14-tert-Butoxycarbonylamino-16-chloro-12-oxo-8-oxa-11,17,18-triaza-tricyclo[13.3.1.0$^{2,7}$]nonadeca-1(19),2,4,6,15,17-hexaene-5-carboxylic acid methyl ester: To a solution of BOP reagent (36.3 mg, 0.082 mmol), DIEA (0.036 mL, 0.205 mmol) and DMAP (5.02 mg, 0.041 mmol) in DCM (30 mL) was added a solution of 94C (25 mg, 0.041 mmol) in DMF (2.0 mL) through a syringe pump over 2 h at rt. Upon addition, the reaction was stirred for another 30 min and the solvent was removed. The crude product was purified by reverse phase chromatography to give 94D (3.0 mg, 15.32% yield) as a tan solid. LC-MS (ESI) m/z: 477.1 (M+H)$^+$.

94E. Example 94 was prepared by following the procedures described in step 3C, by replacing 3B with 94D; followed by step 1G. $^1$H NMR (400 MHz, DMF-d$_7$) δ ppm 9.84 (1H, s), 8.80 (1H, d, J=8.03 Hz), 8.33 (1H, s), 8.19-8.28 (1H, m), 8.11 (1H, s), 7.83 (1H, d, J=8.28 Hz), 7.73-7.80 (4H, m), 7.00-7.09 (1H, m), 6.90-6.99 (1H, m), 5.47-5.63 (1H, m), 4.24 (2H, dd, J=5.65, 1.88 Hz), 3.94 (3H, s), 3.61 (2H, t, J=5.90 Hz), 3.03-3.14 (2H, m). LC-MS (ESI) m/z: 609.2 (M+H)$^+$. Analytical HPLC: RT=7.620 min.

Example 95

{(E)-(S)-14-[(E)-3-(5-Chloro-2-tetrazol-1-yl-phenyl)-acryloylamino]-9-oxo-8,16-diaza-tricyclo[13.3.1.0$^{2,7}$]nonadeca-1(19),2(7),3,5,11,15,17-heptaen-5-yl}-carbamic Acid methyl ester, 1 TFA Salt

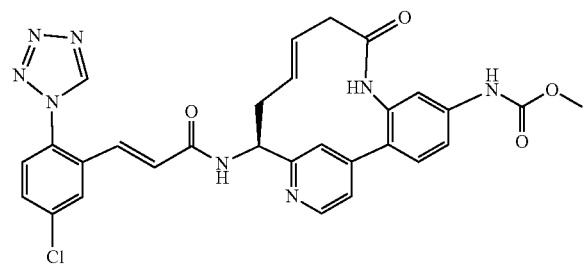 [SMILES: COC(=O)Nc1ccc2c(c1)NC(=O)C/C=C/C[C@H](NC(=O)/C=C/c1cc(Cl)ccc1-n1cnnn1)c1cc-2ccn1]

95A. ((E)-(S)-14-tert-Butoxycarbonylamino-9-oxo-8,16-diaza-tricyclo[13.3.1.0$^{2,7}$]nonadeca-1(19),2(7),3,5,11,15,17-heptaen-5-yl)-carbamic acid methyl ester, 1 TFA salt: This compound was prepared following the procedures described in step 88E, by replacing pent-4-enoic acid with but-3-enoic acid; followed by steps 88F; and 88G. MS (ESI) m/z: 453.3 (M+H)$^+$.

95B. Example 95 was prepared following the procedures described in step 3C, by replacing 3B with 95A; followed by step 1G. $^1$H NMR (500 MHz, CD$_3$OD) δ ppm 9.65 (s, 1H), 9.49 (s, 1H), 8.64 (d, J=6.0 Hz, 1H), 7.99 (d, J=2.2 Hz, 1H), 7.71 (dd, J=6.0, 1.6 Hz, 1H), 7.66 (dd, J=8.8, 2.7 Hz, 1H), 7.63 (br. s., 1H), 7.57 (d, J=8.2 Hz, 1H), 7.46-7.52 (m, 2H), 7.38 (s, 1H), 7.10 (d, J=15.4 Hz, 1H), 6.83 (d, J=15.4 Hz, 1H), 5.79-5.90 (m, 1H), 5.08 (dd, J=9.6, 4.1 Hz, 1H), 4.89-4.99 (m, 1H), 3.76 (s, 3H), 2.98 (dd, J=11.5, 8.8 Hz, 1H), 2.75-2.89 (m, 2H), 2.40-2.53 (m, 1H). MS (ESI) m/z: 585.3 (M+H)$^+$. Analytical HPLC (Method D): RT=5.07 min.

Example 96

{(S)-14-[(E)-3-(5-Chloro-2-tetrazol-1-yl-phenyl)-acryloylamino]-9-oxo-8,16-diaza-tricyclo[13.3.1.0$^{2,7}$]nonadeca-1(19),2(7),3,5,15,17-hexaen-5-yl}-carbamic Acid methyl ester, 1 TFA Salt

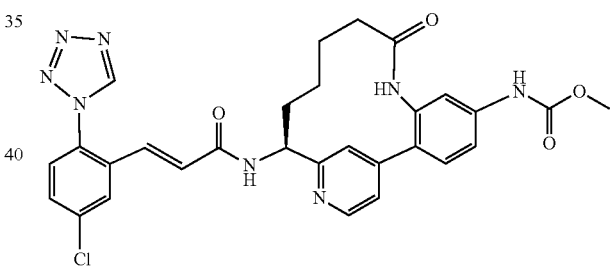

96A. ((S)-14-Amino-9-oxo-8,16-diaza-tricyclo[13.3.1.0$^{2,7}$]nonadeca-1(19),2(7),3,5,15,17-hexaen-5-yl)-carbamic acid methyl ester, 2 TFA salt: Compound 96A was prepared following the procedures described in step 2G, by replacing 2E/2F with 95A; followed by step 3C. MS (ESI) m/z: 355.2 (M+H)$^+$.

96B. Example 96 was prepared following the procedures described in step 1G, by replacing 1F with 96A. $^1$H NMR (500 MHz, CD$_3$OD) δ ppm 9.66 (s, 1H), 9.49 (s, 1H), 8.68 (d, J=6.0 Hz, 1H), 8.04 (s, 1H), 7.97 (d, J=1.6 Hz, 1H), 7.80 (d, J=5.5 Hz, 1H), 7.66 (dd, J=8.5, 1.9 Hz, 1H), 7.61 (d, J=8.2 Hz, 1H), 7.54-7.58 (m, 2H), 7.50 (dd, J=8.2, 1.6 Hz, 1H), 7.10 (d, J=15.4 Hz, 1H), 6.79 (d, J=15.4 Hz, 1H), 5.06-5.15 (m, 1H), 3.76 (s, 3H), 2.47-2.56 (m, 1H), 2.08-2.19 (m, 1H), 1.63-2.02 (m, 4H), 1.33-1.44 (m, 1H), 0.66-0.81 (m, 1H). MS (ESI) m/z: 587.3 (M+H)$^+$. Analytical HPLC (Method D): RT=4.37 min.

Example 113

{(R)-16-[(E)-3-(5-Chloro-2-tetrazol-1-yl-phenyl)-acryloylamino]-9-oxo-14-oxa-8,18,20-triaza-tricyclo[15.2.1.0$^{2,7}$]icosa-1(19),2,4,6,17(20)-pentaen-5-yl}-carbamic Acid methyl ester 1 TFA Salt

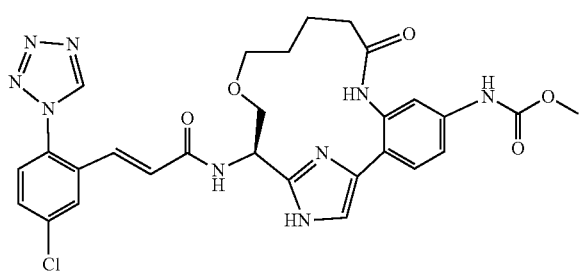 [SMILES: COC(=O)Nc1ccc2c(c1)NC(=O)CCCCOC[C@H](NC(=O)/C=C/c1cc(Cl)ccc1-n1cnnn1)c1nc-2c[nH]1]

Example 113 was prepared following the procedures described in step 10D, by replacing 10C with 52F; followed by steps 2E/2F; 2G; 10H; and 1G. $^1$H NMR (400 MHz, CD$_3$OD) δ ppm 9.59 (s, 1H) 9.52 (s, 1H) 7.97 (d, J=2.26 Hz, 1H) 7.77 (d, J=1.76 Hz, 1H) 7.66-7.70 (m, 1H) 7.56-7.61 (m, 1H) 7.45-7.48 (m, 1H) 7.44 (d, J=2.01 Hz, 1H) 7.36-7.42 (m, 1H) 7.16 (d, J=15.81 Hz, 1H) 6.80 (d, J=15.56 Hz, 1H) 5.29 (t, J=4.14 Hz, 1H) 3.84-3.97 (m, 2H) 3.75 (s, 3H) 3.58-3.69 (m, 1H) 3.43-3.55 (m, 1H) 2.26-2.44 (m, 2H) 1.54-1.75 (m, 4H). MS(ESI) m/z: 606.3 (M+H)$^+$. Analytical HPLC: RT=5.28 min.

Example 115

{(S)-16-[(E)-3-(5-Chloro-2-tetrazol-1-yl-phenyl)-acryloylamino]-14-oxo-8,13,18,20-tetraaza-tricyclo[15.2.1.0$^{2,7}$]icosa-1(19),2,4,6,17(20)-pentaen-5-yl}-carbamic Acid methyl ester, 2 TFA Salt

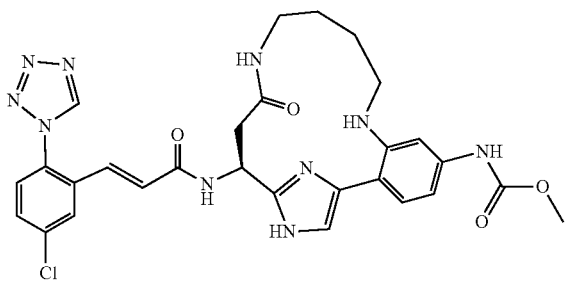 [SMILES: COC(=O)Nc1ccc2c(c1)NCCCCNC(=O)C[C@H](NC(=O)/C=C/c1cc(Cl)ccc1-n1cnnn1)c1nc-2c[nH]1]

Example 115 was prepared following the procedures described in Example 79 by replacing benzyl 3-aminopropylcarbamate HCl salt with benzyl 4-aminobutylcarbamate HCl salt in 79A. $^1$H NMR (400 MHz, MeOD) δ ppm 9.52 (1H, s), 8.00 (1H, d, J=2.26 Hz), 7.68 (1H, dd, J=8.53, 2.26 Hz), 7.57-7.62 (2H, m), 7.54 (1H, d, J=8.53 Hz), 7.51 (1H, s), 7.19 (1H, d, J=15.56 Hz), 7.15 (1H, dd, J=8.53, 2.01 Hz), 6.77 (1H, d, J=15.81 Hz), 5.54 (1H, dd, J=8.53, 5.02 Hz), 3.75 (3H, s), 3.19-3.43 (4H, m), 2.80-2.93 (1H, m), 1.56-1.81 (4H, m). LC-MS (ESI) m/z: 605.2 (M+H)$^+$. Analytical HPLC, RT=4.950 min.

Example 116

{(10R,14S)-14-[(E)-3-(5-Chloro-2-tetrazol-1-yl-phenyl)-acryloylamino]-10-methyl-9-oxo-8,16,18-triaza-tricyclo[13.2.1.02,7]octadeca-1(17),2,4,6,15(18)-pentaen-5-yl}-carbamic Acid methyl ester, 1TFA Salt, diastereomer A

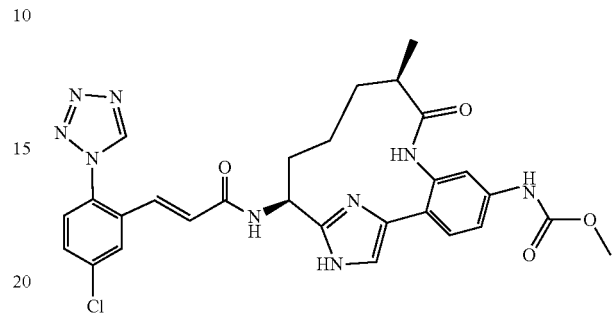

116A. A solution of Example 10C (5 g, 9.40 mmol) and triethylamine (1.564 ml, 11.28 mmol) in EtOAc (Volume: 30 ml) was cooled down to 0° C. under Ar, 2,2,2-trifluoroacetic anhydride (1.458 ml, 10.34 mmol) was added dropwise. After 1 hr, the reaction mixture was washed with water and brine, dried over Na$_2$SO$_4$, filtered off solid, concentrated. Purification by normal phase chromatography gave 5.26 g (97%) of 116A as a pale yellow solid. MS (ESI) m/z: 628.1 (M+H)$^+$.

116B. Benzyl 2-methylbut-3-enoate: To a solution of 2-methylbut-3-enoic acid (2 g, 18.98 mmol) in CH$_2$Cl$_2$ (38.0 ml) was added phenylmethanol (1.966 ml, 18.98 mmol), DCC (3.92 g, 18.98 mmol) and DMAP (0.232 g, 1.898 mmol) (slight exotherm). The reaction was stirred at rt for four hours. The reaction was filtered off solid, rinsed with hexane, concentrated. Purification by normal phase chromatography gave 3.55 g (98%) of 116B as a colorless oil.

116C. (6S,E)-Benzyl 6-(tert-butoxycarbonylamino)-6-(4-(4-(methoxycarbonylamino)-2-(2,2,2-trifluoroacetamido)phenyl)-1-((2-(trimethylsilyl)ethoxy)methyl)-1H-imidazol-2-yl)-2-methylhex-3-enoate: A solution of 116A (0.841 g, 1.340 mmol) in DCM (Volume: 26.8 ml) was added pTsOH (0.255 g, 1.340 mmol). The reaction mixture was degassed by bubbling into Ar for 30 mins, then the mixture was stirred under Ar at 40° C. for 40 mins, 116B (1.53 g, 8.04 mmol) was added, followed by Grubbs(II) (0.341 g, 0.402 mmol) in 2 ml degassed DCM dropwise. The reaction was stirred at 40° C. overnight. The reaction was quenched with sat. aq. NaHCO$_3$, extracted with DCM, washed with brine, and dried the organic layer over MgSO$_4$, filtered off solid, concentrated. Purification by normal phase chromatography gave 522 mg (49%) of 116C as a light brownish oil. MS (ESI) m/z: 790.4 (M+H)$^+$.

116D. (6S)-6-(tert-Butoxycarbonylamino)-6-(4-(4-(methoxycarbonylamino)-2-(2,2,2-trifluoroacetamido)phenyl)-1-((2-(trimethylsilyl)ethoxy)methyl)-1H-imidazol-2-yl)-2-methylhexanoic acid: A solution of 116C (810 mg, 1.025 mmol) in MeOH (20.5 ml) was vacuumed and refilled with Ar, then Pd/C 10% wt (109 mg, 0.103 mmol) was added, vacuumed and refilled with H$_2$, stirred under H$_2$ balloon at rt overnight. The reaction mixture was filtered, rinsed and concentrated to give 116D as light greenish foam (709 mg, 99%) without further purification. MS (ESI) m/z: 702.5 (M+H)$^+$.

116E. (6S)-6-(4-(2-Amino-4-(methoxycarbonylamino)phenyl)-1-((2-(trimethylsilyl)ethoxy)methyl)-1H-imidazol-2-yl)-6-(tert-butoxycarbonylamino)-2-methylhexanoic acid: To a solution of 116D (709 mg, 1.010 mmol) in MeOH (10.100 ml) was added lithium hydroxide (2N aq) (3.54 ml, 7.07 mmol), sealed and heated at 60° C. for 5 hr. The reaction was cooled down and concentrated. The residue was adjusted with 1N HCl in aq to pH ~6, extracted with EtOAc until no more product in aqueous layer. EtOAc layer washed with brine, dried over $MgSO_4$, filtered off solid, concentrated to give 116E as a dark black foam (640 mg, 100%) and used in next step without further purification. MS (ESI) m/z: 606.4 $(M+H)^+$.

116F. To a solution of BOP (1.117 g, 2.53 mmol) and DMAP (0.518 g, 4.24 mmol) in $CH_2Cl_2$ (Ratio: 25, Volume: 324 ml) and DMF (Ratio: 1.000, Volume: 12.95 ml) was added dropwise via syringe pump a solution of 116E (0.612 g, 1.010 mmol) and DIEA (1.235 ml, 7.07 mmol) in 8 ml DMF over 8 hrs. Stirred at rt overnight. The reaction was transferred to a sealed bottle and heated at 60° C. for 5 hrs then cooled down to rt and stirred at rt over the weekend. MeOH was added to quench the reaction. The reaction was concentrated, diluted with EtOAc, washed with $H_2O$ (2×), brine, dried over $MgSO_4$, filtered and concentrated. Purification by normal phase chromatography gave 116F (287 mg, 48%) as a light yellow solid. Separation of 116F by reverse phase chromatography provided two diastereomers.

116G. [(10R,14S)-5-Methoxycarbonylamino-10-methyl-9-oxo-16-(2-trimethylsilanyl-ethoxymethyl)-8,16,18-triaza-tricyclo[13.2.1.02,7]octadeca-1(17),2,4,6,15(18)-pentaen-14-yl]-carbamic acid tert-butyl ester: fast eluting isomer. MS (ESI) m/z: 588.3 $(M+H)^+$.

116H. [(10S,14S)-5-Methoxycarbonylamino-10-methyl-9-oxo-16-(2-trimethylsilanyl-ethoxymethyl)-8,16,18-triaza-tricyclo[13.2.1.02,7]octadeca-1(17),2,4,6,15(18)-pentaen-14-yl]-carbamic acid tert-butyl ester: slow eluting isomer. MS (ESI) m/z: 588.3 $(M+H)^+$.

116I. Example 116 was prepared following the procedures described in 1F, by replacing 1D with 116G; followed by 1G. $^1$H NMR (400 MHz, $CD_3OD$) δ ppm 9.51 (s, 1H), 7.96 (d, J=2.2 Hz, 1H), 7.67 (dd, J=8.8, 2.2 Hz, 1H), 7.58 (d, J=8.8 Hz, 2H), 7.48-7.54 (m, 1H), 7.41-7.48 (m, 2H), 7.13 (d, J=15.4 Hz, 1H), 6.74 (d, J=15.9 Hz, 1H), 5.02 (dd, J=10.4, 6.0 Hz, 1H), 3.75 (s, 3H), 2.43-2.56 (m, 1H), 2.16-2.29 (m, 1H), 1.83-1.97 (m, 1H), 1.57 (d, J=9.3 Hz, 1H), 1.21-1.36 (m, 2H), 1.18 (d, J=7.1 Hz, 3H), 1.05-1.18 (m, 1H). MS (ESI) m/z: 590.3 $(M+H)^+$. Analytical HPLC: RT=4.16 min. (Method B).

Example 117

{(S)-14-[(E)-3-(5-Chloro-2-tetrazol-1-yl-phenyl)-acryloylamino]-11-methyl-9-oxo-8,11,16,18-tetraaza-tricyclo[13.2.1.0^{2,7}]octadeca-1(17),2,4,6,15(18)-pentaen-5-yl}-carbamic Acid methyl ester, 2 TFA Salt

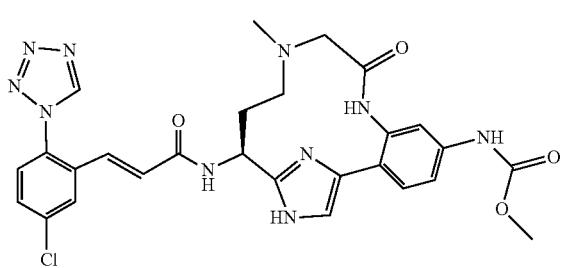 [SMILES: COC(=O)Nc1ccc2c(c1)NC(=O)CN(C)CC[C@H](NC(=O)/C=C/c1cc(Cl)ccc1-n1cnnn1)c1nc-2c[nH]1]

117A. {3-Bromo-4-[2-((S)-1-tert-butoxycarbonylamino-3-oxo-propyl)-1-(2-trimethylsilanyl-ethoxymethyl)-1H-imidazol-4-yl]-phenyl}-carbamic acid methyl ester: To a solution of 10B(100 mg, 0.168 mmol) in acetonitrile (4.00 ml) were added water (1 ml), sodium periodate (144 mg, 0.672 mmol) and osmium tetroxide (0.105 ml, 8.39 μmol) at 0° C. The reaction mixture was stirred and allowed to warm slowly to rt, then diluted with ethyl acetate, and washed with water and brine. The organic phase was dried over magnesium sulfate, filtered and concentrated to a brown solid. Normal phase chromatography gave 117A as a brown solid (50 mg, 49.8% yield). MS (ESI) m/z: 631.5 $(M+H)^+$.

117B. ({(S)-3-[4-(2-Bromo-4-methoxycarbonylamino-phenyl)-1-(2-trimethylsilanyl-ethoxymethyl)-1H-imidazol-2-yl]-3-tert-butoxycarbonylamino-propyl}-methyl-amino)-acetic acid: To a solution of 117A (300 mg, 0.502 mmol) in DCE (6 mL) was added 2-(methylamino)acetic acid (67.1 mg, 0.753 mmol) and 1 drop of acetic acid (0.01 mL, 0.175 mmol). The reaction mixture was sonicated and stirred at room temperature for 2 hours. Sodium triacetoxyborohydride (319 mg, 1.506 mmol) was added and the reaction was stirred at room temperature for 3 days. The reaction was quenched with saturated aqueous sodium bicarbonate. The aqueous layer was extracted with ethyl acetate. The combined organic layers were washed with brine and dried over magnesium sulfate, filtered and concentrated to yield 117B. MS (ESI) m/z: 672.3 $(M+H)^+$.

117C. Example 117 was prepared following the procedure described in step 10C alternate), by replacing 10B with 117B; followed by steps 20F; 10H; and 1G. $^1$H NMR (400 MHz, MeOD-$d_4$) δ ppm 9.52 (s, 1H) 7.97 (d, J=2.2 Hz, 1H) 7.67 (dd, J=8.53, 2.2 Hz, 1H) 7.59 (m, 2H) 7.55 (s, 1H) 7.46 (s, 1H) 7.37 (dd, J=8.52, 2.2 Hz, 1H) 7.19 (d, J=15.68 Hz, 1H) 6.69 (d, J=15.41 Hz, 1H) 5.26 (br s, 1H) 3.93 (m, 1H) 3.75 (m, 4H) 3.27 (m, 1H) 3.00 (m, 1H) 2.82 (s, 3H) 2.44 (br s, 1H) 2.37 (br s, 1H). MS (ESI) m/z: 591.3 $(M+H)^+$. Analytical HPLC: RT=4.48 min.

Example 118

{(10S,14S)-14-[(E)-3-(5-Chloro-2-tetrazol-1-yl-phenyl)-acryloylamino]-10-methyl-9-oxo-8,16,18-triaza-tricyclo[13.2.1.02,7]octadeca-1(17),2,4,6,15(18)-pentaen-5-yl}-carbamic Acid methyl ester 1 TFA Salt

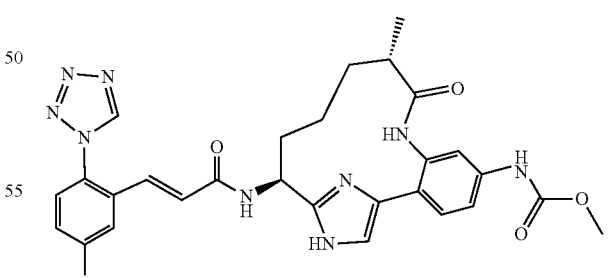

Example 118 was prepared following the procedures described in step 1F, by replacing 1D with 116H; followed by step 1G. $^1$H NMR (400 MHz, $CD_3OD$) δ ppm 9.51 (s, 1H), 7.97 (d, J=2.2 Hz, 1H), 7.68 (dd, 2.5 Hz, 1H), 7.56-7.62 (m, 2H), 7.50 (d, J=8.2 Hz, 1H), 7.45 (s, 1H), 7.35-7.42 (m, 1H), 7.14 (d, J=15.4 Hz, 1H), 6.75 (d, J=15.4 Hz, 1H), 5.14 (dd, J=9.9, 6.6 Hz, 1H), 3.76 (s, 3H), 2.68-2.80 (m, 1H), 2.12-2.26 (m, 1H), 1.90-2.05 (m, 1H), 1.51-1.72 (m, 3H), 1.03 (d, J=7.1 Hz, 3H), 0.70 (br. s., 1H). MS (ESI) m/z: 590.3 (M+H)⁺. Analytical HPLC: RT=4.08 min. (Method B).

Example 119

{(S)-14-[(E)-3-(5-Chloro-2-tetrazol-1-yl-phenyl)-acryloylamino]-12-oxo-8,11,16,18-tetraaza-tricyclo[13.2.1.0²,⁷]octadeca-1(17),2,4,6,15(18)-pentaen-5-yl}-carbamic Acid methyl ester, 2 TFA Salt

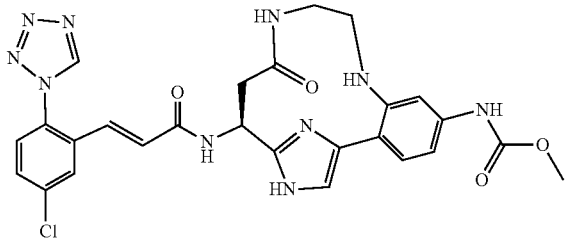 [SMILES: COC(=O)Nc1ccc2c(c1)NCCNC(=O)C[C@H](NC(=O)/C=C/c1cc(Cl)ccc1-n1cnnn1)c1nc-2c[nH]1]

Example 119 was prepared following the procedures described in Example 79 by replacing benzyl 3-aminopropylcarbamate HCl salt with benzyl 2-aminoethylcarbamate in 79A. ¹H NMR (400 MHz, CD₃OD) δ ppm 9.52 (1H, s), 7.99 (1H, d, J=2.26 Hz), 7.92 (1H, d, J=1.51 Hz), 7.75 (1H, d, J=8.53 Hz), 7.67 (1H, dd, J=8.53, 2.26 Hz), 7.55-7.61 (2H, m), 7.34 (1H, dd, J=8.53, 2.01 Hz), 7.21 (1H, d, J=15.81 Hz), 6.76 (1H, d, J=15.56 Hz), 5.48-5.64 (1H, m), 3.78-3.93 (1H, m), 3.77 (3H, s), 3.33-3.72 (3H, m), 2.81 (2H, d, J=7.03 Hz). LC-MS (ESI) m/z: 577.2 (M+H)⁺. Analytical HPLC: RT=4.621 min.

Example 120

(E)-N-((E)-(S)-5-Amino-9-oxo-8,17,19-triaza-tricyclo[14.2.1.0²,⁷]nonadeca-1(18),2,4,6,12,16(19)-hexaen-15-yl)-3-(5-chloro-2-tetrazol-1-yl-phenyl)-acrylamide, 2 TFA Salt

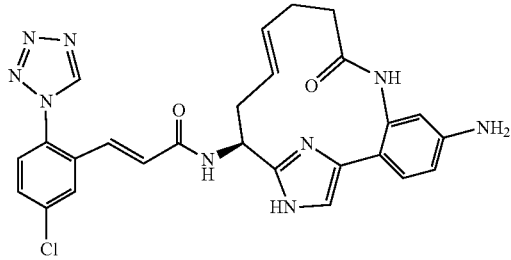 [SMILES: Nc1ccc2c(c1)NC(=O)CC/C=C/C[C@H](NC(=O)/C=C/c1cc(Cl)ccc1-n1cnnn1)c1nc-2c[nH]1]

Example 120 was prepared following the procedure described in step 10H, by replacing 10G with 39A and by running the reaction at 75° C. for 20 h; followed by step 1G. ¹H NMR (400 MHz, CD₃OD) δ ppm 9.52 (s, 1H), 7.97 (d, J=2.2 Hz, 1H), 7.68 (dd, J=8.8, 2.2 Hz, 1H), 7.58 (d, J=8.8 Hz, 1H), 7.31 (s, 1H), 7.24 (d, J=8.2 Hz, 1H), 7.14 (d, J=15.4 Hz, 1H), 6.71-6.80 (m, 3H), 5.50-5.60 (m, 1H), 5.35-5.44 (m, 1H), 5.08 (dd, J=9.9, 4.9 Hz, 1H), 2.74-2.83 (m, 1H), 2.31-2.61 (m, 5H). MS (ESI) m/z: 530.2 (M+H)⁺. Analytical HPLC: RT=4.24 min.

Example 121

(E)-N-((E)-(S)-18-Chloro-9-oxo-10-oxa-8,17,19-triaza-tricyclo[14.2.1.0²,⁷]nonadeca-1(18),2,4,6,12,16(19)-hexaen-15-yl)-3-(5-chloro-2-tetrazol-1-yl-phenyl)-acrylamide, 1 TFA Salt

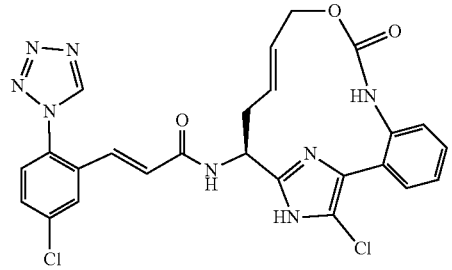 [SMILES: O=C(/C=C/c1cc(Cl)ccc1-n1cnnn1)N[C@H]1C/C=C/COC(=O)Nc2ccccc2-c2nc1[nH]c2Cl]

Example 121 was prepared following the procedure described in 17A, by replacing 16A with Example 87. ¹H NMR (500 MHz, CD₃OD) δ ppm 2.48-2.60 (m, 1H), 2.81-2.93 (m, 1H), 4.37 (br. s., 2H), 5.05 (dd, J=10.5, 5.0 Hz, 1H), 5.60-5.73 (m, 1H), 5.76-5.89 (m, 1H), 6.77 (d, J=15.7 Hz, 1H), 7.16 (d, J=15.4 Hz, 1H), 7.24 (d, J=8.0 Hz, 1H), 7.40 (td, J=7.4, 1.2 Hz, 1H), 7.49 (td, J=7.8, 1.2 Hz, 1H), 7.52-7.56 (m, 1H), 7.59 (d, J=8.5 Hz, 1H), 7.68 (dd, J=8.5, 2.2 Hz, 1H), 7.99 (d, J=1.9 Hz, 1H), 9.52 (s, 1H) MS (ESI) m/z: 551.2 (M+H)⁺. Analytical HPLC: RT=7.25 min.

Example 122

(E)-3-(5-Chloro-2-tetrazol-1-yl-phenyl)-N—((S)-9-oxo-19-oxa-8,17,18-triaza-tricyclo[14.2.1.02,7]nonadeca-1(18),2,4,6,12,16-hexaen-15-yl)-acrylamide, and (Z)-3-(5-Chloro-2-tetrazol-1-yl-phenyl)-N—((S)-9-oxo-19-oxa-8,17,18-triaza-tricyclo[14.2.1.02,7]nonadeca-1(18),2,4,6,12,16-hexaen-15-yl)-acrylamide

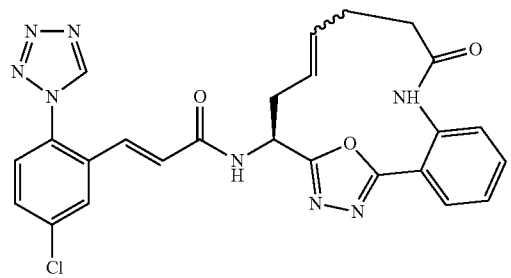 [SMILES: O=C(/C=C/c1cc(Cl)ccc1-n1cnnn1)N[C@H]1CC=CCCC(=O)Nc2ccccc2-c2nnc1o2]

122A. (S)-tert-Butyl 1-(2-(2-nitrobenzoyl)hydrazinyl)-1-oxopent-4-en-2-ylcarbamate: A mixture of [(S)-2-(tert-butoxycarbonylamino)pent-4-enoic acid (0.500 g, 2.323 mmol), HATU (1.060 g, 2.79 mmol), and DIPEA (1.623 mL, 9.29 mmol) in DCM (15 mL) was stirred at rt under nitrogen for 3 d. Reaction mixture was diluted with additional DCM, then washed with water, 5% aq. citric acid, sat'd aq. NaHCO₃ and brine, then dried over anhydrous Mg₂SO₄, filtered and evaporated. Residue was purified by normal phase chromatography to provide the acylhydrazide (0.7 g 79.6.0% yield). MS (ESI) m/z: 379.3 (M+H)⁺; 323.3 (M+H-tBu)⁺; 279.3 (M+H-Boc)⁺.

122B. (S)-tert-Butyl 1-(5-(2-nitrophenyl)-1,3,4-oxadiazol-2-yl)but-3-enylcarbamate: Into a 150 mL pressure vessel was charged a solution of 122A (0.57 g, 1.506 mmol) in anhydrous THF (30 mL), and Burgess reagent (1.077 g, 4.52 mmol) was added. The vessel was sealed under Ar, and the mixture was heated in a 75° C. oil bath with stirring behind a blast shield for 2 hrs. Reaction was cooled to room temperature, vented and then left standing at room temperature overnight. Reaction mixture was transferred to a round bottom flask with the aid of a little MeOH and evaporated to dryness. Residue was purified by silica gel chromatography to provide the oxadiazole product (0.327 g, 0.907 mmol, 60.2% yield) MS (ESI) m/z 383.3 (M+Na)$^+$305.3 (M+H-tBu)$^+$.

122C. (S)-tert-Butyl 1-(5-(2-aminophenyl)-1,3,4-oxadiazol-2-yl)but-3-enylcarbamate: 122B (0.325 g, 0.902 mmol) was dissolved in ethanol (4.5 mL) and iron powder (1.007 g, 18.04 mmol) was added. The mixture was stirred at room temperature for 1-2 min then 0.1 M HCl (4.51 mL, 0.451 mmol) was added, and the reaction was heated with stirring under nitrogen in a 50° C. oil bath for 1.5 h. Reaction was cooled to room temperature and then filtered twice through a pad of CELITE® and solids washed with water, EtOH and EtOAc then discarded. Filtrate was evaporated and remaining aqueous was diluted with NaHCO$_3$ (to pH 8), and extracted 3× with EtOAc. Combined extracts were washed with saturated aq. NaHCO$_3$ solution and brine, dried over anhydrous Na$_2$SO$_4$, filtered and evaporated to provide the amine as a white crystalline solid, (0.216 g, 0.654 mmol, 72.5% yield). MS (ESI) m/z: 331.4 (M+H)$^+$; 275.3 (M+H-tBu)$^+$; 231.3 (M+H-Boc)$^+$.

122D. (S)-tert-Butyl 1-(5-(2-pent-4-enamidophenyl)-1,3,4-oxadiazol-2-yl)but-3-enylcarbamate: 122C was dissolved in DCM (3.5 mL) and pyridine (0.105 mL, 1.302 mmol) was added. The solution was cooled in an ice/salt water bath to 0° C., then 4-pentenoyl chloride (0.072 mL, 0.651 mmol) was added dropwise with stirring under nitrogen. The resulting mixture was stirred at 0-5° C. for 1 h then allowed to warm to room temperature. After 2h, the reaction was diluted with EtOAc and washed with water, 1M HCl, saturated aq. NaHCO$_3$ and brine, then dried over anhydrous Na$_2$SO$_4$, filtered and evaporated. Residue was purified by silica gel chromatography to provide the amide (0.242 g, 0.587 mmol, 90% yield). MS (ESI) m/z: 413.4 (M+H)$^+$; 357.3 (M+H-tBu)$^+$; 313,4 (M+H-Boc)$^+$.

122E. ((E)-(S)-9-Oxo-19-oxa-8,17,18-triaza-tricyclo[14.2.1.0$^{2,7}$]nonadeca-1(18),2,4,6,12,16-hexaen-15-yl)-carbamic acid tert-butyl ester; and ((Z)-(S)-9-Oxo-19-oxa-8,17,18-triaza-tricyclo[14.2.1.0$^{2,7}$]nonadeca-1(18),2,4,6,12,16-hexaen-15-yl)-carbamic acid tert-butyl ester: 122D (135 mg, 0.327 mmol) was divided between five-20 mL microwave vials. The vials were then flushed with argon for 10-15 min followed by addition of anhydrous DCM (4.8 mM) and Grubbs (II) (36 mol %). All operations were carried out under argon and the fully charged vials were flushed for an additional few minutes with argon, then capped, sealed, and heated for 90 min at 75° C. in the microwave then left standing overnight. Contents of the five vials were combined and concentrated to remove DCM, redissolved in MeOH, filtered and purified by reverse phase HPLC to provide the macrocyclic alkene as a mixture of trans/cis isomers (34 mg, 27%). MS (ESI) m/z: 385.2 (M+H)$^+$; 329.1 (M+H-tBu)$^+$.

122E. Example 122: 122E (34 mg, 0.088 mmol) was dissolved in DCM (2 mL) and TFA (0.5 mL, 6.49 mmol) was added. The resulting mixture was stirred at room temperature under N$_2$ for ~5 h, then stripped to dryness. Residue was taken up in MeOH and stripped (2×) then dried on vacuum pump. The crude trifluoroacetic acid salt of the amine (MS (ESI) m/z: 285.2 (M+H)$^+$; 33 mg, 0.116 mmol) was dissolved in DMF (1 mL) and (E)-2,5-dioxopyrrolidin-1-yl 3-(5-chloro-2-(1H-tetrazol-1-yl)phenyl)acrylate (46 mg, 0.132 mmol) and DIPEA (0.1 mL, 0.573 mmol) were added. The resulting dark solution was stirred under a blanket of argon overnight. Reaction mixture was diluted with water and extracted 3× with EtOAc. Combined extracts were washed with 5% aq. citric acid soln, saturated aq. NaHCO$_3$ soln and brine, then dried over anhydrous sodium sulfate, filtered and evaporated. Residue was suspended in MeOH, sonicated and filtered. Solid was dissolved in a 1:1 mixture of DMSO/MeOH, filtered and purified by reverse phase HPLC to provide the title compound (14 mg, 23%). MS (ESI) m/z: 517.3 (M+H)$^+$ as an ~5:1 mixture of the trans/cis double bond isomers as determined by nmr and HPLC. Analytical HPLC: major trans isomer: RT=7.53 min; minor isomer RT=7.41.

Example 123

{(S)-15-[(E)-3-(5-Chloro-2-tetrazol-1-yl-phenyl)-acryloylamino]-9-oxo-8,13,17,19-tetraaza-tricyclo[14.2.1.0$^{2,7}$]nonadeca-1(18),2,4,6,16(19)-pentaen-5-yl}-carbamic Acid methyl ester, 2 TFA Salt

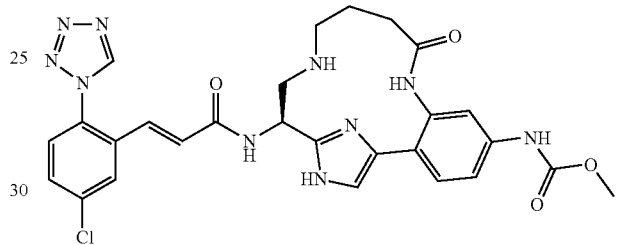

Example 123 was prepared following the procedures described in step 117B, by replacing 117A with 4-oxobutanoic acid and by replacing 2-(methylamino) acetic acid with 20B; followed by steps 20D; 10C (alternate); 20F; 2G; 1G; and 10H. $^1$H NMR (400 MHz, MeOD-d$_4$) δ ppm 9.54 (s, 1H), 7.99 (d, J=2.2 Hz, 1H), 7.69 (dd, J=8.8, 2.2 Hz, 1H), 7.60 (d, J=8.8 Hz, 1H), 7.48-7.56 (m, 2H), 7.44 (s, 1H), 7.37-7.43 (m, 1H), 7.24 (d, J=15.9 Hz, 1H), 6.69 (d, J=15.4 Hz, 1H), 5.52 (dd, J=8.2, 3.8 Hz, 1H), 3.74 (s, 3H), 3.42-3.61 (m, 2H), 3.24-3.29 (m, 2H), 2.50-2.78 (m, 2H), 2.02-2.33 (m, 2H). MS (ESI) m/z: 591.3 (M+H)$^+$. Analytical HPLC: RT=3.88 min. (Method B).

Example 124

(E)-3-(5-Chloro-2-tetrazol-1-yl-phenyl)-N-((E)-(S)-5-fluoro-9-oxo-8,17,19-triaza-tricyclo[14.2.1.0$^{2,7}$]nonadeca-1(18),2,4,6,12,16(19)-hexaen-15-yl)-acrylamide, 1 TFA Salt

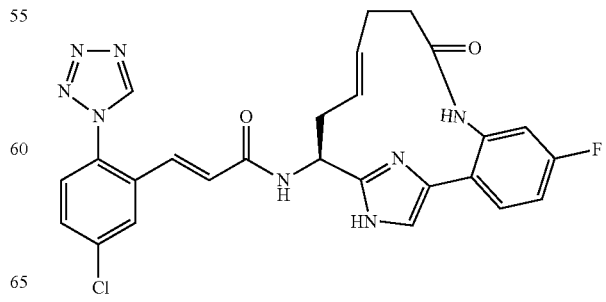

Example 124 was prepared following the procedures described in step 2A, by replacing 2-bromo-1-(2-bromophenyl)ethanone with Intermediate 17; followed by steps 2B; 2C; 10C; 10D, by replacing with but-3-enoic acid with pent-4-enoic acid; 2E; 10H; and 15D. $^1$H NMR (500 MHz, CD$_3$OD) δ ppm 2.33-2.62 (m, 5H), 2.75-2.84 (m, 1H), 5.05-5.12 (m, 1H), 5.37-5.47 (m, 1H), 5.52-5.62 (m, 1H), 6.76 (d, J=15.7 Hz, 1H), 7.11-7.21 (m, 3H), 7.43 (br. s., 1H), 7.50-7.56 (m, 1H), 7.56-7.61 (m, 1H), 7.66-7.71 (m, 1H), 7.97 (br. s., 1H), 9.51 (br. s., 1H). $^{19}$F NMR (471 MHz, CD$_3$OD) δ ppm −111.20. MS (ESI) m/z: 533.1 (M+H)$^+$. Analytical HPLC: RT=5.03 min.

Example 125

{(Z)-(S)-15-[(E)-3-(5-Chloro-2-tetrazol-1-yl-phenyl)-acryloylamino]-9-oxo-8,17,19-triaza-tricyclo[14.2.1.0$^{2,7}$]nonadeca-1(18),2,4,6,12,16(19)-hexaen-5-yl}-carbamic Acid methyl ester, 1 TFA Salt

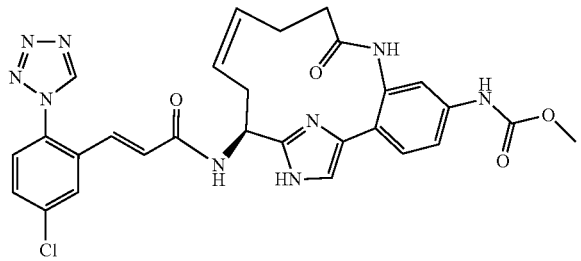 [SMILES: COC(=O)Nc1ccc2c(c1)NC(=O)CC/C=C\C[C@H](NC(=O)/C=C/c1cc(Cl)ccc1-n1cnnn1)c1nc-2c[nH]1]

Example 125 was prepared following the procedures described in step 10D, by replacing but-3-enoic acid with pent-4-enoic acid; followed by steps 2F; 10H, by running the reaction at 75° C.; and 1G. $^1$H NMR (500 MHz, 50° C., CD$_3$OD) δ ppm 9.46 (s, 1H), 7.95 (d, J=2.2 Hz, 1H), 7.64-7.68 (m, 2H), 7.57 (d, J=8.2 Hz, 1H), 7.41 (d, J=8.8 Hz, 1H), 7.35 (dd, J=8.3, 2.2 Hz, 1H), 7.31 (s, 1H), 7.18 (d, J=15.4 Hz, 1H), 6.70 (d, J=15.4 Hz, 1H), 5.57-5.64 (m, 1H), 5.42-5.50 (m, 1H), 5.16-5.22 (m, 1H), 3.76 (s, 3H), 2.87-2.97 (m, 1H), 2.68-2.77 (m, 1H), 2.47-2.64 (m, 2H), 2.31-2.43 (m, 2H). MS (ESI) m/z: 588.2 (M+H)$^+$. Analytical HPLC: RT=4.86 min.

Example 126

(E)-N-((E)-(S)-18-Chloro-5-fluoro-9-oxo-8,17,19-triaza-tricyclo[14.2.1.0$^{2,7}$]nonadeca-1(18),2,4,6,12,16(19)-hexaen-15-yl)-3-(5-chloro-2-tetrazol-1-yl-phenyl)-acrylamide, 1 TFA Salt

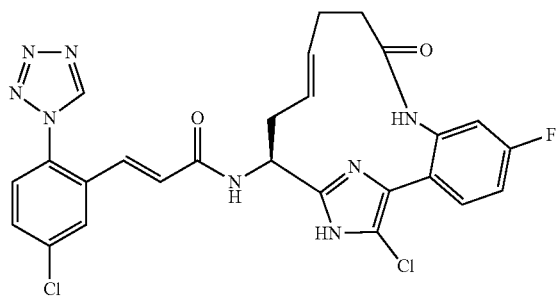 [SMILES: O=C(/C=C/c1cc(Cl)ccc1-n1cnnn1)N[C@H]1C/C=C/CCC(=O)Nc2cc(F)ccc2-c2nc1[nH]c2Cl]

Example 126 was prepared following the procedure described in 17A, by replacing 16A with Example 124. $^1$H NMR (500 MHz, CD$_3$OD) δ ppm 2.31-2.50 (m, 5H), 2.66-2.74 (m, 1H), 4.96 (dd, J=10.5, 4.4 Hz, 1H), 5.30-5.40 (m, 1H), 5.50-5.59 (m, 1H), 6.77 (d, J=15.4 Hz, 1H), 7.11-7.18 (m, 3H), 7.48-7.53 (m, 1H), 7.57 (d, J=8.5 Hz, 1H), 7.67 (dd, J=8.5, 2.2 Hz, 1H), 7.98 (d, J=2.2 Hz, 1H), 9.51 (s, 1H). $^{19}$F NMR (471 MHz, CD$_3$OD) δ ppm −112.21. MS (ESI) m/z: 567.2 (M+H)$^+$. Analytical HPLC: RT=7.41 min.

Example 127

{(S)-15-[(E)-3-(5-Chloro-2-tetrazol-1-yl-phenyl)-acryloylamino]-12-methyl-9-oxo-8,12,17,19-tetraaza-tricyclo[14.2.1.0$^{2,7}$]nonadeca-1(18),2,4,6,16(19)-pentaen-5-yl}-carbamic Acid methyl ester, 2 TFA Salt

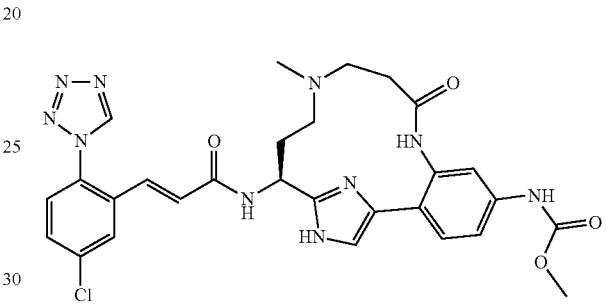

127A. [4-[2-((S)-1-tert-Butoxycarbonylamino-but-3-enyl)-1-(2-trimethylsilanyl-ethoxymethyl)-1H-imidazol-4-yl]-3-(2,2,2-trifluoro-acetylamino)-phenyl]-carbamic acid methyl ester: To a suspension of 10C (200 mg, 0.376 mmol) in DCM (3 ml) at 0° C. was added triethylamine (0.157 ml, 1.128 mmol), followed by trifluoroacetic anhydride (0.064 ml, 0.451 mmol). The reaction mixture was allowed to stir at rt for 1 h, then diluted with EtOAc, washed with 1 N HCl and brine, and dried over magnesium sulfate. The solvent was removed under reduced pressure to give 127A (271 mg, 0.432 mmol, 115% yield) as a yellow foam. MS (EST) m/z: 628.5 (M+H)$^+$.

127B. [4-[2-((S)-1-tert-Butoxycarbonylamino-3-oxo-propyl)-1-(2-trimethylsilanyl-ethoxymethyl)-1H-imidazol-4-yl]-3-(2,2,2-trifluoro-acetylamino)-phenyl]-carbamic acid methyl ester: This compound was prepared following the procedures described in 117A, by replacing 10B with 127A. MS (ESI) m/z: 630.4 (M+H)$^+$.

127C. 3-({(S)-3-tert-Butoxycarbonylamino-3-[4-[4-methoxycarbonylamino-2-(2,2,2-trifluoro-acetylamino)-phenyl]-1-(2-trimethylsilanyl-ethoxymethyl)-1H-imidazol-2-yl]-propyl}-methyl-amino)-propionic acid: To a solution of 127B (97 mg, 0.154 mmol) in MeOH (2 ml) was added 3-(methylamino)propanoic acid (23.83 mg, 0.231 mmol) and 1 drop acetic acid, then sodium cyanoborohydride (4.84 mg, 0.077 mmol) was added and the reaction was stirred at rt overnight. The reaction was quenched with sat. sodium bicarbonate, extracted with EtOAc and washed the organic layer with brine. The organic layer was dried over MgSO$_4$, filtered and concentrated to give 127C (86 mg, 0.120 mmol, 78% yield) as a light orange solid. MS (ESI) m/z: 717.5 (M+H)$^+$.

127D. [(S)-5-Methoxycarbonylamino-11-methyl-9-oxo-16-(2-trimethylsilanyl-ethoxymethyl)-8,11,16,18-tetraaza-tricyclo[13.2.1.0$^{2,7}$]octadeca-1(17),2,4,6,15(18)-pentaen- 14-yl]-carbamic acid tert-butyl ester: To a mixture of 127C (86 mg, 0.120 mmol) in methanol (3 mL) was added potassium carbonate (116 mg, 0.840 mmol). The resulting mixture was stirred at rt for 1 h, then stored at −10° C. over the weekend. Water (0.150 mL) and 1 N aq. sodium hydroxide (0.4 mL, 0.400 mmol) were added and the reaction was heated to 50° C. for four hours. Purification by reverse phase chromatography afforded 127D (41 mg, 0.066 mmol, 55.0% yield) as a dark orange solid. MS (ESI) m/z: 621.2 (M+H)$^+$.

127E. Example 127 was prepared following the procedures described in step 23E, by replacing 23D with 127D; followed by steps 10H; and 15D. $^1$H NMR (500 MHz, CD$_3$OD) δ ppm 9.52 (1H, s), 7.96 (1H, d, J=2.5 Hz), 7.66 (1H, dd, J=8.5, 2.2 Hz), 7.58 (2H, d, J=8.5 Hz), 7.53 (1H, d, J=8.5 Hz), 7.48 (1H, s), 7.33 (1H, dd, J=8.5, 2.2 Hz), 7.19 (1H, d, J=15.7 Hz), 6.69 (1H, d, J=15.7 Hz), 5.40 (1H, dd, J=7.4, 3.9 Hz), 3.71-3.78 (3H, m), 3.60 (1H, br. s.), 3.39-3.49 (1H, m), 3.01 (3H, s), 2.84-2.92 (2H, m), 2.38-2.46 (2H, m). MS (ESI) m/z: 605.4 (M+H)$^+$. Analytical HPLC: RT=4.55 min.

Example 128

{(E)-15-[(E)-3-(5-Chloro-2-tetrazol-1-yl-phenyl)-acryloyl amino]-17-fluoro-9-oxo-8-aza-tricyclo[14.3.1.0$^{2,7}$]icosa-1(20),2,4,6,12,16,18-heptaen-5-yl}-carbamic Acid methyl ester

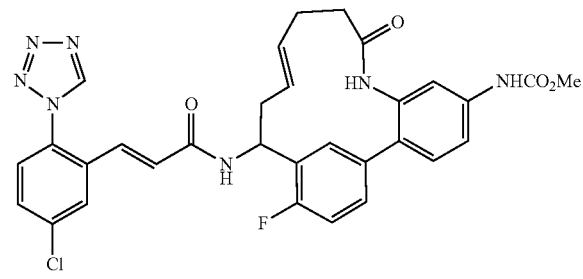

Example 128 was prepared following the procedures described in step 93A, by replacing 3-bromobenzaldehyde with 3-bromo-6-fluorobenzaldehyde; followed by steps 88C; 88E; 88F, by replacing methanol with acetone and by replacing solid ammonium chloride with a saturated aqueous solution of ammonium chloride; 88G, by running the reaction without pTsOH; 3C; and 1G. $^1$H NMR (400 MHz, MeOD/DMSO-d$_6$) δ ppm 9.38 (s, 1H), 8.60 (s, 1H), 7.01 (d, J=2.0 Hz, 1H), 6.72-6.63 (dd, J=2.0 & 8.3 Hz, 3H), 6.63 (dd, J=2.0 & 8.2 Hz, 1H), 6.32-6.20m, 5H), 6.09-6.05 (d, J=15.4 Hz, 1H), 5.94-5.91 (d, J=15.6 Hz, 1H), 4.58 (m, 1H), 4.47 (m, 2H), 2.80 (s, 3H), 1.67 (m, 1H), 1.51-1.46 (m, 4H)ppm. MS (ESI) m/z: 616.0 (M+H)$^+$. Analytical HPLC: RT=8.55 min.

Example 129

{(E)-(S)-15-[(4-Aminomethyl-cyclohexanecarbonyl)-amino]-10,10-difluoro-9-oxo-8,17,19-triaza-tricyclo[14.2.1.0$^{2,7}$]nonadeca-1(18),2,4,6,12,16(19)-hexaen-5-yl}-carbamic Acid methyl ester, 2 TFA Salt

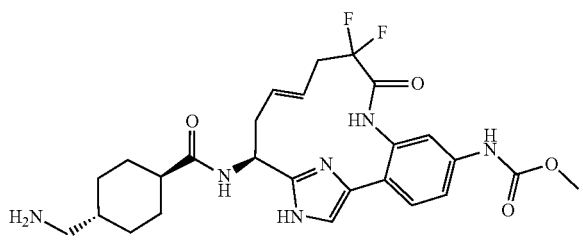

Example 129 was prepared following the procedures described in step 10D, by replacing but-3-enoic acid with 2,2-difluoropent-4-enoic acid; followed by steps 2E; 10H; 3B; and 3C. $^1$H NMR (400 MHz, CD$_3$OD) δ ppm 9.67 (s, 1H), 7.58 (d, J=2.2 Hz, 1H), 7.53 (dd, J=8.2, 2.2 Hz, 1H), 7.38-7.46 (m, 2H), 5.66-5.80 (m, 1H), 5.20-5.31 (m, 1H), 4.99 (dd, J=11.0, 4.4 Hz, 1H), 3.76 (s, 3H), 2.73-3.00 (m, 5H), 2.48-2.61 (m, 1H), 2.26-2.39 (m, 1H), 1.83-2.00 (m, 3H), 1.54-1.69 (m, 1H), 1.38-1.54 (m, 2H), 1.01-1.19 (m, 2H). MS (ESI) m/z: 531.3 (M+H)$^+$. Analytical HPLC: RT=1.73 min. (Method B).

Example 130

(E)-3-(5-Chloro-2-tetrazol-1-yl-phenyl)-N—((S)-5-fluoro-9-oxo-8,17,19-triaza-tricyclo[14.2.1.0$^{2,7}$]nonadeca-1(18),2,4,6,16(19)-pentaen-15-yl)-acrylamide, 1 TFA Salt

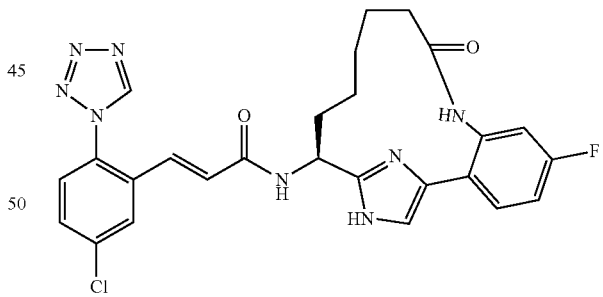

Example 130 was prepared following the procedures step 2A, by replacing 2-bromo-1-(2-bromophenyl)ethanone with Intermediate 17; followed by steps 2B; 2C; 10C; 10D, by replacing with but-3-enoic acid with pent-4-enoic acid; 2F; 10G, by replacing the hydrogen balloon with hydrogen (55 psi); 10H; and 15D. $^1$H NMR (500 MHz, CD$_3$OD) δ ppm 0.81-0.91 (m, 1H), 0.94-1.05 (m, 1H), 1.41-1.60 (m, 2H), 1.61-1.78 (m, 2H), 1.99-2.09 (m, 1H), 2.16-2.24 (m, 1H), 2.30-2.42 (m, 2H), 5.03 (dd, J=10.2, 4.7 Hz, 1H), 6.74 (d, J=15.7 Hz, 1H), 7.10-7.19 (m, 2H), 7.22 (dd, J=9.5, 2.3 Hz, 1H), 7.48 (s, 1H), 7.55-7.62 (m, 2H), 7.68 (dd, J=8.5, 2.2 Hz, 1H), 7.97 (d, J=2.2 Hz, 1H), 9.51 (s, 1H). $^{19}$F NMR (471

MHz, CD$_3$OD) δ ppm −111.56. MS (ESI) m/z: 535.2 (M+H)$^+$. Analytical HPLC: RT=5.18 min.

Example 131

{15-[(E)-3-(5-Chloro-2-tetrazol-1-yl-phenyl)-acryloylamino]-17-fluoro-9-oxo-8-aza-tricyclo[14.3.1.0$^{2,7}$]icosa-1(20),2,4,6,16,18-hexaen-5-yl}-carbamic Acid methyl ester

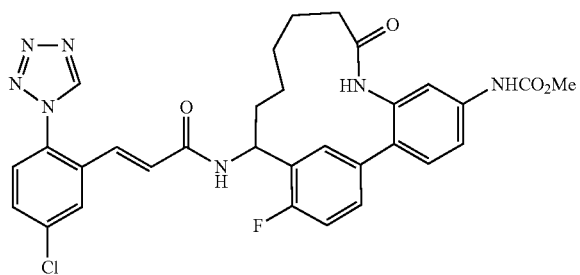

Example 131 was prepared following the procedures described in step 93A, by replacing 3-bromobenzaldehyde with 3-bromo-6-fluorobenzaldehyde; followed by steps 88C; 88E; 88F, by replacing methanol with acetone and by replacing solid ammonium chloride with a saturated aqueous solution of ammonium chloride; 88G, by running the reaction without pTsOH; 2G, by replacing the hydrogen balloon with hydrogen (55 psi); 3C, replacing TFA and DCM with 4M HCl in dioxane; and 1G. $^1$H NMR (400 MHz, DMSO-d$_6$) δ ppm 9.83 (s, 1H), 9.76 (s, 1H), 9.20 (s, 1H), 8.77 (bs, 1H), 8.54 (d, 1H), 7.90 (s, 1H), 7.73-7.69 (m, 2H), 7.50-7.42 (m, 2H), 7.29-7.23 (m, 3H), 6.83 (s, 2H), 4.98 (m, 1H), 3.69 (s, 3H), 2.50-2.25 (m, 4H), 1.90 (m, 1H), 1.7 (m, 1H), 1.50-1.01 (m, 4H). MS (ESI) m/z: 618.1 (M+Na)$^+$. Analytical HPLC: RT=7.95 min.

Example 132

(E)-3-(5-Chloro-2-tetrazol-1-yl-phenyl)-N-((E)-(S)-5-fluoro-9-oxo-8,17-diaza-tricyclo[14.3.1.0$^{2,7}$]icosa-1(20),2(7),3,5,12,16,18-heptaen-15-yl)-acrylamide, 1 TFA Salt

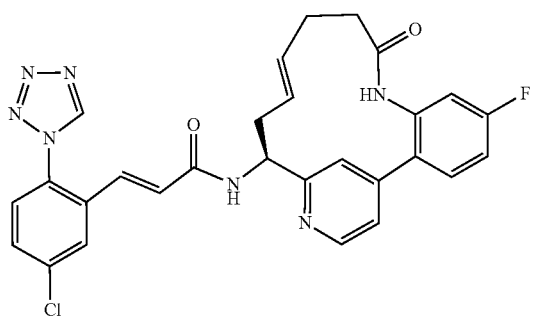 [SMILES: O=C(/C=C/c1cc(Cl)ccc1-n1cnnn1)N[C@H]1C/C=C/CCC(=O)Nc2cc(F)ccc2-c2ccnc1c2]

132A. 2-(5,5-Dimethyl-1,3,2-dioxaborinan-2-yl)-5-fluoro-phenylamine: This compound was prepared following the procedure described in Intermediate 12, by replacing 2-bromo-5-nitroaniline with 2-bromo-5-fluoroaniline. MS (ESI) m/z: 224.3 (M+H)$^+$.

132B. 2-Methyl-propane-2-sulfinic acid {(S)-1-[4-(2-amino-4-fluoro-phenyl)-pyridin-2-yl]-but-3-enyl}-amide: A round bottom flask was charged with 88B (0.377 g, 1.314 mmol), 132A (0.586 g, 2.63 mmol), PdCl$_2$(dppf)-CH$_2$Cl$_2$Adduct (0.107 g, 0.131 mmol), and Potassium phosphate, tribasic (0.558 g, 2.63 mmol), then evacuated and flushed with Ar three times. DMSO (6.57 mL) and water (0.118 mL, 6.57 mmol) were added, and the reaction was once again evacuated and flushed with Ar three times. The reaction was heated at 90° C. for 2 hours, then left at room temperature overnight. The reaction was diluted with water and extracted three times with EtOAc. The combined organic layer was washed with water and brine, then dried over MgSO$_4$, filtered, and condensed to yield a brown residue. The crude residue was redissolved in MeOH, filtered through a small pad of CELITE® and purified by reverse phase chromatography. Fractions from main peak were neutralized with saturated NaHCO$_3$, partially condensed to remove the MeOH, then extracted three times with EtOAc. The organic layer was washed with brine, dried over anhydrous magnesium sulfate, filtered, and evaporated to yield an orange residue, 132B (0.280 g, 0.775 mmol, 58.9% yield). MS (ESI) 362.3 (M+H)$^+$.

132C. ((E)-(S)-5-Fluoro-9-oxo-8,17-diaza-tricyclo[14.3.1.0$^{2,7}$]icosa-1(20),2(7),3,5,12,16,18-heptaen-15-yl)-carbamic acid tert-butyl ester: This compound was prepared from 132B in four steps by cleavage of the t-butylsulfinamide and introduction of a Boc-protection group, reduction of the nitro to the corresponding aniline, coupling with 4-pentenoic acid and subsequent RCM of the resulting diene, following the procedures described for compounds 88D, 52D, 88E and 88G. MS (ESI) m/z: 412.3 (M+H)$^+$.

132D. Example 132 was prepared from 132C by removal of the Boc protecting group and coupling to Intermediate 1, following the procedures described in steps 3C and 1G. $^1$H NMR (400 MHz, DMSO-d$_6$) δ ppm 9.85 (1H, s) 9.46 (1H, s) 8.64 (1H, d, J=7.70 Hz) 8.61 (1H, d, J=4.95 Hz) 7.97 (1H, d, J=1.65 Hz) 7.69-7.76 (2H, m) 7.40 (1H, dd, J=7.97, 6.32 Hz) 7.28 (1H, d, J=4.95 Hz) 7.17-7.25 (2H, m) 7.06 (1H, d, J=15.39 Hz) 7.01 (1H, s) 6.81 (1H, d, J=15.39 Hz) 5.44 (1H, ddd, J=15.12, 7.42, 7.15 Hz) 5.22 (1H, ddd, J=15.53, 5.22, 5.08 Hz) 4.87-4.96 (1H, m) 2.19-2.40 (6H, m). MS (ESI) m/z: 544.3 (M+H)$^+$. Analytical HPLC: RT=6.18 min.

Example 133

(E)-3-(5-Chloro-2-tetrazol-1-yl-phenyl)-N—((S)-5-fluoro-9-oxo-8,17-diaza-tricyclo[14.3.1.0$^{2,7}$]icosa-1(20),2(7),3,5,16,18-hexaen-15-yl)-acrylamide, 1 TFA Salt

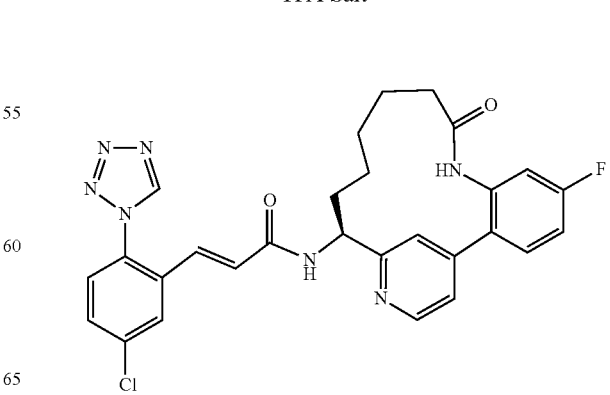

Example 133 was prepared from 132C by hydrogenation of the double bond, deprotection of the Boc-protecting group and coupling with Intermediate 1, following the procedures described in steps 2G, 3C and 1G. $^1$H NMR (400 MHz, DMSO-$d_6$) δ ppm 9.84 (1H, s) 9.50 (1H, s) 8.67 (1H, d, J=4.95 Hz) 8.62 (1H, d, J=7.70 Hz) 7.94 (1H, d, J=1.65 Hz) 7.69-7.77 (2H, m) 7.48 (1H, dd, J=9.07, 6.32 Hz) 7.33 (1H, dd, J=4.95, 1.65 Hz) 7.21-7.28 (2H, m) 7.15 (1H, s) 6.99 (1H, d, J=15.39 Hz) 6.79 (1H, d, J=15.94 Hz) 4.88 (1H, ddd, J=11.54, 7.42, 4.12 Hz) 2.21 (2H, t, J=5.77 Hz) 1.88 (1H, dd, J=13.19, 9.34 Hz) 1.71 (2H, t, J=12.09 Hz) 1.42 (1H, dd, J=13.74, 4.40 Hz) 1.32 (1H, br. s.) 1.11-1.26 (2H, m) 0.91 (1H, d, J=4.40 Hz). MS (ESI) m/z: 546.4 (M+H)$^+$. Analytical HPLC: RT=6.34 min.

Example 134

(E)-N—((S)-18-Chloro-5-fluoro-9-oxo-8,17,19-tri-aza-tricyclo[14.2.1.0$^{2,7}$]nonadeca-1(18),2,4,6,16(19)-pentaen-15-yl)-3-(5-chloro-2-tetrazol-1-yl-phenyl)-acrylamide, 1 TFA Salt

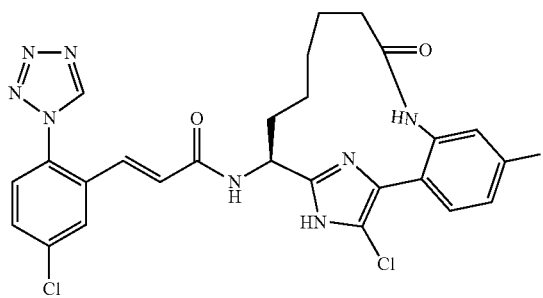

Example 134 was prepared following the procedure described in 17A, by replacing 16A with Example 130. $^1$H NMR (500 MHz, CD$_3$OD) δ ppm 0.81-0.94 (m, 1H), 1.04-1.21 (m, 1H), 1.34-1.54 (m, 2H), 1.63-1.72 (m, 2H), 1.90-2.01 (m, 1H), 2.04-2.15 (m, 1H), 2.28-2.38 (m, 2H), 4.91-4.95 (m, 1H), 6.74 (d, J=15.4 Hz, 1H), 7.10 (d, J=15.7 Hz, 1H), 7.13-7.20 (m, 2H), 7.52-7.58 (m, 2H), 7.64 (dd, J=8.5, 2.2 Hz, 1H), 7.93 (d, J=2.5 Hz, 1H), 9.49 (s, 1H). $^{19}$F NMR (471 MHz, CD$_3$OD) δ ppm −112.04. MS (ESI) m/z: 569.2 (M+H)$^+$. Analytical HPLC: RT=7.54 min.

Example 135

{(E)-(S)-14-[(E)-3-(5-Chloro-2-tetrazol-1-yl-phenyl)-acryloylamino]-8,16,18-triaza-tricyclo[13.2.1.0$^{2,7}$]octadeca-1(17),2,4,6,11,15(18)-hexaen-5-yl}-carbamic Acid methyl ester, 2 TFA Salt

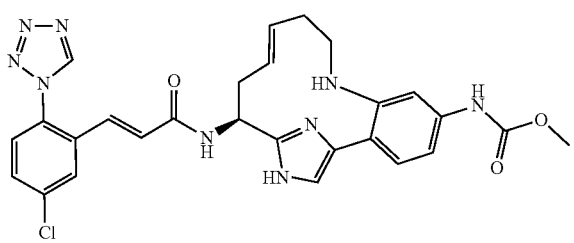 [SMILES: COC(=O)Nc1ccc2c(c1)NCC/C=C/C[C@H](NC(=O)/C=C/c1cc(Cl)ccc1-n1cnnn1)c1nc-2c[nH]1]

Example 135 was prepared following the procedures described in step 10C, by replacing ammonium hydroxide with but-3-enylamine and running the reaction at 90° C.; followed by steps 10E; 1F, by replacing ethanol with methanol and running the reaction at 75° C.; and 1G. $^1$H NMR (500 MHz, 50° C., CD$_3$OD) δ ppm 9.47 (s, 1H), 7.96 (d, J=1.6 Hz, 1H), 7.79 (s, 1H), 7.66 (dd, J=8.8, 2.2 Hz, 1H), 7.55-7.62 (m, 2H), 7.41 (s, 1H), 7.30 (dd, J=8.2, 2.2 Hz, 1H), 7.19 (d, J=15.4 Hz, 1H), 6.77 (d, J=15.9 Hz, 1H), 5.87-5.96 (m, 1H), 5.20-5.28 (m, 1H), 5.13 (ddd, J=15.3, 7.6, 7.4 Hz, 1H), 3.77 (s, 3H), 3.29-3.35 (m, 2H), 2.54-2.68 (m, 2H), 2.43-2.50 (m, 2H). MS (ESI) m/z: 560.2 (M+H)$^+$. Analytical HPLC: RT=5.53 min.

Example 136

[(E)-(S)-18-Chloro-15-(4-cyano-benzoylamino)-9-oxo-8,17,19-triaza-tricyclo[14.2.1.0$^{2,7}$]nonadeca-1(18),2,4,6,12,16(19)-hexaen-5-yl]-carbamic Acid methyl ester, 1 TFA Salt

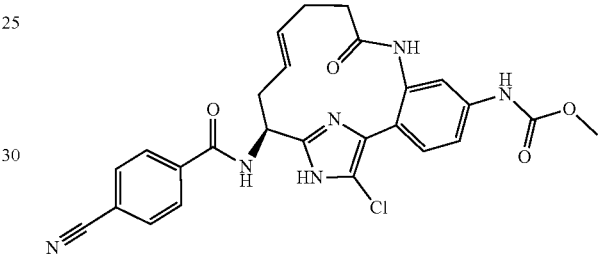

Example 136 was prepared following the procedure described in step 15D, by replacing 15C with 76B, by replacing Intermediate 2 with 4-cyano-benzoic acid, by replacing Hunig's base with triethylamine and running the reaction at 55° C. $^1$H NMR (400 MHz, DMSO-$d_6$, 1 drop of D$_2$O) δ ppm 8.01 (d, J=8.2 Hz, 2H), 7.93 (d, J=8.8 Hz, 2H), 7.45 (s, 1H), 7.29-7.37 (m, 2H), 5.51 (ddd, J=15.3, 7.6, 7.4 Hz, 1H), 5.22-5.32 (m, 1H), 5.07 (dd, J=9.9, 4.4 Hz, 1H), 3.65 (s, 3H), 2.19-2.61 (m, 6H). MS (ESI) m/z: 519.0 (M+H)$^+$. Analytical HPLC: RT=6.12 min.

Example 137

{(S)-14-[(E)-3-(5-Chloro-2-tetrazol-1-yl-phenyl)-acryloylamino]-11,12-dihydroxy-9-oxo-8,16,18-triaza-tricyclo[13.2.1.0$^{2,7}$]octadeca-1(17),2,4,6,15(18)-pentaen-5-yl}-carbamic Acid methyl ester, 1 TFA Salt, Diastereomers A:B (1:1.3)

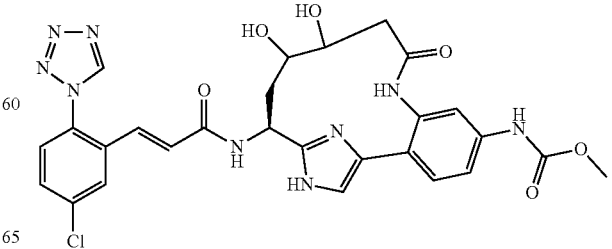

137A. [(S)-11,12-Dihydroxy-5-methoxycarbonylamino-9-oxo-16-(2-trimethylsilanyl-ethoxymethyl)-8,16,18-triaza-tricyclo[13.2.1.0$^{2,7}$]octadeca-1(17),2,4,6,15(18)-pentaen-14-yl]-carbamic acid tert-butyl ester, 1 TFA salt, Diastereomers A:B (1:1.3) and 137B. [(S)-11,12-Dihydroxy-5-methoxycarbonylamino-9-oxo-16-(2-trimethylsilanyl-ethoxymethyl)-8,16,18-triaza-tricyclo[13.2.1.0$^{2,7}$]octadeca-1(17),2,4,6,15(18)-pentaen-14-yl]-carbamic acid tert-butyl ester, 1 TFA salt, Diastereomer C: The content of 1 g sealed vial of OsO$_4$ was dissolved in 200 ml t-Butanol. The pale green solution was treated with 3 drops of 30% H$_2$O$_2$, and allowed to remain at rt overnight. If the solution turned dark, the dropwise addition of 30% H$_2$O$_2$ was repeated, until the pale green persisted. Compound 10E (67 mg, 0.117 mmol) in acetone (1.17 mL) was cooled down to 0° C. Subsequently H$_2$O (0.021 mL, 1.172 mmol), NMO (21.23 mg, 0.176 mmol) and osmium tetroxide (0.293 mL, 5.86 µmol) were added. The reaction was stirred at 0° C. and gradually warmed up to rt overnight. MgSO$_4$ was added to the reaction mixture. The solid was filtered off, rinsed with MeOH and the filtrate was concentrated to yield a black crude product. Purification by reverse phase chromatography provided 9 mg of 137A, as a mixture Diastereomers A:B (1:1.3), as a white solid and 7 mg of 137B (Diastereomer C), as a white solid. For 137A: MS (ESI) m/z: 606.4 (M+H)$^+$. For 137B: MS (ESI) m/z: 606.4 (M+H)$^+$.

137C. Example 137 was prepared following the procedures described in step 1F, by replacing 1D with 137A; followed by step 1G. MS (ESI) m/z: 608.3 (M+H)$^+$. Analytical HPLC: RT=3.90, 4.06 min, ratio 1.3:1. (Method B).

Example 138

(E)-3-(5-Chloro-2-tetrazol-1-yl-phenyl)-N—((S)-9-oxo-5,8,16-triaza-tricyclo[13.3.1.02,7]nonadeca-1(19)2,4,6,15,17-hexaen-14-yl)-acrylamide, 2 TFA Salt

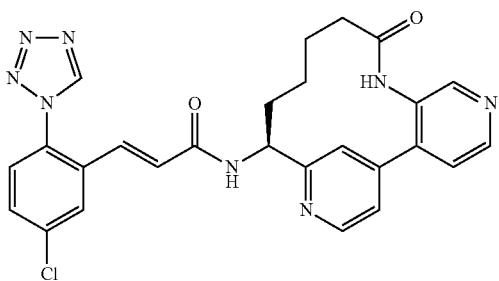 [SMILES: O=C(/C=C/c1cc(Cl)ccc1-n1cnnn1)N[C@H]1CCCCC(=O)Nc2cnccc2-c2ccnc1c2]

138A. 2-Methyl-propane-2-sulfinic acid [(S)-1-(3'-amino-[4,4']bipyridinyl-2-yl)-but-3-enyl]-amide: 088B (591 mg, 2.483 mmol) in a microwave tube was added Dioxane (9 ml) and potassium phosphate tribasic (2.483 ml, 4.97 mmol). The mixture was degassed by bubbling through Ar for several minutes. Tetrakis(triphenylphosphine)palladium (0) (191 mg, 0.166 mmol) was added and continued to bubble for a few minutes. Capped and heated at 100° C. overnight. More Tetrakis(triphenylphosphine)palladium (0) (80 mg) was added and the reaction was heated at 100° C. for additional 5 hrs. The reaction was cooled down to rt and concentrated to remove dioxane, diluted with EtOAc/H$_2$O, extracted 2 more times with EtOAc. The combined organic layers were washed with brine, dried over MgSO$_4$, filtered and concentrated. Purification by normal phase chromatography gave 350 mg (50%) of 138A as slightly brownish foam. MS (ESI) m/z: 345.2 (M+H)$^+$.

138B. Example 138 was prepared following the procedures described in step 88D, by replacing 88C with 138A; followed by steps 88E, by replacing pentenoic acid with but-3-enoic acid; 88G, by replacing 1.1 eq. of pTsOH with 2.2 eq. of pTsOH; 2G; 3C; and 1G. $^1$H NMR (400 MHz, CD$_3$OD) δ ppm 9.49 (1H, s), 8.82 (1H, d, J=5.5 Hz), 8.75 (1H, d, J=5.5 Hz), 8.62 (1H, s), 7.98 (1H, d, J=2.2 Hz), 7.87-7.95 (2H, m), 7.74 (1H, dd, J=5.5, 2.2 Hz), 7.66 (1H, dd, J=8.8, 2.2 Hz), 7.56 (1H, d, J=8.8 Hz), 7.08 (1H, d, J=15.4 Hz), 6.81 (1H, d, J=15.4 Hz), 5.12 (1H, dd, J=11.0, 5.5 Hz), 2.47-2.59 (1H, m), 2.04-2.18 (1H, m), 1.53-2.01 (5H, m), 1.29-1.49 (1H, m), 0.63 (1H, none). MS (ESI) m/z: 515.5 (M+H)$^+$. Analytical HPLC: RT=4.17 min (Method B).

Example 144

(E)-3-(5-Chloro-2-tetrazol-1-yl-phenyl)-N—((S)-9-oxo-6,8,16-triaza-tricyclo[13.3.1.0$^{2,7}$]nonadeca-1(19),2,4,6,15,17-hexaen-14-yl)-acrylamide, 2 TFA Salt

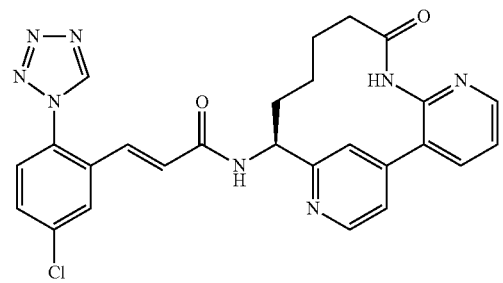 [SMILES: O=C(/C=C/c1cc(Cl)ccc1-n1cnnn1)N[C@H]1CCCCC(=O)Nc2ncccc2-c2ccnc1c2]

Example 144 was prepared following the procedures described in step 138A, by replacing tert-butyl 4-(4,4,5,5-tetramethyl-1,3,2-dioxaborolan-2-yl)pyridin-3-ylcarbamate with tert-butyl 3-(4,4,5,5-tetramethyl-1,3,2-dioxaborolan-2-yl)pyridin-2-ylcarbamate; followed by steps 88D; 88E, by replacing pentenoic acid with but-3-enoic acid; 88G, by replacing 1.1 eq. of pTsOH with 2.2 eq. of pTsOH; 2G; 3C; and 1G. MS (ESI) m/z: 515.2 (M+H)$^+$.

Example 145

{(S)-14-[(E)-3-(5-Chloro-2-tetrazol-1-yl-phenyl)-acryloylamino]-11,12-dihydroxy-9-oxo-8,16,18-triaza-tricyclo[13.2.1.0$^{2,7}$]octadeca-1(17),2,4,6,15(18)-pentaen-5-yl}-carbamic Acid methyl ester, 1 TFA Salt, Diastereomer C

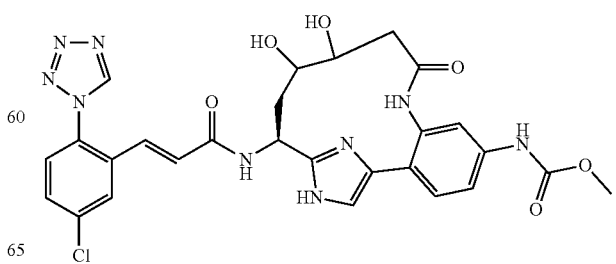

Example 145 was prepared following the procedures described in step 1F, by replacing 1D with 137B; followed by step 1G. ¹H NMR (400 MHz, CD₃OD) δ ppm 9.51 (s, 1H), 7.98 (d, J=2.2 Hz, 1H), 7.69 (dd, J=8.8, 2.2 Hz, 1H), 7.56-7.62 (m, 2H), 7.43-7.50 (m, 2H), 7.38 (dd, J=8.8, 2.2 Hz, 1H), 7.13 (d, J=15.4 Hz, 1H), 6.76 (d, J=15.4 Hz, 1H), 5.10 (dd, J=10.4, 6.6 Hz, 1H), 3.91-3.97 (m, 1H), 3.75 (s, 3H), 3.01 (m, 1H), 2.63 (dd, J=11.6, 3.3 Hz, 1H), 2.42-2.58 (m, 2H), 2.02-2.12 (m, 1H). MS (ESI) m/z: 608.3 (M+H)⁺. Analytical HPLC: RT=4.21 min. (Method B).

Example 152

{(S)-14-[(E)-3-(5-Chloro-2-tetrazol-1-yl-phenyl)-acryloylamino]-12-hydroxy-9-oxo-8,16,18-triaza-tricyclo[13.2.1.0²,⁷]octadeca-1(17),2,4,6,15(18)-pentaen-5-yl}-carbamic Acid methyl ester, 1 TFA Salt

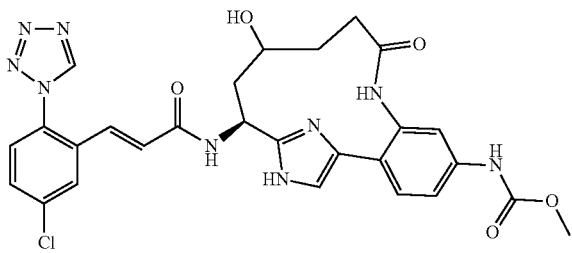 [SMILES: COC(=O)Nc1ccc2c(c1)NC(=O)CCC(O)C[C@H](NC(=O)/C=C/c1cc(Cl)ccc1-n1cnnn1)c1nc-2c[nH]1]

152A. [(S)-11-Hydroxy-5-methoxycarbonylamino-9-oxo-16-(2-trimethylsilanyl-ethoxymethyl)-8,16,18-triaza-tricyclo[13.2.1.0²,⁷]octadeca-1(17),2,4,6,15(18)-pentaen-14-yl]-carbamic acid tert-butyl ester: To a solution of 10E/10F (56 mg, 0.098 mmol) in THF (1 mL) was added borane tetrahydrofuran complex (0.294 mL, 0.294 mmol) at 0° C. dropwise. After addition, the ice water bath was removed and the reaction was warmed up to room temperature. After 2 hrs, reaction mixture was recooled to 0° C. and aqueous solution of sodium acetate (0.653 mL, 1.959 mmol) was added. Hydrogen peroxide (0.300 mL, 2.94 mmol) was added dropwise. After addition, the reaction was warmed up to room temperature and stirred at room temperature for 2 hrs. The reaction was extracted with EtOAc twice. Combined EtOAc layer washed with brine, dried over Na₂SO₄, filtered off solid, concentrated. Purification by reverse phase chromatography gave 152A (3.8 mg, pale yellow solid), 152B (3 mg, pale yellow solid) and 152C (7.8 mg, pale yellow solid).

152A: MS (ESI) m/z: 590.4 (M+H)⁺. Analytical HPLC (Method B): RT=6.09 min.

152B: MS (ESI) m/z: 590.4 (M+H)⁺. Analytical HPLC (Method B): RT=6.17 min.

152C: MS (ESI) m/z: 590.4 (M+H)⁺. Analytical HPLC (Method B): RT=6.44 min.

152D. Example 152 was prepared following the procedures described in step 1F, by replacing 1D with 152A; followed by step 1G. ¹H NMR (500 MHz, CD₃OD) δ ppm 9.50 (s, 1H), 7.93-8.00 (m, 1H), 7.67 (dd, J=8.5, 2.5 Hz, 1H), 7.55-7.60 (m, 2H), 7.46-7.52 (m, 1H), 7.42-7.46 (m, 1H), 7.41 (s, 1H), 7.18 (d, J=15.7 Hz, 1H), 6.72 (d, J=15.4 Hz, 1H), 5.11-5.18 (m, 1H), 3.75 (s, 3H), 3.19-3.27 (m, 1H), 2.42-2.49 (m, 2H), 2.16-2.24 (m, 2H), 1.86-1.95 (m, 1H), 1.21-1.34 (m, 1H). MS (ESI) m/z: 592.2 (M+H)⁺. Analytical HPLC: RT=3.76 min (Method B).

Example 153

(E)-3-(5-Chloro-2-tetrazol-1-yl-phenyl)-N—((S)-5-fluoro-9-oxo-8,16-diaza-tricyclo[13.3.1.0²,⁷]nona-deca-1(19),2(7),3,5,15,17-hexaen-14-yl)-acrylamide, 1 TFA Salt

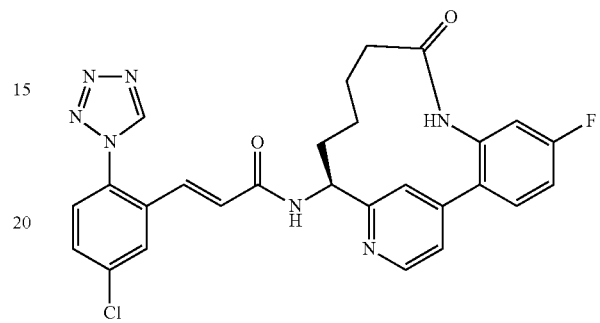

153A. ((E)-(S)-5-Fluoro-9-oxo-8,16-diaza-tricyclo[13.3.1.0²,⁷]nonadeca-1(19),2(7),3,5,11,15,17-heptaen-14-yl)-carbamic acid tert-butyl ester: This compound was prepared from 132B by cleavage of the t-butylsulfinamide and introduction of a Boc-protection group, coupling with 3-butenoic acid and subsequent RCM of the resulting diene, following the procedures described for compounds 88D, 88E (replacing pentenoic acid with but-3-enoic acid), and 88G. MS (ESI) m/z: 398.3 (M+H)⁺.

153B. Example 153 was prepared from 153A by hydrogenation, Boc-deprotection and coupling to Intermediate 1 following the procedures described for compounds 2G, 3C and 1G. ¹H NMR (500 MHz, DMSO-d₆) δ ppm 9.85 (1H, s) 9.84 (1H, s) 8.74 (1H, d, J=6.60 Hz) 8.71 (1H, d, J=5.23 Hz) 7.93 (1H, d, J=2.20 Hz) 7.70-7.77 (2H, m) 7.62-7.68 (2H, m) 7.53 (1H, d, J=4.40 Hz) 7.31 (1H, td, J=8.46, 2.61 Hz) 7.11 (1H, dd, J=9.77, 2.61 Hz) 6.93-6.99 (1H, m) 6.81-6.86 (1H, m) 4.99-5.06 (1H, m) 2.35 (1H, dd, J=10.32, 6.74 Hz) 1.85-1.93 (1H, m) 1.73-1.81 (1H, m) 1.61-1.73 (2H, m) 1.48 (1H, ddd, J=11.14, 6.74, 4.40 Hz) 1.21 (1H, dd, J=6.33, 4.40 Hz) 0.51-0.62 (1H, m). MS (ESI) m/z: 532.2 (M+H)⁺. Analytical HPLC: RT=5.90 min.

Example 154

{(9R,14S)-14-[(E)-3-(5-Chloro-2-tetrazol-1-yl-phenyl)-acryloylamino]-9-trifluoromethyl-8,16,18-triaza-tricyclo[13.2.1.0²,⁷]octadeca-1(17),2,4,6,15(18)-pentaen-5-yl}-carbamic Acid methyl ester, 2 TFA Salt

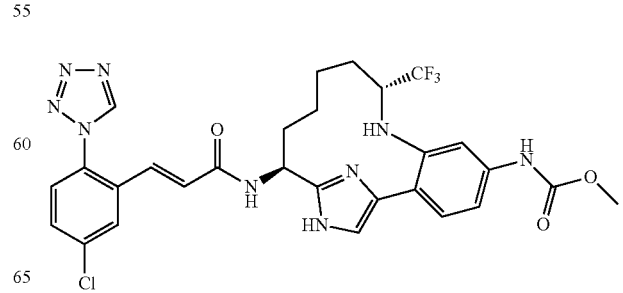

154A. {4-[2-((S)-1-tert-Butoxycarbonylamino-but-3-enyl)-1-(2-trimethylsilanyl-ethoxymethyl)-1H-imidazol-4-yl]-3-[2,2,2-trifluoro-eth-(E)-ylideneamino]-phenyl}-carbamic acid methyl ester: To a solution of 10C (0.805 g, 1.514 mmol) in DCM (30.3 mL) was added 1-ethoxy-2,2,2-trifluoroethanol (0.436 g, 3.03 mmol), 5 A molecular sieves (5 g, 1.514 mmol) and p-toluenesulfonic acid monohydrate (0.014 g, 0.076 mmol). The reaction was warmed to 40° C. After 2 days additional 1-ethoxy-2,2,2-trifluoroethanol (0.436 g, 3.03 mmol) was added. After 12 days, the reaction was filtered through a 0.45 micron GMF filter and the filter cake was rinsed with DCM. The filtrate was concentrated and then toluene (3 mL) was added and then concentrated. This process repeated one more time to afford 154A (0.926 g, 100% yield) as a brown oil and as a mixture of diastereomers. MS (ESI) m/z: 612.6 (M+H)$^+$. This was used in the next step without further purification.

154B. [4-[2-((S)-1-tert-Butoxycarbonylamino-but-3-enyl)-1-(2-trimethylsilanyl-ethoxymethyl)-1H-imidazol-4-yl]-3-(1-trifluoromethyl-but-3-enylamino)-phenyl]-carbamic acid methyl ester: To a cooled (0° C.) solution of 154A (0.926 g, 1.514 mmol) in THF (30 mL) was added allylmagnesium bromide (1M in Et$_2$O, 5.00 mL, 5.00 mmol). After 30 min, the reaction was allowed to warm to rt. After 1.5 h, the reaction was quenched with sat. NH$_4$Cl. Then the reaction mixture was diluted with EtOAc, washed with water, brine, dried over Na$_2$SO$_4$, filtered and concentrated. Purification by normal phase chromatography afforded 154B (0.49 g, 49.5% yield) as a yellow solid and as a mixture of diastereomers. MS (ESI) m/z: 654.5 (M+H)$^+$.

154C. [(9R,14S)-14-tert-Butoxycarbonylamino-9-trifluoromethyl-16-(2-trimethylsilanyl-ethoxymethyl)-8,16,18-triaza-tricyclo[13.2.1.0$^{2,7}$]octadeca-1(17),2,4,6,15(18)-pentaen-5-yl]-carbamic acid methyl ester, 2 TFA salt (Diastereomer A) and 154D. [(9S,14S)-14-tert-Butoxycarbonylamino-9-trifluoromethyl-16-(2-trimethylsilanyl-ethoxymethyl)-8,16,18-triaza-tricyclo[13.2.1.0$^{2,7}$]octadeca-1(17),2,4,6,15(18)-pentaen-5-yl]-carbamic acid methyl ester, 2 TFA salt (Diastereomer B). The ring-closing methathesis products (a mixture of E- and Z-alkene isomers as well as diastereomers at the alpha amine) were prepared following the procedures described in step 2E/2F, by replacing 2D with 154B. To a solution of the ring-closing methathesis product (1.01 g, 1.614 mmol) in EtOAc (32.3 mL) was added TFA (0.249 mL, 3.23 mmol) and 10% palladium on carbon (0.172 g, 0.161 mmol). The reaction vessel was pressurized with hydrogen to 55 psi. After 3 days the reaction was stopped and the reaction was filtered through a 0.45 μm GMF and the catalyst was rinsed with MeOH. The filtrate was concentrated. Purification by reverse phase chromatography afforded 0.074 g (5.4%) of 154 C (diastereomer A) and 0.410 g (30%) of 154 D (diastereomer B). MS (ESI) m/z: 628.4 (M+H)$^+$. Alternatively, the palladium on carbon catalyst can be replaced with platinum oxide.

154E. ((9R,14S)-14-Amino-9-trifluoromethyl-8,16,18-triaza-tricyclo[13.2.1.0$^{2,7}$]octadeca-1(17),2,4,6,15(18)-pentaen-5-yl)-carbamic acid methyl ester. A high-pressure vial, with a teflon-coated screw cap, containing a slightly cloudy mixture of 154D (diastereomer B) (0.0590 g, 0.069 mmol) and 2-amino-3-mercaptopropanoic acid (0.042 g, 0.345 mmol) in 4M HCl in dioxane (1.551 mL, 6.20 mmol) was warmed to 75° C. A white precipitate forms overtime. After 1.5 h, the reaction was stopped and concentrated to give a solid. The solid was dissolved in sat. NaHCO$_3$ and then extracted with EtOAc (3×). The combined organic layers were washed with brine, dried over Na$_2$SO$_4$, filtered and concentrated to give 154E as a pale-yellow foam. MS (ESI) m/z: 398.1 (M+H)$^+$.

154F. Example 154 was prepared following the procedure described in 15D, by replacing 15C with 154 E. $^1$H NMR (500 MHz, CD$_3$OD) δ ppm 9.50 (s, 1H), 7.94 (d, J=2.2 Hz, 1H), 7.66 (dd, J=8.8, 2.2 Hz, 1H), 7.57 (d, J=8.2 Hz, 1H), 7.50 (s, 1H), 7.34 (s, 1H), 7.27 (d, J=8.2 Hz, 1H), 7.06-7.14 (m, 2H), 6.76 (d, J=15.4 Hz, 1H), 5.13 (t, J=7.1 Hz, 1H), 3.73 (s, 3H), 2.93-3.01 (m, 1H), 2.34-2.43 (m, 1H), 1.95-2.04 (m, 1H), 1.62-1.75 (m, 2H), 1.48-1.59 (m, 2H), 1.35-1.46 (m, 1H), 0.48-0.59 (m, 1H). $^{19}$F NMR (470 MHz, CD$_3$OD) δ ppm −75.22. MS (ESI) m/z: 630.4 (M+H)$^+$. Analytical HPLC: RT=6.13 min.

Alternatively, 10C can be condensed with 1-ethoxy-2,2,2-trifluoroethanol to give the 154G rather than the imine (154A) according to the following procedure. Compound 154G can replace 154A in step 154B.

154G. [4-[2-((S)-1-tert-Butoxycarbonylamino-but-3-enyl)-1-(2-trimethylsilanyl-ethoxymethyl)-1H-imidazol-4-yl]-3-(1-ethoxy-2,2,2-trifluoro-ethylamino)-phenyl]-carbamic acid methyl ester: To a clear, dull yellow solution of 10C (2.0 g, 3.76 mmol) in EtOH (7.52 mL) was added 1-ethoxy-2,2,2-trifluoroethanol (1.734 ml, 15.05 mmol). The reaction was heated at 120° C. in a microwave for 3 h. The reaction was cooled to RT and then the reaction was concentrated. Purification by normal phase chromatography gave 1.75 g (66%) of 154A, as an orange foam and as a mixture of diastereomers. MS (ESI) m/z: 658.4 (M+H)$^+$.

Example 155

{(9S,14S)-14-[(E)-3-(5-Chloro-2-tetrazol-1-yl-phenyl)-acryloylamino]-9-trifluoromethyl-8,16,18-triaza-tricyclo[13.2.1.0$^{2,7}$]octadeca-1(17),2,4,6,15 (18)-pentaen-5-yl}-carbamic Acid methyl ester, 2 TFA Salt

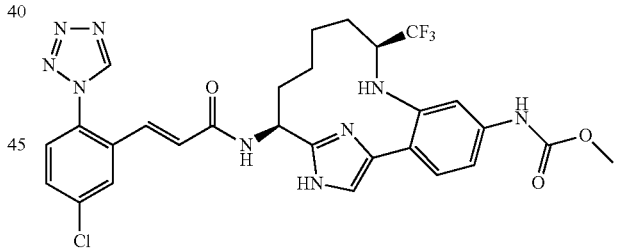

155A. (9S,14S)-14-Amino-9-trifluoromethyl-8,16,18-triaza-tricyclo[13.2.1.0$^{2,7}$]octadeca-1(17),2,4,6,15(18)-pentaen-5-yl)-carbamic acid methyl ester. Compound 155A was prepared following the procedure described in 154E, by replacing 154D with 154C (diastereomer A). MS (EST) m/z: 398.1 (M+H)$^+$.

155B. Example 155 was prepared following the procedure described in 15D, by replacing 15C with 155A. $^1$H NMR (500 MHz, CD$_3$OD) δ ppm 9.51 (s, 1H), 7.98 (d, J=2.2 Hz, 1H), 7.68 (dd, J=8.5, 2.5 Hz, 1H), 7.58 (d, J=8.8 Hz, 1H), 7.54 (s, 1H), 7.39 (s, 1H), 7.31 (d, J=8.2 Hz, 1H), 7.09-7.18 (m, 2H), 6.76 (d, J=15.4 Hz, 1H), 5.24 (dd, J=11.0, 7.1 Hz, 1H), 3.75 (s, 3H), 2.90-2.99 (m, 1H), 2.24-2.37 (m, 1H), 1.97-2.08 (m, 1H), 1.67-1.84 (m, 2H), 1.43-1.63 (m, 3H), 0.30-0.42 (m, 1H). $^{19}$F NMR (470 MHz, CD$_3$OD) δ ppm −74.66. MS (ESI) m/z: 630.4 (M+H)$^+$. Analytical HPLC: RT=6.29 min.

Example 156

{(S)-17-Chloro-14-[(E)-3-(5-chloro-2-tetrazol-1-yl-phenyl)-acryloylamino]-8,16,18-triaza-tricyclo[13.2.1.0²,⁷]octadeca-1(17),2,4,6,15(18)-pentaen-5-yl}-carbamic Acid methyl ester, 2 TFA Salt

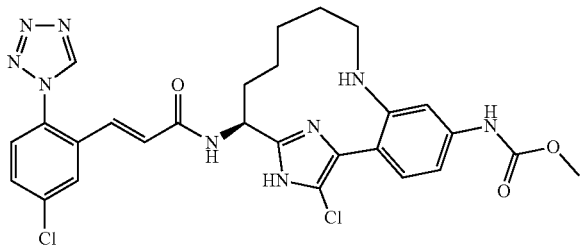 [SMILES: COC(=O)Nc1ccc2c(c1)NCCCCC[C@H](NC(=O)/C=C/c1cc(Cl)ccc1-n1cnnn1)c1nc-2c(Cl)[nH]1]

Example 156 was synthesized according to the procedure described in Example 7, by replacing Example 6 with Example 11. $^1$H NMR (500 MHz, CD$_3$OD) δ ppm 9.54 (s, 1H), 8.02 (d, J=2.5 Hz, 1H), 7.91 (br. s., 1H), 7.84 (d, J=8.8 Hz, 1H), 7.69 (dd, J=8.5, 2.2 Hz, 1H), 7.61 (d, J=8.5 Hz, 1H), 7.32 (dd, J=8.5, 2.2 Hz, 1H), 7.26 (d, J=15.7 Hz, 1H), 6.81 (d, J=15.7 Hz, 1H), 5.20 (dd, J=11.0, 6.3 Hz, 1H), 3.72 (s, 3H), 3.18-3.25 (m, 1H), 2.92-3.00 (m, 1H), 1.97-2.19 (m, 3H), 1.82-1.90 (m, 1H), 1.62-1.72 (m, 2H), 1.33-1.43 (m, 1H), 0.76-0.87 (m, 1H). MS (ESI) m/z: 596.5 (M+H)$^+$. Analytical HPLC: RT=6.01 min.

Example 159

{(S)-14-[(E)-3-(5-Chloro-2-tetrazol-1-yl-phenyl)-acryloylamino]-9-oxo-8,16-diaza-tricyclo[13.3.1.0²,⁷]nonadeca-1(19),2(7),3,5,15,17-hexaen-5-ylmethyl}-carbamic Acid methyl ester, TFA Salt

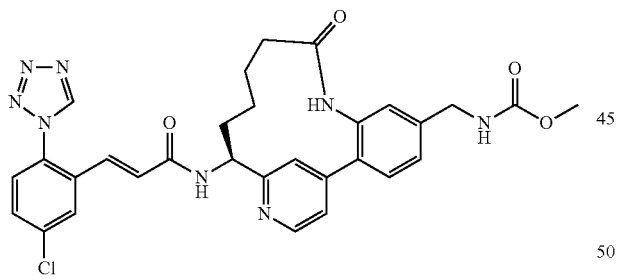

159A. 3-Amino-4-(5,5-dimethyl-1,3,2-dioxaborinan-2-yl)-benzonitrile: This compound was prepared following the procedures described for Intermediate 12, by replacing 2-bromo-5-nitroaniline with 3-amino-4-bromobenzonitrile. MS (ESI) m/z: 163.1 (M+H)$^+$.

159B. ((E)-(S)-5-Cyano-9-oxo-8,16-diaza-tricyclo[13.3.1.0²,⁷]nonadeca-1(19),2(7),3,5,11,15,17-heptaen-14-yl)-carbamic acid tert-butyl ester: This compound was prepared from 159A in four steps by Suzuki coupling to 88B, cleavage of the t-butylsulfinamide and introduction of a Boc-protection group, coupling with 3-butenoic acid and subsequent RCM of the resulting diene, following the procedures described for compounds 88C, 88D, 88E (substituting 3-butenoic acid for 4-pentenoic acid), and 88G. MS (ESI) m/z: 405.2 (M+H)$^+$.

159C. ((S)-5-Aminomethyl-9-oxo-8,16-diaza-tricyclo[13.3.1.0²,⁷]nonadeca-1(19),2(7),3,5,15,17-hexaen-14-yl)-carbamic acid tert-butyl ester: 155B (0.023 g, 0.057 mmol) was dissolved in MeOH (2.0 mL) and transferred to a flask containing a suspension of 10% Pd/C in 1-2 mL MeOH under argon. The mixture was evacuated and back-filled with Ar 3×, then stirred under 1 atm of hydrogen for 3 days. The catalyst was removed by filtration through CELITE® and washed with MeOH; the filtrate was condensed to yield 155C (0.023 g, 99%), MS (ESI) m/z 411.3 (M+H)$^+$.

159D. [(S)-5-(Methoxycarbonylamino-methyl)-9-oxo-8,16-diaza-tricyclo[13.3.1.0²,⁷]nonadeca-1(19),2(7),3,5,15,17-hexaen-14-yl]-carbamic acid tert-butyl ester: 155C (0.023 g, 0.056 mmol) was dissolved in CH$_2$Cl$_2$ (0.5 mL), and TEA (0.016 mL, 0.112 mmol) was added. This mixture was stirred under Ar in an ice/salt water bath. Methyl chloroformate (4.56 μL, 0.059 mmol) was added dropwise to the cold mixture. The reaction was allowed to gradually assume room temperature over 2 hours as the ice bath melted. The reaction was quenched with water and diluted with EtOAc. The organic layer was then washed with saturated NaHCO$_3$ and brine, dried briefly over anhydrous MgSO$_4$, filtered and evaporated to yield 159D as a light yellow glass (0.017 g, 64.8%). MS (ESI) m/z: 469.3 (M+H)$^+$.

159E. Example 159 was prepared from 159D by Boc-deprotection and coupling with Intermediate 1, following the procedures described for steps 3C and 1G. $^1$H NMR (500 MHz, MeOD) δ ppm 9.48 (1H, s) 8.71 (1H, d, J=5.78 Hz) 7.97 (2H, d, J=1.93 Hz) 7.77 (1H, dd, J=5.64, 1.51 Hz) 7.62-7.69 (2H, m) 7.57 (1H, d, J=8.53 Hz) 7.42 (1H, d, J=7.98 Hz) 7.23 (1H, s) 7.10 (1H, d, J=15.68 Hz) 6.79 (1H, d, J=15.68 Hz) 5.11 (1H, dd, J=10.87, 5.64 Hz) 4.36 (2H, s) 3.67 (3H, s) 2.46-2.53 (1H, m) 2.07-2.18 (1H, m) 1.83-2.00 (2H, m) 1.70-1.81 (1H, m) 1.60-1.70 (1H, m) 1.35-1.44 (1H, m) 0.70-0.81 (1H, m). MS (ESI) m/z: 601.3 (M+H)$^+$. Analytical HPLC: RT=5.54 min.

Example 160

{(S)-14-[(E)-3-(5-Chloro-2-tetrazol-1-yl-phenyl)-acryloylamino]-11-hydroxy-9-oxo-8,16,18-triaza-tricyclo[13.2.1.02,7]octadeca-1(17),2,4,6,15(18)-pentaen-5-yl}-carbamic Acid methyl ester, 1 TFA Salt

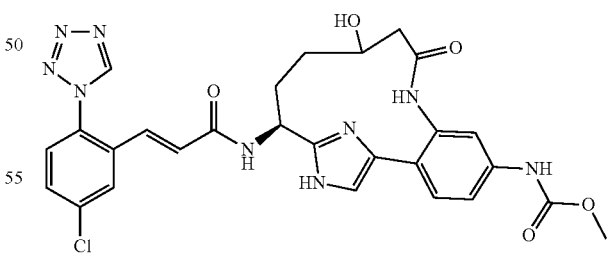

Example 160 was prepared following the procedures described in step 1F, by replacing 1D with 152B; followed by step 1G. $^1$H NMR (500 MHz, CD$_3$OD) δ ppm 9.49 (s, 1H), 7.91-8.01 (m, 1H), 7.65-7.72 (m, 1H), 7.55-7.63 (m, 2H), 7.43-7.52 (m, 2H), 7.34-7.43 (m, 1H), 7.15 (d, J=15.7 Hz, 1H), 6.73 (d, J=15.7 Hz, 1H), 5.08-5.19 (m, 1H), 3.85-3.95 (m, 1H), 3.76 (s, 3H), 2.68-2.76 (m, 1H), 2.40-2.54 (m, 1H), 2.12-2.23 (m, 1H), 1.93-2.06 (m, 1H), 1.39-

1.51 (m, 1H), 1.21-1.34 (m, 1H). MS (ESI) m/z: 592.2 (M+H)⁺. Analytical HPLC: RT=3.86 min (Method B).

Example 161

{(S)-14-[(E)-3-(5-Chloro-2-tetrazol-1-yl-phenyl)-acryloylamino]-11-hydroxy-9-oxo-8,16,18-triaza-tricyclo[13.2.1.0²,⁷]octadeca-1(17),2,4,6,15(18)-pentaen-5-yl}-carbamic Acid methyl ester, 1 TFA Salt

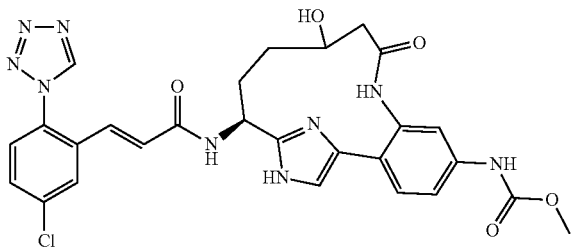 [SMILES: COC(=O)Nc1ccc2c(c1)NC(=O)CC(O)CC[C@H](NC(=O)/C=C/c1cc(Cl)ccc1-n1cnnn1)c1nc-2c[nH]1]

Example 161 was prepared following the procedures described in step 1F, by replacing 1D with 152C; followed by step 1G. ¹H NMR (500 MHz, CD₃OD) δ ppm 9.52 (s, 1H), 7.92-8.04 (m, 1H), 7.64-7.72 (m, 1H), 7.56-7.63 (m, 2H), 7.50-7.56 (m, 1H), 7.41-7.49 (m, 2H), 7.17 (d, J=15.4 Hz, 1H), 6.77 (d, J=15.4 Hz, 1H), 5.26-5.38 (m, 1H), 3.76 (s, 3H), 3.63-3.72 (m, 1H), 2.51-2.64 (m, 1H), 2.30-2.44 (m, 2H), 1.95-2.05 (m, 1H), 1.65-1.78 (m, 1H), 1.30-1.47 (m, 1H). MS (ESI) m/z: 592.2 (M+H)⁺. Analytical HPLC: RT=3.69 min (Method B).

Example 167

{(E)-14-[(E)-3-(5-Chloro-2-tetrazol-1-yl-phenyl)-acryloylamino]-17-methyl-9-oxo-8,16,18-triaza-tricyclo[13.3.1.0²,⁷]nonadeca-1(19),2,4,6,11,15,17-heptaen-5-yl}-carbamic Acid methyl ester

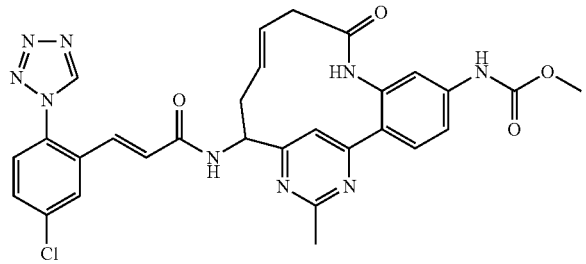 [SMILES: COC(=O)Nc1ccc2c(c1)NC(=O)C/C=C/CC(NC(=O)/C=C/c1cc(Cl)ccc1-n1cnnn1)c1cc-2nc(C)n1]

167A. (S)-4-tert-Butoxycarbonylamino-3-oxo-hept-6-enoic acid ethyl ester. To a solution of (S)-2-(tert-butoxycarbonylamino)pent-4-enoic acid (5.0g, 23.23 mmol) in THF (40 mL) was added carbonyldiimide (4.52 g, 27.9 mmol) at rt. The reaction was stirred under argon at rt for 5 h. To another flask containing a solution of 3-ethoxy-3-oxopropanoic acid (4.60 g, 34.8 mmol) in THF (40 mL) was added dropwise isopropylmagnesium chloride (34.8 mL, 69.7 mmol). Following the addition, the reaction was stirred at 0° C. for 30 min, at rt for 30 min and then at 48° C. for 30 min. The reaction was cooled to rt and transferred to the cooled solution (0° C.) prepared in the first flask to give a milky suspension. The reaction was allowed to stir at rt over night. The reaction mixture was slowly poured into 1.0N HCl (200 ml) at 0° C. and gas was evolved. The reaction mixture was extracted with EtOAc, washed with sat NaHCO₃ and brine. The organic phase was dried over sodium sulfate, filtered and concentrated to give a clear colorless oil. The crude product was purified by normal phase chromatography to give 167A (5.36 g, 81% yield) as a white solid. ¹H NMR (400 MHz, CDCl₃) δ ppm 5.61-5.78 (1H, m), 5.17 (1H, d, J=3.26 Hz), 5.13 (2H, d, J=2.26 Hz), 4.32-4.50 (1H, m), 4.20 (2H, q, J=7.28 Hz), 3.47-3.64 (2H, m), 2.52-2.70 (1H, m), 2.35-2.52 (1H, m), 1.44 (9H, s), 1.28 (3H, t, J=7.15 Hz). MS (ESI) m/z: 308.1 (M+Na)⁺.

167B. [1-(6-Hydroxy-2-methyl-pyrimidin-4-yl)-but-3-enyl]-carbamic acid tert-butyl ester. To a solution of acetimidamide HCl salt (0.928 g, 9.81 mmol) in MeOH (30 mL) were added sodium methoxide solution (25% wt/wt, 4.49 mL, 19.63 mmol) and a solution of 167A(2.0g, 7.01 mmol) dissolved in MeOH (15 mL) at rt. The reaction was stirred under argon at rt for 3 h. The reaction was neutralized with 1.0 N HCl. Most solvent was removed. The reaction mixture was extracted with chloroform. The organic phase was washed with brine and dried over sodium sulfate, filtered and concentrated. The crude product was purified by normal phase chromatography to give 167B (1.82 g, 93% yield) as a white solid. MS (ESI) m/z: 280.1 (M+H)⁺.

167C. [1-(6-Chloro-2-methyl-pyrimidin-4-yl)-but-3-enyl]-carbamic acid tert-butyl ester. To a flask containing 167B (1.82 g, 6.52 mmol) was added POCl₃ (12.15 mL, 130 mmol) at rt. The suspension was stirred under argon at 50° C. and the suspension turned a clear light brown solution. After 2 h, excess POCl₃ was removed under reduced pressure and the residue was co-evaporated twice with toluene to give a dark tar. This intermediate was dissolved in acetonitrile (30 mL), to which were added Na₂CO₃ (3.46 g, 32.6 mmol) and BOC₂O (1.817 mL, 7.82 mmol) at 0° C. The reaction was stirred under argon at 0° C. for 1.5 h. The reaction mixture was diluted with EtOAc, washed with H₂O and brine. The organic phase was dried over sodium sulfate, filtered and concentrated. The crude product was purified by normal phase chromatography to give 167C (0.65 g, 34% yield) as a light yellow solid. ¹H NMR (400 MHz, CD₃OD) δ ppm 7.30 (1H, s), 5.70-5.88 (1H, m, J=17.13, 10.16, 6.93, 6.93 Hz), 5.02-5.15 (2H, m), 4.63 (1H, dd, J=8.28, 5.27 Hz), 2.64 (3H, s), 2.54-2.62 (1H, m), 2.36-2.49 (1H, m), 1.43 (9H, s). MS (ESI) m/z: 298.1 (M+H)⁺.

167D. {3-But-3-enoylamino-4-[6-(1-tert-butoxycarbonylamino-but-3-enyl)-2-methyl-pyrimidin-4-yl]-phenyl}-carbamic acid methyl ester: This compound was prepared following the procedures described in step 88C, by replacing 88B with 167C; followed by steps 88E; and 88F. ¹H NMR (400 MHz, CDCl₃) δ ppm 8.23 (1H, s), 7.63-7.72 (2H, m), 7.40 (1H, s), 5.92-6.07 (1H, m, J=17.07, 10.10, 7.00, 7.00 Hz), 5.61-5.72 (1H, m), 5.19-5.30 (2H, m), 5.08 (2H, d, J=12.05 Hz), 4.62-4.78 (1H, m), 3.75 (3H, s), 3.18 (2H, d, J=7.03 Hz), 2.73 (3H, s), 2.45-2.64 (2H, m), 1.40 (9H, br. s.). MS (ESI) m/z: 496.1 (M+H)⁺.

167E. ((E)-5-Methoxycarbonylamino-17-methyl-9-oxo-8,16,18-triaza-tricyclo[13.3.1.0²,⁷]nonadeca-1(19),2,4,6,11,15,17-heptaen-14-yl)-carbamic acid tert-butyl ester. A solution of 167D (25 mg, 0.050 mmol) in DCM (100 mL) was purged with argon and then was added 4 M HCl in dioxane (0.1 mL, 0.400 mmol) at rt. The solution was heated up to reflux and then Grubbs (II) catalyst (17.13 mg, 0.020 mmol) was added. The reaction was stirred under argon at reflux for 4 h. The reaction was cooled to rt and solvent was removed. Purification by reverse phase chromatography gave 167E (5.1 mg, 22% yield) as a dark brown solid. MS (ESI) m/z: 468.0 (M+H)$^+$.

167F. Example 167 was prepared following the procedures described in step 3C, by replacing 3B with 167E; followed by step 1G. $^1$H NMR (400 MHz, CD$_3$OD) δ ppm 9.55 (1H, s), 9.50 (1H, s), 8.01 (1H, d, J=2.26 Hz), 7.66 (1H, dd, J=8.53, 2.26 Hz), 7.59-7.63 (2H, m), 7.56 (1H, d, J=8.53 Hz), 7.48 (1H, dd, J=8.66, 2.13 Hz), 7.11 (1H, d, J=15.56 Hz), 6.96 (1H, s), 6.89 (1H, d, J=15.56 Hz), 5.74-5.85 (1H, m), 4.96-5.03 (2H, m), 3.76 (3H, s), 3.00 (1H, dd, J=11.80, 9.29 Hz), 2.75-2.85 (2H, m), 2.74 (3H, s), 2.21-2.33 (1H, m). MS (ESI) m/z: 600.1 (M+H)$^+$. Analytical HPLC: RT=6.383 min.

Example 168

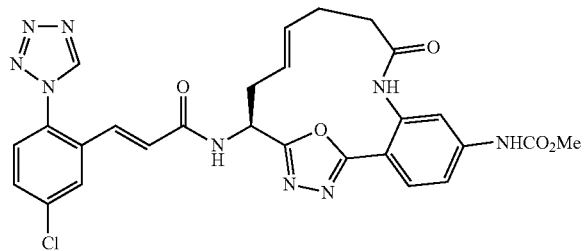

168A. Methyl 4-amino-2-nitrobenzoate: A suspension of 4-amino-2-nitrobenzoic acid (1.0 g, 5.49 mmol) in MeOH (25 mL) was cooled in an ice/salt water bath with stirring under nitrogen while SOCl$_2$ (0.601 mL, 8.24 mmol) was slowly added dropwise. The resulting amber solution was heated at reflux overnight. Reaction was cooled to room temperature and evaporated to remove MeOH. Residue was partitioned between EtOAc and sat'd aq. NaHCO$_3$ solution, and aq. layer reextracted 2× with EtOAc. Combined organic extracts were washed with brine, dried over anh. Na$_2$SO$_4$, filtered and evaporated to give the ester as a yellow-orange solid (0.95 g, 88%). $^1$H NMR (500 MHz, DMSO-d$_6$) d ppm 7.61 (1H, d, J=8.53 Hz) 6.83 (1H, d, J=2.20 Hz) 6.74 (1H, dd, J=8.67, 2.34 Hz) 6.54 (2H, s) 3.72 (3H, s).

168B. Methyl 4-(hydrazinecarbonyl)-3-nitrophenylcarbamate: 168A (0.94 g, 4.79 mmol) was suspended in DCM (25 mL), pyridine (0.775 mL, 9.58 mmol) was added, and the mixture was cooled in an ice bath with stirring under nitrogen. Methylchloroformate (0.390 mL, 5.03 mmol) was then added dropwise to the cold mixture. Stirring was continued for ~30 min in the ice bath then at room temperature for 4 h. Reaction was diluted with additional DCM, washed 2× with 1M HCl, water and brine, then dried over anh. Na$_2$SO$_4$, filtered and evaporated to a light orange solid. The solid obtained (1.2 g, 4.72 mmol) was suspended in ethanol (24 ml), and hydrazine (2.4 ml, 76 mmol) was added. The mixture was heated at reflux under nitrogen with stirring overnight in an 80° C. oil bath, then cooled to room temperature and filtered. Pale yellow solid was washed with EtOH and Et$_2$O then air-dried. The filtrate was evaporated and residue suspended in EtOAc/H$_2$O. Solid which separated was collected by filtration, washed with EtOAc and Et$_2$O, dried and combined with initial solid. The crude hydrazide was suspended in MeOH and sonicated for 10-15, insoluble solid removed by filtration and washed with MeOH. Evaporation of the filtrate gave the product, 168B, as a bright yellow solid. (0.363 g, 30.2%). $^1$H NMR (500 MHz, DMSO-d$_6$) d ppm 10.28 (1H, s) 9.60-9.71 (1H, m) 8.13 (1H, d, J=1.93 Hz) 7.71 (1H, dd, J=8.39, 2.06 Hz) 7.51 (1H, d, J=8.53 Hz) 4.45 (2H, d, J=4.13 Hz) 3.72 (3H, s).

168C. {4-[5-((S)-1-tert-Butoxycarbonylamino-but-3-enyl)-1,3,4-oxadiazol-2-yl]-3-nitro-phenyl}-carbamic acid methyl ester: 168B (0.3 g, 0.393 mmol) and (S)-2-(tert-butoxycarbonylamino)pent-4-enoic acid (0.085 g, 0.393 mmol) were dissolved in DMF (2 mL) in a 15 mL rbf and TEA (0.274 mL, 1.967 mmol) was added. Mixture was stirred under nitrogen at room temperature while propane phosphonic acid anhydride (T3P), 50% in EtOAc (0.293 mL, 0.983 mmol) was added dropwise. The flask was fitted with a reflux condenser, and the resulting mixture was stirred in an 80° C. oil bath for 5 h. Reaction mixture was poured into ice water and extracted 3× with EtOAc. Combined extracts were washed with sat'd aq. NaHCO$_3$, water and brine, dried over anh. Na$_2$SO$_4$, filtered and evaporated to provide {4-[N'—((S)-2-tert-butoxycarbonylamino-pent-4-enoyl)-hydrazinocarbonyl]-3-nitro-phenyl}-carbamic acid methyl ester, (0.46 g, 86%) as a light yellow solid which was used without further purification. The solid (0.46 g, 1.019 mmol) was dissolved in anhydrous THF (20 mL) under argon and the solution transferred to a 75 mL pressure flask. Burgess reagent (1.33 g, 5.58 mmol) was added, the flask was sealed with a pressure relief cap and then heated in a 75° C. oil bath for 2h behind a blast shield then left standing overnight at room temperature. Reaction mixture was evaporated on rotary evaporator. Residue was purified by normal phase chromatography to give 168C as a light yellow foam (0.315 g, 71.3%). MS (ESI) m/z: 434.3 (M+H)$^+$ 378.3 (M+H-tBu)$^+$.

168D. {3-Amino-4-[5-((S)-1-tert-butoxycarbonylamino-but-3-enyl)-1,3,4-oxadiazol-2-yl]-phenyl}-carbamic acid methyl ester: 168C (0.315 g, 0.727 mmol) was dissolved in ethanol (4.5 mL) and iron powder (0.812 g, 14.54 mmol) was added. The mixture was stirred at room temperature for 1-2 min, then 0.1 M HCl (3.63 mL, 0.363 mmol) was added, and the reaction was heated with stirring under nitrogen in a 50° C. oil bath for 1.5 h. Reaction was cooled to room temperature and filtered through a pad of CELITE,® and solids washed with water, EtOH and EtOAc, then discarded. Filtrate was evaporated and remaining aqueous was diluted with NaHCO$_3$ to pH 8, then extracted 3× with EtOAc. Combined extracts were washed with saturated NaHCO$_3$ solution and brine, dried over anhydrous Na$_2$SO$_4$ and filtered. Evaporation of solvents provided 168D as a crystalline solid. (0.257 g, 88%). MS (ESI) m/z: 404.3 (M+H)$^+$ 348.3 (M+H-tBu)$^+$.

168E. -[5-((S)-1-tert-Butoxycarbonylamino-but-3-enyl)-1,3,4-oxadiazol-2-yl]-3-pent-4-enoylamino-phenyl}-carbamic acid methyl ester: 168D (0.275 g, 0.682 mmol) was dissolved in DCM (3.5 mL) and pyridine (0.110 mL, 1.363 mmol) was added. The solution was cooled in an ice/salt water bath to ~0° C., then 4-pentenoyl chloride (0.075 mL, 0.682 mmol) was added dropwise. The resulting mixture was stirred at 0-5° C. for 1 h then allowed to warm to room temperature. After an additional 2 h at room temperature, the reaction was diluted with EtOAc and washed with water, 1M HCl, sat'd NaHCO$_3$ and brine, then dried over anhydrous Na$_2$SO$_4$, filtered and evaporated. The crude product was purified by normal phase chromatography to provide 168E as a white solid (0.276 g, 83%). MS (ESI) m/z: 486.3 (M+H)$^+$ 430.3 (M+H-tBu)$^+$ 168F. ((E)-(S)-15-tert-Butoxycarbonylamino-9-oxo-19-oxa-8,17,18-triaza-tricyclo[14.2.1.0$^{2,7}$]nonadeca-1(18),2,4,6,12,16-hexaen-5-yl)-carbamic acid methyl ester: 168E (0.15 g, 0.309 mmol) was dissolved in DCE (500 mL) in a 1 L flame-dried 3-neck flask fitted with a septum, reflux condenser and argon inlet. The solution was degassed by bubbling Ar through the solution for 30 min. Grubbs (II) (0.094 g, 0.111 mmol) catalyst was weighed out under argon and dissolved in 5 mL of degassed DCE and the dark red solution was added dropwise over 5-10 min to the above solution. The resulting mixture was heated in a 75° C. oil bath for 2 h. Reaction was cooled to room temperature and solvent removed on rotary evaporator. Residue was taken back up in DCM and 0.375 g tris(hydroxymethyl)phosphine and 0.78 mL TEA were added. Mixture was stirred for 10 min then water was added and vigorous stirring was continued for 15 min. Phases were separated and organic layer washed with brine and dried over anhydrous $Na_2SO_4$. The crude product mixture was purified by silica gel chromatography to provide 168F, the trans isomer, as the major product (27 mg, 19.1%). MS (ESI) m/z: 458.3 $(M+H)^+$402.1 $(M+H-tBu)^+$.

168G: Example 168 was prepared from 168F by removal of the Boc protecting group and coupling with Intermediate 1, following the procedures described for compounds 3C and 1G. $^1$H NMR (400 MHz, DMSO-$d_6$) δ ppm 10.04 (1H, s) 9.91 (1H, s) 9.84 (1H, s) 9.04 (1H, d, J=7.33 Hz) 7.96 (1H, d, J=1.77 Hz) 7.64-7.81 (3H, m) 7.52 (1H, s) 7.41 (1H, dd, J=8.46, 1.64 Hz) 6.91 (1H, d, J=16.00 Hz) 6.81 (1H, d, J=16.00 Hz) 5.43-5.63 (2H, m) 5.11-5.22 (1H, m) 3.70 (3H, s) 2.57-2.70 (1H, m) 2.35-2.47 (3H, m) 2.15-2.27 (2H, m). MS (ESI) m/z: 590.2 $(M+H)^+$. Analytical HPLC RT=5.80 min.

Unless otherwise stated, the compounds listed in the following tables can be prepared by one skilled in the art of organic synthesis using the procedures described in Examples 1-168.

Examples I-1 to I-17 (Table I-1) were prepared by coupling 10H with appropriately substituted carboxylic acid derivatives (R—CO$_2$H) using coupling conditions described in step 15D. In the case of Examples I-4, I-12, and I-15, an additional Boc-deprotection step as described in step 3C was required. Example I-18 was prepared by coupling 10H with an appropriately substituted carboxylic acid derivative (R—CO$_2$H) using coupling conditions described in step 15D followed by chlorination as described in Example 7.

Example I-20

{(S)-14-[(E)-3-(5-Chloro-2-tetrazol-1-yl-phenyl)-acryloylamino]-17-fluoro-9-oxo-8,16,18-triaza-tricyclo[13.2.1.0$^{2,7}$]octadeca-1(17),2,4,6,15 (18)-pentaen-5-yl}-carbamic Acid methyl ester, trifluoroacetic Acid Salt

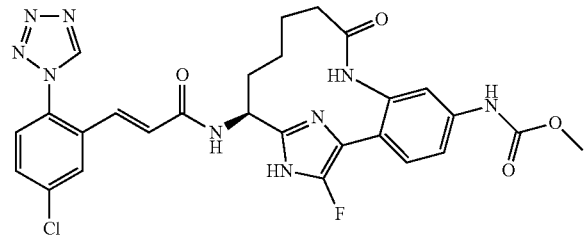 [SMILES: COC(=O)Nc1ccc2c(c1)NC(=O)CCCC[C@H](NC(=O)/C=C/c1cc(Cl)ccc1-n1cnnn1)c1nc-2c(F)[nH]1]

I-20A. ((S)-14-tert-Butoxycarbonylamino-9-oxo-8,16,18-triaza-tricyclo[13.2.1.0$^{2,7}$]octadeca-1(17),2,4,6,15(18)-pentaen-5-yl)-carbamic acid methyl ester: To a brown solution of 10H (74.1 mg, 0.178 mmol) in THF (4 mL) and water (2 mL) was added potassium carbonate (98 mg, 0.712 mmol), followed by di-tert-butyl dicarbonate (0.062 mL, 0.267 mmol). The reaction was stirred at rt for 12 h. To the solution was added aq. NH$_4$Cl (10 mL) and 100 ul sat NH$_4$OH to quench the reaction. The reaction mixture was then extracted with EtOAc (30 mL×2). Organic solution was dried over MgSO$_4$ and concentrated in vacuo, yielding oily mixture, which was purified on normal phase column chromatography (EtOAc/Hex) to provide 40 mg (0.090 mmol, 50.7% yield) of I-20A as light brown oil. MS (ESI) m/z: 444.2 $(M+1)^+$.

I-20B. ((S)-14-Amino-17-fluoro-9-oxo-8,16,18-triaza-tricyclo[13.2.1.0$^{2,7}$]octadeca-1(17),2,4,6,15(18)-pentaen-5-yl)-carbamic acid methyl ester: To a solution of I-20A (40 mg, 0.090 mmol) in DMF (3 mL) was added sodium carbonate (12.43 mg, 0.117 mmol) and 1-Fluoro-4-hydroxy-1,4 diazoniabicyclo[2,2,2]octanebis(tetrafluoroborate) (50% in alumina) (62.9 mg, 0.090 mmol) in a portion, respectively and the resulting solution was stirred for 2 h at rt. The reaction mixture was diluted with MeOH and purified by reverse phase chromatography which gave both ((S)-14-tert-Butoxycarbonylamino-17-fluoro-9-oxo-8,16,18-triaza-tricyclo[13.2.1.0$^{2,7}$]octadeca-1(17),2,4,6,15(18)-pentaen-5-yl)-carbamic acid methyl ester and ((S)-14-Amino-17-fluoro-9-oxo-8,16,18-triaza-tricyclo[13.2.1.0$^{2,7}$]octadeca-1 (17),2,4,6,15(18)-pentaen-5-yl)-carbamic acid methyl ester. The mixture was dissolved in 4N HCl dioxane (10 mL) and stirred overnight at 50° C. Concentration of the solution provided 11 mg of I-20B (34%).

I-20C. Example I-20 was prepared following the procedures described in step 1G, by replacing 1F with I-20B. $^1$H NMR (400 MHz, CD$_3$OD) δ ppm 9.40-9.59 (m, 1H), 7.88-8.10 (m, 1H), 7.62-7.85 (m, 1H), 7.53-7.62 (m, 1H), 7.31-7.52 (m, 2H), 7.07-7.22 (m, 1H), 6.71-6.94 (m, 1H), 4.92-5.03 (m, 1H), 2.36-2.50 (m, 1H), 1.94-2.30 (m, 2H), 1.75 (br. s., 2H), 1.45 (br. s., 2H), 0.99 (br. s., 1H). MS(ESI) m/z: 594.2 $(M+H)^+$. Analytical HPLC: RT=6.79 min.

Example I-22

Methyl N-[(14S)-14-[(2E)-3-[5-chloro-2-(1H-1,2,3,4-tetrazol-1-yl)phenyl]prop-2-enamido]-17-methyl-9-oxo-8,16,18-triazatricyclo[13.2.1.0$^{2,7}$]octadeca-1 (17),2(7),3,5,15(18)-pentaen-5-yl]carbamate, trifluoroacetic Acid

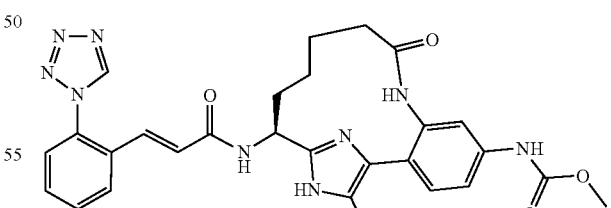

I-22A. tert-Butyl N-[(14S)-17-bromo-5-[(methoxycarbonyl)amino]-9-oxo-16-{[2-(trimethylsilyl)ethoxy]methyl}-8,16,18-triazatricyclo[13.2.1.0$^{2,7}$]octadeca-1(17),2(7),3,5,15 (18)-pentaen-14-yl]carbamate: To a cooled (<0° C.) solution of 10G (0.53 g, 0.924 mmol) in CHCl$_3$ (10 mL) was added NBS (0.164 g, 0.924 mmol). The reaction was stirred under argon at 0° C. for 30 min. The solvent was removed. The crude product was purified by normal phase chromatography to give I-22A (0.58 g, 96%) as a solid. MS (ESI) m/z: 652.2 (M+H)⁺ and 654.2 (M+2+H)⁺.

I-22B. tert-Butyl N-[(14S)-5-[(methoxycarbonyl)amino]-17-methyl-9-oxo-16-{[2-(trimethylsilyl)ethoxy]methyl}-8,16,18-triazatricyclo[13.2.1.0$^{2,7}$]octadeca-1(17),2(7),3,5,15(18)-pentaen-14-yl]carbamate: To a solution of I-22A (0.53g, 0.812 mmol) in dioxane (15 mL) were added Na$_2$CO$_3$ (0.430 g, 4.06 mmol), methylboronic acid (0.097 g, 1.624 mmol) and bis(tri-t-butylphosphine) palladium(0) (0.042 g, 0.081 mmol) at RT. The reaction mixture was purged with argon and then the reaction was stirred under argon at 80° C. for 5 h. The reaction was cooled to RT. The reaction mixture was diluted with EtOAc, washed with sat NaHCO$_3$ and brine. The organic phase was dried over sodium sulfate, filtered and concentrated. In order to remove the des-Br by-product for better purification, it was converted back to bromoimidazole starting material following the procedure described in I-22A. The crude product was purified by reverse phase chromatography to give I-22B (44 mg, 10% yield). MS (ESI) m/z: 588.4 (M+H)⁺.

I-22C. Example I-22 was prepared following the procedures described in 10H, by replacing 10G with I-22B; followed by step 1G. ¹H NMR (400 MHz, MeOD) δ ppm 9.57 (1H, s, br), 9.50 (1H, s), 7.96 (1H, d, J=2.01 Hz), 7.68 (1H, dd, J=8.53, 2.26 Hz), 7.55-7.61 (2H, m), 7.39-7.47 (2H, m), 7.14 (1H, d, J=15.56 Hz), 6.73 (1H, d, J=15.81 Hz), 5.03 (1H, dd, J=10.16, 6.40 Hz), 3.76 (3H, s), 2.37-2.48 (1H, m), 2.31 (3H, s), 2.15-2.28 (1H, m), 2.00-2.12 (1H, m), 1.84-1.97 (1H, m), 1.41-1.66 (3H, m), 0.96-1.18 (1H, m). MS (ESI) m/z: 590.2 (M+H)⁺. Analytical HPLC: RT=4.38 min.

TABLE I-1

Examples I-1 to I-23

| Ex. # | R | R³ | LCMS [M + H]⁺ | HPLC RT (min) (method) |
|---|---|---|---|---|
| I-1 | tetrazole-phenyl-Cl with propyl linker | H | 578.2 | 4.7 |
| I-2 | triazole-phenyl-Cl with propenyl linker | H | 575.2 | 4.5 |
| I-3 | triazole-phenyl-Cl with propenyl linker | H | 575.2 | 4.2 |
| I-4 | amidine-phenyl | H | 490.1 | 2.0 (B) |
| I-5 | triazole-phenyl-Cl with propenyl linker | H | 575.2 | 5.0 |
| I-6 | OCHF$_2$-phenyl-Cl with propenyl linker | H | 574.2 | 6.1 |

TABLE I-1-continued

Examples I-1 to I-23

| Ex. # | R | R³ | LCMS [M + H]⁺ | HPLC RT (min) (method) |
|---|---|---|---|---|
| I-7 | 3-chlorophenyl-4,5-dihydroisoxazol-5-yl | H | 551.1 | 5.0 / 4.8 (B) |
| I-8 | 3-chlorophenyl-4,5-dihydroisoxazol-5-yl | H | 551.1 | 5.0 / 4.9 (B) |
| I-9 | 3-chlorophenyl-isoxazol-5-yl | H | 549.2 | 6.2 |
| I-10 | 1-(3-chlorophenyl)-1H-1,2,3-triazol-4-yl | H | 549.2 | 5.6 |
| I-11 | 2,6-difluoro-4-methylphenyl | H | 498.2 | 4.0 |
| I-12 | 4-(aminomethyl)-2,6-difluorophenyl | H | 513.2 | 6.2 (C) |
| I-13 | 1,2,3,4-tetrahydroquinolin-6-yl | H | 503.4 | 5.2 |
| I-14 | quinolin-6-yl | H | 499.2 | 3.7 |
| I-15 | 1,2,3,4-tetrahydroisoquinolin-6-yl | H | 503.3 | 4.0 |
| I-16 | naphthalen-2-yl | H | 498.3 | 5.9 |
| I-17 | naphthalen-1-yl | H | 498.3 | 5.6 |
| I-18 | 2-acetyl-4-chlorophenyl-vinyl | Cl | 584.3 | 5.9 (B) |
| I-19 | 4-chloro-2-(difluoromethoxy)phenyl-vinyl | Cl | 608.2 | 8.0 |

TABLE I-1-continued

Examples I-1 to I-23

| Ex. # | R | R³ | LCMS [M + H]⁺ | HPLC RT (min) (method) |
|---|---|---|---|---|
| I-20 | (1-(4-chloro-2-((E)-3-methylbut-1-en-1-yl)phenyl)-1H-tetrazol-5-yl) | F | 594.2 | 6.8 |
| I-21 | (4,6-difluoro-1-methyl-1H-benzo[d]imidazol-5-yl, methyl) | F | 556.2 | 4.9 |
| I-22 | (1-(4-chloro-2-((E)-3-methylbut-1-en-1-yl)phenyl)-1H-tetrazol-5-yl) | Me | 590.2 | 4.4 |
| I-23 | (1-(4-chloro-3-fluoro-2-((E)-3-methylbut-1-en-1-yl)phenyl)-1H-tetrazol-5-yl) | Me | 608.2 | 5.2 |

Examples I-24 and I-25 (Table I-2) were prepared following the procedures described in Example 116 and 118 by replacing 2-methylbut-3-enoic acid with 3-methylbut-3-enoic acid.

TABLE I-2

Examples I-24 and I-25

| Ex. # | R⁷ | LCMS [M + H]⁺ | HPLC RT (min) (method) |
|---|---|---|---|
| I-24 | Me (homochiral) | 590.3 | 5.0 |
| I-25 | Me (homochiral) | 590.3 | 5.0 |

Examples I-26 to I-34 (Table I-3) were prepared following the general procedures described in Examples 116 and 118. Example I-26 and I-27 were prepared by replacing benzyl 2-methylbut-3-enoate with methyl 2-hydroxybut-3-enoate as described in Example 116C, followed by 116D, additional step of replacement of hydroxyl group with fluoride by DAST; followed by steps 116E; 116F; and 116I. Examples I-30 and I-31 were prepared by replacing benzyl 2-methylbut-3-enoate with methyl 2-methoxybut-3-enoate as described in Example 116C. Examples I-28, I-29 and I-33 were prepared by replacing benzyl 2-methylbut-3-enoate with benzyl 2-ethylbut-3-enoate or benzyl 2-isopropylbut-3-enoate as described in Example 116C. Example I-32 was prepared by replacing benzyl 2-methylbut-3-enoate with methyl 2-hydroxybut-3-enoate as described in Example 116C; followed by 116D; additional step of oxidation of the hydroxyl group to the ketone by Dess-Martin's reagent followed by fluorination with DAST; followed by steps 116E; 116F; and 116I. Examples I35-I38 were prepared by clorination of Examples 116G, 116H, I-33, and I-34 as described in Example 7. Examples I-39 to I-59 were prepared by coupling macrocyclic cores with appropriately substituted carboxylic acid derivatives (R-CO₂H) using coupling conditions described in step 15D. Example I-40, I-44, I-49 to I-51, I-54, I-55, I-57, I-59 were prepared by coupling macrocyclic core with an appropriately substituted carboxylic acid derivative (R—CO₂H) using coupling conditions described in step 15D followed by chlorination as described in Example 7.

TABLE 1-3

Examples I-26 to I-59

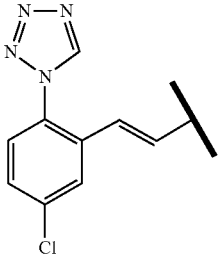

| Ex. # | R | R⁷ | R³ | LCMS [M + H]⁺ | HPLC RT (min) (method) |
|---|---|---|---|---|---|
| I-26 | 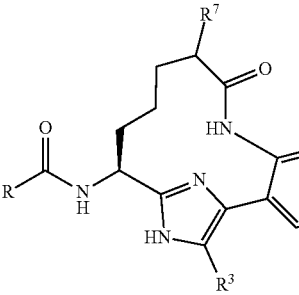 | F (homochiral) | H | 593.9 | 3.7 (B) |
| I-27 | 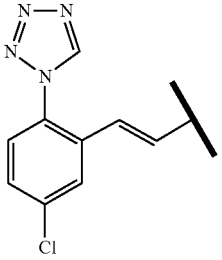 | F (homochiral) | H | 593.9 | 3.6 (B) |
| I-28 | 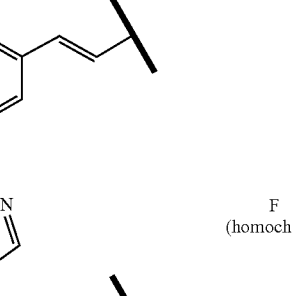 | Et | H | 604.1 | 4.2 (B) |

TABLE 1-3-continued
Examples I-26 to I-59
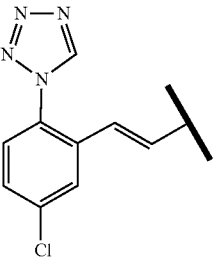
| Ex. # | R | R⁷ | R³ | LCMS [M + H]⁺ | HPLC RT (min) (method) |
|---|---|---|---|---|---|
| I-29 | 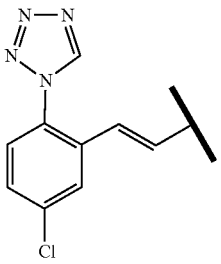 | Et | H | 604.1 | 4.2 (B) |
| I-30 | 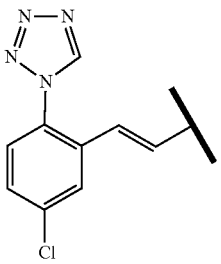 | OMe (homochiral) | H | 606.2 | 5.3 |
| I-31 | 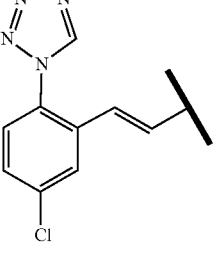 | OMe (homochiral) | H | 606.3 | 6.0 |
| I-32 | | Bis-F | H | 612.1 | 3.8 (B) |

TABLE 1-3-continued
Examples I-26 to I-59
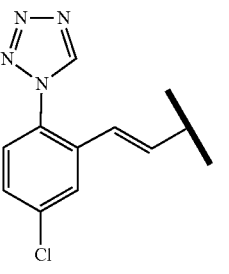
| Ex. # | R | R⁷ | R³ | LCMS [M + H]⁺ | HPLC RT (min) (method) |
|---|---|---|---|---|---|
| I-33 |  | 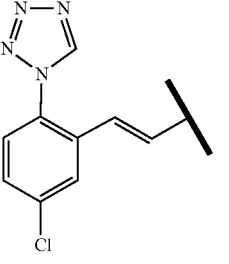<br>(diastereomer A) | H | 618.3 | 4.5 (B) |
| I-34 |  | 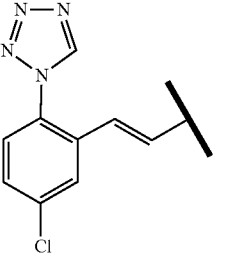<br>(diastereomer B) | H | 618.3 | 4.5 (B) |
| I-35 |  | Me (dashed wedge) | Cl | 624.3 | 7.0 |
| I-36 | 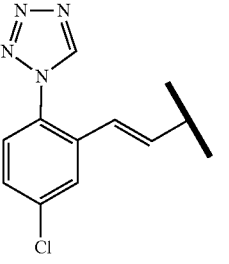 | Me (solid wedge) | Cl | 624.3 | 6.7 |

TABLE 1-3-continued

Examples I-26 to I-59

| Ex. # | R | R⁷ | R³ | LCMS [M + H]⁺ | HPLC RT (min) (method) |
|---|---|---|---|---|---|
| I-37 | tetrazolyl-(4-chloro-2-((E)-but-2-en-1-yl)phenyl) (diastereomer B) | isopropyl | Cl | 652.3 | 5.8 (B) |
| I-38 | tetrazolyl-(4-chloro-2-((E)-but-2-en-1-yl)phenyl) (diastereomer A) | isopropyl | Cl | 652.3 | 5.8 (B) |
| I-39 | 2,6-difluoro-4-methylphenyl | Me | H | 512.2 | 4.8 |
| I-40 | 2,6-difluoro-4-methylphenyl | Me | Cl | 546.2 | 6.9 |
| I-41 | 4,6-difluoro-1-methyl-1H-benzimidazol-5-yl | Me | H | 552.2 | 3.5 |

TABLE 1-3-continued
Examples I-26 to I-59
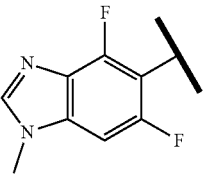
| Ex. # | R | R⁷ | R³ | LCMS [M + H]⁺ | HPLC RT (min) (method) |
|---|---|---|---|---|---|
| I-42 | 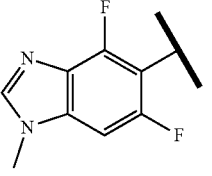 | Me (diastereomer mixture) | H | 552.4 | 3.3 |
| I-43 |  | 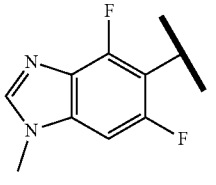 (diastereomer A) | H | 580.3 | 4.3 |
| I-44 | 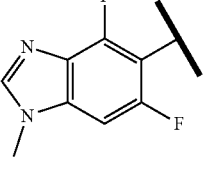 | Me (diastereomer mixture) | Cl | 586.3 | 4.7 4.9 |
| I-45 |  | Me | H | 552.3 | 2.9 |
| I-46 | 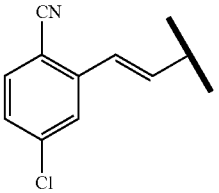 | Me | H | 547.3 | 5.2 |
| I-47 |  | Et | H | 561.3 | 5.7 |

TABLE 1-3-continued
Examples I-26 to I-59
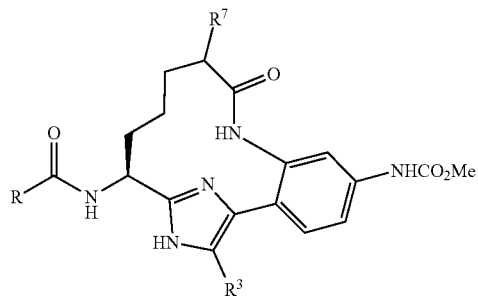
| Ex. # | R | R⁷ | R³ | LCMS [M + H]⁺ | HPLC RT (min) (method) |
|---|---|---|---|---|---|
| I-48 | 2-CN, 5-Cl phenyl CH=CH-CH(Me)- | iPr (diastereomer A) | H | 575.3 | 5.3 (B) |
| I-49 | 2-CN, 5-Cl phenyl CH=CH-CH(Me)- | Me | Cl | 581.3 | 7.5 |
| I-50 | 2-CN, 5-Cl phenyl CH=CH-CH(Me)- | Et | Cl | 595.3 | 7.7 |
| I-51 | 2-CN, 3-F, 4-Cl phenyl CH=CH-CH(Me)- | Me | Cl | 599.2 | 7.8 |
| I-52 | 2-OCHF₂, 5-Cl phenyl CH=CH-CH(Me)- | Et | H | 602.3 | 6.4 |

TABLE 1-3-continued
Examples I-26 to I-59
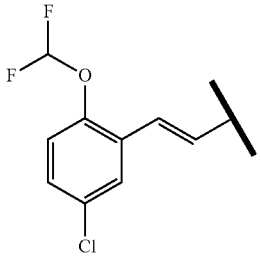
| Ex. # | R | R⁷ | R³ | LCMS [M + H]⁺ | HPLC RT (min) (method) |
|---|---|---|---|---|---|
| I-53 | 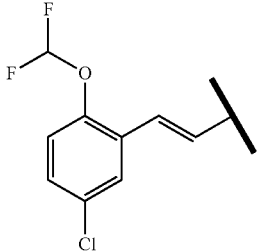 | Me | H | 588.2 | 5.9 |
| I-54 | 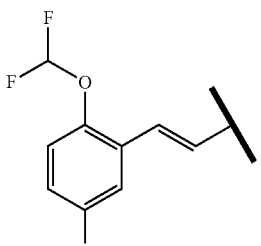 | Me | Cl | 622.3 | 7.9 |
| I-55 | 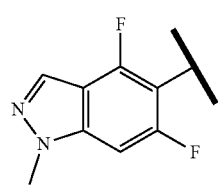 | Et | Cl | 636.3 | 8.4 |
| I-56 | 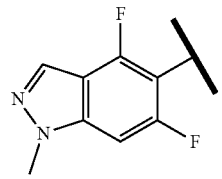 | Me | H | 552.3 | 3.8 (B) |
| I-57 |  | Me | Cl | 586.2 | 4.9 (B) |

TABLE 1-3-continued

Examples I-26 to I-59

| Ex. # | R | R⁷ | R³ | LCMS [M + H]⁺ | HPLC RT (min) (method) |
|---|---|---|---|---|---|
| I-58 | ![4-fluoro-6-fluoro-1-methyl-5-yl indazole] | Et | H | 566.4 | 4.6 |
| I-59 | ![4-fluoro-6-fluoro-1-methyl-5-yl indole] | Me | Cl | 585.4 | 7.7 |

Example I-60 was prepared following the procedures described in Example 7, by replacing Example 6 with Example 154.

Example I-61

{(9S,14S)-17-Chloro-14-[(E)-3-(5-chloro-2-tetrazol-1-yl-phenyl)-acryloylamino]-9-trifluoromethyl-8,16,18-triaza-tricyclo[13.2.1.0²,⁷]octadeca-1(17),2,4,6,15(18)-pentaen-5-yl}-carbamic Acid methyl ester, 2 TFA Salt

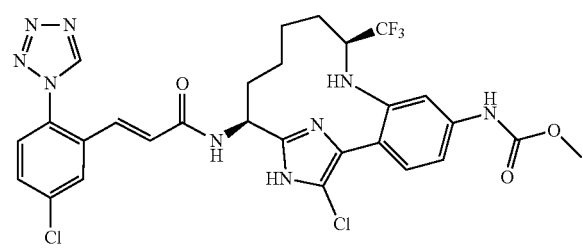 [SMILES: COC(=O)Nc1ccc2c(c1)N[C@H](C(F)(F)F)CCCC[C@H](NC(=O)/C=C/c1cc(Cl)ccc1-n1cnnn1)c1nc-2c(Cl)[nH]1]

I-61A and I-61AA. [(9S,14S)-17-Chloro-5-methoxycarbonylamino-9-trifluoromethyl-16-(2-trimethylsilanyl-ethoxymethyl)-8,16,18-triaza-tricyclo[13.2.1.0²,⁷]octadeca-1(17),2,4,6,15(18)-pentaen-14-yl]-carbamic acid tert-butyl ester, 2TFA salt (I-61A) and [(9S,14S)-4,17-Dichloro-5-methoxycarbonylamino-9-trifluoromethyl-16-(2-trimethyl-silanyl-ethoxymethyl)-8,16,18-triaza-tricyclo[13.2.1.0²,⁷] octadeca-1(17),2,4,6,15(18)-pentaen-14-yl]-carbamic acid tert-butyl ester, 2TFA salt (I-61AA): To the solution of 154C (diastereomer A) (0.124 g, 0.145 mmol) in acetonitrile (1 mL)/chloroform (1.000 mL) was added NCS (0.029 g, 0.217 mmol) and DIPEA (0.076 mL, 0.435 mmol). The reaction mixture was stirred at rt for 44 h. Another NCS (0.029 g, 0.217 mmol) added. After another 2.5 h, the reaction mixture was concentrated. Purification by reverse phase chromatography gave 0.024 g (18.6%) of I-61A as a yellow solid and 0.010 g (7.5%) of I-61AA as a white solid. For I-61A: MS (ESI) m/z: 662.4 (M+H)⁺. For I-61AA: MS (ESI) m/z: 696.3 (M+H)⁺.

I-61B. ((49S,14S)-14-Amino-17-chloro-9-trifluoromethyl-8,16,18-triaza-tricyclo[13.2.1.0²,⁷]octadeca-1(17),2,4,6,15(18)-pentaen-5-yl)-carbamic acid methyl ester, 3TFA salt: To the solution of I-61A (0.032 g, 0.036 mmol) in MeOH (0.5 mL) was added 5 N HCl (0.5 mL, 2.5 mmol) and methoxylamine hydrochloride (25-30 wt. % in water, 0.055 mL, 0.180 mmol). The reaction mixture was warmed to 75° C. for 1 h and then it was cooled to rt. Purification by reverse phase chromatography gave I-61B (0.02 g, 71.9%) as a white solid. MS (ESI) m/z: 432.2 (M+H)⁺.

I-61C. Example I-61 was prepared following the procedure described in 15D, by replacing 15C with I-61B. ¹H NMR (500 MHz, CD₃OD) δ ppm 9.50 (s, 1H), 7.98 (d, J=2.5 Hz, 1H), 7.66 (dd, J=8.5, 2.5 Hz, 1H), 7.57 (d, J=8.5 Hz, 1H), 7.30-7.34 (m, 2H), 7.12 (d, J=15.7 Hz, 1H), 7.07 (dd, J=8.3, 2.2 Hz, 1H), 6.77 (d, J=15.7 Hz, 1H), 5.14 (dd, J=10.6, 7.0 Hz, 1H), 3.74 (s, 3H), 2.84-2.92 (m, 1H), 2.13-2.22 (m, J=13.0, 13.0, 7.1, 2.9 Hz, 1H), 1.87-1.95 (m, 1H), 1.63-1.81 (m, 2H), 1.39-1.55 (m, 3H), 0.44-0.55 (m, 1H). ¹⁹F NMR (471MHz, CD₃OD) δ −74.96, −77.49. MS (ESI) m/z: 664.3 (M+H)⁺. Analytical HPLC, RT=8.89 min.

Examples I-62 to I-64 were synthesized by coupling the amine 155A, with appropriately substituted carboxylic acid derivatives (R—CO₂H) using coupling conditions described in step 15D. In the case of Examples I-62 and I-63 an additional Boc-deprotection step as described in step 3C was required.

Example I-67

(9S,14S)-14-[(E)-3-(5-Chloro-2-tetrazol-1-yl-phenyl)-acryloylamino]-5-methoxycarbonylamino-8,16,18-triaza-tricyclo[13.2.1.0$^{2,7}$]octadeca-1(17),2,4,6,15(18)-pentaene-9-carboxylic Acid ethyl ester, 2 TFA Salt

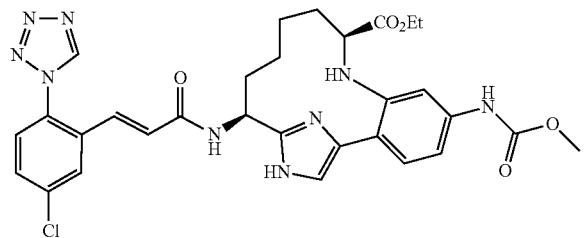 [SMILES: CCOC(=O)[C@@H]1CCCC[C@H](NC(=O)/C=C/c2cc(Cl)ccc2-n2cnnn2)c2nc(c[nH]2)-c2ccc(NC(=O)OC)cc2N1]

I-67A. 2-{2-[2-((S)-1-tert-Butoxycarbonylamino-but-3-enyl)-1-(2-trimethylsilanyl-ethoxymethyl)-1H-imidazol-4-yl]-5-methoxycarbonylamino-phenylamino}-pent-4-enoic acid ethyl ester. To a clear yellowish-brown solution of 10C (4.50 g, 8.46 mmol) and maleic acid (0.982 g, 8.46 mmol) in acetonitrile (33.9 mL) was added a 50% solution ethyl 2-oxoacetate in toluene (2.52 mL, 12.69 mmol) followed by allyltributyltin (4.72 mL, 15.23 mmol). The resulting orange solution was stirred vigorously. After 18 h, the reaction was diluted with EtOAc and then the reaction was washed with 1.0 N NaOH (75 mL×2), brine, dried over Na₂SO₄, filtered and concentrated to give a viscous, orange oil. Purification by normal phase chromatography gave 3.96 g (76%) of I-67A as an orange foam. ¹H NMR indicated approximately a 1:1 mixture of diastereomers. MS (ESI) m/z: 658.4 (M+H)⁺.

I-67B. (9R,14S)-14-tert-Butoxycarbonylamino-5-methoxycarbonylamino-16-(2-trimethylsilanyl-ethoxymethyl)-8,16,18-triaza-tricyclo[13.2.1.0$^{2,7}$]octadeca-1(17),2,4,6,15(18)-pentaene-9-carboxylic acid ethyl ester (Diastereomer A), 2 TFA salt and I-67C. (9S,14S)-14-tert-Butoxycarbonylamino-5-methoxycarbonylamino-16-(2-trimethylsilanyl-ethoxymethyl)-8,16,18-triaza-tricyclo[13.2.1.0$^{2,7}$]octadeca-1(17),2,4,6,15(18)-pentaene-9-carboxylic acid ethyl ester (Diastereomer B), 2 TFA salt.

Compounds I-67B (diastereomer A) and I-67C (diastereomer B) were prepared following the procedures described in I-74C, by replacing I-74B with I-67A; followed by step I-74D. The diastereomers were separated by reverse phase chromatography. MS (ESI) m/z: 632.5 (M+H)⁺.

I-67D. Example I-67 was prepared following the procedures described in 154E, by replacing 154D with I-67C (diastereomer B); followed by step 15D. ¹H NMR (500 MHz, CD₃OD) δ ppm 9.50 (s, 1H), 9.39 (s, 1H), 7.94 (d, J=2.2 Hz, 1H), 7.67 (dd, J=8.2, 2.2 Hz, 1H), 7.55-7.60 (m, 1H), 7.51 (s, 1H), 7.41 (s, 1H), 7.28-7.35 (m, J=8.2 Hz, 1H), 7.09-7.15 (m, 2H), 6.77 (d, J=15.4 Hz, 1H), 5.15 (t, J=6.6 Hz, 1H), 3.96-4.12 (m, 2H), 3.73 (s, 3H), 3.09 (d, J=10.4 Hz, 1H), 2.31-2.42 (m, 1H), 1.94-2.07 (m, 1H), 1.56-1.79 (m, 2H), 1.44-1.55 (m, 3H), 1.14 (t, J=7.2 Hz, 3H), 0.54-0.66 (m, 1H). MS (ESI) m/z: 634.3 (M+H)⁺ and 636.2 (M+2+H)⁺. Analytical HPLC (Method D): RT=4.9 min.

Example I-68

(9R,14S)-14-[(E)-3-(5-Chloro-2-tetrazol-1-yl-phenyl)-acryloylamino]-5-methoxycarbonylamino-8,16,18-triaza-tricyclo[13.2.1.0$^{2,7}$]octadeca-1(17),2,4,6,15(18)-pentaene-9-carboxylic Acid ethyl ester, 2 TFA Salt

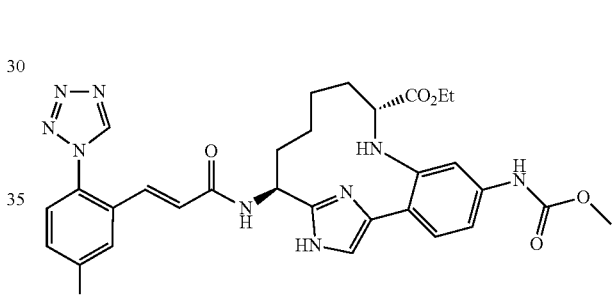

I-68A. (9R,14S)-14-Amino-5-methoxycarbonylamino-8,16,18-triaza-tricyclo[13.2.1.0$^{2,7}$]octadeca-1(17),2,4,6,15(18)-pentaene-9-carboxylic acid ethyl ester: Compound I-68A was prepared following the procedure described in 154E, by replacing 154D with I-67B (diastereomer A). MS (ESI) m/z: 632.5 (M+H)⁺.

I-68B. Example I-68 was prepared following the procedures described in 15D, by replacing 15C with I-68A. ¹H NMR (500 MHz, CD₃OD) δ ppm 9.51 (s, 1H), 9.41 (s, 1H), 7.98 (d, J=2.2 Hz, 1H), 7.68 (dd, J=8.8, 2.2 Hz, 1H), 7.58 (d, J=8.2 Hz, 1H), 7.56 (s, 1H), 7.44 (s, 1H), 7.35 (d, J=8.2 Hz, 1H), 7.12-7.19 (m, 2H), 6.77 (dd, J=15.4, 2.2 Hz, 1H), 5.20-5.30 (m, 1H), 3.94-4.11 (m, 2H), 3.74 (s, 3H), 3.05 (d, J=10.4 Hz, 1H), 2.22-2.37 (m, 1H), 1.96-2.07 (m, 1H), 1.72-1.93 (m, 2H), 1.37-1.62 (m, 3H), 1.12 (t, J=7.2 Hz, 3H), 0.30-0.43 (m, 1H). MS (ESI) m/z: 634.3 (M+H)⁺ and 636.2 (M+2+H)⁺. Analytical HPLC (Method D): RT=5.2 min.

Example I-69 was prepared by following the procedure described in 15D, by replacing 15C with I-68A and by replacing Intermediate 2 with Intermediate 3A.

TABLE 1-4
Examples I-60 to I-69
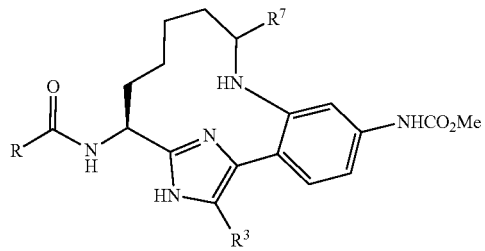
| Ex. # | R | R⁷ | R³ | LCMS [M + H]⁺ | HPLC RT (min) (method) |
|---|---|---|---|---|---|
| I-60 | 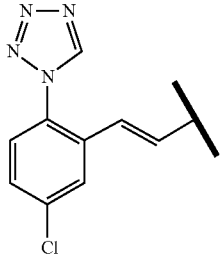 | CF₃ | Cl | 664.1 | 8.6 |
| I-61 | 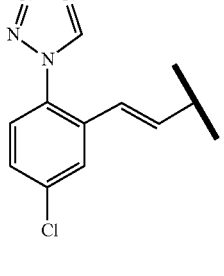 | CF₃ | Cl | 664.3 | 8.9 |
| I-62 | 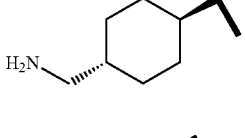 | CF₃ | H | 537.2 | 3.8 |
| I-63 | 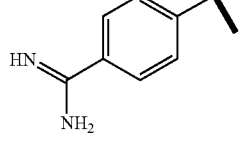 | CF₃ | H | 544.4 | 4.1 |
| I-64 | 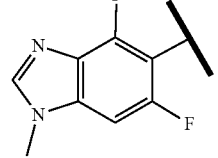 | CF₃ | H | 592.3 | 4.4 (D) |
TABLE 1-4-continued
Examples I-60 to I-69
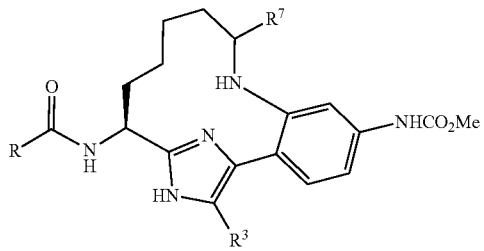
| Ex. # | R | R⁷ | R³ | LCMS [M + H]⁺ | HPLC RT (min) (method) |
|---|---|---|---|---|---|
| I-65 | 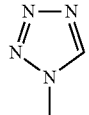 | CF₃ | F | 648.2 | 8.8 |
| I-66 | 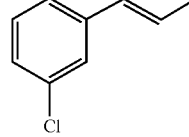 | CF₃ | F | 610.2 | 7.1 |
| I-67 | 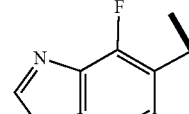 | CO₂Et | H | 634.3 | 4.9 (D) |
| I-68 | 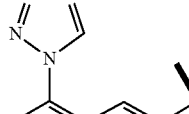 | CO₂Et | H | 634.3 | 5.2 (D) |

TABLE 1-4-continued

Examples I-60 to I-69

| Ex. # | R | R⁷ | R³ | LCMS [M + H]⁺ | HPLC RT (min) (method) |
|---|---|---|---|---|---|
| I-69 | (N—N tetrazole-phenyl with propenyl, F, Cl substituents) | CO₂Et | H | 652.3 | 5.7 (D) |

Examples I-72 and I-73 were prepared according to the procedures described for Example I-67, by replacing ethyl 2-oxoacetate with the appropriately substituted aldehydes.

Example I-74

(9R,14S)-14-[(E)-3-(5-Chloro-2-tetrazol-1-yl-phenyl)-acryloylamino]-5-methoxycarbonylamino-8,16,18-triaza-tricyclo[13.2.1.0²,⁷]octadeca-1(17),2,4,6,15 (18)-pentaene-9-carboxylic Acid methyl ester, 2 TFA Salt

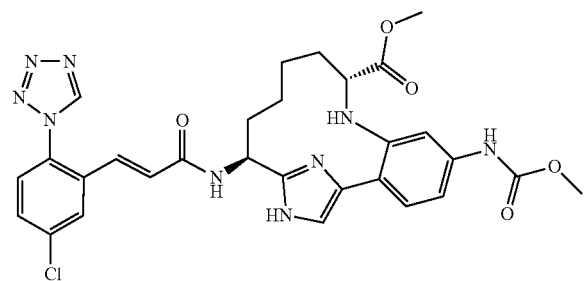 [SMILES: COC(=O)Nc1ccc2c(c1)N[C@@H](C(=O)OC)CCCC[C@H](NC(=O)/C=C/c1cc(Cl)ccc1-n1cnnn1)c1nc-2c[nH]1]

I-74A. (R)-2-(2-(2-((S)-1-(tert-Butoxycarbonylamino) but-3-enyl)-1-((2-(trimethylsilyl)ethoxy)methyl)-1H-imidazol-4-yl)-5-(methoxycarbonylamino)phenylamino)pent-4-enoic acid: A thick-walled flask was charged with 10B (5 g, 8.39 mmol), copper(I) iodide (0.160 g, 0.839 mmol), potassium carbonate (2.90 g, 20.99 mmol), (R)-2-aminopent-4-enoic acid (1.160 g, 10.07 mmol) and DMSO (16.8 mL). The flask was vacuumed and back-filled with argon three times and then the flask was sealed with a teflon screw cap. The reaction was capped, heated to 90° C. for 18 h, and then the reaction was cooled to RT. The reaction mixture was diluted with ethyl acetate and water and the layers were separated. The aqueous layer was extracted with EtOAc (2×). The combined organic layers were washed with brine, dried over $Na_2SO_4$ and concentrated to give I-74A (5.5 g, 83%) as a yellow solid. MS (ESI) m/z: 630.4 (M+H)⁺. The material was carried onto the next step without further purification.

I-74B. (R)-2-{2-[2-((S)-1-tert-Butoxycarbonylamino-but-3-enyl)-1-(2-trimethylsilanyl-ethoxymethyl)-1H-imidazol-4-yl]-5-methoxycarbonylamino-phenylamino}-pent-4-enoic acid methyl ester: To a solution of I-74A (5.5 g, 6.99 mmol) in DMF (100 mL) was added $K_2CO_3$ (0.966 g, 6.99 mmol) and MeI (0.437 mL, 6.99 mmol). The reaction was stirred at RT for 24 h. The reaction was partitioned between EtOAc and water and the layers were separated. The aqueous layer was extracted with EtOAc (1×). The combined organic layers were washed with water, brine, dried over $Na_2SO_4$, filtered and concentrated. Purification by normal phase chromatography gave I-74B (2.36 g, 52.5%) as brown solid. MS (ESI) m/z: 644.5 (M+H)⁺.

I-74C. (9R,14S)-14-tert-Butoxycarbonylamino-5-methoxycarbonylamino-16-(2-trimethylsilanyl-ethoxymethyl)-8,16,18-triaza-tricyclo[13.2.1.0²,⁷]octadeca-1(17),2,4,6,11,15(18)-hexaene-9-carboxylic acid methyl ester: A solution of I-74B (0.4 g, 0.621 mmol), Grubbs (II) (0.211 g, 0.249 mmol) in DCE (15.53 ml) was heated in a microwave at 120° C. for 20 min. The reaction was cooled to RT. The same reaction was repeated eight more times. All nine reactions were combined, washed with sat. $NaHCO_3$, brine, dried over $MgSO_4$, filtered and concentrated. Purification by normal phase chromatography gave I-74C (1.03 g, 30%) as a brown solid. MS (ESI) m/z: 616.5 (M+H)⁺.

I-74D. (9R,14S)-14-tert-Butoxycarbonylamino-5-methoxycarbonylamino-16-(2-trimethylsilanyl-ethoxymethyl)-8,16,18-triaza-tricyclo[13.2.1.0²,⁷]octadeca-1(17),2,4,6,15(18)-pentaene-9-carboxylic acid methyl ester (diastereomer A), 2 TFA salt and I-74E. (9S,14S)-14-tert-Butoxycarbonylamino-5-methoxy carbonylamino-16-(2-trimethylsilanyl-ethoxymethyl)-8,16,18-triaza-tricyclo [13.2.1.0²,⁷]octadeca-1(17),2,4,6,15(18)-pentaene-9-carboxylic acid methyl ester (diastereomer B), 2 TFA salt. To the solution of I-74C (1.03 g, 1.673 mmol) in EtOAc (15 mL)/EtOH (5.00 mL) was added TFA (0.258 ml, 3.35 mmol) and 10% palladium on carbon (0.178 g, 0.167 mmol). Hydrogen was bubbled through the reaction mixture for 5 min. The reaction was stirred under a hydrogen balloon for 4 days. The reaction was filtered through a 0.45pin GMF containing CELITE®. The solid was rinsed with MeOH, and the filtrate was concentrated. The residue was dissolved in EtOAc, washed with sat. $NaHCO_3$, brine, dried over $Na_2SO_4$, filtered and concentrated. Purification by normal phase chromatography gave I-74D (0.3 g, 29.0% yield) as a yellow solid. MS (ESI) m/z: 618.4 (M+H)⁺. A mixture of I-74D and I-74E (0.55 g) was also obtained as a yellow solid. This mixture was purified by reverse phase chromatography to give 0.325 g (23.0%) of I-74D (diastereomer A) as a white solid and 0.23 g (16.3%) I-74E (diastereomer B) as a white solid. For I-74D: MS (ESI) m/z: 618.5 (M+H)⁺. ¹H NMR (500 MHz, $CD_3OD$) δ ppm 7.73 (s, 1H), 7.37 (d, J=1.9 Hz, 1H), 7.30 (d, J=8.3 Hz, 1H), 7.17 (dd, J=8.4, 2.1 Hz, 1H), 5.66 (d, J=10.5 Hz, 1H), 5.53 (d, J=10.5 Hz, 1H), 5.12 (t, J=9.1 Hz, 1H), 3.65-3.77 (m, 5H), 3.51 (s, 3H), 3.03 (d, J=10.7 Hz, 1H), 2.07-2.16 (m, 2H), 1.68-1.81 (m, 2H), 1.31-1.55 (m, 12H), 0.90-1.04 (m, 2H), 0.26-0.38 (m, 1H), 0.01 (s, 9H). [α]=−6.9 (c=1.23, MeOH).

For I-74E: MS (ESI) m/z: 618.4 (M+H)⁺. ¹H NMR (500 MHz, $CD_3OD$) δ ppm 7.71 (s, 1H), 7.39 (s, 1H), 7.32 (d, J=8.3 Hz, 1H), 7.13-7.17 (m, 1H), 5.85 (d, J=10.7 Hz, 1H), 5.51 (d, J=11.0 Hz, 1H), 5.13 (t, J=6.3 Hz, 1H), 3.70-3.76

(m, 5H), 3.52-3.57 (m, 3H), 3.09 (dd, J=9.4, 3.3 Hz, 1H), 2.27-2.36 (m, 1H), 1.91-2.00 (m, 1H), 1.70-1.79 (m, 1H), 1.31-1.69 (m, 13H), 0.89-1.07 (m, 2H), 0.43-0.54 (m, 1H), 0.00 (s, 9H).

I-74F. (9R,14S)-14-Amino-5-methoxycarbonylamino-8,16,18-triaza-tricyclo[13.2.1.0$^{2,7}$]octadeca-1(17),2,4,6,15(18)-pentaene-9-carboxylic acid methyl ester: Compound I-74F was prepared following the procedure described in 154E, by replacing 154D with I-74D (diastereomer A). MS (ESI) m/z: 388.1 (M+H)$^+$.

I-74G. Example I-74 was prepared following the procedure described in 1G, by replacing 1F with I-74F. $^1$H NMR (400 MHz, CD$_3$OD) δ ppm 9.51 (s, 1H), 7.98 (d, J=2.2 Hz, 1H), 7.68 (dd, J=8.8, 2.2 Hz, 1H), 7.55-7.60 (m, 2H), 7.41 (d, J=2.2 Hz, 1H), 7.35 (d, J=8.2 Hz, 1H), 7.12-7.21 (m, 2H), 6.76 (d, J=15.4 Hz, 1H), 5.25 (dd, J=11.0, 7.1 Hz, 1H), 3.75 (s, 3H), 3.57 (s, 3H), 3.07 (d, J=10.4 Hz, 1H), 2.25-2.36 (m, 1H), 1.97-2.06 (m, 1H), 1.72-1.90 (m, 2H), 1.38-1.62 (m, 3H), 0.30-0.43 (m, 1H). MS (ESI) m/z: 620.3 (M+H)$^+$. Analytical HPLC: RT=5.66 min.

Example I-75 was prepared by following the procedure described in Example 7, by replacing Example 6 with Example I-74 and by running the reaction at rt in acetonitrile.

Example I-76

(9R,14S)-14-[(E)-3-(5-Chloro-2-tetrazol-1-yl-phenyl)-acryloylamino]-5-methoxycarbonylamino-8,16,18-triaza-tricyclo[13.2.1.0$^{2,7}$]octadeca-1(17),2,4,6,15(18)-pentaene-9-carboxylic Acid, 2 TFA Salt

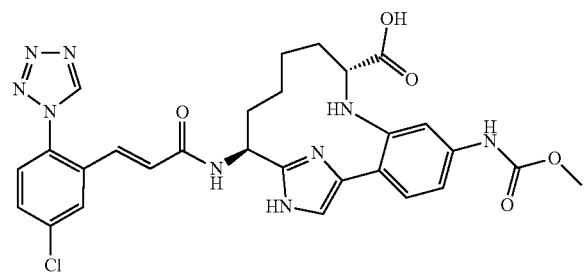 [SMILES: COC(=O)Nc1ccc2c(c1)N[C@@H](C(=O)O)CCCC[C@H](NC(=O)/C=C/c1cc(Cl)ccc1-n1cnnn1)c1nc-2c[nH]1]

I-76A. (9R,14S)-14-Amino-5-methoxycarbonylamino-8,16,18-triaza-tricyclo[13.2.1.0$^{2,7}$]octadeca-1(17),2,4,6,15(18)-pentaene-9-carboxylic acid, 3 HCl salt: To a clear, pale yellow solution of I-74F (0.079 g, 0.204 mmol) in MeOH (2.0 mL) was added 1N sodium hydroxide (0.408 ml, 0.408 mmol). The solution was stirred vigorously at 55° C. for 1.5 h, cooled to RT, acidified with 1.0 N HCl (1 mL), and concentrated to give I-76A (0.098 g, 0.187 mmol, 92% yield) as an off-white solid. MS (ESI) m/z: 374.1 (M+H)$^+$. The material was carried onto the next step without further purification.

I-76B. Example I-76 was prepared following the procedure described in 1G, by replacing 1F with I-76A. $^1$H NMR (500 MHz, CD$_3$OD) δ ppm 9.51 (s, 1H), 7.98 (d, J=2.2 Hz, 1H), 7.68 (dd, J=8.5, 2.2 Hz, 1H), 7.58 (d, J=8.5 Hz, 1H), 7.55 (s, 1H), 7.40 (d, J=1.9 Hz, 1H), 7.36 (d, J=8.5 Hz, 1H), 7.21 (dd, J=8.4, 2.1 Hz, 1H), 7.16 (d, J=15.7 Hz, 1H), 6.76 (d, J=15.7 Hz, 1H), 5.26 (dd, J=11.0, 7.2 Hz, 1H), 3.74 (s, 3H), 3.04 (d, J=10.2 Hz, 1H), 2.26-2.35 (m, J=13.3, 13.3, 7.2, 3.0 Hz, 1H), 1.98-2.06 (m, 1H), 1.73-1.94 (m, 2H), 1.44-1.63 (m, 3H), 0.35-0.46 (m, 1H). MS (ESI) m/z: 606.3 (M+H)$^+$. Analytical HPLC: RT=5.47 min.

Example I-77

{(9R,14S)-14-[(E)-3-(5-Chloro-2-tetrazol-1-yl-phenyl)-acryloylamino]-9-hydroxymethyl-8,16,18-triaza-tricyclo[13.2.1.0$^{2,7}$]octadeca-1(17),2,4,6,15(18)-pentaen-5-yl}-carbamic Acid methyl ester, 2 TFA Salt

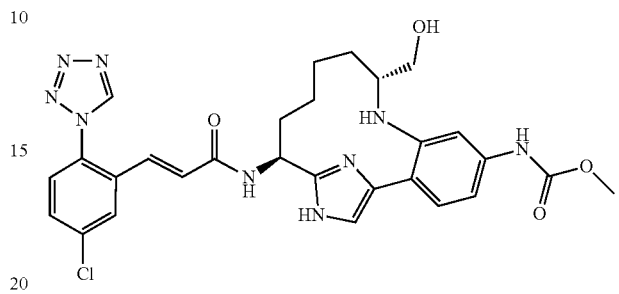

I-77A. [(9R,14S)-14-tert-Butoxycarbonylamino-9-hydroxymethyl-16-(2-trimethylsilanyl-ethoxymethyl)-8,16,18-triaza-tricyclo[13.2.1.0$^{2,7}$]octadeca-1(17),2,4,6,15(18)-pentaen-5-yl]-carbamic acid methyl ester: To a cooled (0° C.) solution of I-74D (0.22 g, 0.356 mmol) in THF (5 mL) was added LAH (0.178 ml, 0.356 mmol) (2M in THF). The reaction was allowed to stir at 0° C. After 1 h, additional LAH (0.05 ml, 0.1 mmol) (2M in THF) was added. After an additional 1 h, the reaction was quenched with 1 N HCl (aq, 1 mL). The reaction was diluted with EtOAc, washed with sat. NaHCO$_3$, brine, dried over Na$_2$SO$_4$, filtered and concentrated to give 0.217 g (103%) of I-77A as a yellow solid. MS (ESI) m/z: 590.5 (M+H)$^+$. The material was carried onto the next step without further purification.

I-77B. Example I-77 was prepared following the procedures described in 154E, by replacing 154D with I-77A; followed by step 15D. $^1$H NMR (500 MHz, CD$_3$OD) δ ppm 9.51 (s, 1H), 7.99 (d, J=2.2 Hz, 1H), 7.65-7.71 (m, 2H), 7.53-7.61 (m, 2H), 7.49 (s, 1H), 7.30 (dd, J=8.5, 2.2 Hz, 1H), 7.16 (d, J=15.7 Hz, 1H), 6.77 (d, J=15.7 Hz, 1H), 5.29 (dd, J=11.1, 6.7 Hz, 1H), 3.76 (s, 3H), 3.52 (dd, J=11.6, 4.7 Hz, 1H), 3.39-3.43 (m, 1H), 2.82-2.88 (m, 1H), 2.16-2.26 (m, J=13.0, 13.0, 6.9, 3.4 Hz, 1H), 1.98-2.09 (m, 2H), 1.86-1.94 (m, 1H), 1.44-1.64 (m, 3H), 0.58-0.69 (m, 1H). MS (ESI) m/z: 592.4 (M+H)$^+$. Analytical HPLC: RT=5.62 min.

Example I-78

{(9R,14S)-14-[(E)-3-(5-Chloro-2-tetrazol-1-yl-phenyl)-acryloylamino]-9-dimethylcarbamoyl-8,16,18-triaza-tricyclo[13.2.1.0$^{2,7}$]octadeca-1(17),2,4,6,15(18)-pentaen-5-yl}-carbamic Acid methyl ester, 2 TFA Salt

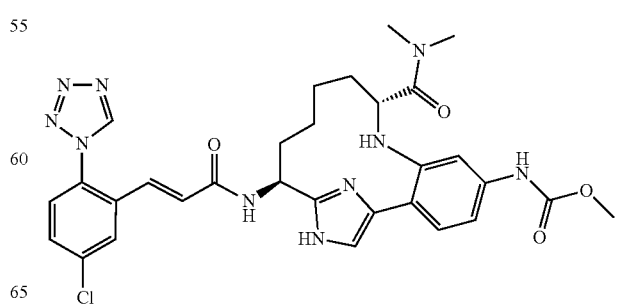

I-78A. (9R,14S)-14-tert-Butoxycarbonylamino-5-methoxycarbonylamino-16-(2-trimethylsilanyl-ethoxymethyl)-8,16,18-triaza-tricyclo[13.2.1.0$^{2,7}$]octadeca-1(17),2,4,6,15(18)-pentaene-9-carboxylic acid, 2 HCl salt: Compound I-78A was prepared by following the procedure described in I-76A, by replacing I-74F with I-74D. MS (ESI) m/z: 604.5 (M+H)$^+$. The material was carried onto the next step without further purification.

I-78B. [(9R,14S)-9-Dimethylcarbamoyl-5-methoxycarbonylamino-16-(2-trimethylsilanyl-ethoxymethyl)-8,16,18-triaza-tricyclo[13.2.1.0$^{2,7}$]octadeca-1(17),2,4,6,15(18)-pentaen-14-yl]-carbamic acid tert-butyl ester: To the solution of I-78A (0.088 g, 0.074 mmol) in DMF (2 mL) was added EDC (0.028 g, 0.148 mmol), HOBT (0.023 g, 0.148 mmol), dimethylamine, HCl (7.26 mg, 0.089 mmol) and TEA (0.041 mL, 0.297 mmol). The reaction was stirred at RT. After 18 h, the reaction was diluted with EtOAc and then washed with water, sat. NaHCO$_3$, brine, dried over Na$_2$SO$_4$, filtered and concentrated to give 0.047 g (100%) of I-78B as a brown solid. MS (ESI) m/z: 631.5 (M+H)$^+$. The material was carried onto the next step without further purification.

I-78C. Example I-78 was prepared following the procedures described in 154E, by replacing 154D with I-78B; followed by step 1G. $^1$H NMR (500 MHz, CD$_3$OD) δ ppm 9.51 (s, 1H), 7.98 (d, J=2.2 Hz, 1H), 7.68 (dd, J=8.5, 2.2 Hz, 1H), 7.56-7.63 (m, 2H), 7.38 (d, J=8.5 Hz, 1H), 7.29 (dd, J=8.3, 1.9 Hz, 1H), 7.24 (d, J=1.4 Hz, 1H), 7.16 (d, J=15.7 Hz, 1H), 6.76 (d, J=15.7 Hz, 1H), 5.27 (dd, J=11.3, 7.2 Hz, 1H), 3.75 (s, 3H), 3.52 (d, J=10.7 Hz, 1H), 2.80 (s, 3H), 2.66 (s, 3H), 2.26-2.36 (m, 1H), 1.87-2.06 (m, 2H), 1.68-1.77 (m, 1H), 1.56-1.66 (m, 1H), 1.43-1.54 (m, 1H), 1.25-1.33 (m, 1H), 0.32-0.43 (m, 1H). MS (ESI) m/z: 633.5 (M+H)$^+$.

Analytical HPLC: RT=6.64 min.

Example I-79

{(9R,14S)-14-[(E)-3-(5-Chloro-2-tetrazol-1-yl-phenyl)-acryloylamino]-9-methylcarbamoyl-8,16,18-triaza-tricyclo[13.2.1.0$^{2,7}$]octadeca-1(17),2,4,6,15(18)-pentaen-5-yl}-carbamic Acid methyl ester, 2 TFA Salt

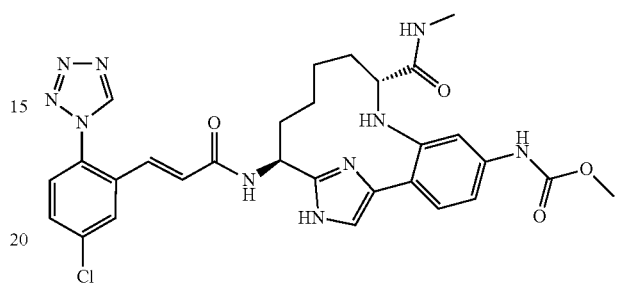

Example I-79 was prepared following the procedure described in 15D, by replacing Intermediate 2 with Example I-76 and by replacing 15C with methanamine hydrochloride. $^1$H NMR (500 MHz, CD$_3$OD) δ ppm 9.51 (s, 1H), 7.98 (d, J=2.5 Hz, 1H), 7.68 (dd, J=8.5, 2.2 Hz, 1H), 7.58 (d, J=8.5 Hz, 1H), 7.53 (s, 1H), 7.37-7.41 (m, 1H), 7.25-7.29 (m, 2H), 7.16 (d, J=15.7 Hz, 1H), 6.76 (d, J=15.7 Hz, 1H), 5.26 (dd, J=11.1, 7.0 Hz, 1H), 3.74 (s, 3H), 3.03 (dd, J=11.7, 1.5 Hz, 1H), 2.57 (s, 3H), 2.24-2.33 (m, 1H), 1.76-2.03 (m, 3H), 1.41-1.58 (m, 2H), 1.26-1.34 (m, 1H), 0.43-0.54 (m, 1H). MS (ESI) m/z: 619.4 (M+H)$^+$. Analytical HPLC: RT=4.78 min.

Examples I-80 and I-81 were prepared according to Example I-79 by replacing methanamine hydrochloride with the appropriately substituted amines. Examples I-82 to I-85 were prepared according to the procedures described for Examples I-74 to I-77. Examples I-86 to I-100 were prepared according to the procedures described for Example I-67, by replacing ethyl 2-oxoacetate with the appropriately substituted aldehydes. For the preparation of compounds I-99 and I-100, the Boc and SEM deprotection was accomplished by replacing the 4M HCl in dioxane, cysteine at 75° C. with 5M aqueous H$_2$SO$_4$, cysteine in methanol at 75° C.

TABLE 1-5

Examples I-70 to I-100

| Ex. # | R$^7$ | R$^3$ | LCMS [M + H]$^+$ | HPLC RT (min) (method) |
|---|---|---|---|---|
| I-70 | CF$_3$ | Me | 644.4 | 6.3 |

TABLE 1-5-continued
Examples I-70 to I-100
| Ex. # | R⁷ | R³ | LCMS [M + H]⁺ | HPLC RT (min) (method) |
|---|---|---|---|---|
| I-71 | CF₃ (wedge) | Me | 644.4 | 6.5 |
| I-72 | CHF₂ (hash) | H | 612.2 | 6.0 |
| I-73 | CHF₂ (wedge) | H | 612.2 | 6.1 |
| I-74 | CO₂Me (hash) | H | 620.3 | 5.6 |
| I-75 | CO₂Me (hash) | Cl | 654.3 | 6.9 (D) |
| I-76 | CO₂H (hash) | H | 606.3 | 4.6 |
| I-77 | CH₂OH (hash) | H | 592.4 | 5.6 |
| I-78 | CON(Me)₂ (hash) | H | 633.3 | 5.5 |
| I-79 | CONHMe (hash) | H | 619.4 | 4.8 |
| I-80 | pyrrolidine amide (hash) | H | 659.4 | 6.5 (D) |
| I-81 | N-methyl-N-(2-dimethylaminoethyl)amide (hash) | H | 690.4 | 5.6(D) |
| I-82 | CO₂Me (wedge) | H | 620.2 | 5.6 |
| I-83 | CO₂Me (wedge) | Cl | 654.2 | 7.5 |
| I-84 | CO₂H (wedge) | H | 606.3 | 5.1 |

TABLE 1-5-continued
Examples I-70 to I-100
| Ex. # | R[7] | R[3] | LCMS [M + H]+ | HPLC RT (min) (method) |
|---|---|---|---|---|
| I-85 | CH₂OH | H | 592.3 | 4.3 |
| I-86 | 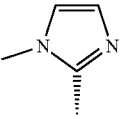 | H | 642.3 | 4.6 |
| I-87 | 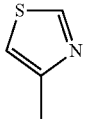<br>(diastereomer mixture) | H | 645.2 | 5.4<br>6.0 |
| I-88 | 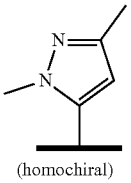<br>(homochiral) | H | 656.3 | 5.4 |
| I-89 | 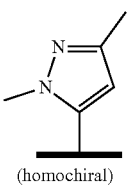<br>(homochiral) | H | 656.4 | 5.4 |
| I-90 | 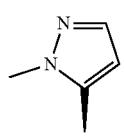 | H | 642.3 | 5.3 |
| I-91 | 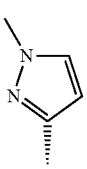 | H | 642.3 | 5.8 |
| I-92 | 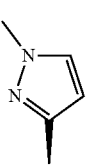 | H | 642.3 | 5.7 |

TABLE 1-5-continued
Examples I-70 to I-100
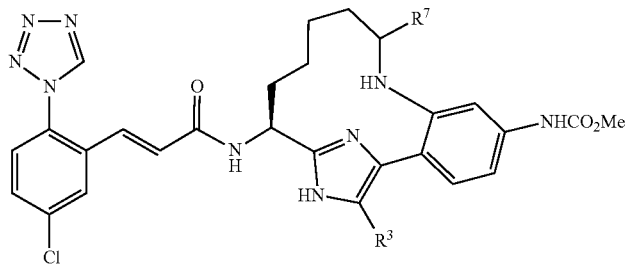
| Ex. # | R⁷ | R³ | LCMS [M + H]⁺ | HPLC RT (min) (method) |
|---|---|---|---|---|
| I-93 | 4-chloro-1-methylpyrazol-3-yl (dashed wedge) | H | 676.3 | 7.2 |
| I-94 | 4-chloro-1-methylpyrazol-3-yl (solid wedge) | H | 676.3 | 7.1 |
| I-95 | 1-propylpyrazol-3-yl (solid wedge) | H | 670.4 | 7.3 |
| I-96 | 1-propylpyrazol-3-yl (dashed wedge) | H | 670.3 | 7.3 |
| I-97 | Me (diastereomer A) | H | 576.3 | 5.6 |
| I-98 | Me (diastereomer B) | H | 576.3 | 5.5 |
| I-99 | 3-methyloxetan-3-yl (diastereomer B) | H | 632.4 | 6.8 |
| I-100 | 3-methyloxetan-3-yl (diastereomer A) | H | 632.3 | 9.3 |

Example I-103

(S)-14-[(E)-3-(5-Chloro-2-tetrazol-1-yl-phenyl)-acryloylamino]-5-methoxycarbonylamino-9-trifluoromethyl-8,16,18-triaza-tricyclo[13.2.1.0²,⁷]octadeca-1(17),2,4,6,15(18)-pentaene-9-carboxylic Acid methyl ester

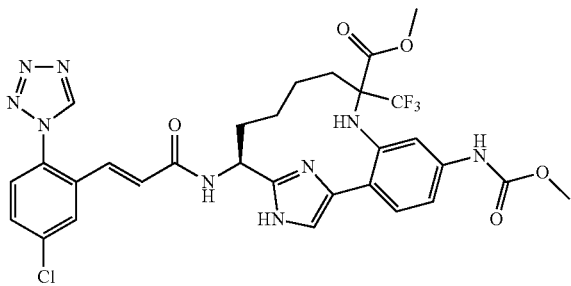 [SMILES: COC(=O)Nc1ccc2c(c1)NC(C(=O)OC)(C(F)(F)F)CCCC[C@H](NC(=O)/C=C/c1cc(Cl)ccc1-n1cnnn1)c1nc-2c[nH]1]

I-103A. 2-{(E)-2-[2-((S)-1-tert-Butoxycarbonylamino-but-3-enyl)-1-(2-trimethylsilanyl-ethoxymethyl)-1H-imidazol-4-yl]-5-methoxycarbonylamino-phenylimino}-3,3,3-trifluoro-propionic acid methyl ester: To a solution of Example 10C (164 mg, 0.308 mmol), methyl 3,3,3-trifluoro-2-oxopropanoate (39 mg, 0.250 mmol) and triethylamine (95 µl, 0.679 mmol) in 1 ml Toluene (Volume: 1028 µl) at 0° C. under Ar was added titanium(IV) chloride (1M in DCM) (308 µl, 0.308 mmol) dropwise. After addition, the ice bath was removed and the reaction was stirred at rt overnight. The reaction mixture was quenched with 1N NaOH (aq), partitioned between water and DCM, DCM layer dried over Na2SO₄, filtered off solid, concentrated to yield an orange oil. Purification by normal phase chromatography gave I-103A (95 mg, 46%) as an orange solid. MS (ESI) m/z: 670.4 (M+H)⁺.

I-103B. 2-{2-[2-((S)-1-Amino-but-3-enyl)-1-(2-trimethylsilanyl-ethoxymethyl)-1H-imidazol-4-yl]-5-methoxycarbonylamino-phenylamino}-2-trifluoromethyl-pent-4-enoic acid methyl ester: To a solution of I-103A (87 mg, 0.130 mmol) in CH₂Cl₂ (Volume: 2 mL) was added allyltrimethylsilane (0.15 mL, 0.940 mmol). The reaction was cooled down to −78° C. under Ar. Perchlorostannane (1M in DCM) (0.162 mL, 0.162 mmol) was added dropwise. After addition, the dry ice acetone bath was removed and the reaction was warmed up to rt and stirred for 2 days. The reaction mixture was concentrated under vacuo to yield a crude solid product. Purification by reverse phase chromatography gave I-103B (35 mg, 44%) as a pale yellow solid. MS (ESI) m/z: 612.3 (M+H)⁺.

I-103C. 2-{2-[2-((S)-1-tert-Butoxycarbonylamino-but-3-enyl)-1-(2-trimethylsilanyl-ethoxymethyl)-1H-imidazol-4-yl]-5-methoxycarbonylamino-phenylamino}-2-trifluoromethyl-pent-4-enoic acid methyl ester: To a solution of I-103B (35 mg, 0.057 mmol) in Dioxane (Volume: 0.3 mL) was added di-tert-butyl dicarbonate (0.020 mL, 0.086 mmol) and sodium hydroxide (1N in aq) (0.229 mL, 0.229 mmol). The reaction was stirred at RT for 3 hrs, diluted with EtOAc, washed with water and brine, dried over Na₂SO₄, filtered, and concentrated. Purification by normal phase chromatography gave I-103C (20 mg, 49%) as a pale yellow solid. MS (ESI) m/z: 712.5 (M+H)⁺.

I-103D. Example I-103 was prepared following the procedures described in I-74C by replacing I-74B with I-103C; followed by steps I-74D/I-74E; I-74F; I-74G. ¹H NMR (500 MHz, CD₃OD) δ ppm 9.51 (s, 1H), 7.98 (d, J=1.9 Hz, 1H), 7.67 (d, J=2.2 Hz, 1H), 7.54-7.61 (m, 1H), 7.36 (s, 3H), 7.11-7.22 (m, 2H), 6.71-6.81 (m, 1H), 5.03-5.12 (m, 1H), 3.73 (s, 3H), 3.67 (s, 3H), 2.77-2.90 (m, 1H), 1.99-2.17 (m, 2H), 1.55-1.73 (m, 2H), 1.42-1.54 (m, 1H), 0.93-1.07 (m, 1H), 0.80-0.93 (m, 1H). MS (ESI) m/z: 688.3 (M+H)⁺.

Example I-106

{(S)-14-[(E)-3-(5-Chloro-2-tetrazol-1-yl-phenyl)-acryloylamino]-9-oxo-8,16,18-triaza-tricyclo[13.2.1.0²,⁷]octadeca-1(17),2,4,6,10,15(18)-hexaen-5-yl}-carbamic Acid methyl ester (90755-098)

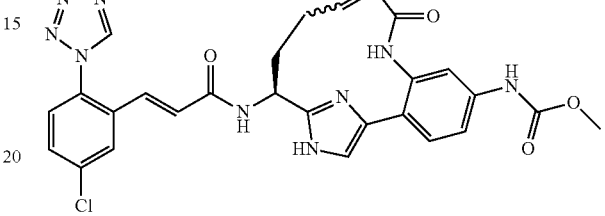

I-106A. [(S)-5-Methoxycarbonylamino-9-oxo-16-(2-trimethylsilanyl-ethoxymethyl)-8,16,18-triaza-tricyclo[13.2.1.0²,⁷]octadeca-1(17),2,4,6,10,15(18)-hexaen-14-yl]-carbamic acid tert-butyl ester: To a solution of mixture of 152A,152B and 152C (20 mg, 0.034 mmol) in 0.5 ml DCM at −78° C. under Ar was added methanesulfonyl chloride (5.83 mg, 0.051 mmol) in 0.5 ml DCM dropwise. After 5 mins, triethylamine (10.29 mg, 0.102 mmol) was added dropwise. The reaction bath was replaced with ice-salt bath, gradually warmed up to 0° C. The reaction mixture was partitioned between water and DCM. DCM layer washed with brine, dried over Na₂SO₄, filtered, and concentrated. Purification by reverse phase chromatography gave I-106A (5.3 mg, 27%) as a pale yellow solid. MS (ESI) m/z: 572.3 (M+H)⁺.

I-106B. Example I-106 was prepared following the procedures described in 1F, by replacing 1D with I-106A; followed by step 1G. ¹H NMR (500 MHz, CD₃OD) δ ppm 9.65-9.77 (m, 1H), 9.51-9.56 (m, 1H), 7.92-8.06 (m, 1H), 7.65-7.74 (m, 1H), 7.56-7.64 (m, 2H), 7.36-7.55 (m, 3H), 7.18-7.28 (m, 1H), 6.61-6.76 (m, 1H), 5.21-5.48 (m, 1H), 4.40-4.64 (m, 1H), 3.74-3.80 (m, 3H), 2.09-2.61 (m, 4H). MS (ESI) m/z: 574.1 (M+H)⁺. Analytical HPLC: RT=3.91 min. (Method B).

Example I-107

{(E)-(S)-14-[(E)-3-(5-Chloro-2-tetrazol-1-yl-phenyl)-acryloylamino]-17-fluoro-8,16,18-triaza-tricyclo[13.2.1.0²,⁷]octadeca-1(17),2,4,6,8,15(18)-hexaen-5-yl}-carbamic Acid methyl ester, trifluoroacetic Acid Salt

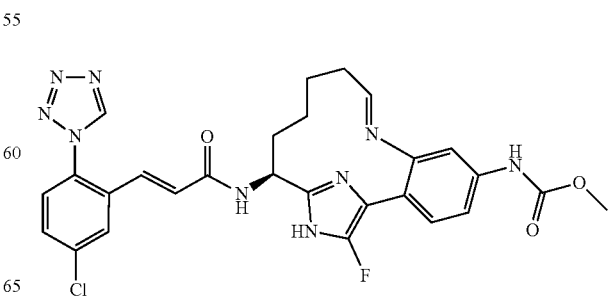

I-107A. ((E)-(S)-14-Amino-17-fluoro-8,16,18-triaza-tricyclo[13.2.1.0²,⁷]octadeca-1(17),2,4,6,8,15(18)-hexaen-5-yl)-carbamic acid methyl ester: To a yellow suspension of I-20B (18.67 mg, 0.043 mmol) in THF (4 mL) was added borane-THF complex (1M) (0.430 mL, 0.430 mmol) dropwise. It was sealed and heated at 60° C. for 1 hr and then cooled down to rt. To the solution was added MeOH, followed by 0.5 ml HCl (4M in dioxane). The reaction mixture was sealed and stored at rt overnight. The reaction mixture was then concentrated and purified by reverse phase chromatography to yield I-107A (4 mg, 25%). ¹H NMR (400 MHz, CD₃OD) δ ppm 7.31 (d, J=8.34 Hz, 1H) 7.16 (d, J=1.52 Hz, 1H) 6.79 (dd, J=8.46, 2.15 Hz, 1H) 5.69 (dd, J=9.98, 3.41 Hz, 1H) 4.69 (dd, J=11.37, 4.04 Hz, 1H) 3.68-3.77 (m, 3H) 2.11-2.32 (m, 1H) 1.43-2.03 (m, 6H) 0.68-0.97 (m, 1H). MS (ESI) m/z: 329.3 (M+H−NH₃)⁺.

I-107B. Example I-107 was prepared following the procedures described in step 1G, by replacing 1F with I-107A. ¹H NMR (400 MHz, CD₃OD) δ ppm 9.52 (s, 1H) 8.02 (d, J=2.26 Hz, 1H) 7.66 (dd, J=8.53, 2.26 Hz, 1H) 7.50-7.59 (m, 1H) 7.27 (d, J=8.03 Hz, 1H) 7.13 (d, J=15.56 Hz, 2H) 6.73-6.90 (m, 2H) 5.74 (br. s., 1H) 5.18 (br. s., 1H) 3.72 (s, 3H) 2.03-2.19 (m, 1H) 1.55-1.97 (m, 5H) 1.07-1.23 (m, 2H). ¹⁹F NMR (376 MHz, CD₃OD) δ ppm −139.71 (br. s., 1F). MS(ESI) m/z: 578.3 (M+H)⁺.

Example I-109

{(10R,14S)-14-[(E)-3-(5-Chloro-2-tetrazol-1-yl-phenyl)-acryloylamino]-10-methyl-8,16,18-triaza-tricyclo[13.2.1.02,7]octadeca-1(17),2,4,6,15(18)-pentaen-5-yl}-carbamic Acid methyl ester, 2TFA Salt

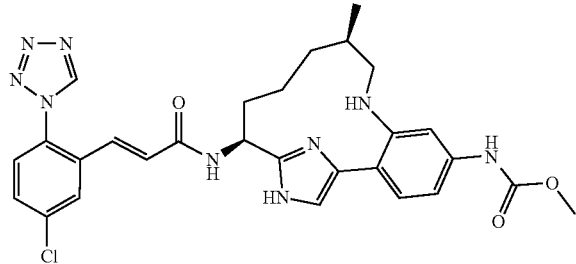

I-109A. ((10R,14S)-14-Amino-10-methyl-9-oxo-8,16,18-triaza-tricyclo[13.2.1.02,7]octadeca-1(17),2,4,6,15(18)-pentaen-5-yl)-carbamic acid methyl ester, 3 HCl salt: I-109A was prepared following the procedure described in 1F, by replacing 1D with 116G.

I-109B. ((10R,14S)-14-Amino-10-methyl-8,16,18-triaza-tricyclo[13.2.1.02,7]octadeca-1(17),2,4,6,15(18)-pentaen-5-yl)-carbamic acid methyl ester, 3 TFA salt: To a yellow suspension of I-109A HCl salt (0.05 g, 0.116 mmol) in tetrahydrofuran (5 mL) was added Borane-THF complex (1M) (1.162 mL, 1.162 mmol), The reaction became clear colorless. It was sealed and heated at 60° C. for 1 hr before cooling down to rt. MeOH was added followed by addition of 1 ml HCl (4M in dioxane). The reaction was sealed and heated at 60° C. overnight. The reaction mixture was concentrated, dissolved in MeOH, filtered off solid. Purification by reverse phase chromatography gave I-109B (5.3 mg, 27%) as a pale yellow solid. MS (ESI) m/z: 344.3 (M+H)⁺.

I-109C. Example I-109 was prepared following the procedures described in 1G, by replacing 1F with I-109B. ¹H NMR (500 MHz, CD₃OD) δ ppm 9.54 (s, 1H), 8.03 (d, J=2.5 Hz, 1H), 7.71-7.76 (m, 1H), 7.69 (dd, J=8.5, 2.2 Hz, 1H), 7.61 (d, J=8.5 Hz, 1H), 7.43-7.49 (m, 1H), 7.23-7.32 (m, 3H), 6.83 (d, J=15.7 Hz, 1H), 5.31 (dd, J=11.3, 6.3 Hz, 1H), 3.69 (s, 3H), 3.02-3.04 (m, 1H), 2.99-3.02 (m, 1H), 2.67-2.74 (m, 1H), 2.24-2.39 (m, 2H), 2.05-2.15 (m, 1H), 1.83-1.92 (m, 1H), 1.54-1.65 (m, 1H), 1.40-1.51 (m, 1H), 0.96 (d, J=7.2 Hz, 3H). MS (ESI) m/z: 576.2 (M+H)⁺. Analytical HPLC: RT=6.26 min.

Example I-115

{(S)-14-[(E)-3-(5-Chloro-2-tetrazol-1-yl-phenyl)-acryloylamino]-17-cyano-8,16,18-triaza-tricyclo [13.2.1.0²,⁷]octadeca-1(17),2,4,6,15 (18)-pentaen-5-yl}-carbamic Acid methyl ester, 2 TFA Salt

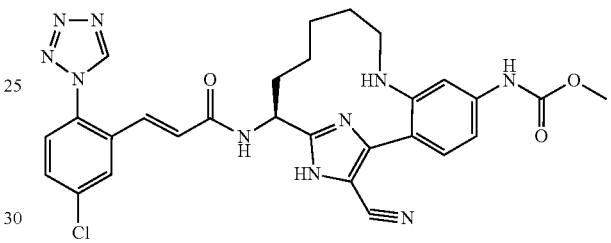

I-115A. [(S)-5-Methoxycarbonylamino-16-(2-trimethyl-silanyl-ethoxymethyl)-8,16,18-triaza-tricyclo[13.2.1.0²,⁷] octadeca-1(17),2,4,6,15(18)-pentaen-14-yl]-carbamic acid tert-butyl ester: I-115A was prepared from 10B following the procedures described in step 10C, by replacing ammonium hydroxide with but-3-enylamine and running the reaction at 90° C.; followed by steps 2E/F; and 10G, by adding 2 equiv. of TFA and replacing the methanol/EtOAc mixture with EtOAc. MS (ESI) m/z: 560.5 (M+H)⁺.

I-115B. [(S)-5-Methoxycarbonylamino-8-(2,2,2-trifluoro-acetyl)-16-(2-trimethylsilanyl-ethoxymethyl)-8,16, 18-triaza-tricyclo[13.2.1.0²,⁷]octadeca-1(17),2,4,6,15(18)-pentaen-14-yl]-carbamic acid tert-butyl ester: A mixture of 115A (1.21 g, 2.162 mmol) and TEA (0.362 ml, 2.59 mmol) in EtOAc (10.81 ml) was cooled to 0° C. under Argon, and then TFAA (0.336 ml, 2.378 mmol) was added dropwise. After ~2 h at 0° C., the reaction mixture was diluted with EtOAc, washed with water (2x) and brine, dried over MgSO₄, filtered, and concentrated. Residue was purified by flash column chromatography to yield I-115B as an off-white foam (1.14 g, 80%). MS (ESI) m/z: 656.5 (M+H)⁺.

I-115C. [(S)-17-Bromo-5-methoxycarbonylamino-8-(2,2, 2-trifluoro-acetyl)-16-(2-trimethylsilanyl-ethoxymethyl)-8, 16,18-triaza-tricyclo[13.2.1.0²,⁷]octadeca-1(17),2,4,6,15 (18)-pentaen-14-yl]-carbamic acid tert-butyl ester: To a cooled (<0° C.) solution of I-115B (1.14 g, 1.738 mmol) in CHCl₃ (5.79 ml) was added NBS (0.325 g, 1.825 mmol). The reaction was stirred under argon at 0° C. for 20 min. Reaction mixture was evaporated and residue purified by flash column chromatography to yield I-115C as a light peach foam (1.3 g, 102%). MS (ESI) m/z: 734.5 (M+H)⁺.

I-115D. [(S)-17-Cyano-5-methoxycarbonylamino-8-(2,2, 2-trifluoro-acetyl)-16-(2-trimethylsilanyl-ethoxymethyl)-8, 16,18-triaza-tricyclo[13.2.1.0²,⁷]octadeca-1(17),2,4,6,15 (18)-pentaen-14-yl]-carbamic acid tert-butyl ester: In a microwave vial, I-115C (0.1 g, 0.136 mmol) was added to a solution of zinc cyanide (0.016 g, 0.136 mmol) in DMF (2.72 ml). The mixture was evacuated/flushed with Ar three times, and then tetrakis(triphenylphosphine)palladium(0) (7.86 mg, 6.81 µmol) was added. The vial was again evacuated/flushed with Ar three times, then capped and heated at 120° C. in the microwave for 20 min. Another 0.05 eq. of catalyst (7.86 mg) was added, the reaction vial was capped and evacuated/flushed with Ar three times, then heated at 120° C. in the microwave for another 20 min. Reaction was evaporated to dryness and the residue was purified by normal phase chromatography to yield I-115D as a white foam, (0.088 g, 95%). MS (ESI) m/z: 681.5 (M+H)$^+$.

I-115E. Example I-115 was prepared from I-115D following the procedures described in step I-61B and 1G to provide Example 115 as a white solid (0.0077 g, 19.8%). $^1$H NMR (500 MHz, CD$_3$OD) δ ppm 9.91 (1H, s) 9.55 (1H, d, J=1.10 Hz) 8.07 (1H, br. s.) 8.02 (1H, d, J=2.20 Hz) 7.97 (1H, dd, J=8.25, 4.40 Hz) 7.69 (1H, dd, J=8.80, 2.20 Hz) 7.59-7.63 (1H, m) 7.41 (1H, dd, J=8.80, 2.20 Hz) 7.19-7.25 (1H, m) 6.83 (1H, dd, J=15.95, 2.20 Hz) 5.29 (1H, dd, J=11.00, 6.05 Hz) 3.76 (3H, s) 3.28 (1H, br. s.) 2.99-3.07 (1H, m) 2.14-2.23 (1H, m) 2.04-2.14 (2H, m) 1.85-1.93 (1H, m) 1.69 (2H, t, J=12.92 Hz) 1.42 (1H, t, J=9.62 Hz) 0.88 (1H, q, J=11.18 Hz). MS (ESI) m/z: 587.3 (M+H)$^+$. Analytical HPLC: RT=5.83 min.

Example I-116

{(S)-17-Bromo-14-[(E)-3-(5-chloro-2-tetrazol-1-yl-phenyl)-acryloylamino]-8,16,18-triaza-tricyclo[13.2.1.0$^{2,7}$]octadeca-1(17),2,4,6,15(18)-pentaen-5-yl}-carbamic Acid methyl ester, 2 TFA

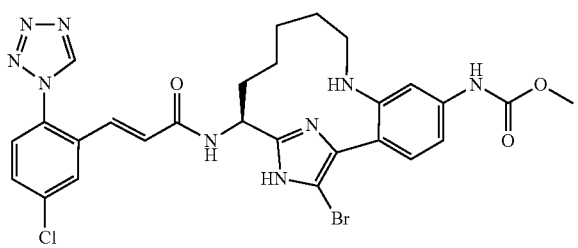 [SMILES: COC(=O)Nc1ccc2c(c1)NCCCCC[C@H](NC(=O)/C=C/c1cc(Cl)ccc1-n1cnnn1)c1nc-2c(Br)[nH]1]

Example I-116 was prepared from I-115C following the procedures described in step I-61B and 1G, as a white solid (0.046 g, 78%). $^1$H NMR (500 MHz, CD$_3$OD) δ ppm 9.75 (1H, s) 9.55 (1H, s) 8.88 (1H, d, J=4.40 Hz) 8.02 (1H, d, J=2.20 Hz) 7.98 (1H, d, J=8.80 Hz) 7.96 (1H, br. s.) 7.70 (1H, dd, J=8.80, 2.20 Hz) 7.60-7.64 (1H, m) 7.33 (1H, dd, J=8.80, 2.20 Hz) 7.24 (1H, d, J=15.40 Hz) 6.81 (1H, d, J=15.40 Hz) 5.22 (1H, dd, J=11.00, 6.60 Hz) 3.73 (3H, s) 3.19-3.25 (1H, m) 2.95 (1H, t, J=12.10 Hz) 2.10-2.19 (1H, m) 1.97-2.09 (2H, m) 1.82-1.91 (1H, m) 1.68 (2H, t, J=12.37 Hz) 1.37 (1H, br. s.) 0.72-0.84 (1H, m). MS (ESI) m/z: 640.3 (M+H)$^+$. Analytical HPLC: RT=6.34 min.

Example I-118

(S)-14-[(E)-3-(5-Chloro-2-tetrazol-1-yl-phenyl)-acryloylamino]-5-methoxycarbonylamino-8,16,18-triaza-tricyclo[13.2.1.0$^{2,7}$]octadeca-1(17),2,4,6,15(18)-pentaene-17-carboxylic Acid ethyl ester, 2 TFA

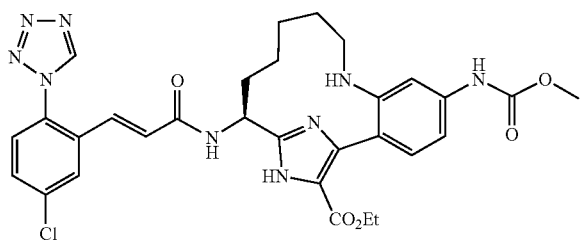 [SMILES: CCOC(=O)c1[nH]c2nc1-c1ccc(NC(=O)OC)cc1NCCCCC[C@@H]2NC(=O)/C=C/c1cc(Cl)ccc1-n1cnnn1]

I-118A. (S)-14-Amino-5-methoxycarbonylamino-8,16,18-triaza-tricyclo[13.2.1.0$^{2,7}$]octadeca-1(17),2,4,6,15(18)-pentaene-17-carboxylic acid ethyl ester, 3TFA: I-115D (0.086 g, 0.126 mmol) was dissolved in EtOH (0.5 ml), and then concentrated H$_2$SO$_4$ (10.10 µl, 0.189 mmol) was added at room temperature. The reaction was refluxed at 90° C. under Ar overnight. Additional EtOH (2 mL) and conc. H$_2$SO$_4$ (0.2 mL) were added, and the reaction was heated at 90° C. for an additional 18 h then cooled to room temperature and poured into cold water. The aqueous layer was adjusted to pH ~10 with 1N NaOH and extracted 3× with EtOAc; the combined organic layers were washed with brine, dried over MgSO$_4$, filtered, and evaporated. The residue was purified by reverse phase HPLC to provide I-118A (0.019 g, 20.2%). MS (ESI) m/z: 402.3 (M+H)$^+$.

I-118B. Example I-118 was obtained as a light yellow solid from I-118A following the procedure described in Step 1G (0.014 g, 58.5%). $^1$H NMR (500 MHz, CD$_3$OD) δ ppm 9.78 (1H, s) 9.52 (1H, s) 8.32 (1H, dd, J=8.67, 1.51 Hz) 8.03 (1H, d, J=2.20 Hz) 8.01 (1H, d, J=2.20 Hz) 7.68 (1H, dd, J=8.39, 2.34 Hz) 7.60 (1H, d, J=8.53 Hz) 7.32 (1H, d, J=8.80 Hz) 7.19 (1H, d, J=15.41 Hz) 6.80 (1H, d, J=15.41 Hz) 5.32 (1H, dd, J=10.04, 6.46 Hz) 4.32-4.41 (2H, m) 3.77 (3H, s) 3.21 (1H, ddd, J=12.52, 4.13, 3.99 Hz) 2.93-3.03 (1H, m) 2.09-2.19 (1H, m) 1.81-2.05 (3H, m) 1.68 (2H, t, J=12.24 Hz) 1.37 (3H, t, J=7.15 Hz) 1.30 (1H, d, J=6.88 Hz) 0.69-0.81 (1H, m). MS (ESI) m/z: 634.4 (M+H)$^+$. Analytical HPLC: RT=6.46 min.

Example I-119

(S)-14-[(E)-3-(5-Chloro-2-tetrazol-1-yl-phenyl)-acryloylamino]-5-methoxycarbonylamino-9,16,18-triaza-tricyclo[13.2.1.02,7]octadeca-1(17),2,4,6,15(18)-pentaene-9-carboxylic Acid methyl ester, 1TFA Salt

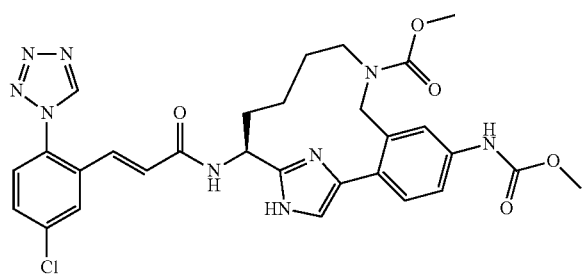 [SMILES: COC(=O)Nc1ccc2c(c1)CN(C(=O)OC)CCCC[C@H](NC(=O)/C=C/c1cc(Cl)ccc1-n1cnnn1)c1nc-2c[nH]1]

I-119A. {4-[2-((S)-1-tert-Butoxycarbonylamino-but-3-enyl)-1-(2-trimethylsilanyl-ethoxymethyl)-1H-imidazol-4-yl]-3-formyl-phenyl}-carbamic acid methyl ester: To a solution of 10B (351 mg, 0.589 mmol) in THF (3 ml) at −78° C. was added methyllithium (0.786 ml, 1.179 mmol). The reaction was stirred at −78° C. for 30 min, then butyllithium (0.552 ml, 0.884 mmol) in hexanes was added dropwise. After 30 mins, DMF (0.055 ml, 0.707 mmol) was added to the reaction mixture. The reaction was stirred at −78° C. before it was quenched with conc. NH$_4$Cl (aq), extracted with ether (2×), combined ether layers was washed with brine, dried over MgSO$_4$, filtered, and concentrated to yield a yellow oil. Purification by normal phase chromatography gave I-119A as a pale yellow foam (187 mg, 58%). MS (ESI) m/z: 545.2 (M+H)$^+$.

I-119B. {3-Allylaminomethyl-4-[2-((S)-1-tert-butoxycarbonylamino-but-3-enyl)-1-(2-trimethylsilanyl-ethoxymethyl)-1H-imidazol-4-yl]-phenyl}-carbamic acid methyl ester: To a solution of I-119A (187 mg, 0.343 mmol) in DCM (3.433 ml) was added prop-2-en-1-amine (19.60 mg, 0.343 mmol) and a drop of AcOH. The reaction was stirred at rt for 30 min, sodium triacetoxyborohydride (109 mg, 0.515 mmol) was added. After 3 hrs, the reaction was diluted with DCM, washed with sat. Na$_2$CO$_3$, brine, dried over MgSO$_4$. Filtered and concentrated. Purification by normal phase chromatography gave I-119B as a white foam (145 mg, 72%). MS (ESI) m/z: 586.5 (M+H)$^+$.

I-119C. [(S)-5-Methoxycarbonylamino-16-(2-trimethylsilanyl-ethoxymethyl)-9,16,18-triaza-tricyclo[13.2.1.02,7]octadeca-1(17),2,4,6,15(18)-pentaen-14-yl]-carbamic acid tert-butyl ester: I-119C was prepared following the procedures described in 2E/2F, by replacing 2D with I-119B; followed by 2G. MS (ESI) m/z: 560.4 (M+H)$^+$.

I-119D. (S)-14-tert-Butoxycarbonylamino-5-methoxycarbonylamino-16-(2-trimethylsilanyl-ethoxymethyl)-9,16,18-triaza-tricyclo[13.2.1.02,7]octadeca-1(17),2,4,6,15(18)-pentaene-9-carboxylic acid methyl ester: To a solution of I-119C (14 mg, 0.021 mmol) in CH$_2$Cl$_2$ (Volume: 1 mL) was added methyl chloroformate (1.967 µl, 0.025 mmol) in 0.4 ml DCM, followed by TEA (0.014 mL, 0.099 mmol). The reaction was stirred at rt. for 30 min. The reaction mixture was concentrated, redissolved in EtOAc, washed with water and brine, dried over Na$_2$SO$_4$, filtered off solid, concentrated. Purification by normal phase chromatography gave I-119D as a white solid (7 mg, 55%). MS (ESI) m/z: 618.5 (M+H)$^+$.

I-119E. Example I-119 was prepared following the procedures described in 1F, by replacing 1D with I-119D; followed by 1G. $^1$H NMR (500 MHz, CD$_3$OD) δ ppm 9.51-9.53 (m, 1H), 7.98 (d, J=2.5 Hz, 1H), 7.67-7.72 (m, 2H), 7.55-7.61 (m, 2H), 7.49 (s, 1H), 7.40 (d, J=8.2 Hz, 1H), 7.18 (d, J=15.7 Hz, 1H), 6.76 (d, J=15.7 Hz, 1H), 4.92-4.98 (m, 1H), 4.31-4.52 (m, 1H), 3.77 (s, 3H), 3.62-3.65 (m, 2H), 3.61 (s, 3H), 3.04-3.18 (m, 1H), 2.98-3.01 (m, 1H), 2.13-2.28 (m, 1H), 1.77-1.92 (m, 1H), 1.51-1.69 (m, 1H), 1.20-1.43 (m, 2H). MS (ESI) m/z: 620.3 (M+H)$^+$. Analytical HPLC: RT=4.56 min. (Method B).

TABLE I-6

Examples I-101 to I-121

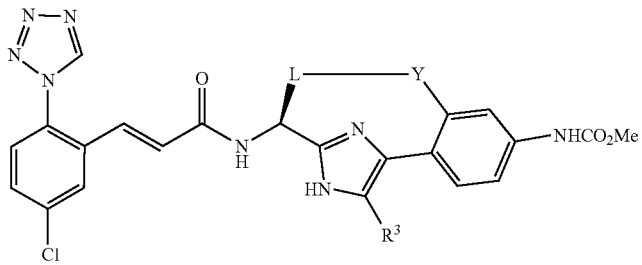

| Ex. # | L-Y | R$^3$ | LCMS [M + H]$^+$ | HPLC RT (min) (method) |
|---|---|---|---|---|
| I-101 | ⸺CO$_2$Me (structure) | H | 634.3 | 4.5(B) |

TABLE I-6-continued

Examples I-101 to I-121

| Ex. # | L-Y | R³ | LCMS [M + H]⁺ | HPLC RT (min) (method) |
|---|---|---|---|---|
| I-102 | (CO₂Me, NH; stereochem shown) | H | 634.3 | 5.0(B) |
| I-103 | (CO₂Me, NH; homochiral) | H | 688.3 | 5.1(B) |
| I-104 | (F₃C, CO₂Me, NH; homochiral) | H | 688.3 | 5.8(B) |
| I-105 | (N-methyl pyrazole linker, NH; diastereomer mixture) | H | 640.2 | 5.4 |
| I-106 | (α,β-unsaturated amide linker) | H | 573.9 | 3.9(B) |
| I-107 | (imine linker) | F | 578.3 | 8.6 |
| I-108 | (N-CO₂Me linker) | H | 620.2 | 5.5 |
| I-109 | (methyl-branched NH linker; diastereomer mixture) | H | 576.3 | 4.8(B) |

TABLE I-6-continued
Examples I-101 to I-121
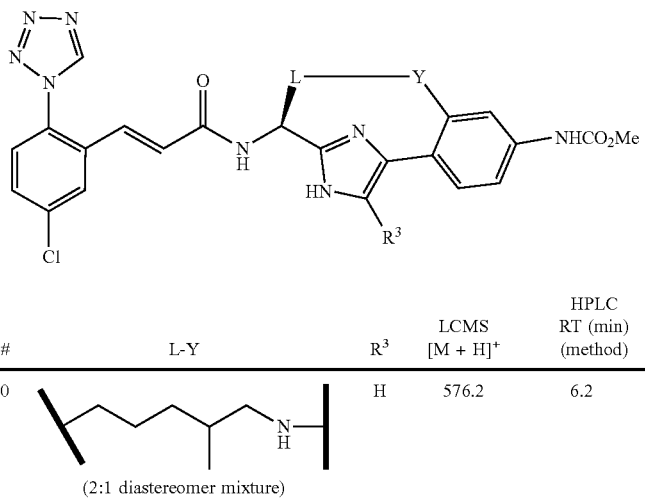
| Ex. # | L-Y | R³ | LCMS [M + H]⁺ | HPLC RT (min) (method) |
|---|---|---|---|---|
| I-110 | 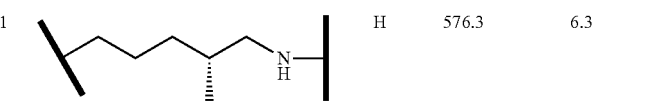<br>(2:1 diastereomer mixture) | H | 576.2 | 6.2 |
| I-111 | 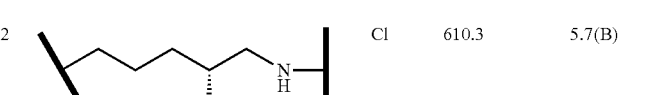 | H | 576.3 | 6.3 |
| I-112 | 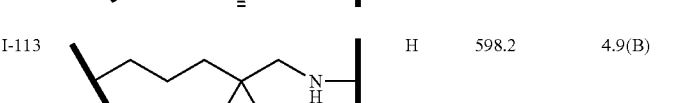 | Cl | 610.3 | 5.7(B) |
| I-113 | 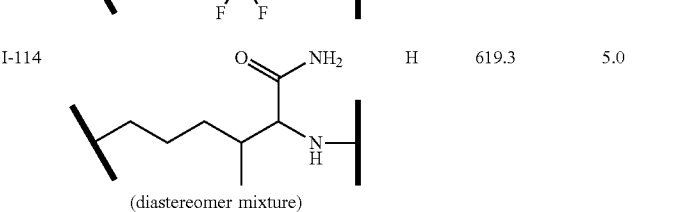 | H | 598.2 | 4.9(B) |
| I-114 | 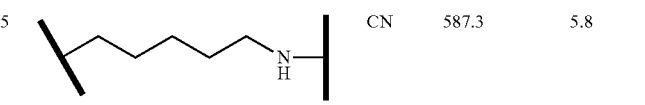<br>(diastereomer mixture) | H | 619.3 | 5.0 |
| I-115 |  | CN | 587.3 | 5.8 |
| I-116 | 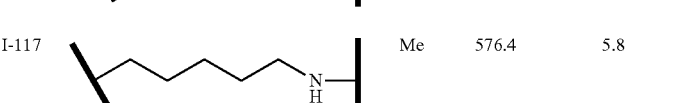 | Br | 640.3 | 6.3 |
| I-117 | 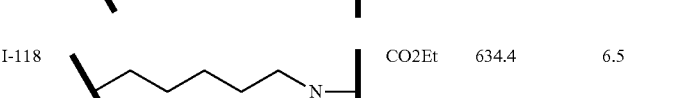 | Me | 576.4 | 5.8 |
| I-118 | 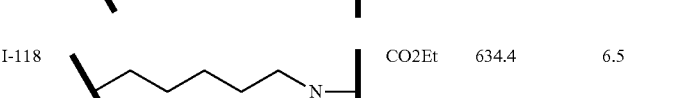 | CO2Et | 634.4 | 6.5 |
| I-119 | 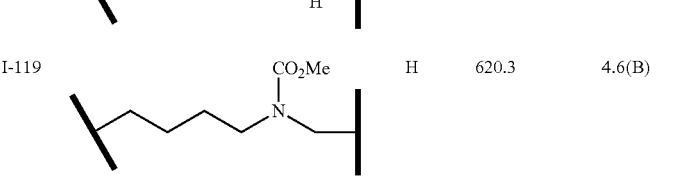 | H | 620.3 | 4.6(B) |

TABLE I-6-continued

Examples I-101 to I-121

[Structure: tetrazole-phenyl-chloro acrylamide linked to imidazole with L-Y and phenyl-NHCO2Me]

| Ex. # | L-Y | R³ | LCMS [M + H]⁺ | HPLC RT (min) (method) |
|---|---|---|---|---|
| I-120 | [structure] | H | 576.4 | 7.2 |
| I-121 | [structure with CO₂Et] | H | 648.5 | 7.6 |

Example I-123

{(S)-17-Chloro-14-[(E)-3-(5-chloro-2-tetrazol-1-yl-phenyl)-acryloylamino]-8,16,18-triaza-tricyclo[13.2.1.0$^{2,7}$]octadeca-1(17),2,4,6,15 (18)-pentaen-5-yl}-carbamic acid 2-methoxy-ethyl ester, 2 TFA

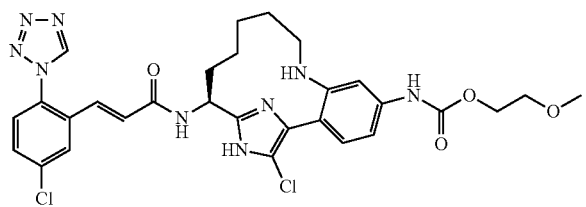 [SMILES: COCCOC(=O)Nc1ccc2c(c1)NCCCCC[C@H](NC(=O)/C=C/c1cc(Cl)ccc1-n1cnnn1)c1nc-2c(Cl)[nH]1]

I-123A. {(S)-1-[4-(4-Amino-2-bromo-phenyl)-1-(2-trimethylsilanyl-ethoxymethyl)-1H-imidazol-2-yl]-but-3-enyl}-carbamic acid tert-butyl ester: To a stirred solution of 10B (1.5 g, 2.52 mmol) dissolved in MeOH (36 mL) was added 1N NaOH (50.4 mL, 50.4 mmol) dropwise at room temperature. The reaction was stirred at 85° C. under a reflux condenser overnight. Solvent was removed under reduced pressure and the residue was partitioned between EtOAc/water. Aqueous layer was extracted with EtOAc 3×, combined organic phases were washed with brine, dried with sodium sulfate, filtered and evaporated to yield the crude product, I-123A (1.42 g, 105%), as a yellow solid. MS (ESI) m/z:=537.2 (M+H)⁺.

I-123B. {3-Bromo-4-[2-((S)-1-tert-butoxycarbonylamino-but-3-enyl)-1-(2-trimethylsilanyl-ethoxymethyl)-1H-imidazol-4-yl]-phenyl}-carbamic acid 2-methoxy-ethyl ester: I-123A (1.42 g, 2.64 mmol) was dissolved in DCM (26.4 ml). Pyridine (0.855 ml, 10.57 mmol) was added followed by dropwise addition of 2-methoxyethyl carbonochloridate at 0° C. The reaction was allowed to warm to RT and stirred ON. Another 2 equiv. of 2-methoxyethyl carbonochloridate (0.439 g, 3.17 mmol) was added and stirring was continued at RT for 2 hours. The reaction was quenched with sat.'d sodium bicarbonate and extracted with EtOAc 3×. Combined organic phases were washed with brine, dried over sodium sulfate, filtered and concentrated. Crude product was purified by silica gel chromatography to provide I-123B (1.23 g, 72.8%) as a yellow, oily solid. MS (ESI) m/z:=639.3/641.3 (M+H)⁺.

I-123C. {(S)-14-[(E)-3-(5-Chloro-2-tetrazol-1-yl-phenyl)-acryloylamino]-8,16,18-triaza-tricyclo[13.2.1.0$^{2,7}$]octadeca-1(17),2,4,6,15 (18)-pentaen-5-yl}-carbamic acid 2-methoxy-ethyl ester: I-123C was prepared from I-123B using the procedures described for 115A, 61B and 1G. Crude product was used without purification in the next step. MS (ESI) m/z:=606.4 (M+H)⁺.

I-123D. Example I-123: I-123C (.085 g, 0.140 mmol) was dissolved in acetonitrile (1 ml)/chloroform (1 ml) and TFA (0.086 ml, 1.122 mmol) was added followed by NCS (0.022 g, 0.168 mmol), and the mixture was stirred at 65° C. under Ar for 1.75 h. Reaction was diluted with water and extracted with EtOAc 2×. Combined organics were washed with brine, dried over sodium sulfate, filtered and concentrated. The crude product was purified by reverse phase chromatography to provide Example I-123 (0.056 g, 44.6%) as a yellow solid. ¹H NMR (500 MHz, CD₃OD) δ ppm 9.79 (1H, br. s.), 9.54 (1H, s), 8.90 (1H, d, J=5.50 Hz), 8.02 (1H, d, J=2.20 Hz), 7.93 (1H, br. s.), 7.86 (1H, d, J=8.80 Hz), 7.67-7.72 (1H, m), 7.58-7.64 (1H, m), 7.32 (1H, dd, J=8.80, 2.20 Hz), 7.18-7.28 (1H, m), 6.81 (1H, d, J=15.95 Hz), 5.20 (1H, dd, J=11.27, 6.32 Hz), 4.17-4.29 (2H, m), 3.61 (2H, t, J=4.67 Hz), 3.37 (3H, s), 3.18-3.26 (1H, m), 2.90-3.02 (1H, m), 1.94-2.21 (3H, m), 1.78-1.91 (1H, m), 1.62-1.74 (2H, m), 1.30-1.45 (1H, m), 0.72-0.91 (1H, m). MS (ESI) m/z:=640.3 (M+H)⁺. Analytical HPLC: RT=5.9 min.

TABLE I-7
Examples I-122 to I-127
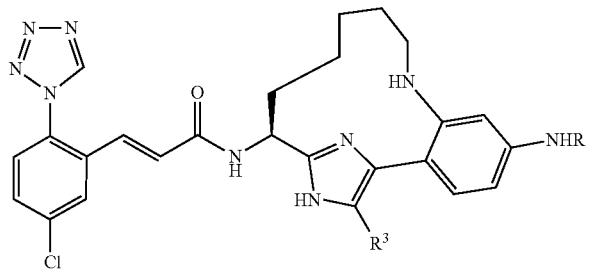
| Ex. # | R | R³ | LCMS [M + H]⁺ | HPLC RT (min) |
|---|---|---|---|---|
| I-122 | methyl 2-(2-methoxyethoxy)carbonyl | H | 606.3 | 6.2 |
| I-123 | methyl 2-(2-methoxyethoxy)carbonyl | Cl | 640.3 | 5.9 |
| I-124 | tetrahydrofuranylmethyl ester | H | 632.4 | 5.9 |
| I-125 | 2-ethoxyethyl ester | H | 620.4 | 5.9 |
| I-126 | 2-methoxybutyl ester | H | 634.4 | 6.3 |
| I-127 | 2-hydroxyethyl ester | H | 592.4 | 5.2 |

Example I-134

Methyl N-[(14S)-14-[(2E)-3-[5-chloro-2-(1H-1,2,3,4-tetrazol-1-yl)phenyl]prop-2-enamido]-9-oxo-18-oxa-8,16-diazatricyclo[13.2.1.0$^{2,7}$]octadeca-1(17),2(7),3,5,15-pentaen-5-yl]carbamate, trifluoroacetic Acid Salt

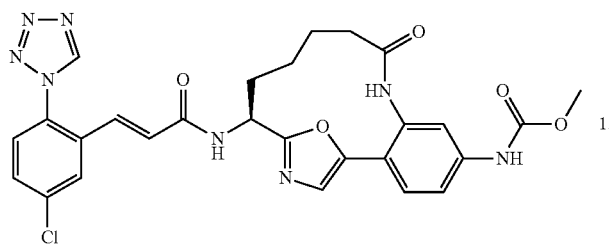

I-134A. Methyl 4-(2-aminoacetyl)-3-bromophenylcarbamate: To a solution of Intermediate 8 (3.0 g, 8.55 mmol) in acetonitrile (40 mL) was added sodium diformylamide (0.975 g, 10.26 mmol). The suspension was stirred under argon at RT for 5 hrs. The mixture was filtered and the solid was washed with warm MeCN. The filtrate was concentrated to give a tan solid. Next, aq. 4 N HCl (25 mL) was added and the resulting suspension was warmed to reflux. After 2 h, the clear reaction was cooled to RT and the solution was concentrated to give 2.45 g (100%) of I-134A as a light tan solid. MS (ESI) m/z: 287.0 (M+H)$^+$ and 288.9 (M+2+H)$^+$.

I-134B. tert-Butyl N-[(1S)-1-[(2-{2-bromo-4-[(methoxycarbonyl)amino]phenyl}-2-oxoethyl)carbamoyl]but-3-en-1-yl]carbamate: To a solution of (S)-2-(tert-butoxycarbonylamino)pent-4-enoic acid (515 mg, 2.393 mmol) in DMF (15 mL) was added HOBt (476 mg, 3.11 mmol) and EDC (596 mg, 3.11 mmol). After 5 min, a solution of I-134A (774 mg, 2.393 mmol) and DIEA (0.418 ml, 2.393 mmol) in DMF (5 mL) was added. The reaction was stirred under argon at RT for 2 h. The reaction mixture was diluted with EtOAc, washed with 1M HCl, sat NaHCO$_3$ and brine. The organic phase was dried over sodium sulfate, filtered and concentrated. Purification by normal phase chromatography gave 1.05 g (91%) of I-134B as a tan solid. MS (ESI) m/z: 484.0 (M+H)$^+$ and 485.9 (M+2+H)$^+$.

I-134C. tert-Butyl N-[(1S)-1-(5-{2-bromo-4-[(methoxycarbonyl)amino]phenyl}-1,3-oxazol-2-yl)but-3-en-1-yl]carbamate: A solution of I-134B (900 mg, 1.858 mmol) and Burgess reagent (1771 mg, 7.43 mmol) in THF(10 mL) was microwaved at 120° C. for 12 min. The reaction mixture was diluted with EtOAc, washed with H$_2$O and brine. The organic phase was dried over sodium sulfate, filtered and concentrated. The crude product was purified by normal phase chromatography which gave 398 mg (46%) of I-134C as a solid. MS (ESI) m/z: 466.0 (M+H)$^+$ and 468.0 (M+2+H)$^+$.

I-134D. Example I-134 was prepared following the procedures described in 10C (alternative), by replacing 10B with I-134C; followed by steps 10D; 2E/2F, by replacing DCM with DCE and running the reaction at 70° C.; 2G; 3C; and 1G. $^1$H NMR (400 MHz, DMSO-d$_6$) δ ppm 9.72 (1H, s), 9.70 (1H, s), 9.59 (1H, s), 8.64 (1H, d, J=7.53 Hz), 7.78 (1H, d, J=2.01 Hz), 7.60 (1H, dd, J=8.53, 2.26 Hz), 7.57 (1H, d, J=8.53 Hz), 7.38 (1H, d, J=8.53 Hz), 7.27 (1H, dd, J=8.66, 1.88 Hz), 7.16 (1H, d, J=1.76 Hz), 7.13 (1H, s), 6.75 (1H, d, J=15.56 Hz), 6.68 (1H, d, J=15.56 Hz), 4.91-5.02 (1H, m), 3.53 (3H, s), 1.84-1.94 (1H, m), 1.73-1.84 (1H, m), 1.60-1.73 (2H, m), 1.40-1.54 (1H, m), 1.12-1.25 (1H, m), 0.73-0.91 (1H, m). MS (ESI) m/z: 577.2 (M+H)$^+$. Analytical HPLC: RT=6.39 min.

Example I-136

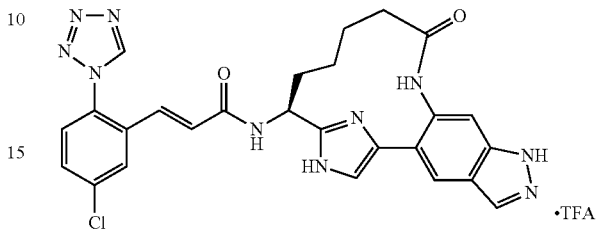

I-136A. 5-Bromo-6-nitro-1H-indazole: A solution of sodium nitrite (2.189 g, 31.7 mmol) in water (6.29 mL) was added dropwise to a solution of 4-bromo-2-methyl-5-nitroaniline prepared according to J. Org. Chem., 44:4609 (1979) (7.33 g, 31.7 mmol) in glacial acetic acid (793 ml), and the reaction mixture was stirred under argon at room temperature overnight. The mixture was concentrated to give an oily residue. Water was added to precipitate the crude product which was collected via filtration and washed with water, then dried in vacuo to yield an orange solid. The solid was dried by lyophilization to yield I-136A (6.77 g, 88%). (M+H)$^+$ MS (ESI) m/z: 242.1 (M+H)$^+$.

I-136B. 5-(1-Ethoxyvinyl)-6-nitro-1H-indazole: A solution of I-136A (7.65 g, 31.6 mmol), tributyl(1-ethoxyvinyl)stannane (12.81 ml, 37.9 mmol), and (Ph$_3$P)$_2$PdCl$_2$ (1.109 g, 1.580 mmol) in toluene (63.2 ml) was heated at 115° C. under Ar. The reaction was cooled to room temperature and filtered. The filtrate was concentrated and dried under vacuum to yield a dark brown oil, which was dissolved in DCM and absorbed on a dry pad of silica gel. The pad was washed sequentially with Hex and EtOAc. The EtOAc fraction was condensed to a dark brown oil, which was further purified by normal phase chromatography to provide an ~3:1 mixture of SM to product. This mixture was dissolved in dioxane, and tributyl(1-ethoxyvinyl)stannane (3.46 ml, 10.23 mmol), CuI (0.162 g, 0.852 mmol), and tetrakis(triphenylphosphine)palladium(0) (0.492 g, 0.426 mmol) were added. The mixture was degassed and then heated at 110° C. under Ar for 3 hrs, then allowed to sit at rt overnight. The reaction mixture was filtered and solids washed with EtOAc. Filtrate was stripped to a brown oil which was purified by flash chromatography to yield I-136B as an orange oil, (1.93 g, 61.1%). MS (ESI) m/z: 234.1 (M+H)$^+$.

I-136C. 2-Bromo-1-(6-nitro-1H-indazol-5-yl)ethanone: To a soln of I-136B (1.39 g, 5.96 mmol) in THF (8.83 ml) and water (3.09 ml) was added NBS (1.061 g, 5.96 mmol). The reaction was stirred at rt for ~45 min, then partitioned between EtOAc/brine. The brine layer was re-extracted with EtOAc, and the combined organic layer was dried over MgSO$_4$, filtered, concentrated, and dried under vacuum to yield an 2.01 g of an orange solid which was combined with 0.698 g from a second prep and dissolved in a small amount of methylene chloride. The insoluble tan solid was filtered off to provide 0.381 g (16.6%) of product. The filtrate was purified by normal phase chromatography to provide and additional 0.783 of I-136C (34%). MS (ESI) m/z: 284.1 (M+H)$^+$.

Example I-136D. The title compound was prepared from I-136C following the procedures described for 2A; 1B; 10B; 122C; 10D; 2E; 2G; 10H; and 1G. $^1$H NMR (500 MHz, DMSO-d$_6$) δ ppm 14.27 (1H, br. s.) 13.26 (1H, s) 9.86 (1H, s) 9.63 (1H, br. s.) 8.89 (1H, br. s.) 8.17 (1H, s) 7.99 (1H, s) 7.92 (1H, d, J=2.20 Hz) 7.72-7.80 (2H, m) 7.64 (1H, br. s.) 7.43 (1H, br. s.) 6.91-6.97 (1H, m) 6.80-6.85 (1H, m) 5.04 (1H, dt, J=9.83, 4.85 Hz) 2.34-2.40 (1H, m) 2.10 (1H, br. s.) 2.00 (1H, br. s.) 1.82 (1H, br. s.) 1.63 (1H, br. s.) 1.39 (1H, br. s.) 1.28 (1H, br. s.) 0.89 (1H, br. s.). MS (ESI) m/z: 543.3 (M+H)$^+$. Analytical HPLC: RT=4.8 min.

Example I-140

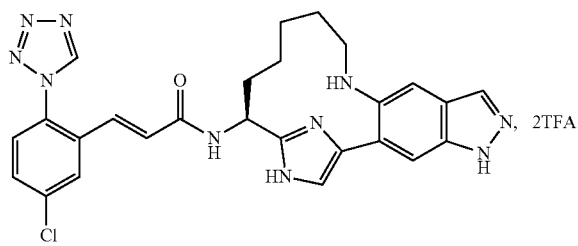 [SMILES: O=C(/C=C/c1cc(Cl)ccc1-n1cnnn1)N[C@H]1CCCCCNc2cc3cn[nH]c3cc2-c2c[nH]c1n2]

I-140A. 3-Amino-N-methoxy-N,4-dimethylbenzamide: 3-amino-4-methylbenzoic acid (5.0 g, 33.1 mmol) was dissolved in DMF (165 ml) and TEA (23.05 ml, 165 mmol), EDC (7.93 g, 41.3 mmol), HOBT (6.33 g, 41.3 mmol), and N,O-dimethylhydroxylamine hydrochloride (8.07 g, 83 mmol) were added. The reaction was stirred under Ar at room temperature overnight. The mixture was diluted with EtOAc and washed 3× with water. The combined aq. washes were re-extracted with EtOAc. The organic layers were combined and washed with brine, then dried over MgSO$_4$, filtered and concentrated. The resulting orange residue was purified by normal phase chromatography to yield the product as a colorless oil (2.87 g, 44.7%). MS (ESI) m/z: 195.1 m/z (M+H)$^+$.

I-140B. 5-Amino-2-bromo-N-methoxy-N,4-dimethyl-benzamide: NBS (2.52 g, 14.16 mmol) was added to a solution of I-140A (2.75 g, 14.16 mmol) in DMF (28.3 ml), and the mixture was stirred overnight at room temperature. The reaction mixture was diluted with H$_2$O and extracted 3× with EtOAc. The organic extracts were combined and washed with brine, then dried over MgSO$_4$, filtered, and evaporated. Residue was dissolved in a small amount of methylene chloride and the precipitate was filtered off to provide product as a white solid (1.53 g, 39.6%). The filtrate was purified by normal phase chromatography to provide additional product (1.13g, 29.2%). MS (ESI) m/z: 273.1 m/z (M+H)$^+$.

I-140C. 5-Bromo-N-methoxy-N-methyl-1H-indazole-6-carboxamide: This compound was prepared from I-140B (2.66 g, 9.74 mmol) following the procedure described for step I-136A The product was isolated as a yellow solid (2.55g, 92%). MS (ESI) m/z: 284.1 m/z (M+H)$^+$.

I-140D. tert-Butyl 5-bromo-6-(methoxy(methyl)carbamoyl)-1H-indazole-1-carboxylate: A solution of I-140C (2.55 g, 8.98 mmol), (Boc)$_2$O (4.79 ml, 20.64 mmol), TEA (5.00 ml, 35.9 mmol), and DMAP (0.658 g, 5.39 mmol) in THF (44.9 ml) was stirred under Ar at rt overnight. The reaction mixture was concentrated to remove THF and partitioned between EtOAc and saturated aq. NH$_4$Cl solution. Layers were separated, and aqueous phase re-extracted with EtOAc. The org layers were combined and washed with brine, then dried over MgSO$_4$, filtered, and evaporated. Crude product was purified by normal phase chromatography to provide I-140D as a light yellow foam (3.23 g, 94%). MS (ESI) m/z: 384.1 m/z (M+H)$^+$ I-140E. 1-(5-Bromo-1H-indazol-6-yl)ethanone: To a solution of I-140D (3.1 g, 8.07 mmol) in THF (81 ml) in a 3-neck rbf at 0° C. was added 4 eq. of methylmagnesium bromide (1.4 M in THF:Toluene, 23.05 ml, 32.3 mmol) dropwise over 20 min. The resulting yellow soln was stirred under argon at 0° C. After ~1.5 hrs from the start of the addition an additional 3 eq of methylmagnesium bromide (1.4 M in THF:Toluene, 17.29 ml, 24.20 mmol) was added dropwise to the cold soln. The mixture was then stirred under Ar overnight allowing the reaction to gradually assume room temperature. Another 1.5 eq. of methylmagnesium bromide (1.4 M in THF:Toluene. 8.64 ml, 12.10 mmol) was then added dropwise over ~10 min at rt, and the reaction was stirred at rt under Ar for an additional 3 h prior to workup. The reaction was quenched at 0° C. with MeOH followed by a little water, then diluted with EtOAc. The suspension was adjusted to pH5 to dissolve the solids and then evaporated to remove THF. Additional EtOAc was added, and organics were washed with dilute aq. acid (pH ~5), sat. NaHCO$_3$, and brine, then dried over MgSO$_4$, filtered and concentrated. The crude product was purified by normal phase chromatography to provide I-140E as a white solid (1.45 g, 75%). MS (ESI) m/z: 239.1 m/z (M+H)$^+$ I-140F. 2-Bromo-1-(5-bromo-1H-indazol-6-yl)ethanone: I-140E (1.45 g, 6.07 mmol) was taken up in THF (30.3 ml), and pyridinium tribromide (1.959 g, 6.13 mmol) was added. The mixture was stirred under Ar at rt for 15 min then at 40° C. for 20 min. The reaction was evaporated and the resulting pale yellow solid was partitioned between EtOAc/water. The organic layer was washed with water and brine, dried over MgSO$_4$, filtered, and evaporated. The residue was purified by flash chromatography to provide the desired monobromo product, I-140F (1.14 g, 59%). MS (ESI) m/z: 319.0 m/z (M+H)$^+$ Example I-140. The title compound was prepared from I-140F following the procedures described for steps 2A; 1B; 10B; 10C by substituting 3-butenamine for ammonium hydroxide; 2E/F; 154C/D; I-61B; and 1G. $^1$H NMR (500 MHz, CD$_3$OD) δ ppm 9.56 (1H, s) 8.18 (1H, d, J=1.10 Hz) 8.02 (1H, d, J=2.75 Hz) 7.79 (1H, s) 7.69 (1H, dd, J=8.80, 2.20 Hz) 7.62 (1H, d, J=8.25 Hz) 7.60 (1H, br. s.) 7.51 (1H, s) 7.25 (1H, d, J=15.40 Hz) 6.85 (1H, d, J=15.95 Hz) 5.28 (1H, dd, J=11.00, 6.60 Hz) 3.20 (1H, d, J=12.65 Hz) 2.94 (1H, t, J=12.37 Hz) 2.13-2.22 (1H, m) 2.09 (2H, t, J=12.65 Hz) 1.86-1.94 (1H, m) 1.61-1.79 (2H, m) 1.30-1.40 (1H, m) 0.73 (1H, d, J=12.65 Hz). MS (ESI) m/z: 529.4 m/z (M+H)$^+$. Analytical HPLC: RT=5.43 min.

Example I-141

(S)-14-[(E)-3-(5-Chloro-2-tetrazol-1-yl-phenyl)-acryloylamino]-8,16,18-triaza-tricyclo[13.2.1.02,7]octadeca-1(17),2,4,6,15(18)-pentaene-5-carboxylic Acid amide, 2 TFA

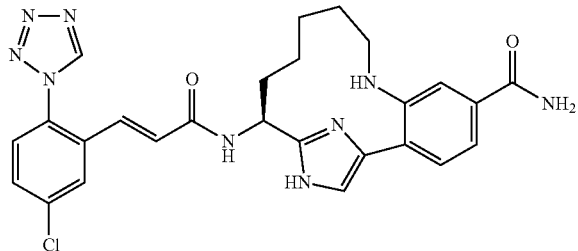 [SMILES: NC(=O)c1ccc2c(c1)NCCCCC[C@H](NC(=O)/C=C/c1cc(Cl)ccc1-n1cnnn1)c1nc-2c[nH]1]

I-141-A. (S)-14-[(E)-3-(5-Chloro-2-tetrazol-1-yl-phenyl)-acryloylamino]-8,16,18-triaza-tricyclo[13.2.1.02,7]octadeca-1(17),2,4,6,15(18)-pentaene-5-carboxylic acid, 2 TFA: I-141A was prepared following the procedures described for Example 142 substituting 3-bromo-4-methylbenzoic for 4-bromo-3-methylbenzoic acid. MS (ESI) m/z: 533.3 m/z (M+H)+.

Example I-141. I-141A (.012 g, 0.016 mmol) was dissolved in DMF (1 mL). Hunig's base (0.028 mL, 0.158 mmol) was added, followed by ammonium chloride (8.43 mg, 0.158 mmol), HOBT (2.90 mg, 0.019 mmol) and EDC (3.63 mg, 0.019 mmol). The reaction was stirred at room temperature for 48 h, stripped to dryness, and residue purified by reverse phase chromatography to provide the title compound as a white solid. $^1$H NMR (500 MHz, CD$_3$OD) δ ppm 9.53 (1H, s), 8.87 (1H, d, J=5.50 Hz), 8.00 (1H, d, J=2.20 Hz), 7.91-7.98 (2H, m), 7.86 (1H, d, J=7.70 Hz), 7.65-7.70 (2H, m), 7.59 (1H, d, J=8.25 Hz), 7.18 (1H, d, J=15.40 Hz), 6.80 (1H, d, J=15.95 Hz), 5.30 (1H, dd, J=10.72, 6.32 Hz), 3.24-3.29 (1H, m), 2.95-3.06 (1H, m), 1.98-2.22 (3H, m), 1.80-1.96 (1H, m), 1.58-1.78 (2H, m), 1.24-1.44 (1H, m), 0.76-1.00 (1H, m). MS (ESI) m/z: 532.4 (M+H)+. Analytical HPLC: RT=4.94 min.

Example I-142

(S)-14-[(E)-3-(5-Chloro-2-tetrazol-1-yl-phenyl)-acryloylamino]-8,16,18-triaza-tricyclo[13.2.1.02,7]octadeca-1(17),2,4,6,15(18)-pentaene-4-carboxylic Acid, 2TFA

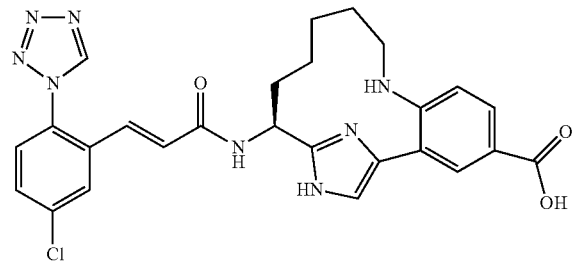 [SMILES: O=C(/C=C/c1cc(Cl)ccc1-n1cnnn1)N[C@H]1CCCCCNc2ccc(C(=O)O)cc2-c2c[nH]c1n2]

I-142A. tert-Butyl 4-bromo-3-methylbenzoate: To a suspension of 4-bromo-3-methylbenzoic acid (2.8 g, 13.02 mmol) in THF (20 mL) and hexane (20 mL) in an ice bath under N$_2$, was added tert-butyl 2,2,2-trichloroacetimidate (3.50 mL, 19.53 mmol). After 10 min, BF$_3$·OEt$_2$ (0.165 mL, 1.302 mmol) was added. The resulting mixture was allowed slowly to warm to rt and stirred overnight. The mixture was diluted with Et$_2$O, washed with 1.5 M K$_2$HPO$_4$ solution, dried over anh. Na$_2$SO$_4$, filtered and evaporated. The residue was triturated with 20% Et$_2$O/hexane, and the solid was filtered off. Filtrate was evaporated. Residue was purified by flash chromatography to provide I-142A as a light peach color oil (2.141 g, 60.6%). MS (ESI) m/z: 293.1/295.1 (M+Na)+271.2/273.1 (M+H)+215,1/217.1 (M+H-tBu)+.

I-142B. tert-Butyl 4-bromo-3-formylbenzoate: I-142A (2.14 g, 7.89 mmol) was dissolved in CCl$_4$ (39.5 ml) and NBS (3.09 g, 17.36 mmol) and benzoyl peroxide (0.191 g, 0.789 mmol) were added. The mixture was stirred under nitrogen at reflux in a 90° C. oil bath overnight. Reaction was diluted with EtOAc and washed with water and brine, dried over anh. Na$_2$SO$_4$, filtered and evaporated. Crude product (3.39 g, 7.90 mmol) was dissolved in morpholine (10 ml, 115 mmol), and the mixture was heated with stirring in a 60° C. oil bath under nitrogen overnight. After cooling to room temperature, the mixture was diluted with EtOAc, then stirred for 30 min. Solids were removed by filtration and washed with EtOAc. The filtrate was transferred to a separatory funnel and washed 3× with 5% aq. citric acid and once with brine, then dried over anh. Na$_2$SO$_4$, filtered and evaporated. The residue was purified by flash chromatography to provide I-142B as a white solid (1.885 g, 84%). $^1$H NMR (500 MHz, CDCl$_3$) δ ppm 10.39 (1H, s) 8.47 (1H, d, J=2.20 Hz) 8.05 (1H, dd, J=8.25, 2.20 Hz) 7.73 (1H, d, J=8.53 Hz) 1.61 (9H, s).

I-142C. tert-Butyl 4-bromo-3-(1-hydroxyethyl)benzoate: I-142B was dissolved in THF (50 mL) and cooled in a dry ice/acetone bath. To the cold solution was added methylmagnesium chloride (3.0 M in THF, 2.86 ml, 8.59 mmol) dropwise over 10-15 min. Stirring was continued at −78° C. for 1 h at which point the reaction was quenched with 10% aqueous KHSO$_4$ solution and warmed to room temperature. The mixture was diluted with water and extracted 3× with EtOAc. Extracts were combined and washed with water and brine, dried over anh. Na$_2$SO$_4$, filtered and evaporated. Residue was purified by flash chromatography to provide the desired product (1.18 g, 59.6%) along with recovered starting material (0.425g, 22%). MS (ESI) m/z: 301.1/303.1 (M+H)+245.1/247.1 (M+H-tBu)+.

I-142D. tert-Butyl 3-acetyl-4-bromobenzoate: I-142C (1.186 g, 3.94 mmol) was dissolved in DCM (50 ml) and treated with PCC (1.02 g, 4.73 mmol) with stirring under nitrogen. The resulting mixture was stirred at room temperature for 4 h then filtered through a pad of CELITE®. Filtrate was evaporated to dryness, and residue was purified by flash chromatography to provide the product as a colorless liquid (0.938 g, 80%). $^1$H NMR (500 MHz, CDCl$_3$) δ ppm 8.04 (1H, d, J=2.20 Hz) 7.88 (1H, dd, J=8.25, 2.20 Hz) 7.67 (1H, d, J=8.25 Hz) 2.65 (3H, s) 1.59 (9H, s).

I-142E. tert-Butyl 4-bromo-3-(2-bromoacetyl)benzoate: I-142D (0.209 g, 0.699 mmol) was dissolved in THF (3.5 ml) and pyridinium tribromide (0.226 g, 0.706 mmol) was added with stirring under nitrogen. Mixture was stirred at room temperature for ~30 min. Reaction was diluted with EtOAc and washed with brine, dried over anh. Na$_2$SO$_4$, filtered and evaporated. The residue was purified by flash chromatography to yield I-142E (0.214 g, 81%) contaminated with a small amount of starting material. MS (ESI) m/z: 323.0 (M+H-tBu)+.

Example 142. I-142E was converted into the title compound using the same series of steps described for conversion of I-140F into Example 140. $^1$H NMR (500 MHz, CD₃OD) δ ppm 9.52 (1H, s) 8.29 (1H, d, J=1.65 Hz) 7.95-8.03 (2H, m) 7.64-7.74 (2H, m) 7.59 (1H, d, J=8.53 Hz) 7.43 (1H, d, J=8.53 Hz) 7.18 (1H, d, J=15.68 Hz) 6.78 (1H, d, J=15.68 Hz) 5.28 (1H, dd, J=10.45, 6.33 Hz) 3.07-3.17 (1H, m) 2.83-2.94 (1H, m) 2.10-2.26 (1H, m) 1.86-2.05 (3H, m) 1.55-1.72 (2H, m) 1.32-1.45 (1H, m) 0.78-0.95 (1H, m). MS (ESI) m/z: 533.2 (M+H)⁺ Analytical HPLC: RT=5.71 min.

TABLE I-8

Examples I-128 to I-142

| Ex. # | Structure | LCMS [M + H]⁺ | HPLC RT (min) |
|---|---|---|---|
| I-128 | 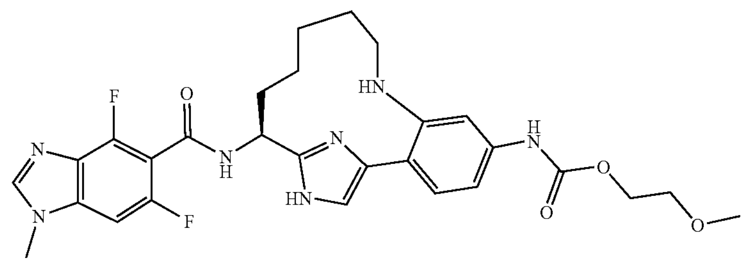 [SMILES: COCCOC(=O)Nc1ccc2c(c1)NCCCCC[C@H](NC(=O)c1c(F)cc3c(ncn3C)c1F)c1nc-2c[nH]1] | 568.4 | 4.2 |
| I-129 | 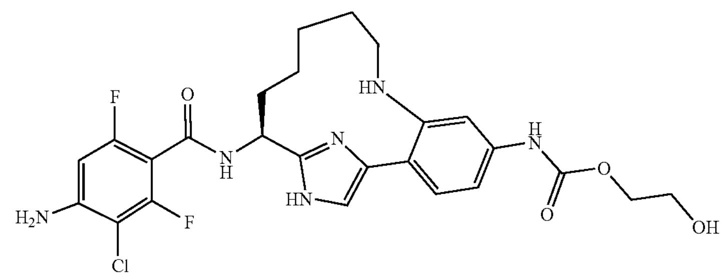 [SMILES: Nc1cc(F)c(C(=O)N[C@H]2CCCCCNc3cc(NC(=O)OCCO)ccc3-c3c[nH]c2n3)c(F)c1Cl] | 549.3 | 4.7 |
| I-130 | 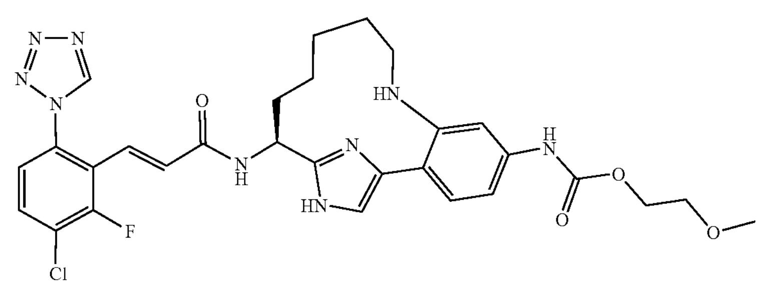 [SMILES: COCCOC(=O)Nc1ccc2c(c1)NCCCCC[C@H](NC(=O)/C=C/c1c(-n3cnnn3)ccc(Cl)c1F)c1nc-2c[nH]1] | 624.3 | 5.7 |
| I-131 | 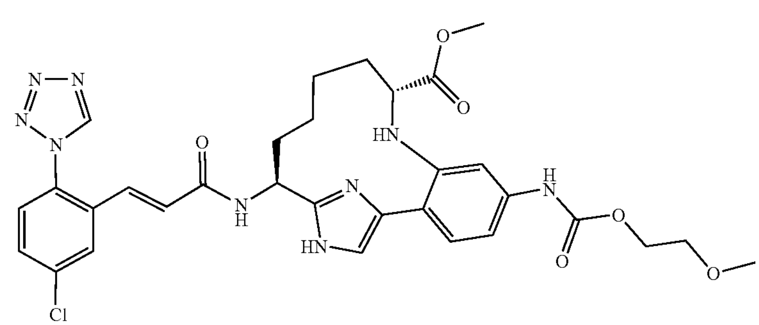 [SMILES: COCCOC(=O)Nc1ccc2c(c1)N[C@@H](C(=O)OC)CCCC[C@H](NC(=O)/C=C/c1cc(Cl)ccc1-n1cnnn1)c1nc-2c[nH]1] | 664.4 | 6.2 |

TABLE I-8-continued

Examples I-128 to I-142

| Ex. # | Structure | LCMS [M + H]+ | HPLC RT (min) |
|---|---|---|---|
| I-132 | 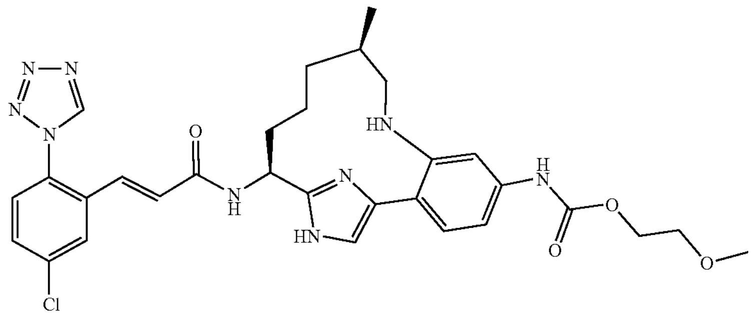 [SMILES: COCCOC(=O)Nc1ccc2c(c1)NC[C@H](C)CCC[C@H](NC(=O)/C=C/c1cc(Cl)ccc1-n1cnnn1)c1nc-2c[nH]1] | 620.3 | 6.0 |
| I-133 | 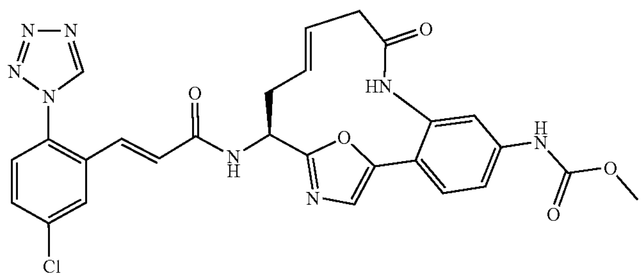 [SMILES: COC(=O)Nc1ccc2c(c1)NC(=O)C/C=C/C[C@H](NC(=O)/C=C/c1cc(Cl)ccc1-n1cnnn1)c1ncc-2o1] | 575.2 | 7.2 |
| I-134 | 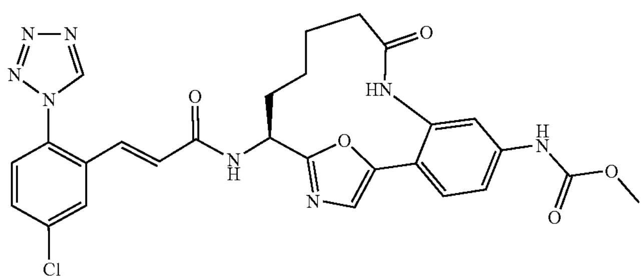 [SMILES: COC(=O)Nc1ccc2c(c1)NC(=O)CCCC[C@H](NC(=O)/C=C/c1cc(Cl)ccc1-n1cnnn1)c1ncc-2o1] | 577.2 | 6.4 |
| I-135 | 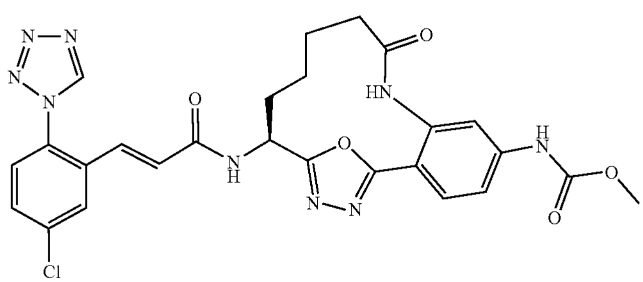 [SMILES: COC(=O)Nc1ccc2c(c1)NC(=O)CCCC[C@H](NC(=O)/C=C/c1cc(Cl)ccc1-n1cnnn1)c1nnc-2o1] | 578.0 | 7.2 |
| I-136 | 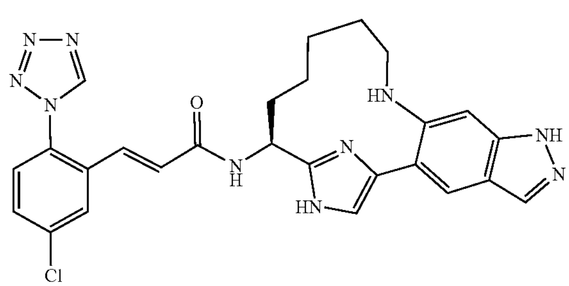 [SMILES: O=C(/C=C/c1cc(Cl)ccc1-n1cnnn1)N[C@H]1CCCCCNc2cc3[nH]ncc3cc2-c2c[nH]c1n2] | 543.3 | 4.8 |

TABLE I-8-continued

Examples I-128 to I-142

| Ex. # | Structure | LCMS [M + H]+ | HPLC RT (min) |
|---|---|---|---|
| I-137 | 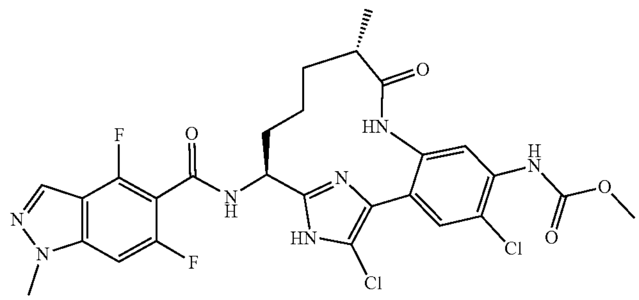 [SMILES: COC(=O)Nc1cc2c(cc1Cl)-c1nc([nH]c1Cl)[C@@H](NC(=O)c1c(F)cc3c(cnn3C)c1F)CCC[C@H](C)C(=O)N2] | 586.2 | 5.7(B) |
| I-138 | 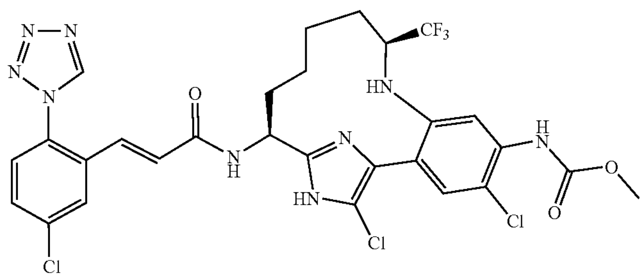 [SMILES: COC(=O)Nc1cc2c(cc1Cl)-c1nc([nH]c1Cl)[C@@H](NC(=O)/C=C/c1cc(Cl)ccc1-n1cnnn1)CCCC[C@@H](C(F)(F)F)N2] | 698.1 | 10.0 |
| I-139 | 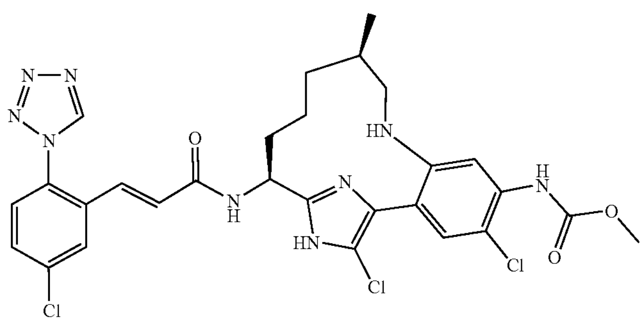 [SMILES: COC(=O)Nc1cc2c(cc1Cl)-c1nc([nH]c1Cl)[C@@H](NC(=O)/C=C/c1cc(Cl)ccc1-n1cnnn1)CCC[C@@H](C)CN2] | 644.3 | 5.9 |
| I-140 | 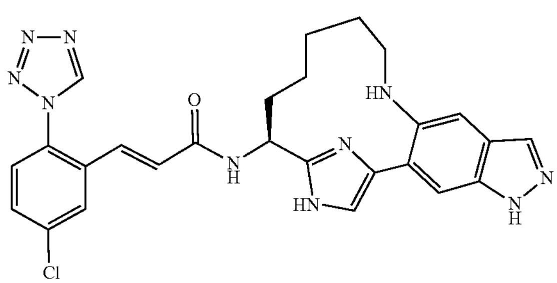 [SMILES: O=C(/C=C/c1cc(Cl)ccc1-n1cnnn1)N[C@H]1CCCCCNc2cc3cn[nH]c3cc2-c2c[nH]c1n2] | 529.4 | 5.4 |
| I-141 | 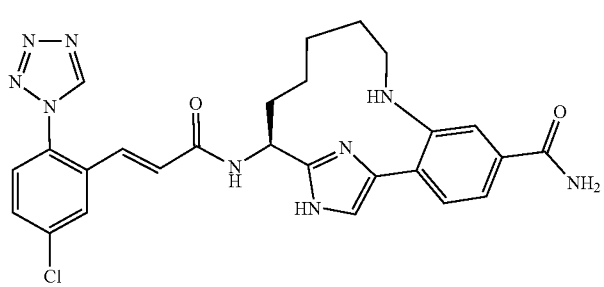 [SMILES: NC(=O)c1ccc2c(c1)NCCCCC[C@H](NC(=O)/C=C/c1cc(Cl)ccc1-n1cnnn1)c1nc-2c[nH]1] | 532.4 | 4.9 |

TABLE I-8-continued

Examples I-128 to I-142

| Ex. # | Structure | LCMS [M + H]+ | HPLC RT (min) |
|---|---|---|---|
| I-142 | (structure) | 533.0 | 5.7 |

Examples I-143 to I-147 were prepared following the sequence of procedures described in step 10H, by replacing 10G with 39A; followed by step 15D, by replacing Intermediate 2 with appropriately substituted carboxylic acid derivatives (R—CO₂H). Examples I-148 to I-157 were prepared following the sequence of procedures described in step 10H, by replacing 10G with 39A; followed by step 15D, by replacing Intermediate 2 with appropriately substituted carboxylic acid derivatives (R—CO₂H); and finally Boc-deprotection according to the procedure described in 3C. Examples I-158 to I-161 were prepared by coupling 76B with appropriately substituted carboxylic acid derivatives (R—CO₂H) using coupling conditions described in step 15D. In the case of Example I-158, an additional Boc-deprotection step as described in step 3C was required. Examples I-162 to I-176 were prepared in a similar manner as described above.

TABLE I-9

Examples I-143 to I-176

| Ex. # | R | R³ | LCMS [M + H]+ | HPLC RT (min) (method) |
|---|---|---|---|---|
| I-143 | (cyclohexyl) | H | 480.2 | 4.2(D) |
| I-144 | (2,6-difluoro-4-methylphenyl) | H | 510.1 | 3.6(D) |
| I-145 | (4-methylphenyl) | H | 474.1 | 3.8(D) |
| I-146 | (2,6-difluoro-4-hydroxyphenyl) | H | 512.1 | 3.8 |
| I-147 | (2,6-difluoro-4-methoxyphenyl) | H | 526.2 | 4.4 |
| I-148 | (4-aminomethylphenyl) | H | 489.2 | 3.0(D) |
| I-149 | (3-fluoro-4-aminomethylphenyl) | H | 507.1 | 3.0(D) |

TABLE I-9-continued
Examples I-143 to I-176
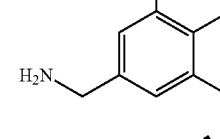
| Ex. # | R | R³ | LCMS [M + H]⁺ | HPLC RT (min) (method) |
|---|---|---|---|---|
| I-150 | 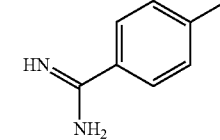 | H | 495.2 | 6.3(C) |
| I-151 | | H | 515.2 | 7.4(C) |
| I-152 | | H | 529.2 | 8.3(C) |
| I-153 | | H | 529.2 | 8.3(C) |
| I-154 | | H | 515.2 | 7.7(C) |
| I-155 | | H | 515.2 | 7.7(C) |
| I-156 | | H | 502.2 | 6.4(C) |
TABLE I-9-continued
Examples I-143 to I-176
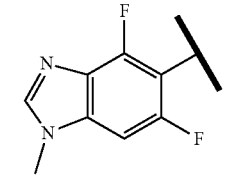
| Ex. # | R | R³ | LCMS [M + H]⁺ | HPLC RT (min) (method) |
|---|---|---|---|---|
| I-157 | 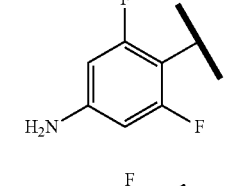 | H | 525.2 | 6.7(C) |
| I-158 | | Cl | 536.1 | 3.5 |
| I-159 | 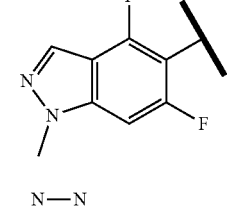 | Cl | 584.0 | 5.0 |
| I-160 | | Cl | 545.2 | 5.2 |
| I-161 | | Cl | 584.0 | 6.1 |
| I-162 | 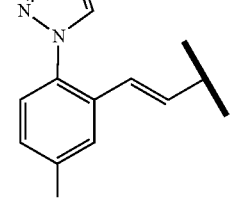 | F | 606.0 | 7.1 |

TABLE I-9-continued

Examples I-143 to I-176

| Ex. # | R | R³ | LCMS [M + H]⁺ | HPLC RT (min) (method) |
|---|---|---|---|---|
| I-163 | (trans-dimethylcyclohexyl) | F | 498.2 | 7.7 |
| I-164 | 4,6-difluoro-1-methylbenzimidazol-5-yl | F | 568.2 | 5.3 |
| I-165 | 3,5-difluoro-4-(aminomethyl)phenyl | F | 543.1 | 3.5 |
| I-166 | 4,6-difluoro-1-(2-fluoroethyl)benzimidazol-5-yl | F | 600.2 | 10.1 |
| I-167 | 2-OMe-5-Cl-phenyl-CH=CH- | F | 568.2 | 8.1 |
| I-168 | 4,6-difluoro-7-chloro-1-methylbenzimidazol-5-yl | F | 602.1 | 6.4 |
| I-169 | imidazol-4-yl-CH=CH- | F | 494.3 | 4.0 |
| I-170 | 4,6-difluoro-1-(fluoromethyl)benzimidazol-5-yl | F | 584.4 | 6.1 |
| I-171 | 4-Cl-2-(tetrazol-1-yl)phenyl-CH=CH- | Me | 602.2 | 4.8 |
| I-172 | (trans-dimethylcyclohexyl) | Me | 494.3 | 5.3 |
| I-173 | 4-Cl-3-F-2-(tetrazol-1-yl)phenyl-CH=CH- | Me | 620.3 | 5.2 |
| I-174 | 2-CN-5-Cl-phenyl-CH=CH- | Me | 559.3 | 6.4 |

TABLE I-9-continued

Examples I-143 to I-176

[Structure diagram]

| Ex. # | R | R³ | LCMS [M + H]⁺ | HPLC RT (min) (method) |
|---|---|---|---|---|
| I-175 | [structure with F, F, O, Cl] | Me | 600.3 | 6.0 |
| I-176 | [structure with triazole, Cl] | CN | 613.2 | 6.9 |

Example I-177

N-((E)-(S)-5-Acetylamino-18-chloro-9-oxo-8,17,19-triaza-tricyclo[14.2.1.02,7]nonadeca-1(18),2,4,6,12,16(19)-hexaen-15-yl)-2,6-difluoro-4-methyl-benzamide, TFA

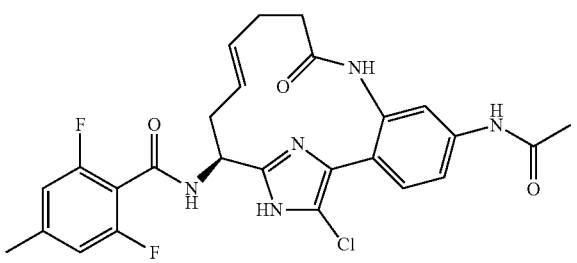 [SMILES: CC(=O)Nc1ccc2c(c1)NC(=O)CC/C=C/C[C@H](NC(=O)c1c(F)cc(C)cc1F)c1nc-2c(Cl)[nH]1]

I-177A and 177-B. (E)-(S)-5,15-Diamino-18-chloro-8,17,19-triaza-tricyclo[14.2.1.02,7]nonadeca-1(18),2,4,6,12,16(19)-hexaen-9-one and ((E)-(S)-15-amino-18-chloro-9-oxo-8,17,19-triaza-tricyclo[14.2.1.02,7]nonadeca-1(18),2,4,6,12,16(19)-hexaen-5-yl)-carbamic acid ethyl ester: 76B (0.377 g, 0.815 mmol) was dissolved in a mixture of ethanol (3.3 ml), water (9.8 ml), and THF (3.3 ml), and LiOH (0.156 g, 6.52 mmol) was added. The reaction was stirred at 60° C. for 48 h, cooled to room temperature, neutralized with 1M HCl and concentrated. The crude products were isolated by reverse phase chromatography to provide I-177A (0.559 g) and I-177B (30 mg) which were used without further purification.

I-177C. 2,5-Dioxopyrrolidin-1-yl 2,6-difluoro-4-methyl-benzoate: To a solution of 2,6-difluoro-4-methylbenzoic acid (2.0 g, 11.62 mmol) in THF (61.8 mL) was added 1-hydroxypyrrolidine-2,5-dione (1.471 g, 12.78 mmol) and 1,3-diisopropylcarbodiimide (2.00 mL, 12.78 mmol) at rt. The reaction mixture was stirred under $N_2$ at rt overnight. Reaction mixture was filtered, and the filtrate was evaporated. The residue was resuspended in MeOH, filtered, and washed several times with MeOH. The remaining white solid was dried under vacuum to yield I-177C (2.80 g, 90%). MS (ESI) m/z: 155.1 (M+H)⁺.

I-177D (Example I-184. N-((E)-(S)-5-Amino-18-chloro-9-oxo-8,17,19-triaza-tricyclo[14.2.1.02,7]nonadeca-1(18),2,4,6,12,16(19)-hexaen-15-yl)-2,6-difluoro-4-methyl-benzamide): I-177D was prepared from I-177A following the procedure described in step 1G, by replacing Intermediate 1 with I-177C. ¹H NMR (500 MHz, CD₃OD) δ ppm 7.17 (1H, d, J=8.25 Hz), 6.89 (2H, d, J=8.80 Hz), 6.68 (1H, dd, J=8.25, 2.20 Hz), 6.60 (1H, d, J=2.20 Hz), 5.49-5.61 (1H, m), 5.23-5.34 (1H, m), 5.14 (1H, dd, J=9.35, 3.85 Hz), 2.55-2.66 (1H, m), 2.41-2.52 (1H, m), 2.33-2.41 (7H, m). MS (ESI) m/z: 486.1 (M+H)⁺. Analytical HPLC: RT=4.92 min.

Example I-177. I-177D (0.03 g, 0.062 mmol) was dissolved in DCM (0.5 ml) and a solution of acetic anhydride (6.30 mg, 0.062 mmol) in DCM (0.1 mL) was added dropwise. The reaction was stirred overnight at room temperature. Reaction mixture was concentrated, and residue was purified by reverse phase chromatography to provide the title compound (12.6 mg, 31.6%) as a white solid. ¹H NMR (500 MHz, DMSO-d₆) δ ppm 11.45 (1H, br. s.), 10.08-10.13 (1H, m), 9.32 (1H, br. s.), 9.21 (1H, d, J=7.70 Hz), 7.63 (1H, br. s.), 7.44 (1H, d, J=10.45 Hz), 7.33 (1H, d, J=8.25 Hz), 6.98 (2H, d, J=8.80 Hz), 5.41-5.61 (1H, m), 5.20-5.35 (1H, m), 5.04-5.19 (1H, m), 2.39-2.45 (1H, m), 2.32 (3H, s), 2.29-2.40 (2H, m), 2.16-2.31 (2H, m), 2.04 (3H, s). MS (ESI) m/z: 528.2 (M+H)⁺. Analytical HPLC: RT=6.05 min.

Example I-178

[(E)-(S)-18-Chloro-15-(2,6-difluoro-4-methyl-benzoylamino)-9-oxo-8,17,19-triaza-tricyclo[14.2.1.02,7]nonadeca-1(18),2,4,6,12,16(19)-hexaen-5-yl]-carbamic acid 2-methoxy-ethyl ester, TFA

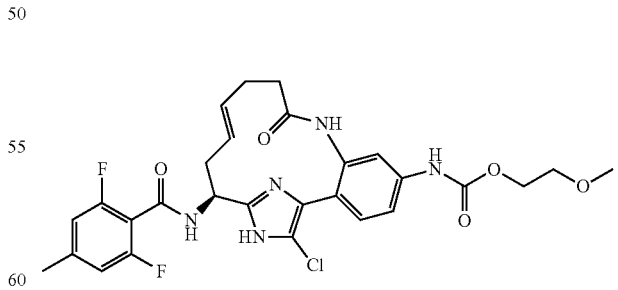

I-177C was dissolved in DCM (5 mL) and pyridine (0.02 mL, 0.247 mmol) was added, followed by dropwise addition of a solution of 2-methoxyethyl carbonochloridate (8.55 mg, 0.062 mmol) in DCM (0.5 mL). The resulting mixture was stirred overnight at room temperature. The reaction was concentrated to dryness, and residue purified by reverse phase HPLC to provide Example I-178 as a white solid (10.6 mg, 24.21%). ¹H NMR (500 MHz, DMSO-d₆) δ ppm 11.38 (1H, br. s.), 9.96 (1H, br. s.), 9.33 (1H, br. s.), 9.22 (1H, d, J=8.25 Hz), 7.45 (1H, br. s.), 7.35-7.41 (1H, m), 7.27-7.35 (1H, m), 6.99 (2H, d, J=8.25 Hz), 5.45-5.58 (1H, m), 5.20-5.34 (1H, m), 5.05-5.18 (1H, m), 4.17-4.27 (2H, m), 3.47-3.61 (2H, m), 3.27 (3H, s), 2.43-2.50 (2H, m), 2.31-2.38 (2H, m), 2.33 (3H, s), 2.18-2.28 (2H, m). MS (ESI) m/z: 588.3 (M+H)⁺. Analytical HPLC: RT=6.8 min.

Example I-179

[(E)-(S)-18-Chloro-15-(2,6-difluoro-4-methyl-benzoylamino)-9-oxo-8,17,19-triaza-tricyclo[14.2.1.02,7]nonadeca-1(18),2,4,6,12,16(19)-hexaen-5-yl]-carbamic Acid ethyl ester, TFA

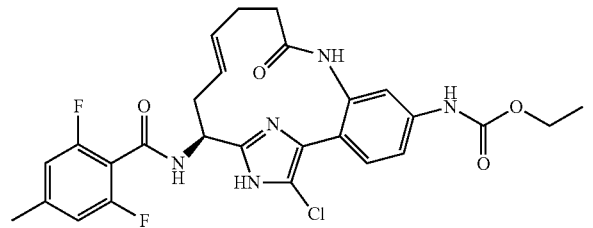 [SMILES: CCOC(=O)Nc1ccc2c(c1)NC(=O)CC/C=C/C[C@H](NC(=O)c1c(F)cc(C)cc1F)c1nc-2c(Cl)[nH]1]

Example I-179 was prepared following the procedure described for I-177D by replacing I-177A with I-177B. ¹H NMR (500 MHz, DMSO-d₆) δ ppm 11.26 (1H, br. s.), 9.65 (1H, s), 9.19 (1H, br. s.), 9.00 (1H, d, J=7.70 Hz), 7.50 (1H, br. s.), 7.38-7.45 (1H, m), 7.31-7.36 (1H, m), 6.92-7.03 (2H, m), 5.49-5.62 (1H, m), 5.23-5.36 (1H, m), 5.07-5.22 (1H, m), 4.16 (2H, q, J=6.97 Hz), 2.40-2.50 (2H, m), 2.33-2.43 (5H, m), 2.25-2.33 (2H, m), 1.27 (3H, t, J=7.02 Hz). MS (ESI) m/z: 558.2 (M+H)⁺. Analytical HPLC: RT=7.35 min.

Example I-180

[(E)-(S)-18-Chloro-15-(2,6-difluoro-4-methyl-benzoylamino)-9-oxo-8,17,19-triaza-tricyclo[14.2.1.02,7]nonadeca-1(18),2,4,6,12,16(19)-hexaen-5-yl]-carbamic Acid (R)-1-(tetrahydro-furan-2-yl)methyl ester, TFA

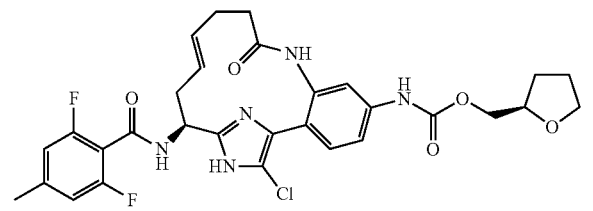 [SMILES: Cc1cc(F)c(C(=O)N[C@H]2C/C=C/CCC(=O)Nc3cc(NC(=O)OC[C@H]4CCCO4)ccc3-c3nc2[nH]c3Cl)c(F)c1]

I-180A. (R)-4-Nitrophenyl (tetrahydrofuran-2-yl)methyl carbonate: A solution of 4-nitrophenyl carbonochloridate (0.2 g, 1.998 mmol) in DCM (8 mL) was added dropwise to a solution of (R)-hydroxy(tetrahydrofuran-2-yl)methylium (0.2 g, 1.998 mmol) in DCM (6.66 ml)/pyridine (0.162 ml, 1.998 mmol) at 0° C. The reaction was maintained at 0° C. for 2 hours then allowed to warm to RT overnight. Reaction was quenched with water and diluted with DCM. Organic phase was washed 3× with sat'd. sodium bicarbonate, and once with brine, dried over sodium sulfate, filtered and concentrated. I-180A (0.442 g, 83%), was obtained as a white solid. MS (ESI) m/z: 290.2 (M+Na)⁺

Example I-180. I-177D (0.026 g, 0.054 mmol) was dissolved in pyridine. I-180A (0.029 g, 0.107 mmol) was added followed by DMAP (6.54 mg, 0.054 mmol). Reaction was stirred at RT overnight. Another 2 equiv. of I-180A was added, and the mixture was stirred for 2 more hours, then evaporated. Residue was purified by reverse phase chromatography to provide the title compound (5.6 mg, 13.80%) as a white solid. ¹H NMR (500 MHz, CD₃OD) δ ppm 9.63 (1H, br. s.), 7.55 (1H, s), 7.36-7.46 (2H, m), 6.91 (2H, d, J=8.80 Hz), 5.45-5.64 (1H, m), 5.29-5.46 (1H, m), 5.06-5.23 (1H, m), 4.04-4.32 (3H, m), 3.85-3.96 (1H, m), 3.70-3.84 (1H, m), 2.70-2.84 (1H, m), 2.21-2.62 (8H, m), 2.00-2.14 (1H, m), 1.81-2.01 (2H, m), 1.52-1.80 (1H, m). MS (ESI) m/z: 614.2 (M+H)⁺. Analytical HPLC: RT=7.65 min.

Examples I-181

[(E)-(S)-18-Chloro-15-(2,6-difluoro-4-methyl-benzoylamino)-9-oxo-8,17,19-triaza-tricyclo[14.2.1.02,7]nonadeca-1(18),2,4,6,12,16(19)-hexaen-5-yl]-carbamic Acid pyridin-2-ylmethyl ester, TFA

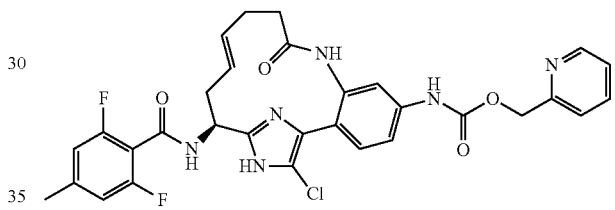

and

Example I-182

N-[(E)-(S)-18-Chloro-9-oxo-5-(2,2,2-trifluoro-acetylamino)-8,17,19-triaza-tricyclo[14.2.1.02,7]nonadeca-1(18),2,4,6,12,16(19)-hexaen-15-yl]-2,6-difluoro-4-methyl-benzamide, TFA

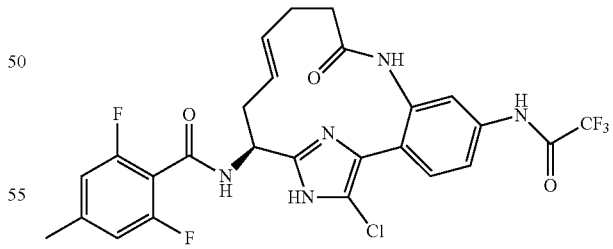

I-177D (0.013 g, 0.018 mmol) was dissolved in DCM (0.5 ml). TEA (0.018 ml, 0.127 mmol) was added, followed by triphosgene (10.81 mg, 0.036 mmol). The mixture was stirred for 30 min at RT, and then a solution of pyridin-2-ylmethanol (9.93 mg, 0.091 mmol) in DCM (0.1 mL) was added. Stirring was continued at RT overnight. Reaction mixture was evaporated, and residue was purified by reverse phase chromatography to provide Example I-181 (1.6 mg, 9.83%). ¹H NMR (500 MHz, CD₃OD) δ ppm 8.68 (1H, d, J=4.95 Hz), 8.22 (1H, td, J=7.84, 1.37 Hz), 7.82 (1H, d, J=7.70 Hz), 7.64-7.70 (1H, m), 7.56-7.60 (1H, m), 7.43-7.46 (2H, m), 6.91 (2H, d, J=8.80 Hz), 5.47-5.61 (1H, m), 5.41 (2H, s), 5.26-5.40 (1H, m), 5.08-5.17 (1H, m), 2.67-2.80 (1H, m), 2.26-2.55 (8H, m). MS (ESI) m/z: 623.1 (M+H)⁺. Analytical HPLC: RT=5.31 min., and Example I-182 (5.6 mg, 43.8%). ¹H NMR (500 MHz, CD₃OD) δ ppm 7.79 (1H, d, J=2.20 Hz), 7.65 (1H, dd, J=8.53, 2.20 Hz), 7.56 (1H, d, J=8.53 Hz), 6.91 (2H, d, J=8.80 Hz), 5.48-5.60 (1H, m), 5.32-5.44 (1H, m), 5.09-5.19 (1H, m), 2.69-2.79 (1H, m), 2.29-2.57 (8H, m). MS (ESI) m/z: 582.3 (M+H)⁺. Analytical HPLC: RT=8.06 min.

Example 183

[(E)-(S)-18-Chloro-15-(2,6-difluoro-4-methyl-benzoylamino)-9-oxo-8,17,19-triaza-tricyclo[14.2.1.02,7]nonadeca-1(18),2,4,6,12,16(19)-hexaen-5-yl]-carbamic Acid 2-dimethylamino-ethyl ester, 2 TFA

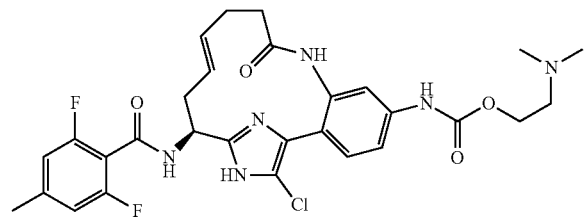

Example I-183 was prepared using the procedure described for Example I-181 by replacing pyridin-2-yl-methanol with 2-(dimethylamino)ethanol. ¹H NMR (500 MHz, CD₃OD) δ ppm 8.10 (1H, s), 7.58 (1H, s), 7.44-7.47 (2H, m), 6.90 (2H, d, J=8.80 Hz), 5.49-5.59 (1H, m), 5.28-5.41 (1H, m), 5.07-5.15 (1H, m), 4.49-4.55 (2H, m), 3.46-3.56 (2H, m), 3.00 (6H, s), 2.60-2.75 (2H, m), 2.25-2.56 (7H, m). MS (ESI) m/z: 601.3 (M+H)⁺. Analytical HPLC: RT=4.66 min.

Example 185

[(E)-(S)-18-Chloro-15-(2,6-difluoro-4-methyl-benzoylamino)-9-oxo-8,17,19-triaza-tricyclo[14.2.1.02,7]nonadeca-1(18),2,4,6,12,16(19)-hexaen-5-yl]-carbamic acid azetidin-3-yl ester, 2 TFA

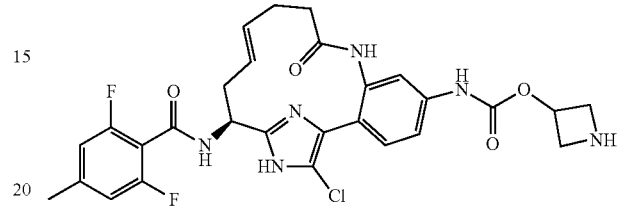

Example 186 was dissolved in DCM (1 mL) and TFA (0.25 mL) was added. After stirring for 1 h at RT, the reaction mixture was evaporated to dryness to provide the title compound. ¹H NMR (500 MHz, CD₃OD) δ ppm 7.44-7.50 (1H, m), 7.33-7.41 (2H, m), 6.80-6.86 (2H, m), 5.38-5.52 (1H, m), 5.23-5.34 (2H, m), 5.00-5.07 (1H, m), 4.33-4.43 (2H, m), 4.09-4.19 (2H, m), 2.61-2.73 (1H, m), 2.17-2.49 (8H, m). MS (ESI) m/z: 585.2 (M+H)⁺. Analytical HPLC: RT=4.53 min.

Example 186

3-[(E)-(S)-18-Chloro-15-(2,6-difluoro-4-methyl-benzoylamino)-9-oxo-8,17,19-triaza-tricyclo[14.2.1.02,7]nonadeca-1(18),2,4,6,12,16(19)-hexaen-5-ylcarbamoyloxy]-azetidine-1-carboxylic Acid tert-butyl ester, TFA

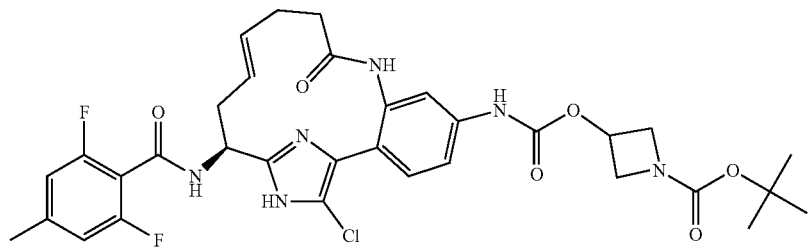 [SMILES: Cc1cc(F)c(C(=O)N[C@H]2C/C=C/CCC(=O)Nc3cc(NC(=O)OC4CN(C(=O)OC(C)(C)C)C4)ccc3-c3nc2[nH]c3Cl)c(F)c1]

Example 186 was prepared using the procedures described for Ex. I-180, by replacing (R)-hydroxy(tetrahydrofuran-2-yl)methylium with tert-butyl 3-hydroxyazetidine-1-carboxylate in step I-180A. ¹H NMR (500 MHz, CD₃OD) δ ppm 9.81 (1H, br. s.), 7.52-7.58 (1H, m), 7.37-7.48 (2H, m), 6.90 (2H, d, J=8.80 Hz), 5.45-5.59 (1H, m), 5.29-5.41 (1H, m), 5.16-5.24 (1H, m), 5.07-5.16 (1H, m), 4.23-4.35 (2H, m), 3.85-3.99 (2H, m), 2.68-2.78 (1H, m), 2.25-2.56 (8H, m), 1.44 (9H, s). MS (ESI) m/z: 685.3 (M+H)⁺. Analytical HPLC: RT=8.63 min.

Example I-187

[(E)-(S)-18-Chloro-15-(2,6-difluoro-4-methyl-benzoylamino)-9-oxo-8,17,19-triaza-tricyclo[14.2.1.0 2,7]nonadeca-1(18),2,4,6,12,16(19)-hexaen-5-ylcarbamoyloxy]-acetic Acid, TFA

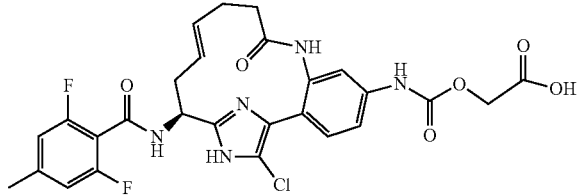 [SMILES: Cc1cc(F)c(C(=O)N[C@H]2C/C=C/CCC(=O)Nc3cc(NC(=O)OCC(=O)O)ccc3-c3nc2[nH]c3Cl)c(F)c1]

Example I-187 was prepared following the procedure described for Example 181, by replacing pyridin-2-ylmethanol with ethyl 2-hydroxyacetate, followed by hydrolysis of the crude ethyl ester with LiOH in THF. $^1$H NMR (500 MHz, CD$_3$OD) δ ppm 9.80 (1H, br. s.), 7.57 (1H, s), 7.43 (2H, s), 6.90 (2H, d, J=8.80 Hz), 5.47-5.62 (1H, m), 5.29-5.41 (1H, m), 5.01-5.20 (1H, m), 4.66 (2H, s), 2.68-2.79 (1H, m), 2.25-2.56 (8H, m). MS (ESI) m/z: 588.2 (M+H)$^+$. Analytical HPLC: RT=6.08 min.

Example I-188

[(E)-(S)-18-Chloro-15-(2,6-difluoro-4-methyl-benzoylamino)-9-oxo-8,17,19-triaza-tricyclo[14.2.1.0 2,7]nonadeca-1(18),2,4,6,12,16(19)-hexaen-5-yl]-carbamic Acid 2-tert-butoxy-ethyl ester, TFA

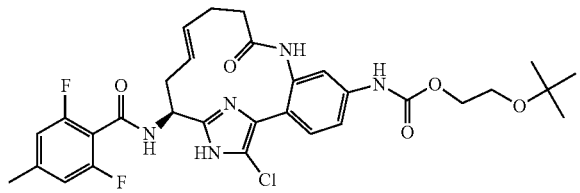 [SMILES: Cc1cc(F)c(C(=O)N[C@H]2C/C=C/CCC(=O)Nc3cc(NC(=O)OCCOC(C)(C)C)ccc3-c3nc2[nH]c3Cl)c(F)c1]

Example 188 was prepared similarly to Ex. I-180, by replacing (R)-hydroxy(tetrahydrofuran-2-yl)methylium with 2-tert-butoxyethanol in step I-180A $^1$H NMR (500 MHz, CD$_3$OD) δ ppm 9.51 (1H, br. s.), 7.50 (1H, s), 7.37 (2H, s), 6.86 (2H, d, J=8.80 Hz), 5.40-5.58 (1H, m), 5.22-5.33 (1H, m), 5.08 (1H, dd, J=10.17, 4.12 Hz), 4.13-4.21 (2H, m), 3.56-3.64 (2H, m), 2.59-2.70 (1H, m), 2.34 (8H, s), 1.17 (9H, s). MS (ESI) m/z: 630.3 (M+H)$^+$. Analytical HPLC: RT=8.0 min.

Example I-189

[(E)-(S)-18-Chloro-15-(2,6-difluoro-4-methyl-benzoylamino)-9-oxo-8,17,19-triaza-tricyclo[14.2.1.0 2,7]nonadeca-1(18),2,4,6,12,16(19)-hexaen-5-yl]-carbamic Acid 2-hydroxy-ethyl ester, TFA

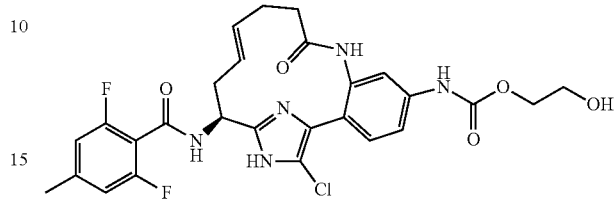

I-189A. 2-tert-Butoxyethyl carbonochloridate: To a solution of 2-tert-butoxyethanol (0.444 mL, 3.38 mmol) and pyridine (0.274 mL, 3.38 mmol) in ether (10 mL) was added triphosgene (0.331 g, 1.117 mmol) dissolved in 2 mL of ether. The reaction mixture was maintained at 0° C. for one hour. Reaction mixture was filtered and concentrated to provide the crude 2-tert-butoxyethyl carbonochloridate (0.424 g, 69.3%), as a clear oil. $^1$H NMR (500 MHz, CDCl$_3$) δ ppm 4.38-4.43 (2H, m), 3.60-3.65 (2H, m), 1.20 (9H, s).

Example I-189. This compound was prepared from I-177D according to the procedure described for step I-123B, by replacing 2-methoxyethyl carbonochloridate with I-189A, followed by deprotection of the crude t-butyl ether with TFA/DCM. $^1$H NMR (500 MHz, CD$_3$OD) δ ppm 9.57 (1H, br. s.), 7.55-7.66 (1H, m), 7.39-7.51 (2H, m), 6.94 (2H, d, J=8.80 Hz), 5.48-5.61 (1H, m), 5.32-5.46 (1H, m), 5.16 (1H, dd, J=10.59, 4.54 Hz), 4.21-4.34 (2H, m), 3.77-3.86 (2H, m), 2.74-2.84 (1H, m), 2.31-2.59 (8H, m). MS (ESI) m/z: 574.2 (M+H)$^+$. Analytical HPLC: RT=5.77 min.

Example 190

[(E)-(S)-18-Chloro-15-(2,6-difluoro-4-methyl-benzoylamino)-9-oxo-8,17,19-triaza-tricyclo[14.2.1.0 2,7]nonadeca-1(18),2,4,6,12,16(19)-hexaen-5-yl]-carbamic Acid tetrahydro-furan-3-ylmethyl ester, TFA

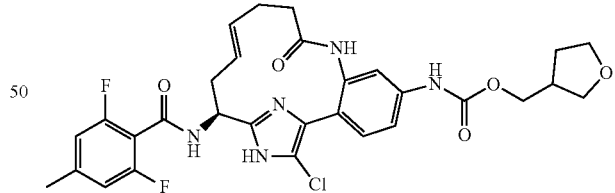

Example I-190 was prepared following the procedures described for Ex. I-189, by replacing 2-tert-butoxyethanol with (tetrahydrofuran-3-yl)methanol in step I-189A and omitting the TFA treatment. $^1$H NMR (500 MHz, CD$_3$OD) δ ppm 9.54 (1H, br. s.), 8.25 (1H, d, J=9.35 Hz), 7.47-7.53 (1H, m), 7.24-7.45 (2H, m), 6.85 (2H, d, J=8.80 Hz), 5.41-5.57 (1H, m), 5.24-5.35 (1H, m), 5.06 (1H, dd, J=10.72, 4.12 Hz), 4.06-4.28 (1H, m), 3.94-4.04 (1H, m), 3.74-3.87 (2H, m), 3.63-3.73 (1H, m), 3.53-3.62 (1H, m), 2.62-2.74 (1H, m), 2.53-2.63 (1H, m), 2.20-2.50 (8H, m), 1.90-2.10 (1H, m), 1.58-1.75 (1H, m). MS (ESI) m/z: 614.3 (M+H)$^+$. Analytical HPLC: RT=6.86 min.

TABLE I-10
Examples I-177 to I-190
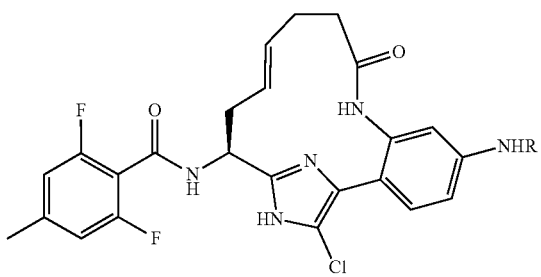
| Ex. # | R | LCMS [M + H]+ | HPLC RT (min) |
|---|---|---|---|
| I-177 | | 528.2 | 6.1 |
| I-178 | | 588.3 | 6.8 |
| I-179 | | 558.2 | 7.3 |
| I-180 | | 614.2 | 7.7 |
| I-181 | | 621.3 | 5.3 |
| I-182 | | 582.3 | 8.1 |
| I-183 | | 601.3 | 4.7 |

TABLE I-10-continued

Examples I-177 to I-190

| Ex. # | R | LCMS [M + H]⁺ | HPLC RT (min) |
|---|---|---|---|
| I-184 | H | 486.1 | 4.9 |
| I-185 | (azetidin-3-yl ester of propanoate) | 585.2 | 4.5 |
| I-186 | (N-Boc-azetidin-3-yl ester of propanoate) | 685.3 | 8.6 |
| I-187 | (carboxymethyl ester of propanoate) | 588.2 | 6.1 |
| I-188 | (2-tert-butoxyethyl ester of propanoate) | 630.3 | 8.0 |
| I-189 | (2-hydroxyethyl ester of propanoate) | 574.2 | 5.8 |
| I-190 | ((tetrahydrofuran-3-yl)methyl ester of propanoate) | 614.3 | 6.9 |

Example I-192 was prepared following the procedure described in Example 47. Examples I-193 to I-195 were prepared following the procedures described in Example 53, by replacing 15B with 10C.

Example I-196

{(E)-(S)-15-[(E)-3-(5-Chloro-2-tetrazol-1-yl-phenyl)-acryloylamino]-11-hydroxy-9-oxo-8,17,19-triaza-tricyclo[14.2.1.0$^{2,7}$]nonadeca-1(18),2,4,6,12,16(19)-hexaen-5-yl}-carbamic Acid methyl ester, trifluoroacetic Acid Salt

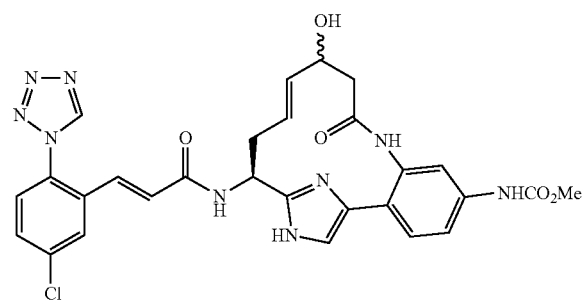

I-196A. {3-Amino-4-[2-((S)-1-tert-butoxycarbonylamino-but-3-enyl)-1-(2-trimethylsilanyl-ethoxymethyl)-1H-imidazol-4-yl]-phenyl}-carbamic acid methyl ester (0.15 g, 0.28 mmol) was dissolved in DMF (3 mL). To this solution was added 3-Hydroxy-pent-4-enoic acid (0.064 g, 0.55 mmol), followed by T3P (0.326 g, 0.423 mmol) and Hunig's base (0.073 g, 0.56 mmol) and the reaction mixture was stirred at room temperature overnight. Quenched the reaction with water (100 ml), and extracted organics with EtOAc (2×100 mL), dried (MgSO$_4$) and evaporated to a greenish semi-solid mass. Purified the crude via normal phase chromatography. Pure fractions were collected and concentrated to a pale yellow solid (0.11g, 62%). $^1$H NMR (500 MHz, CD$_3$OD) δ ppm 8.39 (m, 1H), 7.58-7.43 (m, 2H), 7.21 (s, 1H), 5.80 (m, 1H), 5.55-5.05 (m, 8H), 3.76 (s, 3H), 3.54 (m. 2H), 2.80 (m, 2H), 1.46 (s, 9H), 0.94 (m, 2H), 0.00 (s, 9H). MS (ESI) m/z: 630.3 (M+H)$^+$.

I-196 B. The product from I-196A was dissolved in DCM (35 mL) and degassed. After 0.5 h pTsOH (0.03 g, 0.18 mmol) was added and the reaction mixture was stirred for an additional 0.5 h while being degassed. To this solution was added Grubbs II catalyst (0.06 g, 0.07 mmol) and the reaction mixture was heated to 40° C. overnight. Reaction mixture was cooled and quenched with sodium phase phase solution (10%, 50 mL) and the organics layer separated. The aqueous layer was further extracted with EtOAc (2×100 ml), and the combined extracts was dried (MgSO$_4$) and evaporated to a brown oil. The crude material was purified via normal phase chromatography to afford the desired macrocycle as a colorless oil. MS (ESI) m/z: 602.2 (M+H)$^+$.

I-196C. The removal of the Boc and Sem protecting groups as in Example 1 (step 1F) of the product from I-196B, followed by the coupling of the crude amino macrocycle with Intermediate 1 as described for Example 1 (step 1G) afforded the title compound as a white solid (10 mg, 23%). $^1$H NMR (500 MHz, CD$_3$OD) δ ppm 9.55 (s, 1H), 9.50 (d, J=2.5 Hz, 1H), 7.98 (m, 1H), 7.69 (dd, J=2.3 & 8.5 Hz, 1H), 7.60-7.57 (m, 2H), 7.41-7.37 (m, 2H), 7.18-7.13 (dd, J=4.3 & 8.7 Hz, 1H), 6.77 (d, J=15.8 Hz, 1H), 5.84-5.73 (m, 1H), 5.55-5.43 (m, 1H), 5.17-5.09 (m, 1H), 4.44 (m, 1H), 3.75 (s, 3H), 2.9-2.45 (m, 5H). MS (ESI) m/z: 604.3 (M+H)$^+$. Analytical HPLC: RT=5.12 min.

Example I-197

{(S)-15-[(E)-3-(5-Chloro-2-tetrazol-1-yl-phenyl)-acryloylamino]-11-hydroxy-9-oxo-8,17,19-triaza-tricyclo[14.2.1.0$^{2,7}$]nonadeca-1(18),2,4,6,16(19)-pentaen-5-yl}-carbamic Acid methyl ester, trifluoroacetic Acid Salt

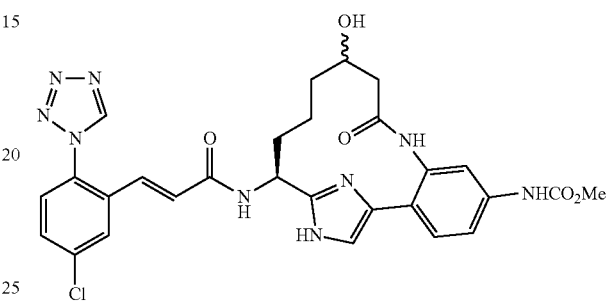

The reduction of I-196B as in Example 2 (step 2G), deprotection of the Boc and Sem protecting groups as in Example 1 (step 1F), and coupling with Intermediate 1 as described for Example 1 (step 1G) afforded the title compound as a brown solid (7 mg, 13%). $^1$H NMR (500 MHz, CD$_3$OD) δ ppm 9.51 (s, 1H), 9.51 (s, 1H), 7.98 (dd, J=2.3 & 8.3 Hz, 1H), 7.69-7.66 (m, 1H), 7.61-7.56 (m, 1H), 7.44-7.41 (m, 2H), 7.16-7.10 (t, 1H), 6.79-6.69 (dd, J=15.6 Hz, 2H), 5.05-4.97 (m, 1H), 4.00 (m, 1H), 3.76 (s, 3H), 2.66-2.63 (m, 1H), 2.34-2.22 (m, 2H), 2.05 (m, 1H), 1.80 (m, 1H), 1.62 (m, 1H), 1.58 (m, 1H), 1.38-1.22 (m, 2H), 1.00-0.74 (m, 2H). MS (ESI) m/z: 606.4 (M+H)$^+$. Analytical HPLC: RT=4.36 min.

Example I-198

{(S)-15-[(E)-3-(5-Chloro-2-tetrazol-1-yl-phenyl)-acryloylamino]-9,11-dioxo-8,17,19-triaza-tricyclo [14.2.1.0$^{2,7}$]nonadeca-1(18),2,4,6,16(19)-pentaen-5-yl}-carbamic Acid methyl ester, trifluoroacetic Acid Salt

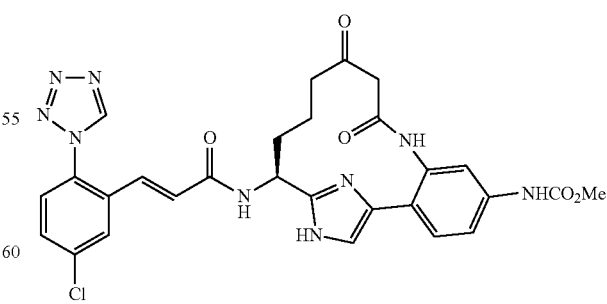

The reduction of I-196B as in Example 2 (step 2G), followed by the oxidation of the reduced product (0.04 g, 0.06 mmol) with Dess-Martin periodinane (0.03 g, 0.076 mmol) in DCM (5 mL), deprotection of the Boc and SEM protecting groups as in Example 1 (step 1F), and coupling with Intermediate 1 as described for Example 1 (step 1G) afforded the title compound as a brown solid (6 mg, 15%). $^1$H NMR (500 MHz, CD$_3$OD) δ ppm 9.41 (s, 1H), 7.87 (d, J=2.7 Hz, 1H), 7.52-7.45 (m, 4H), 7.40-7.30 (m, 4H), 7.04 (d, J=16.4 Hz, 1H), 6.65 (d, J=15.4 Hz, 1H), 4.97 (m, 1H), 3.66 (s, 3H), 3.63 (t, 1H). 3.18-3.10 (m, 1H), 2.25-2.05 (m, 2H), 1.75 (bm, 2H). MS (ESI) m/z: 604.2 (M+H)$^+$. Analytical HPLC: RT=5.79 min.

Example I-199

Acetic Acid (S)-15-[(E)-3-(5-chloro-2-tetrazol-1-yl-phenyl)-acryloylamino]-5-methoxycarbonylamino-9-oxo-8,17,19-triaza-tricyclo[14.2.1.0$^{2,7}$]nonadeca-1(18),2,4,6,16(19)-pentaen-11-yl ester, trifluoroacetic Acid Salt

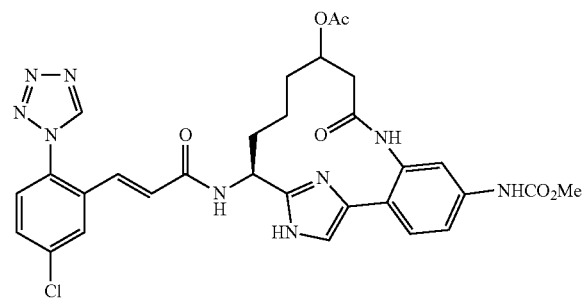

The reduction of I-196B as in Example 2 (step 2G), followed by the acetylation with acetic anhydride of the reduced product, deprotection of the Boc and SEM protecting groups as in Example 1 (step 1F), and coupling with Intermediate 1 as described for Example 1 (step 1G) afforded the title compound as a brown solid (4 mg, 5%). $^1$H NMR (500 MHz, CD$_3$OD) δ ppm 9.39 (s, 1H), 7.88-7.85 (dd, J=2.3 & 8.8 Hz, 1H), 7.63-7.56 (m, 1H), 7.54-7.47 (m, 2H), 7.48-7.39 (m, 2H), 7.08-7.03 (m, 1H), 6.69-6.57 (q, 2H), 5.12-4.98 (m, 1H), 4.48 (m, 1H), 3.66 (s, 3H), 2.78 (dd, 2H), 2.40-2.30 (m, 1H), 2.12 (bm, 1H), 1.95 (s, 3H), 1.51-1.00 (m, 4H). MS (ESI) m/z: 648.2 (M+H)$^+$. Analytical HPLC: RT=4.93 min.

Examples I-200 and I-201 were prepared following the procedures described in step 10D, by replacing but-3-enoic acid with 2-methylpent-4-enoic acid; followed by steps 2E/2F; 10H; and 1G. Examples I-202 and I-203 were prepared following the procedures described in step 10D, by replacing but-3-enoic acid with 2-methylpent-4-enoic acid; followed by steps 2E/2F; 2G; 10H; and 1G.

Examples I-205 and I-206

{(S)-15-[(E)-3-(5-Chloro-2-tetrazol-1-yl-phenyl)-acryloylamino]-11-methyl-8-oxa-17,19-diaza-tricyclo[14.2.1.0$^{2,7}$]nonadeca-1(18),2,4,6,16(19)-pentaen-5-yl}-carbamic Acid methyl ester, TFA, Diastereomer A and Diastereomer B

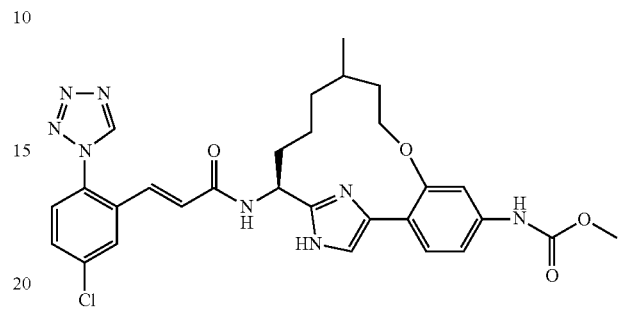

I-205A. Methyl 2-hydroxy-4-(methoxycarbonylamino)benzoate: Methyl 4-amino-2-hydroxybenzoate (10 g, 59.8 mmol) was dissolved in DCM (120 mL), and pyridine (5.32 mL, 65.8 mmol) was added. The mixture was cooled to 0° C., and methyl chloroformate (4.87 mL, 62.8 mmol) was added dropwise. The reaction was stirred for 1.5 h, then quenched with 1.5M dibasic potassium phosphate solution, and extracted 2× with DCM. The combined org. phases were washed 2× with 1M HCl and 1× with brine, dried with sodium sulfate, filtered and concentrated to yield I-205A (14.2 g) which was used without further purification in the next step. MS (ESI) m/z: 226.2 (M+H)$^+$.

I-205B. Methyl 2-(allyloxy)-4-(methoxycarbonylamino)benzoate: I-205A (14.22 g, 63.1 mmol) was dissolved in acetone (210 mL). Allyl bromide (16.39 mL, 189 mmol) was added followed by potassium carbonate (43.6 g, 316 mmol). The reaction was heated at 60° C. under Ar and a reflux condensor for 8 hours. The reaction was concentrated under reduced pressure and diluted with EtOAc/water. The aq. phase was washed with EtOAc 2×, then the combined organic phases were washed with brine and dried with sodium sulfate and concentrated. Residue was purified by normal phase chromatography to provide I-205B (8.03 g, 47.9%), as a yellow solid. MS (ESI) m/z: 266.1 (M+H)$^+$ I-205C. Methyl 3-(allyloxy)-4-(2-chloroacetyl)phenylcarbamate: To trimethylsulfoxonium chloride (12.12 g, 94 mmol) and 1 M potassium t-butoxide (99 mL, 99 mmol) was added an additional 80 mL of THF. The mixture was refluxed for 2 hours, then allowed to cool to room temperature. A solution of I-205B (5 g, 18.85 mmol) dissolved in 100 mL of THF was added dropwise. The reaction was allowed to stir at RT overnight under Ar. The reaction mixture and was concentrated, and the residue was partitioned between EtOAc and water. Aqueous phase was extracted 2× with EtOAc. Combined organic phases were washed with brine, dried with sodium sulfate, filtered and concentrated. Residue was taken up in methylene chloride and filtered. Filtrate was purified by normal phase chromatography, and fractions containing product combined with the insoluble solid above to provide the intermediate sulfonium species (5.76 g, 94%, MS (ESI) m/z: 326.1 (M+H)$^+$), which was dissolved in THF (89 mL). a solution of 4M HCl in Dioxane (8.85 mL, 35.4 mmol) was added, and the mixture was stirred at 70° C. overnight in a sealed tube. The reaction mixture was concentrated, and residue was purified by normal phase chromatography to provide I-205C (2.01 g, 40.0%) as a yellow solid. MS (ESI) m/z: 284.1 (M+H)$^+$ I-205D. {3-Allyloxy-4-[2-((S)-1-tert-butoxycarbonylamino-but-3-enyl)-1-(2-trimethylsilanyl-ethoxymethyl)-1H-imidazol-4-yl]-phenyl}-carbamic acid methyl ester: I-205D was prepared in three steps following the procedures described for steps 2A, by replacing 2-bromo-1-(2-bromophenyl)ethanone with I-205C; 2B; and 10B. MS (ESI) m/z: 573.4 (M+H)$^+$.

I-205E. {4-[2-((S)-1-tert-Butoxycarbonylamino-but-3-enyl)-1-(2-trimethylsilanyl-ethoxymethyl)-1H-imidazol-4-yl]-3-hydroxy-phenyl}-carbamic acid methyl ester: I-205D (0.663 g, 1.158 mmol) was dissolved in methanol (5.79 ml) and added to a 3 neck flask along with potassium carbonate (0.480 g, 3.47 mmol). The flask was degassed and backfilled with Ar 3×. (Ph$_3$P)$_4$Pd (0.134 g, 0.116 mmol) was added under a stream of Ar. The mixture was degassed and backfilled 3 more times with Ar. The reaction was stirred for 10 min at RT, then an additional portion of potassium carbonate (0.480 g, 3.47 mmol) was added under a stream of Ar, and the mixture was stirred for 1 hr under Ar. Reaction was diluted with EtOAc/water; aq. phase was extracted 2× with EtOAc; combined organic phases were washed with brine, dried with sodium sulfate concentrated. Residue was purified by flash chromatography to provide I-205E (0.45 g, 0.845 mmol, 73.0%) as a white solid. MS (ESI) m/z: 533.4 (M+H)$^+$.

I-205F. 5-Iodo-3-methylpent-1-ene: To a cooled solution (0° C.) of 1M lithium aluminum hydride in Et$_2$O (21.90 mL, 21.90 mmol) and 10 mL of additional ether, was added dropwise 3-methylpent-4-enoic acid (1.064 mL, 8.76 mmol) dissolved in 15 mL of ether. Reaction was allowed to warm to RT and stirred overnight. The reaction was carefully poured onto ice in small portions, and 15 mL of 5M H$_2$SO$_4$ was added to dissolve most of the salts. The aq. phase was extracted 2× with ether and combined organic phases were washed with brine, dried with sodium sulfate, filtered and concentrated to provide the crude 3-methylpent-4-en-1-ol, which was taken on without further purification. The alcohol (0.877 g, 8.76 mmol) was dissolved in 20 mL of anhydrous DCM, and triphenylphosphine (2.99 g, 11.38 mmol) and imidazole (0.894 g, 13.13 mmol) were added. The reaction mixture was cooled to 0° C., and a solution of iodine (2.89 g, 11.38 mmol) in 20 mL of DCM was added dropwise. After 30 min at 0° C., the reaction was warmed to RT and stirred overnight. The reaction was washed 3× with 10% aq. sodium sulfite and 1× with brine, dried with sodium sulfate, filtered and concentrated. Residue was purified on a pad of silica gel eluted with pentane to provide the iodide (0.937 g, 4.46 mmol, 50.9%) as a clear oil.

I-205G. [4-[2-((S)-1-tert-Butoxycarbonylamino-but-3-enyl)-1-(2-trimethylsilanyl-ethoxymethyl)-1H-imidazol-4-yl]-3-(3-methyl-pent-4-enyloxy)-phenyl]-carbamic acid methyl ester: I-205E (.206 g, 0.335 mmol, 79%) was dissolved in acetone (3 mL) and potassium carbonate (0.292 g, 2.112 mmol) and I-205F (0.444 g, 2.112 mmol) were added. Reaction mixture was stirred at 55° C. in a sealed vial for 1 h, then at 70° C. overnight. The reaction was concentrated and partitioned between water and EtOAc. Aq. phase was re-extracted 2× with EtOAc, and combined organic extracts were washed with brine dried with sodium sulfate, filtered and concentrated. Residue was purified by normal phase chromatography to provide I-205G (0.206 g, 79%) as a white solid. MS (ESI) m/z: 615.5 (M+H)$^+$.

Examples I-205 and I-206. The title compounds were prepared in four steps from I-205G using the procedures described in steps 2E/F and 2G, at which point the diastereomers were separated by reverse phase chromatography and carried on individually through the deprotection and amide coupling steps using the procedures described in steps 10H and 1G. Example I-205 (Diastereomer A): $^1$H NMR (500 MHz, CD$_3$OD) δ ppm 9.52 (1H, s), 7.99 (1H, d, J=2.20 Hz), 7.69 (1H, dd, J=8.53, 2.48 Hz), 7.60 (1H, d, J=8.53 Hz), 7.40 (1H, s), 7.33-7.40 (2H, m), 7.19 (1H, d, J=15.41 Hz), 7.02-7.09 (1H, m), 6.80 (1H, d, J=15.41 Hz), 5.14 (1H, dd, J=8.80, 4.40 Hz), 3.99-4.13 (2H, m), 3.76 (3H, s), 2.22-2.41 (1H, m), 1.71-1.91 (3H, m), 1.55-1.71 (2H, m), 1.41-1.55 (1H, m), 0.94-1.05 (2H, m), 0.95 (3H, d, J=6.60 Hz). MS (ESI) m/z: 591.2 (M+H)$^+$. Analytical HPLC: RT=6.98 min. Example I-206 (Diastereomer B): $^1$H NMR (400 MHz, CD$_3$OD) δ ppm 9.51 (1H, s), 7.95 (1H, d, J=2.20 Hz), 7.67 (1H, dd, J=8.79, 2.20 Hz), 7.52-7.62 (1H, m), 7.40-7.43 (1H, m), 7.37-7.40 (1H, m), 7.36 (1H, d, J=8.25 Hz), 7.14 (1H, d, J=15.39 Hz), 7.05 (1H, dd, J=8.25, 1.65 Hz), 6.70 (1H, d, J=15.94 Hz), 5.01 (1H, dd, J=9.89, 4.95 Hz), 3.94-4.12 (2H, m), 3.75 (3H, s), 1.99-2.25 (2H, m), 1.47-1.81 (4H, m), 0.96-1.34 (3H, m), 0.94-1.03 (3H, m). MS (ESI) m/z: 591.2 (M+H)$^+$. Analytical HPLC: RT=6.976 min Examples I-207 and I-208 were prepared in a similar manner as Examples I-205 and I-206 starting from Intermediate I-205E and substituting 2-methylpent-4-enoic acid for 3-methylpent-4-enoic acid in step I-205F.

Examples I-209 to I-212 were prepared following the procedures described for the preparation of Examples 154 and 155, replacing allylmagnesium bromide with but-3-enylmagnesium bromide. Examples I-213 to I-215 were prepared following the procedures described for the preparation of Examples 125, 39, and 34, replacing pent-4-enoic acid with hex-5-enoic acid.

TABLE I-11
Examples I-191 to I-215
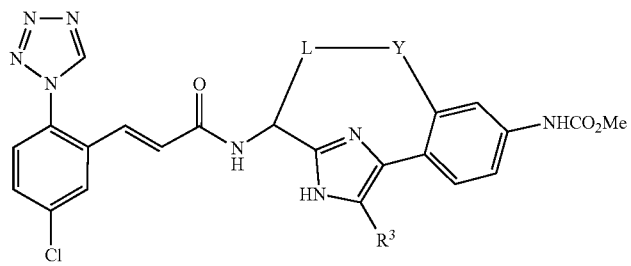
| Ex. # | L-Y | R³ | LCMS [M + H]⁺ | HPLC RT (min) |
|---|---|---|---|---|
| I-191 | —(CH₂)₅—C(O)NH— | F | 608.3 | 7.0 |
| I-192 | 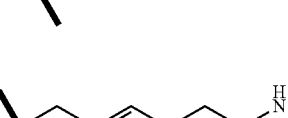 | H | 602.0 | 5.4 |
| I-193 |  | H | 602.2 | 5.5 |
| I-194 | 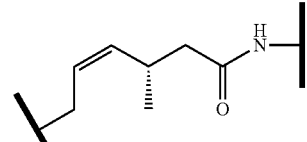 | H | 602.2 | 5.4 |
| I-195 | 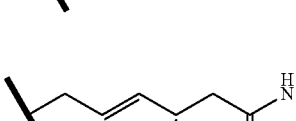 | H | 602.2 | 5.4 |
| I-196 | 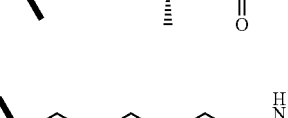 (diastereomer mixture) | H | 604.2 | 5.1 |
| I-197 | 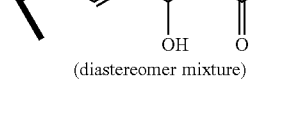 (diastereomer mixture) | H | 604.4 [M − H]⁺ | 4.4 |
| I-198 | 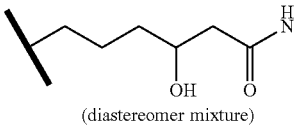 | H | 604.2 | 5.8 |

TABLE I-11-continued

Examples I-191 to I-215

| Ex. # | L-Y | R³ | LCMS [M + H]⁺ | HPLC RT (min) |
|---|---|---|---|---|
| I-199 | (diastereomer mixture) | H | 648.2 | 4.9 |
| I-200 | (diastereomer B) | H | 602.2 | 5.4 |
| I-201 | (diastereomer A) | H | 602.3 | 5.3 |
| I-202 | (diastereomer B) | H | 604.3 | 4.9 |
| I-203 | (diastereomer A) | H | 604.3 | 4.9 |
| I-204 | | Cl | 638.2 | 6.9 |
| I-205 | (homochiral) | H | 591.2 | 7.0 |
| I-206 | (homochiral) | H | 591.2 | 7.0 |

TABLE I-11-continued

Examples I-191 to I-215

| Ex. # | L-Y | R³ | LCMS [M + H]⁺ | HPLC RT (min) |
|---|---|---|---|---|
| I-207 | (homochiral) | H | 591.3 | 6.8 |
| I-208 | (homochiral) | H | 591.2 | 6.8 |
| I-209 | (homochiral) | H | 642.3 | 7.3 |
| I-210 | (homochiral) | H | 644.3 | 7.2 |
| I-211 | (homochiral) | H | 642.3 | 5.7 |
| I-212 | (homochiral) | H | 644.3 | 6.3 |
| I-213 | | H | 602.1 | 5.3 |

TABLE I-11-continued

Examples I-191 to I-215

| Ex. # | L-Y | R³ | LCMS [M + H]⁺ | HPLC RT (min) |
|---|---|---|---|---|
| I-214 | (alkenyl amide linker) | H | 602.2 | 5.6 |
| I-215 | (alkyl amide linker) | H | 604.2 | 5.5 |

Example I-216 was prepared following the procedures described in step 10D, by replacing but-3-enoic acid with 3-methyl-4-pentenoic; followed by steps 2E; 10H; and 15D, by replacing Intermediate 2 with 2,6-difluoro-4-methylbenzoic acid. Example I-217 was prepared following the procedures described in step 10D, by replacing but-3-enoic acid with 3-methyl-4-pentenoic; followed by steps 2E/2F; 10G; 10H; and 15D, by replacing Intermediate 2 with 2,6-difluoro-4-methylbenzoic acid. Examples I-218 to I-219 were prepared following the procedures described in step 10D, by replacing but-3-enoic acid with 3-ethyl pent-4-enoic acid; followed by steps 2E/2F; 10H; and 15D, by replacing Intermediate 2 with 2,6-difluoro-4-methylbenzoic acid. Examples I-220 and I-221 were prepared following the procedures described in step 10D, by replacing but-3-enoic acid with 2-methyl-4-pentenoic acid; followed by steps 2E/2F; 10H; and 15D, by replacing Intermediate 2 with 2,6-difluoro-4-methylbenzoic acid.

TABLE I-12

Examples I-216 to I-221

| Ex. # | L-Y | R³ | LCMS [M + H]⁺ | HPLC RT (min) |
|---|---|---|---|---|
| I-216 | (alkenyl methyl amide linker) | Cl | 558.1 | 7.5 |
| I-217 | (alkyl methyl amide linker) | Cl | 560.0 | 7.1 |

TABLE I-12-continued

Examples I-216 to I-221

| Ex. # | L-Y | R³ | LCMS [M + H]⁺ | HPLC RT (min) |
|---|---|---|---|---|
| I-218 | (diastereomer A) | H | 538.2 | 4.9 |
| I-219 | (diastereomer B) | H | 538.2 | 4.9 |
| I-220 | (diastereomer B) | H | 524.3 | 5.1 |
| I-221 | (diastereomer A) | H | 524.2 | 5.0 |

Example I-226

(E)-3-(5-Chloro-2-tetrazol-1-yl-phenyl)-N-((E)-(S)-4-fluoro-9-oxo-8,17,19-triaza-tricyclo[14.2.1.0$^{2,7}$]nonadeca-1(18),2,4,6,12,16(19)-hexaen-15-yl)-acrylamide, trifluoroacetic Acid Salt

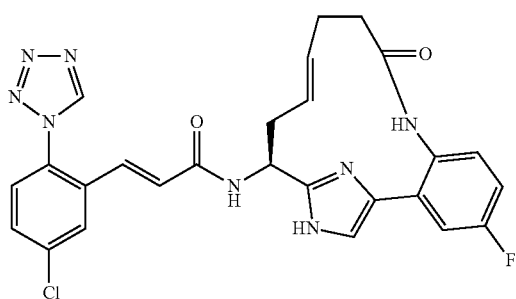 [SMILES: O=C(/C=C/c1cc(Cl)ccc1-n1cnnn1)N[C@H]1C/C=C/CCC(=O)Nc2ccc(F)cc2-c2c[nH]c1n2]

I-226A. 2-Methyl-propane-2-sulfinic acid {(S)-1-[4-(5-fluoro-2-nitro-phenyl)-1-(2-trimethylsilanyl-ethoxymethyl)-1H-imidazol-2-yl]-but-3-enyl}-amide: A microwave vial containing a mixture of Intermediate 37 (409.6 mg, 0.909 mmol), 5-fluoro-2-nitrophenylboronic acid (336 mg, 1.818 mmol) and potassium carbonate (251 mg, 1.818 mmol) in dioxane (5.82 mL) and water (1.46 mL) was degassed with argon for 5 min. Next, bis(tri-t-butylphosphine)palladium (0) (23.23 mg, 0.045 mmol) was added and the vial was sealed and heated in a microwave to 130° C. for 10 min. Additional 5-fluoro-2-nitrophenylboronic acid (1 eq) and potassium carbonate (1 eq) was added to the vial and the vial was degassed with argon for 5 min. Additional bis(tri-t-butylphosphine)palladium (0) (23.23 mg, 0.045 mmol) was added and the vial was sealed and heated in a microwave at 130° C. for 10 min. Additional 5-fluoro-2-nitrophenylboronic acid (1 eq) and potassium carbonate (1 eq) was added to the vial and the vial was degassed with argon for 5 min. Additional bis(tri-t-butylphosphine)palladium (0) (23.23 mg, 0.045 mmol) was added and the vial was sealed and heated in a microwave at 130° C. for 10 min. The reaction was partitioned between water and ethyl acetate and the layers were separated. The aqueous layer was extracted with EtOAc (2×). The combined organic layers were washed with sat. NaHCO₃(aq), brine, dried over Na₂SO₄, filtered and concentrated to a thick brown oil. Purification by normal phase chromatography gave 168.4 mg (36.3%) of I-226A as a yellow oil. MS (ESI) m/z: 511.2 (M+H)⁺.

I-226B. {(S)-1-[4-(5-Fluoro-2-nitro-phenyl)-1-(2-trimethylsilanyl-ethoxymethyl)-1H-imidazol-2-yl]-but-3-enyl}- carbamic acid tert-butyl ester: To a dark yellow solution of I-226A (314.6 mg, 0.616 mmol) in MeOH (6.16 mL) was added dropwise 4M HCl in dioxane (0.77 mL, 3.08 mmol). The reaction was allowed to stir at RT. After 30 min, the reaction was quenched with the dropwise addition of sat. NaHCO$_3$(aq) and then it was concentrated to give a light brown oil. The oil was then partitioned between sat. NaHCO$_3$(aq) and DCM and the layers were separated. The aqueous layer was extracted with DCM (1×). The organic layers were combined, washed with brine, dried over MgSO$_4$, filtered and concentrated to give 204.7 mg (82%) of the amine as an orange oil. MS (ESI) m/z: 407.1 (M+H)$^+$.

To a solution of amine (196.9 mg, 0.444 mmol) in DCM (1.4 mL) was added triethylamine (0.248 mL, 1.778 mmol). Next, BOC$_2$O (0.114 mL, 0.489 mmol) was added. After 30 min, the reaction was partitioned between DCM and sat. NaHCO$_3$(aq) and the layers were separated. The aqueous layer was extracted with DCM. The combined organic layers were washed with brine, dried over Na$_2$SO$_4$, filtered and concentrated to an orange oil. Purification by normal phase chromatography gave 195.7 mg (87%) of I-226B as a yellow-green residue. MS (ESI) m/z: 507.3 (M+H)$^+$.

I-226C. Example I-226 was prepared following the procedures described in 15B, by replacing 15A with I-226B; followed by steps 10D, by replacing but-3-enoic acid with pent-4-enoic acid; 2E/2F; 10H; and 15D. MS (ESI) m/z: 533.1 (M+H)$^+$. $^1$H NMR (500 MHz, CD$_3$OD) δ: 2.33-2.51 (m, 4H), 2.53-2.61 (m, 1H), 2.77-2.86 (m, 1H), 5.09 (dd, J=9.9, 4.7 Hz, 1H), 5.37-5.46 (m, 1H), 5.52-5.60 (m, 1H), 6.76 (d, J=15.7 Hz, 1H), 7.15 (d, J=15.7 Hz, 1H), 7.27-7.38 (m, 3H), 7.49 (s, 1H), 7.59 (d, J=8.5 Hz, 1H), 7.68 (dd, J=8.5, 2.2 Hz, 1H), 7.98 (d, J=2.5 Hz, 1H), 9.51 (s, 1H).

TABLE I-13

Examples I-222 to I-230

| Ex. # | Structure | LCMS [M + H]$^+$ | HPLC RT (min) |
|---|---|---|---|
| I-222 | 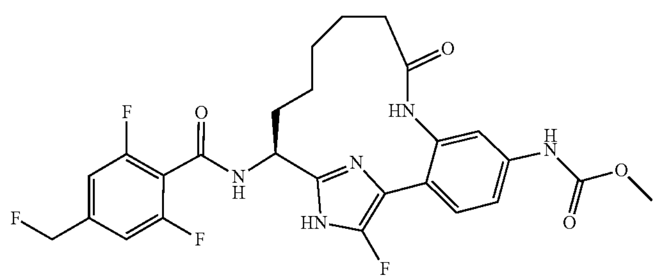 [SMILES: COC(=O)Nc1ccc2c(c1)NC(=O)CCCCC[C@H](NC(=O)c1c(F)cc(CF)cc1F)c1nc-2c(F)[nH]1] | 548.1 | 6.9 |
| I-223 | (diastereomer mixture) | 576.2 | 5.4 |
| I-224 | (diastereomer mixture) | 577.2 | 4.3 |

TABLE I-13-continued
Examples I-222 to I-230
| Ex. # | Structure | LCMS [M + H]+ | HPLC RT (min) |
|---|---|---|---|
| I-225 | 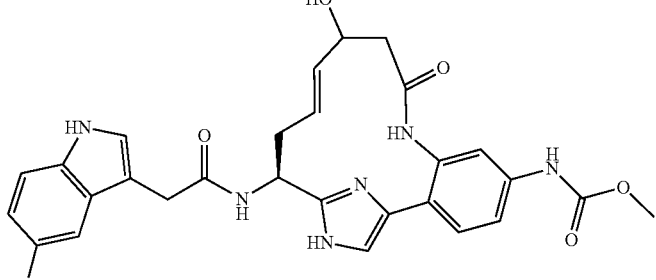 (diastereomer mixture) | 563.2 | 4.1 |
| I-226 | 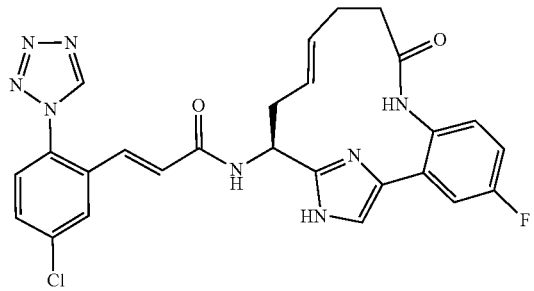 [SMILES: O=C(/C=C/c1cc(Cl)ccc1-n1cnnn1)N[C@H]1C/C=C/CCC(=O)Nc2ccc(F)cc2-c2c[nH]c1n2] | 533.1 | 5.2 |
| I-227 | 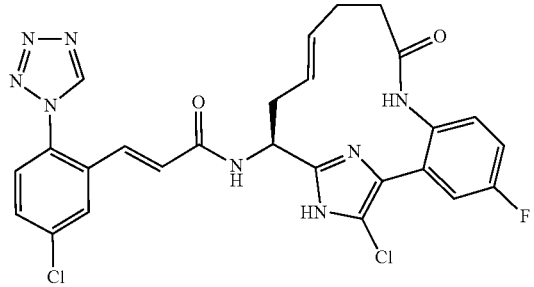 [SMILES: O=C(/C=C/c1cc(Cl)ccc1-n1cnnn1)N[C@H]1C/C=C/CCC(=O)Nc2ccc(F)cc2-c2nc1[nH]c2Cl] | 567.0 | 7.5 |
| I-228 | 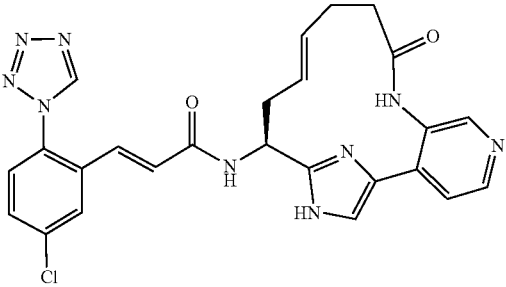 [SMILES: O=C(/C=C/c1cc(Cl)ccc1-n1cnnn1)N[C@H]1C/C=C/CCC(=O)Nc2cnccc2-c2c[nH]c1n2] | 516.1 | 5.4 |
| I-229 | 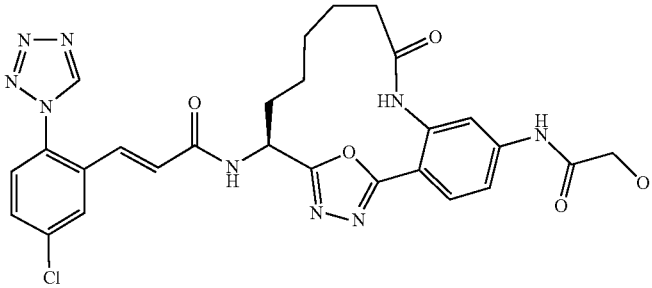 [SMILES: O=C(/C=C/c1cc(Cl)ccc1-n1cnnn1)N[C@H]1CCCCCC(=O)Nc2cc(NC(=O)CO)ccc2C2=NN=C1O2] | 592.0 | 7.6 |

Examples I-241 and I-242

(9S,14S)-14-[(E)-3-(5-Chloro-2-tetrazol-1-yl-phenyl)-acryloylamino]-5-methoxycarbonylamino-17-methyl-8,16,18-triaza-tricyclo[13.2.1.0$^{2,7}$]octadeca-1(17),2,4,6,15(18)-pentaene-9-carboxylic acid ethyl ester, bis-trifluoroacetic acid salt, and (9R,14S)-14-[(E)-3-(5-Chloro-2-tetrazol-1-yl-phenyl)-acryloylamino]-5-methoxycarbonylamino-17-methyl-8,16,18-triaza-tricyclo[13.2.1.0$^{2,7}$]octadeca-1(17),2,4,6,15(18)-pentaene-9-carboxylic Acid ethyl ester, bis-trifluoroacetic Acid Salt

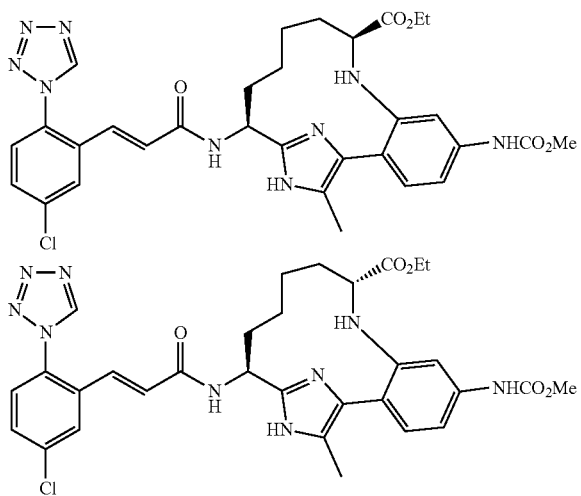

These compounds were prepared using a variation of the procedures employed to make compounds I-67 and I-68.

I-241A. [4-[2-((S)-1-tert-Butoxycarbonylamino-but-3-enyl)-1-(2-trimethylsilanyl-ethoxymethyl)-1H-imidazol-4-yl]-3-(2,2,2-trifluoro-acetylamino)-phenyl]-carbamic acid methyl ester: To a suspension of Example 10C (3 g, 5.64 mmol) in CH$_2$Cl$_2$ (40 ml) at 0° C. was added Et$_3$N (0.944 ml, 6.77 mmol), followed by (CF$_3$CO)$_2$O (0.797 ml, 5.64 mmol). The solvent was removed in vacuo and the residue was purified by normal phase chromatography to give to give a yellow foam (3.0 g, 4.54 mmol, 80% yield): MS (ESI) m/z: 628.5.

I-241B. [4-[5-Bromo-2-((S)-1-tert-butoxycarbonylamino-but-3-enyl)-1-(2-trimethylsilanyl-ethoxymethyl)-1H-imidazol-4-yl]-3-(2,2,2-trifluoro-acetylamino)-phenyl]-carbamic acid methyl ester: To a solution of Example I-241A (1.0 g, 1.593 mmol) in CHCl$_3$ (10 mL) at 0° C. was added 1-bromopyrrolidine-2,5-dione (0.284 g, 1.593 mmol) and stirred at the same temperature for 10 min. The reaction mixture was concentrated in vacuo and purified by normal phase chromatography: MS (ESI) m/z:708.

I-241C. [4-[2-((S)-1-tert-Butoxycarbonylamino-but-3-enyl)-5-methyl-1-(2-trimethylsilanyl-ethoxymethyl)-1H-imidazol-4-yl]-3-(2,2,2-trifluoro-acetylamino)-phenyl]-carbamic acid methyl ester: To a mixture of Example I-241C (200 mg, 0.283 mmol), methylboronic acid (85 mg, 1.415 mmol) and K$_3$PO$_4$ (148 mg, 0.849 mmol) in a microwave vial was added dioxane (5 mL), which had been degassed by bubbling argon through it for 30 min. The reaction mixture was again degassed for 15 mins. To this mixture was then added PdCl$_2$(dppf)-CH$_2$Cl$_2$ adduct (46.2 mg, 0.057 mmol) and sealed immediately and subjected to microwave heating for 25 mins at 150° C. The reaction mixture was diluted with EtOAc and washed with brine. Drying over Na$_2$SO$_4$, filtration, removal of solvent in vacuo and purification of the residue by normal phase chromatography gave an oil: MS (ESI) m/z=642.3.

I-241D. {3-Amino-4-[2-((S)-1-tert-butoxycarbonylamino-but-3-enyl)-5-methyl-1-(2-trimethylsilanyl-ethoxymethyl)-1H-imidazol-4-yl]-phenyl}-carbamic acid methyl ester: To a solution of I-241C (420 mg, 0.654 mmol) in MeOH (5 mL) was added a solution of LiOH (7 mL, 7 mmol) and stirred at 60° C. for 1.5 h. The reaction mixture was acidified to pH 6 with 1N HCl and extracted with EtOAc three times. The combined organic layers were dried over Na$_2$SO$_4$, filtered and concentrated in vacuo. The residue was purified by normal phase chromatography to give an oil. MS (ESI) m/z: 546.3.

Examples I-241 and I-242. The synthesis followed the procedures for I-67 and I-68 using Example I-241D instead of Example 10C. This gave rise to ethyl ester diastereomers instead of methyl ester diastereomers. Each diastereomer was separately carried on through the rest of the sequence as described for Examples I-67 and I-68.

For Example I-241: $^1$H NMR (500MHz, CD$_3$CN) δ 9.11 (s, 1H), 8.81 (d, J=6.1 Hz, 1H), 7.85-7.79 (m, 2H), 7.61 (dd, J=8.5, 2.5 Hz, 1H), 7.50 (d, J=8.5 Hz, 1H), 7.29 (d, J=2.2 Hz, 1H), 7.20-7.16 (m, 1H), 7.08 (dd, J=8.3, 2.2 Hz, 1H), 6.98 (d, J=15.4 Hz, 1H), 6.66 (d, J=15.7 Hz, 1H), 5.33 (m, 1H), 4.09-3.94 (m, 2H), 3.70 (s, 3H), 3.07 (dd, J=9.8, 2.9 Hz, 1H), 2.30-2.21 (m, 5H), 1.94 (m, 1H), 1.85 (br. s., 1H), 1.63-1.50 (m, 2H), 1.45-1.31 (m, 2H), 1.11 (t, J=7.2 Hz, 4H), 0.75-0.65 (m, 1H).

For Example I-242, $^1$H NMR (500 MHz, CD$_3$CN) δ: 10.02 (d, J=8.5 Hz, 1H), 9.08 (s, 1H), 7.82 (d, J=2.2 Hz, 1H), 7.66 (s, 1H), 7.60 (dd, J=8.5, 2.5 Hz, 1H), 7.48 (d, J=8.5 Hz, 1H), 7.21-7.15 (m, 2H), 7.15-7.10 (m, 1H), 6.79-6.72 (m, 1H), 6.63-6.58 (m, 1H), 5.84 (dt, J=10.9, 8.2 Hz, 1H), 4.02-3.88 (m, 2H), 3.74-3.67 (m, 3H), 2.96 (d, J=11.3 Hz, 1H), 2.39-2.31 (m, 4H), 2.17-2.02 (m, 2H), 1.94 (m, 1H), 1.76-1.63 (m, 2H), 1.56-1.44 (m, 2H), 1.44-1.32 (m, 1H), 1.11-1.02 (m, 3H), 0.44-0.32 (m, 1H).

Example I-243

(9R,14 S)-14-[(E)-3-(5-Chloro-2-tetrazol-1-yl-phenyl)-acryloylamino]-5-methoxycarbonylamino-17-methyl-8,16,18-triaza-tricyclo[13.2.1.0$^{2,7}$]octadeca-1(17),2,4,6,15(18)-pentaene-9-carboxylic Acid methyl ester, bis-trifluoroacetic Acid Salt

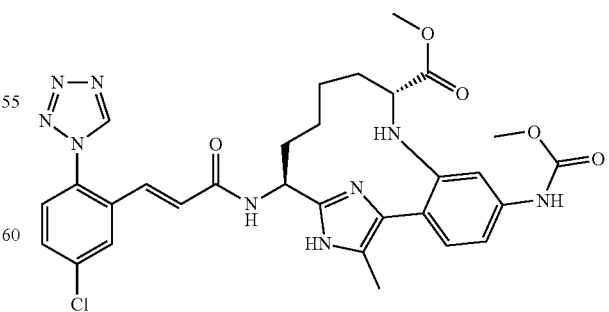

I-243A. (R)-Methyl 2-(N-(2-(2-((S)-1-(tert-butoxycarbonylamino)but-3-enyl)-1-42-(trimethylsilyl)ethoxy)methyl)-1H-imidazol-4-yl)-5-(methoxycarbonylamino)phenyl)-2,2, 2-trifluoroacetamido)pent-4-enoate: Example I-74B (3.66 g, 5.68 mmol) was dissolved in EtOAc (50 mL) and the reaction mixture was cooled to 0° C. Et₃N (1.585 ml, 11.37 mmol) was added followed by (CF₃CO)₂O (0.964 ml, 6.82 mmol). The reaction mixture was allowed to warm to RT over 72 h. The reaction mixture was diluted with water and extracted three times with EtOAc. The combined organic layers were washed with brine, dried over sodium sulfate, filtered and concentrated in vacuo. The residue was purified by normal phase chromatography: Wt=500 mg; MS (ESI) m/z: 740.

I-243B. (E)-(9R,14S)-14-tert-Butoxycarbonylamino-5-methoxycarbonylamino-8-(2,2,2-trifluoro-acetyl)-16-(2-trimethylsilanyl-ethoxymethyl)-8,16,18-triaza-tricyclo[13.2.1.0$^{2,7}$]octadeca-1(17),2,4,6,11,15(18)-hexaene-9-carboxylic acid methyl ester: Example I-243A (500 mg, 0.676 mmol) was dissolved in DCE (15 ml) and reacted with Grubbs II catalyst according to the procedure described for I-74C. Workup and purification by normal phase chromatography provided a solid (Wt=730 mg): MS (ESI) m/z: 712.5.

I-243C. (9R,14S)-14-tert-Butoxycarbonylamino-5-methoxycarbonylamino-8-(2,2,2-trifluoro-acetyl)-16-(2-trimethylsilanyl-ethoxymethyl)-8,16,18-triaza-tricyclo[13.2.1.0$^{2,7}$]octadeca-1(17),2,4,6,15(18)-pentaene-9-carboxylic acid methyl ester: Example I-243C was prepared according to the procedure described for I-74D using precursor I-243B (730 mg). Workup and normal phase chromatography provided the desired intermediate (Wt=520 mg): MS (ESI) m/z: 714.

I-243D. (9R,14S)-17-Bromo-14-tert-butoxy carbonylamino-5-methoxycarbonylamino-8-(2,2,2-trifluoro-acetyl)-16-(2-trimethylsilanyl-ethoxymethyl)-8,16,18-triaza-tricyclo[13.2.1.0$^{2,7}$]octadeca-1(17),2,4,6,15(18)-pentaene-9-carboxylic acid methyl ester: Example I-243C (520 mg, 0.628 mmol) was dissolved in CHCl₃ (10 mL). Reaction mixture cooled to 0° C. and NBS (123 mg, 0.691 mmol) was added. The reaction was allowed to stir at 0° C. The reaction mixture was concentrated in vacuo and the residue was purified by normal phase chromatography. (Wt=225 mg): MS (ESI) m/z: 795, 793. ¹H NMR (500 MHz, MeOH-d3) δ ppm 9.57 (1H, br. s.), 7.83-7.95 (1H, m), 7.60 (1H, dd, J=8.25, 1.65 Hz), 7.39 (1H, d, J=8.25 Hz), 5.75 (1H, d, J=11.55 Hz), 5.42 (1H, d, J=11.00 Hz), 4.97-5.02 (1H, m), 4.48-4.62 (1H, m), 3.80 (3H, s), 3.78 (3H, s), 3.58-3.71 (1H, m), 2.22-2.36 (1H, m), 1.84-1.97 (1H, m), 1.64-1.81 (2H, m), 1.44 (9H, s), 0.84-1.05 (3H, m), 0.00 (9H, s).

I-243E. (9R,14S)-14-tert-Butoxycarbonylamino-5-methoxycarbonylamino-17-methyl-8-(2,2,2-trifluoro-acetyl)-16-(2-trimethylsilanyl-ethoxymethyl)-8,16,18-triaza-tricyclo[13.2.1.0$^{2,7}$]octadeca-1(17),2,4,6,15(18)-pentaene-9-carboxylic acid methyl ester: To a mixture of Example I-243D (78 mg, 0.098 mmol), methylboronic acid (10.57 mg, 0.177 mmol) and K₃PO₄ (18.46 mg, 0.106 mmol) in a microwave vial was added dioxane (1 mL) which was degassed by bubbling argon through it for 30 min. The reaction mixture was again degassed for 15 mins. To this mixture was then added PdCl₂(dppf)-CH₂Cl₂ adduct (5.77 mg, 7.06 μmol) and the reaction vial was sealed immediately and subjected to microwave heating for 15 min at 150° C. The reaction mixture was diluted with ethyl acetate and washed with brine. The organic layer was separated, dried over Na₂SO₄, filtered and concentrated in vacuo. Normal phase chromatography provided a solid (Wt=33 mg): MS (ESI) m/z: 696.4.

I-243F. (9R,14S)-14-Amino-5-methoxycarbonylamino-17-methyl-8,16,18-triaza-tricyclo[13.2.1.0$^{2,7}$]octadeca-1(17),2,4,6,15(18)-pentaene-9-carboxylic acid methyl ester, di-hydrochloride salt: Example I-243F was prepared from Example I-243E (42.7 mg, 0.227 mmol) using the procedure described for Example I-61B. Workup and reverse phase chromatography provided a solid which was a trifluoroacetic acid salt (Wt=11 mg): MS (ESI) m/z: 402.3.

Example I-243. Example I-243F (11 mg, 0.015) and (E)-2,5-dioxopyrrolidin-1-yl 3-(5-chloro-2-(1H-tetrazol-1-yl)phenyl)acrylate (5.2 mg, 0.015 mmol) were reacted according to the procedure for Example 1G. Workup and reverse phase chromatography gave the desired product as a bis-trifluoroacetic acid salt (Wt=6 mg): MS (ESI) m/z: 634.4. ¹H NMR (500MHz, CD₃CN) δ 9.91 (d, J=8.3 Hz, 1H), 9.08 (s, 1H), 7.83 (d, J=2.2 Hz, 1H), 7.74-7.42 (m, 3H), 7.26-7.06 (m, 3H), 6.77 (d, J=15.7 Hz, 1H), 6.65-6.57 (m, 1H), 5.80 (dt, J=11.3, 7.8 Hz, 1H), 3.76-3.65 (m, 3H), 3.55-3.46 (m, 3H), 3.01 (d, J=11.6 Hz, 1H), 2.39-2.31 (m, 3H), 2.19-2.02 (m, 2H), 1.94 (m, 2H) 1.77-1.62 (m, 2H), 1.56-1.32 (m, 3H), 0.46-0.29 (m, 1H).

Example I-244

(9R,14S)-14-[(E)-3-(5-Chloro-2-tetrazol-1-yl-phenyl)-acryloylamino]-17-cyclopropyl-5-methoxycarbonylamino-8,16,18-triaza-tricyclo[13.2.1.0$^{2,7}$]octadeca-1(17),2,4,6,15(18)-pentaene-9-carboxylic Acid methyl ester, bis-trifluoroacetic Acid Salt

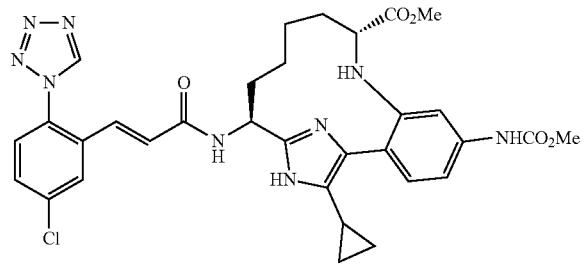

The synthesis for this compound followed the procedure for Example I-243 using cyclopropylboronic acid instead of methyl boronic acid in the step to make Example I-243E. Example I-244 was isolated as a bis-trifluoroacetic acid salt. MS (ESI) m/z: 660.3; ¹H NMR (500MHz, CD₃CN) δ 10.36 (d, J=8.8 Hz, 1H), 9.08 (s, 1H), 7.80 (d, J=2.2 Hz, 1H), 7.65-7.54 (m, 2H), 7.46 (d, J=8.8 Hz, 1H), 7.29 (d, J=8.2 Hz, 1H), 7.18-6.98 (m, 2H), 6.63-6.56 (m, 2H), 5.97-5.86 (m, 1H), 3.71 (s, 3H), 3.48 (s, 3H), 2.87 (d, J=11.5 Hz, 1H), 2.14-2.02 (m, 2H), 1.75-1.42 (m, 6H), 1.34 (t, J=13.2 Hz, 2H), 1.08-0.98 (m, 1H), 0.94-0.77 (m, 3H), 0.32-0.16 (m, 1H).

Example I-245

{(S)-17-Carbamoyl-14-[(E)-3-(5-chloro-2-tetrazol-1-yl-phenyl)-acryloylamino]-8,16,18-triaza-tricyclo[13.2.1.02,7]octadeca-1(17),2,4,6,15(18)-pentaen-5-yl}-carbamic Acid methyl ester, 2 TFA

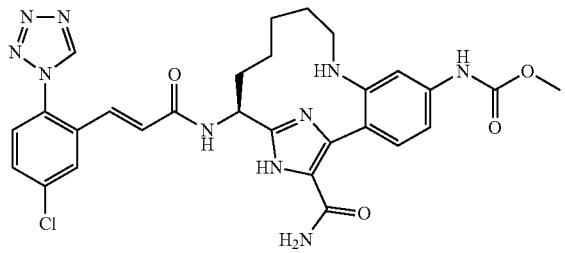 [SMILES: COC(=O)Nc1ccc2c(c1)NCCCCC[C@H](NC(=O)/C=C/c1cc(Cl)ccc1-n1cnnn1)c1nc-2c(C(N)=O)[nH]1]

I-115D (0.050 g, 0.073 mmol) was dissolved in DMSO (0.367 ml) and $K_2CO_3$ (0.030 g, 0.220 mmol) was added followed by dropwise addition of 30% hydrogen peroxide (0.083 ml, 0.808 mmol). A thick white precipitate formed. The reaction was stirred at room temperature for 5.5 h under Ar. Reaction mixture was diluted with EtOAc and washed with water (3×) and brine, then dried over $MgSO_4$, filtered, and evaporated to yield a mixture of product, partially deprotected product (loss of trifluoroacetamide) and SM. This mixture was purified by reverse phase HPLC to remove the unreacted SM, and the product mixture was fully deprotected using the procedure described for step I-61B, followed by coupling of the resulting amine with Intermediate 1 using the procedure described in step 1G to yield Example I-245 as a white solid. $^1$H NMR (500 MHz, $CD_3OD$) δ ppm 9.71 (1H, s) 9.55 (1H, s) 7.94 (1H, d, J=1.65 Hz) 7.89 (1H, d, J=8.25 Hz) 7.86 (1H, br. s.) 7.61-7.67 (1H, m) 7.55-7.60 (1H, m) 7.26 (1H, dd, J=8.52, 1.92 Hz) 7.23 (1H, d, J=15.40 Hz) 6.79 (1H, d, J=15.40 Hz) 5.15 (1H, dd, J=10.45, 6.60 Hz) 3.73 (3H, s) 3.20 (1H, d, J=12.65 Hz) 2.97 (1H, t, J=12.65 Hz) 2.09-2.18 (1H, m) 2.00 (1H, t, J=11.27 Hz) 1.79-1.92 (2H, m) 1.61 (2H, t, J=13.75 Hz) 1.32 (1H, br. s.) 0.62 (1H, d, J=12.65 Hz). MS (ESI) m/z: 605.4 $(M+H)^+$. Analytical HPLC: RT=4.98 min.

Example I-246

(S)-14-[(E)-3-(5-Chloro-2-tetrazol-1-yl-phenyl)-acryloylamino]-5-methoxycarbonylamino-8,16,18-triaza-tricyclo[13.2.1.02,7]octadeca-1(17),2,4,6,15(18)-pentaene-17-carboxylic Acid methyl ester, 2TFA

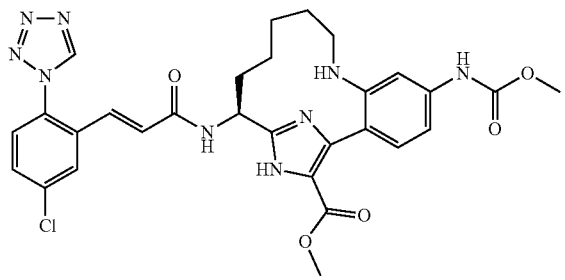 [SMILES: COC(=O)Nc1ccc2c(c1)NCCCCC[C@H](NC(=O)/C=C/c1cc(Cl)ccc1-n1cnnn1)c1nc-2c(C(=O)OC)[nH]1]

I-115D (0.025 g, 0.037 mmol) was dissolved in MeOH (0.5 ml), and then concentrated $H_2SO_4$ (0.050 ml) was added at rt. The reaction was heated at 75° C. under Ar overnight at which point the desired product, (S)-14-amino-5-methoxycarbonylamino-8,16,18-triaza-tricyclo[13.2.1.02,7]octadeca-1(17),2,4,6,15(18)-pentaene-17-carboxylic acid methyl ester (I-246A) was obtained along with (S)-5,14-diamino-8,16,18-triaza-tricyclo[13.2.1.02,7]octadeca-1(17),2,4,6,15(18)-pentaene-17-carboxylic acid methyl ester (I-246B) from cleavage of the methylcarbamate. The reaction mixture was cooled to rt and diluted with MeOH, then filtered and purified by reverse phase HPLC. I-246A was deprotected using the procedure described in step I-61B, and the resulting amine coupled with Intermediate 1 using the procedure described for step 1G to provide Example I-246. $^1$H NMR (500 MHz, DMSO-$d_6$) δ ppm 13.28 (1H, br. s.) 10.76 (1H, br. s.) 10.18 (1H, br. s.) 9.86 (1H, s) 8.43 (1H, d, J=5.50 Hz) 8.03 (1H, d, J=7.15 Hz) 7.99 (1H, d, J=2.20 Hz) 7.95 (1H, br. s.) 7.69-7.79 (2H, m) 7.44 (1H, d, J=7.70 Hz) 6.84-6.93 (2H, m) 5.19-5.28 (1H, m) 3.80 (3H, s) 3.72 (3H, s) 3.05 (1H, d, J=11.00 Hz) 2.83 (1H, t, J=11.28 Hz) 1.91-2.00 (1H, m) 1.79 (2H, br. s.) 1.66 (1H, q, J=10.73 Hz) 1.36-1.49 (2H, m) 1.17 (1H, br. s.) 0.61 (1H, d, J=13.75 Hz). MS (ESI) m/z: 620.4 $(M+H)^+$. Analytical HPLC: RT=5.55 min.

Example I-247

(9R,14S)-14-[(E)-3-(5-Chloro-2-tetrazol-1-yl-phenyl)-acryloylamino]-17-cyano-5-methoxycarbonylamino-8,16,18-triaza-tricyclo[13.2.1.02,7]octadeca-1(17),2,4,6,15(18)-pentaene-9-carboxylic Acid methyl ester, 2TFA

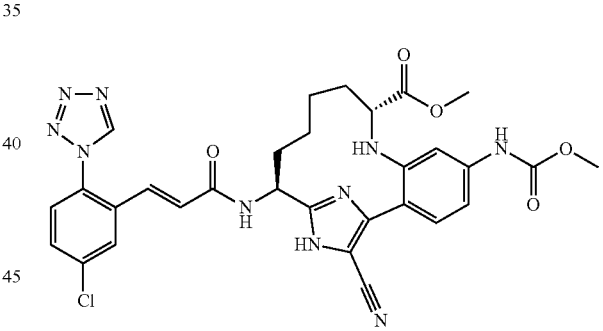

I-247A. (R)-Methyl 2-(N-(2-(2-((S)-1-(tert-butoxycarbonylamino)but-3-enyl)-1-42-(trimethylsilyl)ethoxy)methyl)-1H-imidazol-4-yl)-5-(methoxycarbonylamino)phenyl)-2,2,2-trifluoroacetamido)pent-4-enoate: I-74B (12 g, 13.98 mmol) was dissolved in ethyl acetate (100 ml). Pyridine (1.357 ml, 16.77 mmol) was added, and the reaction was cooled to 0° C. TFAA (2.172 ml, 15.38 mmol) was added dropwise with stirring, and reaction allowed to reach RT, then stirred at room temperature under Ar overnight. Reaction was diluted with EtOAc and water. Aq. phase was extracted 3× with EtOAc, and the combined organic phases were dried with sodium sulfate, filtered and concentrated. Residue was purified by flash chromatography to provide the desired trifluoroacetamide containing minor impurities which do not separate on silica gel. This crude product was taken on without further purification.

I-247B. (9R,14S)-14-tert-Butoxycarbonylamino-5-methoxycarbonylamino-8-(2,2,2-trifluoroacetyl)-16-(2-trimethylsilanylethoxymethyl)-8,16,18-triaza-tricyclo

[13.2.1.0²,⁷]octadeca-1(17),2,4,6,15(18)-pentaene-9-carboxylic acid methyl ester: I-247A (6.15 g, 8.31 mmol) was dissolved in DCE (208 ml) in a rbf equipped with an argon inlet and reflux condenser. The solution was degassed by bubbling with Ar for 15 minutes. The reaction mixture was heated to 84° C., and a solution of Grubbs II (1.059 g, 1.247 mmol) dissolved in 15 mL of DCE was added. Reaction mixture was stirred at 84° C. under Ar for 15 hours. Reaction was quenched by addition of a saturated NaHCO₃ solution and diluted with DCM. The organic layer was extracted one more time with saturated NaHCO₃ solution and once with brine. Organic phase was dried with Na₂SO₄, filtered and concentrated. Residue was purified by flash chromatography to provide the RCM product in 37% yield as a mixture of cis/trans isomers. A portion of this intermediate (1.9 g, 2.67 mmol) was taken up in MeOH (26.7 ml) and Pd/C (0.284 g, 0.267 mmol) added. The mixture was then stirred at room temperature under 50 psi H₂ for 48 h to provide I-127-B (1.66g, 87%) after removal of catalyst and evaporation of solvent. MS (ESI) m/z: 714.3 (M+H)⁺.

I-247C. (9R,14S)-14-tert-Butoxycarbonylamino-17-cyano-5-methoxycarbonylamino-8-(2,2,2-trifluoro-acetyl)-16-(2-trimethylsilanyl-ethoxymethyl)-8,16,18-triaza-tricyclo[13.2.1.0²,⁷]octadeca-1(17),2,4,6,15(18)-pentaene-9-carboxylic acid methyl ester: (9R,14S)-17-Bromo-14-tert-butoxycarbonylamino-5-methoxycarbonylamino-8-(2,2,2-trifluoro-acetyl)-16-(2-trimethylsilanyl-ethoxymethyl)-8,16,18-triaza-tricyclo[13.2.1.0²,⁷]octadeca-1(17),2,4,6,15(18)-pentaene-9-carboxylic acid methyl ester, prepared from I-247B using the procedure described for I-115C, (2.0 g, 2.52 mmol) was dissolved in DMF (12.61 ml). Zinc cyanide (0.178 g, 1.514 mmol) was added and the reaction was degassed by bubbling with Ar for 15 minutes. (Ph₃)₄Pd (0.292 g, 0.252 mmol) was added and the mixture stirred at 120° C. for 10 hours under Ar. Reaction mixture was diluted with EtOAc, washed 4× with 10% LiCl, brine, dried with sodium sulfate, filtered and concentrated. Residue was purified by flash chromatography to provide 1.44 g of a 3:1 mixture cyano product to starting bromide. This mixture was re-subjected to the above reaction conditions and isolation to yield I-247C in 60% yield after chromatography. MS (ESI) m/z: 739.3 (M+H)⁺.

I-247D. (9R,14S)-14-Amino-17-cyano-5-methoxycarbonylamino-8,16,18-triaza-tricyclo[13.2.1.0²,⁷]octadeca-1(17),2,4,6,15(18)-pentaene-9-carboxylic acid methyl ester, 3TFA: I-247C (0.106 g, 0.143 mmol) was dissolved in MeOH (2 mL) and a solution of O-methylhydroxylamine in H₂O (25% w/w, 0.135 mL, 0.717 mmol) was added followed by 6M HCl (2 mL). The mixture was heated with stirring in a sealed tube at 75° C. ON. Reaction mixture was concentrated, and HCl/Dioxane (0.5 mL) and MeOH (2 mL) were added followed by stirring overnight at room temperature. The mixture was concentrated and residue purified by reverse phase HPLC to provide I-247D (0.031 g, 28.6%) as a white solid. MS (ESI) m/z: 413.3 (M+H)⁺.

I-247E. Example I-247 was prepared from I-247D by coupling with Intermediate 1 using the procedure described for step 1G. ¹H NMR (500 MHz, CD₃OD) δ ppm 9.50 (1H, br. s.), 8.00 (1H, d, J=2.20 Hz), 7.65 (1H, dd, J=8.80, 2.20 Hz), 7.56 (1H, d, J=8.80 Hz), 7.46 (1H, d, J=8.25 Hz), 7.42-7.45 (1H, m), 7.16 (1H, dd, J=8.52, 1.92 Hz), 7.10 (1H, d, J=15.40 Hz), 6.80 (1H, d, J=15.95 Hz), 5.19 (1H, dd, J=10.72, 6.87 Hz), 3.74 (3H, s), 3.58 (3H, s), 3.01-3.07 (1H, m), 2.05-2.17 (1H, m), 1.80-1.92 (2H, m), 1.69-1.80 (1H, m), 1.32-1.53 (4H, m), 0.33-0.51 (1H, m). MS (ESI) m/z: 645.4 (M+H)⁺. Analytical HPLC: RT=8.23 min.

Example I-248

(9R,14S)-14-[(E)-3-(5-Chloro-2-tetrazol-1-yl-phenyl)-acryloylamino]-5-methoxycarbonylamino-8,16,18-triaza-tricyclo[13.2.1.0²,⁷]octadeca-1(17),2,4,6,15(18)-pentaene-9,17-dicarboxylic Acid dimethyl ester, 2TFA

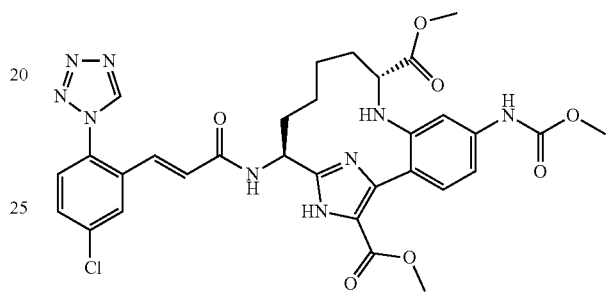

I-248A. (9R,14S)-14-tert-Butoxycarbonylamino-17-carbamoyl-5-methoxycarbonylamino-8-(2,2,2-trifluoroacetyl)-16-(2-trimethylsilanylethoxymethyl)-8,16,18-triaza-tricyclo[13.2.1.0²,⁷]octadeca-1(17),2,4,6,15(18)-pentaene-9-carboxylic acid methyl ester: I-247C (60 mg, 0.081 mmol), acetaldehyde oxime (9.90 µl, 162 mmol), triphenylphosphine (4.26 mg, 0.016 mmol) and palladium(II) acetate (1.823 mg, 8.12 µmol) were weighed into a 1 dram pressure-rated vial, and ethanol (0.2 mL) and water (0.050 mL) were added. The vial was flushed with argon and capped, and the reaction mixture was heated at 80° C. with stirring for ~1 h. Reaction was cooled to room temperature, filtered through a syringe filter, which was further washed with mix of MeOH/CH₂Cl₂, and the filtrate was stripped to dryness. Residue was purified by flash chromatography to provide I-248A (42.1 mg, 68.5%). MS (ESI) m/z: 757.4 (M+H)⁺

I-248B. (9R,14S)-14-Amino-5-methoxycarbonylamino-8,16,18-triaza-tricyclo[13.2.1.0²,⁷]octadeca-1(17),2,4,6,15(18)-pentaene-9,17-dicarboxylic acid dimethyl ester, 3TFA: I-248B was obtained from I-248A using the procedure described for step I-61B and isolated as the tris-TFA salt after reverse phase HPLC.

I-248C. Example I-248 was prepared from I-248B by coupling with Intermediate 1 using the procedure described for step 1G. ¹H NMR (500 MHz, CD₃OD) δ ppm 9.50 (1H, s), 7.98 (1H, d, J=2.2 Hz), 7.67 (1H, dd, J=8.8, 2.2 Hz), 7.59 (1H, s), 7.57 (1H, s), 7.45 (1H, s), 7.09-7.16 (2H, m), 6.76 (1H, d, J=15.4 Hz), 5.18 (1H, dd, J=11.0, 7.1 Hz), 3.88 (3H, s), 3.75 (3H, s), 3.59 (3H, s), 3.05 (1H, d, J=11.5 Hz), 2.21-2.33 (1H, m), 1.99-2.08 (1H, m), 1.67-1.78 (2H, m), 1.51-1.62 (1H, m), 1.37-1.50 (2H, m), 0.40-0.55 (1H, m). MS (ESI) m/z: 678.1 (M+H)⁺. Analytical HPLC: RT=6.52 min.

Example I-250

(9R,14S)-14-[(E)-3-(5-Chloro-2-tetrazol-1-yl-phenyl)-acryloylamino]-17-cyano-5-methoxycarbonylamino-8,16,18-triaza-tricyclo[13.2.1.02,7]octadeca-1(17),2,4,6,15(18)-pentaene-9-carboxylic Acid, 2 TFA

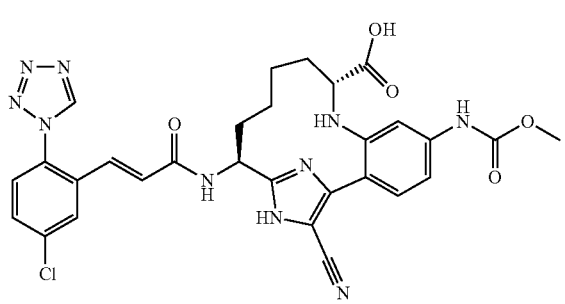 [SMILES: COC(=O)Nc1ccc2c(c1)N[C@@H](C(=O)O)CCCC[C@H](NC(=O)/C=C/c1cc(Cl)ccc1-n1cnnn1)c1nc-2c(C#N)[nH]1]

I-250A. (9R,14S)-14-Amino-17-cyano-5-methoxycarbonylamino-8,16,18-triaza-tricyclo[13.2.1.02,7]octadeca-1(17),2,4,6,15(18)-pentaene-9-carboxylic acid, 3 TFA: A mixture of I-247C (165 mg, 0.193 mmol), O-methoxyamine hydrochloride (30% in water, 0.245 mL, 0.967 mmol), 6M HCl (1.29 ml, 7.74 mmol) and MeOH (1.6 ml) was heated with stirring in a 75° C. oil bath overnight in a sealed 5 mL pressure-rated vial. Reaction was cooled to room temperature and determined by LCMS to be an ~1:1 mixture of methyl ester and acid products. The mixture was stripped to dryness, and residue was redissolved in a mixture of 4 mL THF, 2.5 mL 1M LiOH and ~0.5 mL MeOH, then stirred overnight at room temperature under nitrogen. Reaction mixture was neutralized with 1M HCl and stripped to dryness. Residue was purified by reverse phase HPLC to provide I-250A (29.3 mg, 29.6%) and the corresponding methyl ester, I-247D (23.2 mg, 22.78%). I-250A MS (ESI) m/z: 399.2 (M+H)$^+$.

I-250B. Example I-250 was prepared from I-250A by coupling with Intermediate 1 using the procedure described for step 1G. $^1$H NMR (500 MHz, DMSO-d$_6$) δ ppm 12.98 (1H, br. s.), 9.86 (1H, s), 9.79 (1H, s), 8.76 (1H, d, J=7.7 Hz), 7.93 (1H, d, J=2.2 Hz), 7.67-7.80 (2H, m), 7.34 (1H, br. s.), 7.28 (1H, d, J=8.2 Hz), 7.10 (1H, d, J=8.2 Hz), 6.82-6.96 (2H, m), 5.14-5.27 (1H, m), 5.00 (1H, br. s.), 3.67 (3H, s), 2.68-2.85 (1H, m), 1.99 (1H, br. s.), 1.59-1.79 (3H, m), 1.17-1.36 (3H, m), 0.33 (1H, br. s.). MS (ESI) m/z: 631.4 (M+H)$^+$ Analytical HPLC: RT=7.66 min.

Example I-251

(9R,14S)-14-[(E)-3-(5-Chloro-2-tetrazol-1-yl-phenyl)-acryloylamino]-17-cyano-5-methoxycarbonylamino-8,16,18-triaza-tricyclo[13.2.1.02,7]octadeca-1(17),2,4,6,15(18)-pentaene-9-carboxylic Acid ethyl ester, 2 TFA

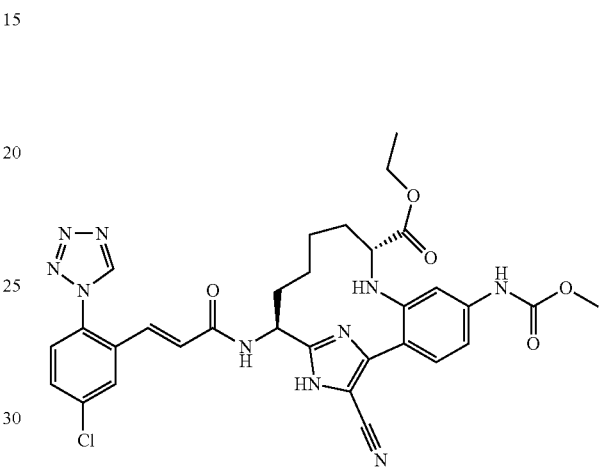

Example I-251. Example I-250 (15.8 mg, 0.018 mmol) was dissolved in EtOH (0.5 ml) and TMS-Cl (5.64 µl, 0.044 mmol) was added under nitrogen. Reaction mixture was stirred at room temperature overnight. Only a small amount of desired product was observed, therefore, the solution was transferred to a pressure-rated vial using ~0.2 mL additional EtOH to rinse. An additional 20 µL TMS-Cl were added, and the vial was capped and heated with stirring at 75° C. for 4 h. LCMS shows complete conversion to ethyl ester. Reaction mixture was stripped to dryness and crude product was redissolved in MeOH, filtered and purified by reverse phase HPLC to provide Example I-251 (6.8 mg, 40.4%) as a white solid. $^1$H NMR (500 MHz, CD$_3$CN) δ ppm 9.10 (1H, s), 7.88 (1H, d, J=2.2 Hz), 7.86 (1H, s), 7.61 (1H, dd, J=8.5, 2.2 Hz), 7.52 (2H, dd, J=11.8, 8.5 Hz), 7.41 (1H, d, J=1.9 Hz), 7.36 (1H, d, J=7.4 Hz), 7.17 (1H, dd, J=8.3, 2.2 Hz), 7.01 (1H, d, J=15.4 Hz), 6.65 (1H, d, J=15.7 Hz), 5.30 (1H, ddd, J=10.9, 7.0, 6.9 Hz), 3.92-4.07 (2H, m), 3.71 (3H, s), 2.94-3.05 (1H, m), 2.05-2.16 (1H, m), 1.66-1.83 (3H, m), 1.32-1.57 (3H, m), 1.10 (3H, t, J=7.2 Hz), 0.42 (1H, d, J=12.7 Hz). MS (ESI) m/z: 659.2 (M+H)$^+$. Analytical HPLC: RT=9.00 min.

TABLE I-14
Examples I-231 to I-251
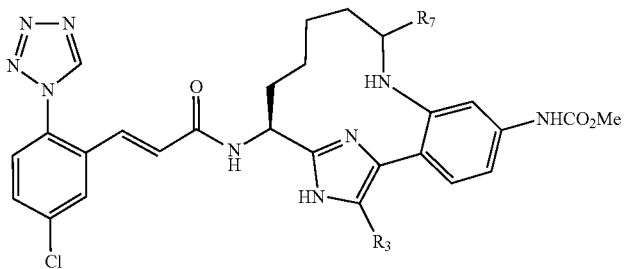
| Ex. # | R7 | R3 | LCMS [M + H]+ | HPLC RT (min.) |
|---|---|---|---|---|
| I-231 | CH₂OMe (homochiral) | H | 606.3 | 9.1 |
| I-232 | CH₂OMe (homochiral) | H | 606.3 | 9.0 |
| I-233 | 4-methylthiazol-2-yl | H | 659.3 | 5.9 |
| I-234 | 2-oxo-2,3-dihydrothiazol-4-yl | H | 661.2 | 5.8 |
| I-235 | 4-methylthiazol-2-yl | H | 659.2 | 5.8 |
| I-236 | azetidin-1-yl carbonyl | H | 645.3 | 5.1 |
| I-237 | morpholin-4-yl carbonyl | H | 675.3 | 5.1 |
| I-238 | N-methoxy carbamoyl | H | 635.2 | 5.4 |

TABLE I-14-continued

Examples I-231 to I-251

| Ex. # | R7 | R3 | LCMS [M + H]+ | HPLC RT (min.) |
|---|---|---|---|---|
| I-239 | -CH(CO2Me)- | H | 634.2 | 6.8 |
| I-240 | -CH(CO2H)- | H | 620.1 | 5.3 |
| I-241 | -CH(CO2Et)- | Me | 648.4 | 6.1 |
| I-242 | -CH(CO2Et)- | Me | 648.4 | 5.9 |
| I-243 | -CH(CO2Me)- | Me | 634.4 | 5.8 |
| I-244 | -CH(CO2Me)- | cyclopropyl | 660.3 | 6.2 |
| I-245 | H | $CONH_2$ | 605.4 | 5.0 |
| I-246 | H | $CO_2Me$ | 620.4 | 5.5 |
| I-247 | -CH(CO2Me)- | CN | 645.4 | 8.2 |

TABLE I-14-continued

Examples I-231 to I-251

| Ex. # | R7 | R3 | LCMS [M + H]⁺ | HPLC RT (min.) |
|---|---|---|---|---|
| I-248 | methyl ester group | CO₂Me | 678.3 | 6.1 |
| I-249 | N-methyl amide group | CN | 658.4 | 7.8 |
| I-250 | carboxylic acid (HO) | CN | 631.4 | 7.7 |
| I-251 | ethyl ester group | CN | 659.2 | 9.0 |

Example I-252

(S)-14-[(E)-3-(5-Chloro-2-tetrazol-1-yl-phenyl)-acryloylamino]-5-methoxycarbonylamino-16,18-diaza-tricyclo[13.2.1.0$^{2,7}$]octadeca-1(17),2,4,6,15(18)-pentaene-9-carboxylic Acid tert-butyl ester, trifluoroacetic Acid Salt

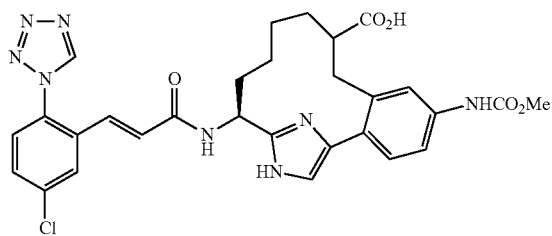

I-252A. 3-{2-[2-((S)-1-tert-Butoxycarbonylamino-but-3-enyl)-1-(2-trimethylsilanyl-ethoxymethyl)-1H-imidazol-4-yl]-5-methoxycarbonylamino-phenyl}-propionic acid tert-butyl ester: (Molander, G. A., *Organic Letters*, 10(9):1795 (2008).) A thick-walled 150-mL screw top flask containing potassium 3-trifluoroboratopropionate tert-butyl ester (2.180 g, 9.23 mmol), 10B (5.0 g, 8.39 mmol), palladium acetate (0.141 g, 0.630 mmol), 2-dicyclohexylphosphino-2',6'-di-i-propoxy-1,1'-biphenyl (Ru-Phos) (0.588 g, 1.259 mmol), and potassium carbonate (3.48 g, 25.2 mmol) was purged with argon for several minutes. Next, degassed toluene (33.6 ml) and degassed water (8.4 ml) were added and under a blanket of argon the septum was replaced with a teflon screw cap possessing a Viton O-ring. The biphasic orange mixture was warmed to 85° C. After 24 h, the reaction was stopped and cooled to RT. The layers were separated and the aqueous layer was extracted with EtOAc (2×). The combined organic layers were washed with brine, dried over Na₂SO₄, filtered and concentrated to give a yellow foam weighing 6.63 g. Purification by normal phase chromatography (gradient elution 0-20% EtOAc/DCM) gave 1.45 g (27%) of I-252A, as a white foam. MS (ESI) m/z: 645.4 (M+H)⁺.

I-252B. 2-{2-[2-((S)-1-tert-Butoxycarbonylamino-but-3-enyl)-1-(2-trimethylsilanyl-ethoxymethyl)-1H-imidazol-4-yl]-5-methoxycarbonylamino-benzyl}-pent-4-enoic acid tert-butyl ester: To a cooled solution (−78° C.) of diisopropylamine (1.167 ml, 8.19 mmol) in degassed THF (14 mL) was added dropwise n-BuLi (4.65 ml, 7.44 mmol). The resulting clear, pale yellow solution was stirred at −78° C. for 45 min. Next, a clear, pale yellow solution of I-252A (1.20 g, 1.86 mmol) in THF (degassed, 9 ml) was added dropwise over 30 min. The resulting yellow suspension was stirred vigorously at −78° C. After 1.5 h, allyl bromide (0.161 ml, 1.861 mmol) was added dropwise. The reaction mixture was stirred at −78° C. After 1 h, the clear, pale yellow solution was allowed to slowly warm to −15° C. The reaction was quenched with the dropwise addition of sat. ammonium chloride and the reaction was allowed to warm to RT. The reaction was partitioned between water and EtOAc and the layers were separated. The aqueous layer was extracted with EtOAc (2×). The combined organic layers were washed with sat. NaHCO$_3$, brine, dried over Na$_2$SO$_4$, filtered and concentrated to give a yellow foam. Purification by normal phase chromatography (gradient elution 0-20% EtOAc/DCM) gave 1.04 g (70%) as a 1:2.6 mixture of I-252A:I-252B. Compound I-252B is a mixture of diastereomers. MS (ESI) m/z: 686.7 (M+H)$^+$.

I-252C. (S)-14-tert-Butoxycarbonylamino-5-methoxycarbonylamino-16-(2-trimethylsilanyl-ethoxymethyl)-16,18-diaza-tricyclo[13.2.1.0$^{2,7}$]octadeca-1(17),2,4,6,15(18)-pentaene-9-carboxylic acid tert-butyl ester, trifluoroacetic acid salt (Diastereomer A) and I-252D. (S)-14-tert-Butoxycarbonylamino-5-methoxycarbonylamino-16-(2-trimethylsilanyl-ethoxymethyl)-16,18-diaza-tricyclo[13.2.1.0$^{2,7}$]octadeca-1(17),2,4,6,15(18)-pentaene-9-carboxylic acid tert-butyl ester, trifluoroacetic acid salt (Diastereomer B). The title compounds I-252C (Diastereomer A) and I-252D (Diastereomer B) were prepared by following the procedures described in 2E/2F, by replacing 2D with the 1:2.6 mixture of I-253A:I-253B; followed by step 2G, by replacing methanol with ethanol. The diastereomers were separated by reverse phase chromatography.

I-252E. Example I-252 was prepared by following the procedures described in step 10H, by replacing 10G with I-252C (diastereomer A) and by running the reaction at 75° C.; followed by step 1G. $^1$H NMR (500 MHz, CD$_3$OD) 50° C., δ ppm 9.46 (s, 1H), 7.94 (d, J=2.2 Hz, 1H), 7.68 (dd, J=8.8, 2.2 Hz, 1H), 7.57 (d, J=8.8 Hz, 1H), 7.45-7.52 (m, 3H), 7.38 (d, J=8.2 Hz, 1H), 7.17 (d, J=15.9 Hz, 1H), 6.74 (d, J=15.9 Hz, 1H), 5.18 (t, J=6.0 Hz, 1H), 3.74 (s, 3H), 2.79-2.91 (m, 2H), 2.18-2.27 (m, 2H), 1.97-2.06 (m, 1H), 1.30-1.67 (m, 4H), 1.05-1.16 (m, 1H), 0.40-0.55 (m, 1H). MS (ESI) m/z: 605.3 (M+H)$^+$. Analytical HPLC: RT=8.82 min.

Examples I-253 to I-255 were prepared from I-252C (diastereomer A) according to the procedures described in the previous examples. Examples I-256 to I-259 were prepared from I-252D (diastereomer B) according to the procedures described in the previous examples.

TABLE I-15

Examples I-252 to I-259

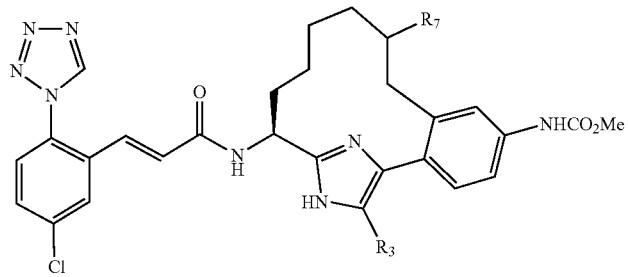

| Ex. # | R7 | R3 | LCMS [M + H]$^+$ | HPLC RT (min.) |
|---|---|---|---|---|
| I-252 | CO$_2$H (homochiral) | H | 605.3 | 8.8 |
| I-253 | CO$_2$Me (homochiral) | H | 619.4 | 9.2 |
| I-254 | CONMe$_2$ (homochiral) | H | 632.5 | 8.7 |
| I-255 | CONMe$_2$ (homochiral) | Cl | 666.2 | 7.4 |
| I-256 | CO$_2$H (homochiral) | H | 605.3 | 8.8 |
| I-257 | CONHMe (homochiral) | H | 618.5 | 8.6 |
| I-258 | CONMe$_2$ (homochiral) | H | 632.5 | 8.7 |
| I-259 | CONH$_2$ (homochiral) | H | 604.4 | 8.5 |

TABLE I-16

Examples I-260 to I-264

[Structure with R, R7, R3, NHCO2Me groups on imidazole-containing scaffold]

| Ex. # | R | R7 | R3 | LCMS [M + H]+ | HPLC RT (min.) |
|---|---|---|---|---|---|
| I-260 | [tetrazolyl-phenyl-propenyl with Me] | H | H | 556.3 | 8.1 |
| I-261 | [H2N-CH2-cyclohexyl] | H | H | 483.4 | 6.5 (C) |
| I-262 | [quinolinyl] | H | H | 499.3 | 3.1 |
| I-263 | [difluoro-methyl-indazolyl] | F | H | 566.3 | 8.0 |
| I-264 | [difluoro-methyl-indazolyl] | F | Cl | 600.3 | 7.5 |

Example 266

(S)-14-[(E)-3-(5-Chloro-2-tetrazol-1-yl-phenyl)-acryloylamino]-5-(2-methoxy-ethoxycarbonylamino)-8,16,18-triaza-tricyclo[13.2.1.02,7]octadeca-1(17),2,4,6,15(18)-pentaene-17-carboxylic Acid methyl ester, 2TFA

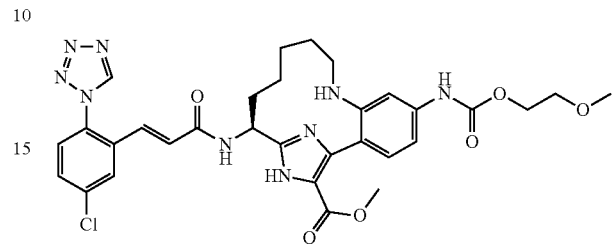

Example I-266 was prepared from aniline, I-246B following a similar procedure to that described for step I-123B. $^1$H NMR (500 MHz, CD$_3$OD) δ ppm 9.53 (1H, s) 8.34 (1H, d, J=8.80 Hz) 8.03 (1H, br. s.) 8.02 (1H, d, J=2.20 Hz) 7.67-7.71 (1H, m) 7.59-7.62 (1H, m) 7.31 (1H, dt, J=8.80, 1.10 Hz) 7.19 (1H, d, J=15.95 Hz) 6.80 (1H, d, J=15.40 Hz) 5.31 (1H, dd, J=10.17, 6.32 Hz) 4.26-4.32 (2H, m) 3.89 (3H, s) 3.65 (2H, t, J=4.67 Hz) 3.39 (3H, s) 3.18-3.24 (1H, m) 2.98 (1H, t, J=11.27 Hz) 2.09-2.19 (1H, m) 1.99 (1H, br. s.) 1.83-1.96 (2H, m) 1.67 (2H, t, J=12.10 Hz) 1.31 (1H, br. s.) 0.69-0.82 (1H, m). MS (ESI) m/z: 664.4 (M+H)$^+$. Analytical HPLC: RT=5.65 min.

Example I-267

(9R,14S)-14-[(E)-3-(5-Chloro-2-tetrazol-1-yl-phenyl)-acryloylamino]-5-(2-methoxy-ethoxycarbonylamino)-8,16,18-triaza-tricyclo[13.2.1.02,7]octadeca-1(17),2,4,6,15(18)-pentaene-9-carboxylic Acid, 2 TFA

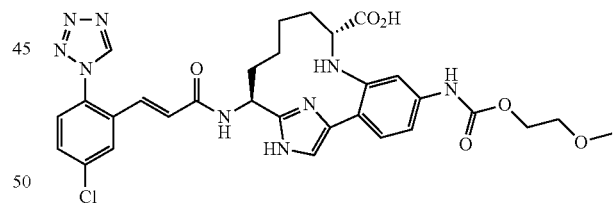

Example I-131 (13 mg, 0.015 mmol) was dissolved in 4M HCl/dioxane (2 mL)/water (0.5 mL) and heated to 55° C. in a sealed vial for 1.5 h. then at 45° C. for 9 h. Reaction mixture was filtered and residue was purified by reverse phase HPLC to provide Example I-267 (4.41 mg, 32.7%) as a yellow solid. $^1$H NMR (500 MHz, CD$_3$CN) δ ppm 9.43 (1H, br. s.), 9.09 (1H, s), 7.73-7.89 (2H, m), 7.60 (1H, dd, J=8.25, 2.20 Hz), 7.47 (1H, d, J=8.25 Hz), 7.39 (1H, s), 7.21-7.29 (2H, m), 7.09-7.18 (1H, m), 6.82-6.93 (1H, m), 6.62 (1H, d, J=15.95 Hz), 5.59-5.76 (1H, m), 4.13-4.31 (2H, m), 3.58 (2H, t, J=4.40 Hz), 3.33 (3H, s), 3.26 (1H, s), 3.01 (1H, d, J=11.55 Hz), 2.08-2.18 (1H, m), 1.97-2.08 (1H, m), 1.64-1.77 (2H, m), 1.35-1.55 (3H, m), 0.21-0.37 (1H, m). MS (ESI) m/z: 650.4 (M+H)$^+$. Analytical HPLC: RT=5.18 min.

Example I-270

{(S)-14-[(E)-3-(5-Chloro-2-tetrazol-1-yl-phenyl)-acryloylamino]-9,9-difluoro-8-oxo-16,18-diaza-tricyclo[13.2.1.0²,⁷]octadeca-1(17),2,4,6,15(18)-pentaen-5-yl}-carbamic Acid methyl ester, TFA Salt

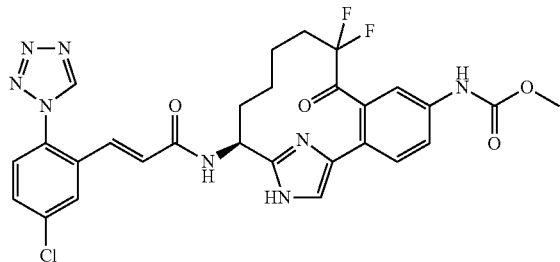 [SMILES: COC(=O)Nc1ccc2c(c1)C(=O)C(F)(F)CCCC[C@H](NC(=O)/C=C/c1cc(Cl)ccc1-n1cnnn1)c1nc-2c[nH]1]

I-270A. 2,2-Difluoro-1-morpholinopent-4-en-1-one: To a solution of 2,2-difluoropent-4-enoic acid (701 mg, 5.15 mmol) in dichloromethane (10 mL) was added catalytic amount of DMF (0.05 ml, 0.646 mmol). Then the reaction mixture was cooled in ice bath. To the solution was added oxalyl chloride (0.460 ml, 5.15 mmol) dropwise. The resulting solution was stirred for 2 hr at rt.

Reaction mixture was then cooled in ice bath, added TEA (1.436 ml, 10.30 mmol) and morpholine (0.497 ml, 5.7 mmol). The resulting solution was stirred for 1.5 h at rt. The reaction mixture was then diluted with EtOAc (30 ml) and washed with aq. $NH_4Cl$. Organic solution was dried over $MgSO_4$ and concentrated in vacuo, yielding oily residue, which was purified on normal phase chromatography to provide 633 mg (3.1 mmol, 60% yield) of I-270A as light brown oil. MS (ESI) m/z: 206.1 $(M+1)^+$.

I-270B. [4-[2-((S)-1-tert-Butoxycarbonylamino-but-3-enyl)-1-(2-trimethylsilanyl-ethoxymethyl)-1H-imidazol-4-yl]-3-(2,2-difluoro-pent-4-enoyl)-phenyl]-carbamic acid methyl ester: To a solution of 10B (0.145 g, 0.243 mmol) in THF (2 mL) under $N_2$ was added BuLi 2.5M in hex (0.487 mL, 1.217 mmol) at −78° C. The resulting solution was stirred for 0.5 h and to the solution was added I-270A in 3 ml of THF dropwise for 10 min. The reaction mixture was allowed to warm up to RT. The reaction was then quenched by adding aq. $NH_4Cl$ (2 mL). The reaction mixture was then diluted with EtOAc (30 ml) and washed with aq. $NH_4Cl$ (10 mL). Organic solution was dried over $MgSO_4$ and concentrated in vacuo, yielding oily residue, which was purified on normal phase chromatography to yield I-270B. TFA to yield I-270B. TFA (43 mg, 0.057 mmol, 23.6%).

I-270C. [(E)-(S)-9,9-Difluoro-5-methoxycarbonylamino-8-oxo-16-(2-trimethylsilanyl-ethoxymethyl)-16,18-diaza-tricyclo[13.2.1.0²,⁷]octadeca-1(17),2,4,6,11,15(18)-hexaen-14-yl]-carbamic acid tert-butyl ester: Compound I-270C was prepared following the procedure described step 2E/2F, by replacing 2D with I-270B. MS (ESI) m/z: 607.2 $(M+1)^+$.

I-270D. [(S)-9,9-Difluoro-5-methoxycarbonylamino-8-oxo-16-(2-trimethylsilanyl-ethoxymethyl)-16,18-diaza-tricyclo[13.2.1.0²,⁷]octadeca-1(17),2,4,6,15(18)-pentaen-14-yl]-carbamic acid tert-butyl ester: A solution of I-270C (14 mg, 0.023 mmol) and $PtO_2$ (3 mg, 0.013 mmol) in EtOAc (5 mL) and MeOH (5 ml) was stirred under $H_2$ (50 psi) for 14 h. The reaction mixture was filtered and concentrated in vacuo to provide I-270D (14 mg, 100%), which was subjected to the following reaction without further purification. MS (ESI) m/z: 609.3 $(M+H)^+$.

I-270E. Example I-270 was prepared following the procedures described in step 10H, by replacing 10G with I-270D; followed by step 1G. $^{19}F$ NMR (376 MHz, acetonitrile-$d_3$) δ ppm −76.47 (2 F, br. s.). MS (ESI) m/z: 611.2 $(M+H)^+$. Analytical HPLC: RT=5.59 min.

Example I-280

[(9R,14S)-14-[(E)-3-(5-Chloro-2-tetrazol-1-yl-phenyl)-acryloylamino]-17-cyano-9-(3-hydroxy-azetidine-1-carbonyl)-8,16,18-triaza-tricyclo[13.2.1.02,7]octadeca-1(17),2,4,6,15(18)-pentaen-5-yl]-carbamic Acid methyl ester, 2TFA A mixture of Example I-250 (0.020 g, 0.023 mmol), azetidin-3-ol hydrochloride (3.83 mg, 0.035 mmol), and BOP reagent (0.015 g, 0.035 mmol) in DMF (0.5 mL), was treated with DIPEA (0.020 mL, 0.116 mmol) and then stirred at room temperature under Ar overnight. Reaction was evaporated to remove DMF, and the residue was purified by reverse phase HPLC to provide Example I-280 (0.0196 g, 92%) as a white solid. $^1H$ NMR (500 MHz, $CD_3OD$) δ ppm 9.52 (1H, s), 8.00 (1H, d, J=2.2 Hz), 7.67 (1H, dd, J=8.8, 2.2 Hz), 7.55-7.61 (2H, m), 7.40 (1H, dd, J=17.9, 1.9 Hz), 7.28-7.33 (1H, m), 7.14 (1H, dd, J=15.7, 1.4 Hz), 6.80 (1H, d, J=15.9 Hz), 5.22 (1H, dd, J=11.0, 6.6 Hz), 4.33-4.47 (1H, m), 4.04-4.12 (1H, m), 3.79-4.06 (1H, m), 3.59-3.67 (1H, m), 3.38-3.62 (1H, m), 3.13-3.18 (1H, m), 2.12-2.21 (1H, m), 1.77-2.01 (3H, m), 1.45-1.56 (2H, m), 1.31 (1H, t, J=14.0 Hz), 0.42-0.55 (1H, m). MS (ESI) m/z: 686.1 $(M+H)^+$. Analytical HPLC: RT=6.98 min.

Example I-283

(9R,14S)-14-[(E)-3-(5-Chloro-2-tetrazol-1-yl-phenyl)-acryloylamino]-17-cyano-5-methoxycarbonylamino-8,16,18-triaza-tricyclo[13.2.1.02,7]octadeca-1(17),2,4,6,15(18)-pentaene-9-carboxylic Acid tert-butyl ester

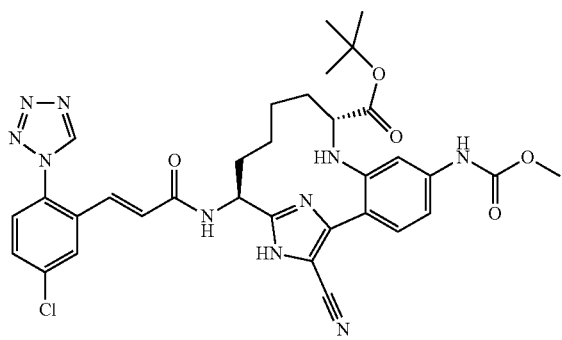 [SMILES: COC(=O)Nc1ccc2c(c1)N[C@@H](C(=O)OC(C)(C)C)CCCC[C@H](NC(=O)/C=C/c1cc(Cl)ccc1-n1cnnn1)c1nc-2c(C#N)[nH]1]

To a solution of Example I-250 (0.03 g, 0.048 mmol) in THF (0.5 ml)/Dichloromethane (0.5 ml) at RT was added t-BuOH (0.500 ml) and a solution of (E)-tert-butyl N,N'-diisopropylcarbamimidate (0.048 g, 0.238 mmol) dissolved in DCM (0.3 mL). Reaction was allowed to stir at RT ON. Reaction was concentrated and residue was purified by reverse phase HPLC. The fractions containing the product were neutralized by passing through a PL-HCO$_3$ MP SPE cartridge prior to evaporating to dryness to yield Example I-283 (12 mg, 36.4%) as a white solid. $^1$H NMR (500 MHz, CD$_3$OD) δ ppm 9.53 (1H, s), 8.02 (1H, d, J=2.48 Hz), 7.68 (1H, dd, J=8.53, 2.20 Hz), 7.59 (1H, d, J=8.53 Hz), 7.46 (2H, d, J=8.25 Hz), 7.05-7.18 (2H, m), 6.83 (1H, d, J=15.68 Hz), 5.22 (1H, dd, J=10.73, 6.88 Hz), 3.77 (3H, s), 2.77-2.87 (1H, m), 2.09-2.19 (1H, m), 1.78-1.96 (2H, m), 1.64-1.78 (1H, m), 1.40-1.53 (2H, m), 1.28-1.40 (10H, m), 0.39-0.55 (1H, m). MS (ESI) m/z: 687.2 (M+H)$^+$. Analytical HPLC: RT=9.28 min.

Example I-284 was prepared according to the procedure described in 88C, by replacing 88B with Intermediate 37 and by replacing Intermediate 12 with Intermediate 39; followed by steps I-226B; 10D, by replacing but-3-enoic acid with pent-4-enoic acid; 2E/2F; 10H; and 1G. Examples I-286 was prepared according to the procedure described in 88C, by replacing 88B with Intermediate 37 and by replacing Intermediate 12 with Intermediate 39; followed by steps I-226B; 10D, by replacing but-3-enoic acid with pent-4-enoic acid; 2E/2F; 10H; saponification of the methyl ester with 1.0 M aqueous sodium hydroxide in methanol at 45° C.; and 1G.

TABLE I-17

Examples I-265 to I-334

| Ex. # | Structure | LCMS [M + H]$^+$ | HPLC RT (min.) (Method) |
|---|---|---|---|
| I-265 | | 579.2 | 6.4 |
| I-266 | | 664.4 | 5.7 |

TABLE I-17-continued
Examples I-265 to I-334
| Ex. # | LCMS [M + H]+ | HPLC RT (min.) (Method) |
|---|---|---|
| I-267 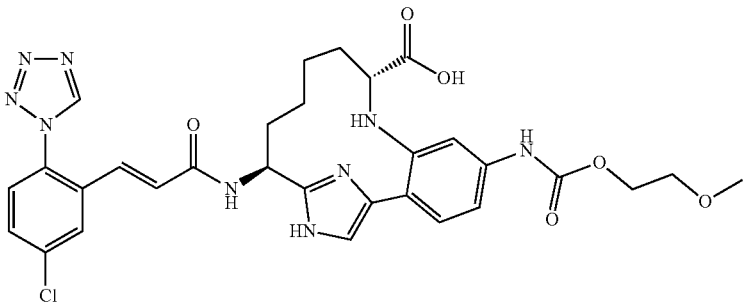 [SMILES: COCCOC(=O)Nc1ccc2c(c1)N[C@@H](C(=O)O)CCCC[C@H](NC(=O)/C=C/c1cc(Cl)ccc1-n1cnnn1)c1nc-2c[nH]1] | 650.4 | 5.2 |
| I-268 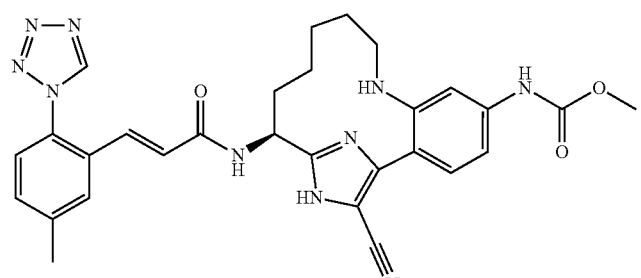 | 567.4 | 5.8 |
| I-269 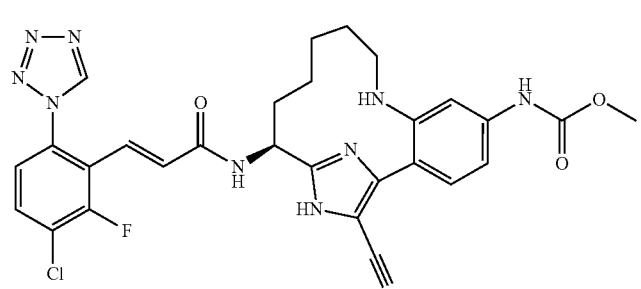 | 605.4 | 5.9 |
| I-270 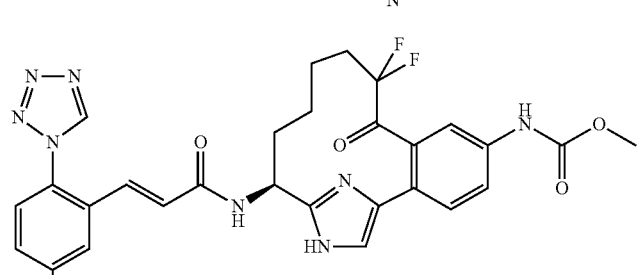 | 611.2 | 6.9 |
| I-271 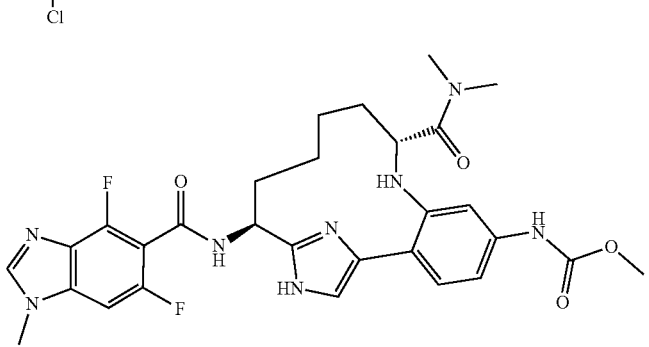 | 595.2 | 5.1 |

TABLE I-17-continued
Examples I-265 to I-334
| Ex. # | | LCMS [M + H]+ | HPLC RT (min.) (Method) |
|---|---|---|---|
| I-272 | 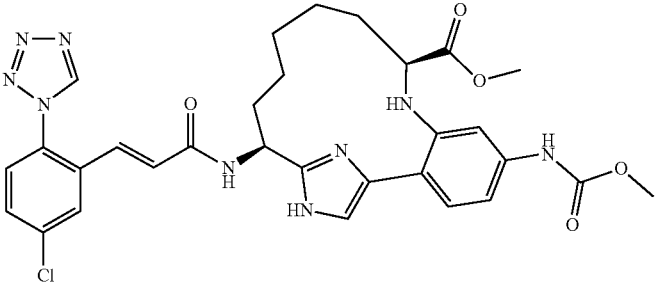 [SMILES: COC(=O)Nc1ccc2c(c1)N[C@H](C(=O)OC)CCCCC[C@H](NC(=O)/C=C/c1cc(Cl)ccc1-n1cnnn1)c1nc-2c[nH]1] | 634.2 | 6.2 |
| I-273 | 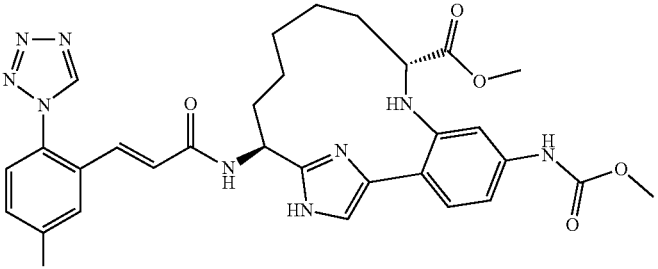 | 634.2 | 7.0 |
| I-274 | 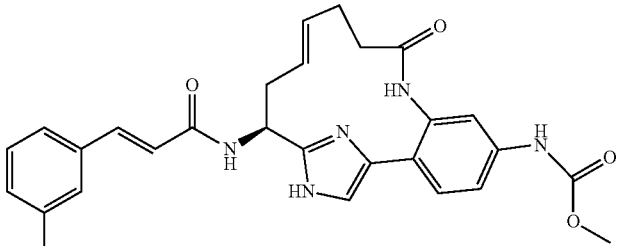 | 520.3 | 5.4 |
| I-275 | 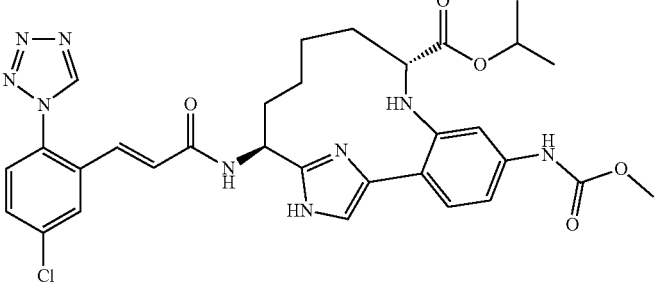 | 648.1 | 7.4 |
| I-276 | 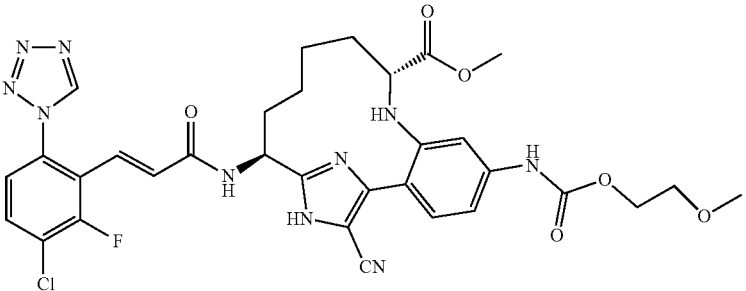 [SMILES: COCCOC(=O)Nc1ccc2c(c1)N[C@@H](C(=O)OC)CCCC[C@H](NC(=O)/C=C/c1c(-n3cnnn3)ccc(Cl)c1F)c1nc-2c(C#N)[nH]1] | 707.3 | 8.8 |

TABLE I-17-continued

Examples I-265 to I-334

| Ex. # | LCMS [M + H]+ | HPLC RT (min.) (Method) |
|---|---|---|
| I-277 | 740.3 | 6.7 |
| I-278 | 689.4 | 8.6 |
| I-279 | 700.3 | 7.7 |
| I-280 | 686.1 | 6.9 |

TABLE I-17-continued

Examples I-265 to I-334

| Ex. # | LCMS [M + H]+ | HPLC RT (min.) (Method) |
|---|---|---|
| I-281 | 670.1 | 7.7 |
| I-282 | 711.2 | 6.2 |
| I-283 | 687.2 | 9.3 |
| I-284 | 573.0 | 5.25(D) |

TABLE I-17-continued

Examples I-265 to I-334

| Ex. # | LCMS [M + H]+ | HPLC RT (min.) (Method) |
|---|---|---|
| I-285 | 673.1 | 8.9 |
| I-286 | 559.0 | 7.50(D) |
| I-287 | 606.1 | 5.55 |
| I-288 | 700.1 | 7.16 |

TABLE I-17-continued
Examples I-265 to I-334
| Ex. # | | LCMS [M + H]+ | HPLC RT (min.) (Method) |
|---|---|---|---|
| I-289 | 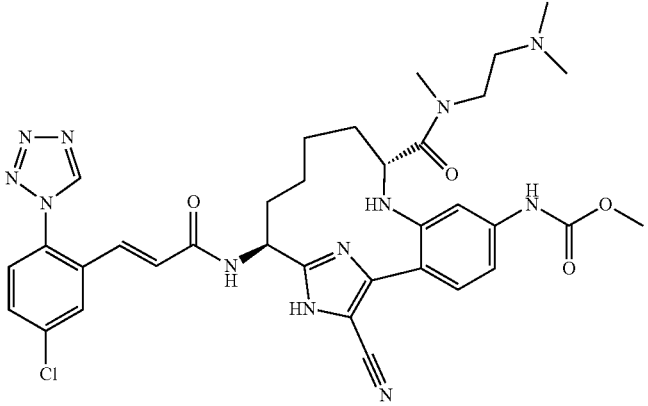 [SMILES: COC(=O)Nc1ccc2c(c1)N[C@@H](C(=O)N(C)CCN(C)C)CCCC[C@H](NC(=O)/C=C/c1cc(Cl)ccc1-n1cnnn1)c1nc-2c(C#N)[nH]1] | 715.2 | 5.35 |
| I-290 | 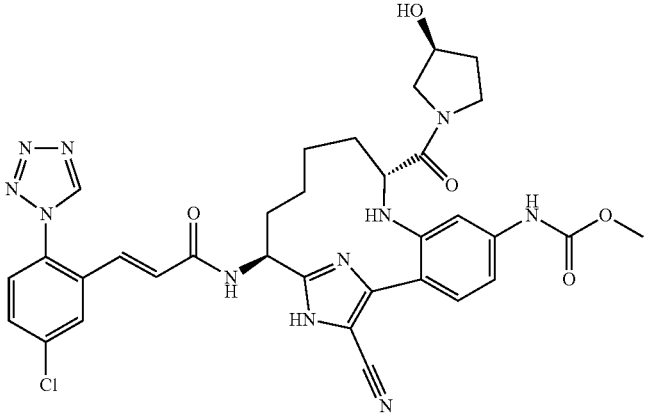 [SMILES: COC(=O)Nc1ccc2c(c1)N[C@@H](C(=O)N1CC[C@H](O)C1)CCCC[C@H](NC(=O)/C=C/c1cc(Cl)ccc1-n1cnnn1)c1nc-2c(C#N)[nH]1] | 700.1 | 7.01 |
| I-291 | 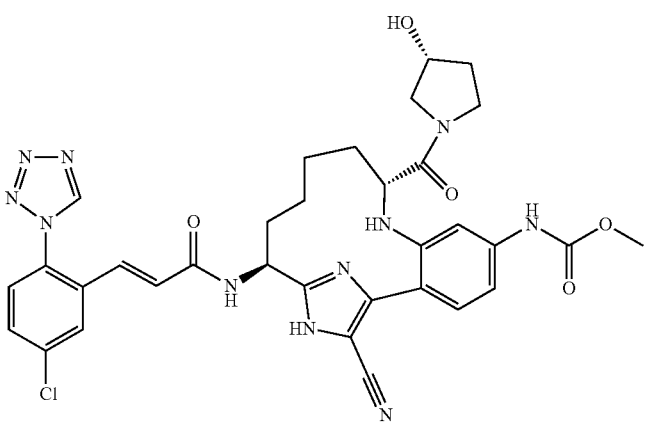 [SMILES: COC(=O)Nc1ccc2c(c1)N[C@@H](C(=O)N1CC[C@@H](O)C1)CCCC[C@H](NC(=O)/C=C/c1cc(Cl)ccc1-n1cnnn1)c1nc-2c(C#N)[nH]1] | 700.1 | 7.00 |

TABLE I-17-continued
Examples I-265 to I-334
| Ex. # | LCMS [M + H]+ | HPLC RT (min.) (Method) |
|---|---|---|
| I-292 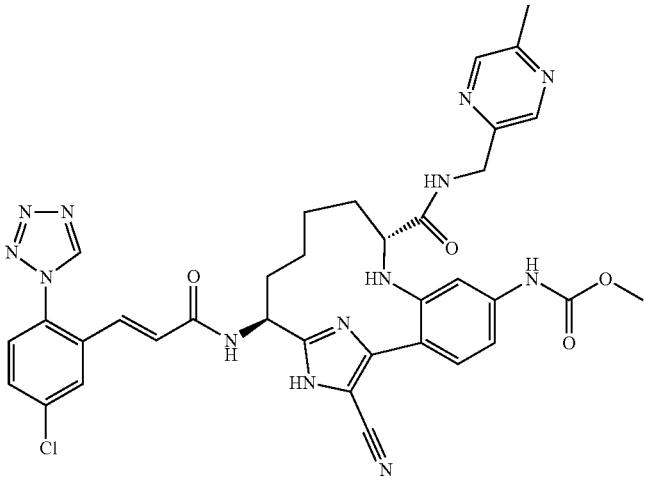 [SMILES: COC(=O)Nc1ccc2c(c1)N[C@@H](C(=O)NCc1cnc(C)cn1)CCCC[C@H](NC(=O)/C=C/c1cc(Cl)ccc1-n1cnnn1)c1nc-2c(C#N)[nH]1] | 736.1 | 6.87 |
| I-293 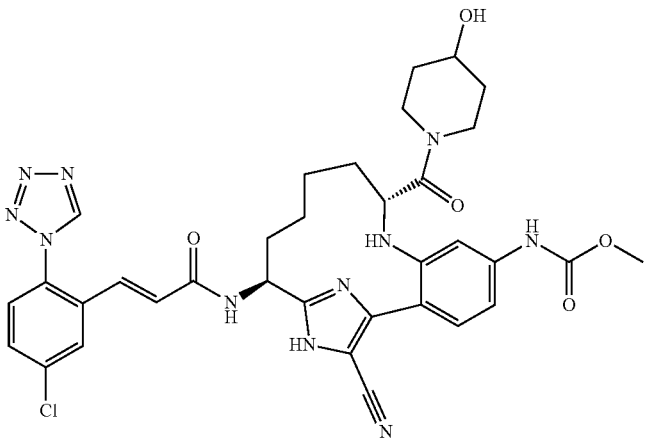 [SMILES: COC(=O)Nc1ccc2c(c1)N[C@@H](C(=O)N1CCC(O)CC1)CCCC[C@H](NC(=O)/C=C/c1cc(Cl)ccc1-n1cnnn1)c1nc-2c(C#N)[nH]1] | 714.2 | 7.01 |
| I-294 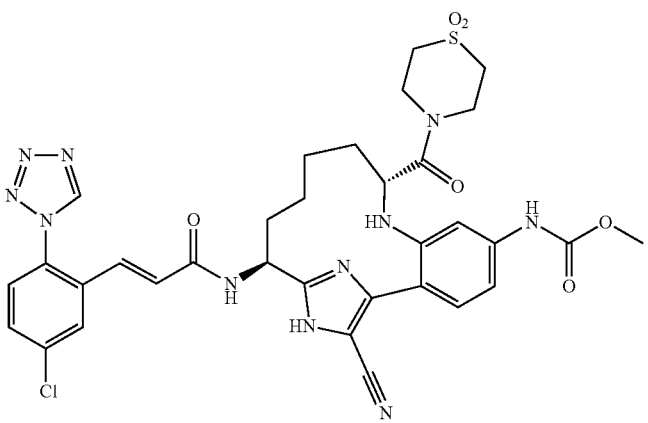 [SMILES: COC(=O)Nc1ccc2c(c1)N[C@@H](C(=O)N1CCS(=O)(=O)CC1)CCCC[C@H](NC(=O)/C=C/c1cc(Cl)ccc1-n1cnnn1)c1nc-2c(C#N)[nH]1] | 748.1 | 7.77 |

TABLE I-17-continued
Examples I-265 to I-334
| Ex. # | | LCMS [M + H]+ | HPLC RT (min.) (Method) |
|---|---|---|---|
| I-295 | 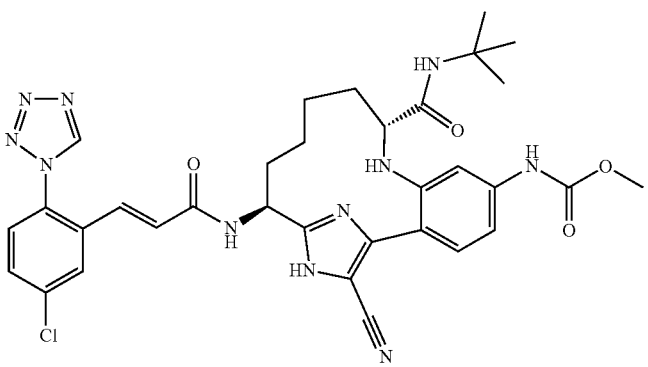 [SMILES: COC(=O)Nc1ccc2c(c1)N[C@@H](C(=O)NC(C)(C)C)CCCC[C@H](NC(=O)/C=C/c1cc(Cl)ccc1-n1cnnn1)c1nc-2c(C#N)[nH]1] | 686.1 | 8.01 |
| I-296 | 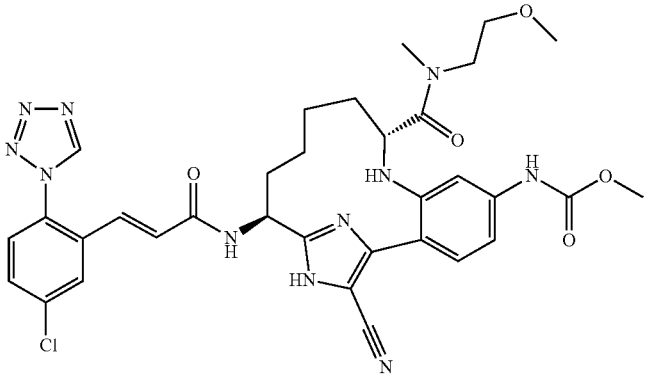 [SMILES: COCCN(C)C(=O)[C@H]1CCCC[C@H](NC(=O)/C=C/c2cc(Cl)ccc2-n2cnnn2)c2nc(c(C#N)[nH]2)-c2ccc(NC(=O)OC)cc2N1] | 702.2 | 7.42 |
| I-297 | 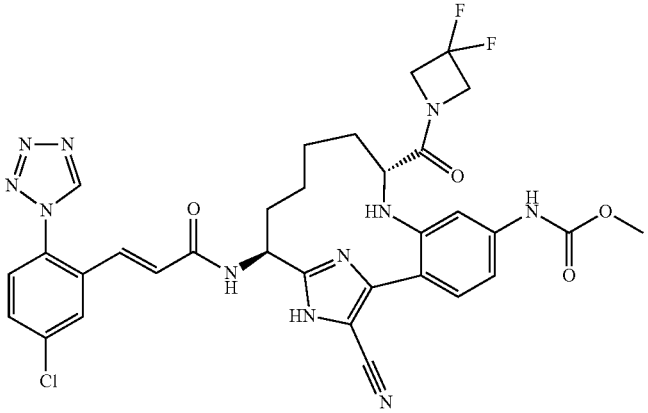 [SMILES: COC(=O)Nc1ccc2c(c1)N[C@@H](C(=O)N1CC(F)(F)C1)CCCC[C@H](NC(=O)/C=C/c1cc(Cl)ccc1-n1cnnn1)c1nc-2c(C#N)[nH]1] | 706.2 | 8.45 |

TABLE I-17-continued

Examples I-265 to I-334

| Ex. # | | LCMS [M + H]+ | HPLC RT (min.) (Method) |
|---|---|---|---|
| I-298 | | 700.2 | 7.75 |
| I-299 | | 633.1 | 5.50 |
| I-300 | | 688.1 | 7.93 |
| I-301 | | 713.1 | 9.13 |

TABLE I-17-continued
Examples I-265 to I-334
| Ex. # | | LCMS [M + H]+ | HPLC RT (min.) (Method) |
|---|---|---|---|
| I-302 | 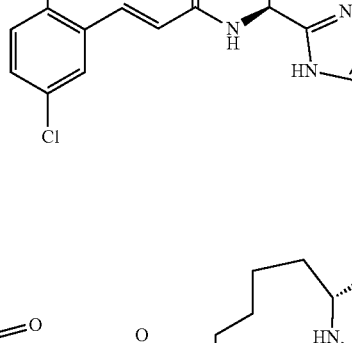 | 687.1 | 7.87 |
| I-303 | 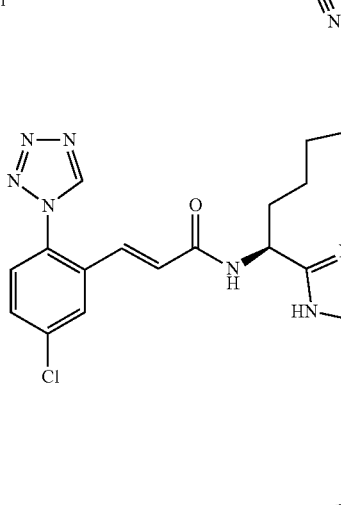 | 681.1 | 8.89 |
| I-304 | 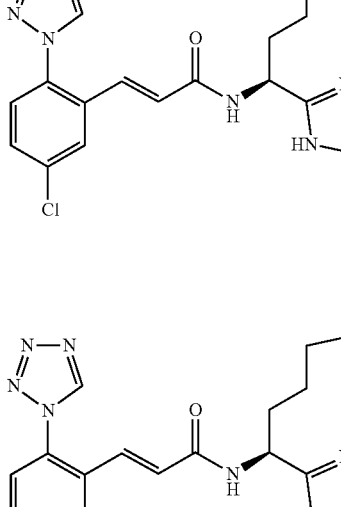 | 737.0 | 7.68 |
| I-305 | 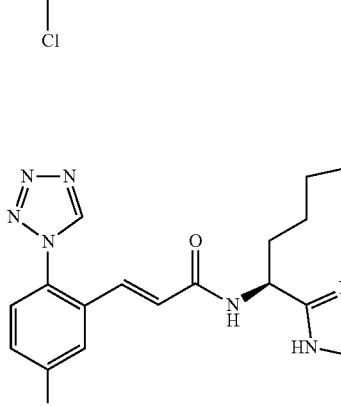 | 680.3 | 7.07 |

TABLE I-17-continued

Examples I-265 to I-334

| Ex. # | | LCMS [M + H]+ | HPLC RT (min.) (Method) |
|---|---|---|---|
| I-306 | | 707.0 | 9.92 |
| I-307 | | 544.0 | 6.8 |
| I-308 | | 615.9 | 7.1 |
| I-309 | | 554.0 | 7.4 |
| I-310 | | 542.0 | 6.9 |

TABLE I-17-continued

Examples I-265 to I-334

| Ex. # | LCMS [M + H]+ | HPLC RT (min.) (Method) |
|---|---|---|
| I-311 | 639.9 | 8.3 |
| I-312 | 570.0 | 4.5 |
| I-313 | 549.0 | 3.5 |
| I-314 | 549.0 | 6.5 |
| I-315 | 545.0 | 4.2 |

TABLE I-17-continued

Examples I-265 to I-334

| Ex. # | LCMS [M + H]+ | HPLC RT (min.) (Method) |
|---|---|---|
| I-316 | 680.2 | 7.44 |
| I-317 | 644.0 | 6.61 |
| I-318 | 644.0 | 6.37 |
| I-319 | 592.9 | 6.41 |

TABLE I-17-continued

Examples I-265 to I-334

| Ex. # | LCMS [M + H]+ | HPLC RT (min.) (Method) |
|---|---|---|
| I-320 | 607.0 | 6.67 |
| I-321 | 545.0 | 3.61 |
| I-322 | 545.0 | 3.75 |
| I-323 | 544.9 | 5.37 |
| I-324 | 568.9 | 7.38 |

TABLE I-17-continued
Examples I-265 to I-334
| Ex. # | | LCMS [M + H]+ | HPLC RT (min.) (Method) |
|---|---|---|---|
| I-325 | 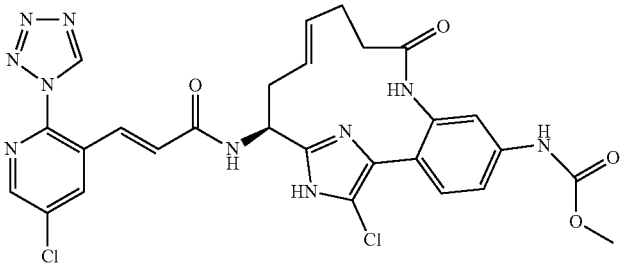 [SMILES: COC(=O)Nc1ccc2c(c1)NC(=O)CC/C=C/C[C@H](NC(=O)/C=C/c1cc(Cl)cnc1-n1cnnn1)c1nc-2c(Cl)[nH]1] | 622.9 | 6.05 |
| I-326 | 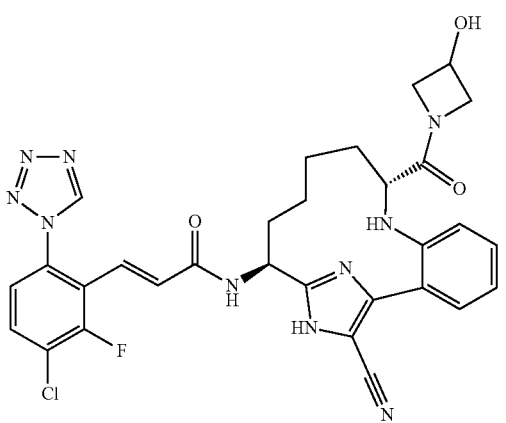 [SMILES: N#Cc1[nH]c2nc1-c1ccccc1N[C@@H](C(=O)N1CC(O)C1)CCCC[C@@H]2NC(=O)/C=C/c1c(-n2cnnn2)ccc(Cl)c1F] | 631.0 | 7.09 |
| I-327 | 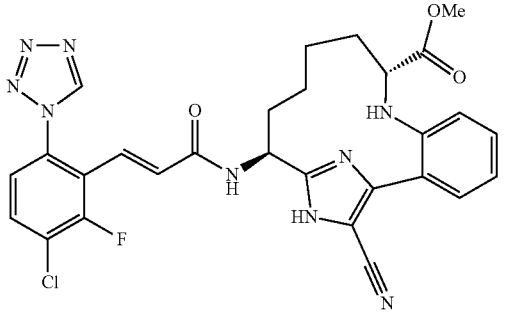 | 590.0 | 9.21 |
| I-328 | 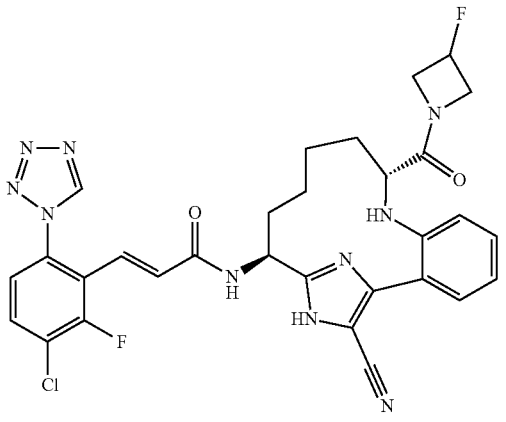 [SMILES: N#Cc1[nH]c2nc1-c1ccccc1N[C@@H](C(=O)N1CC(F)C1)CCCC[C@@H]2NC(=O)/C=C/c1c(-n2cnnn2)ccc(Cl)c1F] | 633.0 | 8.21 |

TABLE I-17-continued
Examples I-265 to I-334
| Ex. # | | LCMS [M + H]+ | HPLC RT (min.) (Method) |
|---|---|---|---|
| I-329 | 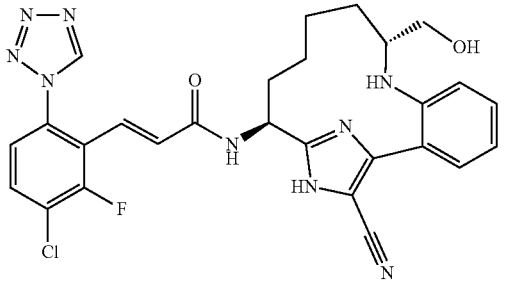 [SMILES: N#Cc1[nH]c2nc1-c1ccccc1N[C@@H](CO)CCCC[C@@H]2NC(=O)/C=C/c1c(-n2cnnn2)ccc(Cl)c1F] | 562.0 | 6.05 |
| I-330 | 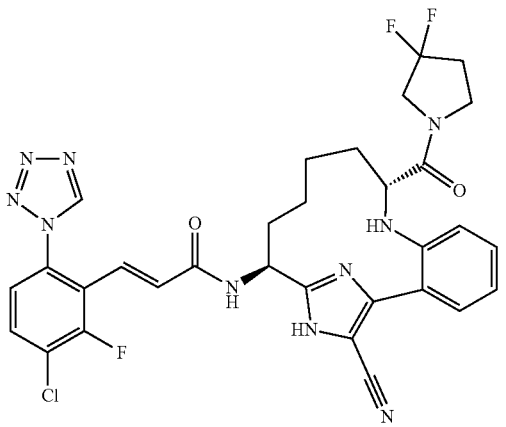 [SMILES: N#Cc1[nH]c2nc1-c1ccccc1N[C@@H](C(=O)N1CCC(F)(F)C1)CCCC[C@@H]2NC(=O)/C=C/c1c(-n2cnnn2)ccc(Cl)c1F] | 665.0 | 8.97 |
| I-331 | 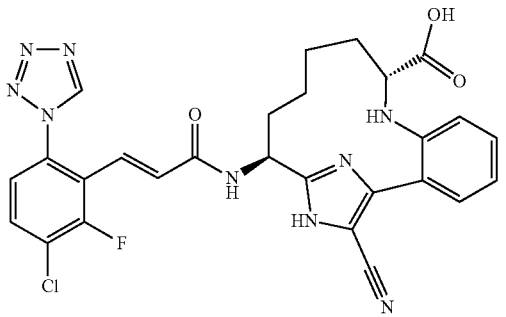 [SMILES: N#Cc1[nH]c2nc1-c1ccccc1N[C@@H](C(=O)O)CCCC[C@@H]2NC(=O)/C=C/c1c(-n2cnnn2)ccc(Cl)c1F] | 575.9 | 8.01 |
| I-332 | 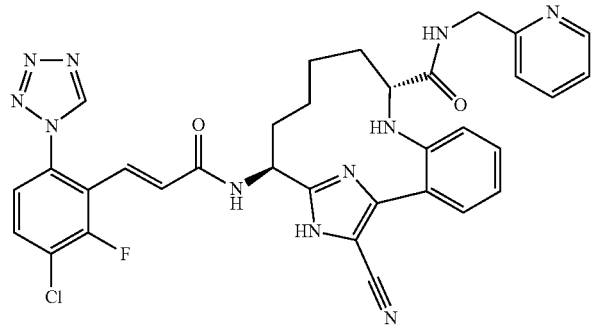 [SMILES: N#Cc1[nH]c2nc1-c1ccccc1N[C@@H](C(=O)NCc1ccccn1)CCCC[C@@H]2NC(=O)/C=C/c1c(-n2cnnn2)ccc(Cl)c1F] | 666.1 | 6.02 |

TABLE I-17-continued

Examples I-265 to I-334

| Ex. # | | LCMS [M + H]+ | HPLC RT (min.) (Method) |
|---|---|---|---|
| I-333 | (structure with OMe ester) | 527.1 | 4.51 |
| I-334 | (structure with OH acid) | 513.1 | 3.88 |

Examples II-1 and II-2 were prepared in two steps by coupling 91A with an appropriately substituted carboxylic acid derivative (R—CO₂H) using coupling conditions described in step 15D, followed by a Boc-deprotection step as described in step 3C. Example II-3 was prepared by following the procedures described in step 3C, by replacing 3B with 88G; followed by step 15D, by replacing Intermediate 2 with an appropriately substituted carboxylic acid; followed by Boc-deprotection step 3C. Examples II-4 and II-5 were prepared by coupling 96A with an appropriately substituted carboxylic acid derivative using coupling conditions described in step 15D. In the case of II-5 an additional Boc-deprotection step as described in step 3C was required.

Example II-6

(S)-14-[(E)-3-(5-Chloro-2-tetrazol-1-yl-phenyl)-acryloylamino]-9-oxo-8,16-diaza-tricyclo[13.3.1.02,7]nonadeca-1(19),2(7),3,5,15,17-hexaene-5-carboxylic Acid amide, TFA

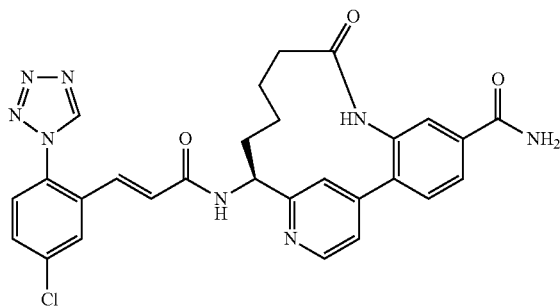 [SMILES: NC(=O)c1ccc2c(c1)NC(=O)CCCC[C@H](NC(=O)/C=C/c1cc(Cl)ccc1-n1cnnn1)c1cc-2ccn1]

II-6A. (S)-Benzyl 1-(4-chloropyridin-2-yl)but-3-enylcarbamate: 88B (1.135 g, 3.96 mmol) was taken up in MeOH (39.6 mL) and 4M HCl in dioxane (19.79 mL, 79 mmol) was added. Reaction was stirred at rt under Ar for 2 hrs then was evaporated to remove MeOH and triturated with Et₂O 2× to yield (S)-1-(4-chloropyridin-2-yl)but-3-en-1-amine, 2 HCl (1.005 g, 99%, MS (ESI) m/z: 183.1 (M+H)+), which was taken up in MeOH (13.11 mL) and treated with benzyl 2,5-dioxopyrrolidin-1-yl carbonate (1.078 g, 4.33 mmol) and DIPEA (2.060 mL, 11.80 mmol). The resulting mixture was stirred at rt for 5 min then stripped to dryness, diluted with EtOAc and washed with brine, dried over MgSO₄, filtered, and evaporated. The residue was purified by flash chromatography to yield II-6A (1.19 g, 96%) as a colorless oil. MS (ESI) m/z: 317.2 (M+H)+

II-6B. (S)-2-(1-(Benzyloxycarbonylamino)but-3-enyl)pyridin-4-ylboronic acid, TFA: A mixture of II-6A (0.75 g, 2.368 mmol), bis(neopentyl glycolato)diboron (0.802 g, 3.55 mmol), potassium acetate (0.697 g, 7.10 mmol), PdCl2(dppf)-CH₂Cl₂ adduct (1:1) (0.193 g, 0.237 mmol) and DMSO (7.89 mL) in a sealed tube was degassed by evacuating and backfilling with Ar 3×, and then the reaction was heated at 80° C. for 6-8 h, then left at room temperature overnight. A second reaction was carried out identically. The two reactions were combined and diluted with EtOAc, then filtered through a small pad of CELITE® which was rinsed several times with EtOAc. The filtrate was transferred to a separatory funnel and washed 3× with H₂O, refiltered again thru CELITE®, then washed with brine, dried and concentrated to yield a dark brown oil which was purified by reverse phase HPLC to yield II-6B as a white foam (1.325 g, 63.6%). MS (ESI) m/z: 327.3 (M+H)+.

II-6C. (S)-Benzyl 1-(4-(2-amino-4-cyanophenyl)pyridin-2-yl)but-3-enylcarbamate, 2 TFA: To II-6B (0.44 g, 1.000 mmol), 3-amino-4-bromobenzonitrile (0.164 g, 0.833 mmol) (81378-051-01), tetrabutylammonium bromide (0.013 g, 0.042 mmol), and 2M sodium carbonate (1.249 mL, 2.499 mmol) in a 20 mL microwave tube was added toluene (6.92 mL) and EtOH (2.88 mL), and the solution was degassed by evacuating/flushing with Ar 3×. (Ph₃P)₄Pd (0.048 g, 0.042 mmol) was added, and the vial was once again evacuated/flushed with Ar 3×. Two more vials were prepared identically. All 3 vials were capped and heated at 95° C. in an oil bath overnight. Then the reaction was allowed to stir at rt for 3 days. Contents of vials were combined and diluted with EtOAc and washed with water, sat. NaHCO$_3$, and brine, then dried over anhydrous magnesium sulfate, filtered, and evaporated. Residue was purified by flash chromatography to yield II-6C (0.758 g, 48.4%) as a light yellow foam. MS (ESI) m/z: 399.3 (M+H)$^+$.

II-6D. ((E)-(S)-5-Cyano-9-oxo-8,16-diaza-tricyclo[13.3.1.0$^{2,7}$]nonadeca-1(19),2(7),3,5,11,15,17-heptaen-14-yl)-carbamic acid benzyl ester: II-6D was prepared in two steps from II-6C using the procedures described for steps 10D and 2E/F. MS (ESI) m/z: 439.2 (M+H)$^+$.

II-6E. ((E)-(S)-5-Carbamoyl-9-oxo-8,16-diaza-tricyclo[13.3.1.0$^{2,7}$]nonadeca-1(19),2(7),3,5,11,15,17-heptaen-14-yl)-carbamic acid benzyl ester: II-6D (0.015 g, 0.034 mmol) (81378-069-01) was dissolved in DMSO (0.171 mL) and K$_2$CO$_3$ (0.014 g, 0.103 mmol) was added. Then 30% H$_2$O$_2$ (0.038 mL, 0.376 mmol) was added dropwise. The light yellow suspension was stirred for 1 h at room temperature under nitrogen. Reaction mixture was diluted with water and extracted 3× with EtOAc. The organic layer was dried over MgSO$_4$, filtered, and condensed to yield the crude amide as a colorless residue (0.022 g) which was taken on to the next step without further purification. MS (ESI) m/z: 457.3 (M+H)$^+$.

Example II-6. The title compound was prepared from II-6E using the procedures described for steps 10F and 1G. $^1$H NMR (500 MHz, CD$_3$OD) δ ppm 9.49 (1H, s) 8.76 (1H, d, J=5.78 Hz) 8.00 (1H, d, J=1.10 Hz) 7.95-7.99 (2H, m) 7.82 (1H, dd, J=5.78, 1.65 Hz) 7.80 (1H, d, J=1.65 Hz) 7.77 (1H, d, J=8.25 Hz) 7.66 (1H, dd, J=8.39, 2.34 Hz) 7.57 (1H, d, J=8.53 Hz) 7.10 (1H, d, J=15.41 Hz) 6.79 (1H, d, J=15.68 Hz) 5.12 (1H, dd, J=10.73, 5.78 Hz) 2.50 (1H, ddd, J=12.52, 6.74, 1.93 Hz) 2.07-2.19 (1H, m) 1.93-2.01 (1H, m) 1.82-1.92 (1H, m) 1.70-1.80 (1H, m) 1.60-1.69 (1H, m) 1.33-1.42 (1H, m) 0.71-0.86 (1H, m). MS (ESI) m/z: 557.3 (M+H)$^+$. Analytical HPLC: RT=4.95 min.

Example II-7 was prepared from 88B following the procedures described for steps II-6A, by replacing benzyl 2,5-dioxopyrrolidin-1-yl carbonate with di-t-butyldicarbonate; 88C, by replacing 88B with (S)-2-(1-(tert-butoxycarbonylamino)but-3-enyl)pyridin-4-ylboronic acid and Intermediate 12 with methyl 4-amino-3-bromobenzoate; 10D; 2E/F; and 2G; followed by hydrolysis of the methyl ester with 1M LiOH in THF; then steps 3A and 1G. Example 11-8 was similarly prepared following the procedures described for steps II-6C, by substituting (S)-2-(1-(tert-butoxycarbonylamino)but-3-enyl)pyridin-4-ylboronic acid for II6-B and 4-amino-3-bromobenzonitrile for 3-amino-4-bromobenzonitrile; 10D, 2E/F, 3C and 1G.

Example II-11

{(E)-(S)-14-[(E)-3-(5-Chloro-2-tetrazol-1-yl-phenyl)-acryloylamino]-9-trifluoromethyl-8,16-diazatricyclo[13.3.1.0$^{2,7}$]nonadeca-1(19),2(7),3,5,11,15,17-heptaen-5-yl}-carbamic Acid methyl ester, 2 TFA Salt

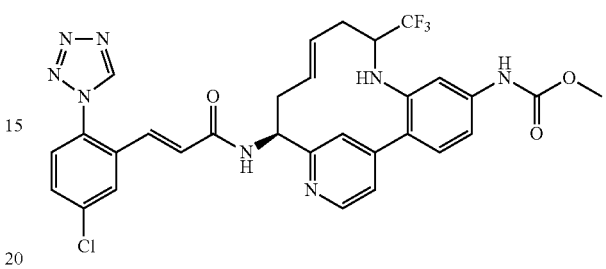

II-11A. (S)-tert-Butyl 1-(4-(2-amino-4-nitrophenyl)pyridin-2-yl)but-3-enylcarbamate: Compound II-11A was prepared by following the procedure described in step 88C, by replacing 88B with (S)-tert-butyl 1-(4-chloropyridin-2-yl)but-3-enylcarbamate. MS (ESI) 385.1 (M+H)$^+$.

II-11B. (S)-tert-Butyl 1-(4-(2,4-diaminophenyl)pyridin-2-yl)but-3-enylcarbamate: To a clear, orange solution of II-11A (2.9 g, 7.54 mmol) in methanol (75 mL) was added sequentially zinc dust (4.93 g, 75 mmol) and ammonium chloride (4.04 g, 75 mmol). The resulting suspension was stirred vigorously for 4 h. The reaction was stopped and filtered through a 0.45 micron GMF eluting with methanol to give a clear, yellow filtrate. Concentration of the filtrate gave a yellow-black residue. The residue was partitioned between EtOAc and 0.25 M HCl (50 mL) and the layers were separated. The organic layer was extracted with 0.25 M HCl (1×50 mL). The combined aqueous layers were basified with 1.5M K$_2$HPO$_4$ and then extracted with EtOAc (3×). The combined organic layers were washed with brine, dried over Na$_2$SO$_4$, filtered and concentrated to give II-11B (2.63 g, 98%) as a brown foam. MS (ESI) m/z: 355.2 (M+H)$^+$.

II-11C. {3-Amino-4-[2-((S)-1-tert-butoxycarbonylamino-but-3-enyl)-pyridin-4-yl]-phenyl}-carbamic acid methyl ester: To a cooled (−78° C.) clear, brown solution of II-11B (2.63 g, 7.42 mmol) and pyridine (0.600 ml, 7.42 mmol) in dichloromethane (74.2 ml) was added dropwise over 30 min methyl chloroformate (0.516 ml, 6.68 mmol). The reaction was stirred at −78° C. After 1.5 h, the reaction was quenched with sat. NH$_4$Cl and the reaction was allowed to warm to RT. The reaction was diluted with DCM and water and the layers were separated. The aqueous layer was extracted with DCM (1×). The combined organic layers were washed with sat. NaHCO$_3$, brine, dried over Na$_2$SO$_4$, filtered and concentrated. The residue dissolved in DCM (~10 mL) and then hexane (~300 mL) was added to give a brown suspension with brown gummy sticky substance at the bottom. The mixture was sonicated to give a mostly clear solution with the brown substance at the bottom. The solution decanted and the bottom substance rinsed with hexane, dried to give II-11C (2.7 g, 88%) as a slightly brown foam. LCMS (ES) 413.2 (M+H)$^+$.

II-11D. [4-[2-((S)-1-tert-Butoxycarbonylamino-but-3-enyl)-pyridin-4-yl]-3-(1-ethoxy-2,2,2-trifluoro-ethyl-amino)-phenyl]-carbamic acid methyl ester: A clear yellow solution of II-11C (2.296 g, 5.57 mmol), pTsOH (0.053 g, 0.278 mmol) and trifluoroacetaldehyde ethyl hemiacetal (2.63 ml, 22.27 mmol) in ethanol (11.13 ml) was microwaved at 120° C. for 3 h. The reaction was concentrated, purified by normal phase chromatography which gave II-11D (1.61 g, 53.7%) as a yellow solid and as a mixture of diastereomers. MS (ESI) m/z: 539.2 (M+H)$^+$.

II-11E. [4-[2-((S)-1-tert-Butoxycarbonylamino-but-3-enyl)-pyridin-4-yl]-3-(1-trifluoromethyl-but-3-enylamino)-phenyl]-carbamic acid methyl ester: To a cooled (−20° C.) solution of II-11D (1.816 g, 3.37 mmol) in THF (33.7 mL) was added dropwise allylmagnesium bromide (1M in Et$_2$O, 15.17 ml, 15.17 mmol). The resulting cloudy, red reaction mixture was stirred at −20° C. After 3 h, another allylmagnesium bromide (0.8 mL, 0.8 mmol) added. After another 20 min, the reaction mixture was quenched with sat. NH$_4$Cl and the reaction was warmed to RT. The reaction was partitioned between water and EtOAc and the layers were separated. The aqueous layer was extracted with EtOAc (2×). The combined organic layers were washed with brine, dried over Na$_2$SO$_4$, filtered and concentrated. Purification by normal phase chromatography gave II-11E (1.45 g, 80%) as a yellow foam and as a mixture of diastereomers. MS (ESI) m/z: 535.3 (M+H)$^+$.

II-11F and II-11G. ((E)-(S)-14-tert-Butoxycarbonylamino-9-trifluoromethyl-8,16-diaza-tricyclo[13.3.1.0$^{2,7}$]nonadeca-1(19),2(7),3,5,11,15,17-heptaen-5-yl)-carbamic acid methyl ester: Compounds II-11F (diastereomer A) and II-11G (diastereomer B) were prepared following the procedure described in 88G, by replacing 88F with II-11E. For II-11F: MS (ESI) m/z: 507.2 (M+H)$^+$. For II-11G: MS (ESI) m/z: 507.3 (M+H)$^+$.

II-11H. Example II-11 was prepared following the procedures described in step 3C, by replacing 3B with II-11F (diastereomer A); followed by step 1G. $^1$H NMR (400 MHz, CD$_3$OD) δ ppm 9.51 (s, 1H), 8.64 (d, J=5.5 Hz, 1H), 8.06 (d, J=1.1 Hz, 1H), 7.98 (d, J=2.2 Hz, 1H), 7.77 (dd, J=6.1, 1.6 Hz, 1H), 7.67 (dd, J=8.3, 2.2 Hz, 1H), 7.58 (d, J=8.8 Hz, 1H), 7.33 (br. s., 1H), 7.27 (d, J=8.2 Hz, 1H), 7.09-7.18 (m, 2H), 6.76 (d, J=15.4 Hz, 1H), 5.59-5.72 (m, 1H), 5.06-5.24 (m, 2H), 3.75 (s, 3H), 3.43-3.57 (m, 1H), 2.83-2.94 (m, 1H), 2.47-2.65 (m, 2H), 2.26-2.39 (m, 1H). $^{19}$F NMR (471 MHz, CD$_3$OD) δ −75.49, −77.15. MS (ESI) m/z: 639.2 (M+H)$^+$. Analytical HPLC, RT=6.74 min.

TABLE II-1

Examples II-1 to II-11

| Ex. # | Structure | LCMS [M + H]$^+$ | HPLC RT (min) (method) |
|---|---|---|---|
| II-1 | 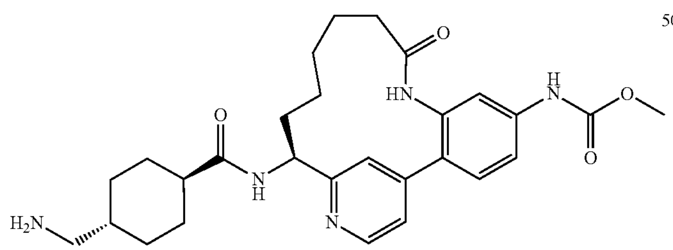 | 508.2 | 6.5 (C) |
| II-2 | 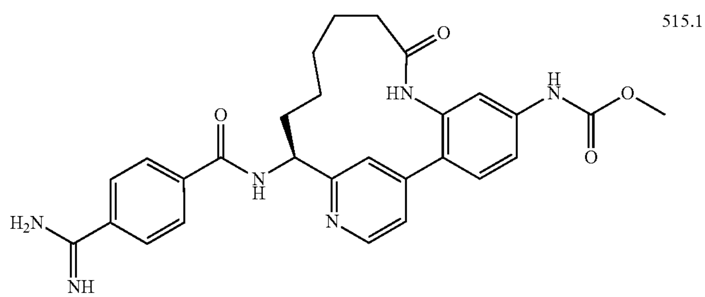 | 515.1 | 6.3 (C) |
| II-3 | 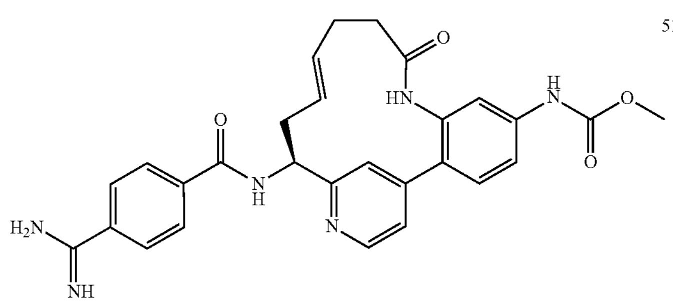 | 513.1 | 6.3 (C) |

TABLE II-1-continued

Examples II-1 to II-11

| Ex. # | Structure | LCMS [M + H]+ | HPLC RT (min) (method) |
|---|---|---|---|
| II-4 | 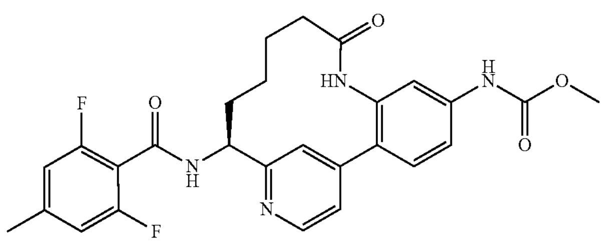 | 509.1 | 4.9 |
| II-5 | 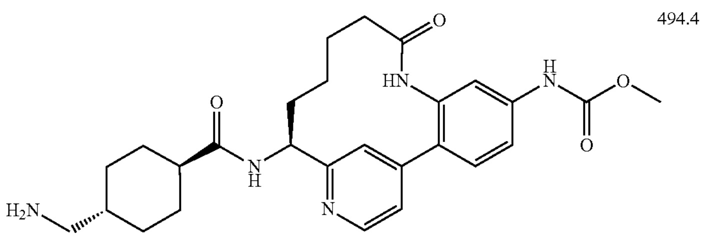 | 494.4 | 6.5 (C) |
| II-6 | 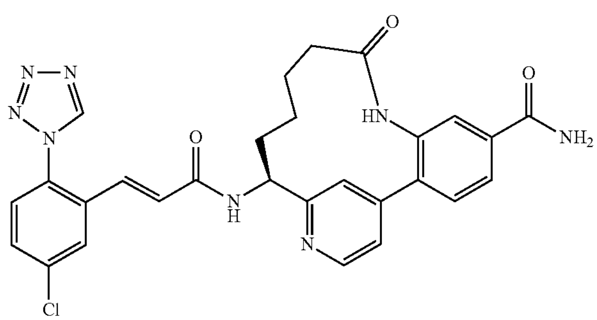 [SMILES: NC(=O)c1ccc2c(c1)NC(=O)CCCC[C@H](NC(=O)/C=C/c1cc(Cl)ccc1-n1cnnn1)c1cc-2ccn1] | 557.3 | 5.0 |
| II-7 | 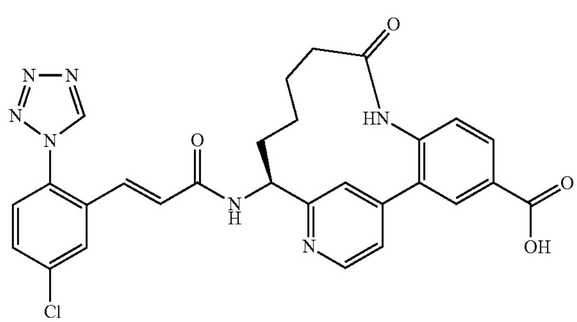 [SMILES: O=C(/C=C/c1cc(Cl)ccc1-n1cnnn1)N[C@H]1CCCCC(=O)Nc2ccc(C(=O)O)cc2-c2ccnc1c2] | 558.2 | 5.2 |
| II-8 | 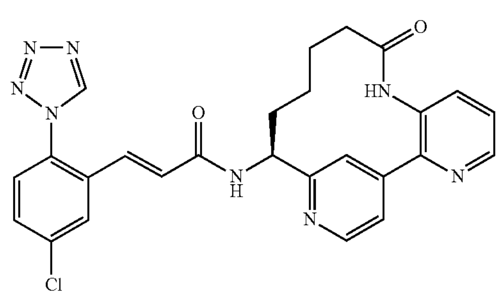 [SMILES: O=C(/C=C/c1cc(Cl)ccc1-n1cnnn1)N[C@H]1CCCCC(=O)Nc2cccnc2-c2ccnc1c2] | 515.2 | 4.1 (B) |

TABLE II-1-continued

Examples II-1 to II-11

| Ex. # | Structure | LCMS [M + H]+ | HPLC RT (min) (method) |
|---|---|---|---|
| II-9 | 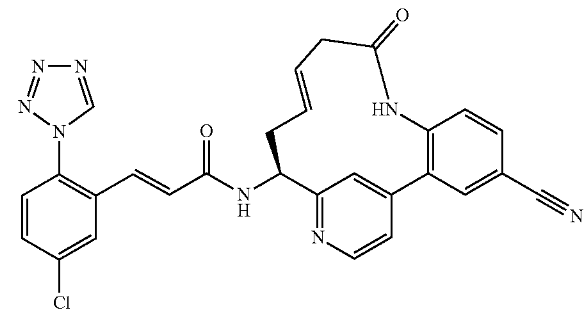 [SMILES: N#Cc1ccc2c(c1)-c1ccnc(c1)[C@@H](NC(=O)/C=C/c1cc(Cl)ccc1-n1cnnn1)C/C=C/CC(=O)N2] | 537.2 | 6.2 |
| II-10 | (racemate) | 602.1 | 6.4 |
| II-11 | (homochiral) | 639.2 | 6.7 |

Example II-12

{(S)-14-[(E)-3-(5-Chloro-2-tetrazol-1-yl-phenyl)-acryloylamino]-9-trifluoromethyl-8,16-diaza-tricyclo[13.3.1.0$^{2,7}$]nonadeca-1(19),2(7),3,5,15,17-hexaen-5-yl}-carbamic Acid methyl ester, 2 TFA Salt

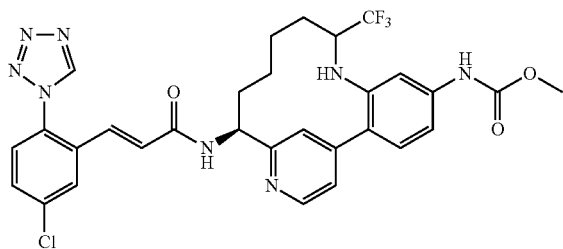

II-12A. ((S)-5-Methoxycarbonylamino-9-trifluoromethyl-8,16-diaza-tricyclo[13.3.1.0$^{2,7}$]nonadeca-1(19),2(7),3,5,15,17-hexaen-14-yl)-carbamic acid tert-butyl ester: To the solution II-11F (diastereomer A) (0.46 g, 0.908 mmol) in EtOH (6 mL) was added TFA (0.070 mL, 0.908 mmol) and 10% palladium on carbon (0.097 g, 0.091 mmol). Hydrogen, from a balloon, was bubbled through the reaction for a few minutes, then the reaction was stirred under H$_2$-balloon for 24 h. Additional TFA (0.070 mL, 0.908 mmol) was added, and the reaction was stirred under a H$_2$-balloon for another 24 h. The reaction was filtered through 0.45 µm GMF rinsing with MeOH. The filtrate was concentrated. The residue was dissolved in EtOAc, washed with sat. NaHCO$_3$, brine, dried over Na$_2$SO$_4$, filtered and concentrated. Purification by normal phase chromatography gave II-12A (0.4 g, 87% yield) as a yellow solid. MS (ESI) m/z: 509.3 (M+H)+.

II-12B. ((S)-14-Amino-9-trifluoromethyl-8,16-diaza-tricyclo[13.3.1.0$^{2,7}$]nonadeca-1(19),2(7),3,5,15,17-hexaen-5-yl)-carbamic acid methyl ester, 3 TFA salt: Compound II-12B was prepared following the procedure described in 3C, by replacing 3B with II-12A. MS (ESI) m/z: 409.1 (M+H)+.

II-12C. Example II-12 was prepared following the procedure described in step 1G by replacing 1F with II-12B. $^1$H NMR (500 MHz, CD$_3$OD) δ ppm 9.48 (s, 1H), 8.73 (d, J=1.4 Hz, 1H), 8.66 (d, J=6.1 Hz, 1H), 7.98 (d, J=2.2 Hz, 1H), 7.89 (dd, J=6.2, 1.8 Hz, 1H), 7.67 (dd, J=8.4, 2.3 Hz, 1H), 7.57 (d, J=8.5 Hz, 1H), 7.48 (d, J=8.5 Hz, 1H), 7.40 (d, J=1.7 Hz, 1H), 7.22 (dd, J=8.5, 1.9 Hz, 1H), 7.11 (d, J=15.7 Hz, 1H), 6.79 (d, J=15.4 Hz, 1H), 5.17 (dd, J=11.7, 6.5 Hz, 1H), 3.76 (s, 3H), 2.95-3.05 (m, 1H), 2.20-2.31 (m, 1H), 1.84-1.99 (m, 2H), 1.71-1.80 (m, 1H), 1.51-1.62 (m, 2H), 1.41-1.50 (m, 1H), 0.33-0.45 (m, 1H). $^{19}$F NMR (471 MHz, CD$_3$OD) δ −75.06, −77.30. MS (ESI) m/z: 641.3 (M+H)$^+$. Analytical HPLC: RT=7.06 min.

Examples II-13 and II-14 were prepared in two steps by coupling II-12B with an appropriately substituted carboxylic acid derivative (R—CO$_2$H) using coupling conditions described in step 15D, followed by a Boc-deprotection step as described in step 3C.

Example II-15 were prepared according to the procedures described in II-12, by replacing II-11F with II-11G; followed by II-14.

Example II-17

(9R,14S)-14-[(E)-3-(5-Chloro-2-tetrazol-1-yl-phenyl)-acryloylamino]-5-methoxycarbonylamino-8,16-diaza-tricyclo[13.3.1.0$^{2,7}$]nonadeca-1(19),2(7),3,5,15,17-hexaene-9-carboxylic Acid ethyl ester, diastereomer A, 2 TFA Salt

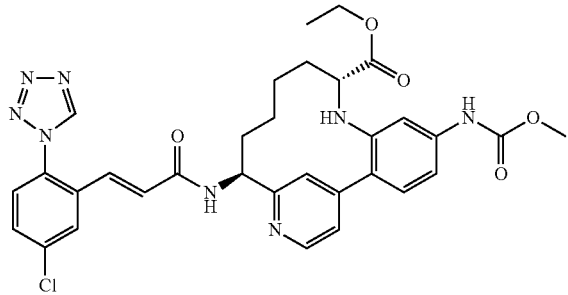 [SMILES: CCOC(=O)[C@H]1CCCC[C@H](NC(=O)/C=C/c2cc(Cl)ccc2-n2cnnn2)c2cc(ccn2)-c2ccc(NC(=O)OC)cc2N1]

II-17A. 2-{2-[2-((S)-1-tert-Butoxycarbonylamino-but-3-enyl)-pyridin-4-yl]-5-methoxycarbonylamino-phenylamino}-pent-4-enoic acid ethyl ester: Compound II-17A was prepared following the procedure described in I-67A, by replacing 10C with II-11C. MS (ESI) m/z: 539 (M+H)$^+$.

II-17B. (E)-(9R,14S)-14-tert-Butoxycarbonylamino-5-methoxycarbonylamino-8,16-diaza-tricyclo[13.3.1.0$^{2,7}$] nonadeca-1(19),2(7),3,5,11,15,17-heptaene-9-carboxylic acid ethyl ester (diastereomer A) and II-17C. (E)-(9 S,14 S)-14-tert-Butoxycarbonylamino-5-methoxycarbonylamino-8,16-diaza-tricyclo[13.3.1.0$^{2,7}$]nonadeca-1(19),2 (7),3,5,11,15,17-heptaene-9-carboxylic acid ethyl ester (diastereomer B): Compounds II-17B (diastereomer A) and II-17C (diastereomer B) were prepared following the procedure described in 88G, by replacing 88F with II-17A. The diastereomers were separated by chiral HPLC (OJ column, 20:20:60 EtOH:MeOH:heptane). For II-17B (diastereomer A): MS (ESI) m/z: 512, 511 (M+H)$^+$. $^1$H NMR (MeOH-d4, 400 MHz): δ ppm 8.56 (d, 1H, J=5), 7.62 (s, 1H), 7.24 (d, 1H, J=5), 7.20 (d, 1H, J=8), 7.03 (s, 1H), 6.98 (d, 1H, J=9), 5.44 (m, 1H), 5.07 (m, 1H), 4.71 (m, 1H), 4.12 (q, 2H, J=7), 3.73 (s, 3H), 3.31 (m, 3H), 2.72 (m, 1H), 2.35 (m, 4H), 1.44 (s, 9H), 1.20 (m, 3H). For II-17C (diastereomer B): MS (ESI) m/z: 512, 511 (M+H)$^+$; $^1$H NMR (MeOH-d4, 400 MHz): δ ppm 8.56 (d, 1H, J=5), 7.49 (s, 1H), 7.21 (m, 2H), 6.99 (s, 1H), 6.94 (d, 1H, J=9), 5.66 (m, 1H), 5.03 (m, 1H), 4.12 (m, 3H), 3.72 (s, 3H), 3.31 (m, 3H), 2.69 (m, 1H), 2.54 (m, 1H), 2.37 (m, 2H), 1.44 (s, 9H), 1.14 (t, 3H, J=7).

II-17D. (9R,14S)-14-tert-Butoxycarbonylamino-5-methoxycarbonylamino-8,16-diaza-tricyclo[13.3.1.0$^{2,7}$] nonadeca-1(19),2(7),3,5,15,17-hexaene-9-carboxylic acid ethyl ester: Compound II-17D was prepared following the procedure described in II-12A, by replacing II-11F with II-17B (diastereomer A). MS (ESI) m/z: 514, 513 (M+H)$^+$.

II-17E. (9R,14S)-14-Amino-5-methoxycarbonylamino-8, 16-diaza-tricyclo[13.3.1.0$^{2,7}$]nonadeca-1(19),2(7),3,5,5,17-hexaene-9-carboxylic acid ethyl ester, 3HCl salt: A mixture of II-17D (175 mg, 0.341 mmol) and hydrogen chloride (1.71 ml, 6.83 mmol) (4 M in dioxane) and ethyl acetate (2 mL) was stirred at room temperature for 1 h. Solvent was removed in vacuo to give a light tan yellow solid (130 mg): MS (ESI) m/z: 414, 413 (M+H)$^+$. The product was taken on without further purification.

II-17F. Example II-17 was prepared following the procedure described in 1G, by replacing 1F with II-17E. MS (ESI) m/z: 647, 645 (M+H)$^+$. $^1$H NMR (MeOH-d4, 400 MHz): 9.49 (s, 1H), 8.79 (s, 1H), 8.64 (d, 1H, J=9), 7.97 (d, 1H, J=2), 7.77 (d, 1H, J=9), 7.67 (dd, 1H, J=9, 2), 7.57 (d, 1H, J=9), 7.47 (d, 1H, J=8), 7.38 (s, 1H), 7.23 (dd, 1H, J=9, 2), 7.11 (d, 1H, J=15), 6.80 (d, 1H, J=15), 5.15 (m, 1H), 4.00 (m, 3H), 3.75 (s, 3H), 3.31 (m, 1H), 3.08 (d, 1H, J=9), 2.20 (m, 2H), 1.94 (m, 2H), 1.77 (m, 2H), 1.50 (m, 2H), 1.39 (m, 1H), 1.12 (t, 3H, J=7), 0.42 (m, 2H).

TABLE II-2

Examples II-12 to II-22

| Ex. # | R | R³ | LCMS [M + H]⁺ | HPLC RT (min) |
|---|---|---|---|---|
| II-12 | 1-(4-chloro-2-((E)-but-2-en-1-yl)phenyl)-1H-tetrazole | CF₃ (From II-11F) | 641.2 | 6.9 |
| II-13 | trans-4-(aminomethyl)cyclohexyl-methyl | CF₃ (from II-11F) 548.4 | 548.4 | 4.8 |
| II-14 | 4-carbamimidoylphenyl-methyl | CF₃ (from II-11F) | 555.4 | 4.8 |
| II-15 | 4-carbamimidoylphenyl-methyl | CF₃ (from II-11G) | 555.3 | 3.9 |
| II-16 | 1-(4-chloro-2-((E)-but-2-en-1-yl)phenyl)-1H-tetrazole | H | 573.3 | 6.2 |

TABLE II-2-continued

Examples II-12 to II-22

| Ex. # | R | $R^3$ | LCMS [M + H]$^+$ | HPLC RT (min) |
|---|---|---|---|---|
| II-17 | 1-(4-chloro-2-(prop-1-en-1-yl)phenyl)-1H-tetrazol-5-yl | ⸺CO$_2$Et | 645.4 | 6.5 |
| II-18 | 1-(4-chloro-2-(prop-1-en-1-yl)phenyl)-1H-tetrazol-5-yl (regioisomer) | ⸺CO$_2$Et | 645.4 | 6.1 |
| II-19 | 1-(4-chloro-2-(prop-1-en-1-yl)phenyl)-1H-tetrazol-5-yl | ⸺CO$_2$H | 617.4 | 5.7 |
| II-20 | 1-(4-chloro-3-fluoro-2-(prop-1-en-1-yl)phenyl)ethan-1-one | ⸺CO$_2$Et | 637.5 | 7.0 |
| II-21 | 2-cyano-5-chloro-(prop-1-en-1-yl)phenyl | ⸺CO$_2$Et | 602.5 | 7.1 |

TABLE II-2-continued

Examples II-12 to II-22

| Ex. # | R | R³ | LCMS [M + H]⁺ | HPLC RT (min) |
|---|---|---|---|---|
| II-22 | (5-chloro-2-tetrazol-1-yl-phenyl with propenyl, F substituent) | CO₂Et (wedge) | 663.4 | 6.9 |

Example II-24

(R)-14-[(E)-3-(5-Chloro-2-tetrazol-1-yl-phenyl)-acryloylamino]-5-methoxycarbonylamino-18-oxo-8,16,17-triaza-tricyclo[13.3.1.02,7]nonadeca-1(19),2(7),3,5,15-pentaene-9-carboxylic Acid ethyl ester

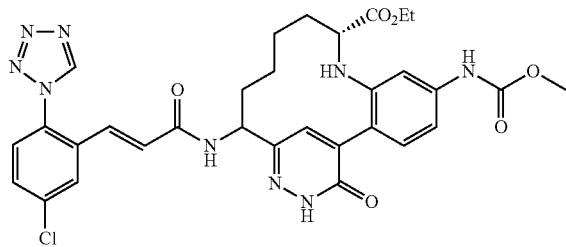 [SMILES: CCOC(=O)[C@H]1CCCCC(NC(=O)/C=C/c2cc(Cl)ccc2-n2cnnn2)c2cc(c(=O)[nH]n2)-c2ccc(NC(=O)OC)cc2N1]

II-24A. ((S)-3-tert-Butoxycarbonylamino-2-oxo-hex-5-enyl)-phosphonic acid dimethyl ester: To a solution of dimethyl methylphosphonate (6.99 ml, 65.4 mmol) in THF (43.6 ml) at −78° C. was added BuLi (40.9 ml, 65.4 mmol) slowly. After addition, the reaction was stirred for 40 min and then a solution of (S)-methyl 2-(tert-butoxy carbonylamino)pent-4-enoate (3 g, 13.08 mmol) in THF (10 mL) was added drop-wise. Stirring was continued for another 40 min at −78° C. The reaction was quenched by adding water, then EtOAc. It was washed with 1M HCl, sat NaHCO₃ and brine. The organic phase was dried over MgSO₄, filtered and concentrated to give a clear oil. Purification by normal phase chromatography gave II-24A as a colorless oil (4.19 g, 99%). MS (ESI) m/z: 344.0 (M+Na)⁺.

II-24B. (4-Methoxycarbonylamino-2-nitro-phenyl)-oxo-acetic acid: To a solution of methyl 4-acetyl-3-nitrophenyl-carbamate (10.5 g, 44.1 mmol) in pyridine (44.1 ml) was added selenium dioxide (7.34 g, 66.1 mmol) in portions. The reaction was stirred under argon at 60° C. overnight. Solvent was evaporated and pumped for several hours to remove most pyridine. 1.0N HCl (60 mL) was added and the mixture was filtered, rinsed with 1N HCl. The solid was put in a vacuum-oven at 45° C. overnight. MeOH (200 mL) was added, filtered, the filtrate was concentrated to give 13.8 g of II-24B as a brownish foam. MS (ESI) m/z: 269.0, 223.0 (M+NH)⁺.

II-24C. (4-Methoxycarbonylamino-2-nitro-phenyl)-oxo-acetic acid methyl ester: To a red oil of II-24B (5 g, 16.03 mmol) in DCM (57.3 ml) at 0° C. was added TEA (3.13 ml, 22.45 mmol). The mixture was sonicated to dissolve into a red-colored solution. Methyl carbonochloridate (1.739 ml, 22.45 mmol) was added dropwise at 0° C. After 5 min, the reaction mixture was diluted with CH₂Cl₂ (100 mL), washed with 1M HCl, sat. NaHCO₃ and brine. The organic phase was dried over MgSO₄, filtered and concentrated to give a red colored solid. Triturated with DCM and EtOAc, filtered. The solid was washed with DCM/Hex and dried in vacuum-oven at 45° C. to give 2.79 g (62%) of II-24C as a light brownish solid. MS (ESI) m/z: 223.0 (fragmentation).

II-24D. {4-[6-((S)-1-tert-Butoxycarbonylamino-but-3-enyl)-3-oxo-2,3-dihydro-pyridazin-4-yl]-3-nitro-phenyl}-carbamic acid methyl ester: To a clear solution of II-24A (911 mg, 2.84 mmol) in EtOH (30 ml) at rt were added potassium carbonate (588 mg, 4.25 mmol). The reaction mixture was stirred for 2 hr. The solvent was removed by rot-vap removed solvent and vacuum pump. THF (Volume: 30.0 ml) was added, followed by addition of II-24C. After 3 hrs, hydrazine (0.356 ml, 11.34 mmol) was added and the rxn was stirred at rt for 3 days. The reaction was diluted with EtOAc, washed with 1 N HCl, brine, dried over MgSO₄, filtered and concentrated. Purification by normal phase chromatography gave II-24D as a yellow foam (380 mg, 29%). MS (ESI) m/z: 460.2 (M+NH)⁺.

II-24E. {4-[6-((S)-1-tert-Butoxycarbonylamino-but-3-enyl)-3-oxo-2,3-dihydro-pyridazin-4-yl]-3-amino-phenyl}-carbamic acid methyl ester: Example II-24E was prepared following the procedures described in 15B by replacing 15A with II-24D.

II-24F. Example II-24 was prepared following the procedures described in I-67A, by replacing 10C with II-24E; followed by procedures described in steps II-17B/II-17C; II-17D; II-17E; and II-17F. $^1$H NMR (500 MHz, CD$_3$OD) d 9.52 (s, 1H), 8.30 (s, 1H), 7.99 (d, J=2.2 Hz, 1H), 7.78-7.65 (m, 1H), 7.58 (d, J=8.5 Hz, 1H), 7.36 (d, J=1.9 Hz, 1H), 7.18-7.01 (m, 1H), 6.80 (d, J=15.4 Hz, 1H), 5.03 (dd, J=11.4, 5.9 Hz, 1H), 4.14-3.92 (m, 2H), 3.83-3.72 (m, 2H), 3.51-3.39 (m, 1H), 2.21-2.01 (m, 1H), 1.63-1.40 (m, 2H), 1.15 (t, J=7.2 Hz, 2H), 0.96-0.81 (m, 1H). MS (ESI) m/z: 662.2 (M+H)$^+$. Analytical HPLC: RT=9.81 min. (Method D).

Example II-26

(9R,14S)-14-[(E)-3-(5-Chloro-2-tetrazol-1-yl-phenyl)-acryloylamino]-5-methoxycarbonylamino-8,17-diaza-tricyclo[13.3.1.0$^{2,7}$]nonadeca-1(19),2(7),3,5,15,17-hexaene-9-carboxylic Acid ethyl ester, diastereomer A, 2 TFA Salt

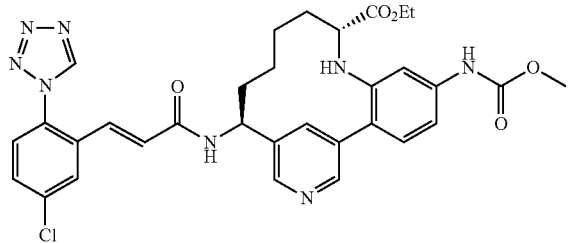 [SMILES: CCOC(=O)[C@H]1CCCC[C@H](NC(=O)/C=C/c2cc(Cl)ccc2-n2cnnn2)c2cncc(c2)-c2ccc(NC(=O)OC)cc2N1]

II-26A. (R,E)-N-((5-Bromopyridin-3-yl)methylene)-2-methylpropane-2-sulfinamide: Example II-26A was prepared following the procedures described in 88A, by replacing 4-chloropicolinaldehyde with 5-bromonicotinaldehyde using (R)-2-methylpropane-2-sulfinamide. MS (ESI) m/z: 291.2 (M+H)$^+$.

II-26B. (R)—N—((S)-1-(5-Bromopyridin-3-yl)but-3-enyl)-2-methylpropane-2-sulfinamide: Reference: Lin (Organic Letters, 10:1259 (2008)). To a sat. aq. solution of sodium bromide (600 ml) was added powdered II-26A (8.3 g, 28.7 mmol) and indium (13.18 g, 115 mmol). Ally bromide (13.66 g, 115 mmol) was added via syringe pump, and the resulting light orange suspension was allowed to stir at rt overnight, generating a beige foam. The reaction was quenched with saturated aqueous NaHCO$_3$ and extracted with EtOAc. The organic layer was dried over anhydrous MgSO$_4$, filtered, concentrated to give a fluffy orange solid weighing 8 g. Purification by normal phase chromatography gave 4.25 g of II-26B as a beige solid. MS (ESI) m/z: 333.0 (M+H)$^+$.

II-26C. Example II-26 was prepared following the procedure described in 88D, by replacing 88C with II-26B; followed by steps as described in 88C; 88F; I-67A; 88G; 2G; II-17E; and 1G. $^1$H NMR (500 MHz, CD$_3$OD) δ ppm 9.49 (1H, s), 9.36 (1H, d, J=13.5 Hz), 8.76 (1H, d, J=5.2 Hz), 8.54 (1H, br. s.), 7.97 (1H, d, J=2.2 Hz), 7.66 (1H, dd, J=8.5, 2.2 Hz), 7.57 (1H, d, J=8.5 Hz), 7.41 (1H, d, J=8.5 Hz), 7.35 (1H, s), 7.23 (1H, d, J=8.3 Hz), 7.11 (1H, d, J=15.7 Hz), 6.75 (1H, d, J=15.7 Hz), 5.11-5.19 (1H, m), 3.94-4.06 (2H, m), 3.75 (3H, s), 3.12 (1H, d, J=11.6 Hz), 2.14-2.22 (1H, m), 1.69-1.95 (1H, m), 1.36-1.51 (3H, m), 1.11 (3H, t, J=7.2 Hz), 0.57 (1H, d, J=11.6 Hz) MS (ESI) m/z: 645.1 (M+H)$^+$. Analytical HPLC: RT=6.82 min. (Method D).

Example II-28

(9R,14S)-14-[(E)-3-(5-Chloro-2-tetrazol-1-yl-phenyl)-acryloylamino]-5-methoxycarbonylamino-17-oxy-8,17-diaza-tricyclo[13.3.1.0$^{2,7}$]nonadeca-1(19),2,4,6,15,17-hexaene-9-carboxylic Acid ethyl ester, diastereomer A, TFA Salt

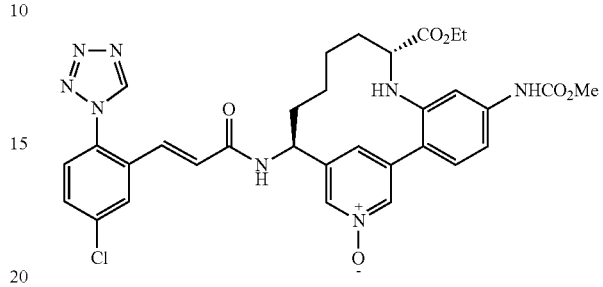

II-28A. Example II-26 (15 mg, 0.017 mmol) was diluted with MeOH and filtered through a cartridge of solid sodium bicarbonate to form the free base. The filtrate was concentrated and to the resulting solid was added DCM (1 mL) and mCPBA (5.78 mg, 0.026 mmol). The solution was stirred at rt for 1 h. The reaction mixture was washed with sat. Sodium sulfite, sat. aq. NaHCO$_3$, and brine, then dried over MgSO$_4$. Filtered and concentrated. Purification by reverse phase chromatography gave II-28 (8.7 mg, 65%) as a pale yellow solid. $^1$H NMR (500 MHz, CD$_3$OD) δ ppm 9.49 (1H, s), 8.53 (1H, s), 8.37 (1H, s), 8.18 (1H, s), 7.98 (1H, d, J=2.2 Hz), 7.66 (1H, dd, J=8.4, 2.3 Hz), 7.56 (1H, d, J=8.5 Hz), 7.27-7.39 (2H, m), 7.05-7.22 (2H, m), 6.73 (1H, d, J=15.4 Hz), 5.01-5.12 (1H, m), 3.88-4.07 (2H, m), 3.74 (3H, s), 3.18 (1H, dd, J=11.8, 1.4 Hz), 2.05-2.19 (1H, m), 1.79-1.94 (1H, m), 1.67-1.79 (2H, m), 1.35-1.53 (3H, m), 1.10 (3H, t, J=7.0 Hz), 0.56-0.72 (1H, m) MS (ESI) m/z: 661.3 (M+H)$^+$. Analytical HPLC: RT=7.91 min. (Method D).

Example II-29

(9R,14S)-14-[(E)-3-(5-Chloro-2-tetrazol-1-yl-phenyl)-acryloylamino]-5-methoxycarbonylamino-16-oxy-8,16-diaza-tricyclo[13.3.1.0$^{2,7}$]nonadeca-1(19),2,4,6,15,17-hexaene-9-carboxylic Acid ethyl ester, trifluoroacetic Acid Salt

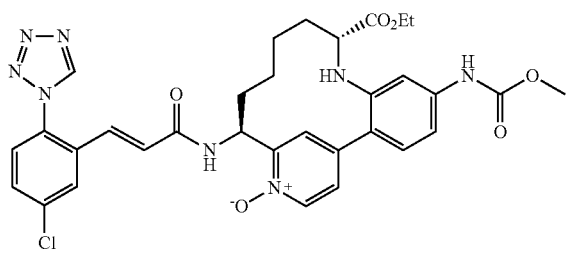

II-29A. 2-(tert-Butoxycarbonyl-{2-[2-((S)-1-tert-butoxycarbonylamino-but-3-enyl)-pyridin-4-yl]-5-methoxycarbonylamino-phenyl}-amino)-pent-4-enoic acid ethyl ester, dihydrochloride salt: To a solution of Example II-17A (125 mg, 0.232 mmol) in dichloromethane (2.5 mL) was added DMAP (28.4 mg, 0.232 mmol) and Boc$_2$O (0.119 mL, 0.511 mmol) followed by DIEA (0.101 mL, 0.580 mmol). The reaction mixture was stirred at rt for 1.5 h. The reaction mixture is concentrated in vacuo, dissolved with ethyl acetate and washed with brine. The crude product is then purified using normal phase chromatography. MS (ESI) m/z: 639.

II-29B. (E)-(S)-14-tert-Butoxycarbonylamino-5-methoxycarbonylamino-8,16-diaza-tricyclo[13.3.1.0$^{2,7}$]nonadeca-1(19),2,4,6,11,15,17-heptaene-8,9-dicarboxylic acid 8-tert-butyl ester 9-ethyl ester: This compound was prepared by the following the procedure described for 88G, replacing 88F with II-29A. The compound as a mixture of diastereomers was purified by reverse phase chromatography. MS (ESI) m/z: 611.

II-29C. (9R,14S)-14-tert-Butoxycarbonylamino-5-methoxycarbonylamino-8,16-diaza-tricyclo[13.3.1.0$^{2,7}$]nonadeca-1(19),2,4,6,15,17-hexaene-8,9-dicarboxylic acid 8-tert-butyl ester 9-ethyl ester: This Example was prepared by the procedure used in II-12A, by replacing II-11F with II-29B. The diastereomers of Example II-29C were separated by reverse phase chromatography. MS (ESI) m/z: 613 for both diastereomer 1 (shorter retention time) and diastereomer 2 (longer retention time); each is a mono-trifluoroacetate salt.

II-29D. (9R,14S)-14-tert-Butoxycarbonylamino-5-methoxycarbonylamino-16-oxy-8,16-diaza-tricyclo[13.3.1.0$^{2,7}$]nonadeca-1(19),2,4,6,15,17-hexaene-8,9-dicarboxylic acid 8-tert-butyl ester 9-ethyl ester: To a solution of Example II-29C, diastereomer 2 (21 mg, 0.034 mmol) in ethyl acetate was added a saturated solution of sodium carbonate in water. After mixing, the layers were separated and the organic layer was dried over magnesium sulfate. Filtration and removal of solvent in vacuo gave the free base. This was then diluted with DCM (0.5 mL). m-Chloroperbenzoic acid (mCPBA) (11.52 mg, 0.051 mmol) was added. The reaction mixture was stirred at RT. The reaction mixture is diluted with ethyl acetate and washed with a saturated Na$_2$SO$_3$ solution, saturated NaHCO$_3$ solution, then brine. The organic layer was dried over Na$_2$SO$_4$, filtered and concentrated in vacuo. The crude product was used without any further purification. MS (ESI) m/z: 629.

II-29E. (9R,14S)-14-Amino-5-methoxycarbonylamino-16-oxy-8,16-diaza-tricyclo[13.3.1.0$^{2,7}$]nonadeca-1(19),2,4,6,15,17-hexaene-9-carboxylic acid ethyl ester: Example II-29D was mixed with a solution of HCl in dioxane and the reaction mixture was stirred at rt for 1 h. The reaction mixture was concentrated in vacuo and used as the di-hydrochloride salt for the next step without any further purification. MS (ESI) m/z: 429.

Example II-29. Following the procedure used to make Example 1G, (E)-2,5-dioxopyrrolidin-1-yl 3-(5-chloro-2-(1H-tetrazol-1-yl)phenyl)acrylate (18 mg, 0.052 mmol) and II-29E (26 mg, 0.052 mmol) were dissolved in DMF (0.5 mL), and then DIPEA (0.090 mL, 0.518 mmol) was added. The reaction mixture was stirred at room temperature under argon for 4 h. The reaction mixture is diluted with ethyl acetate (10 mL) and washed with 10% LiCl solution. Drying over Na$_2$SO$_4$, filtration and removal of solvent in vacuo gave the crude product, which was purified by reverse phase chromatography. Solvent was removed in vacuo by lyophilization to give a solid (wt=9 mg, 21% yield): MS (ESI) m/z: 660.4; $^1$H NMR (500MHz, CD$_3$CN) δ 9.12 (s, 1H), 8.67 (d, J=6.0 Hz, 1H), 8.41-8.23 (m, 2H), 7.96-7.80 (m, 2H), 7.64-7.44 (m, 3H), 7.32-7.21 (m, 2H), 7.11 (d, J=7.7 Hz, 1H), 6.97 (d, J=15.4 Hz, 1H), 6.75 (d, J=15.4 Hz, 1H), 5.50-5.37 (m, 1H), 4.01-3.83 (m, 3H), 3.76-3.69 (m, 4H), 2.95 (s, 1H), 2.32 (br. s., 1H), 1.95 (m, 1H) 1.92-1.72 (m, 1H), 1.61 (br. s., 1H), 1.42 (br. s., 3H), 1.15-0.93 (m, 3H).

TABLE II-3

Examples II-23 to II-29

| Ex. # | x | R7 | LCMS [M + H]$^+$ | HPLC RT (min.) |
|---|---|---|---|---|
| II-23 | 4-methyl-6-pyridazinone | CO$_2$Et (diastereomer mixture) | 662.2 | 9.5 |
| II-24 | 4-methyl-6-pyridazinone | CO$_2$Et (diastereomer mixture) | 662.2 | 9.8 |
| II-25 | 3,5-pyridyl | CO$_2$Et | 645.1 | 6.7 |

TABLE II-3-continued

Examples II-23 to II-29

[Structure: chiral amide macrocycle with 1-tetrazolyl-4-chlorophenyl cinnamoyl group, NHCO₂Me substituent, and X ring with R₇ substituent]

| Ex. # | x | R7 | LCMS [M + H]⁺ | HPLC RT (min.) |
|---|---|---|---|---|
| II-26 | 3,5-dimethylpyridine | ⋯CO₂Et | 645.1 | 6.8 |
| II-27 | 3,5-dimethylpyridine N-oxide | ▲CO₂Et | 661.1 | 8.8 |
| II-28 | 3,5-dimethylpyridine N-oxide | ⋯CO₂Et | 661.3 | 7.9 |
| II-29 | 2,4-dimethylpyridine N-oxide | ⋯CO₂Et | 660.4 | 7.9 |

TABLE II-4

Examples II-30 to II-38

[Structure: chiral amide macrocycle with 1-tetrazolyl-4-chlorophenyl cinnamoyl group, pyridine ring, NHCO₂Me substituent, and R₇ substituent]

| Ex. # | R7 | LCMS [M + H]⁺ | HPLC RT (min.) |
|---|---|---|---|
| II-30 | ▲CO₂H | 617.1 | 6.9 |
| II-31 | ⋯CO₂Me | 631.3 | 7.6 |

TABLE II-4-continued

Examples II-30 to II-38

| Ex. # | R7 | LCMS [M + H]+ | HPLC RT (min.) |
| --- | --- | --- | --- |
| II-32 | azetidine-C(O)- | 656.3 | 7.0 |
| II-33 | morpholine-C(O)- | 686.2 | 6.4 |
| II-34 | pyrrolidine-C(O)- | 670.2 | 6.5 |
| II-35 | 4-methylpiperazine-C(O)- | 699.2 | 6.0 |
| II-36 | MeN(CH2CH2NMe2)-C(O)- | 701.5 | 5.0 |
| II-37 | 2-pyridylmethyl-NH-C(O)- | 707.2 | 5.8 |

TABLE II-4-continued

Examples II-30 to II-38

| Ex. # | R7 | LCMS [M + H]+ | HPLC RT (min.) |
|---|---|---|---|
| II-38 | (Me-N(Me)-CH2CH2-O-C(=O)-) | 688.1 | 9.9 |

Example II-39

(9S,14S)-14-[(E)-3-(5-Chloro-2-tetrazol-1-yl-phenyl)-acryloylamino]-5-(2-methoxy-ethoxycarbonylamino)-8,16-diaza-tricyclo[13.3.1.0²,⁷]nonadeca-1(19),2,4,6,15,17-hexaene-9-carboxylic Acid ethyl ester, bis-trifluoroacetic Acid Salt

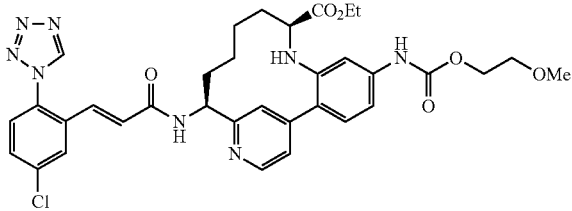 [SMILES: CCOC(=O)[C@@H]1CCCC[C@H](NC(=O)/C=C/c2cc(Cl)ccc2-n2cnnn2)c2cc(ccn2)-c2ccc(NC(=O)OCCOC)cc2N1]

The synthesis of Example II-39 followed the general procedures described for II-17. Example II-39AE (described below) was substituted for compound II-17A. The diastereomers corresponding to Example II-17B, diastereomers A and B, were not separated. They were hydrogenated and then separated by HPLC to give diastereomers corresponding to compound II-17C and its diastereomer. The diastereomers were then separately converted to Examples II-39 and II-40 (described below). The following data were collected for Example II-39: MS (ESI) m/z 689.3, 691.3; ¹H NMR (CD₃OD, 400 MHz): δ 9.37 (s, 1H), 8.55 (d, 1H, J=6), 8.28 (s, 1H), 7.87 (d, 1H, J=2), 7.55 (dd, 1H, J=8, 2), 7.46 (d, 1H, J=8), 7.27 (d, 1H, J=8), 7.24 (d, 1H, J=2), 6.99 (d, 1H, J=16), 6.74 (d, 1H, J=16), 5.07 (m, 1H), 4.17 (t, 2H, J=6), 3.94 (m, 2H), 3.55 (t, 2H, J=6), 3.29 (s, 3H), 3.20 (m, 5H), 3.12 (m, 2H), 2.17 (m, 1H), 1.89 (m, 1H), 1.60 (m, 2H), 1.40 (m, 4H), 1.03 (t, 3H, J=7), 0.58 (m, 1H).

II-39AA. ((S)-1-{4-[4-Nitro-2-(2,2,2-trifluoro-acetylamino)-phenyl]-pyridin-2-yl}-but-3-enyl)-carbamic acid tert-butyl ester: To a solution of Example II-11A (0.40 g, 1.041 mmol) in THF (Volume: 9 mL) at −78° C. was added Et₃N (0.435 mL, 3.12 mmol), followed by (CF₃CO)₂O (0.154 mL, 1.093 mmol). The reaction mixture was warmed gradually to rt and stirred for 20.75 h. The reaction mixture was concentrated in vacuo. The residue was treated with water (10 mL) and extracted three times with EtOAc. The combined organics were washed once with 1 N HCl (3 mL), then dried over MgSO₄. Filtration, removal of solvent in vacuo and purification of the residue by normal phase chromatography provided an oil (Wt=239 mg): MS (ESI) m/z: 481.2.

II-39AB. ((S)-1-{4-[4-Amino-2-(2,2,2-trifluoro-acetylamino)-phenyl]-pyridin-2-yl}-but-3-enyl)-carbamic acid tert-butyl ester: To a clear yellow solution of II-39AA (0.269 g, 0.560 mmol) in MeOH (5.60 ml) was added sequentially zinc (0.366 g, 5.60 mmol) and NH₄Cl (0.300 g, 5.60 mmol). The resulting suspension was stirred vigorously for 6.5 h. The reaction mixture was filtered through a 0.45 micron GMF eluting with methanol to give a clear, yellow filtrate. Concentration gave a dark yellow residue. The residue was partitioned three times between EtOAc and 1 M HCl (10 mL) and the layers were separated. The combined aqueous layers were basified with a 1 N NaOH solution (pH ~8 by paper) and then extracted with EtOAc (3×). The combined organic layers were washed with brine, dried over MgSO₄, filtered and concentrated to give an oil (Wt=200 mg): MS (ESI) m/z=451.3.

II-39AC. [4-[2-((S)-1-tert-Butoxycarbonylamino-but-3-enyl)-pyridin-4-yl]-3-(2,2,2-trifluoro-acetylamino)-phenyl]-carbamic acid 2-methoxy-ethyl ester: A solution of II-39AB (200 mg, 0.444 mmol) and pyridine (0.180 mL, 2.220 mmol) in dichloromethane (4 mL) was cooled to 0° C. under argon with stirring. Then 2-methoxyethyl carbonochloridate (0.103 mL, 0.888 mmol) was added dropwise. The reaction mixture was stirred for 50 min at 0° C. for 2 h. Added 50 μL of the chloroformate reagent and stirred at room temperature for 17.75 h. The reaction mixture was diluted with EtOAc and washed once with 2.2 mL 1 N HCl, then twice with saturated Na₂CO₃ solution. The organic was dried over MgSO₄ and filtered. Solvent was removed in vacuo to give clear pale yellow oil (Wt=160 mg). MS (ESI) m/z=553.3. ¹H NMR (CD₃OD, 500 MHz): δ 11.94 (s, 1H), 10.90 (s, 1H), 9.32 (d, 1H, J=5), 8.44 (s, 1H), 8.36 (dd, 1H, J=10, 2), 8.20 (d, 1H, J=10), 8.17 (s, 1H), 8.01 (m, 1H), 6.55 (m, 1H), 5.87 (d, 1H, J=17), 5.81 (d, 1H, J=9), 5.48 (M, 1H), 5.15 (m, 1H), 5.06 (m, 2H), 4.67 (m, 2H), 3.31 (s, 3H), 3.23 (m, 1H).

II-39AD. {3-Amino-4-[2-((S)-1-tert-butoxycarbonylamino-but-3-enyl)-pyridin-4-yl]-phenyl}-carbamic acid 2-methoxy-ethyl ester: A mixture of Example II-39AC (160 mg, 0.290 mmol), a 1M solution of LiOH in water (0.290 mL, 0.290 mmol) and THF 0.5 mL) was stirred for 20 h. Added 0.2 mL 1M LiOH solution and continued stirring for 24 h. A 1 N HCl solution (0.5 mL) was added and the mixture was extracted three times with EtOAc. The organic layers were washed with a saturated Na₂CO₃ solution, then dried over MgSO₄ and filtered. Solvent was removed in vacuo. The residue was purified by normal phase chromatography to provide a yellow oil (Wt=103 mg): MS (ESI) m/z=457 (ES+) desired product.

II-39AE. 2-[2-[2-((S)-1-tert-Butoxycarbonylamino-but-3-enyl)-pyridin-4-yl]-5-(2-methoxy-ethoxycarbonylamino)-phenylamino]-pent-4-enoic acid ethyl ester: The synthesis of Example II-39AE followed the general procedure described for II-17A where Example II-39AD was substituted for Example II-11C. The crude product was purified by normal phase chromatography to provide a yellow oil: MS (ESI) m/z=583.4 (ES+) desired product.

Example II-40

9R,14S)-14-[(E)-3-(5-Chloro-2-tetrazol-1-yl-phenyl)-acryloylamin]-5-(2-methoxy-ethoxycarbonylamino)-8,16-diaza-tricyclo[13.3.1.0²,⁷]nonadeca-1(19),2,4,6,15,17-hexaene-9-carboxylic Acid ethyl ester, bis-trifluoroacetic Acid Salt

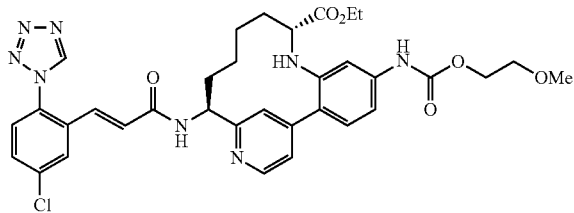 [SMILES: CCOC(=O)[C@H]1CCCC[C@H](NC(=O)/C=C/c2cc(Cl)ccc2-n2cnnn2)c2cc(ccn2)-c2ccc(NC(=O)OCCOC)cc2N1]

The synthesis of Example II-40 followed the general procedures described for II-17. Example II-39AE (described above) was substituted for Example II-17A. The diastereomers corresponding to Example II-17B, diastereomers A and B, were not separated. They were hydrogenated and then separated by normal phase chromatography to give diastereomers corresponding to Example II-17C and its diastereomer. The diastereomers were then separately converted to Examples II-39 and II-40 (described below). The following data were collected for Example II-40: MS (ESI) m/z 689.3, 691.3; ¹H NMR (CD₃OD, 400 MHz): δ 9.49 (s, 1H), 8.71 (s, 1H), 8.64 (d, 1H, J=6), 7.99 (d, 1H, J=2), 7.72 (d, 1H, J=3), 7.67 (dd, 1H, J=8, 2), 7.57 (d, 1H, J=9), 7.46 (d, 1H, J=9), 7.38 (d, 1H, J=2), 7.22 (dd, 1H, J=9, 2), 7.11 (d, 1H, J=16), 6.81 (d, 1H, J=16), 5.15 (dd, 1H, J=11, 5), 4.28 (t, 2H, J=5), 4.00 (m, 2H), 3.66 (t, 2H, J=4), 3.40 (s, 3H), 3.30 (m, 4H), 3.08 (d, 1H, J=11), 2.19 (m, 1H), 1.90 (m, 2H), 1.76 (m, 1H), 1.49 (m, 2H), 1.38 (m, 1H), 1.09 (t, 3H, J=7), 0.37 (m, 1H).

Example II-41

9R,14S)-14-[(E)-3-(5-Chloro-2-tetrazol-1-yl-phenyl)-acryloylamino)-5-(2-methoxy-ethoxycarbonylamino)-16-oxy-8,16-diaza-tricyclo[13.3.1.0²,⁷]nonadeca-1(19),2,4,6,15,17-hexaene-9-carboxylic Acid ethyl ester, trifluoroacetic Acid Salt

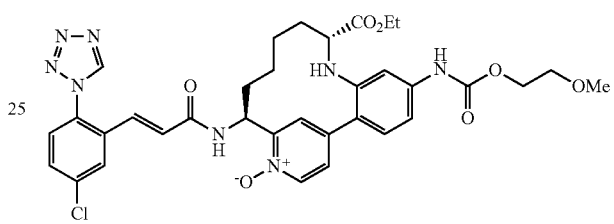

This Example was prepared following the general procedures described for Example II-29.

II-41A (described below) was substituted for Example II-29A. The following data were collected for Example II-41. MS (ESI) m/z=705.3, 707.3. ¹H NMR (CD₃CN, 500 MHz): δ 9.02 (s, 1H), 8.38 (d, 1H, J=8), 8.17 (d, 1H, J=6), 7.85 (d, 1H, J=3), 7.75 (s, 1H), 7.51 (dd, 1H, J=11, 2), 7.41 (d, 1H, J=8), 7.26 (d, 1H, J=3), 7.19 (d, 1H, J=8), 6.92 (d, 1H, J=16), 6.66 (d, 1H, J=16), 5.53 (m, 1H), 4.15 (t, 2H, J=6), 3.86 (m, 2H), 3.49 (t, 2H, J=6), 3.25 (s, 3H), 2.97 (d, 1H, J=12), 2.38 (m, 5H), 1.74 (m, 2H), 1.54 (m, 1H), 1.27 (m, 4H), 0.97 (t, 3H, J=7).

II-41A. 2-{tert-Butoxycarbonyl-[2-[2-((S)-1-tert-butoxycarbonylamino-but-3-enyl)-pyridin-4-yl]-5-(2-methoxy-ethoxycarbonylamino)-phenyl]-amino}-pent-4-enoic acid ethyl ester: To a solution of Example II-39AE (83 mg, 0.142 mmol) in DCM (1.5 mL) was added DMAP (17.40 mg, 0.142 mmol) and Boc₂O (68.4 mg, 0.313 mmol) followed by DIEA (0.062 mL, 0.356 mmol). The reaction mixture was stirred at rt for 3 h. The reaction mixture was concentrated in vacuo, dissolved with EtOAc and washed with brine. The crude product was then purified by normal phase chromatography to give an oil (Wt=98 mg): MS (ESI) m/z=681.3.

Compounds II-47 (diastereomer A) and II-48 (diastereomer B) were prepared following the procedures described in amide coupling step 88E, by replacing 88D with II-11C and by replacing pent-4-enoic acid with 2-methylbut-3-enoic acid; followed by ring-closing metathesis step 88G; hydrogenation step 2G where the diastereomers were separated by chiral prep hplc [Chiralcel OD, eluting with 80% isopropanol/heptane] to give diastereomer A and diastereomer B; Boc-deprotection step 3C; and 1G.

TABLE II-5
Examples II-39 to II-72
| Ex. # | Structure | LCMS [M + H]+ | HPLC RT (min.) |
|---|---|---|---|
| II-39 | 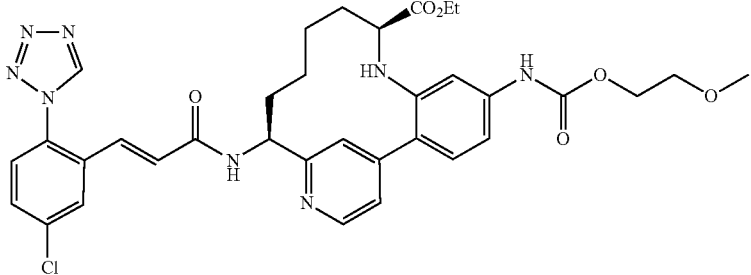 [SMILES: CCOC(=O)[C@@H]1CCCC[C@H](NC(=O)/C=C/c2cc(Cl)ccc2-n2cnnn2)c2cc(ccn2)-c2ccc(NC(=O)OCCOC)cc2N1] | 689.3 | 6.1 |
| II-40 | 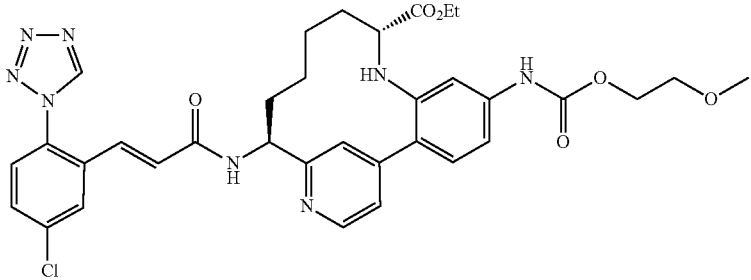 [SMILES: CCOC(=O)[C@H]1CCCC[C@H](NC(=O)/C=C/c2cc(Cl)ccc2-n2cnnn2)c2cc(ccn2)-c2ccc(NC(=O)OCCOC)cc2N1] | 689.3 | 6.5 |
| II-41 | 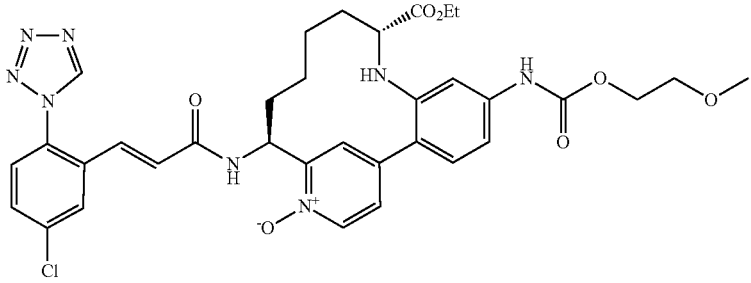 | 705.3 | 7.7 |
| II-42 | 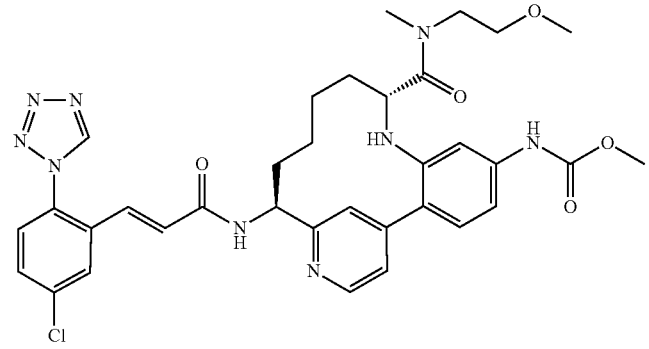 [SMILES: COCCN(C)C(=O)[C@H]1CCCC[C@H](NC(=O)/C=C/c2cc(Cl)ccc2-n2cnnn2)c2cc(ccn2)-c2ccc(NC(=O)OC)cc2N1] | 688.2 | 10.9 |
| II-43 | 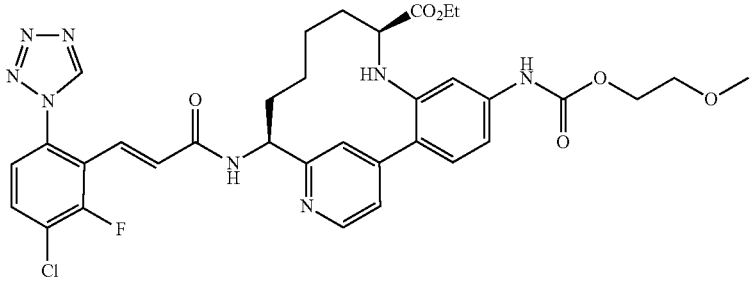 [SMILES: CCOC(=O)[C@@H]1CCCC[C@H](NC(=O)/C=C/c2c(-n3cnnn3)ccc(Cl)c2F)c2cc(ccn2)-c2ccc(NC(=O)OCCOC)cc2N1] | 707.1 | 5.7 |

TABLE II-5-continued

Examples II-39 to II-72

| Ex. # | LCMS [M + H]+ | HPLC RT (min.) |
|---|---|---|
| II-44 | 707.1 | 6.2 |
| II-45 | 601.4 | 4.6/4.7 |
| II-46 | 617.1 | 5.8 |
| II-47 (Diastereomer A) | 601.0 | 5.4 |

TABLE II-5-continued

Examples II-39 to II-72

| Ex. # | LCMS [M + H]+ | HPLC RT (min.) |
|---|---|---|
| II-48 (Diasetereomer B) | 601.0 | 5.4 |
| II-49 | 603.0 | 5.6 |
| II-50 | 631.1 | 5.95 |
| II-51 | 656.1 | 5.40 |

TABLE II-5-continued

Examples II-39 to II-72

| Ex. # | LCMS [M + H]⁺ | HPLC RT (min.) |
|---|---|---|
| II-52 | 660.2 | 5.02 |
| II-53 | 675.1 | 7.1 |
| II-54 | 706.1 | 7.3 |
| II-55 | 708.1 | 6.0 |

TABLE II-5-continued

Examples II-39 to II-72

| Ex. # | LCMS [M + H]+ | HPLC RT (min.) |
|---|---|---|
| II-56 | 656.1 | 5.16 |
| II-57 | 693.1 | 5.22 |
| II-58 | 707.0 | 4.44 |
| II-59 | 672.1 | 5.4 |

TABLE II-5-continued

Examples II-39 to II-72

| Ex. # | Structure | LCMS [M + H]+ | HPLC RT (min.) |
|---|---|---|---|
| II-60 | | 672.1 | 5.2 |
| II-61 | | 686.1 | 5.3 |
| II-62 | | 661.2 | 7.41 |
| II-63 | | 680.2 | 10.21 |

TABLE II-5-continued

Examples II-39 to II-72

| Ex. # | | LCMS [M + H]+ | HPLC RT (min.) |
|---|---|---|---|
| II-64 | | 680.3 | 10.56 |
| II-65 | | 679.0 | 9.46 |
| II-66 | | 646.0 | 8.78 |
| II-67 | | 632.0 | 8.24 |
| II-68 | | 646.0 | 8.37 |

TABLE II-5-continued

Examples II-39 to II-72

| Ex. # | LCMS [M + H]⁺ | HPLC RT (min.) |
|---|---|---|
| II-69 | 646.0 | 9.04 |
| II-70 | 700.0 | 5.61 |
| II-71 | 616.1 | 5.60 |
| II-72 | 674.0 | 6.09 |

What is claimed is:

1. A compound of Formula (I):

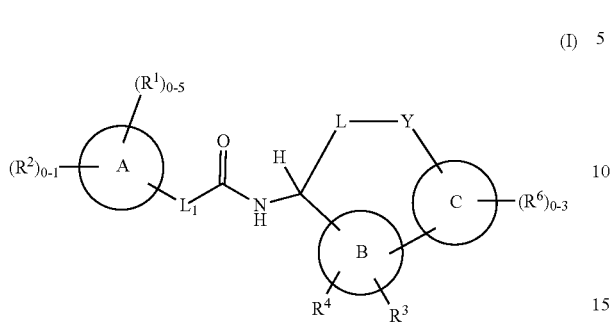

or a stereoisomer, a tautomer, a pharmaceutically acceptable salt, or a solvate thereof, wherein:
ring A is phenyl;
ring B is a 6-membered heteroaryl comprising: carbon atoms and 1-4 heteroatoms selected from N, O, and $S(O)_p$;
ring C is a 6-membered heteroaryl comprising: carbon atoms and 1-4 heteroatoms selected from N, O, and $S(O)_p$;
$L_1$ is $-CR^5=CR^5-$;
L is $C_{3-8}$ alkylene; wherein said alkylene is substituted with 0-2 $R^7$;
Y is $-CONH-$;
$R^1$ is, independently at each occurrence, selected from the group consisting of: halogen, $C_{1-6}$ alkyl, $C_{1-4}$ alkoxy, $C_{1-4}$ alkylthio, and $C_{1-4}$ haloalkyl;
$R^2$ is independently a 5- to 7-membered heterocycle comprising carbon atoms and 1-4 heteroatoms selected from N, NH, N ($C_{1-4}$ alkyl), O, and $S(O)_p$, wherein said heterocycle is substituted with 0-2 $R^{2a}$;
$R^{2a}$ is, independently at each occurrence, selected from the group consisting of: halogen, $C_{1-4}$ alkyl, $-CH_2OH$, $C_{1-4}$ alkoxy, OH, $CF_3$, $OCF_3$, CN, $NH_2$, $CO_2H$, $CO_2(C_{1-4}$ alkyl), $COC_{1-4}$ alkyl, $-CONH_2$, $-CONH(C_{1-4}$ alkyl), $-CON(C_{1-4}$ alkyl)$_2$, $-SO_2(C_{1-4}$ alkyl), $-SO_2NH_2$, $-SO_2NH(C_{1-4}$ alkyl), and $-SO_2N(C_{1-4}$ alkyl)$_2$;
$R^3$ is independently selected from the group consisting of: H, halogen, and CN;
$R^4$ is independently selected from the group consisting of: H, and $C_{1-4}$ alkyl;
$R^5$ is, independently at each occurrence, selected from the group consisting of: H, halogen, OH, and $C_{1-4}$ alkyl;
$R^6$ is, independently at each occurrence, selected from the group consisting of: halogen, $C_{1-4}$ alkyl, CN, OH, and $CF_3$;
$R^7$ is, independently at each occurrence, selected from the group consisting of: halogen, $C_{1-4}$ haloalkyl, $OCH_2F$, $OCHF_2$, $OCF_3$, and $C_{1-4}$ alkoxy; and
p is, independently at each occurrence, selected from the group consisting of: 0, 1, and 2.

2. The compound of claim 1, wherein:
ring B is independently selected from the group consisting of: pyridine, pyridazine, and pyrimidine; and
ring C is pyridine.

3. The compound of claim 2, wherein:

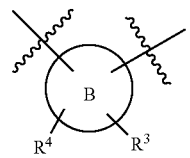

is independently selected from the group consisting of:

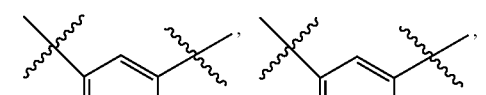

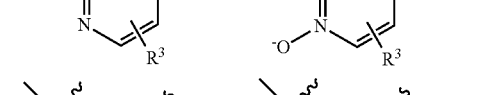

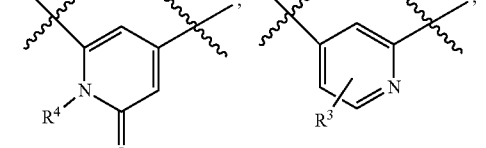

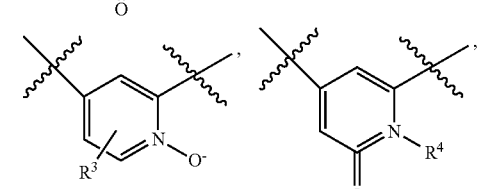

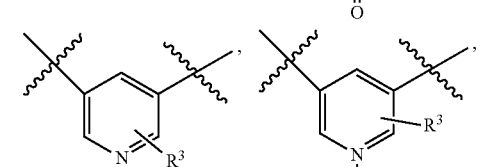

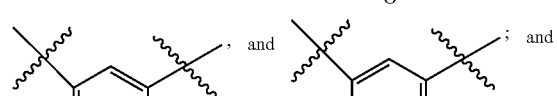

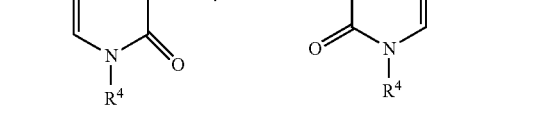

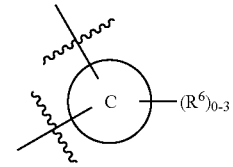

is independently selected from the group consisting of:

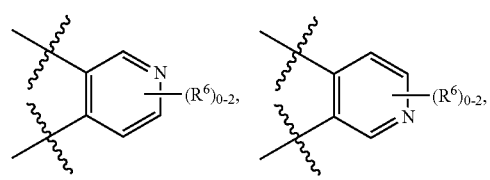

-continued

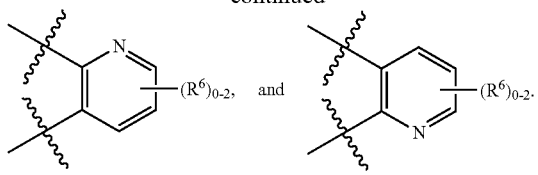

4. The compound of claim 1, wherein:
   $L_1$ is —CH=CH—;
   L is $C_{3-7}$ alkylene;
   $R^1$ is, independently at each occurrence, selected from: halogen and CN;
   $R^3$ is independently selected from the group consisting of: H and halogen; and
   $R^6$ is, independently at each occurrence, halogen.

5. The compound of claim 1, wherein:
   $L_1$ is —CH=CH—;
   L is —$(CH_2)_{3-6}$;
   $R^1$ is, independently at each occurrence, halogen;
   $R^3$ is H; and
   $R^6$ is, independently at each occurrence, halogen.

6. The compound according to claim 1, which is selected from:

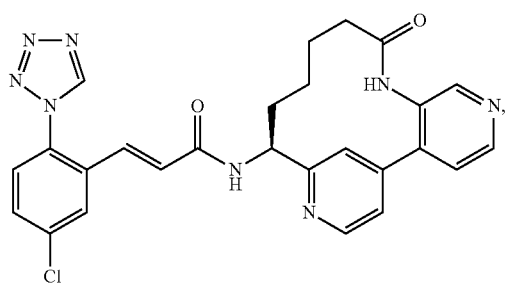 [SMILES: O=C(/C=C/c1cc(Cl)ccc1-n1cnnn1)N[C@H]1CCCCC(=O)Nc2cnccc2-c2ccnc1c2]

(E)-3-(5-Chloro-2-tetrazol-1-yl-phenyl)-N—((S)-9-oxo-5,8,16-triaza-tricyclo[13.3.1.0$^{2,7}$]nonadeca-1(19),2,4,6,15,17-hexaen-14-yl)-acrylamide, 2 TFA salt;

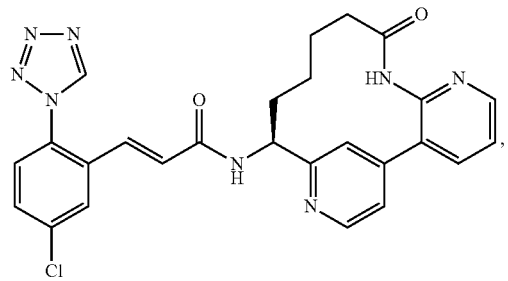 [SMILES: O=C(/C=C/c1cc(Cl)ccc1-n1cnnn1)N[C@H]1CCCCC(=O)Nc2ncccc2-c2ccnc1c2]

(E)-3-(5-Chloro-2-tetrazol-1-yl-phenyl)-N—((S)-9-oxo-6,8,16-triaza-tricyclo[13.3.1.0$^{2,7}$]nonadeca-1(19),2,4,6,15,17-hexaen-14-yl)-acrylamide, 2 TFA salt; and,

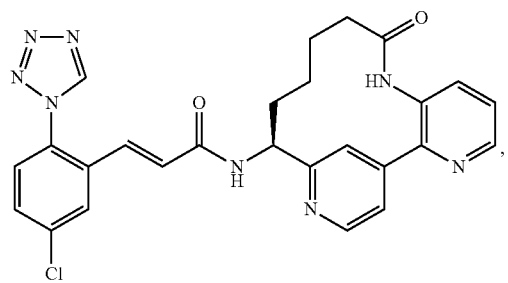 [SMILES: O=C(/C=C/c1cc(Cl)ccc1-n1cnnn1)N[C@H]1CCCCC(=O)Nc2cccnc2-c2ccnc1c2]

(S,E)-3-(5-chloro-2-(1H-tetrazol-1-yl)phenyl)-N-(4-oxo-3-aza-1(4,2),2(2,3)-dipyridinacyclononaphane-9-yl)acrylamide.

7. A pharmaceutical composition comprising one or more compounds of claim 1 and a pharmaceutically acceptable carrier or diluent.

8. A method for the treatment of a thromboembolic disorder, comprising: administering to a patient in need thereof a therapeutically effective amount of a compound of claim 1, or a stereoisomer, a tautomer, or a pharmaceutically acceptable salt thereof.

* * * * *